(12) United States Patent
Bilotta et al.

(10) Patent No.: US 8,501,732 B2
(45) Date of Patent: Aug. 6, 2013

(54) AMINOMETHYL QUINOLONE COMPOUNDS

(75) Inventors: Joseph A. Bilotta, Nutley, NJ (US);
Adrian Wai-Hing Cheung, Glen Rock, NJ (US); Fariborz Firooznia, Florham Park, NJ (US); Kevin Richard Guertin, Malden, MA (US); Stuart Hayden, Manalapan, NJ (US); Nancy-Ellen Haynes, Cranford, NJ (US); Christine M. Lukacs-Lesburg, Short Hills, NJ (US); Nicholas Marcopulos, North Caldwell, NJ (US); Eric Mertz, Fair Lawn, NJ (US); Lida Qi, Killingworth, CT (US); Yimin Qian, Wayne, NJ (US); Sung-Sau So, Verona, NJ (US); Jenny Tan, New Providence, NJ (US); Kshitij C. Thakkar, Clifton, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 13/546,039

(22) Filed: Jul. 11, 2012

(65) Prior Publication Data
US 2013/0018043 A1 Jan. 17, 2013

Related U.S. Application Data

(60) Provisional application No. 61/506,702, filed on Jul. 12, 2011.

(51) Int. Cl.
| | | |
|---|---|---|
| A61K 31/55 | (2006.01) | |
| A61K 31/551 | (2006.01) | |
| A61K 31/5375 | (2006.01) | |
| A61K 31/5377 | (2006.01) | |
| A61K 31/4427 | (2006.01) | |
| A61K 31/435 | (2006.01) | |
| A61K 31/47 | (2006.01) | |
| C07D 243/08 | (2006.01) | |
| C07D 401/02 | (2006.01) | |
| C07D 413/02 | (2006.01) | |
| C07D 413/14 | (2006.01) | |
| C07D 471/00 | (2006.01) | |
| C07D 215/00 | (2006.01) | |

(52) U.S. Cl.
USPC ............ 514/217.07; 514/218; 514/234.5; 514/235.2; 514/300; 514/312; 540/575; 540/597; 544/122; 544/127; 546/113; 546/153

(58) Field of Classification Search
USPC ......... 514/217.07, 218, 234.5, 235.2, 300, 514/312; 540/575, 597; 544/122, 127; 546/113, 546/153
See application file for complete search history.

(56) References Cited

FOREIGN PATENT DOCUMENTS
| | | |
|---|---|---|
| WO | 2005/051301 | 6/2005 |
| WO | 2005/091857 | 10/2005 |
| WO | 2008/138920 | 11/2008 |

OTHER PUBLICATIONS

Baker et al., J. Heterocyclic Chem. 40:353 ( 2003).
Liu, Q. et al., Tetrahedron Letters 42:1445-1447 ( 2001).
Connell et al., J. Org. Chem. 53:3845-3849 ( 1988).
Padwa et al., J. Org. Chem. 62:2786-2797 ( 1997).
Buckley et al., Bioorganic & Medicinal Chemistry Letters 18:3211-3214 ( 2008).
Fotsch et al., J. Med. Chem. 44:2344-2356 ( 2001).
Sasaki et al., J. Org. Chem. 43(12):2320 ( 1978).
Liu, Jia-Ming et al., J. Org. Chem. 51:1120-1123 ( 1986).
Tamaru et al., J. Am. Chem. Soc. 110:3994-4002 ( 1988).
Cairns et al., J. Med. Chem. 28:1832-1842 ( 1985).
Mendelson et al., Synthetic Comm. 26(3):603-610 ( 1996).
Huang et al., Bioorganic & Medicinal Chemistry Letters 15:3701-3706 ( 2005).
Gueret et al., Organic Letters 11(4):963-966 ( 2009).
Gueiffier et al., J. Heterocyclic Chem. 27:421 ( 1990).
Ganellin et al., J. Med. Chem. 38:3342-3350 ( 1995).
Barrett et al., Bioorganic & Medicinal Chemistry Letters 14:4897-4902 ( 2004).
Kiggen et al., Tetrahedron 42(6):1859-1872 ( 1986).
Grehn et al., Synthesis:275 ( 1987).
Barlow et al., J. Med. Chem. 24:315-322 ( 1981).
Gauuan et al., Bioorganic & Medicinal Chemistry 10:3013-3021 ( 2002).
Luo et al., Tetrahedron Letters 43:5739-5742 ( 2002).
Frerot et al., Tetrahedron 47(2):259-270 ( 1991).
Kasuga et al., Bioorganic & Medicinal Chemistry Letters 16:771-774 ( 2006).
Mallakpour et al., Synthetic Communications 37:1927-1934 ( 2007).
Vivier et al., J. Med. Chem. 48:6733l-6740 ( 2005).
Stern et al., J. Med. Chem. 50(22):5471-5484 ( 2007).
(International Search Report for PCT/EP2012/063366 Nov. 26, 2012).

*Primary Examiner* — Samantha Shterengarts

(57) ABSTRACT

The invention relates to JNK inhibitors and corresponding methods, formulations, and compositions for inhibiting JNK and treating JNK-mediated disorders. The application discloses JNK inhibitors, as described below in Formula I:

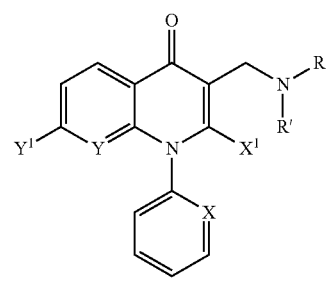

wherein the variables are as defined herein. The compounds and compositions disclosed herein are useful to modulate the activity of JNK and treat diseases associated with JNK activity. Disclosed are methods and formulations for inhibiting JNK and treating JNK-mediated disorders, and the like, with the compounds, and processes for making said compounds, and corresponding compositions, disclosed herein.

15 Claims, No Drawings

AMINOMETHYL QUINOLONE COMPOUNDS

PRIORITY TO RELATED APPLICATIONS

This application is entitled to the benefit of U.S. provisional patent application Ser. No. 61/506,702 filed on Jul. 12, 2011, the disclosure of which is incorporated herein by reference in its entirety.

FIELD OF THE INVENTION

The c-Jun N-terminal kinases (JNKs) are members of the mitogen-activated protein kinase family along with p38 and extracellular signal-regulated kinases (ERKs). Three distinct genes (jnk1, jnk2 and jnk3) encoding 10 splice variants have been identified. JNK1 and JNK2 are expressed in a wide variety of tissues, whereas JNK3 is mainly expressed in neurons, and to a lesser extent in heart and testes. Members of JNK family are activated by pro-inflammatory cytokines such as tumor necrosis factor α (TNF-α) and interleukin-1β (IL-1β), as well as environmental stresses. The activation of JNKs is mediated by its upstream kinases, MKK4 and MKK7, via dual phosphorylation of Thr-183 and Tyr-185. It has been shown that MKK4 and MKK7 can be activated by the diverse upstream kinases, including MEKK1 and MEKK4, depending upon the external stimuli and cellular context. The specificity of JNK signaling is achieved by forming a JNK-specific signaling complex containing multiple components of the kinase cascade by use of scaffold proteins called JNK-interacting proteins. JNKs have been shown to play important roles in inflammation, T cell functions, apoptosis and cellular survival by phosphorylating specific substrates, including transcription factors such as c-Jun, the component of activator protein-1 (AP1) family, and ATF2, as well as non-transcription factors such as IRS-1 and Bcl-2. Over-activation of JNK is believed to be an important mechanism in autoimmune, inflammatory, metabolic, neurological diseases as well as cancer.

Rheumatoid arthritis (RA) is a systemic autoimmune disease characterized by chronic inflammation of the joints. In addition to the joint swelling and pain caused by the inflammatory process, most RA patients ultimately develop debilitating joint damage and deformation. Several lines of compelling pharmacological and genetic evidence in cellular and animal models strongly suggest the relevance and importance of the activated JNK in the pathogenesis of RA. First, abnormal activation of JNK was detected in both human arthritic joints from RA patients and rodent arthritic joints from animal models of arthritis. In addition, inhibition of JNK activation by selective JNK inhibitors blocked proinflammatory cytokines and MMP production in human synoviocytes, macrophages and lymphocytes. Importantly, administration of the selective JNK inhibitors in rats with adjuvant arthritis or in mice with collagen-induced arthritis effectively protected joints from destruction and significantly reduced paw swelling by inhibiting cytokine and collagenase expression.

Asthma is a chronic inflammatory disease of airways, characterized by the presence of a cellular inflammatory process and by bronchial hyper-responsiveness associated with structural changes of the airways. This disorder has been shown to be driven by many cell types in the airways, including T lymphocytes, eosinophils, mast cells, neutrophils and epithelial cells. JNKs have emerged as promising therapeutic targets for asthma based upon the recent proof-of-concept studies: it has been shown that JNK inhibitors significantly blocked RANTES production in activated human airway smooth cells. More importantly, the JNK inhibitors showed good efficacy in chronic rat and mouse models for their abilities to reduce cellular infiltration, inflammation, hyper-responsiveness, smooth muscle proliferation, and IgE production. These observations suggest important roles of JNKs in the allergic inflammation and airway remodeling process associated with hyper-responsiveness. Therefore, blockade of JNK activity is expected to be beneficial for the treatment of asthma.

Type 2 diabetes is the most serious and prevalent metabolic disease characterized by insulin resistance and insulin secretion impairment as a result of chronic low-level inflammation and abnormal lipid metabolism associated with oxidative stress. It has been reported that JNK activity is abnormally elevated in various diabetic target tissues under obese and diabetic conditions. Activation of the JNK pathway by pro-inflammatory cytokines and oxidative stresses negatively regulates insulin signaling via phosphorylation of insulin receptor substrate-1 (IRS-1) at $Ser^{307}$, therefore contributes to insulin resistance and glucose tolerance. Compelling genetic evidence came from elegant animal model studies using $jnk^{-/-}$ mice crossed with either genetic (ob/ob) obese mice or dietary obese mice. Loss of JNK1($JNK1^{-/-}$), but not JNK2 functions ($jnk2^{-/-}$), protected obese mice from body gains, increased steady-state levels of blood glucose, and decreased plasma insulin levels. These studies demonstrated the potential utility of JNK inhibitor in the treatment of obesity/type 2 diabetes.

Neurodegenerative diseases, such as Alzheimer's (AD), Parkinson's (PD) and Stroke are CNS diseases characterized by synaptic loss, neuronal atrophy and death. The JNK pathway leading to c-Jun activation has been shown to play a causal role in apoptosis of isolated primary embryonic neurons and multiple neuronal cell lines upon induction of a variety of stimuli. Over-activation of JNK was observed in human brains from AD patients or rodent brain sections derived from animal models of neurodegenerative diseases. For example, increased phospho-JNKs were detected in the post-mortem brains from the AD patients. Administration of JNK inhibitory peptide (JIP-1 peptide) in the rodent model of AD induced by β-amyloid peptide administration prevented the impairment of synaptic plasticity. In the animal models of PD (MPTP model), elevated phospho-MKK4 and phospho-JNKs were observed concomitantly with the neuronal cell death. Adenoviral gene transfer of JNK inhibitory peptide (JIP-1 peptide) into striatum of mice attenuated behavioral impairment by inhibiting MPTP-mediated JNK, c-Jun and caspase activation, therefore blocking neuronal cell death in the substantia nigra. In addition, in the animal model of ischemic stroke induced by glutamate excitotoxicity, mice deficient in JNK3, but not JNK1 or JNK2, were resistant to kainic acid (glutamate receptor agonist)-mediated seizure or neuronal death. These data suggest JNK3 was mainly responsible for glutamate excitotoxicity, an important component in ischemic conditions. Taken together, data has emerged suggesting JNKs as attractive target for multiple CNS diseases associated with neuronal cell death.

Uncontrolled cellular growth, proliferation and migration along with de-regulated angiogenesis lead to the formation of malignant tumors. The JNK signal transduction pathway may not act exclusively in apoptosis, sustained JNK activation leading to AP1 activation has recently been implicated to contribute to the cellular survival of specific cancer types such as glial tumors and BCL-ABL transformed B lymphoblasts. In the case of glial tumors, enhanced JNK/AP1 activity was seen in most of the primary brain tumor samples. For the transformed B lymphoblasts, BCL-ABL was shown to activate the JNK pathway which in turn up-regulated expression of anti-apoptotic bcl-2 gene. Interestingly, the multi-drug resistance and hyper-proliferation seen in treatment-refractory AML (acute myeloid leukemia) patients has been causally linked to the sustained JNK activity present in these AML samples. Activation of JNK in leukemic cells resulted in induced expression of efflux pumps such as mdr1 and MRP1 responsible for multidrug resistance. Also, genes with a survival benefit in response to oxidative stress including glutathione-S-transferase π and γ-glutamyl cysteine synthase were also upregulated by the activated JNK pathway.

Kidney diseases are characterized by loss of nephron function caused by progressive glomerulosclerosis and tubulointerstitial fibrosis. Renal disease may develop as a consequence of many conditions including inflammation, hypertension, diabetes, or acute tissue damage caused by antibiotics, contrast agents, or other nephrotoxic substances. JNK signaling has been shown to be upregulated in pathology specimens from many human renal diseases, including immune and non-immune mediated glomerulonephritis, diabetic nephropathy, hypertension, acute injury, and appears to play a signaling role in polycystic kidney disease. Compelling evidence for a central role of JNK and the therapeutic potential of JNK inhibitors is supported by studies in animal models of renal injury. JNK was increased in a rat anti-glomerular basement membrane induced glomerulonephritis model and renal function was improved by a specific inhibitor in both acute and chronic disease paradigms. JNK was also increased in the Dahl salt-sensitive hypertensive rat, a model of hypertensive renal disease, as well as in models of renal ischemia-reperfusion injury. The cellular mechanisms by which JNK may contribute to renal injury are, in part, by up-regulation of pro-inflammatory mediators in macrophages, as well as by activation of pro-fibrotic, and pro-apoptotic pathways directly in cells of the renal glomerulus and the tubular epithelium. The ability to improve renal function by inhibition of JNK in multiple disease models, suggests JNKs as attractive targets for therapy of renal diseases of various etiology.

SUMMARY OF THE INVENTION

In one aspect, the application provides a compound of formula I

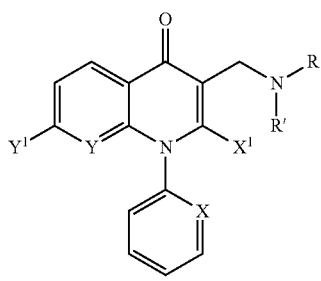

I wherein:
R is —C(=O)A, —C(=O)OA, —C(=O)NHA, —C(=N—C≡N)A, —C(=N—C≡N)NHA, or A;
A is lower alkyl, phenyl, cycloalkyl, adamantyl, heterocycloalkyl, heteroaryl, or bicyclic heteroaryl, optionally substituted with one or more $A^1$;
each $A^1$ is independently $A^2$ or $A^3$;
each $A^2$ is independently hydroxy, halo, or oxo;
each $A^3$ is independently lower alkyl, lower alkoxy, phenyl, benzyl, heterocycloalkyl, bicyclic heterocycloalkyl, heteroaryl, amino, lower alkyl amino, lower dialkyl amino, amido, lower alkyl ester, sulfonyl, sulfonamido, —C(=O), or —C(=O)O, optionally substituted with one or more halo, hydroxy, lower alkyl, lower alkoxy, phenyl, hydroxy cycloalkyl, amino, lower alkyl amino, lower dialkyl amino, carbamic acid tert-butyl ester, sulfonyl, lower alkyl sulfonyl heterocycloalkyl, or hydroxy lower alkyl;
R' is H or methyl;
X is CX';
X' is H or halo;
$X^1$ is H, 2-oxazolyl, dimethyl amido, or lower alkyl ester;
Y is CH or N; and
$Y^1$ is H, halo, lower alkoxy, or halo lower alkyl;
or a pharmaceutically acceptable salt thereof.

In one aspect, the application provides a method of treating a JNK-mediated disorder in a subject having a JNK-mediated disorder, said method comprising administering to a subject in need thereof a therapeutically effective amount of any of the above compounds.

In certain embodiments of the method of treating a JNK-mediated disorder, the JNK-mediated disorder is kidney disease.

In one aspect, the application provides a pharmaceutical composition comprising the compound of any one of the above embodiments, admixed with at least one pharmaceutically acceptable carrier, excipient or diluent.

DETAILED DESCRIPTION OF THE INVENTION

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise. Thus, the phrase 'a" or "an" entity' as used herein refers to one or more of that entity; for example, a compound refers to one or more compounds or at least one compound. As such, the terms "a" (or "an"), "one or more", and "at least one" can be used interchangeably herein.

As used in this specification, whether in a transitional phrase or in the body of the claim, the terms "comprise(s)" and "comprising" are to be interpreted as having an open-ended meaning That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

As used herein, unless specifically indicated otherwise, the word "or" is used in the "inclusive" sense of "and/or" and not the "exclusive" sense of "either/or".

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable (e.g., R, X, $X^1$, $Y^1$, and $Y^2$) occurs more than one time in any moiety or formula depicting and describing compounds employed or claimed in the present invention, its definition on each occurrence is independent of its definition at every other occurrence. Also, combinations of substituents and/or variables are permissible only if such compounds result in stable compounds.

The symbols "*" at the end of a bond or "- - - -" drawn through a bond each refer to the point of attachment of a functional group or other chemical moiety to the rest of the molecule of which it is a part. Thus, for example:

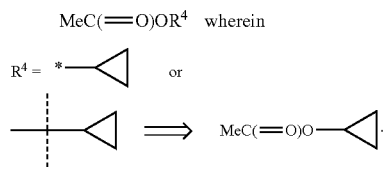

The symbol " ⁄ " as used herein refers to a bond that may be in either the cis or trans configuration.

A bond drawn into ring system (as opposed to connected at a distinct vertex) indicates that the bond may be attached to any of the suitable ring atoms.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen or a substituent.

The term "about" is used herein to mean approximately, in the region of, roughly, or around. When the term "about" is used in conjunction with a numerical range, it modifies that range by extending the boundaries above and below the numerical values set forth.

Certain compounds of the invention may exhibit tautomerism. Tautomeric compounds can exist as two or more interconvertable species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH— $\rightleftharpoons$ —C(—OH)=CH—), amide/imidic acid (—C(=O)—NH— $\rightleftharpoons$ —C(—OH)=N—) and amidine (—C(=NR)—NH— $\rightleftharpoons$ —C(—NHR)=N—) tautomers. The latter two are particularly common in heteroaryl and heterocyclic rings and the present invention encompasses all tautomeric forms of the compounds.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics*, 10th Ed., McGraw Hill Companies Inc., New York (2001). Any suitable materials and/or methods known to those of skill can be utilized in carrying out the present invention. However, preferred materials and methods are described. Materials, reagents and the like to which reference are made in the following description and examples are obtainable from commercial sources, unless otherwise noted.

The definitions described herein may be appended to form chemically-relevant combinations, such as "heteroalkylaryl," "haloalkylheteroaryl," "arylalkylheterocyclyl," "alkylcarbonyl," "alkoxyalkyl," and the like. When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" refers to an alkyl group having one to two phenyl substituents, and thus includes benzyl, phenylethyl, and diphenylmethyl. An "alkylaminoalkyl" is an alkyl group having one to two alkylamino substituents. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth. Accordingly, as used herein, the term "hydroxyalkyl" is used to define a subset of heteroalkyl groups defined below. The term -(ar)alkyl refers to either an unsubstituted alkyl or an aralkyl group. The term (hetero)aryl or (het)aryl refers to either an aryl or a heteroaryl group.

The term "acyl" as used herein denotes a group of formula —C(=O)R wherein R is hydrogen or lower alkyl as defined herein. The term "alkylcarbonyl" as used herein denotes a group of formula C(=O)R wherein R is alkyl as defined herein. The term $C_{1-6}$ acyl refers to a group —C(=O)R wherein R contains 1-6 carbon atoms. The term "arylcarbonyl" as used herein means a group of formula C(=O)R wherein R is an aryl group; the term 'benzoyl" as used herein an "arylcarbonyl" group wherein R is phenyl.

The term "alkyl" as used herein denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-10}$ alkyl" as used herein refers to an alkyl composed of 1 to 10 carbons. Examples of alkyl groups include, but are not limited to, lower alkyl groups include methyl, ethyl, propyl, i-propyl, n-butyl, i-butyl, t-butyl or pentyl, isopentyl, neopentyl, hexyl, heptyl, and octyl.

When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" denotes the radical R'R"-, wherein R' is a phenyl radical, and R" is an alkylene radical as defined herein with the understanding that the attachment point of the phenylalkyl moiety will be on the alkylene radical. Examples of arylalkyl radicals include, but are not limited to, benzyl, phenylethyl, 3-phenylpropyl. The terms "arylalkyl" or "aralkyl" are interpreted similarly except R' is an aryl radical. The terms "(het)arylalkyl" or "(het)aralkyl" are interpreted similarly except R' is optionally an aryl or a heteroaryl radical.

The term "alkylene" as used herein denotes a divalent saturated linear hydrocarbon radical of 1 to 10 carbon atoms (e.g., $(CH_2)_n$) or a branched saturated divalent hydrocarbon radical of 2 to 10 carbon atoms (e.g., —CHMe- or —CH$_2$CH (i-Pr)CH$_2$—), unless otherwise indicated. Except in the case of methylene, the open valences of an alkylene group are not attached to the same atom. Examples of alkylene radicals include, but are not limited to, methylene, ethylene, propylene, 2-methyl-propylene, 1,1-dimethyl-ethylene, butylene, 2-ethylbutylene.

The term "alkoxy" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1-10}$ alkoxy" as used herein refers to an-O-alkyl wherein alkyl is $C_{1-10}$.

The term "amido" as used herein means an amino, alkylamino, or dialkylamino group appended to the parent molecular moiety through a carbonyl group (—C(=O)— group). Representative examples of amido include, but are not limited to, aminocarbonyl, methylaminocarbonyl, dimethylaminocarbonyl, and ethylmethylaminocarbonyl.

The term "amino" as used herein, means a —$NH_2$ group.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, optionally substituted phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof.

The term "base" includes, but is not limited to, NaOH, KOH, LiOH and alkali metal carbonates such as potassium carbonate, sodium carbonate, lithium carbonate, sodium bicarbonate, cesium carbonate and the like.

"Cycloalkyl" or "carbocyclic ring" means a monovalent saturated carbocyclic moiety consisting of monocyclic, bicyclic or tricyclic rings. Cycloalkyl can optionally be substituted with one or more substituents, wherein each substituent is independently hydroxy, alkyl, alkoxy, halo, haloalkyl, amino, monoalkylamino, or dialkylamino, unless otherwise specifically indicated. Examples of cycloalkyl moieties include, but are not limited to, cyclopropyl, cyclobutyl, cyclopentyl, cyclohexyl, cycloheptyl, and the like, including partially unsaturated derivatives thereof.

"Heterocycloalkyl lower alkyl" means a moiety of the formula —$R^a$—$R^b$, where $R^a$ is lower alkylene and $R^b$ is heterocycloalkyl as defined herein.

The term "heteroaryl" or "heteroaromatic" as used herein means a monocyclic or bicyclic radical of 5 to 12 ring atoms having at least one aromatic ring containing four to eight atoms per ring, incorporating one or more N, O, or S heteroatoms, the remaining ring atoms being carbon, with the understanding that the attachment point of the heteroaryl radical will be on an aromatic ring. As well known to those skilled in the art, heteroaryl rings have less aromatic character than their all-carbon counter parts. Thus, for the purposes of the invention, a heteroaryl group need only have some degree of aromatic character. Examples of heteroaryl moieties include monocyclic aromatic heterocycles having 5 to 6 ring atoms and 1 to 3 heteroatoms include, but is not limited to, pyridinyl, pyrimidinyl, pyrazinyl, pyrrolyl, pyrazolyl, imidazolyl, oxazol, isoxazole, thiazole, isothiazole, triazoline, thiadiazole and oxadiaxoline which can optionally be substituted with one or more, preferably one or two substituents selected from hydroxy, cyano, alkyl, alkoxy, thio, lower haloalkoxy, alkylthio, halo, haloalkyl, alkylsulfinyl, alkylsulfonyl, halogen, amino, alkylamino, dialkylamino, aminoalkyl, alkylaminoalkyl, and dialkylaminoalkyl, nitro, alkoxycarbonyl and carbamoyl, alkylcarbamoyl, dialkylcarbamoyl, arylcarbamoyl, alkylcarbonylamino and arylcarbonylamino. Examples of bicyclic moieties include, but are not limited to, quinolinyl, isoquinolinyl, benzofuryl, benzothiophenyl, benzoxazole, benzisoxazole, benzothiazole and benzisothiazole. Bicyclic moieties can be optionally substituted on either ring; however the point of attachment is on a ring containing a heteroatom.

The term "heterocyclyl", "heterocycle", or "heterocycloalkyl" as used herein denotes a monovalent saturated cyclic radical, consisting of one or more rings, preferably one to two rings, of three to eight atoms per ring, incorporating one or more ring heteroatoms (chosen from N,O or $S(O)_{0-2}$), and which can optionally be independently substituted with one or more, preferably one or two substituents selected from hydroxy, oxo, cyano, lower alkyl, lower alkoxy, lower haloalkoxy, alkylthio, halo, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino, arylcarbonylamino, unless otherwise indicated. Examples of heterocyclic radicals include, but are not limited to, azetidinyl, pyrrolidinyl, hexahydroazepinyl, oxetanyl, tetrahydrofuranyl, tetrahydrothiophenyl, oxazolidinyl, thiazolidinyl, isoxazolidinyl, morpholinyl, piperazinyl, piperidinyl, tetrahydropyranyl, thiomorpholinyl, quinuclidinyl and imidazolinyl.

The term "hydroxyalkyl" as used herein denotes an alkyl radical as herein defined wherein one to three hydrogen atoms on different carbon atoms is/are replaced by hydroxyl groups.

Commonly used abbreviations include: acetyl (Ac), azo-bis-isobutyrylnitrile (AIBN), atmospheres (Atm), 9-borabicyclo[3.3.1]nonane (9-BBN or BBN), tert-butoxycarbonyl (Boc), di-tert-butyl pyrocarbonate or boc anhydride ($BOC_2O$), benzyl (Bn), butyl (Bu), Chemical Abstracts Registration Number (CASRN), benzyloxycarbonyl (CBZ or Z), carbonyl diimidazole (CDI), 1,4-diazabicyclo[2.2.2]octane (DABCO), diethylaminosulfur trifluoride (DAST), dibenzylideneacetone (dba), 1,5-diazabicyclo[4.3.0]non-5-ene (DBN), 1,8-diazabicyclo[5.4.0]undec-7-ene (DBU), N,N'-dicyclohexylcarbodiimide (DCC), 1,2-dichloroethane (DCE), dichloromethane (DCM), diethyl azodicarboxylate (DEAD), di-iso-propylazodicarboxylate (DIAD), di-iso-butylaluminumhydride (DIBAL or DIBAL-H), di-iso-propylethylamine (DIPEA), N,N-dimethyl acetamide (DMA), 4-N,N-dimethylaminopyridine (DMAP), N,N-dimethylformamide (DMF), dimethyl sulfoxide (DMSO), 1,1'-bis-(diphenylphosphino)ethane (dppe), 1,1'-bis-(diphenylphosphino)ferrocene (dppf), 1-(3-dimethylaminopropyl)-3-ethylcarbodiimide hydrochloride (EDC), ethyl (Et), ethyl acetate (EtOAc), ethanol (EtOH), 2-ethoxy-2H-quinoline-1-carboxylic acid ethyl ester (EEDQ), diethyl ether ($Et_2O$), O-(7-azabenzotriazole-1-yl)-N,N,N'N'-tetramethyluronium hexafluorophosphate acetic acid (HATU), acetic acid (HOAc), 1-N-hydroxybenzotriazole (HOBt), high pressure liquid chromatography (HPLC), iso-propanol (IPA), lithium hexamethyl disilazane (LiHMDS), methanol (MeOH), melting point (mp), $MeSO_2$— (mesyl or Ms), methyl (Me), acetonitrile (MeCN), m-chloroperbenzoic acid (MCPBA), mass spectrum (ms), methyl t-butyl ether (MTBE), N-bromosuccinimide (NBS), N-carboxyanhydride (NCA), N-chlorosuccinimide (NCS), N-methylmorpholine (NMM), N-methylpyrrolidone (NMP), pyridinium chlorochromate (PCC), pyridinium dichromate (PDC), phenyl (Ph), propyl (Pr), iso-propyl (i-Pr), pounds per square inch (psi), pyridine (pyr), room temperature (rt or RT), tert-butyldimethylsilyl or t-$BuMe_2Si$ (TBDMS), triethylamine (TEA or $Et_3N$), 2,2,6,6-tetramethylpiperidine 1-oxyl (TEMPO), triflate or $CF_3SO_2$— (Tf), trifluoroacetic acid (TFA), O-benzotriazol-1-yl-N,N,N', N'-tetramethyluronium tetrafluoroborate (TBTU), thin layer chromatography (TLC), tetrahydrofuran (THF), trimethylsilyl or $Me_3Si$ (TMS), p-toluenesulfonic acid monohydrate (TsOH or pTsOH), 4-Me-$C_6H_4SO_2$- or tosyl (Ts), N-urethane-N-carboxyanhydride (UNCA). Conventional nomenclature including the prefixes normal (n), iso (i-), secondary (sec-), tertiary (tert-) and neo have their customary meaning when used with an alkyl moiety. (J. Rigaudy and D. P. Klesney, *Nomenclature in Organic Chemistry*, IUPAC 1979 Pergamon Press, Oxford.).

"Heteroalkyl" means an alkyl moiety as defined herein, including a branched $C_4$-$C_7$ alkyl, wherein one, two or three hydrogen atoms have been replaced with a substituent independently selected from the group consisting of —$OR^a$, —$NR^bR^c$, and —$S(O)_nR^d$ (where n is an integer from 0 to 2), with the understanding that the point of attachment of the heteroalkyl radical is through a carbon atom, wherein $R^a$ is hydrogen, acyl, alkyl, cycloalkyl, or cycloalkylalkyl; $R^b$ and $R^c$ are independently of each other hydrogen, acyl, alkyl, cycloalkyl, or cycloalkylalkyl; and when n is 0, $R^d$ is hydrogen, alkyl, cycloalkyl, or cycloalkylalkyl; when n is 1, $R^d$ is alkyl, cycloalkyl, or cycloalkylalkyl; and when n is 2, $R^d$ is alkyl, cycloalkyl, cycloalkylalkyl, amino, acylamino, monoalkylamino, or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like.

"Heteroaryl" means a monocyclic or bicyclic moiety of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, optionally substituted imidazolyl, oxazolyl, isoxazolyl, thiazolyl, isothiazolyl, oxadiazolyl, thiadiazolyl, pyrazinyl, thienyl, thiophenyl, furanyl, pyranyl, pyridinyl, pyrrolyl, pyrazolyl, pyrimidyl, pyridazinyl, quinolinyl, isoquinolinyl, benzofuryl, benzofuranyl, benzothiophenyl, benzothiopyranyl, benzimidazolyl, benzoxazolyl, benzooxadiazolyl, benzothiazolyl, benzothiadiazolyl, benzopyranyl, indolyl, isoindolyl, indazolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, including partially hydrogenated derivatives thereof.

The terms "halo," "halogen," and "halide" are used interchangeably herein and refer to fluoro, chloro, bromo, and iodo.

"Haloalkyl" means alkyl as defined herein in which one or more hydrogen has been replaced with same or different halogen. The term "lower haloalkyl" denotes a straight or branched chain hydrocarbon residue containing 1 to 6 carbon atoms substituted with one or more halogen atom. Exemplary haloalkyls include —$CH_2Cl$, —$CH_2CF_3$, —$CH_2CCl_3$, —$CF_2CF_3$, —$CF_3$, and the like.

"Heterocyclyl" or "heterocycloalkyl" means a monovalent saturated moiety, consisting of one to two rings, incorporating one, two, or three or four heteroatoms (chosen from nitrogen, oxygen or sulfur). The heterocyclyl ring may be optionally fused to a heteroaryl group as defined herein. The heterocyclyl ring may be optionally substituted as defined herein. Examples of heterocyclyl moieties include, but are not limited to, optionally substituted piperidinyl, piperazinyl, homopiperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, quinuclidinyl, quinolinyl, isoquinolinyl, benzimidazolyl, thiadiazolylidinyl, benzothiazolidinyl, benzoazolylidinyl, dihydrofuryl, tetrahydrofuryl, dihydropyranyl, tetrahydropyranyl, thiamorpholinyl, thiamorpholinylsulfoxide, thiamorpholinylsulfone, dihydroquinolinyl, dihydroisoquinolinyl, tetrahydroquinolinyl, tetrahydroisoquinolinyl, octahydro-pyrrolo[1,2-a]pyrazine, octahydro-pyrido[1,2-a]pyrazine, 5,6,7,8-tetrahydro-[1,2,4]triazolo[4,3-a]pyrazine, 5,6,7,8-tetrahydro-imidazo[1,2-a]pyrazine and the like.

"Optionally substituted" means a substituent which is substituted independently with zero to three substituents selected from lower alkyl, halo, OH, cyano, amino, nitro, lower alkoxy, or halo-lower alkyl.

"Leaving group" means a group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Optional" or "optionally" means that the subsequently described event or circumstance may but need not occur, and that the description includes instances where the event or circumstance occurs and instances in which it does not.

"Agonist" refers to a compound that enhances the activity of another compound or receptor site.

"Antagonist" refers to a compound that diminishes or prevents the action of another compound or receptor site.

The term "drug candidate" refers to a compound or preparation which is to be tested for possible effect in the treatment of a disease state in an animal, regardless of whether said drug candidate has any known biological activity.

The term "homologous" as used herein refers to a protein that performs substantially the same function in another subject species and shares substantial sequence identity, to the extent that they are recognized in the art as being different versions of the same protein, differing primarily in the species in which they are found. Thus, for example, human ERG, mouse ERG, and rat ERG are all considered homologous to each other.

"Modulator" means a molecule that interacts with a target. The interactions include, but are not limited to, agonist, antagonist, and the like, as defined herein.

"Disease" and "Disease state" means any disease, condition, symptom, disorder or indication.

The term "cell line" refers to a clone of immortalized mammalian cells. A "stable" cell line is a cell line that exhibits substantially consistent characteristics over time (e.g., with each doubling). A stable cell line within the scope of this invention provides a substantial proportion of cells that are capable of providing a seal resistance of greater than about 50 MOhm, a current amplitude of greater than about 200 pA, and provide a current amplitude that does not vary by more than approximately 20% over one hour under control conditions.

"Pharmaceutically acceptable salts" of a compound means salts that are pharmaceutically acceptable, as defined herein, and that possess the desired pharmacological activity of the parent compound. Such salts include:

(1) acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphthoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or (2) salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

It should be understood that all references to pharmaceutically acceptable salts include solvent addition forms (solvates) or crystal forms (polymorphs) as defined herein, of the same acid addition salt.

The preferred pharmaceutically acceptable salts are the salts formed from acetic acid, hydrochloric acid, sulphuric acid, methanesulfonic acid, maleic acid, phosphoric acid, tartaric acid, citric acid, sodium, potassium, calcium, zinc, and magnesium.

"Solvates" means solvent additions forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Subject" includes mammals and birds. "Mammals" means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. The term "subject" does not denote a particular age or sex.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

"Pharmacological effect" as used herein encompasses effects produced in the subject that achieve the intended purpose of a therapy. For example, a pharmacological effect would be one that results in the prevention, alleviation or reduction of urinary incontinence in a treated subject.

"Treating" or "treatment" of a disease state includes (i) preventing the disease state, i.e. causing the clinical symptoms of the disease state not to develop in a subject that may be exposed to or predisposed to the disease state, but does not yet experience or display symptoms of the disease state; (ii) inhibiting the disease state, i.e., arresting the development of the disease state or its clinical symptoms; or (iii) relieving the disease state, i.e., causing temporary or permanent regression of the disease state or its clinical symptoms.

All patents and publications identified herein are incorporated herein by reference in their entirety.

Inhibitors of JNK

In one aspect, the application provides a compound of formula I

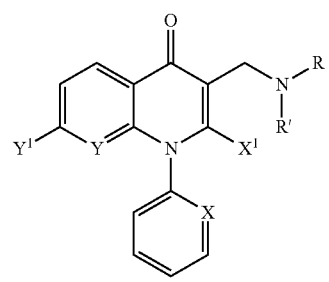

wherein:
R is —C(=O)A, —C(=O)OA, —C(=O)NHA, —C(=N—C≡N)A, —C(=N—C≡N)NHA, or A;
A is lower alkyl, phenyl, cycloalkyl, adamantyl, heterocycloalkyl, heteroaryl, or bicyclic heteroaryl, optionally substituted with one or more $A^1$;
each $A^1$ is independently $A^2$ or $A^3$;
each $A^2$ is independently hydroxy, halo, or oxo;
each $A^3$ is independently lower alkyl, lower alkoxy, phenyl, benzyl, heterocycloalkyl, bicyclic heterocycloalkyl, heteroaryl, amino, lower alkyl amino, lower dialkyl amino, amido, lower alkyl ester, sulfonyl, sulfonamido, —C(=O), or —C(=O)O, optionally substituted with one or more halo, hydroxy, lower alkyl, lower alkoxy, phenyl, hydroxy cycloalkyl, amino, lower alkyl amino, lower dialkyl amino, carbamic acid tert-butyl ester, sulfonyl, lower alkyl sulfonyl heterocycloalkyl, or hydroxy lower alkyl;
R' is H or methyl;
X is CX';
X' is H or halo;
$X^1$ is H, 2-oxazolyl, dimethyl amido, or lower alkyl ester;
Y is CH or N; and
$Y^1$ is H, halo, lower alkoxy, or halo lower alkyl;
or a pharmaceutically acceptable salt thereof.

In one aspect, the application provides a compound of formula I, wherein R' is H.

In one aspect, the application provides a compound of formula I, wherein X is CH.

In one aspect, the application provides a compound of formula I, wherein R' is H and X is CH.

In one aspect, the application provides a compound of formula I, wherein Y is CH.

In one aspect, the application provides a compound of formula I, wherein Y is CH, R' is H and X is CH.

In one aspect, the application provides a compound of formula I, wherein $Y^1$ is Cl.

In one aspect, the application provides a compound of formula I, wherein $Y^1$ is Cl, Y is CH, R' is H and X is CH.

In one aspect, the application provides a compound of formula I, wherein R is —C(=O)A.

In one aspect, the application provides a compound of formula I, wherein R is —C(=O)A, $Y^1$ is Cl, Y is CH, R' is H and X is CH.

In one aspect, the application provides a compound of formula I, wherein A is phenyl, heteroaryl or bicyclic heteroaryl, optionally substituted with one or more $A^1$.

In one aspect, the application provides a compound of formula I, wherein A is phenyl, heteroaryl or bicyclic heteroaryl, optionally substituted with one or more $A^1$, R is —C(=O)A, $Y^1$ is Cl, Y is CH, R' is H and X is CH.

In one aspect, the application provides a compound of formula I, wherein $X^1$ is 2-oxazolyl.

In one aspect, the application provides a compound of formula I, wherein $X^1$ is 2-oxazolyl, A is phenyl, heteroaryl or bicyclic heteroaryl, optionally substituted with one or more $A^1$, R is —C(=O)A, $Y^1$ is Cl, Y is CH, R' is H and X is CH.

In one aspect, the application provides a compound of formula I, wherein $X^1$ is dimethyl amido.

In one aspect, the application provides a compound of formula I, wherein $X^1$ is dimethyl amido, A is phenyl, heteroaryl or bicyclic heteroaryl, optionally substituted with one or more $A^1$, R is —C(=O)A, $Y^1$ is Cl, Y is CH, R' is H and X is CH.

In one aspect, the application provides a compound of formula I, wherein $X^1$ is H.

In one aspect, the application provides a compound of formula I, wherein $X^1$ is H, A is phenyl, heteroaryl or bicyclic heteroaryl, optionally substituted with one or more $A^1$, R is —C(=O)A, $Y^1$ is Cl, Y is CH, R' is H and X is CH.

In one aspect, the application provides a compound of formula I, wherein $X^1$ is methyl ester.

In one aspect, the application provides a compound of formula I, wherein $X^1$ is methyl ester, A is phenyl, heteroaryl or bicyclic heteroaryl, optionally substituted with one or more $A^1$, R is —C(=O)A, $Y^1$ is Cl, Y is CH, R' is H and X is CH.

In one aspect, the application provides a compound of formula I, wherein R' is H, X is CH, Y is N, $Y^1$ is H or $CF_3$, and $X^1$ is 2-oxazolyl In one aspect, the application provides a compound of formula I, wherein R is —C(=O)NHA.

In one aspect, the application provides a compound of formula I, wherein R is —C(=O)NHA, $Y^1$ is Cl, Y is CH, R' is H and X is CH.

In one aspect, the application provides a compound of formula I, wherein A is phenyl, optionally substituted with one or more $A^1$.

In one aspect, the application provides a compound of formula I, wherein A is phenyl, optionally substituted with one or more $A^1$, R is —C(=O)A, $Y^1$ is Cl, Y is CH, R' is H and X is CH.

In one aspect, the application provides a compound of formula I, selected from the group consisting of:

In one aspect, the application provides a compound selected from the group consisting of:

1-Benzyl-2-oxo-1,2-dihydro-pyridine-4-carboxylic acid (7-chloro-2-oxazol-2-yl-4-oxo-1-phenyl-1,4-dihydro-quinolin-3-ylmethyl)-amide;

N-(7-Chloro-2-oxazol-2-yl-4-oxo-1-phenyl-1,4-dihydro-quinolin-3-ylmethyl)-2-morpholin-4-yl-isonicotinamide;

N-(7-Chloro-2-oxazol-2-yl-4-oxo-1-phenyl-1,4-dihydro-quinolin-3-ylmethyl)-6-morpholin-4-yl-nicotinamide;

N-(7-Chloro-2-oxazol-2-yl-4-oxo-1-phenyl-1,4-dihydro-quinolin-3-ylmethyl)-terephthalamide;

5-[(7-Chloro-2-oxazol-2-yl-4-oxo-1-phenyl-1,4-dihydro-quinolin-3-ylmethyl)-carbamoyl]-pyridine-2-carboxylic acid methyl ester;

6-Chloro-N-(7-chloro-2-oxazol-2-yl-4-oxo-1-phenyl-1,4-dihydro-quinolin-3-ylmethyl)-nicotinamide;

3,4,5,6-Tetrahydro-2H-[1,2']bipyridinyl-5'-carboxylic acid (7-chloro-2-oxazol-2-yl-4-oxo-1-phenyl-1,4-dihydro-quinolin-3-ylmethyl)-amide;

Benzo[1,3]dioxole-5-carboxylic acid (7-chloro-2-oxazol-2-yl-4-oxo-1-phenyl-1,4-dihydro-quinolin-3-ylmethyl)-amide;

1-Benzyl-2-oxo-1,2-dihydro-pyridine-4-carboxylic acid (2-oxazol-2-yl-4-oxo-1-phenyl-1,4-dihydro-[1,8]naphthyridin-3-ylmethyl)-amide;

6-Morpholin-4-yl-N-(2-oxazol-2-yl-4-oxo-1-phenyl-1,4-dihydro-[1,8]naphthyridin-3-ylmethyl)-nicotinamide;

1-Methyl-1H-pyrazole-4-carboxylic acid (2-oxazol-2-yl-4-oxo-1-phenyl-1,4-dihydro-[1,8]naphthyridin-3-ylmethyl)-amide;

4-Hydroxymethyl-3,4,5,6-tetrahydro-2H-[1,2]bipyridinyl-5'-carboxylic acid (2-oxazol-2-yl-4-oxo-1-phenyl-1,4-dihydro-[1,8]naphthyridin-3-ylmethyl)-amide;

7-Chloro-3-{[(6-morpholin-4-yl-pyridine-3-carbonyl)-amino]-methyl}-4-oxo-1-phenyl-1,4-dihydro-quinoline-2-carboxylic acid dimethylamide;

7-Chloro-3-{[(2-morpholin-4-yl-thiazole-5-carbonyl)-amino]-methyl}-4-oxo-1-phenyl-1,4-dihydro-quinoline-2-carboxylic acid dimethylamide;

7-Chloro-3-[(4-methoxy-benzoylamino)-methyl]-4-oxo-1-phenyl-1,4-dihydro-quinoline-2-carboxylic acid dimethylamide;

3-{[(Benzothiazole-6-carbonyl)-amino]-methyl}-7-chloro-4-oxo-1-phenyl-1,4-dihydro-quinoline-2-carboxylic acid dimethylamide;

7-Chloro-3-[(4-morpholin-4-yl-benzoylamino)-methyl]-4-oxo-1-phenyl-1,4-dihydro-quinoline-2-carboxylic acid dimethylamide;

7-Chloro-3-[(4-oxazol-5-yl-benzoylamino)-methyl]-4-oxo-1-phenyl-1,4-dihydro-quinoline-2-carboxylic acid dimethylamide;

7-Chloro-3-[(4-methanesulfonyl-benzoylamino)-methyl]-4-oxo-1-phenyl-1,4-dihydro-quinoline-2-carboxylic acid dimethylamide;

7-Chloro-3-[(4-fluoro-benzoylamino)-methyl]-4-oxo-1-phenyl-1,4-dihydro-quinoline-2-carboxylic acid dimethylamide;

7-Chloro-3-{[(2,3-dihydro-benzo[1,4]dioxine-6-carbonyl)-amino]-methyl}-4-oxo-1-phenyl-1,4-dihydro-quinoline-2-carboxylic acid dimethylamide;

3-{[(1-Benzyl-2-oxo-1,2-dihydro-pyridine-4-carbonyl)-amino]-methyl}-7-chloro-4-oxo-1-phenyl-1,4-dihydro-quinoline-2-carboxylic acid dimethylamide;

7-Chloro-3-{[(1-methyl-1H-pyrazole-4-carbonyl)-amino]-methyl}-4-oxo-1-phenyl-1,4-dihydro-quinoline-2-carboxylic acid dimethylamide;

4-Hydroxymethyl-3,4,5,6-tetrahydro-2H-[1,2']bipyridinyl-5'-carboxylic acid (7-chloro-2-dimethylcarbamoyl-4-oxo-1-phenyl-1,4-dihydro-quinolin-3-ylmethyl)-amide;

4-(2-Hydroxy-ethyl)-3,4,5,6-tetrahydro-2H-[1,2']bipyridinyl-5'-carboxylic acid (7-chloro-2-dimethylcarbamoyl-4-oxo-1-phenyl-1,4-dihydro-quinolin-3-ylmethyl)-amide;

7-Chloro-3-({[2-(4-hydroxymethyl-piperidin-1-yl)-thiazole-5-carbonyl]-amino}-methyl)-4-oxo-1-phenyl-1,4-dihydro-quinoline-2-carboxylic acid dimethylamide;

7-Chloro-3-[({2-[4-(2-hydroxy-ethyl)-piperidin-1-yl]-thiazole-5-carbonyl}-amino)-methyl]-4-oxo-1-phenyl-1,4-dihydro-quinoline-2-carboxylic acid dimethylamide;

3,4,5,6-Tetrahydro-2H-[1,2']bipyridinyl-5'-carboxylic acid (7-chloro-2-dimethylcarbamoyl-4-oxo-1-phenyl-1,4-dihydro-quinolin-3-ylmethyl)-amide;

1-Benzyl-2-oxo-1,2-dihydro-pyridine-4-carboxylic acid (7-chloro-4-oxo-1-phenyl-1,4-dihydro-quinolin-3-ylmethyl)-amide;

1-Methyl-1H-pyrazole-4-carboxylic acid (7-chloro-4-oxo-1-phenyl-1,4-dihydro-quinolin-3-ylmethyl)-amide;

N-(7-Chloro-4-oxo-1-phenyl-1,4-dihydro-quinolin-3-ylmethyl)-2-morpholin-4-yl-isonicotinamide;
N-(7-Chloro-4-oxo-1-phenyl-1,4-dihydro-quinolin-3-ylmethyl)-2-pyrrolidin-1-yl-isonicotinamide;
3H-Benzoimidazole-5-carboxylic acid (7-chloro-4-oxo-1-phenyl-1,4-dihydro-quinolin-3-ylmethyl)-amide;
1-(4-Chloro-benzyl)-2-oxo-1,2-dihydro-pyridine-4-carboxylic acid (7-chloro-4-oxo-1-phenyl-1,4-dihydro-quinolin-3-ylmethyl)-amide;
N-(7-Chloro-4-oxo-1-phenyl-1,4-dihydro-quinolin-3-ylmethyl)-6-methoxy-nicotinamide;
N-(7-Chloro-4-oxo-1-phenyl-1,4-dihydro-quinolin-3-ylmethyl)-4-sulfamoyl-benzamide;
1-Phenyl-1H-pyrazole-4-carboxylic acid (7-chloro-4-oxo-1-phenyl-1,4-dihydro-quinolin-3-ylmethyl)-amide;
1-(3-Methoxy-benzyl)-2-oxo-1,2-dihydro-pyridine-4-carboxylic acid (7-chloro-4-oxo-1-phenyl-1,4-dihydro-quinolin-3-ylmethyl)-amide;
1-(2-Chloro-benzyl)-2-oxo-1,2-dihydro-pyridine-4-carboxylic acid (7-chloro-4-oxo-1-phenyl-1,4-dihydro-quinolin-3-ylmethyl)-amide;
N-(7-Chloro-4-oxo-1-phenyl-1,4-dihydro-quinolin-3-ylmethyl)-6-morpholin-4-yl-nicotinamide;
N-(7-Chloro-4-oxo-1-phenyl-1,4-dihydro-quinolin-3-ylmethyl)-2-dimethylamino-isonicotinamide;
Benzothiazole-5-carboxylic acid (7-chloro-4-oxo-1-phenyl-1,4-dihydro-quinolin-3-ylmethyl)-amide;
N-(7-Chloro-4-oxo-1-phenyl-1,4-dihydro-quinolin-3-ylmethyl)-4-(2H-[1,2,4]triazol-3-yl)-benzamide;
1-(3-Chloro-benzyl)-2-oxo-1,2-dihydro-pyridine-4-carboxylic acid (7-chloro-4-oxo-1-phenyl-1,4-dihydro-quinolin-3-ylmethyl)-amide;
3-Methyl-3H-imidazo[4,5-b]pyridine-6-carboxylic acid (7-chloro-4-oxo-1-phenyl-1,4-dihydro-quinolin-3-ylmethyl)-amide;
1H-Indole-6-carboxylic acid (7-chloro-4-oxo-1-phenyl-1,4-dihydro-quinolin-3-ylmethyl)-amide;
N-(7-Chloro-4-oxo-1-phenyl-1,4-dihydro-quinolin-3-ylmethyl)-4-oxazol-5-yl-benzamide;
1-(2-Methoxy-benzyl)-2-oxo-1,2-dihydro-pyridine-4-carboxylic acid (7-chloro-4-oxo-1-phenyl-1,4-dihydro-quinolin-3-ylmethyl)-amide;
1H-Imidazo[4,5-b]pyridine-6-carboxylic acid (7-chloro-4-oxo-1-phenyl-1,4-dihydro-quinolin-3-ylmethyl)-amide;
N-(7-Chloro-4-oxo-1-phenyl-1,4-dihydro-quinolin-3-ylmethyl)-terephthalamide;
3-[(7-Chloro-4-oxo-1-phenyl-1,4-dihydro-quinolin-3-ylmethyl)-carbamoyl]-pyrrolidine-1-carboxylic acid tert-butyl ester;
1-Benzyl-6-oxo-1,6-dihydro-pyridine-3-carboxylic acid (7-chloro-4-oxo-1-phenyl-1,4-dihydro-quinolin-3-ylmethyl)-amide;
1-Methyl-1H-[1,2,3]triazole-4-carboxylic acid (7-chloro-4-oxo-1-phenyl-1,4-dihydro-quinolin-3-ylmethyl)-amide;
1-Methyl-2-oxo-1,2-dihydro-pyridine-4-carboxylic acid (7-chloro-4-oxo-1-phenyl-1,4-dihydro-quinolin-3-ylmethyl)-amide;
1-Benzyl-1H-[1,2,3]triazole-4-carboxylic acid (7-chloro-4-oxo-1-phenyl-1,4-dihydro-quinolin-3-ylmethyl)-amide;
2-Morpholin-4-yl-pyrimidine-5-carboxylic acid (7-chloro-4-oxo-1-phenyl-1,4-dihydro-quinolin-3-ylmethyl)-amide;
N-(7-Chloro-4-oxo-1-phenyl-1,4-dihydro-quinolin-3-ylmethyl)-3,4-dimethoxy-benzamide;
N-(7-Chloro-4-oxo-1-phenyl-1,4-dihydro-quinolin-3-ylmethyl)-3,5-difluoro-benzamide;
N-(7-Chloro-4-oxo-1-phenyl-1,4-dihydro-quinolin-3-ylmethyl)-2,3-difluoro-benzamide;
N-(7-Chloro-4-oxo-1-phenyl-1,4-dihydro-quinolin-3-ylmethyl)-2,5-difluoro-benzamide;
6-Chloro-N-(7-chloro-4-oxo-1-phenyl-1,4-dihydro-quinolin-3-ylmethyl)-nicotinamide;
(1S,4S)-5-{5-[(7-Chloro-4-oxo-1-phenyl-1,4-dihydro-quinolin-3-ylmethyl)-carbamoyl]-pyridin-2-yl}-2,5-diaza-bicyclo[2.2.1]heptane-2-carboxylic acid tert-butyl ester;
4-(2-Hydroxy-ethyl)-3,4,5,6-tetrahydro-2H-[1,2]bipyridinyl-5'-carboxylic acid (7-chloro-4-oxo-1-phenyl-1,4-dihydro-quinolin-3-ylmethyl)-amide;
6-[Bis-(2-hydroxy-ethyl)-amino]-N-(7-chloro-4-oxo-1-phenyl-1,4-dihydro-quinolin-3-ylmethyl)-nicotinamide;
3,4,5,6-Tetrahydro-2H-[1,2]bipyridinyl-5'-carboxylic acid (7-chloro-4-oxo-1-phenyl-1,4-dihydro-quinolin-3-ylmethyl)-amide;
N-(7-Chloro-4-oxo-1-phenyl-1,4-dihydro-quinolin-3-ylmethyl)-6-[(2-hydroxy-ethyl)-methyl-amino]-nicotinamide;
4-Hydroxymethyl-3,4,5,6-tetrahydro-2H-[1,2]bipyridinyl-5'-carboxylic acid (7-chloro-4-oxo-1-phenyl-1,4-dihydro-quinolin-3-ylmethyl)-amide;
6-Azepan-1-yl-N-(7-chloro-4-oxo-1-phenyl-1,4-dihydro-quinolin-3-ylmethyl)-nicotinamide;
4-Methanesulfonyl-3,4,5,6-tetrahydro-2H-[1,2]bipyridinyl-5'-carboxylic acid (7-chloro-4-oxo-1-phenyl-1,4-dihydro-quinolin-3-ylmethyl)-amide;
N-(7-Chloro-4-oxo-1-phenyl-1,4-dihydro-quinolin-3-ylmethyl)-6-((R)-3-hydroxy-pyrrolidin-1-yl)-nicotinamide;
4-Methoxy-3,4,5,6-tetrahydro-2H-[1,2]bipyridinyl-5'-carboxylic acid (7-chloro-4-oxo-1-phenyl-1,4-dihydro-quinolin-3-ylmethyl)-amide;
3,4,5,6-Tetrahydro-2H-[1,2]bipyridinyl-4,5'-dicarboxylic acid 5'-[(7-chloro-4-oxo-1-phenyl-1,4-dihydro-quinolin-3-ylmethyl)-amide]-4-methylamide;
4-{5-[(7-Chloro-4-oxo-1-phenyl-1,4-dihydro-quinolin-3-ylmethyl)-carbamoyl]-pyridin-2-yl}-piperazine-1-carboxylic acid amide;
N-(7-Chloro-4-oxo-1-phenyl-1,4-dihydro-quinolin-3-ylmethyl)-6-(2-methoxy-ethylamino)-nicotinamide;
4-Dimethylamino-3,4,5,6-tetrahydro-2H-[1,2]bipyridinyl-5'-carboxylic acid (7-chloro-4-oxo-1-phenyl-1,4-dihydro-quinolin-3-ylmethyl)-amide;
4-Hydroxy-3,4,5,6-tetrahydro-2H-[1,2]bipyridinyl-5'-carboxylic acid (7-chloro-4-oxo-1-phenyl-1,4-dihydro-quinolin-3-ylmethyl)-amide;
N-(7-Chloro-4-oxo-1-phenyl-1,4-dihydro-quinolin-3-ylmethyl)-6-(2-hydroxy-ethylamino)-nicotinamide;
N-(7-Chloro-4-oxo-1-phenyl-1,4-dihydro-quinolin-3-ylmethyl)-6-(tetrahydro-pyran-4-ylamino)-nicotinamide;
N-(7-Chloro-4-oxo-1-phenyl-1,4-dihydro-quinolin-3-ylmethyl)-6-dimethylamino-nicotinamide;
N-(7-Chloro-4-oxo-1-phenyl-1,4-dihydro-quinolin-3-ylmethyl)-6-(1,1-dioxo-1$\lambda^6$-thiomorpholin-4-yl)-nicotinamide;
{5'-[(7-Chloro-4-oxo-1-phenyl-1,4-dihydro-quinolin-3-ylmethyl)-carbamoyl]-3,4,5,6-tetrahydro-2H[1,2']bipyridinyl-4-yl}-carbamic acid tert-butyl ester;
N-(7-Chloro-4-oxo-1-phenyl-1,4-dihydro-quinolin-3-ylmethyl)-6-(4-methyl-[1,4]diazepan-1-yl)-nicotinamide;
N-(7-Chloro-4-oxo-1-phenyl-1,4-dihydro-quinolin-3-ylmethyl)-6-[4-(2-hydroxy-ethyl)-piperazin-1-yl]-nicotinamide;
N-(7-Chloro-4-oxo-1-phenyl-1,4-dihydro-quinolin-3-ylmethyl)-6-pyrrolidin-1-yl-nicotinamide;
N-(7-Chloro-4-oxo-1-phenyl-1,4-dihydro-quinolin-3-ylmethyl)-6-piperazin-1-yl-nicotinamide;

3,4,5,6-Tetrahydro-2H-[1,2]bipyridinyl-4,5'-dicarboxylic acid 4-amide 5'-[(7-chloro-4-oxo-1-phenyl-1,4-dihydro-quinolin-3-ylmethyl)-amide];

N-(7-Chloro-4-oxo-1-phenyl-1,4-dihydro-quinolin-3-ylmethyl)-6-((S)-3-hydroxy-pyrrolidin-1-yl)-nicotinamide;

N-(7-Chloro-4-oxo-1-phenyl-1,4-dihydro-quinolin-3-ylmethyl)-6-(4-methyl-piperazin-1-yl)-nicotinamide;

N-(7-Chloro-4-oxo-1-phenyl-1,4-dihydro-quinolin-3-ylmethyl)-6-(1S,4S)-2,5-diaza-bicyclo[2.2.1]hept-2-yl-nicotinamide 4-Amino-3,4,5,6-tetrahydro-2H-[1,2]bipyridinyl-5'-carboxylic acid (7-chloro-4-oxo-1-phenyl-1,4-dihydro-quinolin-3-ylmethyl)-amide;

2-Piperidin-1-yl-thiazole-5-carboxylic acid (7-chloro-4-oxo-1-phenyl-1,4-dihydro-quinolin-3-ylmethyl)-amide;

2-(4-Methanesulfonyl-piperidin-1-yl)-thiazole-5-carboxylic acid (7-chloro-4-oxo-1-phenyl-1,4-dihydro-quinolin-3-ylmethyl)-amide;

2-(4-Hydroxymethyl-piperidin-1-yl)-thiazole-5-carboxylic acid (7-chloro-4-oxo-1-phenyl-1,4-dihydro-quinolin-3-ylmethyl)-amide;

2-(4-Hydroxy-piperidin-1-yl)-thiazole-5-carboxylic acid (7-chloro-4-oxo-1-phenyl-1,4-dihydro-quinolin-3-ylmethyl)-amide;

2-(4-Methyl-piperazin-1-yl)-thiazole-5-carboxylic acid (7-chloro-4-oxo-1-phenyl-1,4-dihydro-quinolin-3-ylmethyl)-amide;

2-Morpholin-4-yl-thiazole-5-carboxylic acid (7-chloro-4-oxo-1-phenyl-1,4-dihydro-quinolin-3-ylmethyl)-amide;

2-(1,1-Dioxo-1$\lambda^6$-thiomorpholin-4-yl)-thiazole-5-carboxylic acid (7-chloro-4-oxo-1-phenyl-1,4-dihydro-quinolin-3-ylmethyl)-amide;

N-(7-Chloro-4-oxo-1-phenyl-1,4-dihydro-quinolin-3-ylmethyl)-N-(2-hydroxy-2-methyl-propyl)-terephthalamide;

N-(7-Chloro-4-oxo-1-phenyl-1,4-dihydro-quinolin-3-ylmethyl)-N-((1R,3R)-5-hydroxy-adamantan-2-yl)-terephthalamide;

N-[7-Chloro-1-(2-chloro-phenyl)-4-oxo-1,4-dihydro-quinolin-3-ylmethyl]-6-morpholin-4-yl-nicotinamide;

6-Bromo-N-[7-chloro-1-(2-chloro-phenyl)-4-oxo-1,4-dihydro-quinolin-3-ylmethyl]-nicotinamide;

N-[7-Chloro-1-(2-chloro-phenyl)-4-oxo-1,4-dihydro-quinolin-3-ylmethyl]-6-(1H-pyrazol-4-yl)-nicotinamide;

1-Phenyl-1H-pyrazole-4-carboxylic acid [7-fluoro-1-(2-fluoro-phenyl)-4-oxo-1,4-dihydro-quinolin-3-ylmethyl]-amide;

1-Methyl-1H-pyrazole-4-carboxylic acid [7-fluoro-1-(2-fluoro-phenyl)-4-oxo-1,4-dihydro-quinolin-3-ylmethyl]-amide;

6-Chloro-N-[7-fluoro-1-(2-fluoro-phenyl)-4-oxo-1,4-dihydro-quinolin-3-ylmethyl]-nicotinamide;

4-Hydroxymethyl-3,4,5,6-tetrahydro-2H-[1,2']bipyridinyl-5'-carboxylic acid [7-fluoro-1-(2-fluoro-phenyl)-4-oxo-1,4-dihydro-quinolin-3-ylmethyl]-amide;

6-(1,1-Dioxo-1$\lambda^6$-thiomorpholin-4-yl)-N-[7-fluoro-1-(2-fluoro-phenyl)-4-oxo-1,4-dihydro-quinolin-3-ylmethyl]-nicotinamide;

N-[7-Fluoro-1-(2-fluoro-phenyl)-4-oxo-1,4-dihydro-quinolin-3-ylmethyl]-6-morpholin-4-yl-nicotinamide;

7-Chloro-3-[(4-methanesulfonyl-benzoylamino)-methyl]-4-oxo-1-phenyl-1,4-dihydro-quinoline-2-carboxylic acid methyl ester;

7-Chloro-3-[(4-oxazol-5-yl-benzoylamino)-methyl]-4-oxo-1-phenyl-1,4-dihydro-quinoline-2-carboxylic acid methyl ester;

7-Chloro-4-oxo-1-phenyl-3-{[4-(4H-[1,2,4]triazol-3-yl)-benzoylamino]-methyl}-1,4-dihydro-quinoline-2-carboxylic acid methyl ester;

7-Chloro-3-{[(6-morpholin-4-yl-pyridine-3-carbonyl)-amino]-methyl}-4-oxo-1-phenyl-1,4-dihydro-quinoline-2-carboxylic acid methyl ester;

3-{[(Benzothiazole-5-carbonyl)-amino]-methyl}-7-chloro-4-oxo-1-phenyl-1,4-dihydro-quinoline-2-carboxylic acid methyl ester;

7-Chloro-3-{[4-(1H-imidazol-2-yl)-benzoylamino]-methyl}-4-oxo-1-phenyl-1,4-dihydro-quinoline-2-carboxylic acid methyl ester;

7-Chloro-4-oxo-1-phenyl-3-[(4-sulfamoyl-benzoylamino)-methyl]-1,4-dihydro-quinoline-2-carboxylic acid methyl ester;

7-Chloro-3-{[(2-morpholin-4-yl-thiazole-5-carbonyl)-amino]-methyl}-4-oxo-1-phenyl-1,4-dihydro-quinoline-2-carboxylic acid methyl ester;

3-[(4-Carbamoyl-benzoylamino)-methyl]-7-chloro-4-oxo-1-phenyl-1,4-dihydro-quinoline-2-carboxylic acid methyl ester;

7-Chloro-3-[(4-methylcarbamoyl-benzoylamino)-methyl]-4-oxo-1-phenyl-1,4-dihydro-quinoline-2-carboxylic acid methyl ester;

3-{[(1-Benzyl-1H-pyrazole-4-carbonyl)-amino]-methyl}-7-chloro-4-oxo-1-phenyl-1,4-dihydro-quinoline-2-carboxylic acid methyl ester;

7-Chloro-3-{[(1H-indole-6-carbonyl)-amino]-methyl}-4-oxo-1-phenyl-1,4-dihydro-quinoline-2-carboxylic acid methyl ester;

7-Chloro-3-{[(1-methyl-1H-pyrazole-4-carbonyl)-amino]-methyl}-4-oxo-1-phenyl-1,4-dihydro-quinoline-2-carboxylic acid methyl ester;

7-Chloro-4-oxo-1-phenyl-3-{[4-(1H-pyrazol-3-yl)-benzoylamino]-methyl}-1,4-dihydro-quinoline-2-carboxylic acid methyl ester;

7-Chloro-3-[(4-morpholin-4-yl-benzoylamino)-methyl]-4-oxo-1-phenyl-1,4-dihydro-quinoline-2-carboxylic acid methyl ester;

7-Chloro-4-oxo-1-phenyl-3-[(4-[1,2,3]thiadiazol-5-yl-benzoylamino)-methyl]-1,4-dihydro-quinoline-2-carboxylic acid methyl ester;

7-Chloro-3-{[4-(5-methyl-[1,2,4]oxadiazol-3-yl)-benzoylamino]-methyl}-4-oxo-1-phenyl-1,4-dihydro-quinoline-2-carboxylic acid methyl ester;

7-Chloro-3-{[4-(3-methyl-[1,2,4]oxadiazol-5-yl)-benzoylamino]-methyl}-4-oxo-1-phenyl-1,4-dihydro-quinoline-2-carboxylic acid methyl ester;

7-Chloro-3-{[4-(2-methyl-thiazol-4-yl)-benzoylamino]-methyl}-4-oxo-1-phenyl-1,4-dihydro-quinoline-2-carboxylic acid methyl ester;

3-{[(1-tert-Butoxycarbonyl-piperidine-4-carbonyl)-amino]-methyl}-7-chloro-4-oxo-1-phenyl-1,4-dihydro-quinoline-2-carboxylic acid methyl ester;

7-Chloro-3-{[4-(2-methyl-2H-tetrazol-5-yl)-benzoylamino]-methyl}-4-oxo-1-phenyl-1,4-dihydro-quinoline-2-carboxylic acid methyl ester;

3-{[(1-Acetyl-piperidine-4-carbonyl)-amino]-methyl}-7-chloro-4-oxo-1-phenyl-1,4-dihydro-quinoline-2-carboxylic acid methyl ester;

7-Chloro-3-{[(1-methanesulfonyl-piperidine-4-carbonyl)-amino]-methyl}-4-oxo-1-phenyl-1,4-dihydro-quinoline-2-carboxylic acid methyl ester;

7-Chloro-3-[(4-chloro-benzoylamino)-methyl]-4-oxo-1-phenyl-1,4-dihydro-quinoline-2-carboxylic acid methyl ester;

7-Chloro-3-[(4-methoxycarbonyl-benzoylamino)-methyl]-4-oxo-1-phenyl-1,4-dihydro-quinoline-2-carboxylic acid methyl ester;
7-Chloro-3-[(4-methoxy-benzoylamino)-methyl]-4-oxo-1-phenyl-1,4-dihydro-quinoline-2-carboxylic acid methyl ester;
7-Chloro-3-[(3-methoxy-benzoylamino)-methyl]-4-oxo-1-phenyl-1,4-dihydro-quinoline-2-carboxylic acid methyl ester;
7-Chloro-4-oxo-1-phenyl-3-{[(pyridine-4-carbonyl)-amino]-methyl}-1,4-dihydro-quinoline-2-carboxylic acid methyl ester;
7-Chloro-3-[(3,4-difluoro-benzoylamino)-methyl]-4-oxo-1-phenyl-1,4-dihydro-quinoline-2-carboxylic acid methyl ester;
7-Chloro-3-[(3-fluoro-benzoylamino)-methyl]-4-oxo-1-phenyl-1,4-dihydro-quinoline-2-carboxylic acid methyl ester;
7-Chloro-4-oxo-1-phenyl-3-{[(pyridine-3-carbonyl)-amino]-methyl}-1,4-dihydro-quinoline-2-carboxylic acid methyl ester;
7-Chloro-3-[(4-fluoro-benzoylamino)-methyl]-4-oxo-1-phenyl-1,4-dihydro-quinoline-2-carboxylic acid methyl ester;
7-Chloro-3-[(3-chloro-4-fluoro-benzoylamino)-methyl]-4-oxo-1-phenyl-1,4-dihydro-quinoline-2-carboxylic acid methyl ester;
7-Chloro-3-[(3-chloro-benzoylamino)-methyl]-4-oxo-1-phenyl-1,4-dihydro-quinoline-2-carboxylic acid methyl ester
7-Chloro-3-[(3,4-dimethoxy-benzoylamino)-methyl]-4-oxo-1-phenyl-1,4-dihydro-quinoline-2-carboxylic acid methyl ester
7-Chloro-3-[(3,4-dichloro-benzoylamino)-methyl]-4-oxo-1-phenyl-1,4-dihydro-quinoline-2-carboxylic acid methyl ester;
7-Chloro-3-[(2-fluoro-benzoylamino)-methyl]-4-oxo-1-phenyl-1,4-dihydro-quinoline-2-carboxylic acid methyl ester;
7-Chloro-4-oxo-1-phenyl-3-{[(pyridine-2-carbonyl)-amino]-methyl}-1,4-dihydro-quinoline-2-carboxylic acid methyl ester;
7-Chloro-3-(isobutyrylamino-methyl)-4-oxo-1-phenyl-1,4-dihydro-quinoline-2-carboxylic acid methyl ester;
7-Chloro-3-[(2-chloro-benzoylamino)-methyl]-4-oxo-1-phenyl-1,4-dihydro-quinoline-2-carboxylic acid methyl ester;
7-Chloro-3-[(2-methoxy-benzoylamino)-methyl]-4-oxo-1-phenyl-1,4-dihydro-quinoline-2-carboxylic acid methyl ester;
3-(Benzoylamino-methyl)-7-chloro-4-oxo-1-phenyl-1,4-dihydro-quinoline-2-carboxylic acid methyl ester;
3-(Benzoylamino-methyl)-4-oxo-1-phenyl-1,4-dihydro-quinoline-2-carboxylic acid methyl ester;
3-{[(6-Morpholin-4-yl-pyridine-3-carbonyl)-amino]-methyl}-4-oxo-1-phenyl-7-trifluoromethyl-1,4-dihydro-[1,8]naphthyridine-2-carboxylic acid methyl ester
3-{[4-(1H-Imidazol-2-yl)-benzoylamino]-methyl}-4-oxo-1-phenyl-7-trifluoromethyl-1,4-dihydro-[1,8]naphthyridine-2-carboxylic acid methyl ester;
4-Oxo-1-phenyl-3-[(4-sulfamoyl-benzoylamino)-methyl]-7-trifluoromethyl-1,4-dihydro-[1,8]naphthyridine-2-carboxylic acid methyl ester;
3-[(4-Carbamoyl-benzoylamino)-methyl]-4-oxo-1-phenyl-7-trifluoromethyl-1,4-dihydro-[1,8]naphthyridine-2-carboxylic acid methyl ester;
4-Oxo-1-phenyl-3-{[4-(2H-pyrazol-3-yl)-benzoylamino]-methyl}-7-trifluoromethyl-1,4-dihydro-[1,8]naphthyridine-2-carboxylic acid methyl ester;
3-{[4-(2-Methyl-2H-tetrazol-5-yl)-benzoylamino]-methyl}-4-oxo-1-phenyl-7-trifluoromethyl-1,4-dihydro-[1,8]naphthyridine-2-carboxylic acid methyl ester;
3-{[(1H-Indole-6-carbonyl)-amino]-methyl}-4-oxo-1-phenyl-7-trifluoromethyl-1,4-dihydro-[1,8]naphthyridine-2-carboxylic acid methyl ester;
3-[(3,4-Dichloro-benzoylamino)-methyl]-4-oxo-1-phenyl-7-trifluoromethyl-1,4-dihydro-[1,8]naphthyridine-2-carboxylic acid methyl ester;
3-[(3-Chloro-benzoylamino)-methyl]-7-methoxy-4-oxo-1-phenyl-1,4-dihydro-quinoline-2-carboxylic acid methyl ester;
7-Methoxy-3-[(3-methoxy-benzoylamino)-methyl]-4-oxo-1-phenyl-1,4-dihydro-quinoline-2-carboxylic acid methyl ester;
3-[(3,4-Difluoro-benzoylamino)-methyl]-7-methoxy-4-oxo-1-phenyl-1,4-dihydro-quinoline-2-carboxylic acid methyl ester;
3-[(4-tert-Butyl-benzoylamino)-methyl]-7-methoxy-4-oxo-1-phenyl-1,4-dihydro-quinoline-2-carboxylic acid methyl ester;
7-Methoxy-3-[(4-methoxy-benzoylamino)-methyl]-4-oxo-1-phenyl-1,4-dihydro-quinoline-2-carboxylic acid methyl ester;
7-Methoxy-4-oxo-1-phenyl-3-{[(pyridine-3-carbonyl)-amino]-methyl}-1,4-dihydro-quinoline-2-carboxylic acid methyl ester;
3-[(4-Fluoro-benzoylamino)-methyl]-7-methoxy-4-oxo-1-phenyl-1,4-dihydro-quinoline-2-carboxylic acid methyl ester;
3-[(4-Dimethylamino-benzoylamino)-methyl]-7-methoxy-4-oxo-1-phenyl-1,4-dihydro-quinoline-2-carboxylic acid methyl ester;
3-[(4-Chloro-benzoylamino)-methyl]-7-methoxy-4-oxo-1-phenyl-1,4-dihydro-quinoline-2-carboxylic acid methyl ester;
7-Fluoro-3-{[(6-morpholin-4-yl-pyridine-3-carbonyl)-amino]-methyl}-4-oxo-1-phenyl-1,4-dihydro-quinoline-2-carboxylic acid methyl ester;
3-{[(6-Chloro-pyridine-3-carbonyl)-amino]-methyl}-7-fluoro-4-oxo-1-phenyl-1,4-dihydro-quinoline-2-carboxylic acid methyl ester;
7-Chloro-3-[(6,7-dimethoxy-quinazolin-4-ylamino)-methyl]-1-phenyl-1H-quinolin-4-one;
7-Chloro-3-[(7-fluoro-quinazolin-4-ylamino)-methyl]-1-phenyl-1H-quinolin-4-one;
7-Chloro-1-phenyl-3-[(6-piperidin-1-yl-pyrimidin-4-ylamino)-methyl]-1H-quinolin-4-one;
7-Chloro-1-phenyl-3-[(2-piperidin-1-yl-pyrimidin-4-ylamino)-methyl]-1H-quinolin-4-one;
3-(Benzothiazol-2-ylaminomethyl)-7-chloro-1-phenyl-1H-quinolin-4-one;
3-[(1H-Benzoimidazol-2-ylamino)-methyl]-7-chloro-1-phenyl-1H-quinolin-4-one;
[(7-Chloro-4-oxo-1-phenyl-1,4-dihydro-quinolin-3-ylmethyl)-amino]-morpholin-4-yl-methylene-cyanamide;
[(7-Chloro-4-oxo-1-phenyl-1,4-dihydro-quinolin-3-ylmethyl)-amino]-phenylamino-methylene-cyanamide;
(7-Chloro-4-oxo-1-phenyl-1,4-dihydro-quinolin-3-ylmethyl)-carbamic acid phenyl ester;
4-Phenyl-piperazine-1-carboxylic acid (7-chloro-4-oxo-1-phenyl-1,4-dihydro-quinolin-3-ylmethyl)-amide;

{4-[3-(7-Chloro-4-oxo-1-phenyl-1,4-dihydro-quinolin-3-yl-methyl)-ureido]-cyclohexyl}-carbamic acid tert-butyl ester;
{4-[3-(7-Chloro-4-oxo-1-phenyl-1,4-dihydro-quinolin-3-yl-methyl)-ureido]-cyclohexyl}-carbamic acid tert-butyl ester;
3-[3-(7-Chloro-4-oxo-1-phenyl-1,4-dihydro-quinolin-3-yl-methyl)-ureido]-pyrrolidine-1-carboxylic acid tert-butyl ester;
1-(7-Chloro-4-oxo-1-phenyl-1,4-dihydro-quinolin-3-ylmethyl)-3-cyclopentyl-urea;
4-[3-(7-Chloro-4-oxo-1-phenyl-1,4-dihydro-quinolin-3-yl-methyl)-ureido]-cyclohexanecarboxylic acid methyl ester;
Pyrrolidine-1-carboxylic acid (7-chloro-4-oxo-1-phenyl-1,4-dihydro-quinolin-3-ylmethyl)-amide;
4-Methyl-piperazine-1-carboxylic acid (7-chloro-4-oxo-1-phenyl-1,4-dihydro-quinolin-3-ylmethyl)-amide;
Piperidine-1-carboxylic acid (7-chloro-4-oxo-1-phenyl-1,4-dihydro-quinolin-3-ylmethyl)-amide;
4-[3-(7-Chloro-4-oxo-1-phenyl-1,4-dihydro-quinolin-3-yl-methyl)-ureido]-cyclohexanecarboxylic acid methyl ester;
4-Phenyl-piperidine-1-carboxylic acid (7-chloro-4-oxo-1-phenyl-1,4-dihydro-quinolin-3-ylmethyl)-amide;
1-(7-Chloro-4-oxo-1-phenyl-1,4-dihydro-quinolin-3-ylm-ethyl)-3-((1S,3R,7S)-5-hydroxy-adamantan-2-yl)-urea;
4-[3-(7-Chloro-4-oxo-1-phenyl-1,4-dihydro-quinolin-3-yl-methyl)-ureido]-piperidine-1-carboxylic acid tert-butyl ester
4-[3-(7-Chloro-4-oxo-1-phenyl-1,4-dihydro-quinolin-3-yl-methyl)-ureido]-piperidine-1-carboxylic acid phenyl ester;
1-(1-Benzoyl-piperidin-4-yl)-3-(7-chloro-4-oxo-1-phenyl-1,4-dihydro-quinolin-3-ylmethyl)-urea;
4-[3-(7-Chloro-4-oxo-1-phenyl-1,4-dihydro-quinolin-3-yl-methyl)-ureido]-piperidine-1-carboxylic acid benzyl ester;
1-(1-Benzenesulfonyl-piperidin-4-yl)-3-(7-chloro-4-oxo-1-phenyl-1,4-dihydro-quinolin-3-ylmethyl)-urea;
1-(7-Chloro-4-oxo-1-phenyl-1,4-dihydro-quinolin-3-ylm-ethyl)-3-(1-methanesulfonyl-piperidin-4-yl)-urea;
1-(1-Acetyl-piperidin-4-yl)-3-(7-chloro-4-oxo-1-phenyl-1,4-dihydro-quinolin-3-ylmethyl)-urea;
1-(7-Chloro-4-oxo-1-phenyl-1,4-dihydro-quinolin-3-ylm-ethyl)-3-[1-(4-methanesulfonyl-piperidine-1-carbonyl)-piperidin-4-yl]-urea;
Morpholine-4-carboxylic acid (7-chloro-4-oxo-1-phenyl-1,4-dihydro-quinolin-3-ylmethyl)-amide;
1-(7-Chloro-4-oxo-1-phenyl-1,4-dihydro-quinolin-3-ylm-ethyl)-3-phenyl-urea;
1-(7-Chloro-4-oxo-1-phenyl-1,4-dihydro-quinolin-3-ylm-ethyl)-3-(4-dimethylamino-phenyl)-urea;
1-(7-Chloro-4-oxo-1-phenyl-1,4-dihydro-quinolin-3-ylm-ethyl)-3-(4-methoxy-phenyl)-urea;
1-(3-Chloro-4-fluoro-phenyl)-3-(7-chloro-4-oxo-1-phenyl-1,4-dihydro-quinolin-3-ylmethyl)-urea;
1-(7-Chloro-4-oxo-1-phenyl-1,4-dihydro-quinolin-3-ylm-ethyl)-3-(4-trifluoromethoxy-phenyl)-urea;
4-[3-(7-Chloro-4-oxo-1-phenyl-1,4-dihydro-quinolin-3-yl-methyl)-ureido]-benzoic acid methyl ester;
7-Chloro-3-(isoquinolin-1-ylaminomethyl)-4-oxo-1-phe-nyl-1,4-dihydro-quinoline-2-carboxylic acid methyl ester;
7-Chloro-4-oxo-1-phenyl-3-(quinazolin-4-ylaminomethyl)-1,4-dihydro-quinoline-2-carboxylic acid methyl ester;
7-Chloro-3-{[(morpholine-4-carbonyl)-amino]-methyl}-4-oxo-1-phenyl-1,4-dihydro-quinoline-2-carboxylic acid methyl ester;
7-Chloro-4-oxo-3-(phenoxycarbonylamino-methyl)-1-phe-nyl-1,4-dihydro-quinoline-2-carboxylic acid methyl ester; and
7-Chloro-3-{[(4-methanesulfonyl-benzoyl)-methyl-amino]-methyl}-4-oxo-1-phenyl-1,4-dihydro-quinoline-2-carboxylic acid methyl ester.

In one aspect, the application provides a method of treating a JNK-mediated disorder in a subject having a JNK-mediated disorder, said method comprising administering to a subject in need thereof a therapeutically effective amount of any of the above compounds.

In certain embodiments of the method of treating a JNK-mediated disorder, the JNK-mediated disorder is characterized by cellular proliferation.

In certain embodiments of the method of treating a JNK-mediated disorder, the JNK-mediated disorder is arthritis.

In certain embodiments of the method of treating a JNK-mediated disorder, the JNK-mediated disorder is rheumatoid arthritis.

In certain embodiments of the method of treating a JNK-mediated disorder, the JNK-mediated disorder is asthma.

In certain embodiments of the method of treating a JNK-mediated disorder, the JNK-mediated disorder is diabetes.

In certain embodiments of the method of treating a JNK-mediated disorder, the JNK-mediated disorder is Alzheimer's disease.

In certain embodiments of the method of treating a JNK-mediated disorder, the JNK-mediated disorder is Parkinson's disease.

In certain embodiments of the method of treating a JNK-mediated disorder, the JNK-mediated disorder is ischemic stroke.

In certain embodiments of the method of treating a JNK-mediated disorder, the JNK-mediated disorder is cancer.

In certain embodiments of the method for treating a JNK-mediated disorder, wherein the JNK-mediated disorder is cancer, the cancer is brain cancer.

In certain embodiments of the method for treating a JNK-mediated disorder, wherein the JNK-mediated disorder is cancer, the cancer is leukemia.

In certain embodiments of the method of treating a JNK-mediated disorder, the JNK-mediated disorder is kidney disease.

In one aspect, the application provides a pharmaceutical composition comprising the compound of any one of the above embodiments, admixed with at least one pharmaceutically acceptable carrier, excipient or diluent.

The application provides a use of a compound of Formula I in the preparation of a medicament for the treatment of autoimmune and inflammatory diseases associated with JNK modulation.

A compound, method, or use as described herein.

All publications cited in this disclosure are incorporated herein by reference in their entirety.

Compounds

The compounds described below are JNK inhibitors useful for inhibiting JNK and treating JNK-mediated disorders, and the like. Examples of representative compounds encompassed by the present invention and within the scope of the invention are provided in Table I as compounds.

In general, the nomenclature used in this Application is based on AUTONOM™ v.4.0, a Beilstein Institute computerized system for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

TABLE I

| Compound | Structure | Nomenclature |
| --- | --- | --- |
| I-1 | 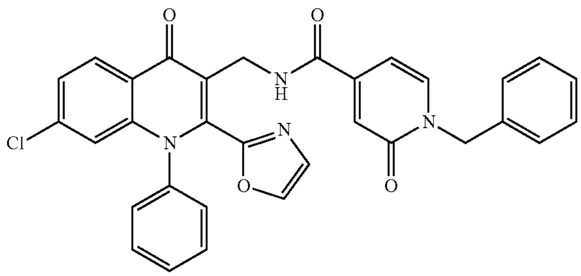 [SMILES: O=C(NCc1c(-c2ncco2)n(-c2ccccc2)c2cc(Cl)ccc2c1=O)c1ccn(Cc2ccccc2)c(=O)c1] | 1-Benzyl-2-oxo-1,2-dihydro-pyridine-4-carboxylic acid (7-chloro-2-oxazol-2-yl-4-oxo-1-phenyl-1,4-dihydro-quinolin-3-ylmethyl)-amide |
| I-2 | 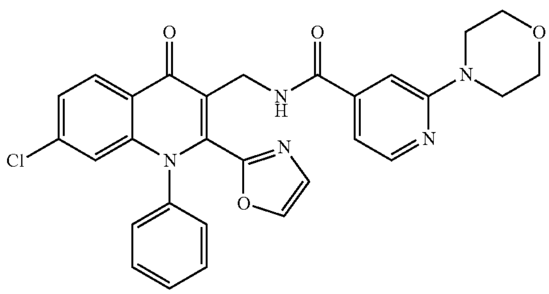 [SMILES: O=C(NCc1c(-c2ncco2)n(-c2ccccc2)c2cc(Cl)ccc2c1=O)c1ccnc(N2CCOCC2)c1] | N-(7-Chloro-2-oxazol-2-yl-4-oxo-1-phenyl-1,4-dihydro-quinolin-3-ylmethyl)-2-morpholin-4-yl-isonicotinamide |
| I-3 | 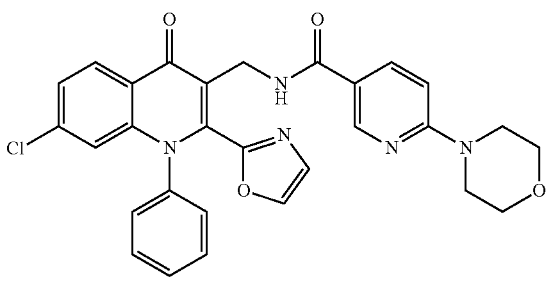 [SMILES: O=C(NCc1c(-c2ncco2)n(-c2ccccc2)c2cc(Cl)ccc2c1=O)c1ccc(N2CCOCC2)nc1] | N-(7-Chloro-2-oxazol-2-yl-4-oxo-1-phenyl-1,4-dihydro-quinolin-3-ylmethyl)-6-morpholin-4-yl-nicotinamide |
| I-4 | 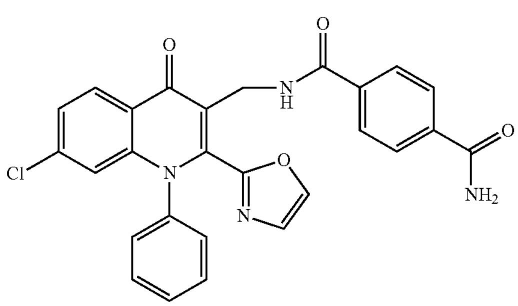 [SMILES: NC(=O)c1ccc(C(=O)NCc2c(-c3ncco3)n(-c3ccccc3)c3cc(Cl)ccc3c2=O)cc1] | N-(7-Chloro-2-oxazol-2-yl-4-oxo-1-phenyl-1,4-dihydro-quinolin-3-ylmethyl)-terephthalamide |
| I-5 | 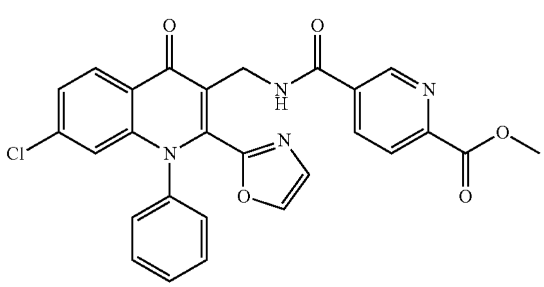 [SMILES: COC(=O)c1ccc(C(=O)NCc2c(-c3ncco3)n(-c3ccccc3)c3cc(Cl)ccc3c2=O)cn1] | 5-[(7-Chloro-2-oxazol-2-yl-4-oxo-1-phenyl-1,4-dihydro-quinolin-3-ylmethyl)-carbamoyl]-pyridine-2-carboxylic acid methyl ester |

TABLE I-continued

| Compound | Structure | Nomenclature |
|---|---|---|
| I-6 | 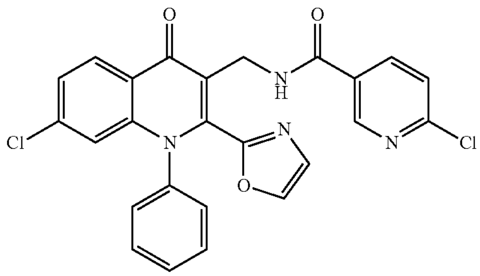 [SMILES: O=C(NCc1c(-c2ncco2)n(-c2ccccc2)c2cc(Cl)ccc2c1=O)c1ccc(Cl)nc1] | 6-Chloro-N-(7-chloro-2-oxazol-2-yl-4-oxo-1-phenyl-1,4-dihydro-quinolin-3-ylmethyl)-nicotinamide |
| I-7 | 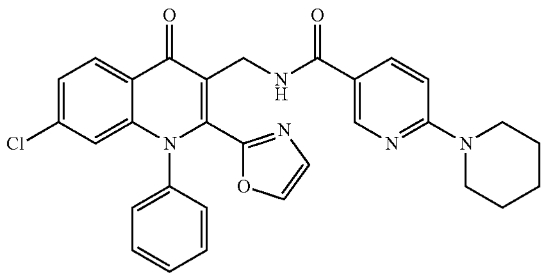 [SMILES: O=C(NCc1c(-c2ncco2)n(-c2ccccc2)c2cc(Cl)ccc2c1=O)c1ccc(N2CCCCC2)nc1] | 3,4,5,6-Tetrahydro-2H-[1,2']bipyridinyl-5'-carboxylic acid (7-chloro-2-oxazol-2-yl-4-oxo-1-phenyl-1,4-dihydro-quinolin-3-ylmethyl)-amide |
| I-8 | 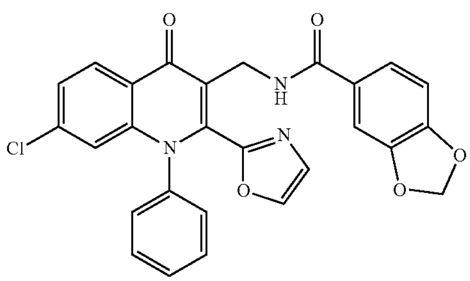 [SMILES: O=C(NCc1c(-c2ncco2)n(-c2ccccc2)c2cc(Cl)ccc2c1=O)c1ccc2c(c1)OCO2] | Benzo[1,3]dioxole-5-carboxylic acid (7-chloro-2-oxazol-2-yl-4-oxo-1-phenyl-1,4-dihydro-quinolin-3-ylmethyl)-amide |
| I-9 | 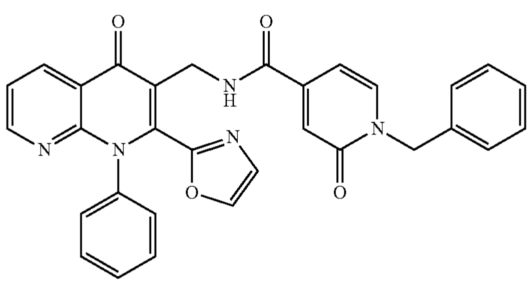 [SMILES: O=C(NCc1c(-c2ncco2)n(-c2ccccc2)c2ncccc2c1=O)c1ccn(Cc2ccccc2)c(=O)c1] | 1-Benzyl-2-oxo-1,2-dihydro-pyridine-4-carboxylic acid (2-oxazol-2-yl-4-oxo-1-phenyl-1,4-dihydro-[1,8]naphthyridin-3-ylmethyl)-amide |
| I-10 | 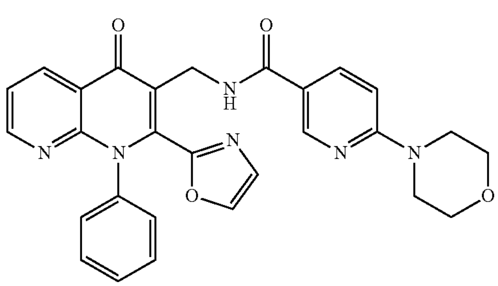 [SMILES: O=C(NCc1c(-c2ncco2)n(-c2ccccc2)c2ncccc2c1=O)c1ccc(N2CCOCC2)nc1] | 6-Morpholin-4-yl-N-(2-oxazol-2-yl-4-oxo-1-phenyl-1,4-dihydro-[1,8]naphthyridin-3-ylmethyl)-nicotinamide |

TABLE I-continued

| Compound | Structure | Nomenclature |
| --- | --- | --- |
| I-11 | 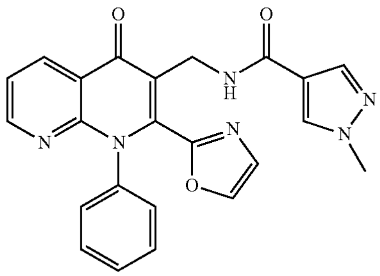 [SMILES: Cn1cc(C(=O)NCc2c(-c3ncco3)n(-c3ccccc3)c3ncccc3c2=O)cn1] | 1-Methyl-1H-pyrazole-4-carboxylic acid (2-oxazol-2-yl-4-oxo-1-phenyl-1,4-dihydro-[1,8]naphthyridin-3-ylmethyl)-amide |
| I-12 | 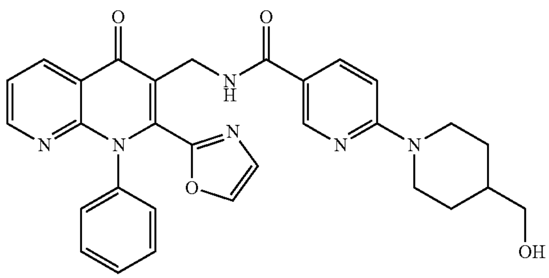 [SMILES: O=C(NCc1c(-c2ncco2)n(-c2ccccc2)c2ncccc2c1=O)c1ccc(N2CCC(CO)CC2)nc1] | 4-Hydroxymethyl-3,4,5,6-tetrahydro-2H-[1,2']bipyridinyl-5'-carboxylic acid (2-oxazol-2-yl-4-oxo-1-phenyl-1,4-dihydro-[1,8]naphthyridin-3-ylmethyl)-amide |
| I-13 | 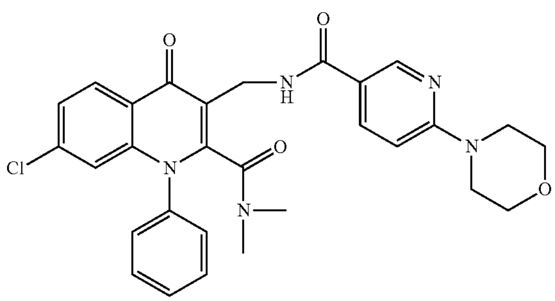 [SMILES: CN(C)C(=O)c1c(CNC(=O)c2ccc(N3CCOCC3)nc2)c(=O)c2ccc(Cl)cc2n1-c1ccccc1] | 7-Chloro-3-{[(6-morpholin-4-yl-pyridine-3-carbonyl)-amino]-methyl}-4-oxo-1-phenyl-1,4-dihydro-quinoline-2-carboxylic acid dimethylamide |
| I-14 | 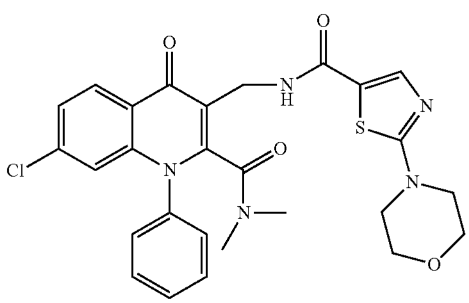 [SMILES: CN(C)C(=O)c1c(CNC(=O)c2cnc(N3CCOCC3)s2)c(=O)c2ccc(Cl)cc2n1-c1ccccc1] | 7-Chloro-3-{[(2-morpholin-4-yl-thiazole-5-carbonyl)-amino]-methyl}-4-oxo-1-phenyl-1,4-dihydro-quinoline-2-carboxylic acid dimethylamide |
| I-15 | 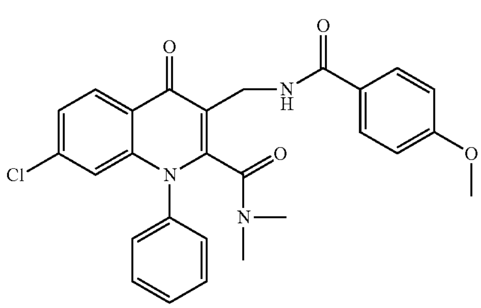 [SMILES: COc1ccc(C(=O)NCc2c(C(=O)N(C)C)n(-c3ccccc3)c3cc(Cl)ccc3c2=O)cc1] | 7-Chloro-3-[(4-methoxy-benzoylamino)-methyl]-4-oxo-1-phenyl-1,4-dihydro-quinoline-2-carboxylic acid dimethylamide |

TABLE I-continued

| Compound | Structure | Nomenclature |
|---|---|---|
| I-16 | 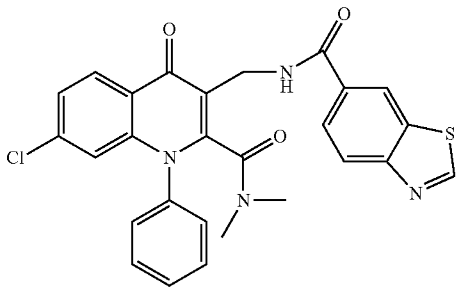 [SMILES: CN(C)C(=O)c1c(CNC(=O)c2ccc3ncsc3c2)c(=O)c2ccc(Cl)cc2n1-c1ccccc1] | 3-{[(Benzothiazole-6-carbonyl)-amino]-methyl}-7-chloro-4-oxo-1-phenyl-1,4-dihydro-quinoline-2-carboxylic acid dimethylamide |
| I-17 | 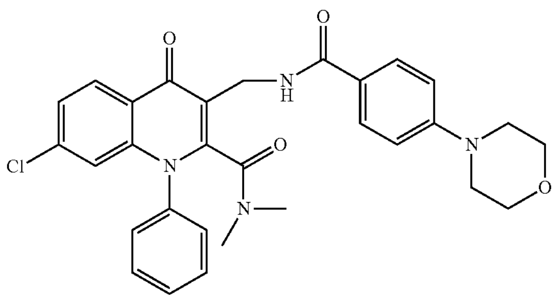 [SMILES: CN(C)C(=O)c1c(CNC(=O)c2ccc(N3CCOCC3)cc2)c(=O)c2ccc(Cl)cc2n1-c1ccccc1] | 7-Chloro-3-[(4-morpholin-4-yl-benzoylamino)-methyl]-4-oxo-1-phenyl-1,4-dihydro-quinoline-2-carboxylic acid dimethylamide |
| I-18 | 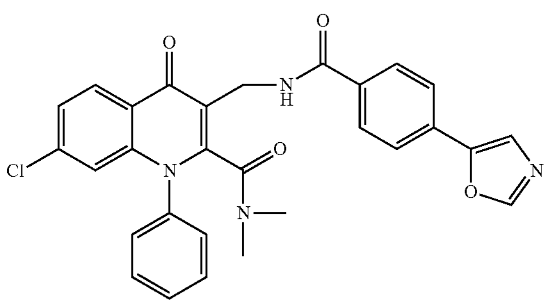 [SMILES: CN(C)C(=O)c1c(CNC(=O)c2ccc(-c3cnco3)cc2)c(=O)c2ccc(Cl)cc2n1-c1ccccc1] | 7-Chloro-3-[(4-oxazol-5-yl-benzoylamino)-methyl]-4-oxo-1-phenyl-1,4-dihydro-quinoline-2-carboxylic acid dimethylamide |
| I-19 | 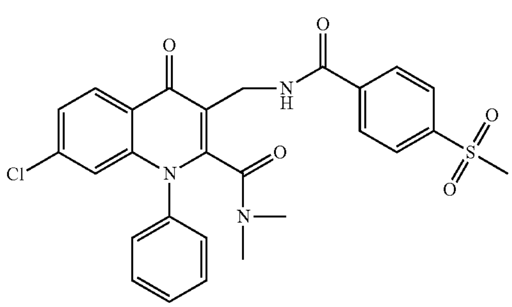 [SMILES: CN(C)C(=O)c1c(CNC(=O)c2ccc(S(C)(=O)=O)cc2)c(=O)c2ccc(Cl)cc2n1-c1ccccc1] | 7-Chloro-3-[(4-methanesulfonyl-benzoylamino)-methyl]-4-oxo-1-phenyl-1,4-dihydro-quinoline-2-carboxylic acid dimethylamide |
| I-20 | 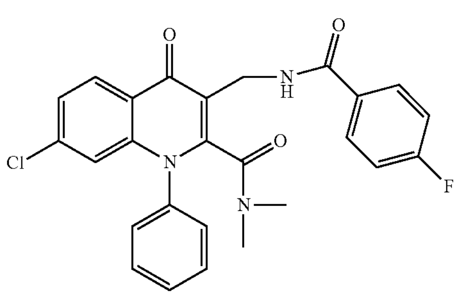 [SMILES: CN(C)C(=O)c1c(CNC(=O)c2ccc(F)cc2)c(=O)c2ccc(Cl)cc2n1-c1ccccc1] | 7-Chloro-3-[(4-fluoro-benzoylamino)-methyl]-4-oxo-1-phenyl-1,4-dihydro-quinoline-2-carboxylic acid dimethylamide |

TABLE I-continued

| Compound | Structure | Nomenclature |
|---|---|---|
| I-21 | 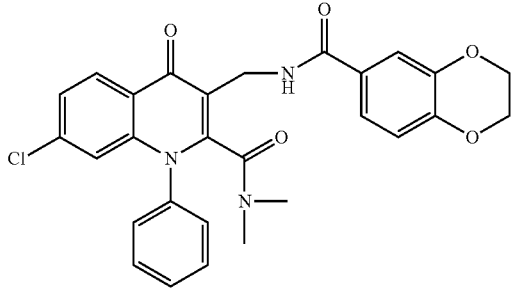 [SMILES: CN(C)C(=O)c1c(CNC(=O)c2ccc3c(c2)OCCO3)c(=O)c2ccc(Cl)cc2n1-c1ccccc1] | 7-Chloro-3-{[(2,3-dihydro-benzo[1,4]dioxine-6-carbonyl)-amino]-methyl}-4-oxo-1-phenyl-1,4-dihydro-quinoline-2-carboxylic acid dimethylamide |
| I-22 | 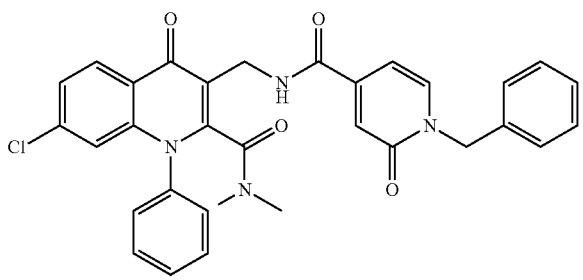 [SMILES: CN(C)C(=O)c1c(CNC(=O)c2ccn(Cc3ccccc3)c(=O)c2)c(=O)c2ccc(Cl)cc2n1-c1ccccc1] | 3-{[(1-Benzyl-2-oxo-1,2-dihydro-pyridine-4-carbonyl)-amino]-methyl}-7-chloro-4-oxo-1-phenyl-1,4-dihydro-quinoline-2-carboxylic acid dimethylamide |
| I-23 | 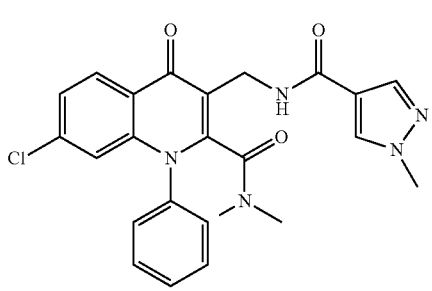 | 7-Chloro-3-{[(1-methyl-1H-pyrazole-4-carbonyl)-amino]-methyl}-4-oxo-1-phenyl-1,4-dihydro-quinoline-2-carboxylic acid dimethylamide |
| I-24 | 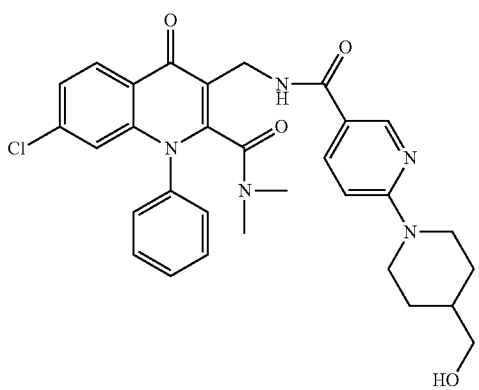 [SMILES: CN(C)C(=O)c1c(CNC(=O)c2ccc(N3CCC(CO)CC3)nc2)c(=O)c2ccc(Cl)cc2n1-c1ccccc1] | 4-Hydroxymethyl-3,4,5,6-tetrahydro-2H-[1,2']bipyridinyl-5'-carboxylic acid (7-chloro-2-dimethylcarbamoyl-4-oxo-1-phenyl-1,4-dihydro-quinolin-3-ylmethyl)-amide |

TABLE I-continued

| Compound | Structure | Nomenclature |
|---|---|---|
| I-25 | 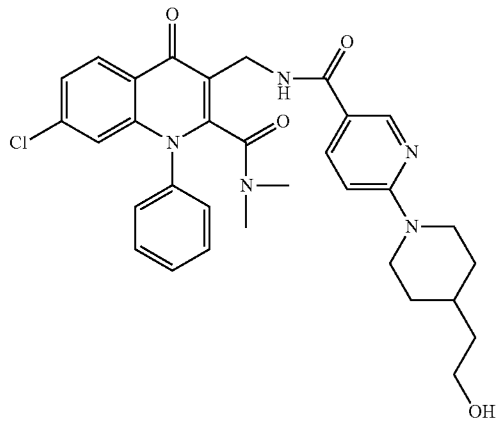 [SMILES: CN(C)C(=O)c1c(CNC(=O)c2ccc(N3CCC(CCO)CC3)nc2)c(=O)c2ccc(Cl)cc2n1-c1ccccc1] | 4-(2-Hydroxy-ethyl)-3,4,5,6-tetrahydro-2H-[1,2']bipyridinyl-5'-carboxylic acid (7-chloro-2-dimethylcarbamoyl-4-oxo-1-phenyl-1,4-dihydro-quinolin-3-ylmethyl)-amide |
| I-26 | 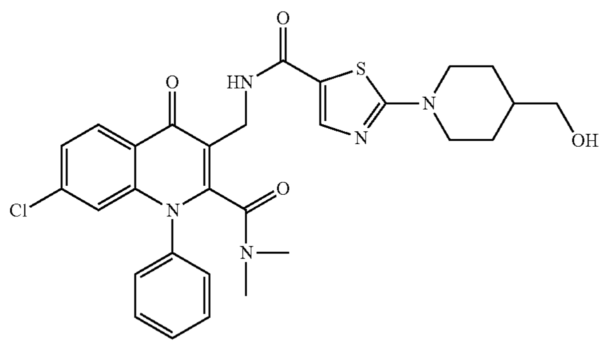 [SMILES: CN(C)C(=O)c1c(CNC(=O)c2cnc(N3CCC(CO)CC3)s2)c(=O)c2ccc(Cl)cc2n1-c1ccccc1] | 7-Chloro-3-({[2-(4-hydroxymethyl-piperidin-1-yl)-thiazole-5-carbonyl]-amino}-methyl)-4-oxo-1-phenyl-1,4-dihydro-quinoline-2-carboxylic acid dimethylamide |
| I-27 | 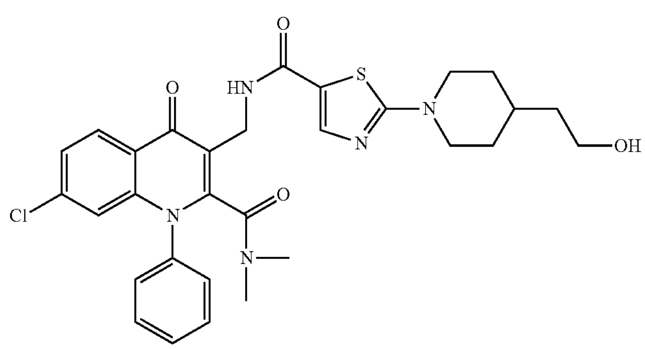 [SMILES: CN(C)C(=O)c1c(CNC(=O)c2cnc(N3CCC(CCO)CC3)s2)c(=O)c2ccc(Cl)cc2n1-c1ccccc1] | 7-Chloro-3-[({2-[4-(2-hydroxy-ethyl)-piperidin-1-yl]-thiazole-5-carbonyl}-amino)-methyl]-4-oxo-1-phenyl-1,4-dihydro-quinoline-2-carboxylic acid dimethylamide |
| I-28 | 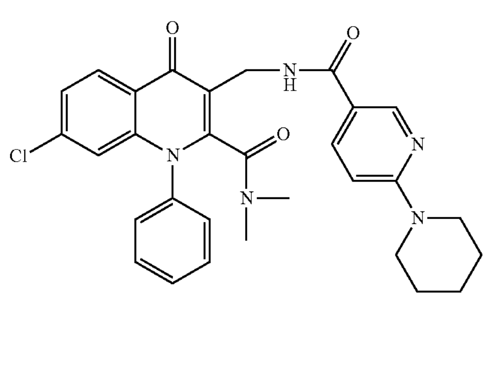 [SMILES: CN(C)C(=O)c1c(CNC(=O)c2ccc(N3CCCCC3)nc2)c(=O)c2ccc(Cl)cc2n1-c1ccccc1] | 3,4,5,6-Tetrahydro-2H-[1,2']bipyridinyl-5'-carboxylic acid (7-chloro-2-dimethylcarbamoyl-4-oxo-1-phenyl-1,4-dihydro-quinolin-3-ylmethyl)-amide |

TABLE I-continued

| Compound | Structure | Nomenclature |
|---|---|---|
| I-29 | 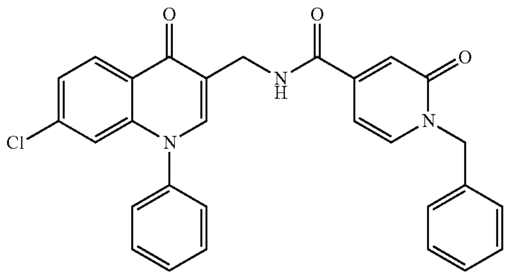 [SMILES: O=C(NCc1cn(-c2ccccc2)c2cc(Cl)ccc2c1=O)c1ccn(Cc2ccccc2)c(=O)c1] | 1-Benzyl-2-oxo-1,2-dihydro-pyridine-4-carboxylic acid (7-chloro-4-oxo-1-phenyl-1,4-dihydro-quinolin-3-ylmethyl)-amide |
| I-30 | 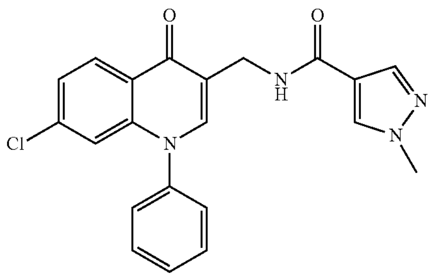 [SMILES: Cn1cc(C(=O)NCc2cn(-c3ccccc3)c3cc(Cl)ccc3c2=O)cn1] | 1-Methyl-1H-pyrazole-4-carboxylic acid (7-chloro-4-oxo-1-phenyl-1,4-dihydro-quinolin-3-ylmethyl)-amide |
| I-31 | 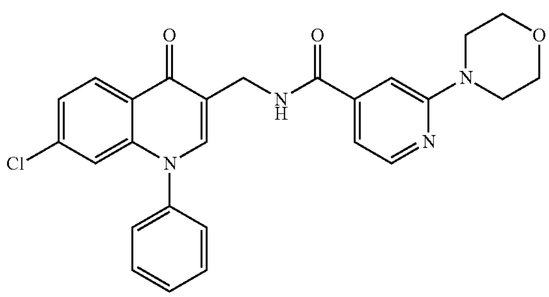 [SMILES: O=C(NCc1cn(-c2ccccc2)c2cc(Cl)ccc2c1=O)c1ccnc(N2CCOCC2)c1] | N-(7-Chloro-4-oxo-1-phenyl-1,4-dihydro-quinolin-3-ylmethyl)-2-morpholin-4-yl-isonicotinamide |
| I-32 | 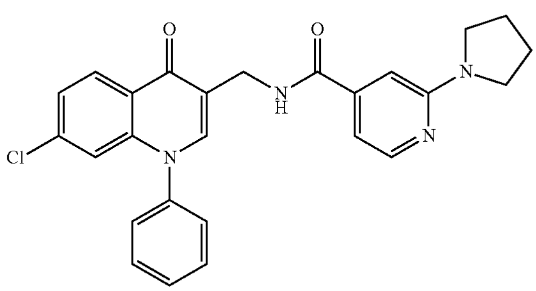 [SMILES: O=C(NCc1cn(-c2ccccc2)c2cc(Cl)ccc2c1=O)c1ccnc(N2CCCC2)c1] | N-(7-Chloro-4-oxo-1-phenyl-1,4-dihydro-quinolin-3-ylmethyl)-2-pyrrolidin-1-yl-isonicotinamide |
| I-33 | 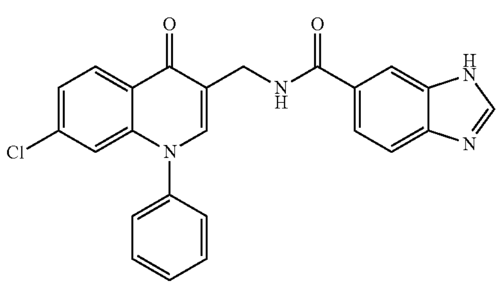 | 3H-Benzoimidazole-5-carboxylic acid (7-chloro-4-oxo-1-phenyl-1,4-dihydro-quinolin-3-ylmethyl)-amide |

TABLE I-continued

| Compound | Structure | Nomenclature |
|---|---|---|
| I-34 | 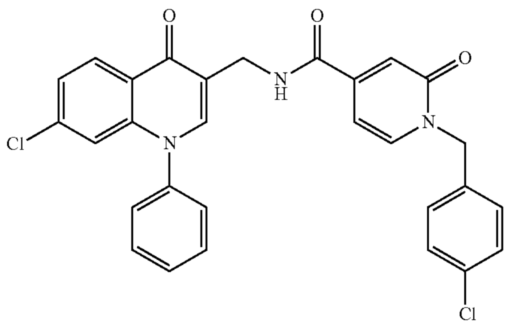 [SMILES: O=C(NCc1cn(-c2ccccc2)c2cc(Cl)ccc2c1=O)c1ccn(Cc2ccc(Cl)cc2)c(=O)c1] | 1-(4-Chloro-benzyl)-2-oxo-1,2-dihydro-pyridine-4-carboxylic acid (7-chloro-4-oxo-1-phenyl-1,4-dihydro-quinolin-3-ylmethyl)-amide |
| I-35 | 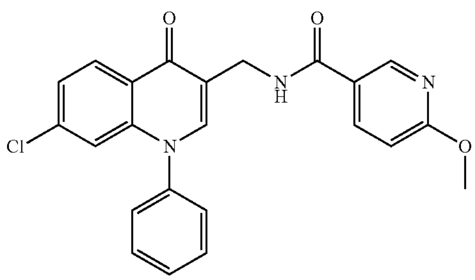 [SMILES: COc1ccc(C(=O)NCc2cn(-c3ccccc3)c3cc(Cl)ccc3c2=O)cn1] | N-(7-Chloro-4-oxo-1-phenyl-1,4-dihydro-quinolin-3-ylmethyl)-6-methoxy-nicotinamide |
| I-36 | 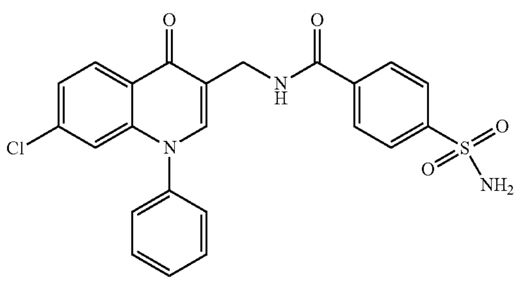 [SMILES: NS(=O)(=O)c1ccc(C(=O)NCc2cn(-c3ccccc3)c3cc(Cl)ccc3c2=O)cc1] | N-(7-Chloro-4-oxo-1-phenyl-1,4-dihydro-quinolin-3-ylmethyl)-4-sulfamoyl-benzamide |
| I-37 | 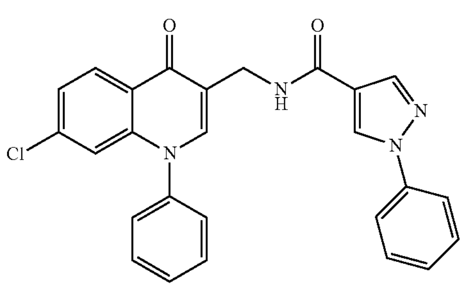 [SMILES: O=C(NCc1cn(-c2ccccc2)c2cc(Cl)ccc2c1=O)c1cnn(-c2ccccc2)c1] | 1-Phenyl-1H-pyrazole-4-carboxylic acid (7-chloro-4-oxo-1-phenyl-1,4-dihydro-quinolin-3-ylmethyl)-amide |
| I-38 | 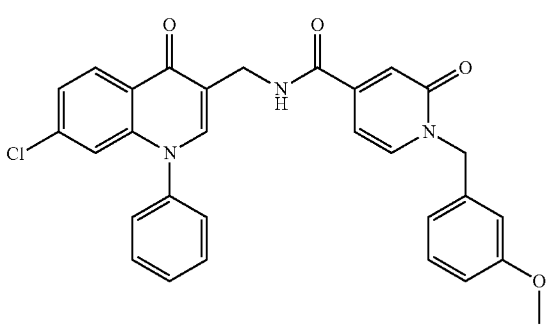 [SMILES: COc1cccc(Cn2ccc(C(=O)NCc3cn(-c4ccccc4)c4cc(Cl)ccc4c3=O)cc2=O)c1] | 1-(3-Methoxy-benzyl)-2-oxo-1,2-dihydro-pyridine-4-carboxylic acid (7-chloro-4-oxo-1-phenyl-1,4-dihydro-quinolin-3-ylmethyl)-amide |

TABLE I-continued

| Compound | Structure | Nomenclature |
|---|---|---|
| I-39 | 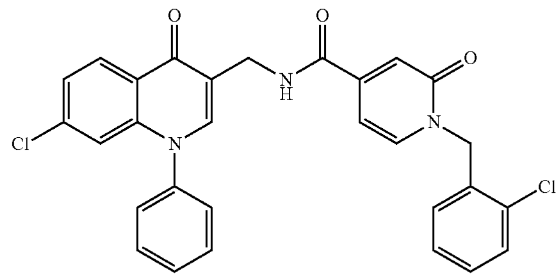 [SMILES: O=C(NCc1cn(-c2ccccc2)c2cc(Cl)ccc2c1=O)c1ccn(Cc2ccccc2Cl)c(=O)c1] | 1-(2-Chloro-benzyl)-2-oxo-1,2-dihydro-pyridine-4-carboxylic acid (7-chloro-4-oxo-1-phenyl-1,4-dihydro-quinolin-3-ylmethyl)-amide |
| I-40 | 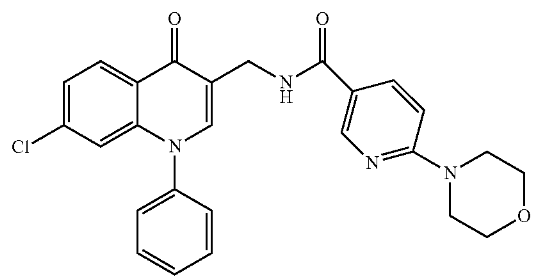 [SMILES: O=C(NCc1cn(-c2ccccc2)c2cc(Cl)ccc2c1=O)c1ccc(N2CCOCC2)nc1] | N-(7-Chloro-4-oxo-1-phenyl-1,4-dihydro-quinolin-3-ylmethyl)-6-morpholin-4-yl-nicotinamide |
| I-41 | 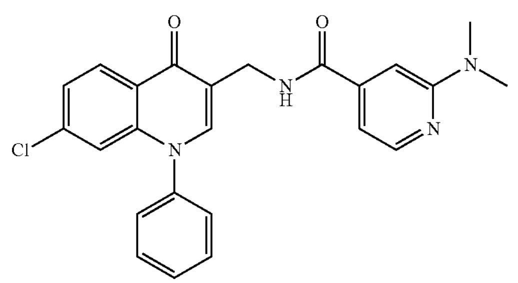 [SMILES: CN(C)c1cc(C(=O)NCc2cn(-c3ccccc3)c3cc(Cl)ccc3c2=O)ccn1] | N-(7-Chloro-4-oxo-1-phenyl-1,4-dihydro-quinolin-3-ylmethyl)-2-dimethylamino-isonicotinamide |
| I-42 | 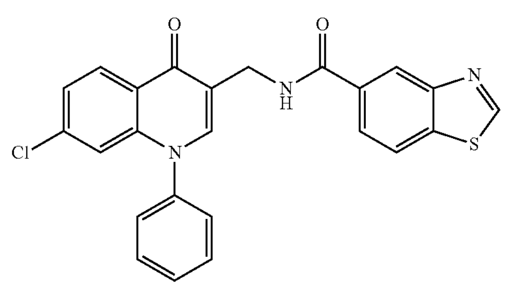 [SMILES: O=C(NCc1cn(-c2ccccc2)c2cc(Cl)ccc2c1=O)c1ccc2scnc2c1] | Benzothiazole-5-carboxylic acid (7-chloro-4-oxo-1-phenyl-1,4-dihydro-quinolin-3-ylmethyl)-amide |
| I-43 | 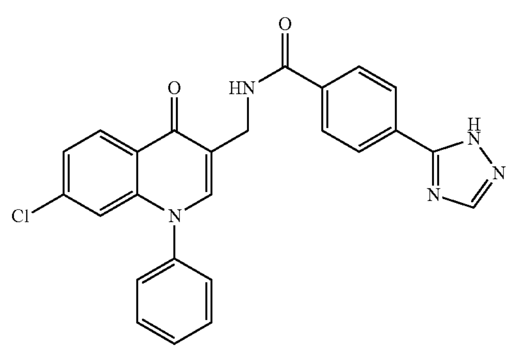 [SMILES: O=C(NCc1cn(-c2ccccc2)c2cc(Cl)ccc2c1=O)c1ccc(-c2ncn[nH]2)cc1] | N-(7-Chloro-4-oxo-1-phenyl-1,4-dihydro-quinolin-3-ylmethyl)-4-(2H-[1,2,4]triazol-3-yl)-benzamide |

TABLE I-continued

| Compound | Structure | Nomenclature |
| --- | --- | --- |
| I-44 | 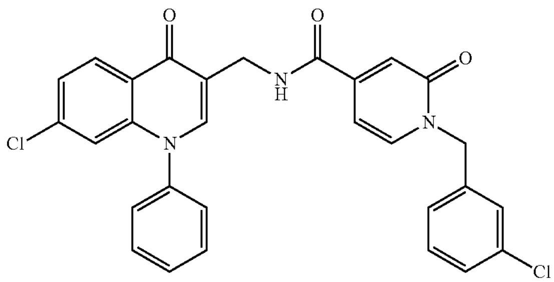 [SMILES: O=C(NCc1cn(-c2ccccc2)c2cc(Cl)ccc2c1=O)c1ccn(Cc2cccc(Cl)c2)c(=O)c1] | 1-(3-Chloro-benzyl)-2-oxo-1,2-dihydro-pyridine-4-carboxylic acid (7-chloro-4-oxo-1-phenyl-1,4-dihydro-quinolin-3-ylmethyl)-amide |
| I-45 | 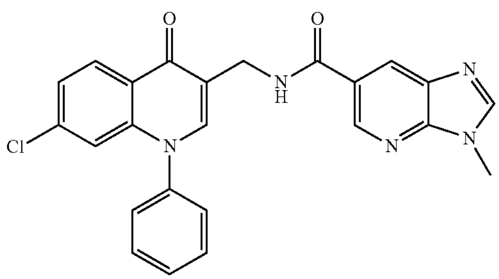 [SMILES: Cn1cnc2cc(C(=O)NCc3cn(-c4ccccc4)c4cc(Cl)ccc4c3=O)cnc21] | 3-Methyl-3H-imidazo[4,5-b]pyridine-6-carboxylic acid (7-chloro-4-oxo-1-phenyl-1,4-dihydro-quinolin-3-ylmethyl)-amide |
| I-46 | 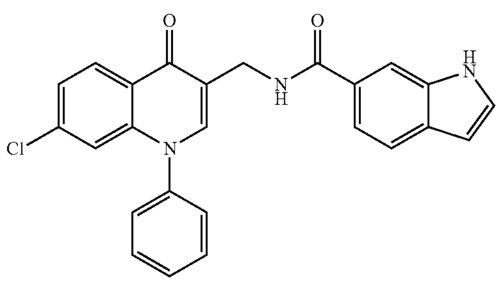 | 1H-Indole-6-carboxylic acid (7-chloro-4-oxo-1-phenyl-1,4-dihydro-quinolin-3-ylmethyl)-amide |
| I-47 | 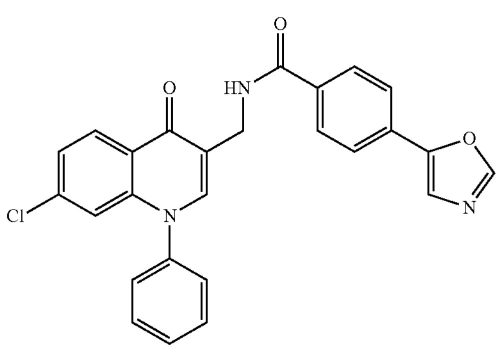 [SMILES: O=C(NCc1cn(-c2ccccc2)c2cc(Cl)ccc2c1=O)c1ccc(-c2cnco2)cc1] | N-(7-Chloro-4-oxo-1-phenyl-1,4-dihydro-quinolin-3-ylmethyl)-4-oxazol-5-yl-benzamide |
| I-48 | 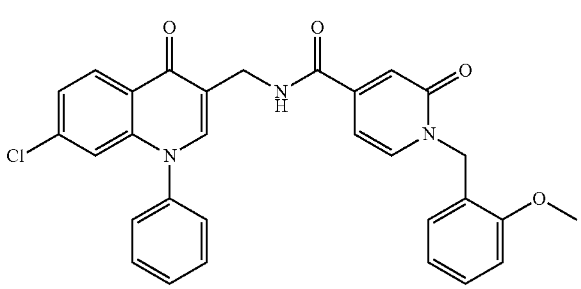 [SMILES: COc1ccccc1Cn1ccc(C(=O)NCc2cn(-c3ccccc3)c3cc(Cl)ccc3c2=O)cc1=O] | 1-(2-Methoxy-benzyl)-2-oxo-1,2-dihydro-pyridine-4-carboxylic acid (7-chloro-4-oxo-1-phenyl-1,4-dihydro-quinolin-3-ylmethyl)-amide |

TABLE I-continued

| Compound | Structure | Nomenclature |
|---|---|---|
| I-49 | 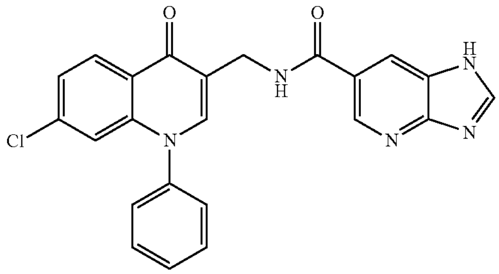 | 1H-Imidazo[4,5-b]pyridine-6-carboxylic acid (7-chloro-4-oxo-1-phenyl-1,4-dihydro-quinolin-3-ylmethyl)-amide |
| I-50 | 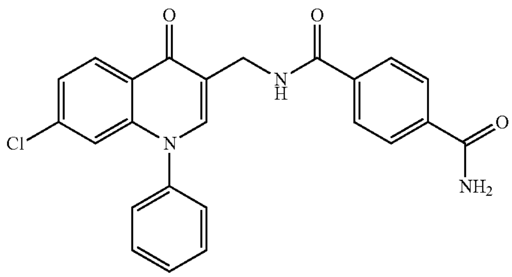 [SMILES: NC(=O)c1ccc(C(=O)NCc2cn(-c3ccccc3)c3cc(Cl)ccc3c2=O)cc1] | N-(7-Chloro-4-oxo-1-phenyl-1,4-dihydro-quinolin-3-ylmethyl)-terephthalamide |
| I-51 | 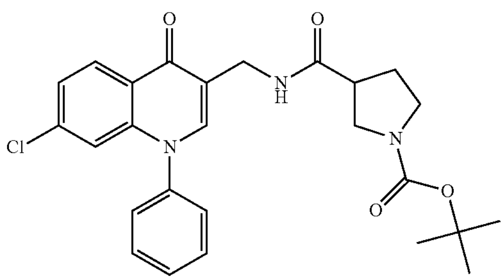 [SMILES: CC(C)(C)OC(=O)N1CCC(C(=O)NCc2cn(-c3ccccc3)c3cc(Cl)ccc3c2=O)C1] | 3-[(7-Chloro-4-oxo-1-phenyl-1,4-dihydro-quinolin-3-ylmethyl)-carbamoyl]-pyrrolidine-1-carboxylic acid tert-butyl ester |
| I-52 | 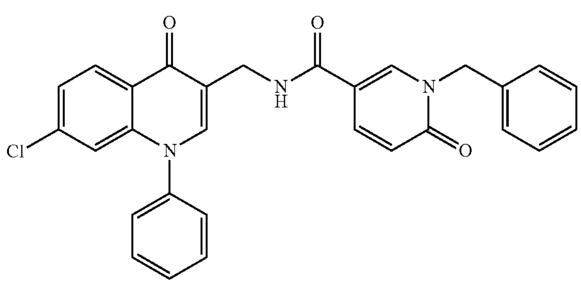 [SMILES: O=C(NCc1cn(-c2ccccc2)c2cc(Cl)ccc2c1=O)c1ccc(=O)n(Cc2ccccc2)c1] | 1-Benzyl-6-oxo-1,6-dihydro-pyridine-3-carboxylic acid (7-chloro-4-oxo-1-phenyl-1,4-dihydro-quinolin-3-ylmethyl)-amide |
| I-53 | 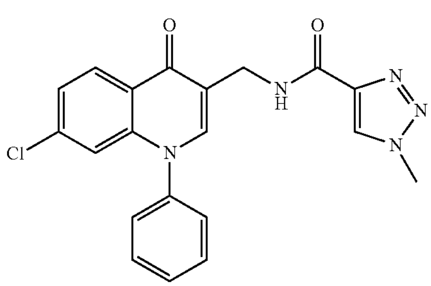 [SMILES: Cn1cc(C(=O)NCc2cn(-c3ccccc3)c3cc(Cl)ccc3c2=O)nn1] | 1-Methyl-1H-[1,2,3]triazole-4-carboxylic acid (7-chloro-4-oxo-1-phenyl-1,4-dihydro-quinolin-3-ylmethyl)-amide |

TABLE I-continued

| Compound | Structure | Nomenclature |
|---|---|---|
| I-54 | 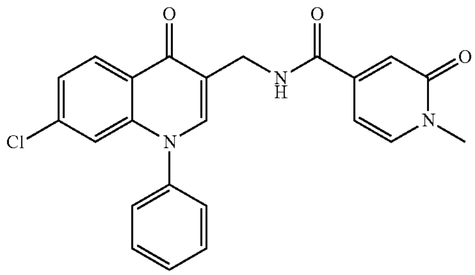 [SMILES: Cn1ccc(C(=O)NCc2cn(-c3ccccc3)c3cc(Cl)ccc3c2=O)cc1=O] | 1-Methyl-2-oxo-1,2-dihydro-pyridine-4-carboxylic acid (7-chloro-4-oxo-1-phenyl-1,4-dihydro-quinolin-3-ylmethyl)-amide |
| I-55 | 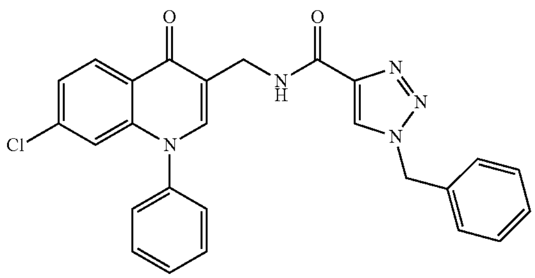 [SMILES: O=C(NCc1cn(-c2ccccc2)c2cc(Cl)ccc2c1=O)c1cn(Cc2ccccc2)nn1] | 1-Benzyl-1H-[1,2,3]triazole-4-carboxylic acid (7-chloro-4-oxo-1-phenyl-1,4-dihydro-quinolin-3-ylmethyl)-amide |
| I-56 | 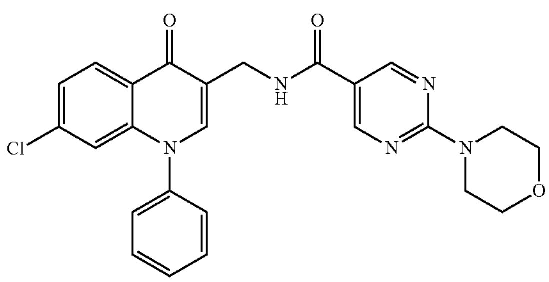 [SMILES: O=C(NCc1cn(-c2ccccc2)c2cc(Cl)ccc2c1=O)c1cnc(N2CCOCC2)nc1] | 2-Morpholin-4-yl-pyrimidine-5-carboxylic acid (7-chloro-4-oxo-1-phenyl-1,4-dihydro-quinolin-3-ylmethyl)-amide |
| I-57 | 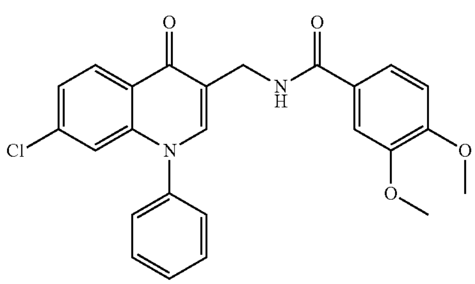 [SMILES: COc1ccc(C(=O)NCc2cn(-c3ccccc3)c3cc(Cl)ccc3c2=O)cc1OC] | N-(7-Chloro-4-oxo-1-phenyl-1,4-dihydro-quinolin-3-ylmethyl)-3,4-dimethoxy-benzamide |
| I-58 | 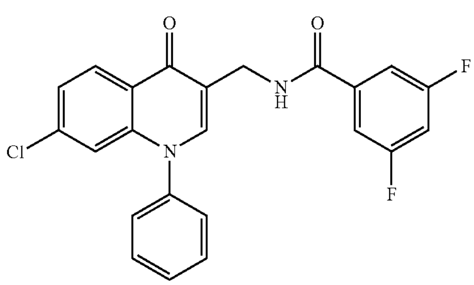 [SMILES: O=C(NCc1cn(-c2ccccc2)c2cc(Cl)ccc2c1=O)c1cc(F)cc(F)c1] | N-(7-Chloro-4-oxo-1-phenyl-1,4-dihydro-quinolin-3-ylmethyl)-3,5-difluoro-benzamide |

TABLE I-continued

| Compound | Structure | Nomenclature |
|---|---|---|
| I-59 | 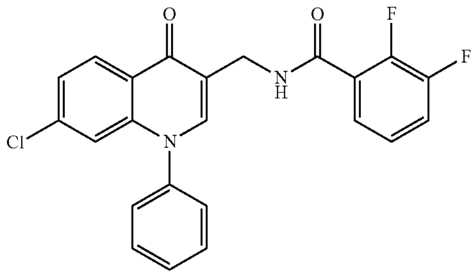 [SMILES: O=C(NCc1cn(-c2ccccc2)c2cc(Cl)ccc2c1=O)c1cccc(F)c1F] | N-(7-Chloro-4-oxo-1-phenyl-1,4-dihydro-quinolin-3-ylmethyl)-2,3-difluoro-benzamide |
| I-60 | 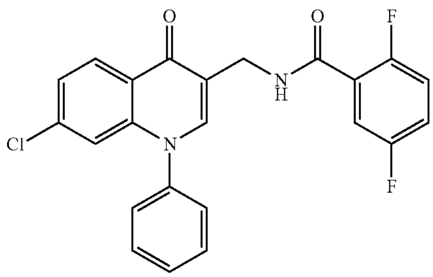 [SMILES: O=C(NCc1cn(-c2ccccc2)c2cc(Cl)ccc2c1=O)c1cc(F)ccc1F] | N-(7-Chloro-4-oxo-1-phenyl-1,4-dihydro-quinolin-3-ylmethyl)-2,5-difluoro-benzamide |
| I-61 | 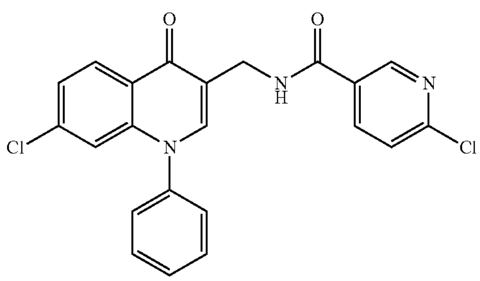 [SMILES: O=C(NCc1cn(-c2ccccc2)c2cc(Cl)ccc2c1=O)c1ccc(Cl)nc1] | 6-Chloro-N-(7-chloro-4-oxo-1-phenyl-1,4-dihydro-quinolin-3-ylmethyl)-nicotinamide |
| I-62 | 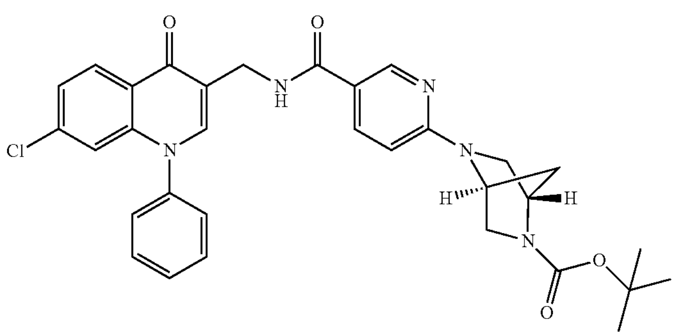 [SMILES: CC(C)(C)OC(=O)N1C[C@@H]2C[C@H]1CN2c1ccc(C(=O)NCc2cn(-c3ccccc3)c3cc(Cl)ccc3c2=O)cn1] | (1S,4S)-5-{5-[(7-Chloro-4-oxo-1-phenyl-1,4-dihydro-quinolin-3-ylmethyl)-carbamoyl]-pyridin-2-yl}-2,5-diaza-bicyclo[2.2.1]heptane-2-carboxylic acid tert-butyl ester |
| I-63 | 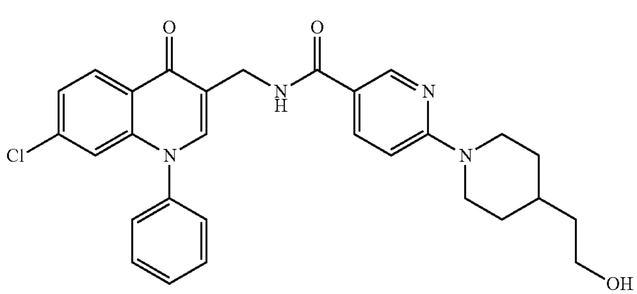 [SMILES: O=C(NCc1cn(-c2ccccc2)c2cc(Cl)ccc2c1=O)c1ccc(N2CCC(CCO)CC2)nc1] | 4-(2-Hydroxy-ethyl)-3,4,5,6-tetrahydro-2H-[1,2']bipyridinyl-5'-carboxylic acid (7-chloro-4-oxo-1-phenyl-1,4-dihydro-quinolin-3-ylmethyl)-amide |

TABLE I-continued

| Compound | Structure | Nomenclature |
|---|---|---|
| I-64 | 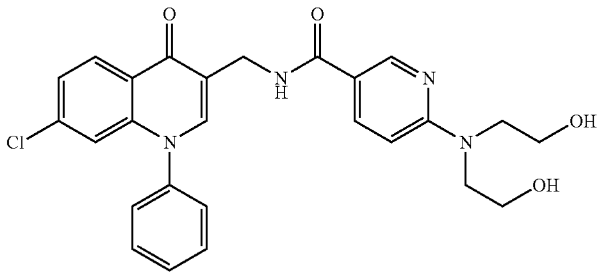 [SMILES: O=C(NCc1cn(-c2ccccc2)c2cc(Cl)ccc2c1=O)c1ccc(N(CCO)CCO)nc1] | 6-[Bis-(2-hydroxy-ethyl)-amino]-N-(7-chloro-4-oxo-1-phenyl-1,4-dihydro-quinolin-3-ylmethyl)-nicotinamide |
| I-65 | 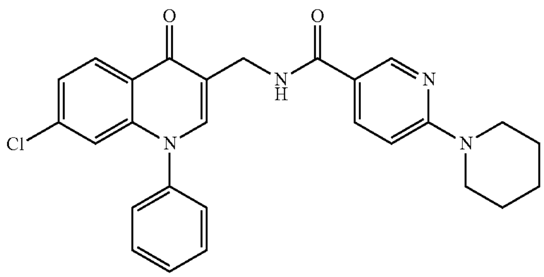 [SMILES: O=C(NCc1cn(-c2ccccc2)c2cc(Cl)ccc2c1=O)c1ccc(N2CCCCC2)nc1] | 3,4,5,6-Tetrahydro-2H-[1,2']bipyridinyl-5'-carboxylic acid (7-chloro-4-oxo-1-phenyl-1,4-dihydro-quinolin-3-ylmethyl)-amide |
| I-66 | 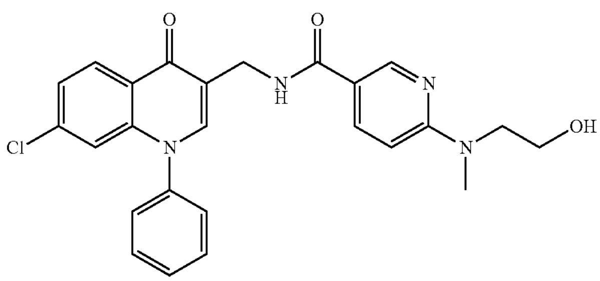 [SMILES: CN(CCO)c1ccc(C(=O)NCc2cn(-c3ccccc3)c3cc(Cl)ccc3c2=O)cn1] | N-(7-Chloro-4-oxo-1-phenyl-1,4-dihydro-quinolin-3-ylmethyl)-6-[(2-hydroxy-ethyl)-methyl-amino]-nicotinamide |
| I-67 | 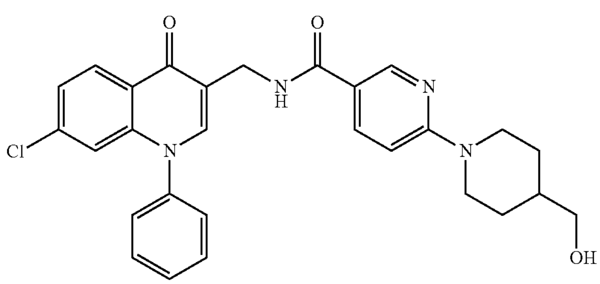 [SMILES: O=C(NCc1cn(-c2ccccc2)c2cc(Cl)ccc2c1=O)c1ccc(N2CCC(CO)CC2)nc1] | 4-Hydroxymethyl-3,4,5,6-tetrahydro-2H-[1,2']bipyridinyl-5'-carboxylic acid (7-chloro-4-oxo-1-phenyl-1,4-dihydro-quinolin-3-ylmethyl)-amide |
| I-68 | 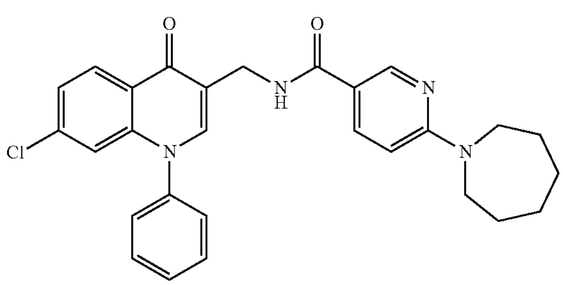 [SMILES: O=C(NCc1cn(-c2ccccc2)c2cc(Cl)ccc2c1=O)c1ccc(N2CCCCCC2)nc1] | 6-Azepan-1-yl-N-(7-chloro-4-oxo-1-phenyl-1,4-dihydro-quinolin-3-ylmethyl)-nicotinamide |

TABLE I-continued

| Compound | Structure | Nomenclature |
|---|---|---|
| I-69 | 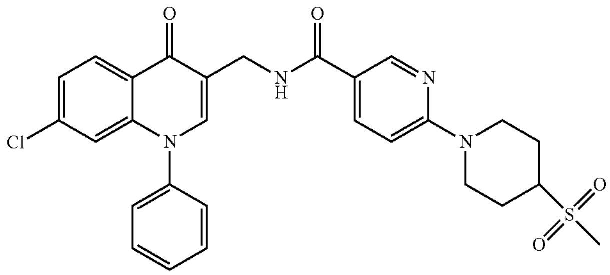 [SMILES: CS(=O)(=O)C1CCN(c2ccc(C(=O)NCc3cn(-c4ccccc4)c4cc(Cl)ccc4c3=O)cn2)CC1] | 4-Methanesulfonyl-3,4,5,6-tetrahydro-2H-[1,2']bipyridinyl-5'-carboxylic acid (7-chloro-4-oxo-1-phenyl-1,4-dihydro-quinolin-3-ylmethyl)-amide |
| I-70 | 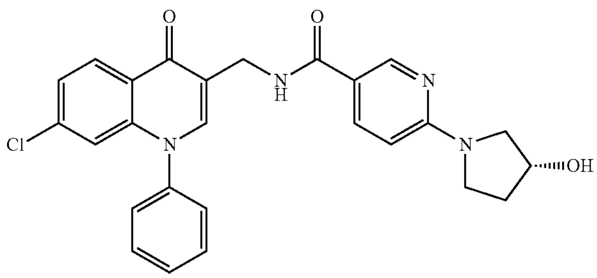 [SMILES: O=C(NCc1cn(-c2ccccc2)c2cc(Cl)ccc2c1=O)c1ccc(N2CC[C@@H](O)C2)nc1] | N-(7-Chloro-4-oxo-1-phenyl-1,4-dihydro-quinolin-3-ylmethyl)-6-((R)-3-hydroxy-pyrrolidin-1-yl)-nicotinamide |
| I-71 | 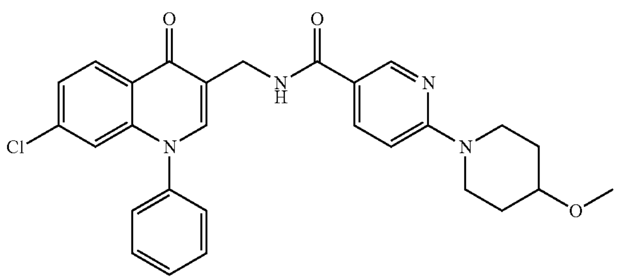 [SMILES: COC1CCN(c2ccc(C(=O)NCc3cn(-c4ccccc4)c4cc(Cl)ccc4c3=O)cn2)CC1] | 4-Methoxy-3,4,5,6-tetrahydro-2H-[1,2']bipyridinyl-5'-carboxylic acid (7-chloro-4-oxo-1-phenyl-1,4-dihydro-quinolin-3-ylmethyl)-amide |
| I-72 | 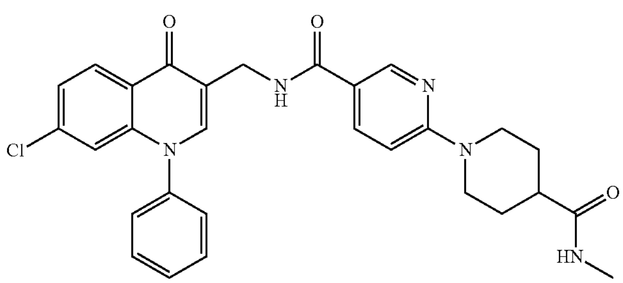 [SMILES: CNC(=O)C1CCN(c2ccc(C(=O)NCc3cn(-c4ccccc4)c4cc(Cl)ccc4c3=O)cn2)CC1] | 3,4,5,6-Tetrahydro-2H-[1,2']bipyridinyl-4,5'-dicarboxylic acid 5'-[(7-chloro-4-oxo-1-phenyl-1,4-dihydro-quinolin-3-ylmethyl)-amide] 4-methylamide |
| I-73 | 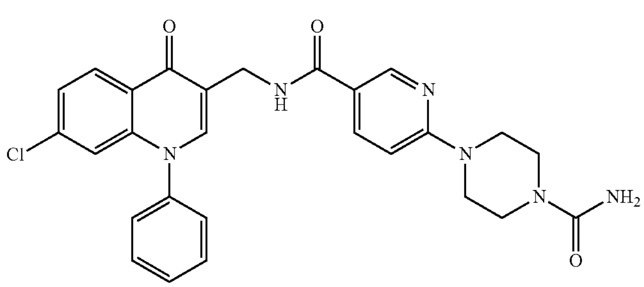 [SMILES: NC(=O)N1CCN(c2ccc(C(=O)NCc3cn(-c4ccccc4)c4cc(Cl)ccc4c3=O)cn2)CC1] | 4-{5-[(7-Chloro-4-oxo-1-phenyl-1,4-dihydro-quinolin-3-ylmethyl)-carbamoyl]-pyridin-2-yl}-piperazine-1-carboxylic acid amide |

TABLE I-continued

| Compound | Structure | Nomenclature |
|---|---|---|
| I-74 | 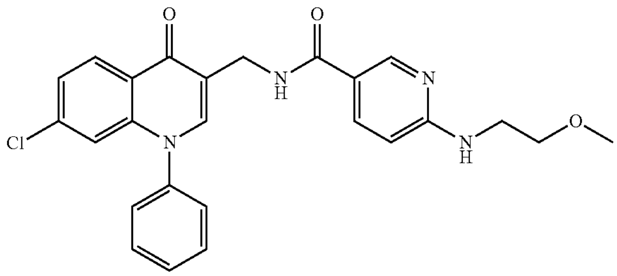 [SMILES: COCCNc1ccc(C(=O)NCc2cn(-c3ccccc3)c3cc(Cl)ccc3c2=O)cn1] | N-(7-Chloro-4-oxo-1-phenyl-1,4-dihydro-quinolin-3-ylmethyl)-6-(2-methoxy-ethylamino)-nicotinamide |
| I-75 | 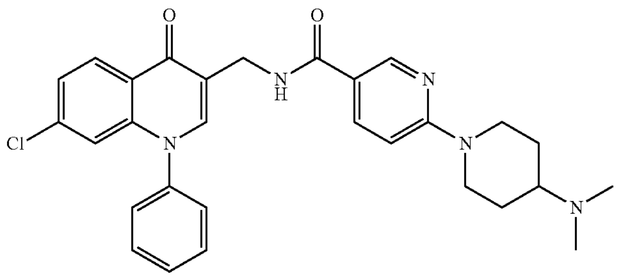 [SMILES: CN(C)C1CCN(c2ccc(C(=O)NCc3cn(-c4ccccc4)c4cc(Cl)ccc4c3=O)cn2)CC1] | 4-Dimethylamino-3,4,5,6-tetrahydro-2H-[1,2']bipyridinyl-5'-carboxylic acid (7-chloro-4-oxo-1-phenyl-1,4-dihydro-quinolin-3-ylmethyl)-amide |
| I-76 | 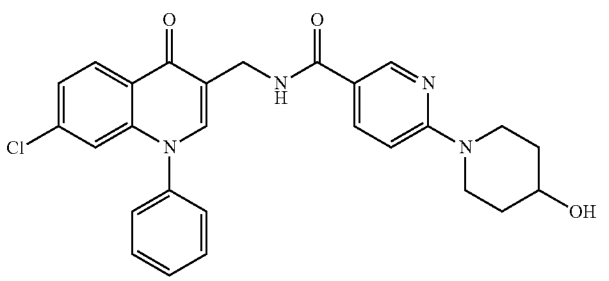 [SMILES: O=C(NCc1cn(-c2ccccc2)c2cc(Cl)ccc2c1=O)c1ccc(N2CCC(O)CC2)nc1] | 4-Hydroxy-3,4,5,6-tetrahydro-2H-[1,2']bipyridinyl-5'-carboxylic acid (7-chloro-4-oxo-1-phenyl-1,4-dihydro-quinolin-3-ylmethyl)-amide |
| I-77 | 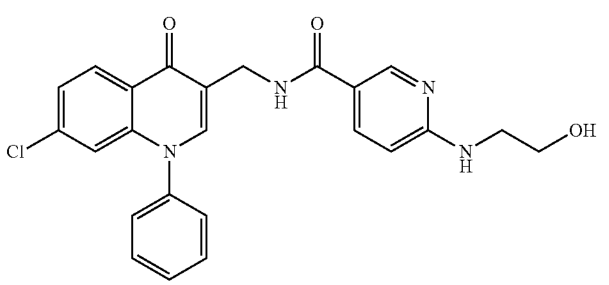 [SMILES: O=C(NCc1cn(-c2ccccc2)c2cc(Cl)ccc2c1=O)c1ccc(NCCO)nc1] | N-(7-Chloro-4-oxo-1-phenyl-1,4-dihydro-quinolin-3-ylmethyl)-6-(2-hydroxy-ethylamino)-nicotinamide |
| I-78 | 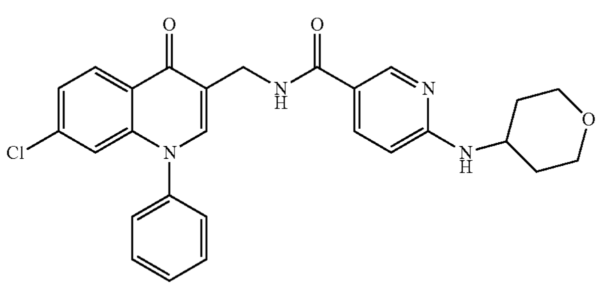 [SMILES: O=C(NCc1cn(-c2ccccc2)c2cc(Cl)ccc2c1=O)c1ccc(NC2CCOCC2)nc1] | N-(7-Chloro-4-oxo-1-phenyl-1,4-dihydro-quinolin-3-ylmethyl)-6-(tetrahydro-pyran-4-ylamino)-nicotinamide |

TABLE I-continued

| Compound | Structure | Nomenclature |
|---|---|---|
| I-79 | 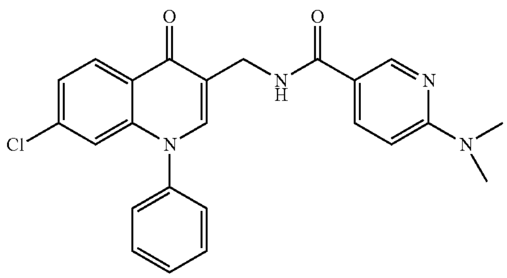 [SMILES: CN(C)c1ccc(C(=O)NCc2cn(-c3ccccc3)c3cc(Cl)ccc3c2=O)cn1] | N-(7-Chloro-4-oxo-1-phenyl-1,4-dihydro-quinolin-3-ylmethyl)-6-dimethylamino-nicotinamide |
| I-80 | 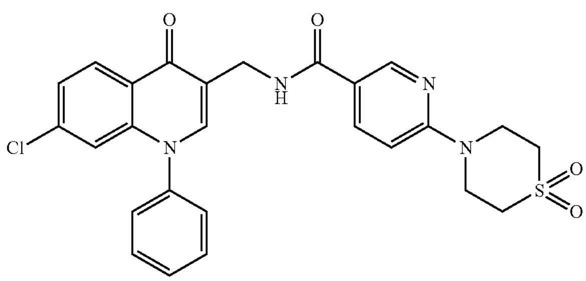 [SMILES: O=C(NCc1cn(-c2ccccc2)c2cc(Cl)ccc2c1=O)c1ccc(N2CCS(=O)(=O)CC2)nc1] | N-(7-Chloro-4-oxo-1-phenyl-1,4-dihydro-quinolin-3-ylmethyl)-6-(1,1-dioxo-1$\lambda^6$-thiomorpholin-4-yl)-nicotinamide |
| I-81 | 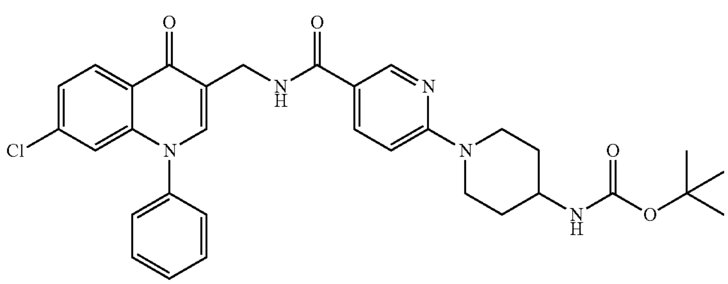 [SMILES: CC(C)(C)OC(=O)NC1CCN(c2ccc(C(=O)NCc3cn(-c4ccccc4)c4cc(Cl)ccc4c3=O)cn2)CC1] | {5'-[(7-Chloro-4-oxo-1-phenyl-1,4-dihydro-quinolin-3-ylmethyl)-carbamoyl]-3,4,5,6-tetrahydro-2H-[1,2']bipyridinyl-4-yl}-carbamic acid tert-butyl ester |
| I-82 | 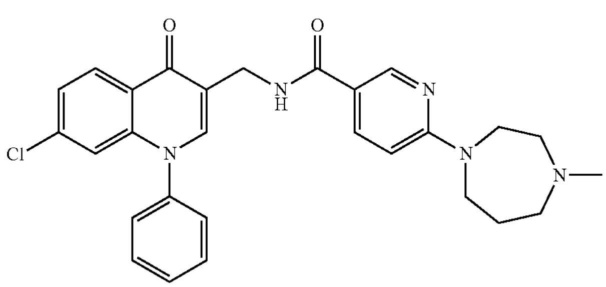 [SMILES: CN1CCCN(c2ccc(C(=O)NCc3cn(-c4ccccc4)c4cc(Cl)ccc4c3=O)cn2)CC1] | N-(7-Chloro-4-oxo-1-phenyl-1,4-dihydro-quinolin-3-ylmethyl)-6-(4-methyl-[1,4]diazepan-1-yl)-nicotinamide |
| I-83 | 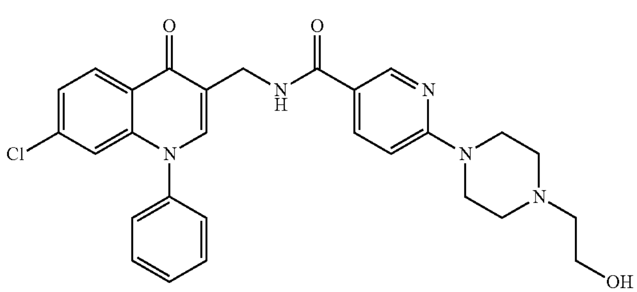 | N-(7-Chloro-4-oxo-1-phenyl-1,4-dihydro-quinolin-3-ylmethyl)-6-[4-(2-hydroxy-ethyl)-piperazin-1-yl]-nicotinamide |

TABLE I-continued

| Compound | Structure | Nomenclature |
|---|---|---|
| I-84 | 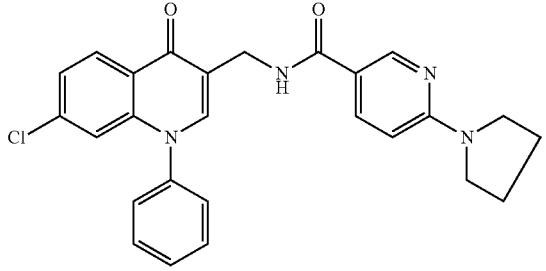 [SMILES: O=C(NCc1cn(-c2ccccc2)c2cc(Cl)ccc2c1=O)c1ccc(N2CCCC2)nc1] | N-(7-Chloro-4-oxo-1-phenyl-1,4-dihydro-quinolin-3-ylmethyl)-6-pyrrolidin-1-yl-nicotinamide |
| I-85 | 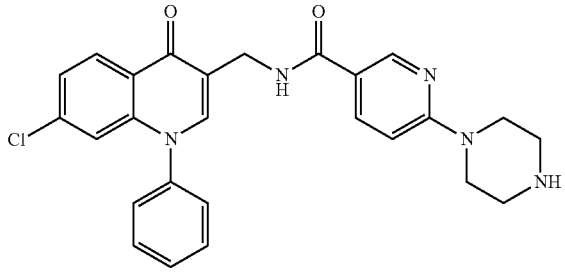 [SMILES: O=C(NCc1cn(-c2ccccc2)c2cc(Cl)ccc2c1=O)c1ccc(N2CCNCC2)nc1] | N-(7-Chloro-4-oxo-1-phenyl-1,4-dihydro-quinolin-3-ylmethyl)-6-piperazin-1-yl-nicotinamide |
| I-86 | 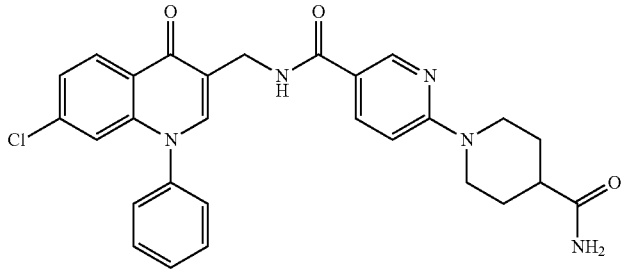 [SMILES: NC(=O)C1CCN(c2ccc(C(=O)NCc3cn(-c4ccccc4)c4cc(Cl)ccc4c3=O)cn2)CC1] | 3,4,5,6-Tetrahydro-2H-[1,2']bipyridinyl-4,5'-dicarboxylic acid 4-amide 5'-[(7-chloro-4-oxo-1-phenyl-1,4-dihydro-quinolin-3-ylmethyl)-amide] |
| I-87 | 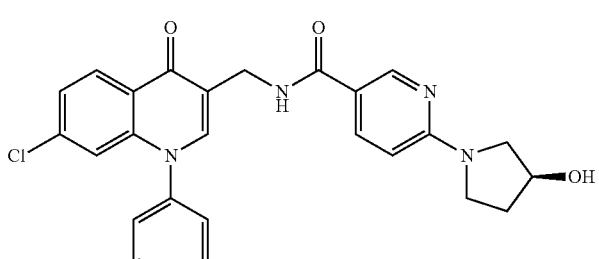 | N-(7-Chloro-4-oxo-1-phenyl-1,4-dihydro-quinolin-3-ylmethyl)-6-((S)-3-hydroxy-pyrrolidin-1-yl)-nicotinamide |
| I-88 | 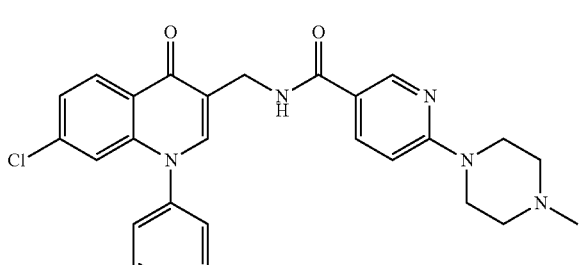 | N-(7-Chloro-4-oxo-1-phenyl-1,4-dihydro-quinolin-3-ylmethyl)-6-(4-methyl-piperazin-1-yl)-nicotinamide |

TABLE I-continued

| Compound | Structure | Nomenclature |
|---|---|---|
| I-89 | 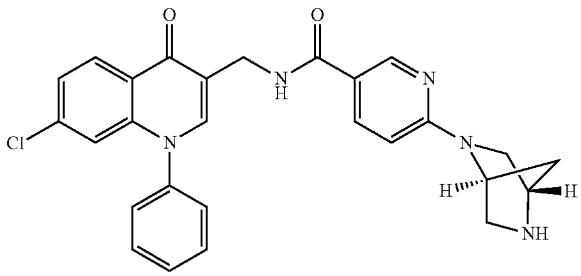 [SMILES: O=C(NCc1cn(-c2ccccc2)c2cc(Cl)ccc2c1=O)c1ccc(N2C[C@@H]3C[C@H]2CN3)nc1] | N-(7-Chloro-4-oxo-1-phenyl-1,4-dihydro-quinolin-3-ylmethyl)-6-(1S,4S)-2,5-diaza-bicyclo[2.2.1]hept-2-yl-nicotinamide |
| I-90 | 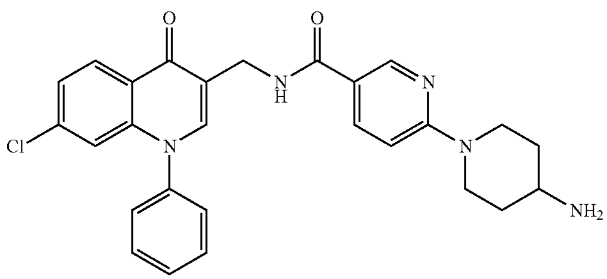 [SMILES: NC1CCN(c2ccc(C(=O)NCc3cn(-c4ccccc4)c4cc(Cl)ccc4c3=O)cn2)CC1] | 4-Amino-3,4,5,6-tetrahydro-2H-[1,2']bipyridinyl-5'-carboxylic acid (7-chloro-4-oxo-1-phenyl-1,4-dihydro-quinolin-3-ylmethyl)-amide |
| I-91 | 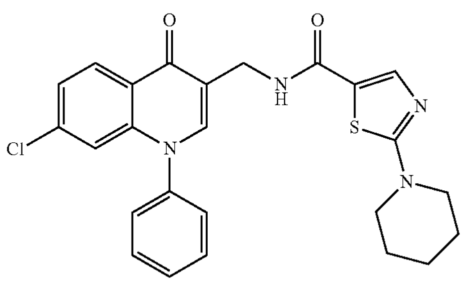 [SMILES: O=C(NCc1cn(-c2ccccc2)c2cc(Cl)ccc2c1=O)c1cnc(N2CCCCC2)s1] | 2-Piperidin-1-yl-thiazole-5-carboxylic acid (7-chloro-4-oxo-1-phenyl-1,4-dihydro-quinolin-3-ylmethyl)-amide |
| I-92 | 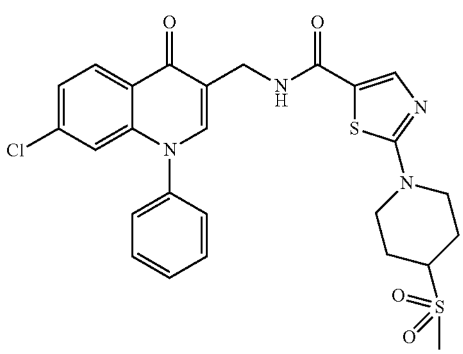 [SMILES: CS(=O)(=O)C1CCN(c2ncc(C(=O)NCc3cn(-c4ccccc4)c4cc(Cl)ccc4c3=O)s2)CC1] | 2-(4-Methanesulfonyl-piperidin-1-yl)-thiazole-5-carboxylic acid (7-chloro-4-oxo-1-phenyl-1,4-dihydro-quinolin-3-ylmethyl)-amide |
| I-93 | 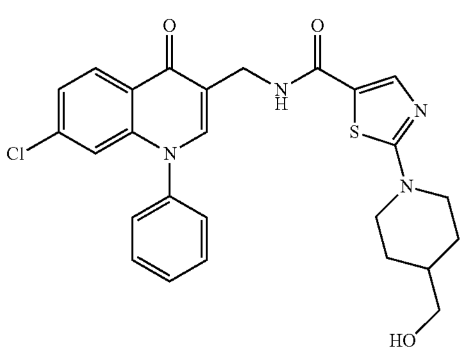 [SMILES: O=C(NCc1cn(-c2ccccc2)c2cc(Cl)ccc2c1=O)c1cnc(N2CCC(CO)CC2)s1] | 2-(4-Hydroxymethyl-piperidin-1-yl)-thiazole-5-carboxylic acid (7-chloro-4-oxo-1-phenyl-1,4-dihydro-quinolin-3-ylmethyl)-amide |

TABLE I-continued

| Compound | Structure | Nomenclature |
|---|---|---|
| I-94 | 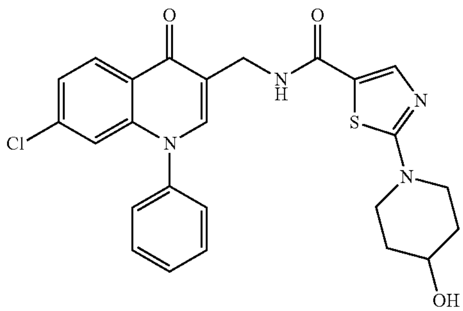 [SMILES: O=C(NCc1cn(-c2ccccc2)c2cc(Cl)ccc2c1=O)c1cnc(N2CCC(O)CC2)s1] | 2-(4-Hydroxy-piperidin-1-yl)-thiazole-5-carboxylic acid (7-chloro-4-oxo-1-phenyl-1,4-dihydro-quinolin-3-ylmethyl)-amide |
| I-95 | 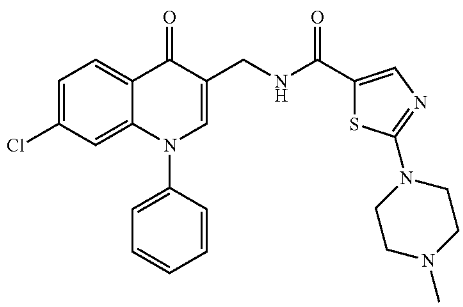 [SMILES: CN1CCN(c2ncc(C(=O)NCc3cn(-c4ccccc4)c4cc(Cl)ccc4c3=O)s2)CC1] | 2-(4-Methyl-piperazin-1-yl)-thiazole-5-carboxylic acid (7-chloro-4-oxo-1-phenyl-1,4-dihydro-quinolin-3-ylmethyl)-amide |
| I-96 | 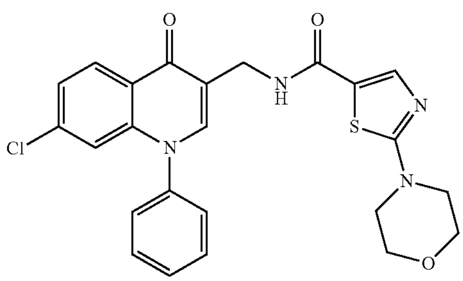 [SMILES: O=C(NCc1cn(-c2ccccc2)c2cc(Cl)ccc2c1=O)c1cnc(N2CCOCC2)s1] | 2-Morpholin-4-yl-thiazole-5-carboxylic acid (7-chloro-4-oxo-1-phenyl-1,4-dihydro-quinolin-3-ylmethyl)-amide |
| I-97 | 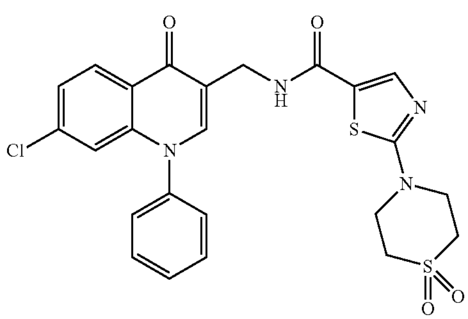 [SMILES: O=C(NCc1cn(-c2ccccc2)c2cc(Cl)ccc2c1=O)c1cnc(N2CCS(=O)(=O)CC2)s1] | 2-(1,1-Dioxo-1$\lambda^6$-thiomorpholin-4-yl)-thiazole-5-carboxylic acid (7-chloro-4-oxo-1-phenyl-1,4-dihydro-quinolin-3-ylmethyl)-amide |
| I-98 | 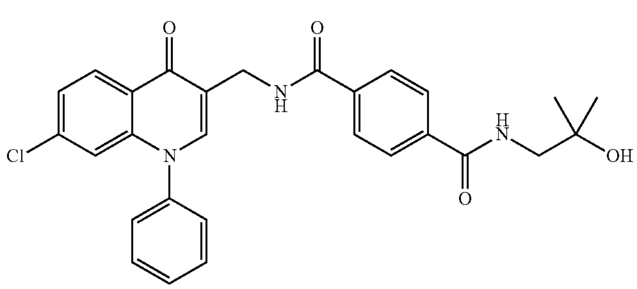 [SMILES: CC(C)(O)CNC(=O)c1ccc(C(=O)NCc2cn(-c3ccccc3)c3cc(Cl)ccc3c2=O)cc1] | N-(7-Chloro-4-oxo-1-phenyl-1,4-dihydro-quinolin-3-ylmethyl)-N'-(2-hydroxy-2-methyl-propyl)-terephthalamide |

TABLE I-continued

| Compound | Structure | Nomenclature |
|---|---|---|
| I-99 | 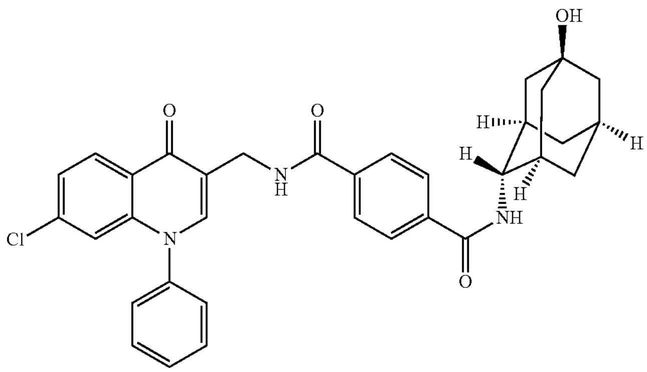 [SMILES: O=C(NCc1cn(-c2ccccc2)c2cc(Cl)ccc2c1=O)c1ccc(C(=O)N[C@H]2[C@@H]3C[C@H]4C[C@@H]2C[C@@](O)(C3)C4)cc1] | N-(7-Chloro-4-oxo-1-phenyl-1,4-dihydro-quinolin-3-ylmethyl)-N'-((1R,3R)-5-hydroxy-adamantan-2-yl)-terephthalamide |
| I-100 | 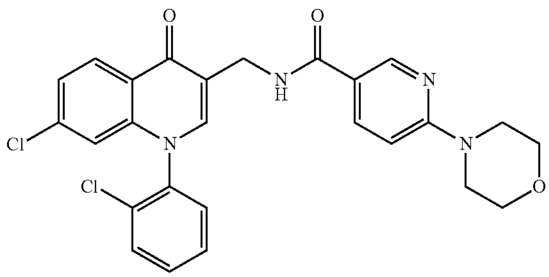 [SMILES: O=C(NCc1cn(-c2ccccc2Cl)c2cc(Cl)ccc2c1=O)c1ccc(N2CCOCC2)nc1] | N-[7-Chloro-1-(2-chloro-phenyl)-4-oxo-1,4-dihydro-quinolin-3-ylmethyl]-6-morpholin-4-yl-nicotinamide |
| I-101 | 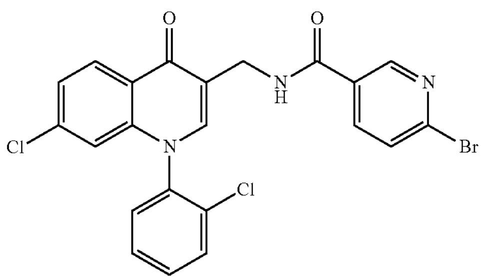 [SMILES: O=C(NCc1cn(-c2ccccc2Cl)c2cc(Cl)ccc2c1=O)c1ccc(Br)nc1] | 6-Bromo-N-[7-chloro-1-(2-chloro-phenyl)-4-oxo-1,4-dihydro-quinolin-3-ylmethyl]-nicotinamide |
| I-102 | 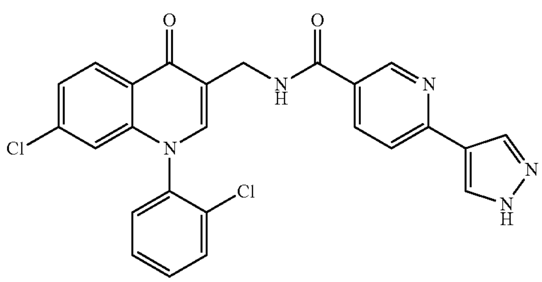 [SMILES: O=C(NCc1cn(-c2ccccc2Cl)c2cc(Cl)ccc2c1=O)c1ccc(-c2cn[nH]c2)nc1] | N-[7-Chloro-1-(2-chloro-phenyl)-4-oxo-1,4-dihydro-quinolin-3-ylmethyl]-6-(1H-pyrazol-4-yl)-nicotinamide |
| I-103 | 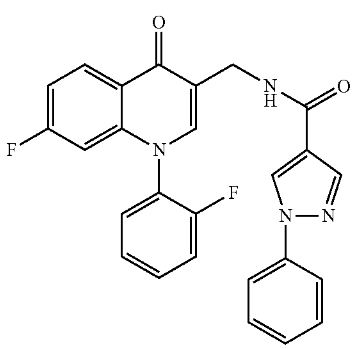 [SMILES: O=C(NCc1cn(-c2ccccc2F)c2cc(F)ccc2c1=O)c1cnn(-c2ccccc2)c1] | 1-Phenyl-1H-pyrazole-4-carboxylic acid [7-fluoro-1-(2-fluoro-phenyl)-4-oxo-1,4-dihydro-quinolin-3-ylmethyl]-amide |

TABLE I-continued

| Compound | Structure | Nomenclature |
| --- | --- | --- |
| I-104 | 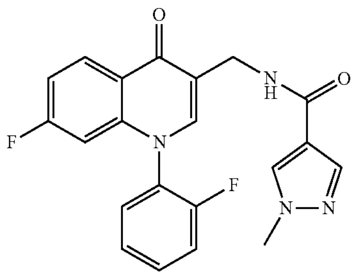 [SMILES: Cn1cc(C(=O)NCc2cn(-c3ccccc3F)c3cc(F)ccc3c2=O)cn1] | 1-Methyl-1H-pyrazole-4-carboxylic acid [7-fluoro-1-(2-fluoro-phenyl)-4-oxo-1,4-dihydro-quinolin-3-ylmethyl]-amide |
| I-105 | 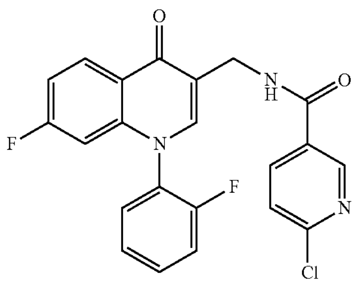 [SMILES: O=C(NCc1cn(-c2ccccc2F)c2cc(F)ccc2c1=O)c1ccc(Cl)nc1] | 6-Chloro-N-[7-fluoro-1-(2-fluoro-phenyl)-4-oxo-1,4-dihydro-quinolin-3-ylmethyl]-nicotinamide |
| I-106 | 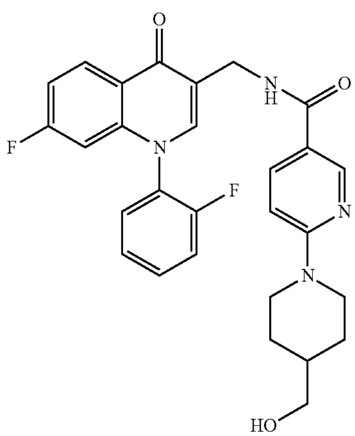 [SMILES: O=C(NCc1cn(-c2ccccc2F)c2cc(F)ccc2c1=O)c1ccc(N2CCC(CO)CC2)nc1] | 4-Hydroxymethyl-3,4,5,6-tetrahydro-2H-[1,2']bipyridinyl-5'-carboxylic acid [7-fluoro-1-(2-fluoro-phenyl)-4-oxo-1,4-dihydro-quinolin-3-ylmethyl]-amide |
| I-107 | 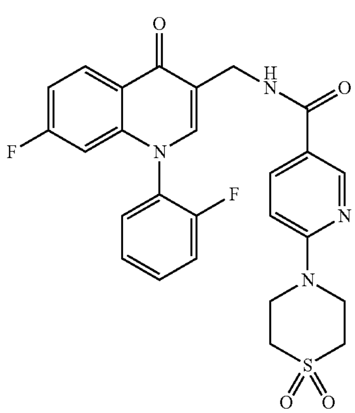 [SMILES: O=C(NCc1cn(-c2ccccc2F)c2cc(F)ccc2c1=O)c1ccc(N2CCS(=O)(=O)CC2)nc1] | 6-(1,1-Dioxo-1$\lambda^6$-thiomorpholin-4-yl)-N-[7-fluoro-1-(2-fluoro-phenyl)-4-oxo-1,4-dihydro-quinolin-3-ylmethyl]-nicotinamide |

TABLE I-continued

| Compound | Structure | Nomenclature |
| --- | --- | --- |
| I-108 | 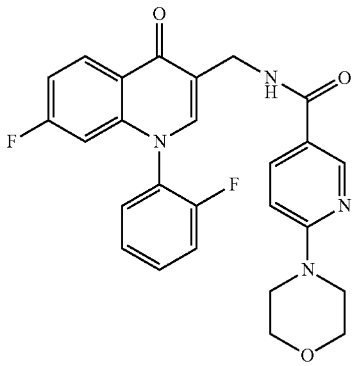 [SMILES: O=C(NCc1cn(-c2ccccc2F)c2cc(F)ccc2c1=O)c1ccc(N2CCOCC2)nc1] | N-[7-Fluoro-1-(2-fluoro-phenyl)-4-oxo-1,4-dihydro-quinolin-3-ylmethyl]-6-morpholin-4-yl-nicotinamide |
| I-109 | 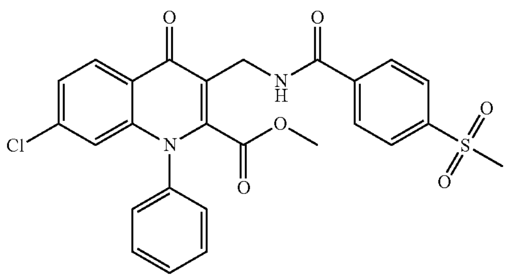 [SMILES: COC(=O)c1c(CNC(=O)c2ccc(S(C)(=O)=O)cc2)c(=O)c2ccc(Cl)cc2n1-c1ccccc1] | 7-Chloro-3-[(4-methanesulfonyl-benzoylamino)-methyl]-4-oxo-1-phenyl-1,4-dihydro-quinoline-2-carboxylic acid methyl ester |
| I-110 | 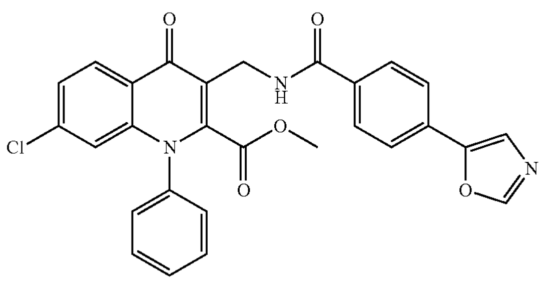 [SMILES: COC(=O)c1c(CNC(=O)c2ccc(-c3cnco3)cc2)c(=O)c2ccc(Cl)cc2n1-c1ccccc1] | 7-Chloro-3-[(4-oxazol-5-yl-benzoylamino)-methyl]-4-oxo-1-phenyl-1,4-dihydro-quinoline-2-carboxylic acid methyl ester |
| I-111 | 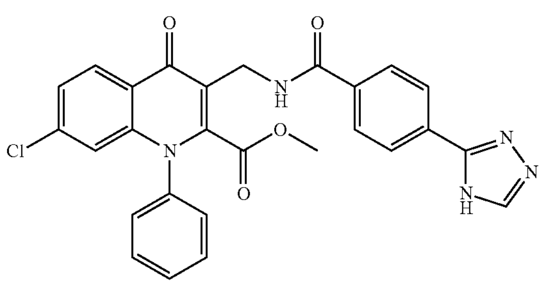 [SMILES: COC(=O)c1c(CNC(=O)c2ccc(-c3nnc[nH]3)cc2)c(=O)c2ccc(Cl)cc2n1-c1ccccc1] | 7-Chloro-4-oxo-1-phenyl-3-{[4-(4H-[1,2,4]triazol-3-yl)-benzoylamino]-methyl}-1,4-dihydro-quinoline-2-carboxylic acid methyl ester |
| I-112 | 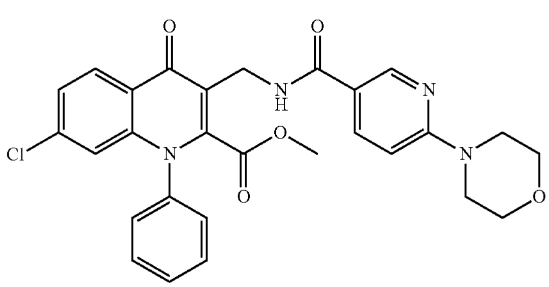 [SMILES: COC(=O)c1c(CNC(=O)c2ccc(N3CCOCC3)nc2)c(=O)c2ccc(Cl)cc2n1-c1ccccc1] | 7-Chloro-3-{[(6-morpholin-4-yl-pyridine-3-carbonyl)-amino]-methyl}-4-oxo-1-phenyl-1,4-dihydro-quinoline-2-carboxylic acid methyl ester |

TABLE I-continued

| Compound | Structure | Nomenclature |
|---|---|---|
| I-113 | 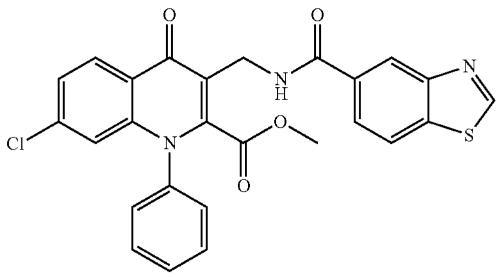 [SMILES: COC(=O)c1c(CNC(=O)c2ccc3scnc3c2)c(=O)c2ccc(Cl)cc2n1-c1ccccc1] | 3-{[(Benzothiazole-5-carbonyl)-amino]-methyl}-7-chloro-4-oxo-1-phenyl-1,4-dihydro-quinoline-2-carboxylic acid methyl ester |
| I-114 | 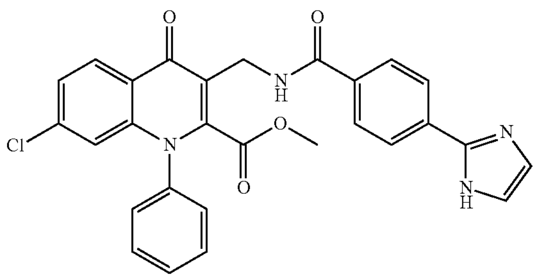 [SMILES: COC(=O)c1c(CNC(=O)c2ccc(-c3ncc[nH]3)cc2)c(=O)c2ccc(Cl)cc2n1-c1ccccc1] | 7-Chloro-3-{[4-(1H-imidazol-2-yl)-benzoylamino]-methyl}-4-oxo-1-phenyl-1,4-dihydro-quinoline-2-carboxylic acid methyl ester |
| I-115 | 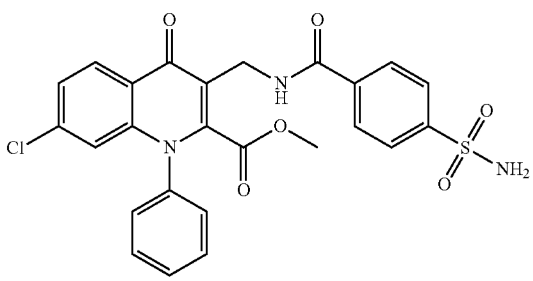 [SMILES: COC(=O)c1c(CNC(=O)c2ccc(S(N)(=O)=O)cc2)c(=O)c2ccc(Cl)cc2n1-c1ccccc1] | 7-Chloro-4-oxo-1-phenyl-3-[(4-sulfamoyl-benzoylamino)-methyl]-1,4-dihydro-quinoline-2-carboxylic acid methyl ester |
| I-116 | 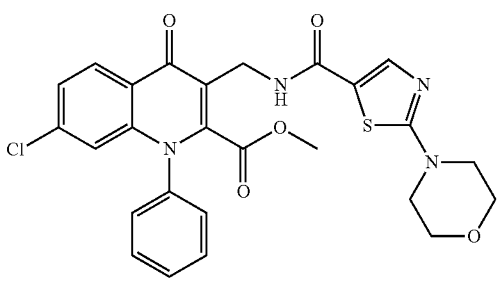 [SMILES: COC(=O)c1c(CNC(=O)c2cnc(N3CCOCC3)s2)c(=O)c2ccc(Cl)cc2n1-c1ccccc1] | 7-Chloro-3-{[(2-morpholin-4-yl-thiazole-5-carbonyl)-amino]-methyl}-4-oxo-1-phenyl-1,4-dihydro-quinoline-2-carboxylic acid methyl ester |
| I-117 | 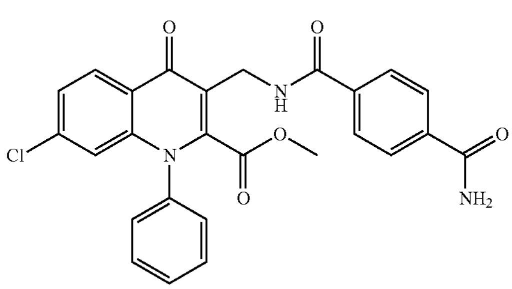 [SMILES: COC(=O)c1c(CNC(=O)c2ccc(C(N)=O)cc2)c(=O)c2ccc(Cl)cc2n1-c1ccccc1] | 3-[(4-Carbamoyl-benzoylamino)-methyl]-7-chloro-4-oxo-1-phenyl-1,4-dihydro-quinoline-2-carboxylic acid methyl ester |

TABLE I-continued

| Compound | Structure | Nomenclature |
|---|---|---|
| I-118 | 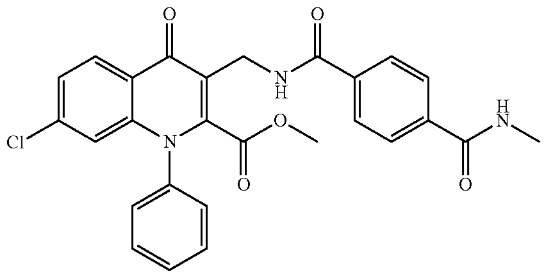 [SMILES: CNC(=O)c1ccc(C(=O)NCc2c(C(=O)OC)n(-c3ccccc3)c3cc(Cl)ccc3c2=O)cc1] | 7-Chloro-3-[(4-methylcarbamoyl-benzoylamino)-methyl]-4-oxo-1-phenyl-1,4-dihydro-quinoline-2-carboxylic acid methyl ester |
| I-119 | 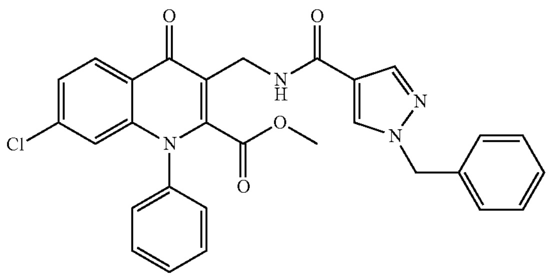 [SMILES: COC(=O)c1c(CNC(=O)c2cnn(Cc3ccccc3)c2)c(=O)c2ccc(Cl)cc2n1-c1ccccc1] | 3-{[(1-Benzyl-1H-pyrazole-4-carbonyl)-amino]-methyl}-7-chloro-4-oxo-1-phenyl-1,4-dihydro-quinoline-2-carboxylic acid methyl ester |
| I-120 | 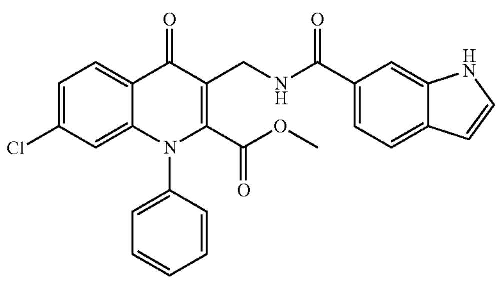 [SMILES: COC(=O)c1c(CNC(=O)c2ccc3cc[nH]c3c2)c(=O)c2ccc(Cl)cc2n1-c1ccccc1] | 7-Chloro-3-{[(1H-indole-6-carbonyl)-amino]-methyl}-4-oxo-1-phenyl-1,4-dihydro-quinoline-2-carboxylic acid methyl ester |
| I-121 | 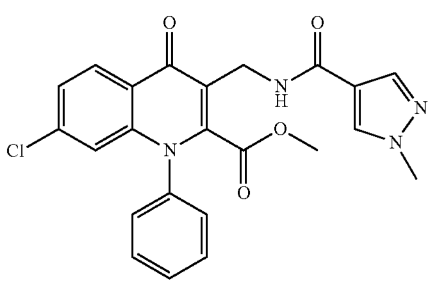 [SMILES: COC(=O)c1c(CNC(=O)c2cnn(C)c2)c(=O)c2ccc(Cl)cc2n1-c1ccccc1] | 7-Chloro-3-{[(1-methyl-1H-pyrazole-4-carbonyl)-amino]-methyl}-4-oxo-1-phenyl-1,4-dihydro-quinoline-2-carboxylic acid methyl ester |
| I-122 | 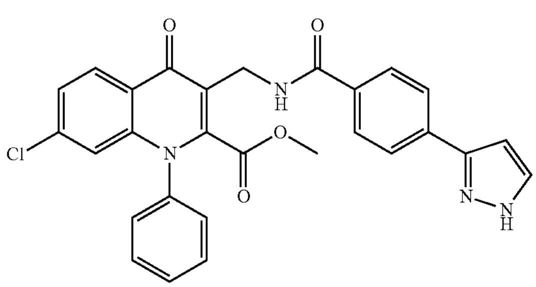 [SMILES: COC(=O)c1c(CNC(=O)c2ccc(-c3cc[nH]n3)cc2)c(=O)c2ccc(Cl)cc2n1-c1ccccc1] | 7-Chloro-4-oxo-1-phenyl-3-{[4-(1H-pyrazol-3-yl)-benzoylamino]-methyl}-1,4-dihydro-quinoline-2-carboxylic acid methyl ester |

TABLE I-continued

| Compound | Structure | Nomenclature |
|---|---|---|
| I-123 | 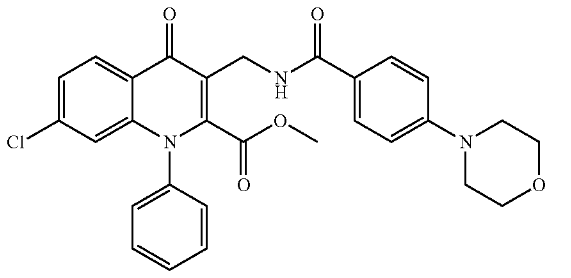 [SMILES: COC(=O)c1c(CNC(=O)c2ccc(N3CCOCC3)cc2)c(=O)c2ccc(Cl)cc2n1-c1ccccc1] | 7-Chloro-3-[(4-morpholin-4-yl-benzoylamino)-methyl]-4-oxo-1-phenyl-1,4-dihydro-quinoline-2-carboxylic acid methyl ester |
| I-124 | 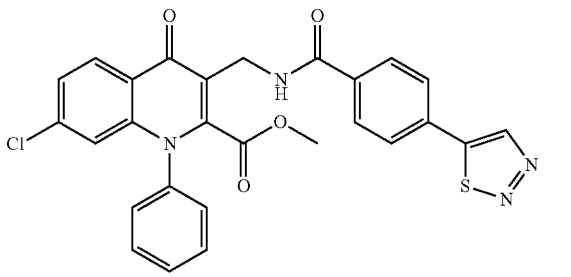 [SMILES: COC(=O)c1c(CNC(=O)c2ccc(-c3cnns3)cc2)c(=O)c2ccc(Cl)cc2n1-c1ccccc1] | 7-Chloro-4-oxo-1-phenyl-3-[(4-[1,2,3]thiadiazol-5-yl-benzoylamino)-methyl]-1,4-dihydro-quinoline-2-carboxylic acid methyl ester |
| I-125 | 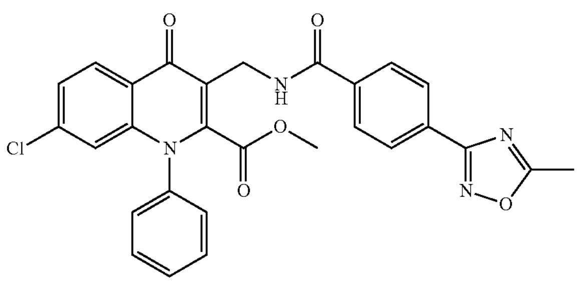 [SMILES: COC(=O)c1c(CNC(=O)c2ccc(-c3noc(C)n3)cc2)c(=O)c2ccc(Cl)cc2n1-c1ccccc1] | 7-Chloro-3-{[4-(5-methyl-[1,2,4]oxadiazol-3-yl)-benzoylamino]-methyl}-4-oxo-1-phenyl-1,4-dihydro-quinoline-2-carboxylic acid methyl ester |
| I-126 | 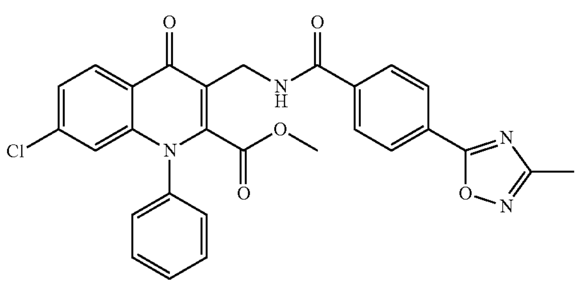 [SMILES: COC(=O)c1c(CNC(=O)c2ccc(-c3nc(C)no3)cc2)c(=O)c2ccc(Cl)cc2n1-c1ccccc1] | 7-Chloro-3-{[4-(3-methyl-[1,2,4]oxadiazol-5-yl)-benzoylamino]-methyl}-4-oxo-1-phenyl-1,4-dihydro-quinoline-2-carboxylic acid methyl ester |
| I-127 | 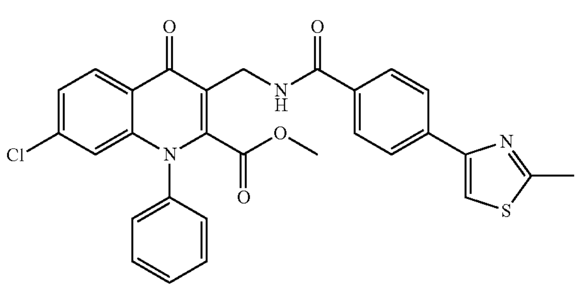 | 7-Chloro-3-{[4-(2-methyl-thiazol-4-yl)-benzoylamino]-methyl}-4-oxo-1-phenyl-1,4-dihydro-quinoline-2-carboxylic acid methyl ester |

TABLE I-continued

| Compound | Structure | Nomenclature |
|---|---|---|
| I-128 | 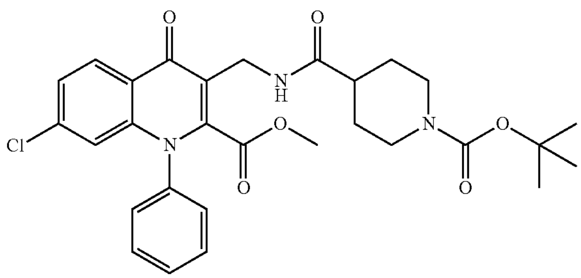 [SMILES: COC(=O)c1c(CNC(=O)C2CCN(C(=O)OC(C)(C)C)CC2)c(=O)c2ccc(Cl)cc2n1-c1ccccc1] | 3-{[(1-tert-Butoxycarbonyl-piperidine-4-carbonyl)-amino]-methyl}-7-chloro-4-oxo-1-phenyl-1,4-dihydro-quinoline-2-carboxylic acid methyl ester |
| I-129 | 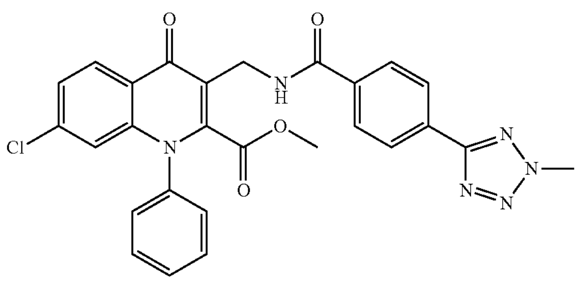 [SMILES: COC(=O)c1c(CNC(=O)c2ccc(-c3nnn(C)n3)cc2)c(=O)c2ccc(Cl)cc2n1-c1ccccc1] | 7-Chloro-3-{[4-(2-methyl-2H-tetrazol-5-yl)-benzoylamino]-methyl}-4-oxo-1-phenyl-1,4-dihydro-quinoline-2-carboxylic acid methyl ester |
| I-130 | 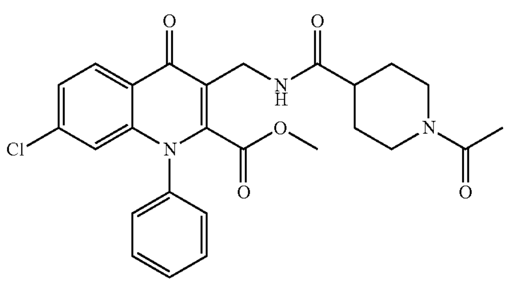 [SMILES: COC(=O)c1c(CNC(=O)C2CCN(C(C)=O)CC2)c(=O)c2ccc(Cl)cc2n1-c1ccccc1] | 3-{[(1-Acetyl-piperidine-4-carbonyl)-amino]-methyl}-7-chloro-4-oxo-1-phenyl-1,4-dihydro-quinoline-2-carboxylic acid methyl ester |
| I-131 | 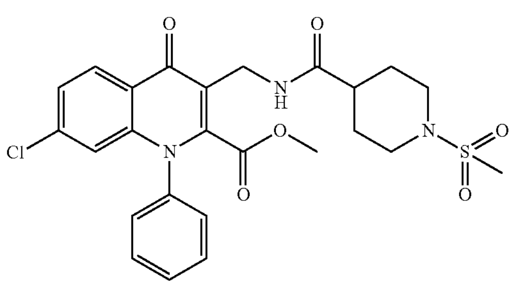 [SMILES: COC(=O)c1c(CNC(=O)C2CCN(S(C)(=O)=O)CC2)c(=O)c2ccc(Cl)cc2n1-c1ccccc1] | 7-Chloro-3-{[(1-methanesulfonyl-piperidine-4-carbonyl)-amino]-methyl}-4-oxo-1-phenyl-1,4-dihydro-quinoline-2-carboxylic acid methyl ester |
| I-132 | 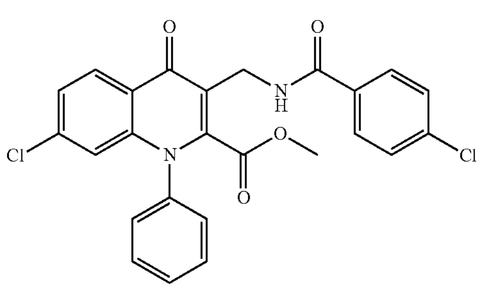 [SMILES: COC(=O)c1c(CNC(=O)c2ccc(Cl)cc2)c(=O)c2ccc(Cl)cc2n1-c1ccccc1] | 7-Chloro-3-[(4-chloro-benzoylamino)-methyl]-4-oxo-1-phenyl-1,4-dihydro-quinoline-2-carboxylic acid methyl ester |

TABLE I-continued

| Compound | Structure | Nomenclature |
|---|---|---|
| I-133 | 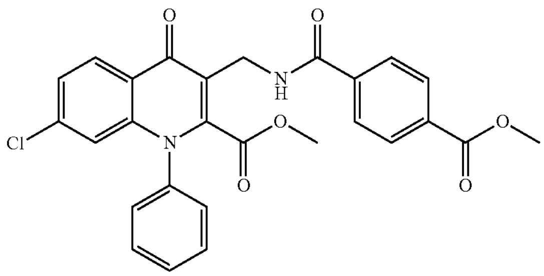 [SMILES: COC(=O)c1ccc(C(=O)NCc2c(C(=O)OC)n(-c3ccccc3)c3cc(Cl)ccc3c2=O)cc1] | 7-Chloro-3-[(4-methoxycarbonyl-benzoylamino)-methyl]-4-oxo-1-phenyl-1,4-dihydro-quinoline-2-carboxylic acid methyl ester |
| I-134 | 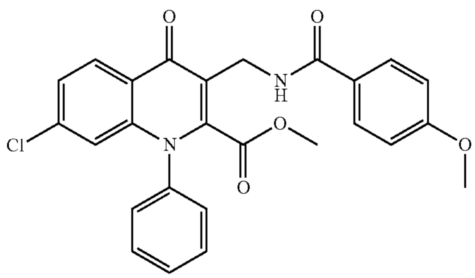 [SMILES: COC(=O)c1c(CNC(=O)c2ccc(OC)cc2)c(=O)c2ccc(Cl)cc2n1-c1ccccc1] | 7-Chloro-3-[(4-methoxy-benzoylamino)-methyl]-4-oxo-1-phenyl-1,4-dihydro-quinoline-2-carboxylic acid methyl ester |
| I-135 | 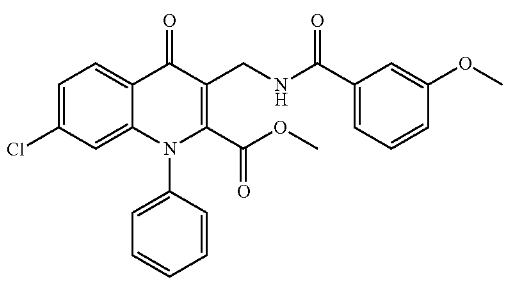 [SMILES: COC(=O)c1c(CNC(=O)c2cccc(OC)c2)c(=O)c2ccc(Cl)cc2n1-c1ccccc1] | 7-Chloro-3-[(3-methoxy-benzoylamino)-methyl]-4-oxo-1-phenyl-1,4-dihydro-quinoline-2-carboxylic acid methyl ester |
| I-136 | 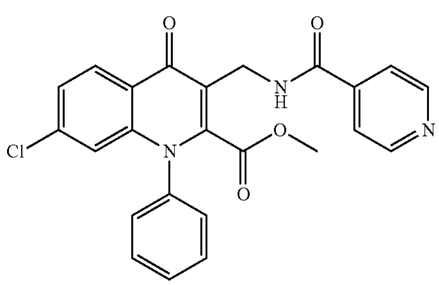 [SMILES: COC(=O)c1c(CNC(=O)c2ccncc2)c(=O)c2ccc(Cl)cc2n1-c1ccccc1] | 7-Chloro-4-oxo-1-phenyl-3-{[(pyridine-4-carbonyl)-amino]-methyl}-1,4-dihydro-quinoline-2-carboxylic acid methyl ester |
| I-137 | 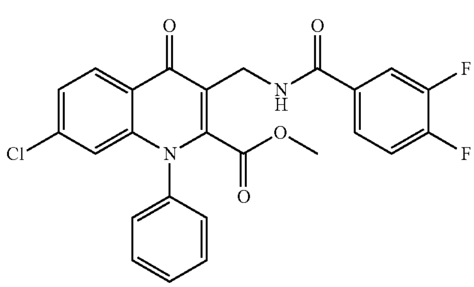 | 7-Chloro-3-[(3,4-difluoro-benzoylamino)-methyl]-4-oxo-1-phenyl-1,4-dihydro-quinoline-2-carboxylic acid methyl ester |

TABLE I-continued

| Compound | Structure | Nomenclature |
| --- | --- | --- |
| I-138 | 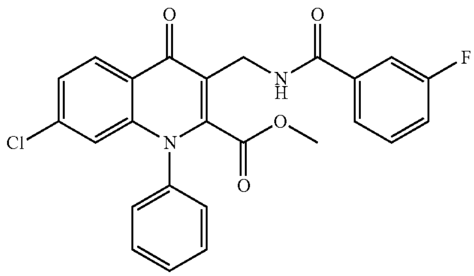 [SMILES: COC(=O)c1c(CNC(=O)c2cccc(F)c2)c(=O)c2ccc(Cl)cc2n1-c1ccccc1] | 7-Chloro-3-[(3-fluoro-benzoylamino)-methyl]-4-oxo-1-phenyl-1,4-dihydro-quinoline-2-carboxylic acid methyl ester |
| I-139 | 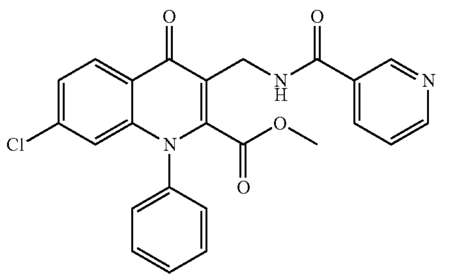 [SMILES: COC(=O)c1c(CNC(=O)c2cccnc2)c(=O)c2ccc(Cl)cc2n1-c1ccccc1] | 7-Chloro-4-oxo-1-phenyl-3-{[(pyridine-3-carbonyl)-amino]-methyl}-1,4-dihydro-quinoline-2-carboxylic acid methyl ester |
| I-140 | 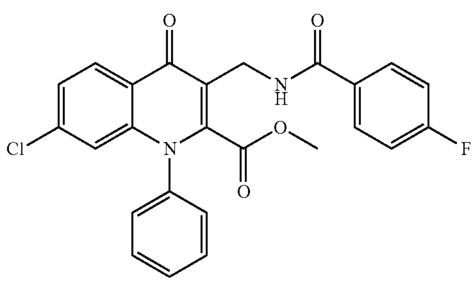 | 7-Chloro-3-[(4-fluoro-benzoylamino)-methyl]-4-oxo-1-phenyl-1,4-dihydro-quinoline-2-carboxylic acid methyl ester |
| I-141 | 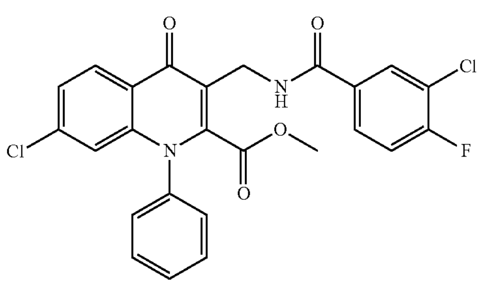 [SMILES: COC(=O)c1c(CNC(=O)c2ccc(F)c(Cl)c2)c(=O)c2ccc(Cl)cc2n1-c1ccccc1] | 7-Chloro-3-[(3-chloro-4-fluoro-benzoylamino)-methyl]-4-oxo-1-phenyl-1,4-dihydro-quinoline-2-carboxylic acid methyl ester |
| I-142 | 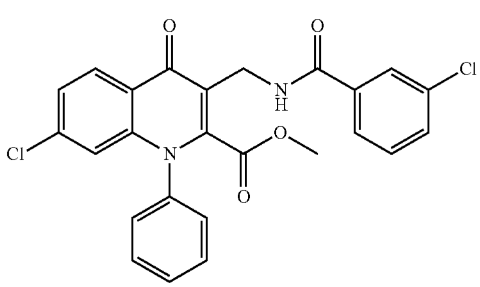 [SMILES: COC(=O)c1c(CNC(=O)c2cccc(Cl)c2)c(=O)c2ccc(Cl)cc2n1-c1ccccc1] | 7-Chloro-3-[(3-chloro-benzoylamino)-methyl]-4-oxo-1-phenyl-1,4-dihydro-quinoline-2-carboxylic acid methyl ester |

TABLE I-continued

| Compound | Structure | Nomenclature |
|---|---|---|
| I-143 | 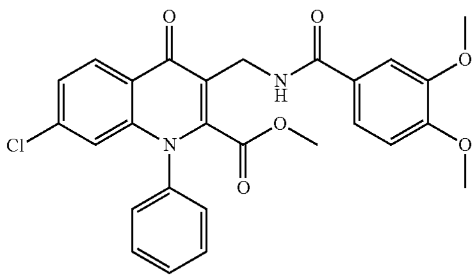 [SMILES: COC(=O)c1c(CNC(=O)c2ccc(OC)c(OC)c2)c(=O)c2ccc(Cl)cc2n1-c1ccccc1] | 7-Chloro-3-[(3,4-dimethoxy-benzoylamino)-methyl]-4-oxo-1-phenyl-1,4-dihydro-quinoline-2-carboxylic acid methyl ester |
| I-144 | 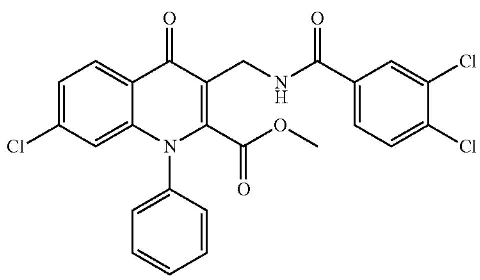 [SMILES: COC(=O)c1c(CNC(=O)c2ccc(Cl)c(Cl)c2)c(=O)c2ccc(Cl)cc2n1-c1ccccc1] | 7-Chloro-3-[(3,4-dichloro-benzoylamino)-methyl]-4-oxo-1-phenyl-1,4-dihydro-quinoline-2-carboxylic acid methyl ester |
| I-145 | 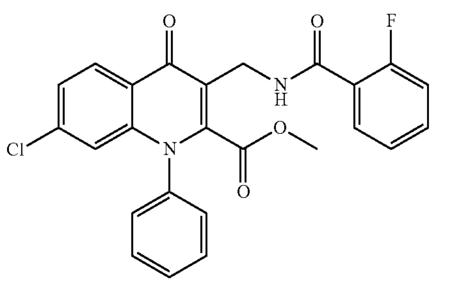 | 7-Chloro-3-[(2-fluoro-benzoylamino)-methyl]-4-oxo-1-phenyl-1,4-dihydro-quinoline-2-carboxylic acid methyl ester |
| I-146 | 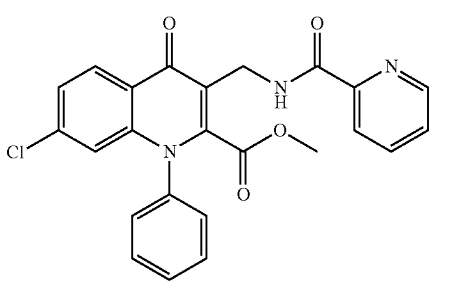 [SMILES: COC(=O)c1c(CNC(=O)c2ccccn2)c(=O)c2ccc(Cl)cc2n1-c1ccccc1] | 7-Chloro-4-oxo-1-phenyl-3-{[(pyridine-2-carbonyl)-amino]-methyl}-1,4-dihydro-quinoline-2-carboxylic acid methyl ester |
| I-147 | 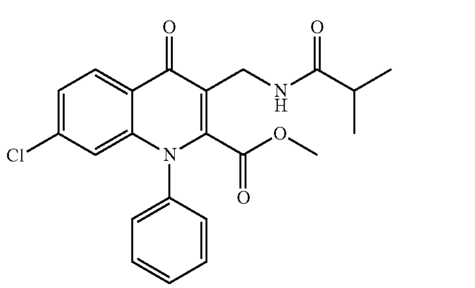 [SMILES: COC(=O)c1c(CNC(=O)C(C)C)c(=O)c2ccc(Cl)cc2n1-c1ccccc1] | 7-Chloro-3-(isobutyrylamino-methyl)-4-oxo-1-phenyl-1,4-dihydro-quinoline-2-carboxylic acid methyl ester |

TABLE I-continued

| Compound | Structure | Nomenclature |
|---|---|---|
| I-148 | 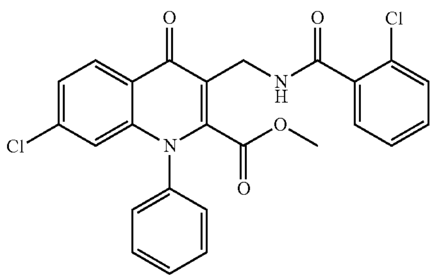 [SMILES: COC(=O)c1c(CNC(=O)c2ccccc2Cl)c(=O)c2ccc(Cl)cc2n1-c1ccccc1] | 7-Chloro-3-[(2-chloro-benzoylamino)-methyl]-4-oxo-1-phenyl-1,4-dihydro-quinoline-2-carboxylic acid methyl ester |
| I-149 | 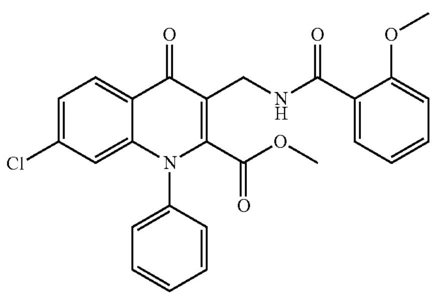 [SMILES: COC(=O)c1c(CNC(=O)c2ccccc2OC)c(=O)c2ccc(Cl)cc2n1-c1ccccc1] | 7-Chloro-3-[(2-methoxy-benzoylamino)-methyl]-4-oxo-1-phenyl-1,4-dihydro-quinoline-2-carboxylic acid methyl ester |
| I-150 | 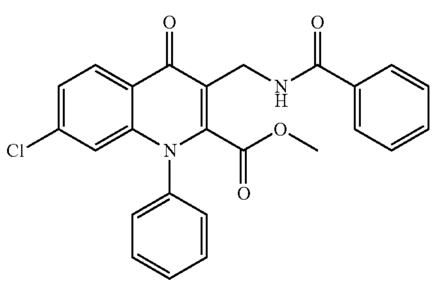 [SMILES: COC(=O)c1c(CNC(=O)c2ccccc2)c(=O)c2ccc(Cl)cc2n1-c1ccccc1] | 3-(Benzoylamino-methyl)-7-chloro-4-oxo-1-phenyl-1,4-dihydro-quinoline-2-carboxylic acid methyl ester |
| I-151 | 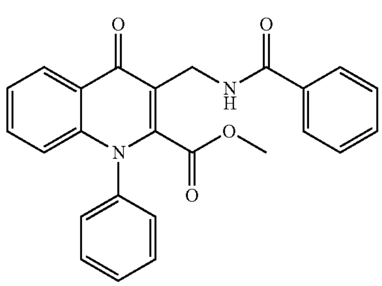 [SMILES: COC(=O)c1c(CNC(=O)c2ccccc2)c(=O)c2ccccc2n1-c1ccccc1] | 3-(Benzoylamino-methyl)-4-oxo-1-phenyl-1,4-dihydro-quinoline-2-carboxylic acid methyl ester |
| I-152 | 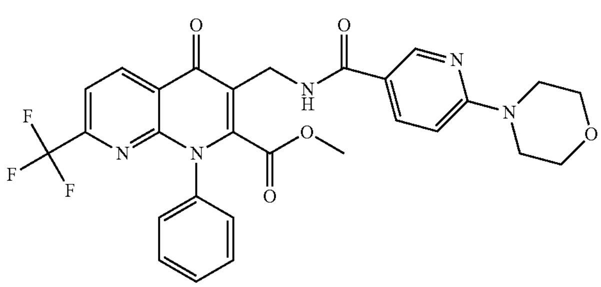 [SMILES: COC(=O)c1c(CNC(=O)c2ccc(N3CCOCC3)nc2)c(=O)c2ccc(C(F)(F)F)nc2n1-c1ccccc1] | 3-{[(6-Morpholin-4-yl-pyridine-3-carbonyl)-amino]-methyl}-4-oxo-1-phenyl-7-trifluoromethyl-1,4-dihydro-[1,8]naphthyridine-2-carboxylic acid methyl ester |

TABLE I-continued

| Compound | Nomenclature |
|---|---|
| I-153 | 3-{[4-(1H-Imidazol-2-yl)-benzoylamino]-methyl}-4-oxo-1-phenyl-7-trifluoromethyl-1,4-dihydro-[1,8]naphthyridine-2-carboxylic acid methyl ester |
| I-154 | 4-Oxo-1-phenyl-3-[(4-sulfamoyl-benzoylamino)-methyl]-7-trifluoromethyl-1,4-dihydro-[1,8]naphthyridine-2-carboxylic acid methyl ester |
| I-155 | 3-[(4-Carbamoyl-benzoylamino)-methyl]-4-oxo-1-phenyl-7-trifluoromethyl-1,4-dihydro-[1,8]naphthyridine-2-carboxylic acid methyl ester |
| I-156 | 4-Oxo-1-phenyl-3-{[4-(2H-pyrazol-3-yl)-benzoylamino]-methyl}-7-trifluoromethyl-1,4-dihydro-[1,8]naphthyridine-2-carboxylic acid methyl ester |
| I-157 | 3-{[4-(2-Methyl-2H-tetrazol-5-yl)-benzoylamino]-methyl}-4-oxo-1-phenyl-7-trifluoromethyl-1,4-dihydro-[1,8]naphthyridine-2-carboxylic acid methyl ester |

TABLE I-continued

| Compound | Nomenclature |
|---|---|
| I-158 | 3-{[(1H-Indole-6-carbonyl)-amino]-methyl}-4-oxo-1-phenyl-7-trifluoromethyl-1,4-dihydro-[1,8]naphthyridine-2-carboxylic acid methyl ester |
| I-159 | 3-[(3,4-Dichloro-benzoylamino)-methyl]-4-oxo-1-phenyl-7-trifluoromethyl-1,4-dihydro-[1,8]naphthyridine-2-carboxylic acid methyl ester |
| I-160 | 3-[(3-Chloro-benzoylamino)-methyl]-7-methoxy-4-oxo-1-phenyl-1,4-dihydro-quinoline-2-carboxylic acid methyl ester |
| I-161 | 7-Methoxy-3-[(3-methoxy-benzoylamino)-methyl]-4-oxo-1-phenyl-1,4-dihydro-quinoline-2-carboxylic acid methyl ester |
| I-162 | 3-[(3,4-Difluoro-benzoylamino)-methyl]-7-methoxy-4-oxo-1-phenyl-1,4-dihydro-quinoline-2-carboxylic acid methyl ester |

TABLE I-continued

| Compound | Structure | Nomenclature |
|---|---|---|
| I-163 | 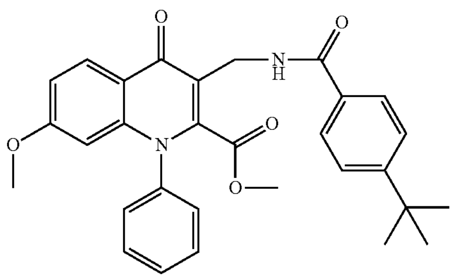 [SMILES: COC(=O)c1c(CNC(=O)c2ccc(C(C)(C)C)cc2)c(=O)c2ccc(OC)cc2n1-c1ccccc1] | 3-[(4-tert-Butyl-benzoylamino)-methyl]-7-methoxy-4-oxo-1-phenyl-1,4-dihydro-quinoline-2-carboxylic acid methyl ester |
| I-164 | 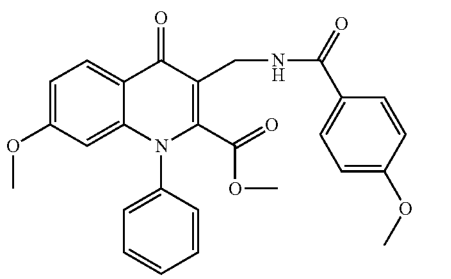 [SMILES: COC(=O)c1c(CNC(=O)c2ccc(OC)cc2)c(=O)c2ccc(OC)cc2n1-c1ccccc1] | 7-Methoxy-3-[(4-methoxy-benzoylamino)-methyl]-4-oxo-1-phenyl-1,4-dihydro-quinoline-2-carboxylic acid methyl ester |
| I-165 | 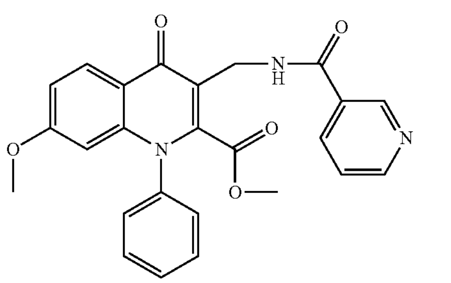 [SMILES: COC(=O)c1c(CNC(=O)c2cccnc2)c(=O)c2ccc(OC)cc2n1-c1ccccc1] | 7-Methoxy-4-oxo-1-phenyl-3-{[(pyridine-3-carbonyl)-amino]-methyl}-1,4-dihydro-quinoline-2-carboxylic acid methyl ester |
| I-166 | 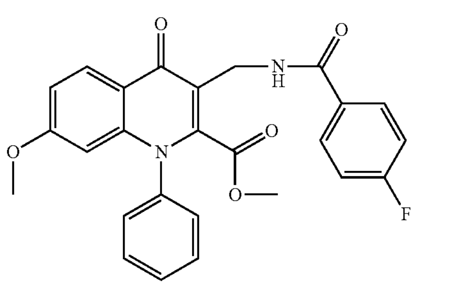 [SMILES: COC(=O)c1c(CNC(=O)c2ccc(F)cc2)c(=O)c2ccc(OC)cc2n1-c1ccccc1] | 3-[(4-Fluoro-benzoylamino)-methyl]-7-methoxy-4-oxo-1-phenyl-1,4-dihydro-quinoline-2-carboxylic acid methyl ester |
| I-167 | 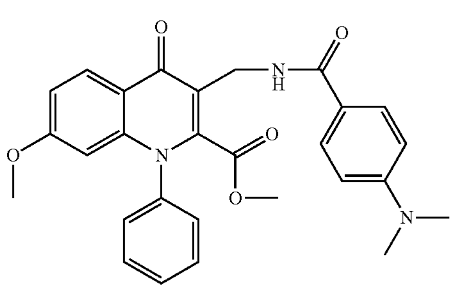 [SMILES: COC(=O)c1c(CNC(=O)c2ccc(N(C)C)cc2)c(=O)c2ccc(OC)cc2n1-c1ccccc1] | 3-[(4-Dimethylamino-benzoylamino)-methyl]-7-methoxy-4-oxo-1-phenyl-1,4-dihydro-quinoline-2-carboxylic acid methyl ester |

TABLE I-continued

| Compound | Structure | Nomenclature |
| --- | --- | --- |
| I-168 | 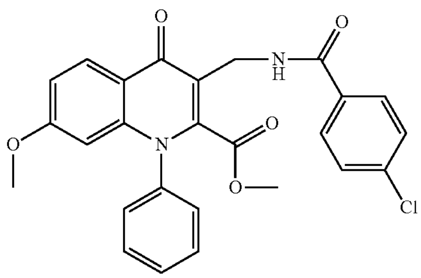 [SMILES: COC(=O)c1c(CNC(=O)c2ccc(Cl)cc2)c(=O)c2ccc(OC)cc2n1-c1ccccc1] | 3-[(4-Chloro-benzoylamino)-methyl]-7-methoxy-4-oxo-1-phenyl-1,4-dihydro-quinoline-2-carboxylic acid methyl ester |
| I-169 | 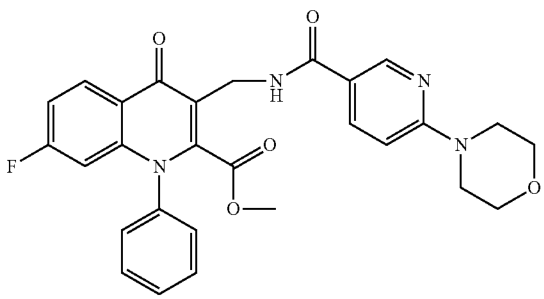 [SMILES: COC(=O)c1c(CNC(=O)c2ccc(N3CCOCC3)nc2)c(=O)c2ccc(F)cc2n1-c1ccccc1] | 7-Fluoro-3-{[(6-morpholin-4-yl-pyridine-3-carbonyl)-amino]-methyl}-4-oxo-1-phenyl-1,4-dihydro-quinoline-2-carboxylic acid methyl ester |
| I-170 | 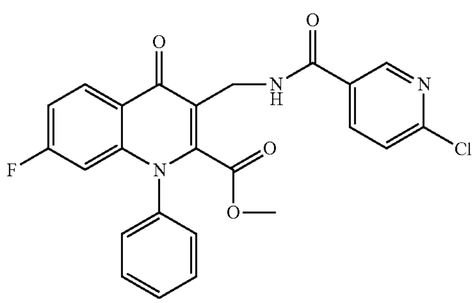 [SMILES: COC(=O)c1c(CNC(=O)c2ccc(Cl)nc2)c(=O)c2ccc(F)cc2n1-c1ccccc1] | 3-{[(6-Chloro-pyridine-3-carbonyl)-amino]-methyl}-7-fluoro-4-oxo-1-phenyl-1,4-dihydro-quinoline-2-carboxylic acid methyl ester |
| I-171 | 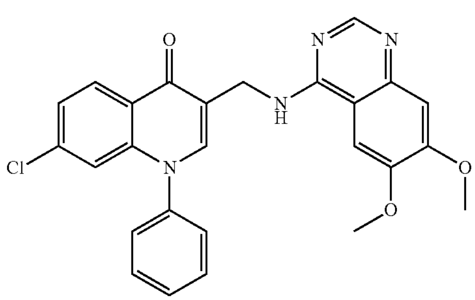 [SMILES: COc1cc2ncnc(NCc3cn(-c4ccccc4)c4cc(Cl)ccc4c3=O)c2cc1OC] | 7-Chloro-3-[(6,7-dimethoxy-quinazolin-4-ylamino)-methyl]-1-phenyl-1H-quinolin-4-one |
| I-172 | 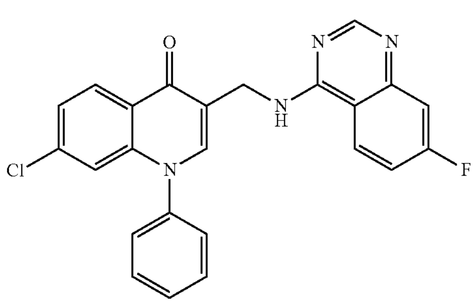 [SMILES: O=c1c(CNc2ncnc3cc(F)ccc23)cn(-c2ccccc2)c2cc(Cl)ccc12] | 7-Chloro-3-[(7-fluoro-quinazolin-4-ylamino)-methyl]-1-phenyl-1H-quinolin-4-one |

TABLE I-continued

| Compound | Structure | Nomenclature |
|---|---|---|
| I-173 | 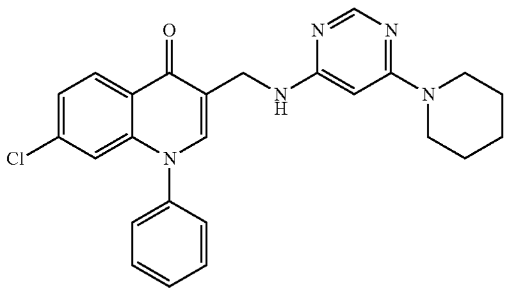 [SMILES: O=c1c(CNc2cc(N3CCCCC3)ncn2)cn(-c2ccccc2)c2cc(Cl)ccc12] | 7-Chloro-1-phenyl-3-[(6-piperidin-1-yl-pyrimidin-4-ylamino)-methyl]-1H-quinolin-4-one |
| I-174 | 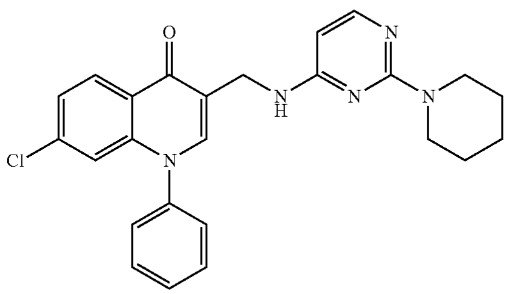 [SMILES: O=c1c(CNc2ccnc(N3CCCCC3)n2)cn(-c2ccccc2)c2cc(Cl)ccc12] | 7-Chloro-1-phenyl-3-[(2-piperidin-1-yl-pyrimidin-4-ylamino)-methyl]-1H-quinolin-4-one |
| I-175 | 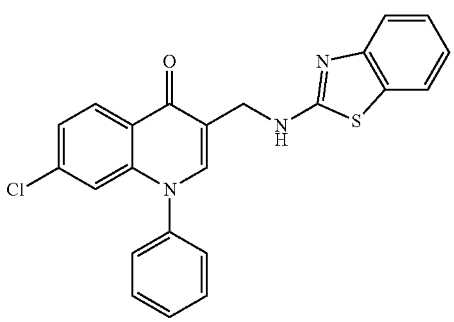 [SMILES: O=c1c(CNc2nc3ccccc3s2)cn(-c2ccccc2)c2cc(Cl)ccc12] | 3-(Benzothiazol-2-ylaminomethyl)-7-chloro-1-phenyl-1H-quinolin-4-one |
| I-176 | 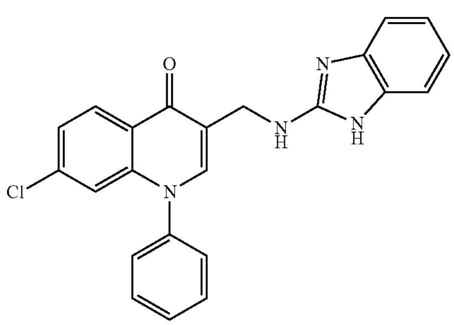 [SMILES: O=c1c(CNc2nc3ccccc3[nH]2)cn(-c2ccccc2)c2cc(Cl)ccc12] | 3-[(1H-Benzoimidazol-2-ylamino)-methyl]-7-chloro-1-phenyl-1H-quinolin-4-one |
| I-177 | 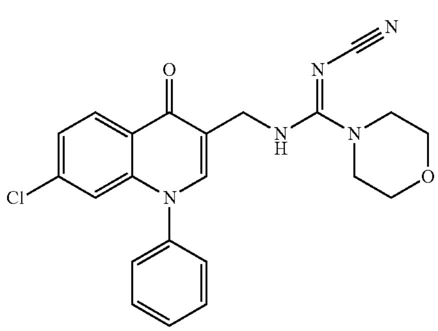 [SMILES: N#C/N=C(/NCc1cn(-c2ccccc2)c2cc(Cl)ccc2c1=O)N1CCOCC1] | [(7-Chloro-4-oxo-1-phenyl-1,4-dihydro-quinolin-3ylmethyl)-amino]-morpholin-4-yl-methylene-cyanamide |

TABLE I-continued

| Compound | Structure | Nomenclature |
|---|---|---|
| I-178 | 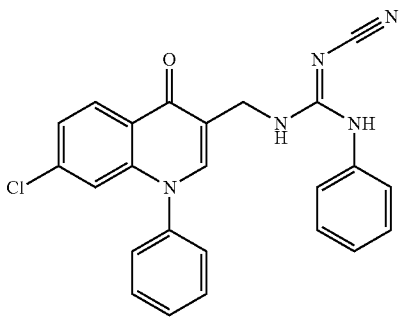 [SMILES: N#C/N=C(/NCc1cn(-c2ccccc2)c2cc(Cl)ccc2c1=O)Nc1ccccc1] | [(7-Chloro-4-oxo-1-phenyl-1,4-dihydro-quinolin-3-ylmethyl)-amino]-phenylamino-methylene-cyanamide |
| I-179 | 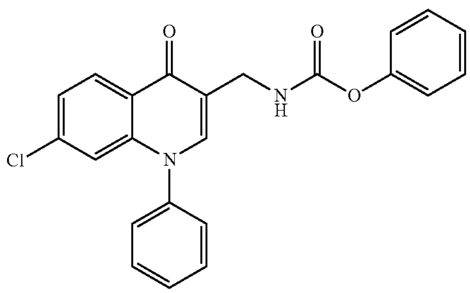 [SMILES: O=C(NCc1cn(-c2ccccc2)c2cc(Cl)ccc2c1=O)Oc1ccccc1] | (7-Chloro-4-oxo-1-phenyl-1,4-dihydro-quinolin-3-ylmethyl)-carbamic acid phenyl ester |
| I-180 | 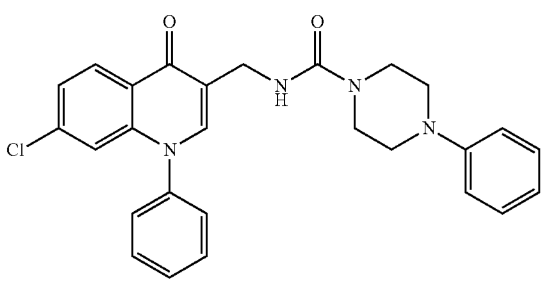 | 4-Phenyl-piperazine-1-carboxylic acid (7-chloro-4-oxo-1-phenyl-1,4-dihydro-quinolin-3-ylmethyl)-amide |
| I-181 | 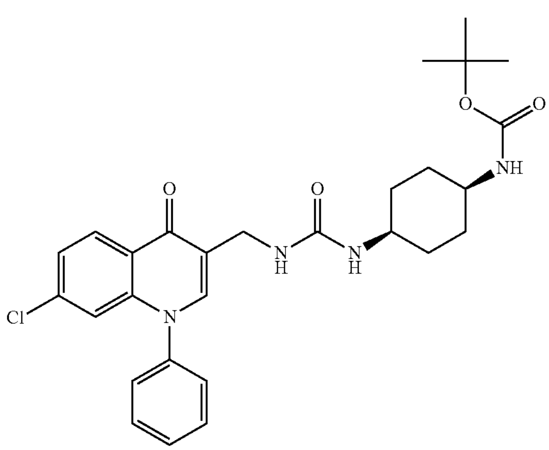 [SMILES: CC(C)(C)OC(=O)N[C@H]1CC[C@@H](NC(=O)NCc2cn(-c3ccccc3)c3cc(Cl)ccc3c2=O)CC1] | {4-[3-(7-Chloro-4-oxo-1-phenyl-1,4-dihydro-quinolin-3-ylmethyl)-ureido]-cyclohexyl}-carbamic acid tert-butyl ester |

TABLE I-continued

| Compound | Structure | Nomenclature |
|---|---|---|
| I-182 | 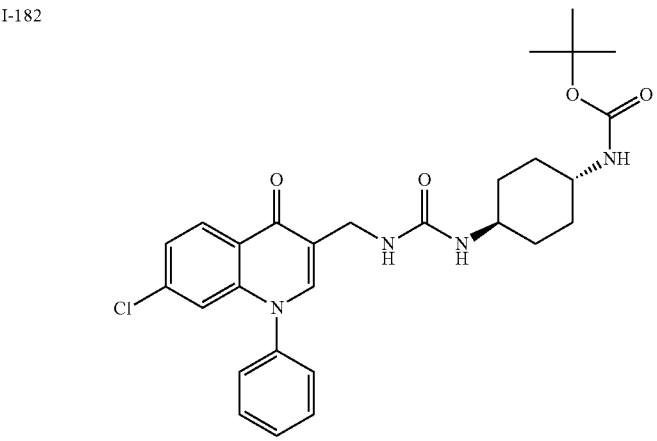 | {4-[3-(7-Chloro-4-oxo-1-phenyl-1,4-dihydro-quinolin-3-ylmethyl)-ureido]-cyclohexyl}-carbamic acid tert-butyl ester |
| I-183 | 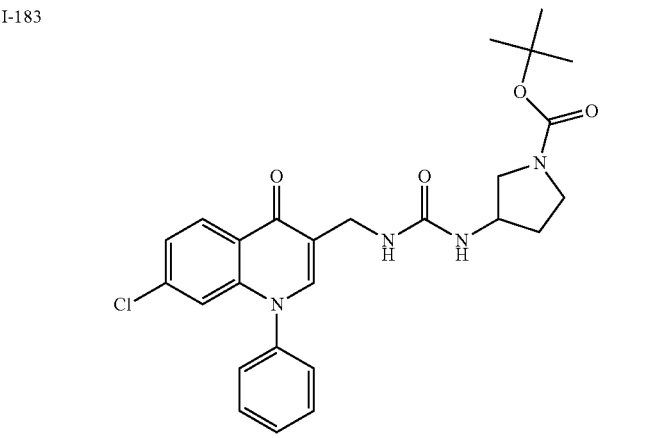 | 3-[3-(7-Chloro-4-oxo-1-phenyl-1,4-dihydro-quinolin-3-ylmethyl)-ureido]-pyrrolidine-1-carboxylic acid tert-butyl ester |
| I-184 | 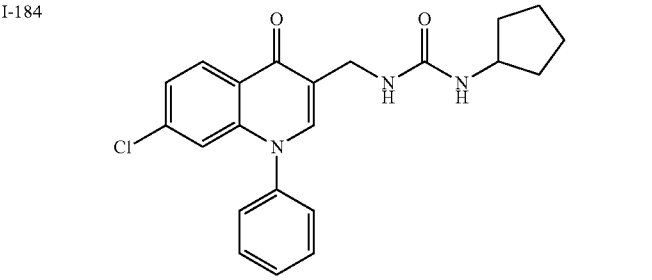 | 1-(7-Chloro-4-oxo-1-phenyl-1,4-dihydro-quinolin-3-ylmethyl)-3-cyclopentyl-urea |
| I-185 | 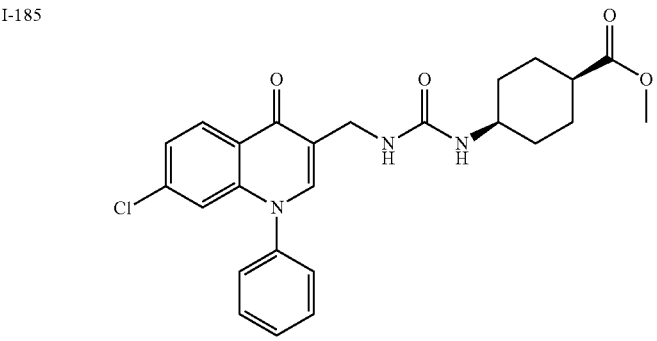 | 4-[3-(7-Chloro-4-oxo-1-phenyl-1,4-dihydro-quinolin-3-ylmethyl)-ureido]-cyclohexanecarboxylic acid methyl ester |

TABLE I-continued

| Compound | Structure | Nomenclature |
|---|---|---|
| I-186 | 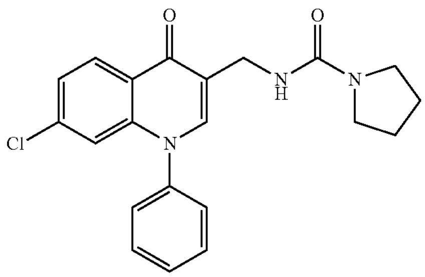 [SMILES: O=C(NCc1cn(-c2ccccc2)c2cc(Cl)ccc2c1=O)N1CCCC1] | Pyrrolidine-1-carboxylic acid (7-chloro-4-oxo-1-phenyl-1,4-dihydro-quinolin-3-ylmethyl)-amide |
| I-187 | 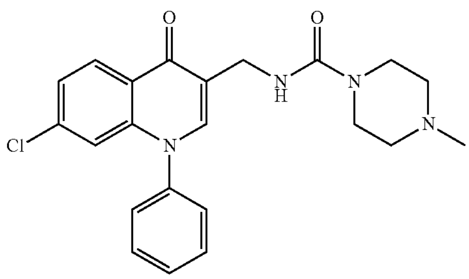 [SMILES: CN1CCN(C(=O)NCc2cn(-c3ccccc3)c3cc(Cl)ccc3c2=O)CC1] | 4-Methyl-piperazine-1-carboxylic acid (7-chloro-4-oxo-1-phenyl-1,4-dihydro-quinolin-3-ylmethyl)-amide |
| I-188 | 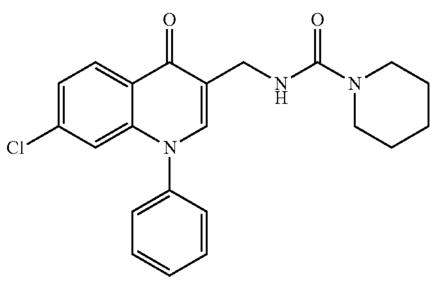 [SMILES: O=C(NCc1cn(-c2ccccc2)c2cc(Cl)ccc2c1=O)N1CCCCC1] | Piperidine-1-carboxylic acid (7-chloro-4-oxo-1-phenyl-1,4-dihydro-quinolin-3-ylmethyl)-amide |
| I-189 | 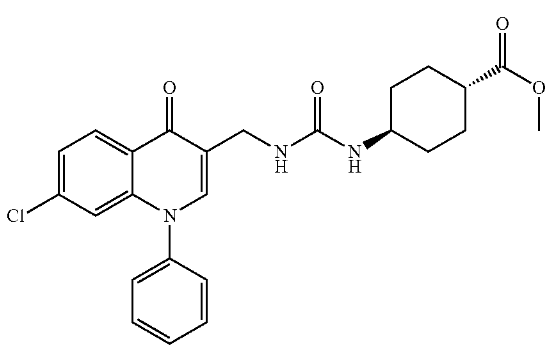 [SMILES: COC(=O)[C@H]1CC[C@H](NC(=O)NCc2cn(-c3ccccc3)c3cc(Cl)ccc3c2=O)CC1] | 4-[3-(7-Chloro-4-oxo-1-phenyl-1,4-dihydro-quinolin-3-ylmethyl)-ureido]-cyclohexanecarboxylic acid methyl ester |
| I-190 | 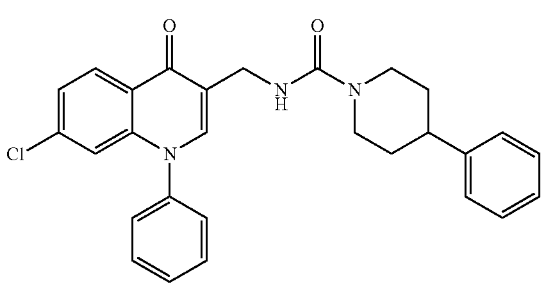 [SMILES: O=C(NCc1cn(-c2ccccc2)c2cc(Cl)ccc2c1=O)N1CCC(c2ccccc2)CC1] | 4-Phenyl-piperidine-1-carboxylic acid (7-chloro-4-oxo-1-phenyl-1,4-dihydro-quinolin-3-ylmethyl)-amide |

TABLE I-continued
| Compound | Structure | Nomenclature |
|---|---|---|
| I-191 | 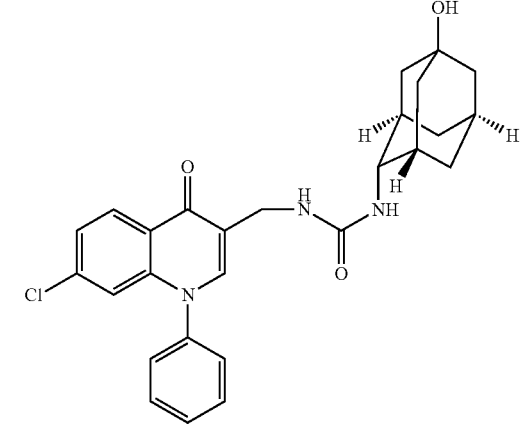 [SMILES: O=C(NCc1cn(-c2ccccc2)c2cc(Cl)ccc2c1=O)NC1[C@@H]2C[C@@H]3C[C@H]1CC(O)(C3)C2] | 1-(7-Chloro-4-oxo-1-phenyl-1,4-dihydro-quinolin-3-ylmethyl)-3-((1S,3R,7S)-5-hydroxy-adamantan-2-yl)-urea |
| I-192 | 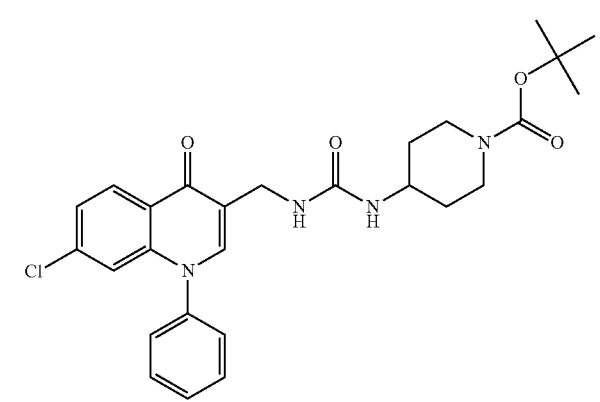 [SMILES: CC(C)(C)OC(=O)N1CCC(NC(=O)NCc2cn(-c3ccccc3)c3cc(Cl)ccc3c2=O)CC1] | 4-[3-(7-Chloro-4-oxo-1-phenyl-1,4-dihydro-quinolin-3-ylmethyl)-ureido]-piperidine-1-carboxylic acid tert-butyl ester |
| I-193 | 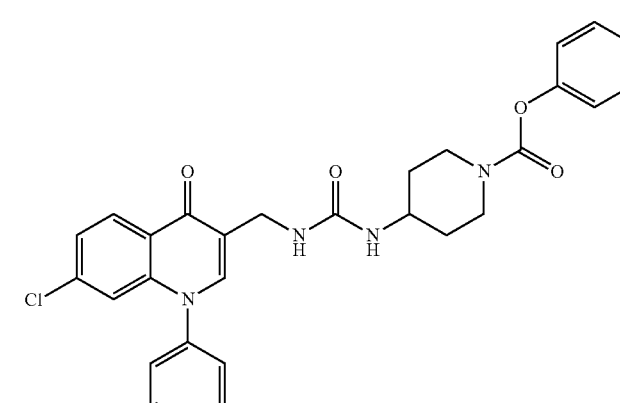 | 4-[3-(7-Chloro-4-oxo-1-phenyl-1,4-dihydro-quinolin-3-ylmethyl)-ureido]-piperidine-1-carboxylic acid phenyl ester |

| Compound | Structure | Nomenclature |
|---|---|---|
| I-194 | 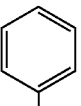 | 1-(1-Benzoyl-piperidin-4-yl)-3-(7-chloro-4-oxo-1-phenyl-1,4-dihydro-quinolin-3-ylmethyl)-urea |
| I-195 | 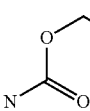 | 4-[3-(7-Chloro-4-oxo-1-phenyl-1,4-dihydro-quinolin-3-ylmethyl)-ureido]-piperidine-1-carboxylic acid benzyl ester |
| I-196 | 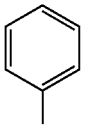 | 1-(1-Benzenesulfonyl-piperidin-4-yl)-3-(7-chloro-4-oxo-1-phenyl-1,4-dihydro-quinolin-3-ylmethyl)-urea |
| I-197 | 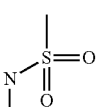 | 1-(7-Chloro-4-oxo-1-phenyl-1,4-dihydro-quinolin-3-ylmethyl)-3-(1-methanesulfonyl-piperidin-4-yl)-urea |

TABLE I-continued

| Compound | Structure | Nomenclature |
|---|---|---|
| I-198 | 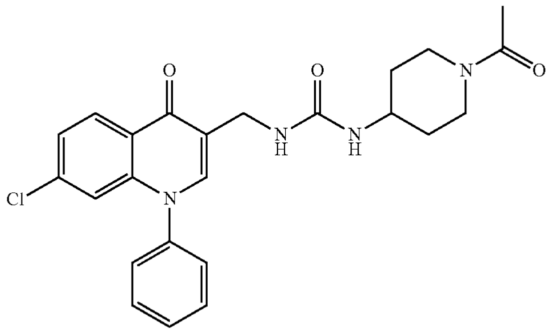 [SMILES: CC(=O)N1CCC(NC(=O)NCc2cn(-c3ccccc3)c3cc(Cl)ccc3c2=O)CC1] | 1-(1-Acetyl-piperidin-4-yl)-3-(7-chloro-4-oxo-1-phenyl-1,4-dihydro-quinolin-3-ylmethyl)-urea |
| I-199 | 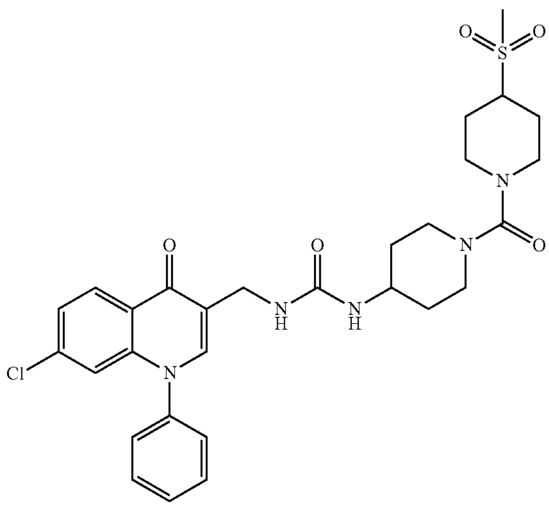 [SMILES: CS(=O)(=O)C1CCN(C(=O)N2CCC(NC(=O)NCc3cn(-c4ccccc4)c4cc(Cl)ccc4c3=O)CC2)CC1] | 1-(7-Chloro-4-oxo-1-phenyl-1,4-dihydro-quinolin-3-ylmethyl)-3-[1-(4-methanesulfonyl-piperidine-1-carbonyl)-piperidin-4-yl]-urea |
| I-200 | 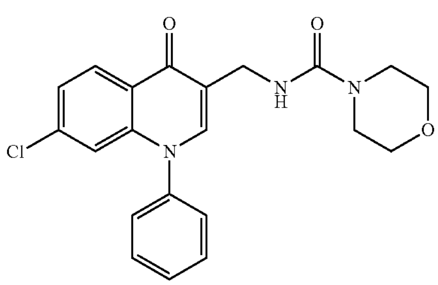 [SMILES: O=C(NCc1cn(-c2ccccc2)c2cc(Cl)ccc2c1=O)N1CCOCC1] | Morpholine-4-carboxylic acid (7-chloro-4-oxo-1-phenyl-1,4-dihydro-quinolin-3-ylmethyl)-amide |
| I-201 | 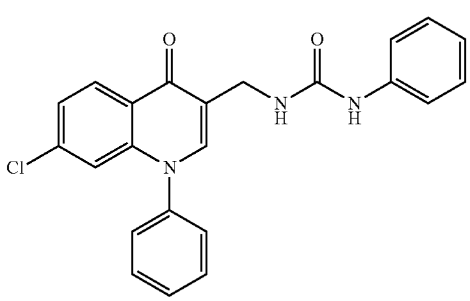 [SMILES: O=C(NCc1cn(-c2ccccc2)c2cc(Cl)ccc2c1=O)Nc1ccccc1] | 1-(7-Chloro-4-oxo-1-phenyl-1,4-dihydro-quinolin-3-ylmethyl)-3-phenyl-urea |

TABLE I-continued

| Compound | Structure | Nomenclature |
|---|---|---|
| I-202 | 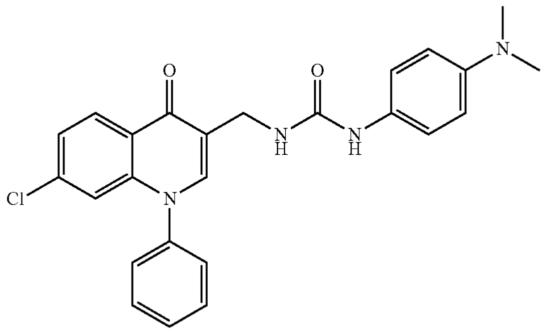 [SMILES: CN(C)c1ccc(NC(=O)NCc2cn(-c3ccccc3)c3cc(Cl)ccc3c2=O)cc1] | 1-(7-Chloro-4-oxo-1-phenyl-1,4-dihydro-quinolin-3-ylmethyl)-3-(4-dimethylamino-phenyl)-urea |
| I-203 | 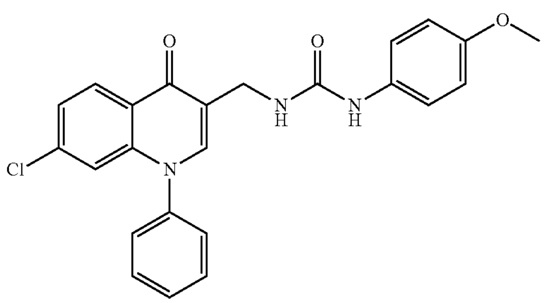 [SMILES: COc1ccc(NC(=O)NCc2cn(-c3ccccc3)c3cc(Cl)ccc3c2=O)cc1] | 1-(7-Chloro-4-oxo-1-phenyl-1,4-dihydro-quinolin-3-ylmethyl)-3-(4-methoxy-phenyl)-urea |
| I-204 | 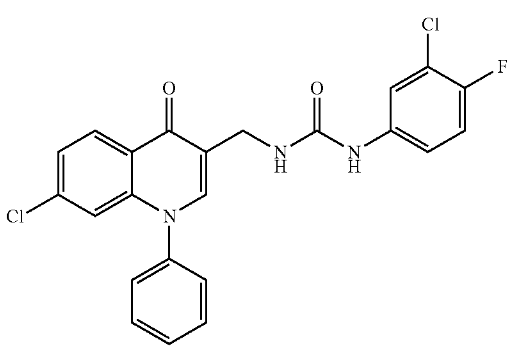 [SMILES: O=C(NCc1cn(-c2ccccc2)c2cc(Cl)ccc2c1=O)Nc1ccc(F)c(Cl)c1] | 1-(3-Chloro-4-fluoro-phenyl)-3-(7-chloro-4-oxo-1-phenyl-1,4-dihydro-quinolin-3-ylmethyl)-urea |
| I-205 | 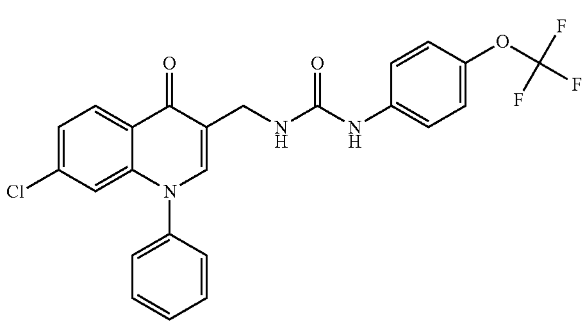 [SMILES: O=C(NCc1cn(-c2ccccc2)c2cc(Cl)ccc2c1=O)Nc1ccc(OC(F)(F)F)cc1] | 1-(7-Chloro-4-oxo-1-phenyl-1,4-dihydro-quinolin-3-ylmethyl)-3-(4-trifluoromethoxy-phenyl)-urea |

TABLE I-continued

| Compound | Structure | Nomenclature |
|---|---|---|
| I-206 | 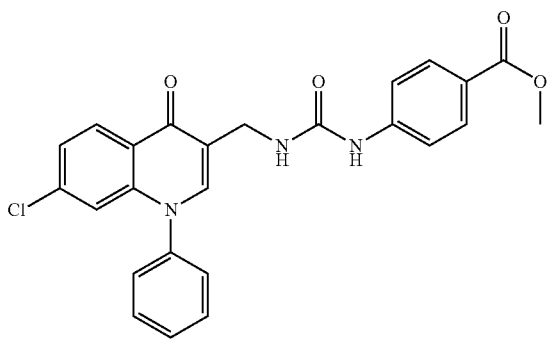 [SMILES: COC(=O)c1ccc(NC(=O)NCc2cn(-c3ccccc3)c3cc(Cl)ccc3c2=O)cc1] | 4-[3-(7-Chloro-4-oxo-1-phenyl-1,4-dihydro-quinolin-3-ylmethyl)-ureido]-benzoic acid methyl ester |
| I-207 | 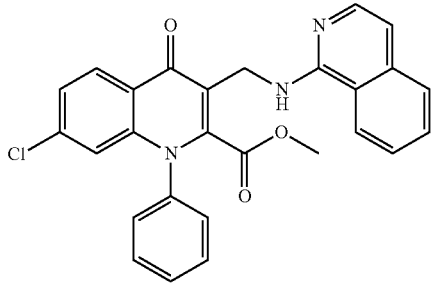 [SMILES: COC(=O)c1c(CNc2nccc3ccccc23)c(=O)c2ccc(Cl)cc2n1-c1ccccc1] | 7-Chloro-3-(isoquinolin-1-ylaminomethyl)-4-oxo-1-phenyl-1,4-dihydro-quinoline-2-carboxylic acid methyl ester |
| I-208 | 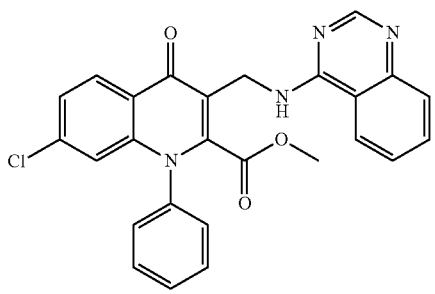 [SMILES: COC(=O)c1c(CNc2ncnc3ccccc23)c(=O)c2ccc(Cl)cc2n1-c1ccccc1] | 7-Chloro-4-oxo-1-phenyl-3-(quinazolin-4-ylaminomethyl)-1,4-dihydro-quinoline-2-carboxylic acid methyl ester |
| I-209 | 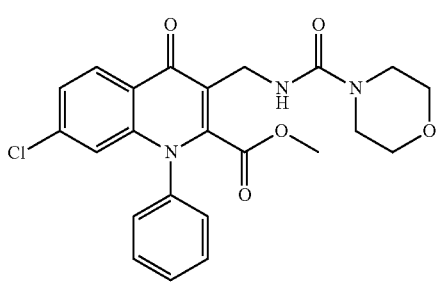 [SMILES: COC(=O)c1c(CNC(=O)N2CCOCC2)c(=O)c2ccc(Cl)cc2n1-c1ccccc1] | 7-Chloro-3-{[(morpholine-4-carbonyl)-amino]-methyl}-4-oxo-1-phenyl-1,4-dihydro-quinoline-2-carboxylic acid methyl ester |
| I-210 | 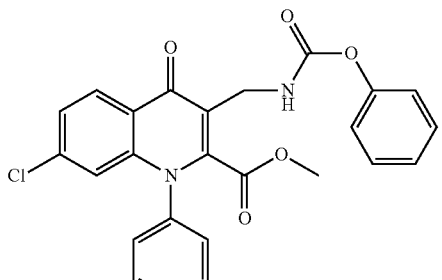 | 7-Chloro-4-oxo-3-(phenoxycarbonylamino-methyl)-1-phenyl-1,4-dihydro-quinoline-2-carboxylic acid methyl ester |

TABLE I-continued

| Compound | Structure | Nomenclature |
|---|---|---|
| I-211 | 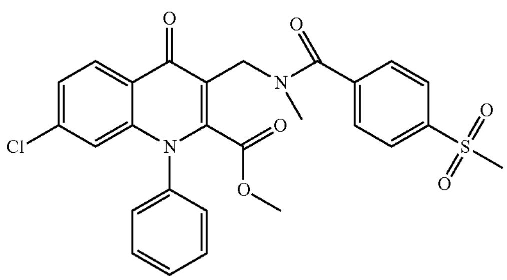 [SMILES: COC(=O)c1c(CN(C)C(=O)c2ccc(S(C)(=O)=O)cc2)c(=O)c2ccc(Cl)cc2n1-c1ccccc1] | 7-Chloro-3-{[(4-methanesulfonyl-benzoyl)-methyl-amino]-methyl}-4-oxo-1-phenyl-1,4-dihydro-quinoline-2-carboxylic acid methyl ester |

Synthesis—General Reaction Schemes

Compounds of the present invention can be prepared from commercially available starting materials or by the use of general synthetic techniques and procedures that are known to those skilled in the art. Outlined below are reaction schemes suitable for the preparation of such compounds. Further exemplification can be found in the specific examples detailed below.

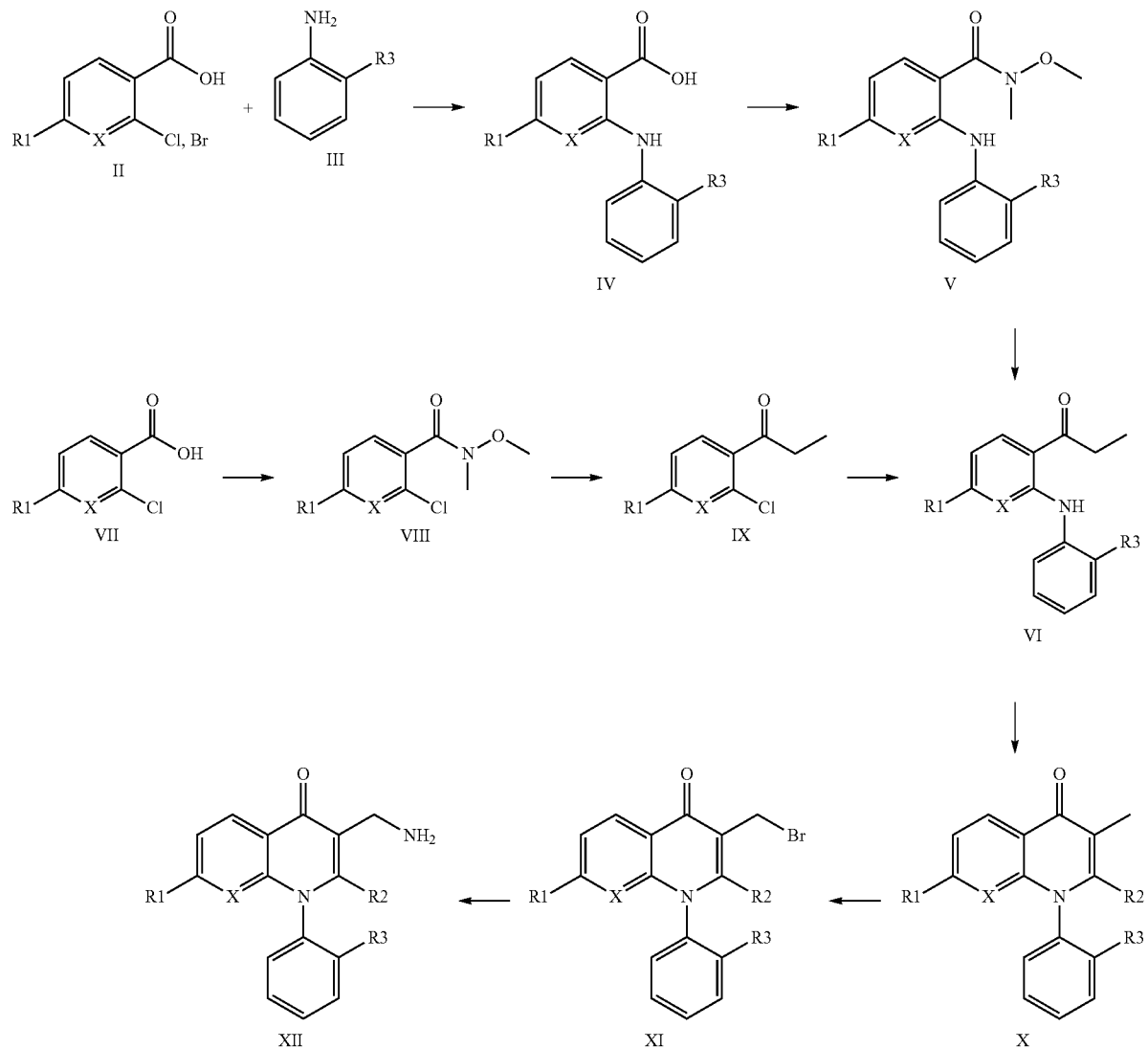

Scheme 1

The compound of formula II where X can be nitrogen or carbon and R1 can be hydrogen, fluorine, chlorine or trifluoromethyl and the compound of formula III where R3 can be hydrogen, fluorine or chlorine are readily available from commercial sources.

The compound of formula IV where X can be nitrogen or carbon, R1 can be hydrogen, fluorine, chlorine or trifluoromethyl and R3 can be hydrogen, fluorine or chlorine can be prepared from the compound of formula II where X can be nitrogen or carbon and R1 can be hydrogen, fluorine, chlorine or trifluoromethyl by treatment with the compound of formula III where R3 can be hydrogen, fluorine or chlorine under standard metal-catalyzed coupling conditions (see for example, PCT WO2008/138920) or basic conditions (see for example, PCT WO2005/051301).

The compound of formula V where X can be nitrogen or carbon, R1 can be hydrogen, fluorine, chlorine or trifluoromethyl and R3 can be hydrogen, fluorine or chlorine can be prepared from the compound of formula IV where X can be nitrogen or carbon, R1 can be hydrogen, fluorine, chlorine or trifluoromethyl and R3 can be hydrogen, fluorine or chlorine and N,O-dimethylhydroxylamine hydrochloride under standard amide coupling conditions (see for example, PCT WO2008/138920).

The compound of formula VI where X can be nitrogen or carbon, R1 can be hydrogen, fluorine, chlorine or trifluoromethyl and R3 can be hydrogen, fluorine or chlorine can be prepared from the compound of formula V where X can be nitrogen or carbon, R1 can be hydrogen, fluorine, chlorine or trifluoromethyl and R3 can be hydrogen, fluorine or chlorine with an ethyl Grignard reagent (see for example, PCT WO2008/138920).

The compound of formula VII where X can be nitrogen and R1 can be hydrogen or trifluoromethyl is readily available from commercial sources.

The compound of formula VIII where X can be nitrogen and R1 can be hydrogen or trifluoromethyl can be prepared from the compound of formula VII where X can be nitrogen and R1 can be hydrogen or trifluoromethyl and N,O-dimethylhydroxylamine hydrochloride under standard amide coupling conditions (see for example, PCT WO2008/138920).

The compound of formula IX where X can be nitrogen and R1 can be hydrogen or trifluoromethyl can be prepared from the compound of formula VIII where X can be nitrogen and R1 can be hydrogen or trifluoromethyl and an ethyl Grignard reagent (see for example, PCT WO2008/138920).

The compound of formula VI where X can be nitrogen and R1 can be hydrogen or trifluoromethyl can be prepared from the compound of formula IX where X can be nitrogen and R1 can be hydrogen or trifluoromethyl and the compound of formula III where R3 can be hydrogen, fluorine or chlorine by displacement with aniline III under acid catalysis (see for example, PCT WO2008/138920).

The compound of formula X where X can be nitrogen or carbon, R1 can be hydrogen, fluorine, chlorine or trifluoromethyl, R3 can be hydrogen, fluorine or chlorine and R2 can be 2-oxazole can be prepared from the compound of formula VI where X can be nitrogen or carbon, R1 can be hydrogen, fluorine, chlorine or trifluoromethyl, R3 can be hydrogen, fluorine or chlorine and 2-oxazole carbonyl chloride under basic conditions (see for example, PCT WO2008/138920).

The compound of formula X where X can be nitrogen or carbon, R1 can be hydrogen, fluorine, chlorine or trifluoromethyl, R3 can be hydrogen, fluorine or chlorine and R2 can be methyl ester can be prepared from the compound of formula VI where X can be nitrogen or carbon, R1 can be hydrogen, fluorine, chlorine or trifluoromethyl, R3 can be hydrogen, fluorine or chlorine and methyl oxalyl chloride under reflux conditions followed by base-mediated cyclization (see for example, PCT WO2008/138920).

The compound of formula X where X can be nitrogen or carbon, R1 can be hydrogen, fluorine, chlorine or trifluoromethyl, R3 can be hydrogen, fluorine or chlorine and R2 can be hydrogen can be prepared from the compound of formula VI where X can be nitrogen or carbon, R1 can be hydrogen, fluorine, chlorine or trifluoromethyl, R3 can be hydrogen, fluorine or chlorine with the Vilsmeier reagent (see for example, Mendelson, W. L.; Hayden, S. *Syn. Comm.* 1996, 26, 603).

The compound of formula X where X can be nitrogen or carbon, R1 can be hydrogen, fluorine, chlorine or trifluoromethyl, R3 can be hydrogen, fluorine or chlorine and R2 can be N,N-dimethylamide can be prepared from the basic hydrolysis of the compound of formula X where X can be nitrogen or carbon, R1 can be hydrogen, fluorine, chlorine or trifluoromethyl, R3 can be hydrogen, fluorine or chlorine and R2 is methyl ester (see for example, Cairns, H.; Cox, D.; Gould, K. J.; Ingall, A. H.; Suschitzky, J. L. *J. Med. Chem.* 1985, 28, 1832), followed by amide formation with dimethylamine.

The compound of formula XI where X can be nitrogen or carbon, R1 can be hydrogen, fluorine, chlorine or trifluoromethyl, R3 can be hydrogen, fluorine or chlorine and R2 can be 2-oxazole, hydrogen, methyl ester, or N,N-dimethylamide can be prepared from the compound of formula X where X can be nitrogen or carbon, R1 can be hydrogen, fluorine, chlorine or trifluoromethyl, R3 can be hydrogen, fluorine or chlorine and R2 can be 2-oxazole, hydrogen, methyl ester, or N,N-dimethylamide under standard radical bromination conditions (see for example, Gauuan, P. J. F.; Trova, M. P.; Gregor-Boros, L.; Bocckino, S. B.; Crapo, J. D.; Day, B. *J. Bioorg. Med. Chem.* 2002, 10, 3013).

The compound of formula XII where X can be nitrogen or carbon, R1 can be hydrogen, fluorine, chlorine or trifluoromethyl, R3 can be hydrogen, fluorine or chlorine and R2 can be hydrogen, methyl ester, or N,N-dimethylamide can be prepared from the compound of formula XI where X can be nitrogen or carbon, R1 can be hydrogen, fluorine, chlorine or trifluoromethyl, R3 can be hydrogen, fluorine or chlorine and R2 can be hydrogen, methyl ester, or N,N-dimethylamide first by treatment with sodium azide (see for example, Liu, J. M.; Young, J. J.; Li, Y. J.; Sha, C. K. *J. Org. Chem.* 1986, 51, 1120) followed by reduction under an atmosphere of hydrogen in the presence of a catalyst (see for example, Gueret, S. M.; O'Connor, P. D.; Brimble, M. A. *Org. Lett.* 2009, 11, 963).

The compound of formula XII where X can be nitrogen or carbon, R1 can be hydrogen, fluorine, chlorine or trifluoromethyl, R3 can be hydrogen, fluorine or chlorine and R2 can be 2-oxazole, hydrogen, methyl ester, or N,N-dimethylamide can alternatively be prepared from the compound of formula XI where X can be nitrogen or carbon, $R_1$ can be hydrogen, fluorine, chlorine or trifluoromethyl, R3 can be hydrogen, fluorine or chlorine and R2 can be 2-oxazole, hydrogen, methyl ester, or N,N-dimethylamide first by treatment with di-t-butyl-iminodicarboxylate (see for example, Grehn, L.; Ragnarsson, U. *Synthesis* 1987, 275) followed by de-protection under acidic conditions (see for example, Connell, R. D.; Rein, T.; Aakermark, B.; Helquist, P. *J. Org. Chem.* 1988, 53, 3845).

The compound of formula XII where X can be nitrogen or carbon, R1 can be hydrogen, fluorine, chlorine or trifluoromethyl, R3 can be hydrogen, fluorine or chlorine and R2 can be 2-oxazole, hydrogen, methyl ester, or N,N-dimethylamide can alternatively be prepared from the compound of formula XI where X can be nitrogen or carbon, R1 can be hydrogen, fluorine, chlorine or trifluoromethyl, R3 can be hydrogen, fluorine or chlorine and R2 can be 2-oxazole, first by treatment with potassium phthalimide, followed by de-protection in the presence of hydrazine (see for example, Sasaki, T.; Minamoto, K.; Itoh, H. *J. Org. Chem.* 1978, 43, 2320).

The compounds of interest of type I-a (Scheme 2) where X can be nitrogen or carbon, R1 can be hydrogen, fluorine, chlorine or trifluoromethyl, R3 can be hydrogen, fluorine or chlorine, R2 can be 2-oxazole, hydrogen, methyl ester, or N,N-dimethylamide and R5 can be hydrogen or methyl can be prepared by the reaction of the compound of formula XI where X can be nitrogen or carbon, R1 can be hydrogen, fluorine, chlorine or trifluoromethyl, R3 can be hydrogen, fluorine or chlorine and R2 can be 2-oxazole, hydrogen, methyl ester, or N,N-dimethylamide with an amide of formula XIII where R5 can be hydrogen or methyl in the presence of a base (see for example, Padwa, A.; Kappe, C. O.; Cochran, J. E.; Snyder, J. P. *J. Org. Chem.* 1997, 62, 2786).

The compounds of interest of type I-b (Scheme 2) where X can be nitrogen or carbon, R1 can be hydrogen, fluorine, chlorine or trifluoromethyl, R3 can be hydrogen, fluorine or chlorine, and R2 can be 2-oxazole, hydrogen, methyl ester, or N,N-dimethylamide can be prepared by the reaction of the compound of formula XII where X can be nitrogen or carbon, R1 can be hydrogen, fluorine, chlorine or trifluoromethyl, R3 can be hydrogen, fluorine or chlorine and R2 can be 2-oxazole, hydrogen, methyl ester, or N,N-dimethylamide with a carboxylic acid of formula XIV under standard amide coupling conditions (see for example, Fréot, E.; Coste, J.; Pantaloni, A.; Dufour, M. N.; Jouin, P. *Tetrahedron,* 1991, 47, 259-270).

Alternatively, the compounds of interest of type I-b (Scheme 2) where X can be nitrogen or carbon, R1 can be hydrogen, fluorine, chlorine or trifluoromethyl, R3 can be hydrogen, fluorine or chlorine, and R2 can be 2-oxazole, hydrogen, methyl ester, or N,N-dimethylamide can be prepared by the reaction of the compound of formula XII where X can be nitrogen or carbon, R1 can be hydrogen, fluorine, chlorine or trifluoromethyl, R3 can be hydrogen, fluorine or chlorine and R2 can be 2-oxazole, hydrogen, methyl ester, or N,N-dimethylamide with an acid chloride of formula XV.

Scheme 2

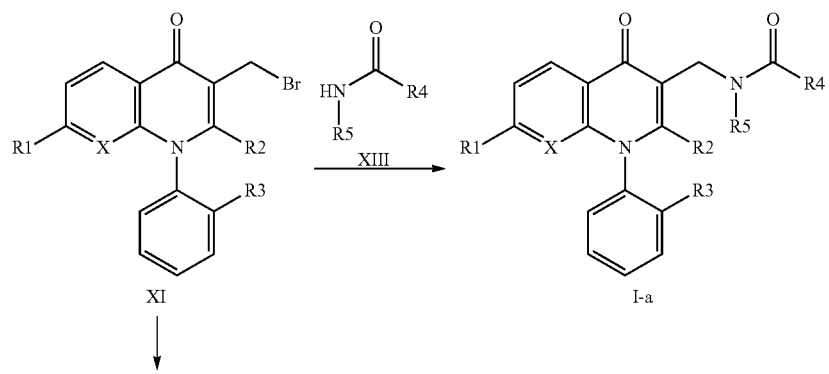

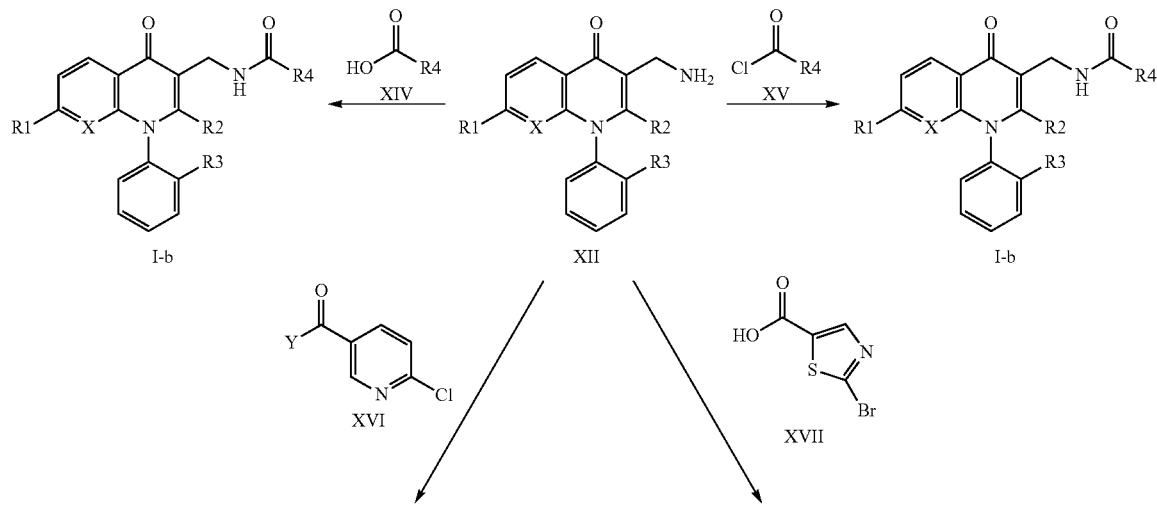

-continued

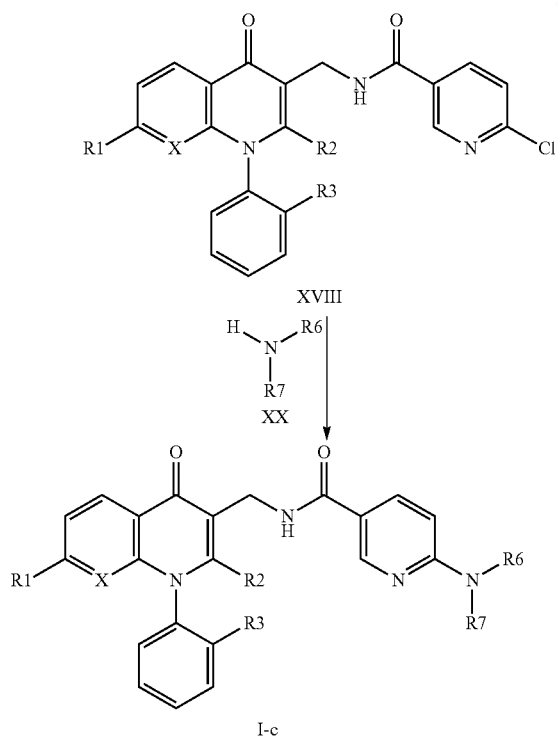

I-c

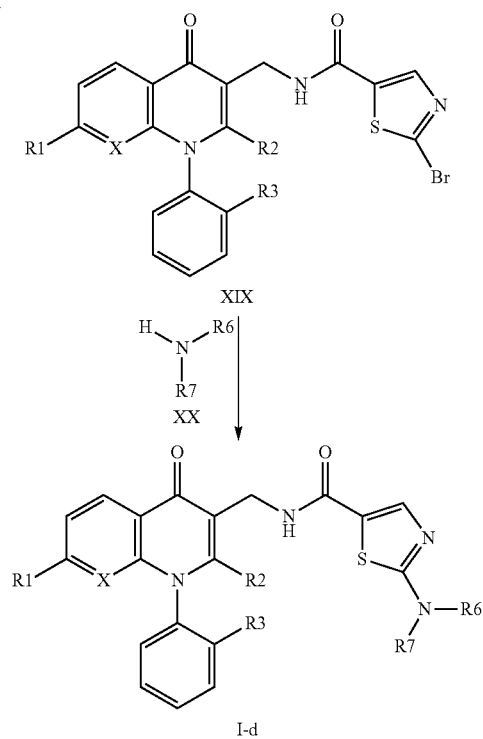

I-d

The compounds of interest of type I-c (Scheme 2) where X can be nitrogen or carbon, R1 can be hydrogen, fluorine, chlorine or trifluoromethyl, R3 can be hydrogen, fluorine or chlorine, R2 can be 2-oxazole, hydrogen, methyl ester, or N,N-dimethylamide can be prepared by the reaction of the compounds of formula XII where X can be nitrogen or carbon, R1 can be hydrogen, fluorine, chlorine or trifluoromethyl, R3 can be hydrogen, fluorine or chlorine and R2 can be 2-oxazole, hydrogen, methyl ester, or N,N-dimethylamide with a compound of formula XVI where Y is chlorine or hydroxyl to give an intermediate of formula XVIII (see for example, Fréot, E.; Coste, J.; Pantaloni, A.; Dufour, M. N.; Jouin, P. *Tetrahedron*, 1991, 47, 259-270). Reaction of compound XVIII with amines of formula XX can provide the compounds of interest I-c (see for example, Huang, C. Q.; Baker, T.; Schwarz, D.; Fan, J.; Heise, C. E.; Zhang, M.; Goodfellow, V. S.; Markison, S.; Gogas, K. R.; Chen, T.; Wang, X-C.; Zhu, Y-F. *Bioorg. Med. Chem. Lett.* 2005, 15, 3701).

Alternatively, the compounds of interest of type I-d where X can be nitrogen or carbon, R1 can be hydrogen, fluorine, chlorine or trifluoromethyl, R3 can be hydrogen, fluorine or chlorine, R2 can be 2-oxazole, hydrogen, methyl ester, or N,N-dimethylamide can be prepared by the reaction of the compounds of formula XII where X can be nitrogen or carbon, R1 can be hydrogen, fluorine, chlorine or trifluoromethyl, R3 can be hydrogen, fluorine or chlorine and R2 can be 2-oxazole, hydrogen, methyl ester, or N,N-dimethylamide with a carboxylic acid of formula XVII to give an intermediate of formula XIX. Reaction of compound XIX with amines of formula XX can provide the compounds of interest I-c (see for example, Huang, C. Q.; Baker, T.; Schwarz, D.; Fan, J.; Heise, C. E.; Zhang, M.; Goodfellow, V. S.; Markison, S.; Gogas, K. R.; Chen, T.; Wang, X-C.; Zhu, Y-F. *Bioorg. Med. Chem. Lett.* 2005, 15, 3701).

The compounds of interest of type I-e (Scheme 3) where X can be nitrogen or carbon, R1 can be hydrogen, fluorine, chlorine or trifluoromethyl, R3 can be hydrogen, fluorine or chlorine, and R2 can be 2-oxazole, hydrogen, methyl ester, or N,N-dimethylamide can be prepared by the reaction of the compound of formula XII where X can be nitrogen or carbon, R1 can be hydrogen, fluorine, chlorine or trifluoromethyl, R3 can be hydrogen, fluorine or chlorine and R2 can be 2-oxazole, hydrogen, methyl ester, or N,N-dimethylamide with a chloroformamide of formula XXI (see for example, Barrett, D. G.; Catalano, J. G.; Deaton, D. N.; Hassell, A. M.; Long, S. T.; Miller, A. B.; Miller, L. R.; Shewchuk, L. M.; Wells-Knecht, K. J.; Willard, D. H., Jr.; Wright, L. L. *Bioorg. Med. Chem. Lett.* 2004, 14, 4897).

The compounds of interest of type I-f (Scheme 3) where X can be nitrogen or carbon, R1 can be hydrogen, fluorine, chlorine or trifluoromethyl, R3 can be hydrogen, fluorine or chlorine, and R2 can be 2-oxazole, hydrogen, methyl ester, or N,N-dimethylamide can be prepared by the reaction of the compound of formula XII where X can be nitrogen or carbon, R1 can be hydrogen, fluorine, chlorine or trifluoromethyl, R3 can be hydrogen, fluorine or chlorine and R2 can be 2-oxazole, hydrogen, methyl ester, or N,N-dimethylamide with an isocyanate of formula XXII (see for example, Tamaru, Y.; Hojo, M.; Higashimura, H.; Yoshida, Z. *J. Am. Chem. Soc.* 1988, 110, 3994).

The compounds of interest of type I-g (Scheme 3) where X can be nitrogen or carbon, R1 can be hydrogen, fluorine, chlorine or trifluoromethyl, R3 can be hydrogen, fluorine or chlorine, and R2 can be 2-oxazole, hydrogen, methyl ester, or N,N-dimethylamide can be prepared by the reaction of the compound of formula XII where X can be nitrogen or carbon, R1 can be hydrogen, fluorine, chlorine or trifluoromethyl, R3 can be hydrogen, fluorine or chlorine and R2 can be 2-oxazole, hydrogen, methyl ester, or N,N-dimethylamide with 4-nitrophenyl chloroformate (XXIII) to give an intermediate of formula XXIV (see for example, Mallakpour, S.; Rafiee, Z. *Syn. Commun.* 2007, 37, 1927). Reaction of compounds of formula XXIV with amines of formula XXV can provide the compounds of interest of type I-g (see for example, Liu, Q.; Luedtke, N. W.; Tor, Y. *Tet. Lett.* 2001, 42, 1445).

or trifluoromethyl, R3 can be hydrogen, fluorine or chlorine, and R2 can be 2-oxazole, hydrogen, methyl ester, or N,N-dimethylamide with boc-protected 4-amino-piperidine (XXVII) can, after acid mediated deprotection, provide an intermediate of formula XXVIII where X can be nitrogen or

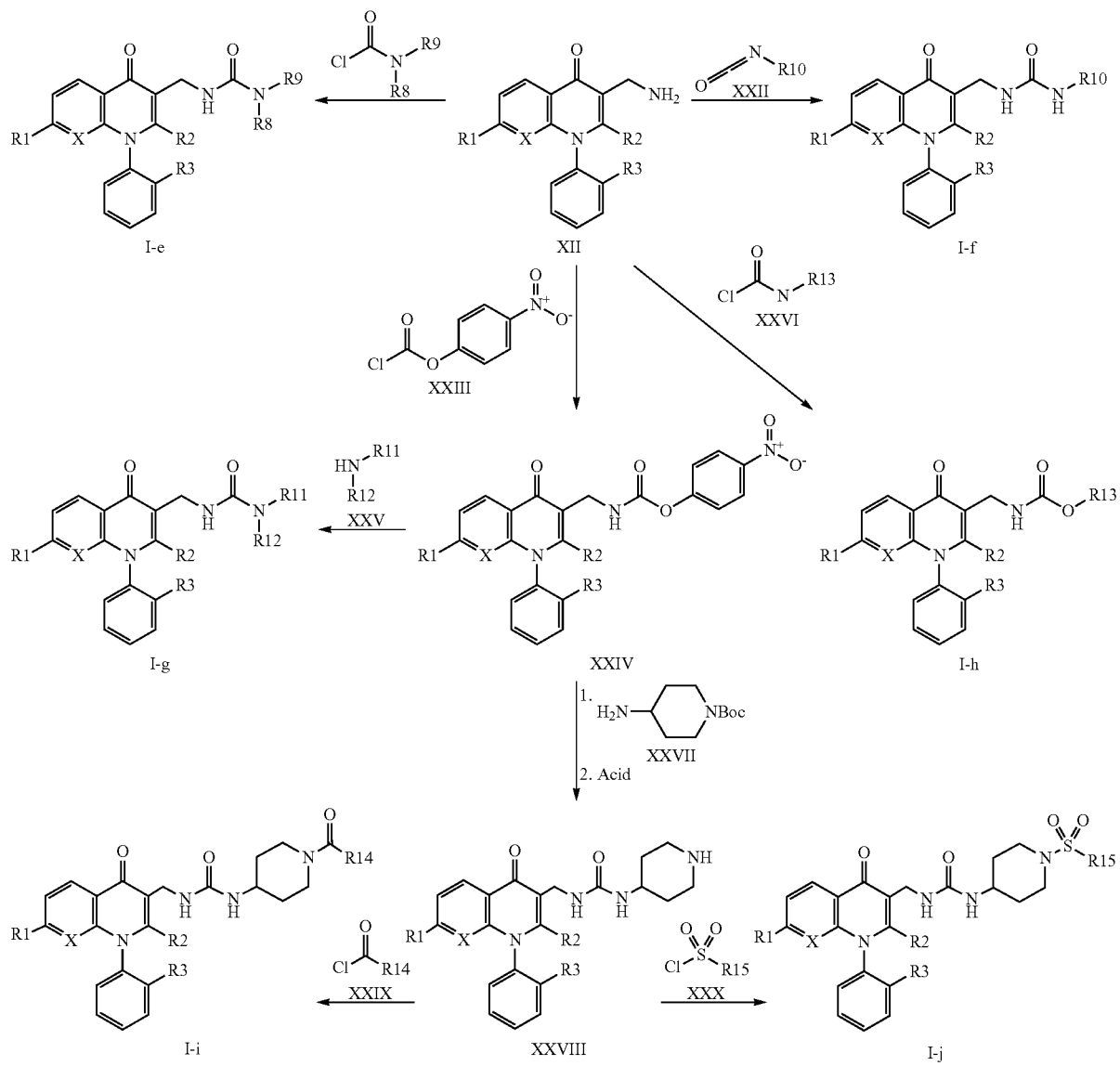

Scheme 3

The compounds of interest of type I-h (Scheme 3) where X can be nitrogen or carbon, R1 can be hydrogen, fluorine, chlorine or trifluoromethyl, R3 can be hydrogen, fluorine or chlorine, and R2 can be 2-oxazole, hydrogen, methyl ester, or N,N-dimethylamide can be prepared by the reaction of the compound of formula XII where X can be nitrogen or carbon, R1 can be hydrogen, fluorine, chlorine or trifluoromethyl, R3 can be hydrogen, fluorine or chlorine and R2 can be 2-oxazole, hydrogen, methyl ester, or N,N-dimethylamide with a chloroformate of formula XXVI (see for example, Mallakpour, S.; Rafiee, Z. *Syn. Commun.* 2007, 37, 1927).

The reaction of compounds of formula XXIV where X can be nitrogen or carbon, R1 can be hydrogen, fluorine, chlorine or trifluoromethyl, R3 can be hydrogen, fluorine or chlorine, and R2 can be 2-oxazole, hydrogen, methyl ester, or N,N-dimethylamide.

The compounds of interest I-i (Scheme 3) where X can be nitrogen or carbon, R1 can be hydrogen, fluorine, chlorine or trifluoromethyl, R3 can be hydrogen, fluorine or chlorine, and R2 can be 2-oxazole, hydrogen, methyl ester, or N,N-dimethylamide can be prepared by the reaction of compounds of formula XXVIII where X can be nitrogen or carbon, R1 can be hydrogen, fluorine, chlorine or trifluoromethyl, R3 can be hydrogen, fluorine or chlorine, and R2 can be 2-oxazole, hydrogen, methyl ester, or N,N-dimethylamide with an acid chloride of formula XXIX.

The compounds of interest 1-j (Scheme 3) where X can be nitrogen or carbon, R1 can be hydrogen, fluorine, chlorine or trifluoromethyl, R3 can be hydrogen, fluorine or chlorine, and R2 can be 2-oxazole, hydrogen, methyl ester, or N,N-dimethylamide can be prepared by the reaction of compounds of formula XXVIII where X can be nitrogen or carbon, R1 can be hydrogen, fluorine, chlorine or trifluoromethyl, R3 can be hydrogen, fluorine or chlorine, and R2 can be 2-oxazole, hydrogen, methyl ester, or N,N-dimethylamide with an sulfonyl chloride of formula XXX.

The compounds of interest I-k (Scheme 4) where X can be nitrogen or carbon, R1 can be hydrogen, fluorine, chlorine or trifluoromethyl, R3 can be hydrogen, fluorine or chlorine, and R2 can be 2-oxazole, hydrogen, methyl ester, or N,N-dimethylamide and Z can be nitrogen or carbon can be prepared by the base-mediated reaction of compounds of formula XI where X can be nitrogen or carbon, R1 can be hydrogen, fluorine, chlorine or trifluoromethyl, R3 can be hydrogen, fluorine or chlorine, and R2 can be 2-oxazole, hydrogen, methyl ester, or N,N-dimethylamide with an amine of formula XXXI where Z can be nitrogen or carbon (see for example, Gueiffier, A.; Viols, H.; Chapat, J. P.; Chavignon, O.; Teulade, J. C.; Dauphin, G. *J. Hetero. Chem.* 1990, 27, 421).

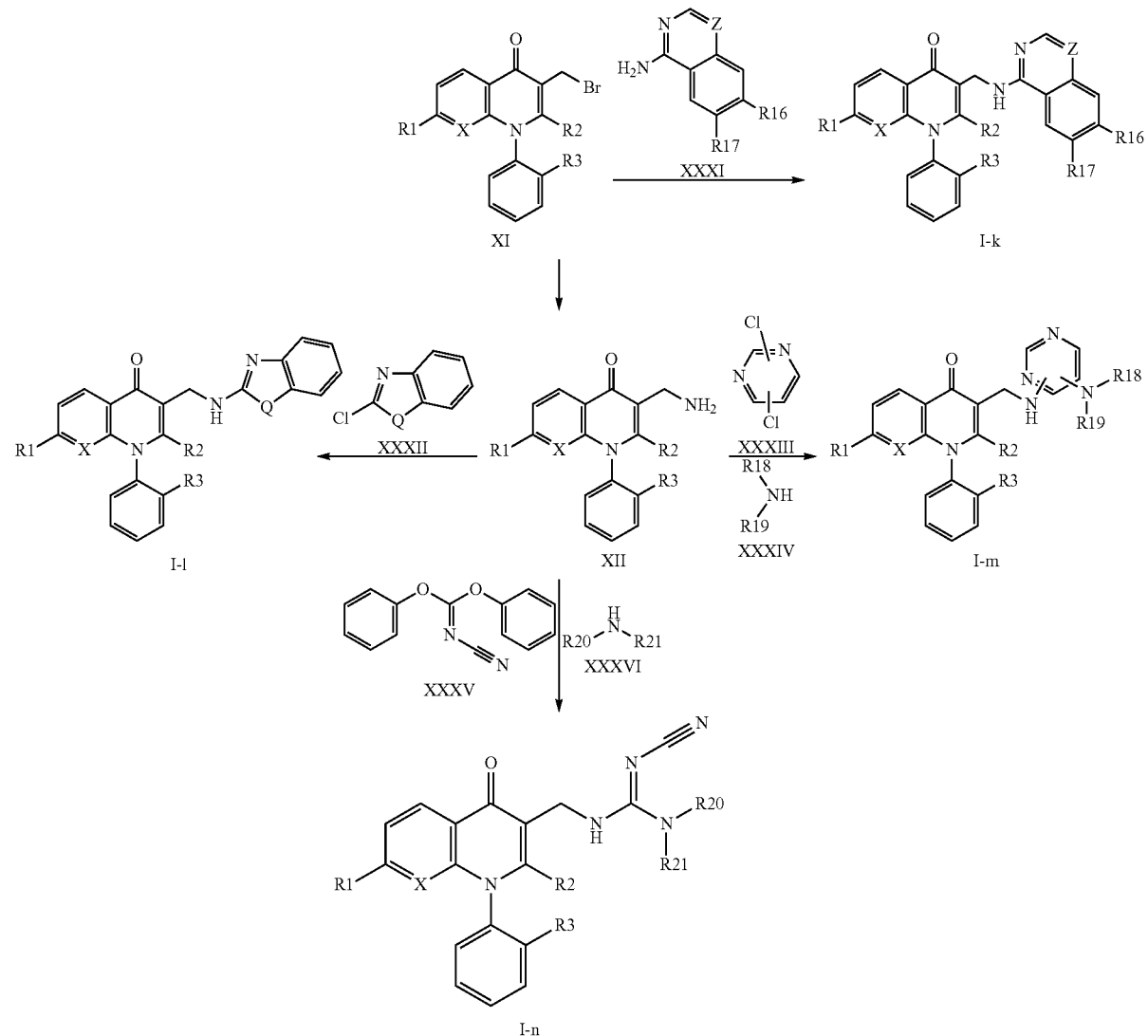

Scheme 4

The compounds of interest I-l (Scheme 4) where X can be nitrogen or carbon, R1 can be hydrogen, fluorine, chlorine or trifluoromethyl, R3 can be hydrogen, fluorine or chlorine, R2 can be 2-oxazole, hydrogen, methyl ester, or N,N-dimethylamide, and Q can be sulfur or nitrogen can be prepared by the base-mediated reaction of compounds of formula XII where X can be nitrogen or carbon, R1 can be hydrogen, fluorine, chlorine or trifluoromethyl, R3 can be hydrogen, fluorine or chlorine, and R2 can be 2-oxazole, hydrogen, methyl ester, or N,N-dimethylamide with compounds of formula XXXII where Q can be sulfur or nitrogen (see for example, Ganellin, C. R.; Hosseini, S. K.; Khalaf, Y. S.; Tertiuk, W.; Arrang, J-M.; Garbarg, M.; Ligneau, X.; Schwartz, J-C. *J. Med. Chem.* 1995, 38, 3342).

The compounds of interest I-m (Scheme 4) where X can be nitrogen or carbon, R1 can be hydrogen, fluorine, chlorine or trifluoromethyl, R3 can be hydrogen, fluorine or chlorine, and R2 can be 2-oxazole, hydrogen, methyl ester, or N,N-dimethylamide can be prepared by the reaction of compounds of formula XII where X can be nitrogen or carbon, R1 can be hydrogen, fluorine, chlorine or trifluoromethyl, R3 can be hydrogen, fluorine or chlorine, and R2 can be 2-oxazole, hydrogen, methyl ester, or N,N-dimethylamide with a dichloropyrimidine of formula XXXIII and an amine of formula XXXIV (see for example, Luo, G.; Chen, L.; Poindexter, G. S. *Tett. Lett.* 2002, 43, 5739).

The compounds of interest I-n (Scheme 4) where X can be nitrogen or carbon, R1 can be hydrogen, fluorine, chlorine or trifluoromethyl, R3 can be hydrogen, fluorine or chlorine, and R2 can be 2-oxazole, hydrogen, methyl ester, or N,N-dimethylamide can be prepared by the reaction of compounds of formula XII where X can be nitrogen or carbon, R1 can be hydrogen, fluorine, chlorine or trifluoromethyl, R3 can be hydrogen, fluorine or chlorine, and R2 can be 2-oxazole, hydrogen, methyl ester, or N,N-dimethylamide with diphenyl N-cyanocarbonimidate (XXXV) a and an amine of formula XXXVI (see for example, Fotsch, C.; Sonnenberg, J. D.; Chen, N.; Hale, C.; Karbon, W.; Norman, M. H. *J. Med. Chem.* 2001, 44, 2344).

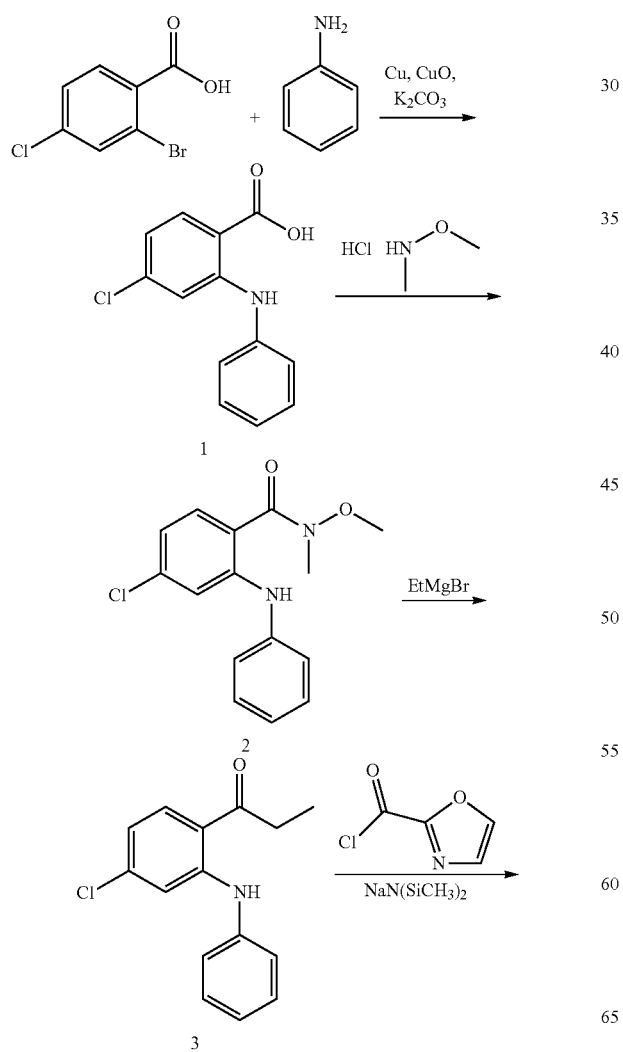

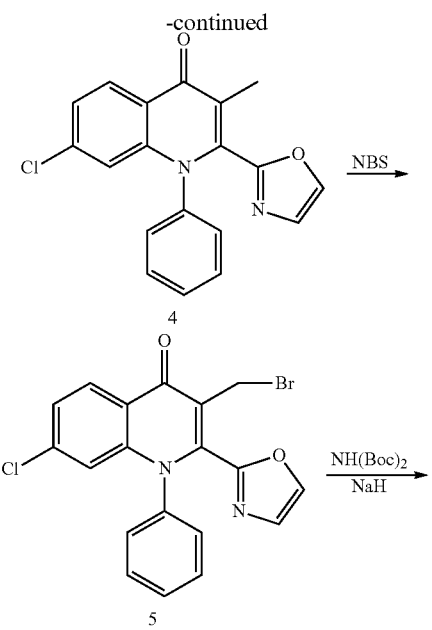

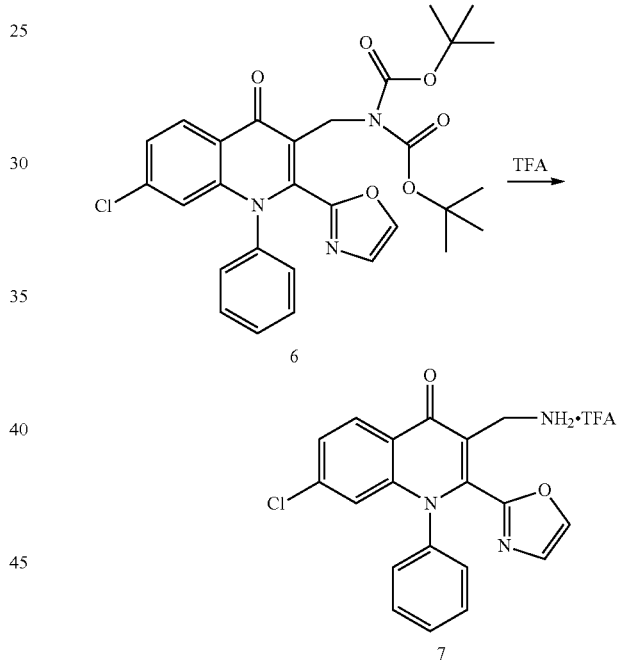

Compound 7 (intermediate A) can be synthesized following the reactions outlined in Scheme 5. Commercially available 2-bromo-4-chlorobenzoic acid can be treated with aniline under standard metal catalyzed aryl halide displacement conditions to provide compound 1 (see for example, PCT WO2008/138920). Compound 1 can be treated with N,O-dimethylhydroxylamine hydrochloride under standard coupling conditions to form the Weinreb amide, compound 2 (see for example, PCT WO2008/138920). Compound 2 can be treated with ethyl magnesium bromide under standard Grignard conditions to provide compound 3 (see for example, PCT WO2008/138920). Compound 3 can be treated with 2-oxazole carbonyl chloride and sodium hexamethyldisilazane to provide compound 4 (see for example, PCT WO2008/138920). Compound 4 can be treated under standard radical bromination conditions to provide compound 5 (see for example, Gauuan, P. J. F.; Trova, M. P.; Gregor-Boros, L.;

Bocckino, S. B.; Crapo, J. D.; Day, B. J. *Bioorg. Med. Chem.* 2002, 10, 3013). Compound 5 can be treated with di-t-butyl-iminodicarboxylate and sodium hydride to provide compound 6 (see for example, Grehn, L.; Ragnarsson, U. *Synthesis* 1987, 275). Compound 6 can then be de-protected under acidic conditions (e.g. trifluoroacetic acid) to afford intermediate A, compound 7 (see for example, Connell, R. D.; Rein, T.; Aakermark, B.; Helquist, P. *J. Org. Chem.* 1988, 53, 3845).

Scheme 6

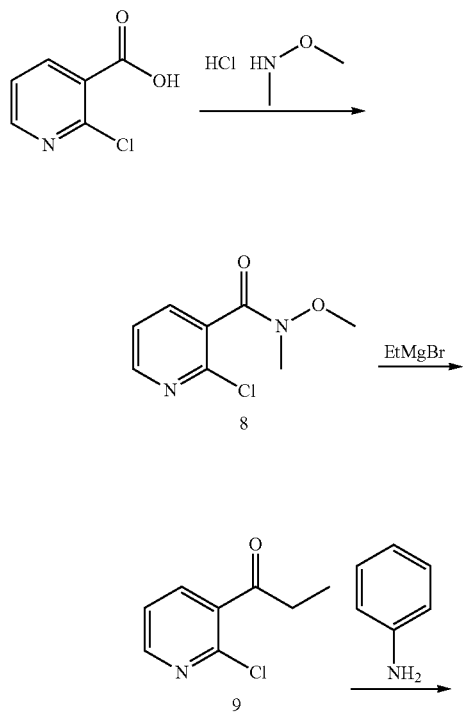

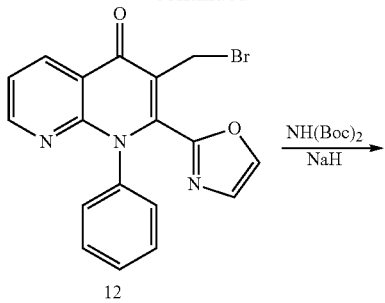

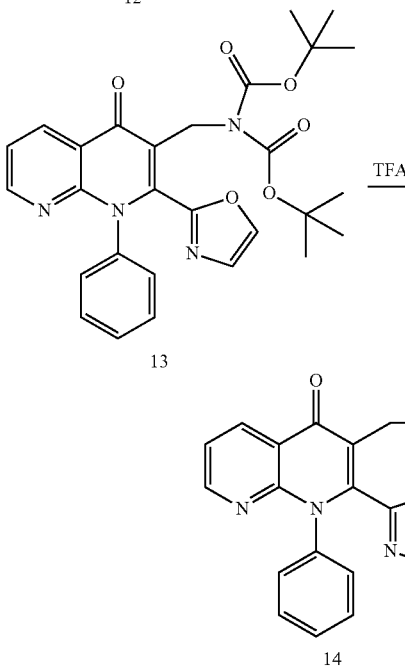

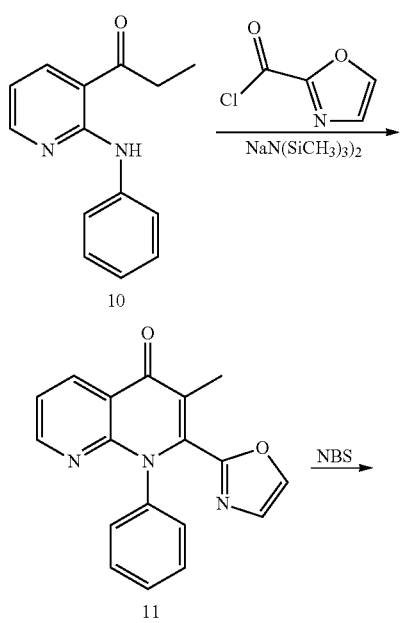

Compound 14 (intermediate B) can be synthesized following the reactions outlined in Scheme 6. Commercially available 2-chloro-nicotinic acid can be treated with N,O-dimethylhydroxylamine hydrochloride under standard coupling conditions to form the Weinreb amide, compound 8 (see for example, PCT WO2008/138920). Compound 8 can be treated with ethyl magnesium bromide under standard Grignard conditions to provide compound 9 (see for example, PCT WO2008/138920). Compound 9 can be treated with aniline under standard displacement conditions to produce compound 10 (see for example, PCT WO2008/138920). Compound 10 can be treated with 2-oxazole carbonyl chloride and sodium hexamethyldisilazane to provide compound 11 (see for example, PCT WO2008/138920). Compound 11 can be treated under standard radical bromination conditions to provide compound 12 (see for example, Gauuan, P. J. F.; Trova, M. P.; Gregor-Boros, L.; Bocckino, S. B.; Crapo, J. D.; Day, B. J. *Bioorg. Med. Chem.* 2002, 10, 3013). Compound 12 can be treated with di-t-butyl-iminodicarboxylate and sodium hydride to provide compound 13 (see for example, Grehn, L.; Ragnarsson, U. *Synthesis* 1987, 275). Compound 13 can then be de-protected under acidic conditions (e.g. trifluoroacetic acid) to afford intermediate B, compound 14 (see for example, Connell, R. D.; Rein, T.; Aakermark, B.; Helquist, P. *J. Org. Chem.* 1988, 53, 3845).

Scheme 7

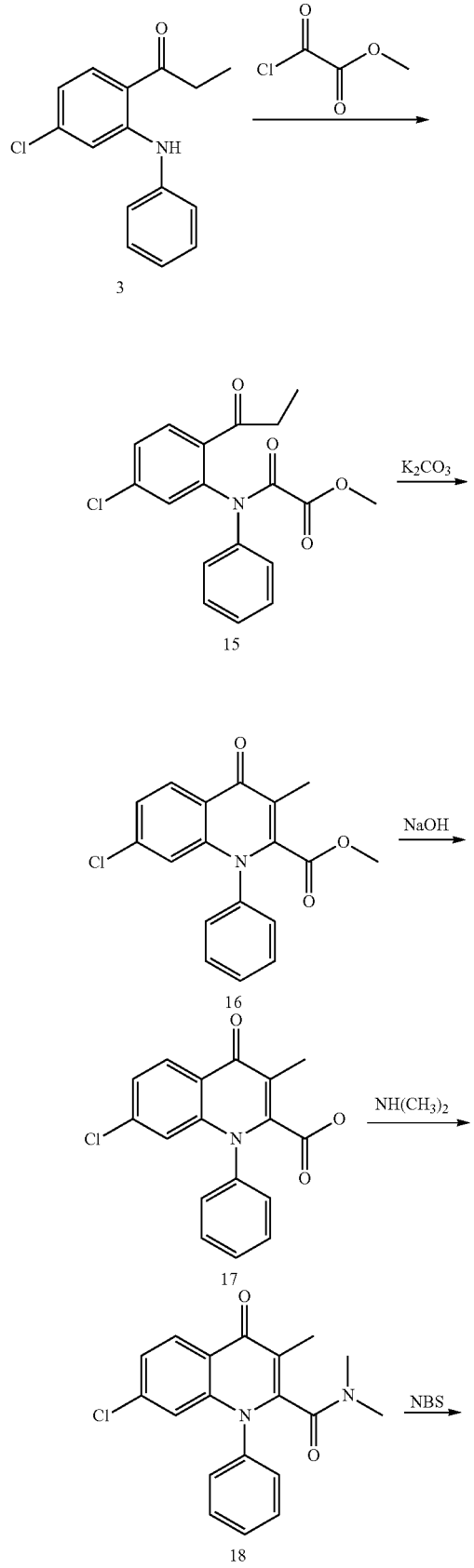

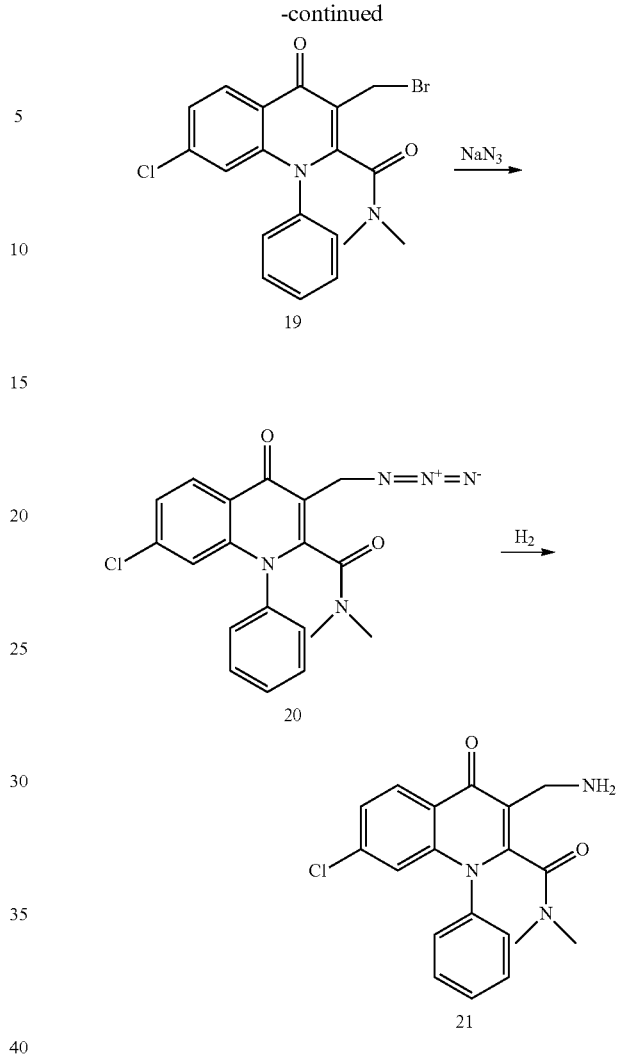

Compound 21 (intermediate C) can be synthesized following the reactions outlined in Scheme 7. Compound 3 can be treated with methyl oxalyl chloride to give compound 15 (see for example, PCT WO2008/138920). The methyl oxalylate, compound 15, can be cyclized using potassium carbonate to give compound 16 (see for example, PCT WO2008/138920). The methyl ester of compound 16 can be treated under basic hydrolysis conditions to form the corresponding carboxylic acid, compound 17 (see for example, Cairns, H.; Cox, D.; Gould, K. J.; Ingall, A. H.; Suschitzky, J. L. *J. Med. Chem.* 1985, 28, 1832). Compound 17, in the presence of dimethylamine can be treated under standard amide bond forming conditions (e.g. PyBrOP) to afford compound 18 (see for example, PCT WO2008/138920). Compound 18 can be treated under standard radical bromination conditions to provide compound 19 (see for example, Gauuan, P. J. F.; Trova, M. P.; Gregor-Boros, L.; Bocckino, S. B.; Crapo, J. D.; Day, B. J. *Bioorg. Med. Chem.* 2002, 10, 3013). Compound 19 can be treated with sodium azide to provide compound 20 (see for example, Liu, J. M.; Young, J. J.; Li, Y. J.; Sha, C. K. *J. Org. Chem.* 1986, 51, 1120). Compound 20 can then be reduced under an atmosphere of hydrogen in the presence of a catalyst (e.g. platinum (IV) oxide) to afford intermediate C, compound 21 (see for example, Gueret, S. M.; O'Connor, P. D.; Brimble, M. A. *Org. Lett.* 2009, 11, 963).

Scheme 8

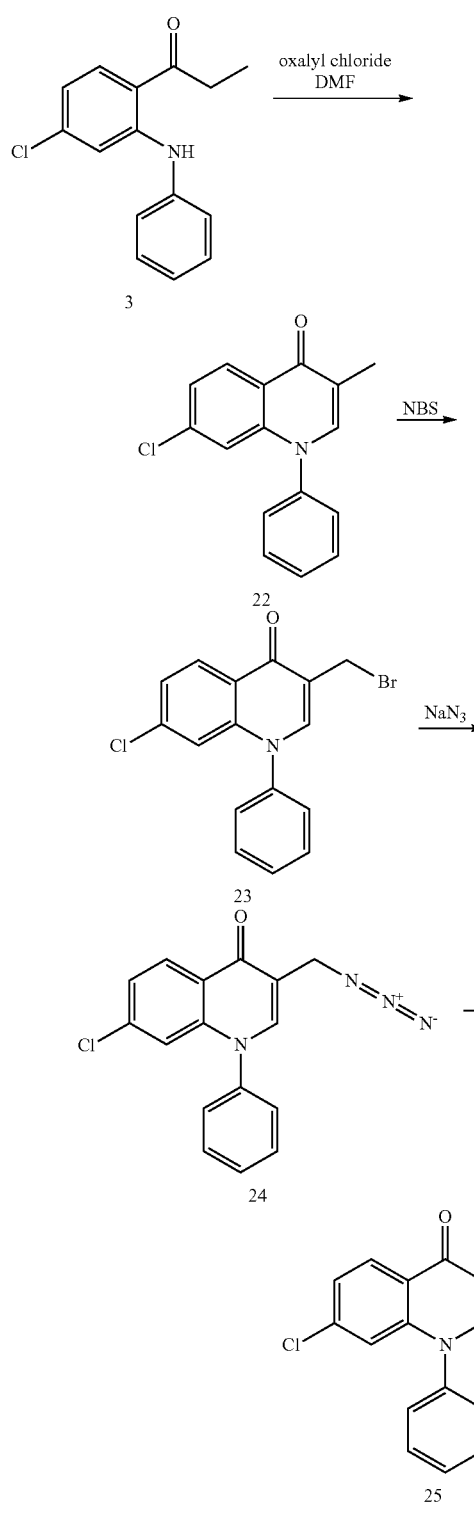

Bocckino, S. B.; Crapo, J. D.; Day, B. J. *Bioorg. Med. Chem.* 2002, 10, 3013). Compound 23 can be treated with sodium azide to provide compound 24 (see for example, Liu, J. M.; Young, J. J.; Li, Y. J.; Sha, C. K. *J. Org. Chem.* 1986, 51, 1120). Compound 24 can then be reduced under an atmosphere of hydrogen in the presence of a catalyst (e.g. platinum (IV) oxide) to afford intermediate D, compound 25 (see for example, Gueret, S. M.; O'Connor, P. D.; Brimble, M. A. *Org. Lett.* 2009, 11, 963).

Scheme 9

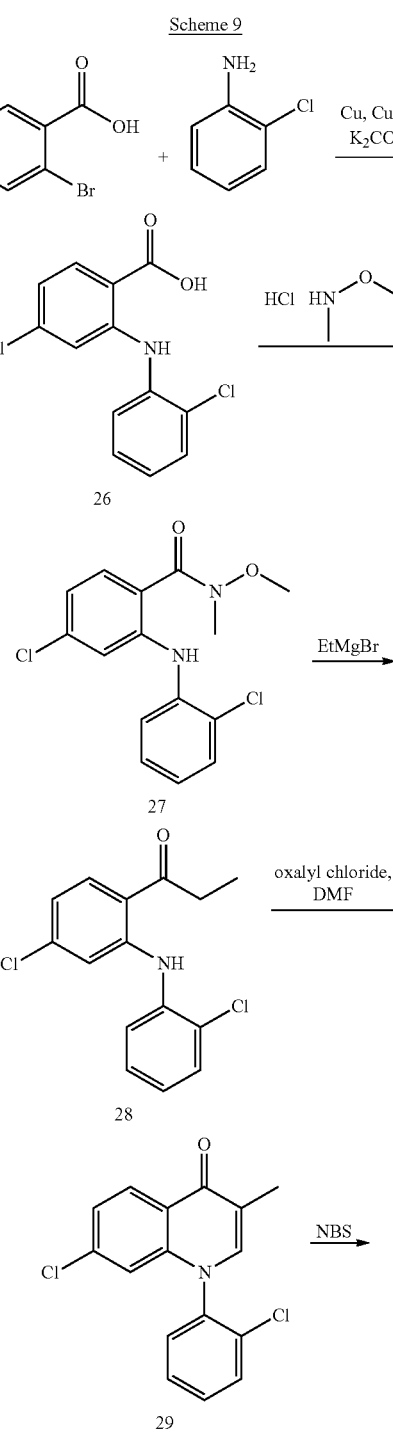

Compound 25 (intermediate D) can be synthesized following the reactions outlined in Scheme 8. Compound 3 can be treated with the Vilsmeier reagent to give compound 22 (see for example, Mendelson, W. L.; Hayden, S. *Syn. Comm.,* 1996, 26, 603). Compound 22 can be treated under standard radical bromination conditions to provide compound 23 (see for example, Gauuan, P. J. F.; Trova, M. P.; Gregor-Boros, L.;

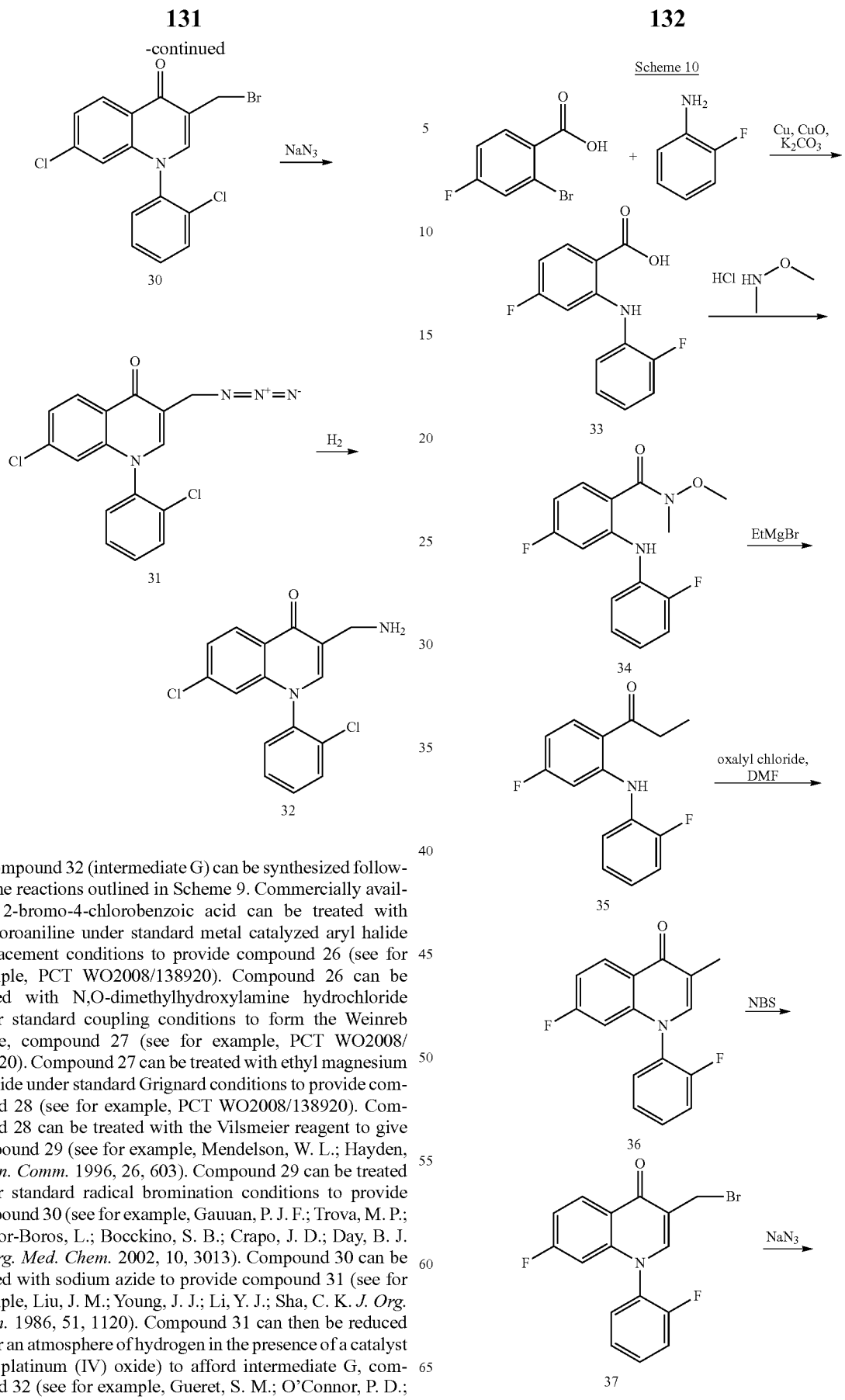

Compound 32 (intermediate G) can be synthesized following the reactions outlined in Scheme 9. Commercially available 2-bromo-4-chlorobenzoic acid can be treated with 2-chloroaniline under standard metal catalyzed aryl halide displacement conditions to provide compound 26 (see for example, PCT WO2008/138920). Compound 26 can be treated with N,O-dimethylhydroxylamine hydrochloride under standard coupling conditions to form the Weinreb amide, compound 27 (see for example, PCT WO2008/138920). Compound 27 can be treated with ethyl magnesium bromide under standard Grignard conditions to provide compound 28 (see for example, PCT WO2008/138920). Compound 28 can be treated with the Vilsmeier reagent to give compound 29 (see for example, Mendelson, W. L.; Hayden, S. *Syn. Comm.* 1996, 26, 603). Compound 29 can be treated under standard radical bromination conditions to provide compound 30 (see for example, Gauuan, P. J. F.; Trova, M. P.; Gregor-Boros, L.; Bocckino, S. B.; Crapo, J. D.; Day, B. J. *Bioorg. Med. Chem.* 2002, 10, 3013). Compound 30 can be treated with sodium azide to provide compound 31 (see for example, Liu, J. M.; Young, J. J.; Li, Y. J.; Sha, C. K. *J. Org. Chem.* 1986, 51, 1120). Compound 31 can then be reduced under an atmosphere of hydrogen in the presence of a catalyst (e.g. platinum (IV) oxide) to afford intermediate G, compound 32 (see for example, Gueret, S. M.; O'Connor, P. D.; Brimble, M. A. *Org. Lett.* 2009, 11, 963).

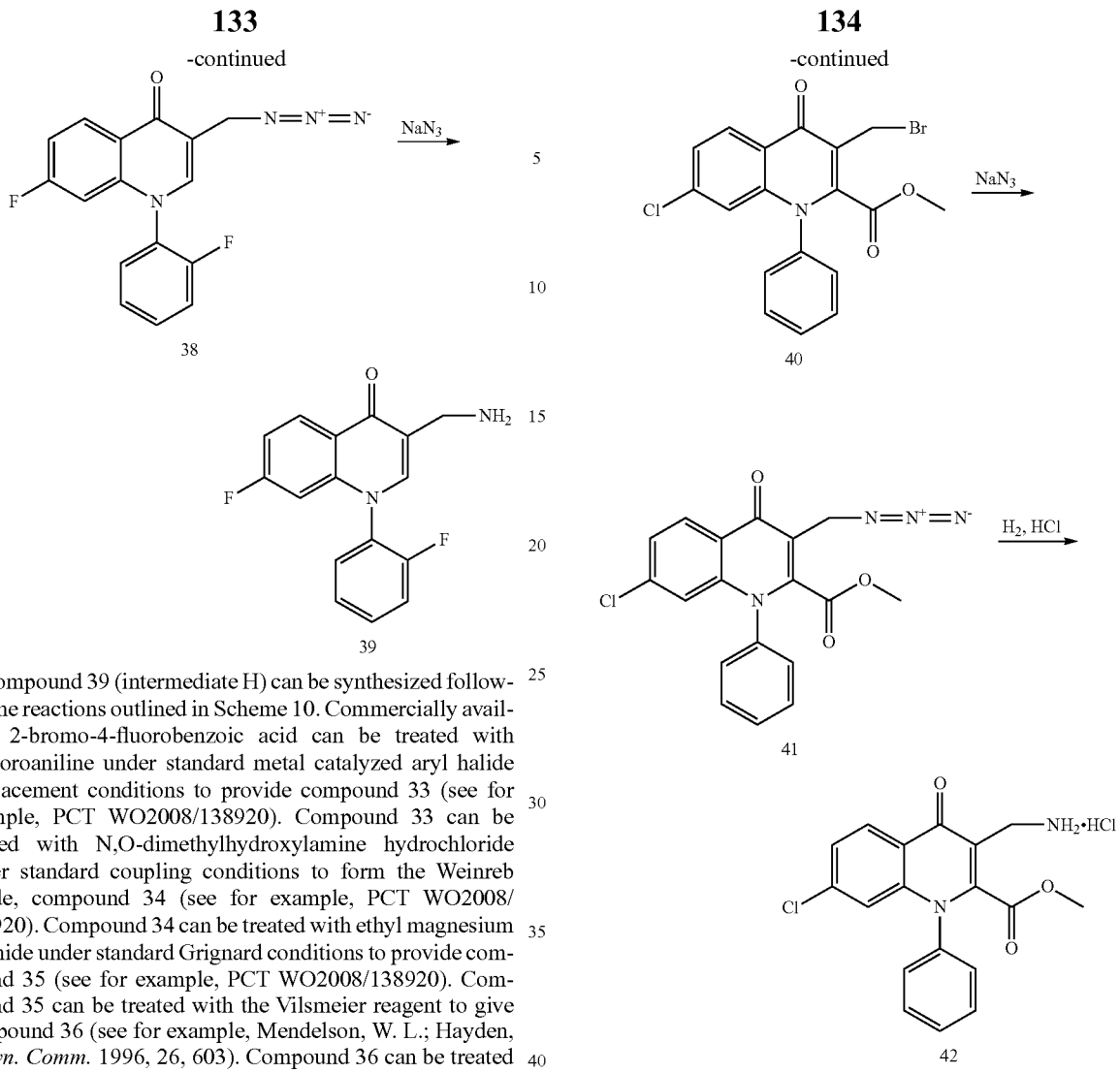

Compound 39 (intermediate H) can be synthesized following the reactions outlined in Scheme 10. Commercially available 2-bromo-4-fluorobenzoic acid can be treated with 2-fluoroaniline under standard metal catalyzed aryl halide displacement conditions to provide compound 33 (see for example, PCT WO2008/138920). Compound 33 can be treated with N,O-dimethylhydroxylamine hydrochloride under standard coupling conditions to form the Weinreb amide, compound 34 (see for example, PCT WO2008/138920). Compound 34 can be treated with ethyl magnesium bromide under standard Grignard conditions to provide compound 35 (see for example, PCT WO2008/138920). Compound 35 can be treated with the Vilsmeier reagent to give compound 36 (see for example, Mendelson, W. L.; Hayden, S. *Syn. Comm.* 1996, 26, 603). Compound 36 can be treated under standard radical bromination conditions to provide compound 37 (see for example, Gauuan, P. J. F.; Trova, M. P.; Gregor-Boros, L.; Bocckino, S. B.; Crapo, J. D.; Day, B. J. *Bioorg. Med. Chem.* 2002, 10, 3013). Compound 37 can be treated with sodium azide to provide compound 38 (see for example, Liu, J. M.; Young, J. J.; Li, Y. J.; Sha, C. K. *J. Org. Chem.* 1986, 51, 1120). Compound 38 can then be reduced under an atmosphere of hydrogen in the presence of a catalyst (e.g. platinum (IV) oxide) to afford intermediate H, compound 39 (see for example, Gueret, S. M.; O'Connor, P. D.; Brimble, M. A. *Org. Lett.* 2009, 11, 963).

Scheme 11

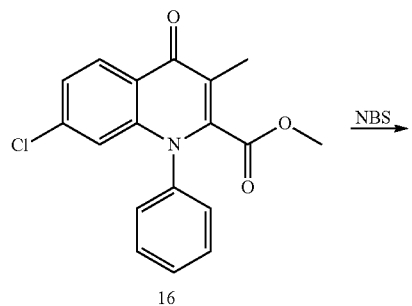

Compound 42 (intermediate I) can be synthesized following the reactions outlined in Scheme 11. Compound 16 can be treated under standard radical bromination condition to provide compound 40 (see for example, Gauuan, P. J. F.; Trova, M. P.; Gregor-Boros, L.; Bocckino, S. B.; Crapo, J. D.; Day, B. J. *Bioorg. Med. Chem.* 2002, 10, 3013). Compound 40 can be treated with sodium azide to provide compound 41 (see for example, Liu, J. M.; Young, J. J.; Li, Y. J.; Sha, C. K. *J. Org. Chem.* 1986, 51, 1120). Compound 41 can then be reduced under an atmosphere of hydrogen in the presence of a catalyst (e.g. platinum (IV) oxide) to afford intermediate I, compound 42 (see for example, Gueret, S. M.; O'Connor, P. D.; Brimble, M. A. *Org. Lett.* 2009, 11, 963).

Scheme 12

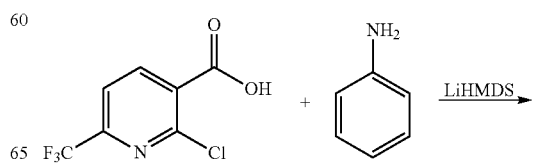

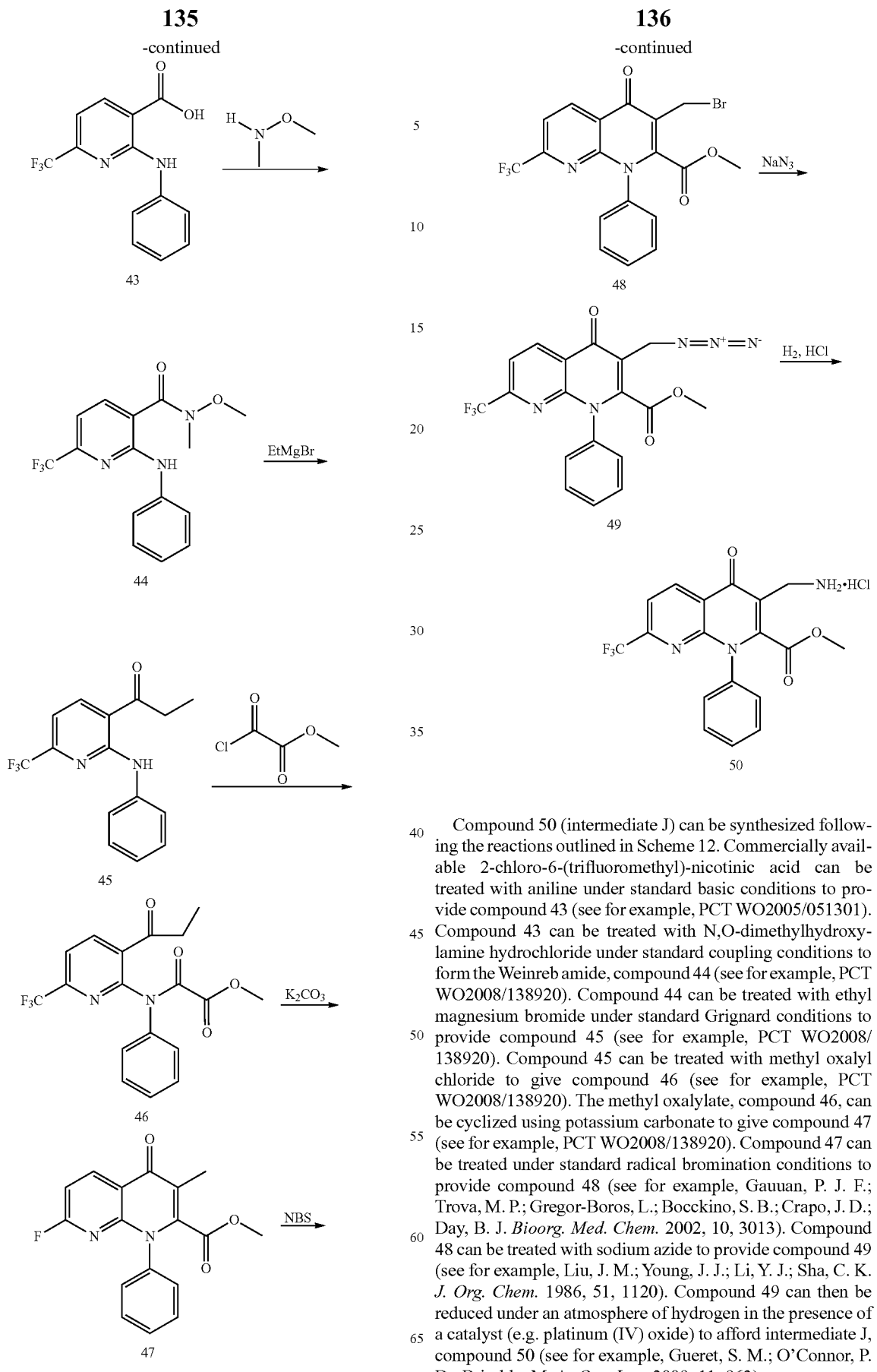

Compound 50 (intermediate J) can be synthesized following the reactions outlined in Scheme 12. Commercially available 2-chloro-6-(trifluoromethyl)-nicotinic acid can be treated with aniline under standard basic conditions to provide compound 43 (see for example, PCT WO2005/051301). Compound 43 can be treated with N,O-dimethylhydroxylamine hydrochloride under standard coupling conditions to form the Weinreb amide, compound 44 (see for example, PCT WO2008/138920). Compound 44 can be treated with ethyl magnesium bromide under standard Grignard conditions to provide compound 45 (see for example, PCT WO2008/138920). Compound 45 can be treated with methyl oxalyl chloride to give compound 46 (see for example, PCT WO2008/138920). The methyl oxalylate, compound 46, can be cyclized using potassium carbonate to give compound 47 (see for example, PCT WO2008/138920). Compound 47 can be treated under standard radical bromination conditions to provide compound 48 (see for example, Gauuan, P. J. F.; Trova, M. P.; Gregor-Boros, L.; Bocckino, S. B.; Crapo, J. D.; Day, B. J. *Bioorg. Med. Chem.* 2002, 10, 3013). Compound 48 can be treated with sodium azide to provide compound 49 (see for example, Liu, J. M.; Young, J. J.; Li, Y. J.; Sha, C. K. *J. Org. Chem.* 1986, 51, 1120). Compound 49 can then be reduced under an atmosphere of hydrogen in the presence of a catalyst (e.g. platinum (IV) oxide) to afford intermediate J, compound 50 (see for example, Gueret, S. M.; O'Connor, P. D.; Brimble, M. A. *Org. Lett.* 2009, 11, 963).

Scheme 13

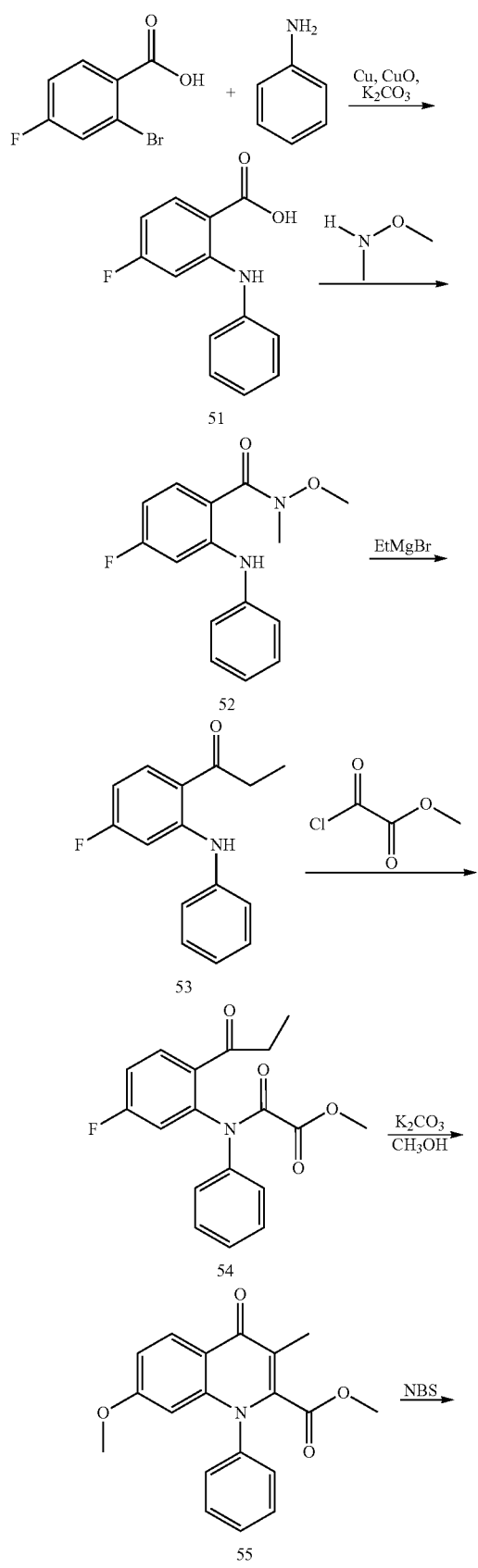

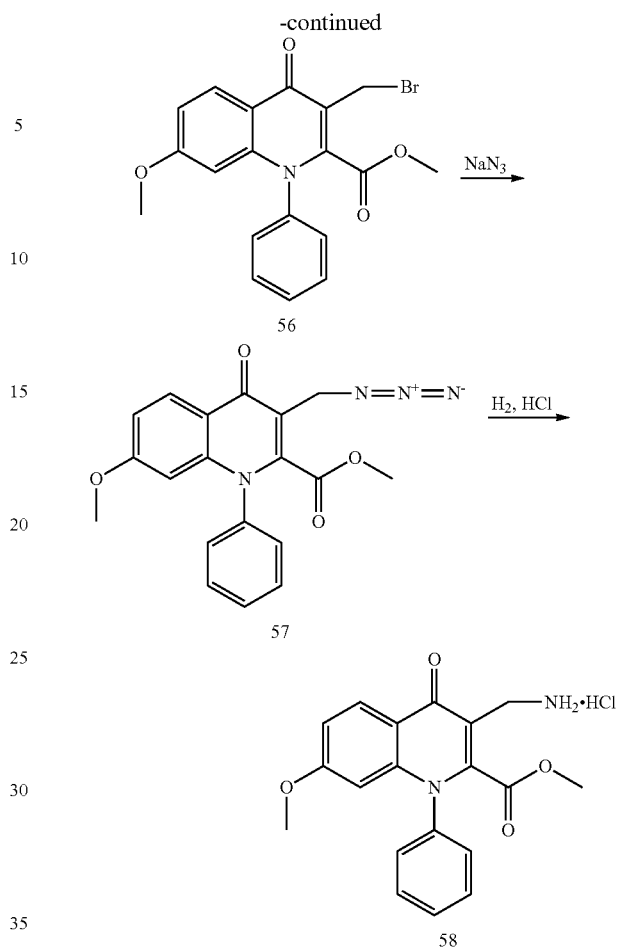

Compound 58 (intermediate K) can be synthesized following the reactions outlined in Scheme 13. Commercially available 2-bromo-4-fluorobenzoic acid can be treated with aniline under standard metal catalyzed aryl halide displacement conditions to provide compound 51 (see for example, PCT WO2008/138920). Compound 51 can be treated with N,O-dimethylhydroxylamine hydrochloride under standard coupling conditions to form the Weinreb amide, compound 52 (see for example, PCT WO2008/138920). Compound 52 can be treated with ethyl magnesium bromide under standard Grignard conditions to provide compound 53 (see for example, PCT WO2008/138920). Compound 53 can be treated with methyl oxalyl chloride to give compound 54 (see for example, PCT WO2008/138920). The methyl oxalylate, compound 54, can be cyclized using potassium carbonate in methanol to give compound 55 (see for example, PCT WO2008/138920). Compound 55 can be treated under standard radical bromination conditions to provide compound 56 (see for example, Gauuan, P. J. F.; Trova, M. P.; Gregor-Boros, L.; Bocckino, S. B.; Crapo, J. D.; Day, B. J. Bioorg. Med. Chem. 2002, 10, 3013). Compound 56 can be treated with sodium azide to provide compound 57 (see for example, Liu, J. M.; Young, J. J.; Li, Y. J.; Sha, C. K. J. Org. Chem. 1986, 51, 1120). Compound 57 can then be reduced under an atmosphere of hydrogen in the presence of a catalyst (e.g. platinum (IV) oxide) to afford intermediate K, compound 58 (see for example, Gueret, S. M.; O'Connor, P. D.; Brimble, M. A. Org. Letters 2009, 11, 963).

Scheme 14

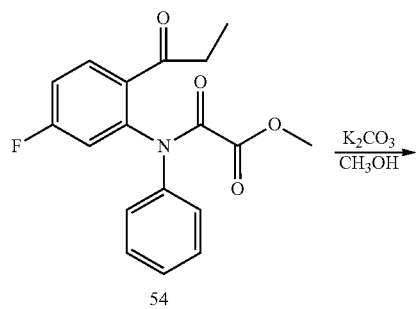

54

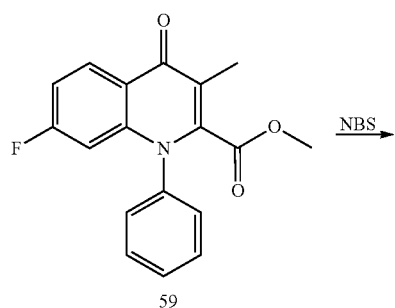

59

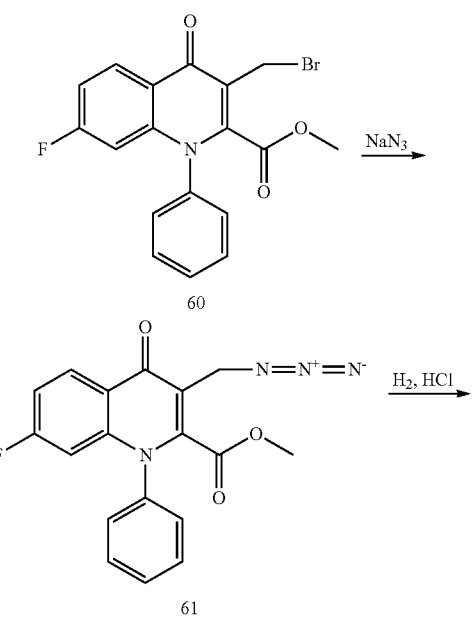

Compound 62 (intermediate L) can be synthesized following the reactions outlined in Scheme 14. The methyl oxalylate, compound 54, can be cyclized using potassium carbonate in methanol to give compound 59 (see for example, PCT WO2008/138920). Compound 59 can be treated under standard radical bromination conditions to provide compound 60 (see for example, Gauuan, P. J. F.; Trova, M. P.; Gregor-Boros, L.; Bocckino, S. B.; Crapo, J. D.; Day, B. J. *Bioorg. Med. Chem.* 2002, 10, 3013). Compound 60 can be treated with sodium azide to provide compound 61 (see for example, Liu, J. M.; Young, J. J.; Li, Y. J.; Sha, C. K. *J. Org. Chem.* 1986, 51, 1120). Compound 61 can then be reduced under an atmosphere of hydrogen in the presence of a catalyst (e.g. platinum (IV) oxide) to afford intermediate L, compound 62 (see for example, Gueret, S. M.; O'Connor, P. D.; Brimble, M. A. *Org. Lett.* 2009, 11, 963).

Scheme 15

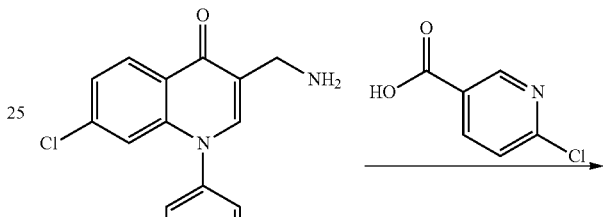

25

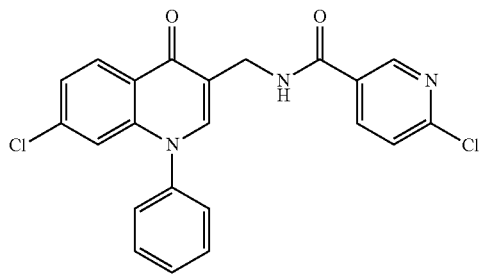

63

Compound 63 (intermediate E) can be synthesized following the reaction outlined in Scheme 15. Compound 25 (intermediate D) can be treated with 6-chloronicotinic acid under standard amide bond forming conditions (e.g. BOP) to afford intermediate E, compound 63 (see for example, PCT WO2008/138920).

Scheme 16

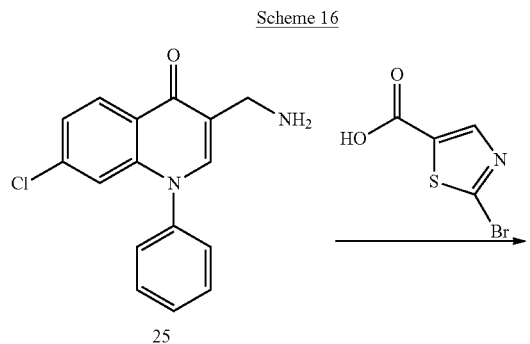

Compound 64 (intermediate F) can be synthesized following the reaction outlined in Scheme 16. Compound 25 (intermediate D) can be treated with 2-bromothiazole-5-carboxylic acid under standard amide bond forming conditions (e.g. BOP) to afford intermediate F, compound 64 (see for example, PCT WO2008/138920).

Scheme 17

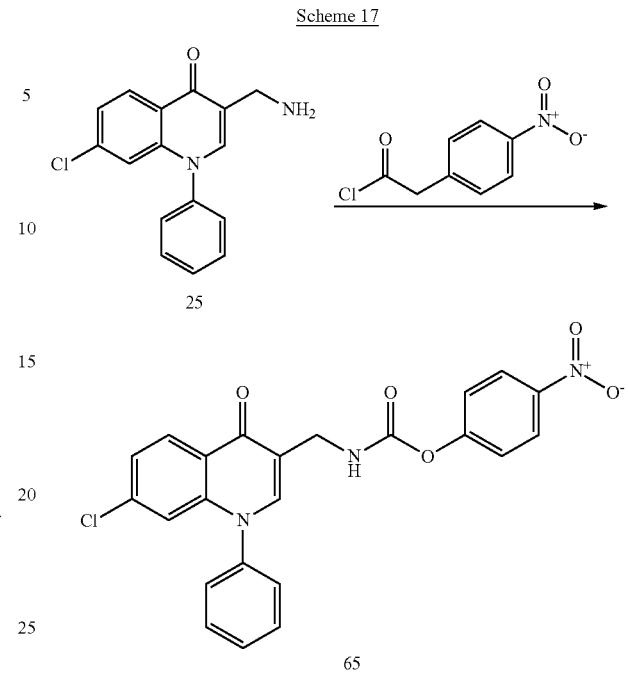

Compound 65 (intermediate M) can be synthesized following the reaction outlined in Scheme 17. Compound 25 (intermediate D) can be treated with 4-nitrophenyl chloroformate to afford intermediate M, compound 65 (see for example, Mallakpour, S.; Rafiee, Z. *Syn. Commun.* 2007, 37, 1927).

Scheme 18

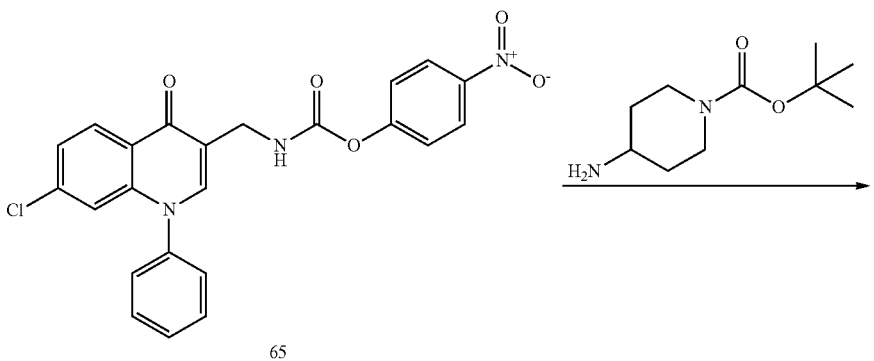

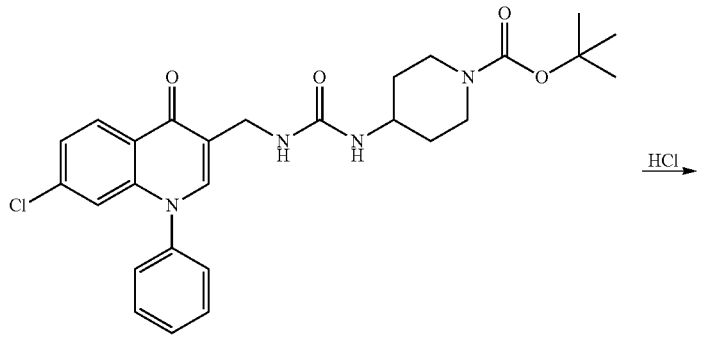

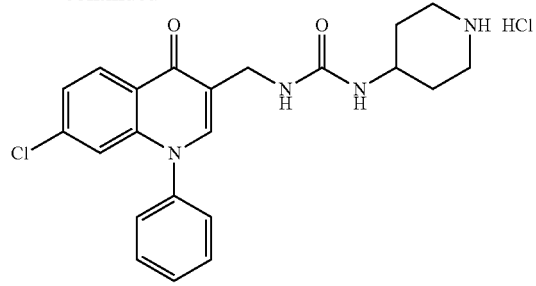

67

Compound 67 (intermediate N) can be synthesized following the reactions outlined in Scheme 18. Compound 65 (intermediate M) can be treated with 4-amino-piperidine-1-carboxylic acid tert-butyl ester to afford compound 66 (see for example, Liu, Q.; Luedtke, N. W.; Tor, Y. *Tetrahedron Lett.* 2001, 42, 1445). Compound 66 can then be treated with hydrogen chloride to afford intermediate N, compound 67 (see for example, PCT WO2008/138920).

Scheme 19

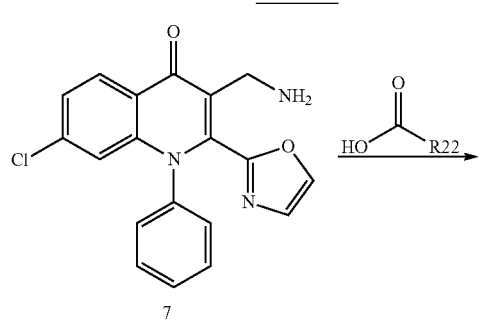

7

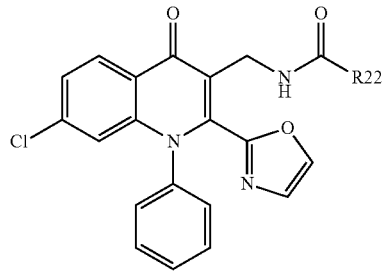

Example I-1 to I-5

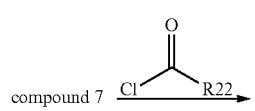

compound 7

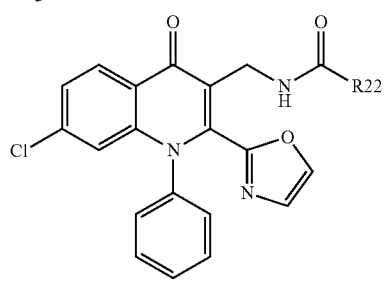

Example I-8

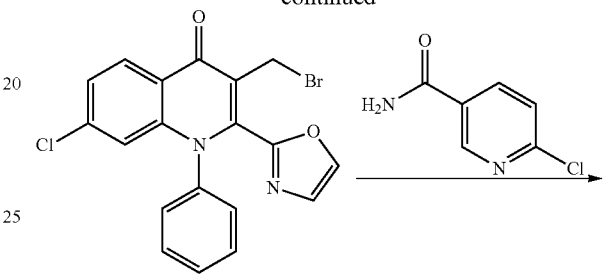

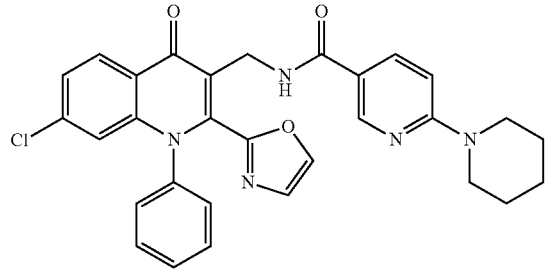

Example I-6

Example I-7

Examples I-1 to I-8 can be synthesized following the reactions outlined in Scheme 19. Compound 7 (intermediate A) can be treated with different carboxylic acids under standard amide bond forming conditions (e.g. BOP, PyBrOP) to afford examples I-1 to I-5 (see for example, PCT WO2008/138920). Compound 7 (intermediate A) can also be treated with an acid chloride under standard amide bond forming conditions to afford example I-8 (see for example, PCT WO2008/138920). Compound 5 can be treated with the anion of 6-chloro-nicotinamide to afford example I-6 (see for example, Kasuga, J.; Hashimoto, Y.; Miyachi, H. *Bioorg. Med. Chem. Lett.* 2006, 16, 771). Example I-6 can then be treated with an amine to afford example I-7 (see for example, Huang, C. Q.; Baker, T.; Schwarz, D.; Fan, J.; Heise, C. E.; Zhang, M.; Goodfellow, V.

S.; Markison, S.; Gogas, K. R.; Chen, T.; Wang, X-C.; Zhu, Y-F. *Bioorg. Med. Chem. Lett.* 2005, 15, 3701).

example, Huang, C. Q.; Baker, T.; Schwarz, D.; Fan, J.; Heise, C. E.; Zhang, M.; Goodfellow, V. S.; Markison, S.; Gogas, K. R.; Chen, T.; Wang, X-C.; Zhu, Y-F. *Bioorg. Med. Chem. Lett.* 2005, 15, 3701).

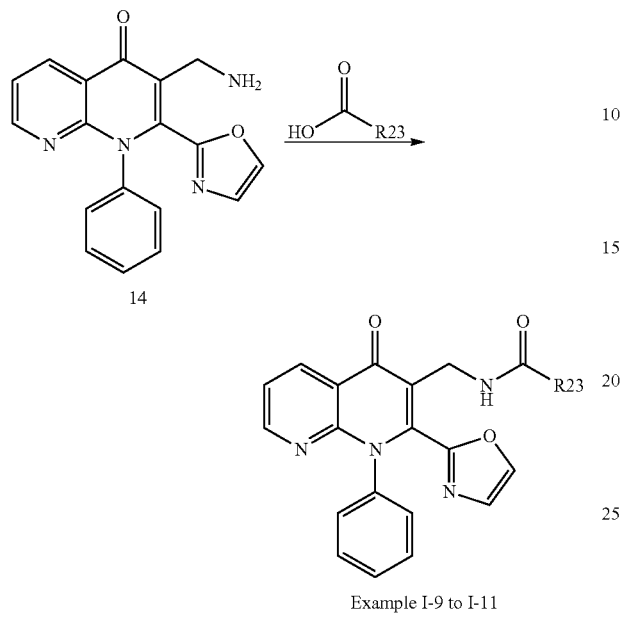

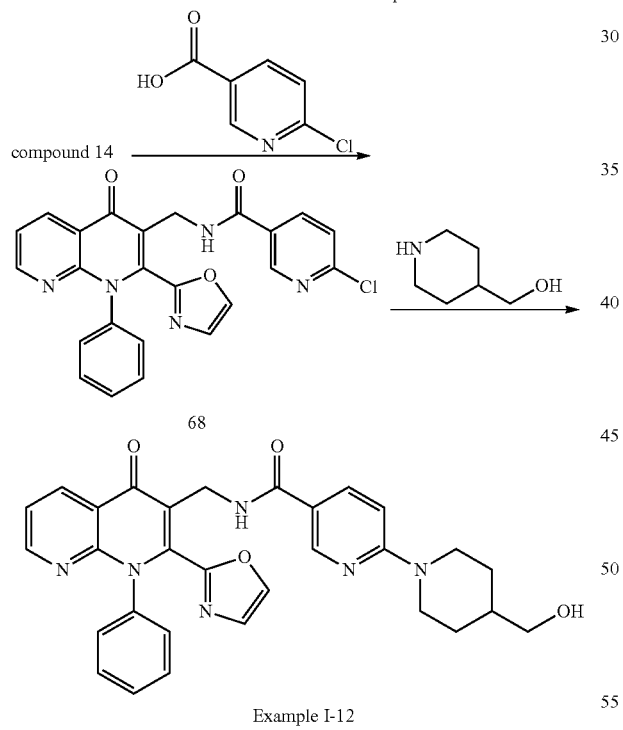

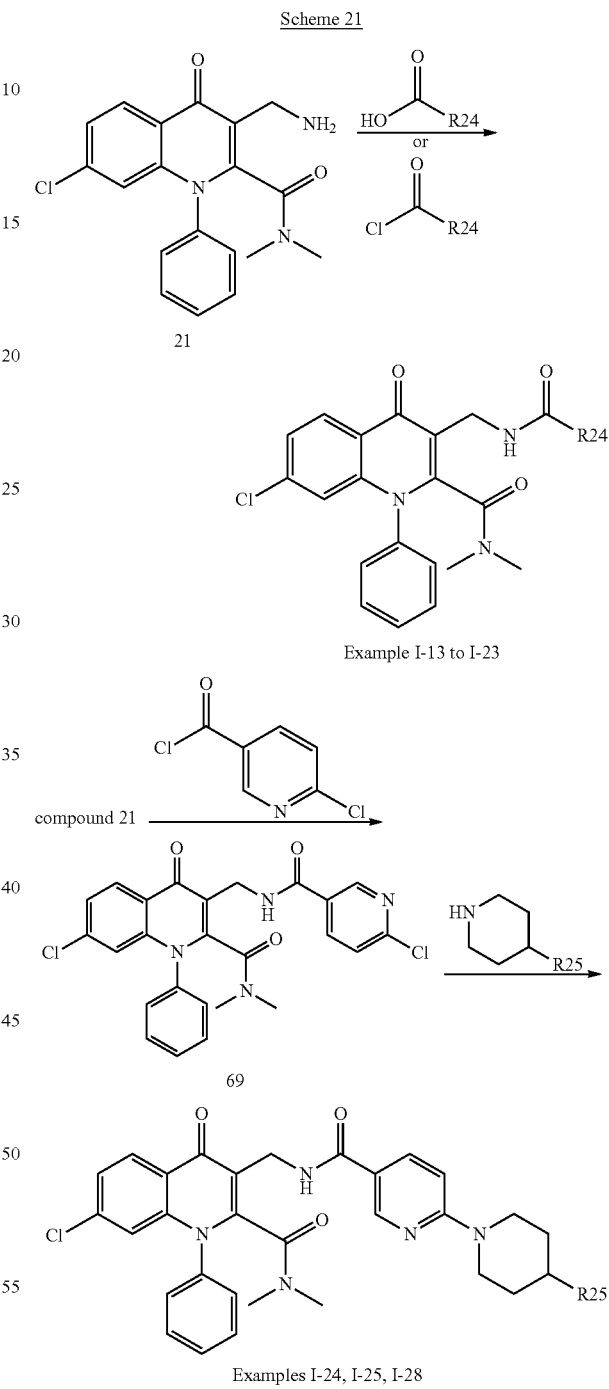

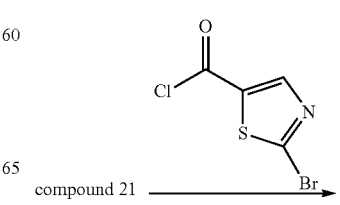

Examples I-9 to I-12 can be synthesized following the reactions outlined in Scheme 20. Compound 14 (intermediate B) can be treated with different carboxylic acids under standard amide bond forming conditions (e.g. BOP, PyBrOP) to afford examples I-9 to I-11 (see for example, PCT WO2008/138920). Compound 14 (intermediate B) can also be treated with 6-chloronicotinic acid under standard amide bond forming conditions to afford compound 68 (see for example, PCT WO2008/138920). Compound 68 can then be treated with piperidin-4-ylmethanol to afford example I-12 (see for

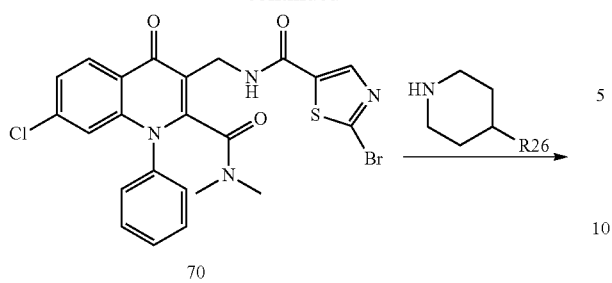

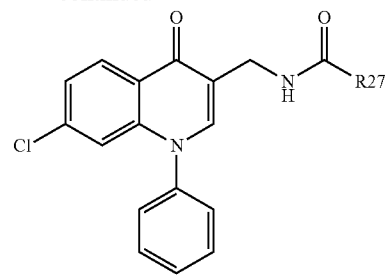

Examples I-29 to I-56, I-61

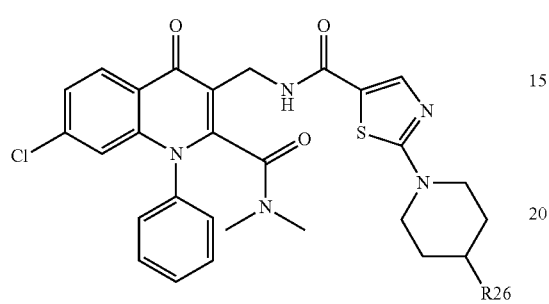

Examples I-26, I-27

Examples I-13 to I-28 can be synthesized following the reactions outlined in Scheme 21. Compound 21 (intermediate C) can be treated with different carboxylic acids under standard amide bond forming conditions (e.g. BOP, PyBrOP) or acid chlorides to afford examples I-13 to I-23 (see for example, PCT WO2008/138920). Compound 21 (intermediate C) can also be treated with 6-chloronicotinoyl chloride under standard amide bond forming conditions to afford compound 69 (see for example, PCT WO2008/138920). Compound 69 can be treated with different amines to afford examples I-24 and I-25 (see for example, Huang, C. Q.; Baker, T.; Schwarz, D.; Fan, J.; Heise, C. E.; Zhang, M.; Goodfellow, V. S.; Markison, S.; Gogas, K. R.; Chen, T.; Wang, X-C.; Zhu, Y-F. *Bioorg. Med. Chem. Lett.* 2005, 15, 3701). Alternatively, compound 21 (intermediate C) can be treated with 6-chloronicotinoyl chloride followed by addition by piperidine in one pot to afford example I-28. Compound 21 (intermediate C) can also be treated with 2-bromothiazole-5-carboxylic acid under standard amide bond forming conditions to afford compound 70 (see for example, PCT WO2008/138920). Compound 70 can be treated with different amines to afford examples I-26 and I-27 (see for example, Baker, L. A.; Williams, C. M. *J. Hetero. Chem.* 2003, 40, 353).

Scheme 22

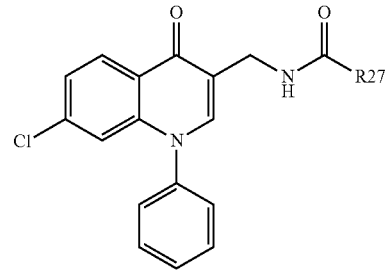

Examples I-57 to I-60

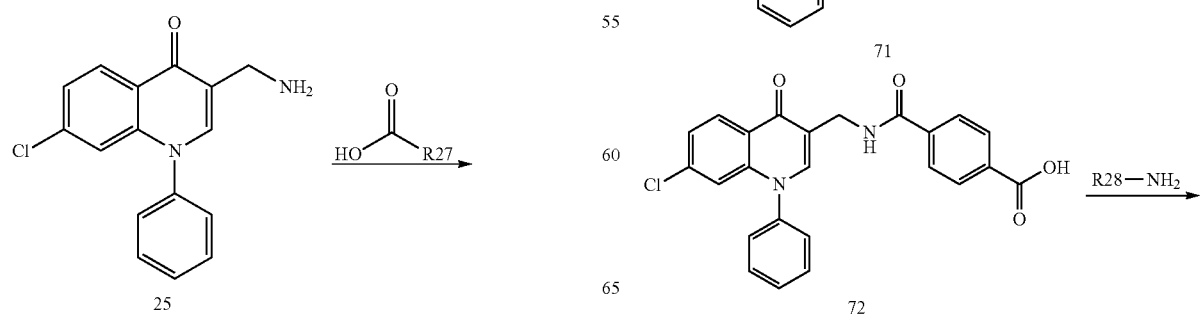

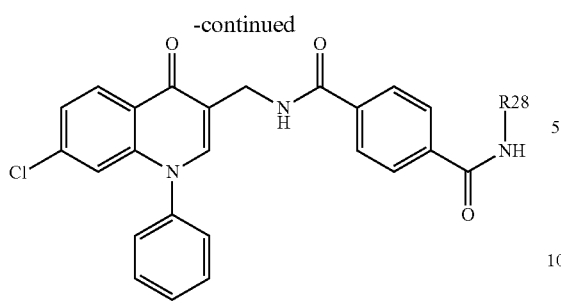

Examples I-98 to I-99

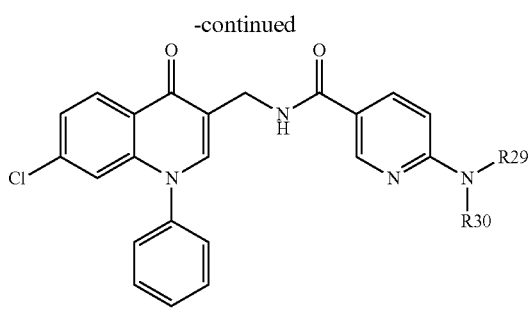

Examples I-62 to I-90

Examples I-29 to I-56 and I-98 to I-99 can be synthesized following the reactions outlined in Scheme 22. Compound 25 (intermediate D) can be treated with different carboxylic acids under standard amide bond forming conditions (e.g. BOP, PyBrOP) to afford examples I-29 to I-56 and I-61 (see for example, PCT WO2008/138920). Compound 25 (intermediate D) can be treated with different acid chlorides under standard amide bond forming conditions to afford examples I-57 to I-60 (see for example, PCT WO2008/138920). Compound 25 (intermediate D) can be treated with methyl 4-(chlorocarbonyl)benzoate to afford compound 71 (see for example, Kiggen, W.; Voegtle, F.; Franken, S.; Puff, H. *Tetrahedron* 1986, 42, 1859). Compound 71 can be hydrolyzed under basic conditions to afford compound 72 (see for example, Vivier, M.; Jarrousse, A.-S.; Bouchon, B.; Galmier, M-J.; Auzeloux, P.; Sauzieres, J.; Madelmont, J-C. *J. Med. Chem.* 2005, 48, 6731). Compound 72 can be treated with different amines under standard amide bond forming conditions to afford examples I-98 and I-99 (see for example, PCT WO2008/138920).

Scheme 23

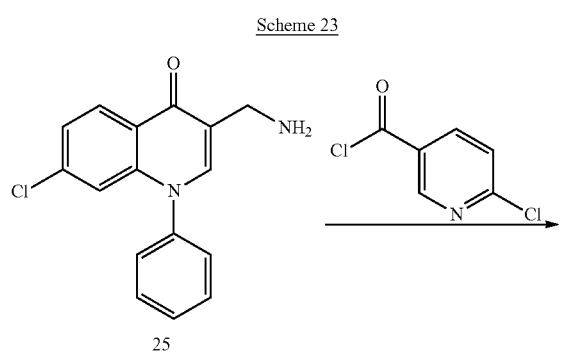

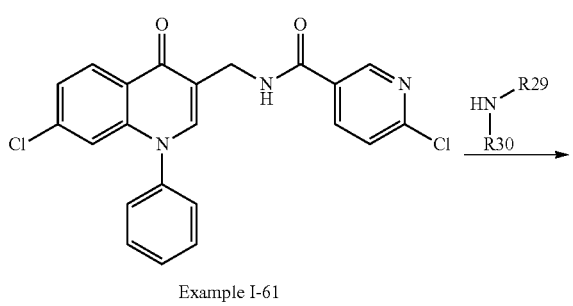

Example I-61

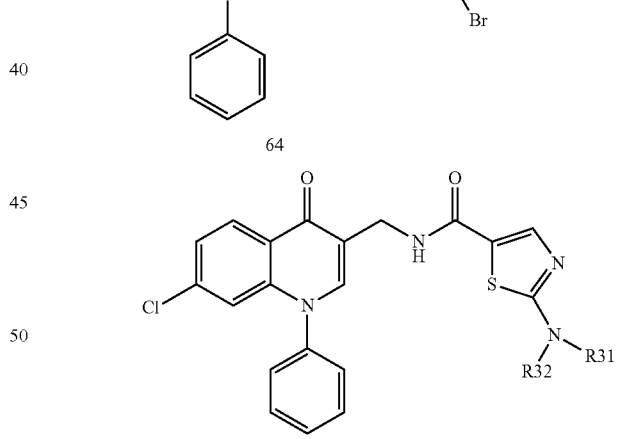

Examples I-91 to I-97

Examples I-62 to I-97 can be synthesized following the reactions outlined in Scheme 23. Compound 51 (intermediate E) can be treated with different amines to afford examples I-62 to I-90 (see for example, Huang, C. Q.; Baker, T.; Schwarz, D.; Fan, J.; Heise, C. E.; Zhang, M.; Goodfellow, V. S.; Markison, S.; Gogas, K. R.; Chen, T.; Wang, X-C.; Zhu, Y-F. *Bioorg. Med. Chem. Lett.* 2005, 15, 3701). Compound 64 (intermediate F) can be treated with different amines to afford examples I-91 and I-97 (see for example, Baker, L. A.; Williams, C. M. *J. Hetero. Chem.* 2003, 40, 353).

Scheme 24

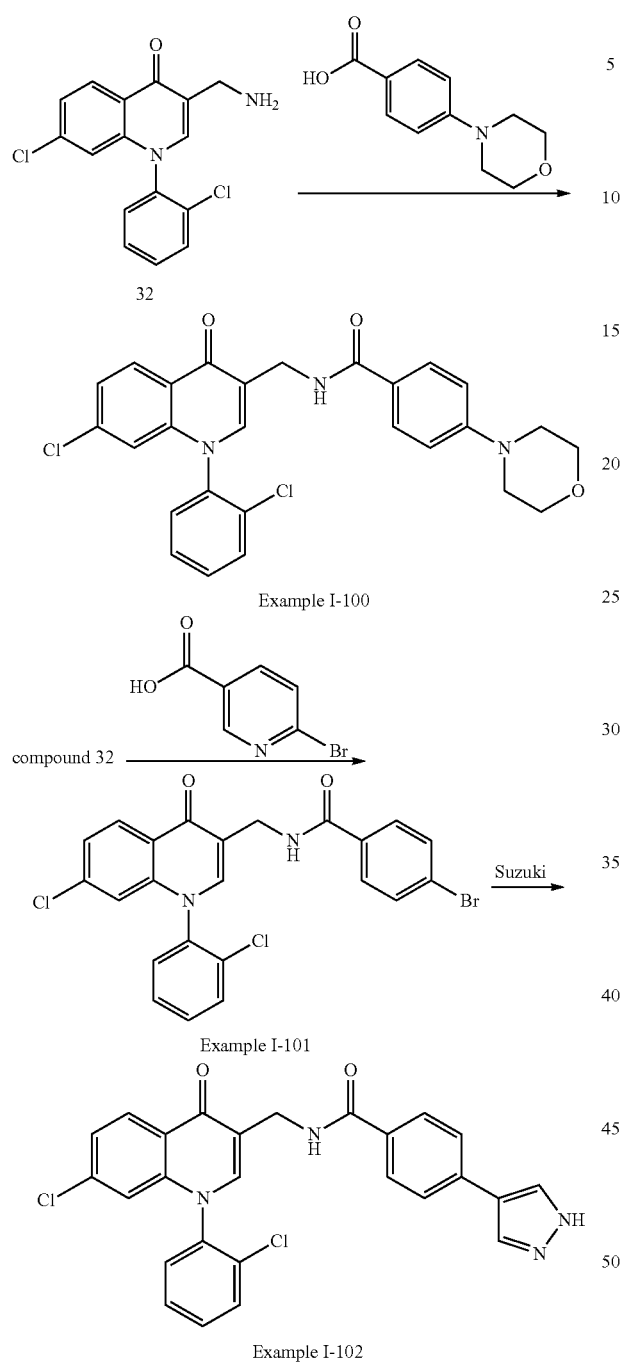

Scheme 25

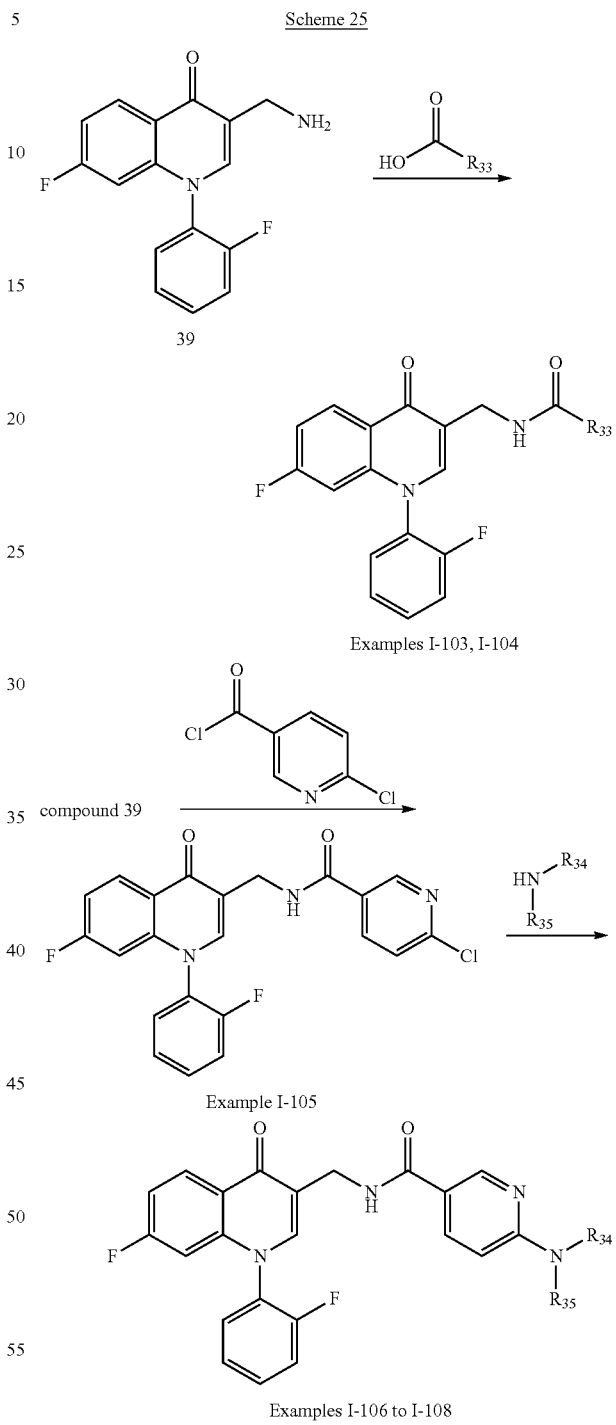

D. M.; Pitt, W. R.; Rausch, O.; Richard, M. D.; Sabin, V.; Fraser, J. L. *Bioorg. Med. Chem. Lett.* 2008, 18, 3211).

Examples I-100 to I-102 can be synthesized following the reactions outlined in Scheme 24. Compound 32 (intermediate G) can be treated with 6-morpholinonicotinic acid under standard amide bond forming conditions to afford example I-100 (see for example, PCT WO2008/138920). Compound 32 (intermediate G) can also be treated with 6-bromonicotinic acid under standard amide bond forming conditions to afford example I-101 (see for example, PCT WO2008/138920). Example I-101 can then be treated with 4-(4,4,5,5-tetramethyl-1,3,2-dioxaborolan-2-yl)-1H-pyrazole to afford example I-102 (see for example, Buckley, G. M.; Gowers, L.; Higueruelo, A. P.; Jenkins, K.; Mack, S. R.; Morgan, T.; Parry, Examples I-103 to I-108 can be synthesized following the reactions outlined in Scheme 25. Compound 39 (intermediate H) can be coupled with different acids under standard amide bond forming conditions to afford examples I-103 and I-104 (see for example, PCT WO2008/138920). Compound 39 (intermediate H) can also be treated with 6-chloronicotinoyl chloride under standard amide bond forming conditions to afford example I-105 (see for example, PCT WO2008/

138920). Compound 1-105 can then be treated with different amines to afford examples I-106 to I-108 (see for example, Huang, C. Q.; Baker, T.; Schwarz, D.; Fan, J.; Heise, C. E.; Zhang, M.; Goodfellow, V. S.; Markison, S.; Gogas, K. R.; Chen, T.; Wang, X-C.; Zhu, Y-F. *Bioorg. Med. Chem. Lett.* 2005, 15, 3701).

Scheme 26

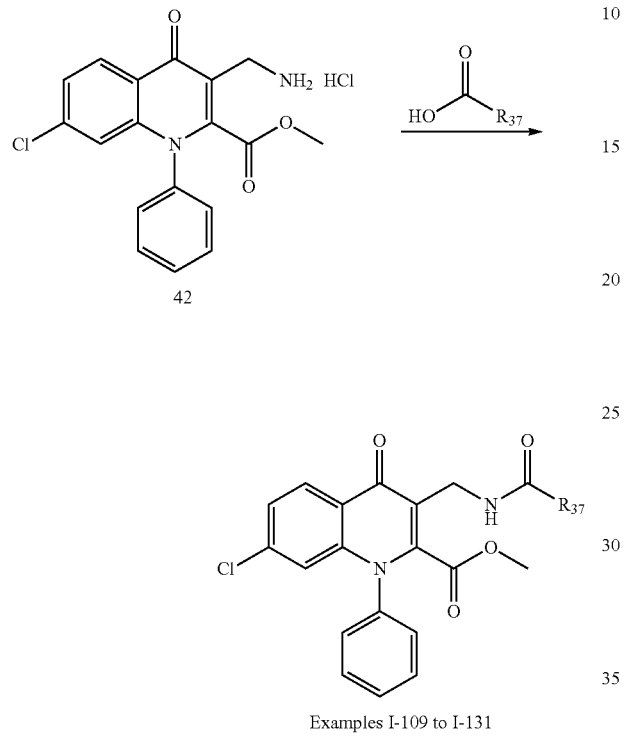

Examples I-109 to I-131

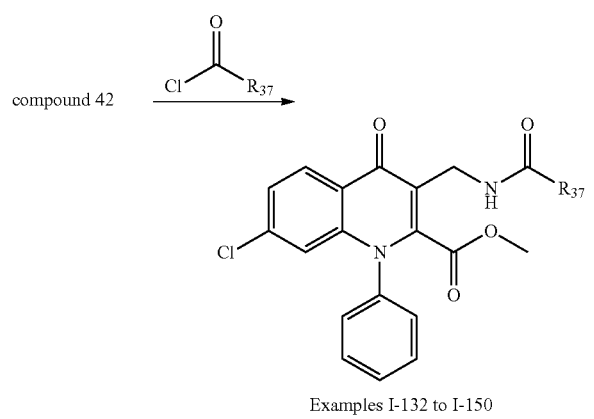

Examples I-132 to I-150

Examples I-109 to I-150 can be synthesized following the reactions outlined in Scheme 26. Compound 42 (intermediate I) can be treated with different carboxylic acids under standard amide bond forming conditions (e.g. BOP, PyBrOP) to afford examples I-109 to I-131 (see for example, PCT WO2008/138920). Compound 42 (intermediate I) can be treated with different acid chlorides under standard amide bond forming conditions to afford examples I-132 to I-150 (see for example, PCT WO2008/138920).

Scheme 27

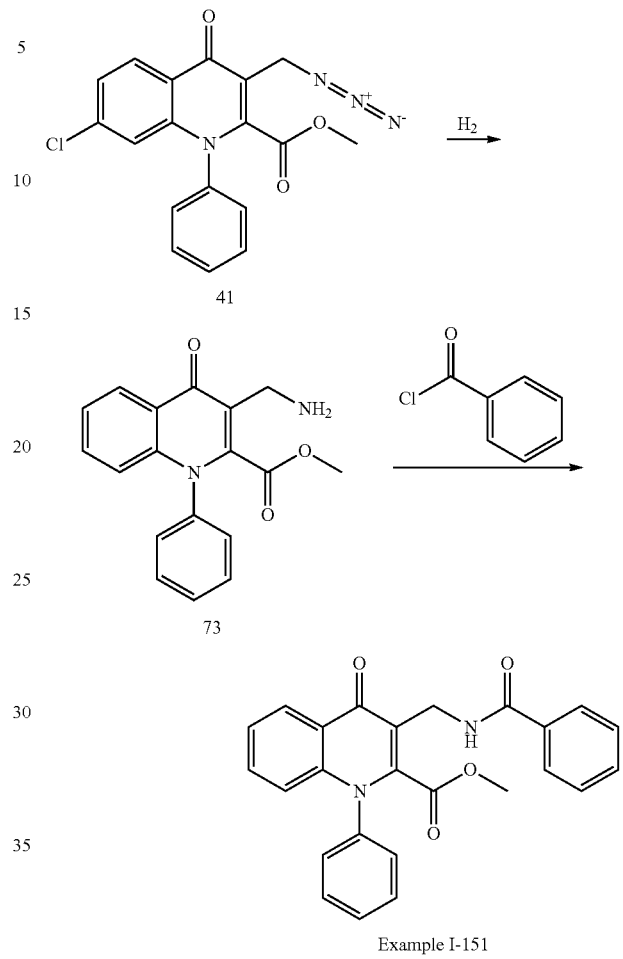

Example I-151

Example I-151 can be synthesized following the reactions outlined in Scheme 27. Compound 41 can be reduced under an atmosphere of hydrogen in the presence of a catalyst (e.g. platinum (IV) oxide) to afford compound 73 as a by-product (see for example, Gueret, S. M.; O'Connor, P. D.; Brimble, M. A. *Org. Lett.* 2009, 11, 963). Compound 73 can be treated with benzoyl chloride under standard amide bond forming conditions to afford example I-151 (see for example, PCT WO2008/138920).

Scheme 28

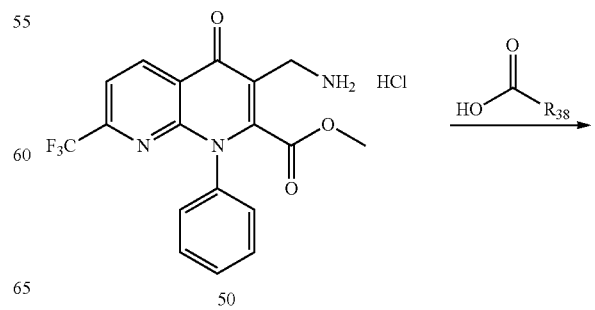

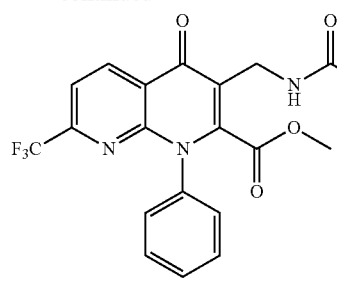

Example I-152 to I-159

Examples I-152 to I-159 can be synthesized following the reactions outlined in Scheme 28. Compound 50 (intermediate J) can be treated with different carboxylic acids under standard amide bond forming conditions (e.g. BOP, PyBrOP) to afford examples I-152 to I-159 (see for example, PCT WO2008/138920).

Scheme 29

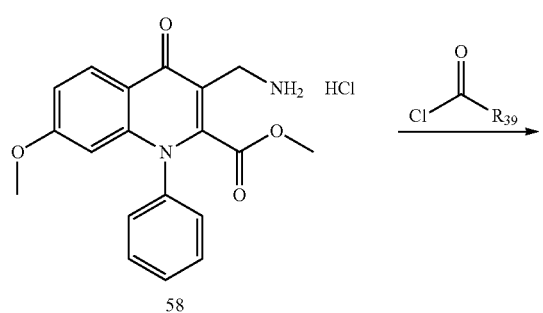

58

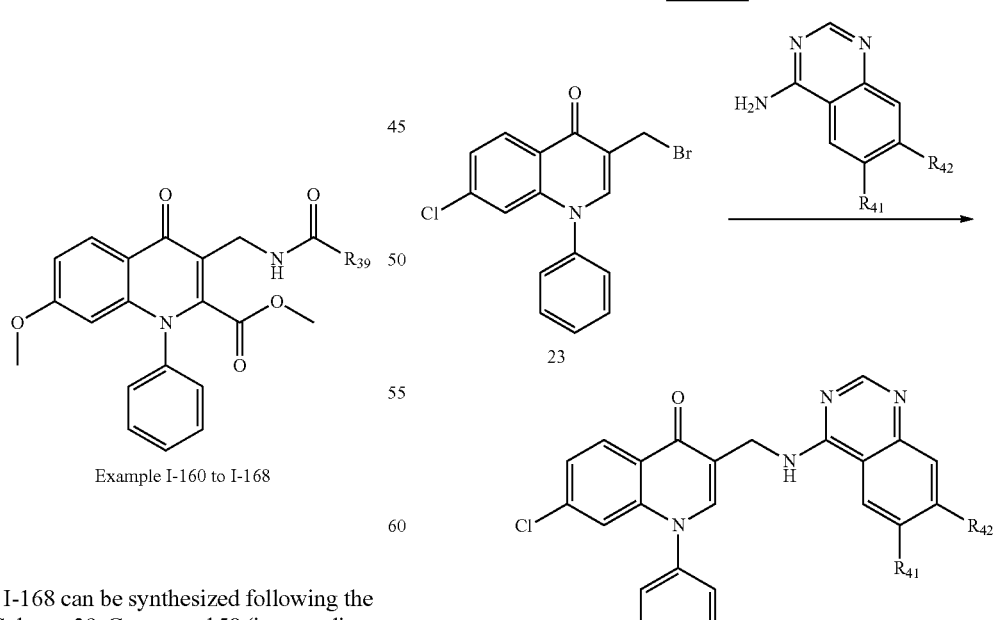

Example I-160 to I-168

Examples I-160 to I-168 can be synthesized following the reactions outlined in Scheme 29. Compound 58 (intermediate K) can be treated with different acid chlorides under standard amide bond forming conditions to afford examples I-160 to I-168 (see for example, PCT WO2008/138920).

Scheme 30

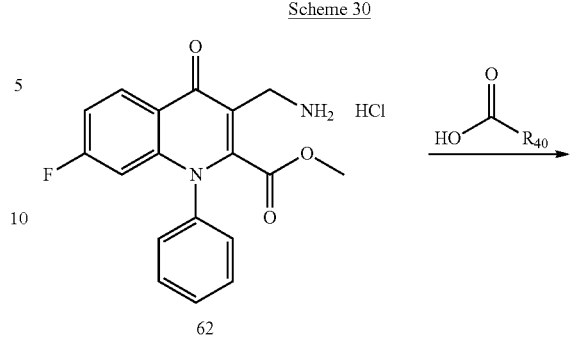

62

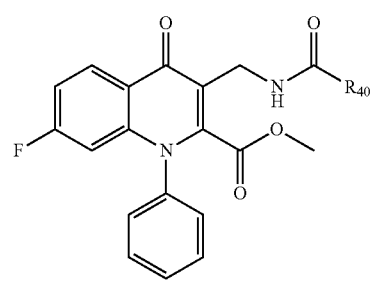

Example I-169 to I-170

Examples I-169 to I-170 can be synthesized following the reactions outlined in Scheme 30. Compound 62 (intermediate L) can be treated with different carboxylic acids under standard amide bond forming conditions (e.g. BOP, PyBrOP) to afford examples I-169 to I-170 (see for example, PCT WO2008/138920).

Scheme 31

23

Examples I-171, I-172

Scheme 32

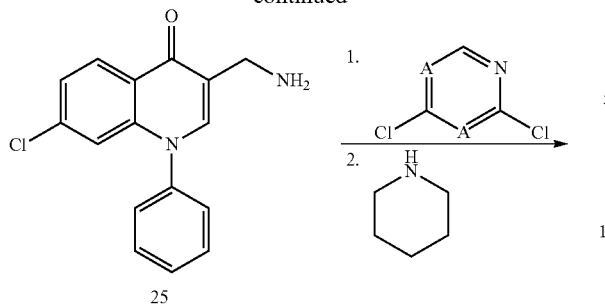

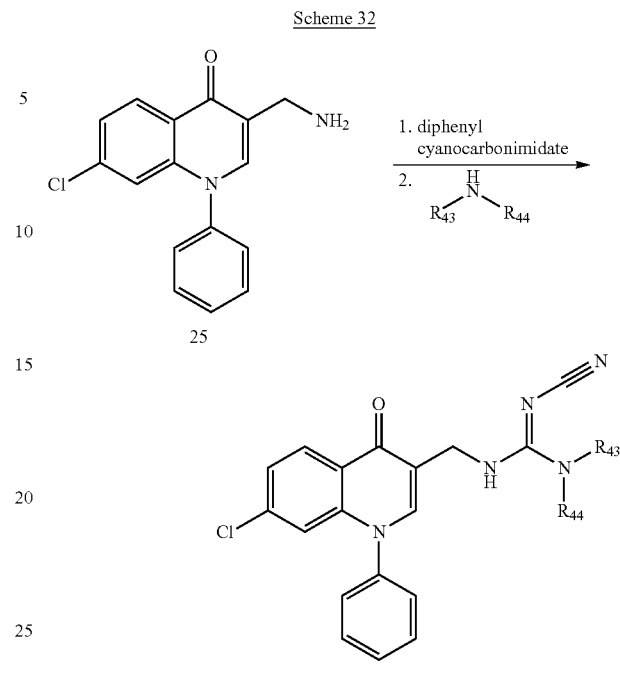

Examples I-177, I-178

Examples I-177 and I-178 can be synthesized following the reactions outlined in Scheme 32. Compound 25 (intermediate D) can be treated with diphenyl cyanocarbonimidate followed by displacement with different amines to afford examples I-177 and I-178 (see for example, Fotsch, C.; Sonnenberg, J. D.; Chen, N.; Hale, C.; Karbon, W.; Norman, M. H. *J. Med. Chem.* 2001, 44, 2344).

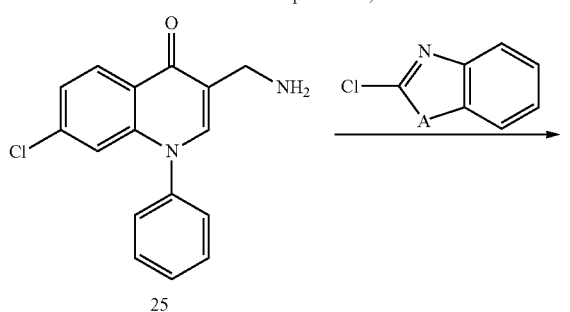

Examples I-173, I-174

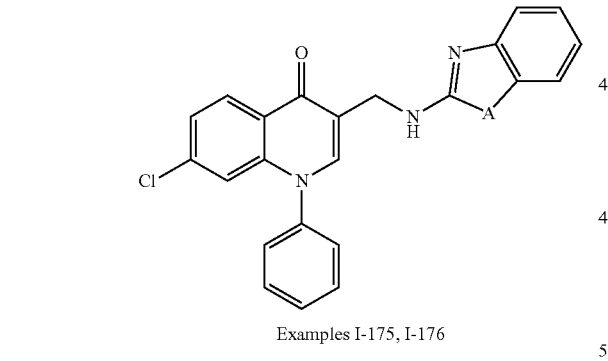

Examples I-175, I-176

Examples I-171 to I-176 can be synthesized following the reactions outlined in Scheme 31. Compound 23 can be treated with different quinazolin-4-amines to afford examples I-171 and I-172 (see for example, Gueiffier, A.; Viols, H.; Chapat, J. P.; Chavignon, O.; Teulade, J. C.; Dauphin, G. *J. Hetero. Chem.* 1990, 27, 421). Compound 25 (intermediate D) can be treated with 4,6-dichloropyrimidine or 2,4-dichloropyrimidine followed by halide displacement with piperidine to afford examples I-173 or I-174 (see for example, Luo, G.; Chen, L.; Poindexter, G. S. *Tett. Lett.* 2002, 43, 5739). Compound 25 (intermediate D) can be treated with 2-chlorobenzothiazole or 2-chlorobenzimidazole to afford examples I-175 or I-176 (see for example, Ganellin, C. R.; Hosseini, S. K.; Khalaf, Y. S.; Tertiuk, W.; Arrang, J-M.; Garbarg, M.; Ligneau, X.; Schwartz, J-C. *J. Med. Chem.* 1995, 38, 3342).

Scheme 33

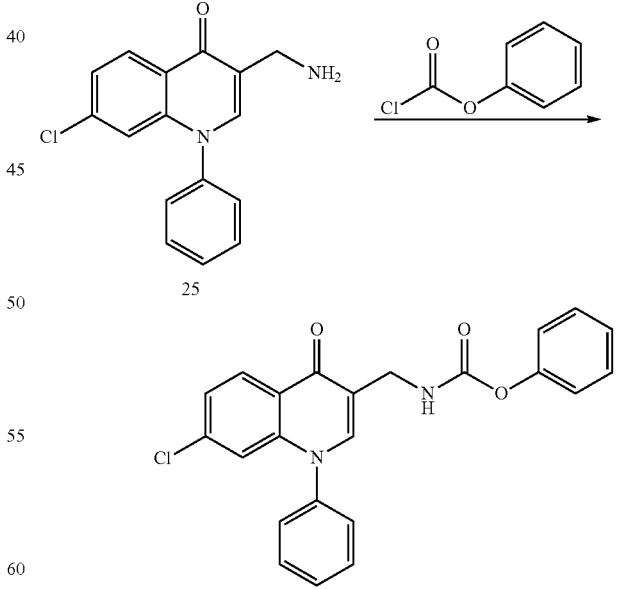

Example I-179

Example I-179 can be synthesized following the reaction outlined in Scheme 33. Compound 25 (intermediate D) can be treated with phenyl chloroformate to afford example I-179 (see for example, Barlow, J. J.; Main, B. G.; Snow, H. M. *J. Med. Chem.* 1981, 24, 315).

Scheme 34
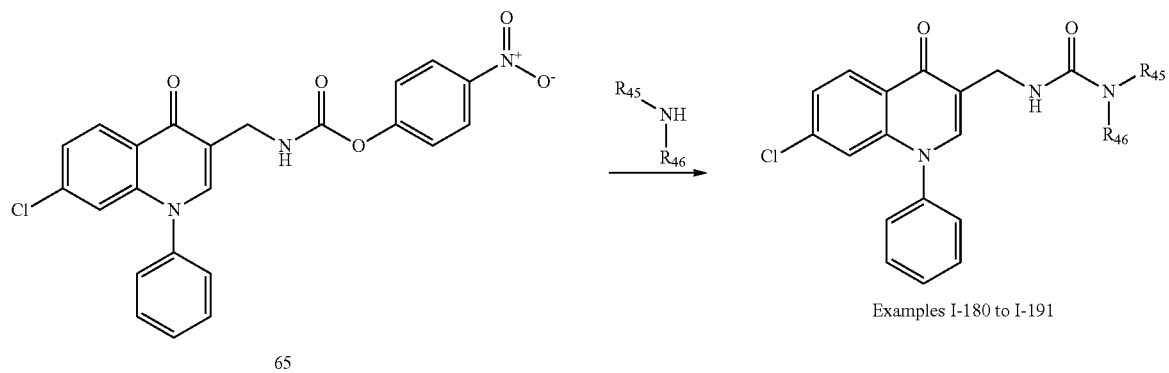
Examples I-180 to I-191
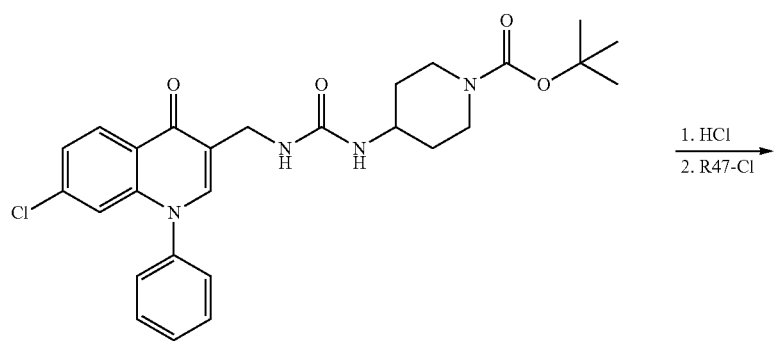
66 (Example I-192)
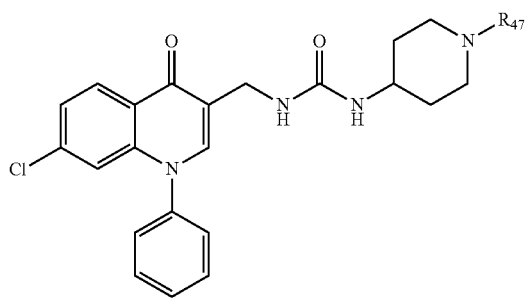
Examples I-193 to I-198
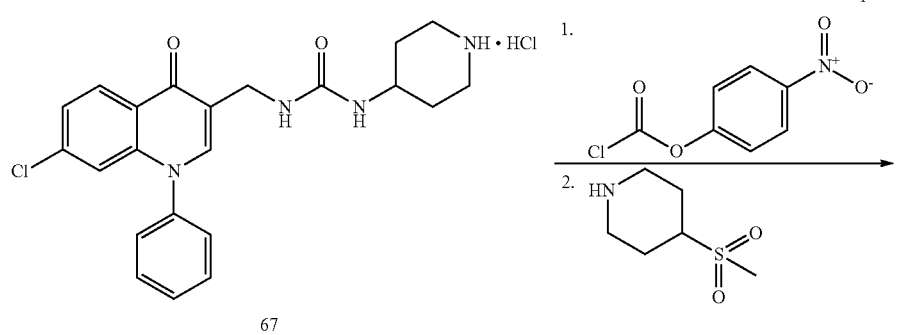
67

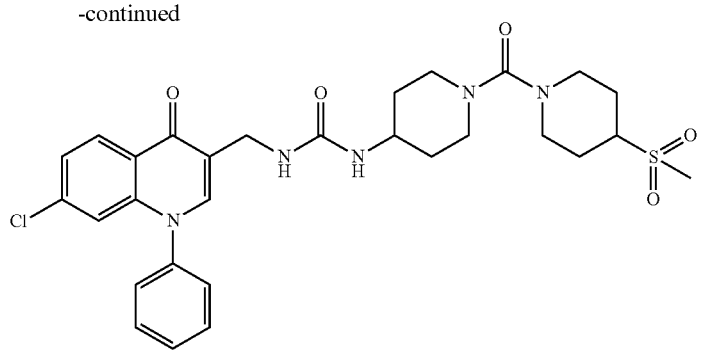

Example I-199

Examples I-180 to I-199 can be synthesized following the reactions outlined in Scheme 34 Compound 65 (intermediate M) can be treated with different amines to afford examples I-180 to I-191 (see for example, Liu, Q.; Luedtke, N. W.; Tor, Y. *Tet. Lett.* 2001, 42, 1445). Example I-192 (compound 66) can be prepared as previously described in Scheme 14. Compound 66 can be treated with hydrogen chloride for Boc-removal followed by capping with different chloroformate, acid chloride or sulfonyl chloride to give examples I-193 to I-198. Compound 67 (intermediate N) can be treated with 4-nitrophenyl chloroformate (see for example, Mallakpour, S.; Rafiee, Z. *Syn. Commun.* 2007, 37, 1927) followed by amine displacement to afford example I-199 (see for example, Liu, Q.; Luedtke, N. W.; Tor, Y. *Tet. Lett.* 2001, 42, 1445).

Scheme 35

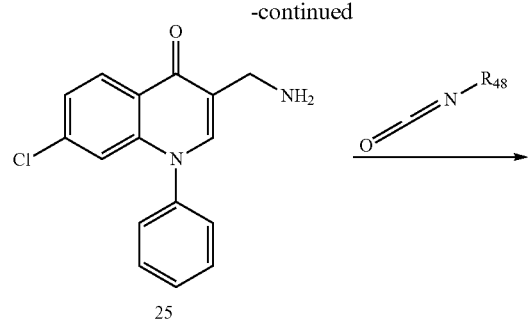

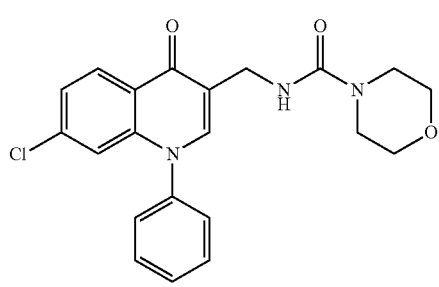

Example I-200

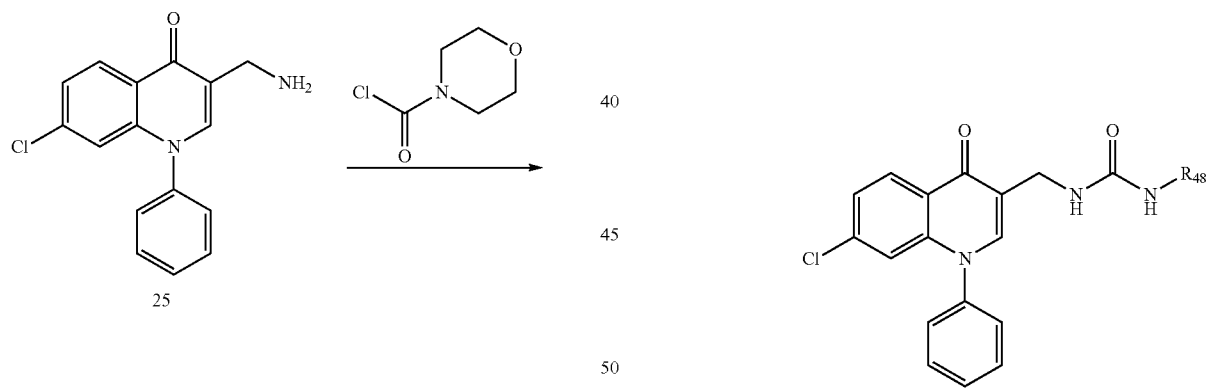

Examples I-201 to I-206

Examples I-200 to I-206 can be synthesized following the reactions outlined in Scheme 35. Compound 25 (intermediate D) can be treated with morpholine-4-carbonyl chloride to afford example I-200 (see for example, Barrett, D. G.; Catalano, J. G.; Deaton, D. N.; Hassell, A. M.; Long, S. T.; Miller, A. B.; Miller, L. R.; Shewchuk, L. M.; Wells-Knecht, K. J.; Willard, D. H., Jr.; Wright, L. L. *Bioorg. Med. Chem. Lett.* 2004, 14, 4897). Compound 25 (intermediate D) can be treated with different isocyanates to afford examples I-201 to I-206 (see for example, Tamaru, Y.; Hojo, M.; Higashimura, H.; Yoshida, Z. *J. Am. Chem. Soc.* 1988, 110, 3994).

Scheme 36

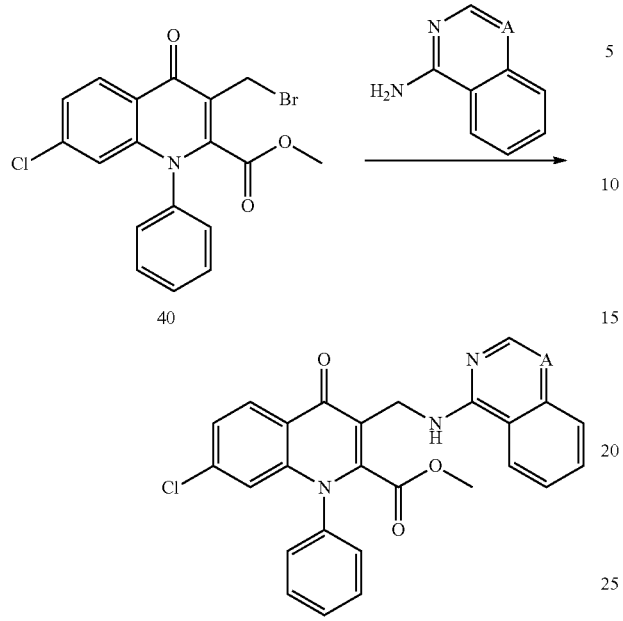

Examples I-207, I-208

Examples I-207 and I-208 can be synthesized following the reaction outlined in Scheme 36. Compound 40 can be treated with 1-aminoisoquinoline or quinazolin-4-ylamine to afford examples I-207 and I-208 (see for example, Gueiffier, A.; Viols, H.; Chapat, J. P.; Chavignon, O.; Teulade, J. C.; Dauphin, G. *J. Hetero. Chem.* 1990, 27, 421).

Scheme 37

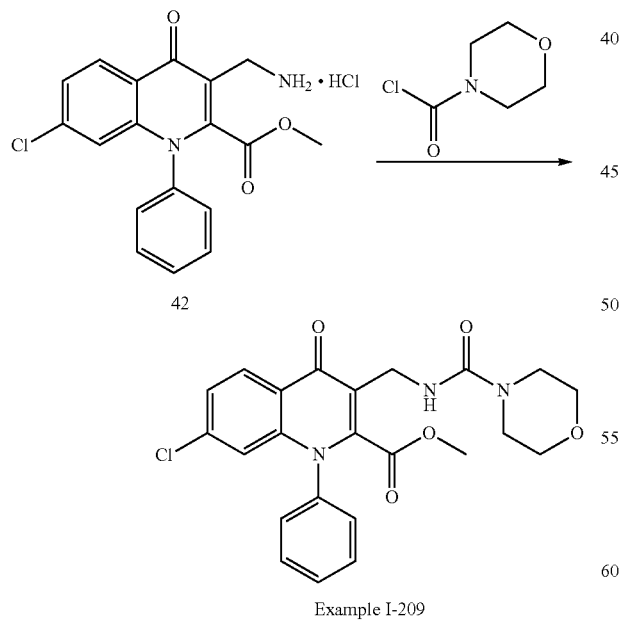

Example I-209

Example I-209 can be synthesized following the reaction outlined in Scheme 37. Compound 42 (intermediate I) can be treated with morpholine-4-carbonyl chloride to afford example I-209 (see for example, Barrett, D. G.; Catalano, J. G.; Deaton, D. N.; Hassell, A. M.; Long, S. T.; Miller, A. B.; Miller, L. R.; Shewchuk, L. M.; Wells-Knecht, K. J.; Willard, D. H., Jr.; Wright, L. L. *Bioorg. Med. Chem. Lett.* 2004, 14, 4897).

Scheme 38

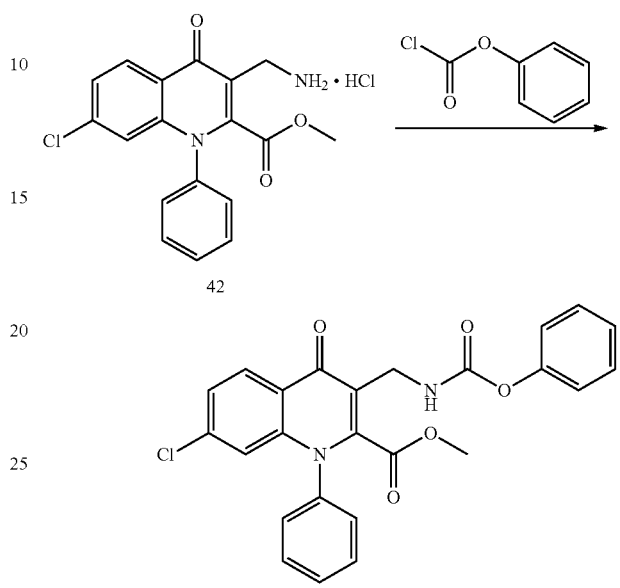

Example I-210

Example I-210 can be synthesized following the reaction outlined in Scheme 38. Compound 42 (intermediate I) can be treated with phenyl chloroformate to afford example I-210 (see for example, Mallakpour, S.; Rafiee, Z. *Syn. Commun.* 2007, 37, 1927).

Scheme 39

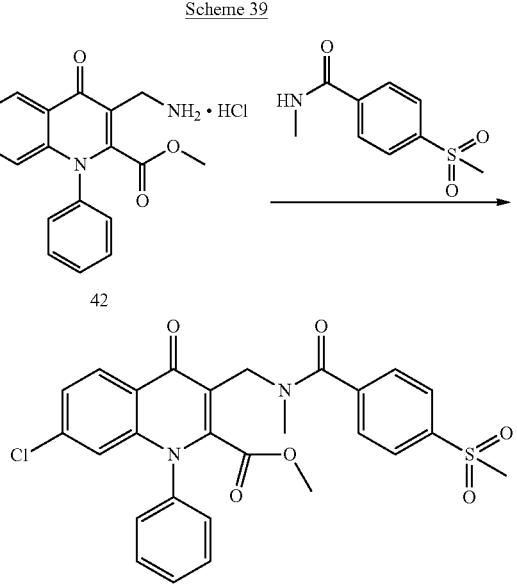

Example I-211

Example I-211 can be synthesized following the reaction outlined in Scheme 39. Compound 42 (intermediate I) can be treated with N-methyl-4-(methylsulfonyl)benzamide and a base (e.g. sodium hydride) to afford example I-211 (see for example, Padwa, A.; Kappe, C. O.; Cochran, J. E.; Snyder, J. P. *J. Org. Chem.* 1997, 62, 2786).

Pharmaceutical Compositions and Administration

The invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the invention will be administered in a therapeutically effective amount by any of the accepted modes of administration for agents that serve similar utilities. Suitable dosage ranges are typically I-500 mg daily, preferably I-100 mg daily, and most preferably I-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

Compounds of the invention may be administered as pharmaceutical formulations including those suitable for oral (including buccal and sub-lingual), rectal, nasal, topical, pulmonary, vaginal, or parenteral (including intramuscular, intraarterial, intrathecal, sub-cutaneous and intravenous) administration or in a form suitable for administration by inhalation or insufflation. The preferred manner of administration is generally oral using a convenient daily dosage regimen which can be adjusted according to the degree of affliction.

A compound or compounds of the invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use.

Formulations containing about one (1) mg of active ingredient or, more broadly, about 0.01 to about one hundred (100) mg, per tablet, are accordingly suitable representative unit dosage forms.

The compounds of the invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatin, tragacanth, methylcellulose, sodium carboxy-methylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the invention may also be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the invention may be formulated for vaginal administration. Pessaries, tampons, creams, gels, pastes, foams or sprays containing in addition to the active ingredient such carriers as are known in the art to be appropriate.

The subject compounds may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chloro-fluorocarbon (CFC), for example, dichlorodifluoromethane, trichlorofluoromethane, or dichloro-tetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to a skin-adhesive solid support. The compound of interest can also be combined with a penetration enhancer, e.g., Azone (1-dodecylazacyclo-heptan-2-one). Sustained release delivery systems are inserted subcutaneously into the sub-dermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described below.

Pharmaceutical compositions of the subject Compounds for administration via several routes are prepared as described in this Example.

| Composition for Oral Administration (A) | |
| --- | --- |
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration (B) | |
| --- | --- |
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration (C) | |
| --- | --- |
| Ingredient | % wt./wt. |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

| Parenteral Formulation (D) | |
|---|---|
| Ingredient | % wt./wt. |
| Active ingredient | 0.25 g |
| Sodium Chloride | qs to make isotonic |
| Water for injection to | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

Additional objects, advantages, and novel features of this invention will become apparent to those skilled in the art upon examination of the following examples thereof, which are not intended to be limiting.

Indications and Methods of Treatment

The compounds of this invention are JNK inhibitors and as such are expected to be effective in the treatment of a wide range of JNK mediated disorders. Exemplary JNK mediated disorders include, but are not limited to, kidney disease, autoimmune disorders, inflammatory disorders, metabolic disorders, neurological disease, and cancer. Accordingly, compounds of the invention can be used to treat one or more of such disorders. In some embodiments, compounds of the invention can be used to treat a JNK mediated disorder such as rheumatoid arthritis, asthma, type II diabetes, Alzheimer's disease, Parkinson's disease or stroke.

In one aspect, the application provides a method of treating a JNK-mediated disorder in a subject having a JNK-mediated disorder, said method comprising administering to a subject in need thereof a therapeutically effective amount of any of the above compounds.

In certain embodiments of the method of treating a JNK-mediated disorder, the JNK-mediated disorder is characterized by cellular proliferation.

In certain embodiments of the method of treating a JNK-mediated disorder, the JNK-mediated disorder is arthritis.

In certain embodiments of the method of treating a JNK-mediated disorder, the arthritis is rheumatoid arthritis.

In certain embodiments of the method of treating a JNK-mediated disorder, the JNK-mediated disorder is asthma.

In certain embodiments of the method of treating a JNK-mediated disorder, the JNK-mediated disorder is diabetes.

In certain embodiments of the method of treating a JNK-mediated disorder, the JNK-mediated disorder is Alzheimer's disease.

In certain embodiments of the method of treating a JNK-mediated disorder, the JNK-mediated disorder is Parkinson's disease.

In certain embodiments of the method of treating a JNK-mediated disorder, the JNK-mediated disorder is ischemic stroke.

In certain embodiments of the method of treating a JNK-mediated disorder, the JNK-mediated disorder is cancer.

In certain embodiments of the method for treating a JNK-mediated disorder, wherein the JNK-mediated disorder is cancer, the cancer is brain cancer.

In certain embodiments of the method for treating a JNK-mediated disorder, wherein the JNK-mediated disorder is cancer, the cancer is leukemia.

In certain embodiments of the method of treating a JNK-mediated disorder, the JNK-mediated disorder is kidney disease.

Combination Therapy (not Just for Inflammation)

In one aspect, the application provides a method for treating a JNK-mediated disorder comprising co-administering to a patient in need thereof a therapeutically effective amount of an anti-inflammatory compound in combination with the compound of any of the above embodiments, variations, or aspects.

EXAMPLES

The following preparations and examples are given to enable those skilled in the art to more clearly understand and to practice the present invention. They should not be considered as limiting the scope of the invention, but merely as being illustrative and representative thereof.

Abbreviations
$Ac_2O$ Acetic anhydride
AcOH Acetic acid
DBU 1,8-Diazabicyclo[5.4.0]undec-7-ene
DCE 1,2-Dichloroethane
DCM Dichloromethane/Methylene chloride
DIPEA Diisopropylethylamine
DMF N,N-dimethylformamide
DMSO Dimethyl sulfoxide
EDCI 1-(3-Dimethylaminopropyl)-3-ethylcarbodiimide hydrochloride
$Et_2O$ Diethyl ether
EtOH Ethanol/Ethyl alcohol
EtOAc Ethyl acetate
HOBt 1-Hydroxybenzotriazole
LDA Lithium diisopropylamide
LiHMDS Lithium bis(trimethylsilyl)amide
m-CPBA 3-Chloroperoxybenzoic acid
MeOH Methanol/Methyl alcohol
MW Microwaves
NMP 1-Methyl-2-pyrrolidinone
PMB 4-Methoxy benzyl
RT Room temperature
TBME tert-Butyl methyl ether
TFA Trifluoroacetic acid
$Tf_2O$ Trifluoromethanesulfonic anhydride
THF Tetrahydrofuran
TLC Thin layer chromatography General Conditions Compounds of the invention can be made by a variety of methods depicted in the illustrative synthetic reactions described below in the Examples section.

The starting materials and reagents used in preparing these compounds generally are either available from commercial suppliers, such as Aldrich Chemical Co., or are prepared by methods known to those skilled in the art following procedures set forth in references such as Fieser and Fieser's *Reagents for Organic Synthesis*; Wiley & Sons: New York, 1991, Volumes 1-15; Rodd's *Chemistry of Carbon Compounds*, Elsevier Science Publishers, 1989, Volumes 1-5 and Supplementals; and *Organic Reactions*, Wiley & Sons: New York, 1991, Volumes 1-40. It should be appreciated that the synthetic reaction schemes shown in the Examples section are merely illustrative of some methods by which the compounds of the invention can be synthesized, and various modifications to these synthetic reaction schemes can be made and will be suggested to one skilled in the art having referred to the disclosure contained in this application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein are typically conducted under an inert atmosphere at atmospheric pressure at a reaction temperature range of from about −78° C. to about 150° C., often from about 0° C. to about 125° C., and more often and conveniently at about room (or ambient) temperature, e.g., about 20° C.

Preparative reverse-phase high-pressure liquid chromatography (RP HPLC) was performed using one of the following systems: (A). a Waters Delta prep 4000 pump/controller, a 486 detector set at 215 nm, and a LKB Ultrorac fraction collector; or (B). a Sciex LC/MS system with a 150 EX single quad mass spec, a Shimadzu LC system, a LEAP autoinjector, and a Gilson fraction collector. The sample was dissolved in a mixture of acetonitrile/20 mM aqueous ammonium acetate or acetonitrile/water/TFA, applied on a Pursuit C-18 20×100 mm column and eluted at 20 mL/min with a linear gradient of 10%-90% B, where (A): 20 mM aqueous ammonium acetate (pH 7.0) and (B): acetonitrile or (A): water with 0.05% TFA and (B): acetonitrile with 0.05% TFA.

Preparative Examples

Part I

Intermediates

Preparation of 3-aminomethyl-7-chloro-2-oxazol-2-yl-1-phenyl-1H-quinolin-4-one trifluoroacetate salt (Intermediate A)

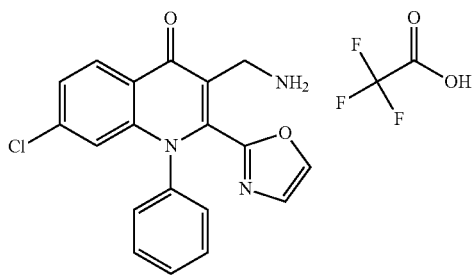 [SMILES: NCc1c(-c2ncco2)n(-c2ccccc2)c2cc(Cl)ccc2c1=O ; O=C(O)C(F)(F)F]

Step 1: Preparation of 4-chloro-2-phenylamino-benzoic acid

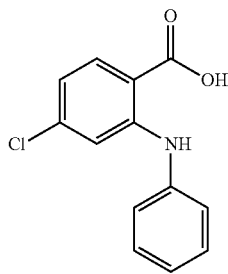 [SMILES: O=C(O)c1ccc(Cl)cc1Nc1ccccc1]

To a solution of 2-bromo-4-chlorobenzoic acid (25.0 g, 106.0 mmol) in 2-ethoxyethanol (40 mL) was added copper powder (0.74 g, 11.6 mmol), copper (I) oxide (0.76 g, 5.3 mmol), potassium carbonate (15.8 g, 114.0 mmol) at room temperature under nitrogen. After stirring for 5 min., aniline (11.2 mL, 124 mmol) was added to the reaction mixture. The reaction mixture was heated at 135° C. for 48 hr. Completion of the reaction was confirmed by silica TLC (mobile phase; hexane:ethyl acetate=1:1; $R_f$=0.6). The reaction mixture was cooled to room temperature, poured into water (30 mL) with continuous shaking and was acidified with aqueous 1N HCl to form a precipitate. The mixture was stirred overnight at room temperature. The mixture was filtered through a sintered glass funnel. The solids were washed with water (2×100 mL). The obtained solids were dried under high vacuum to yield 4-chloro-2-phenylamino-benzoic acid (19.0 g, 72.3% crude yield). The crude product was used in the next step without further purification. MS calcd. for $C_{13}H_{10}ClNO_2$ [(M+H)$^+$] 247, obsd. 248.

Step 2: Preparation of 4-chloro-N-methoxy-N-methyl-2-phenylamino-benzamide

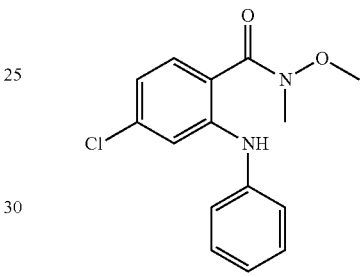

To a solution of 4-chloro-2-phenylamino-benzoic acid (10.1 g, 41.0 mmol) in DMF (200 mL) was added O-benzotriazole-N,N,N',N'-tetramethyl-uronium-hexafluorophosphate (HBTU, 31.2 g, 82.0 mmol), N,O-dimethyl-hydroxylamine hydrochloride (7.94 g, 82.0 mmol), and N,N-diisopropylethylamine (45.0 g, 350.0 mmol) at room temperature. The resulting mixture was stirred for 24 hr. at room temperature. Completion of the reaction was confirmed by silica TLC (mobile phase; hexane:ethyl acetate=7:3; $R_f$=0.5). The reaction mixture was diluted with ethyl acetate (600 mL) and the organic layer was washed with water (4×200 mL) and brine (200 mL). The organic layer was dried over anhydrous $Na_2SO_4$ and volatiles were removed under reduced pressure. The crude material was purified over silica gel (100-200 mesh) column chromatography, using gradient polarity mobile phase (ethyl acetate:hexane=1:9-1:4), to give 4-chloro-N-methoxy-N-methyl-2-phenylamino-benzamide (6.62 g, 56.4% yield) as a yellow solid. $^1$H NMR (DMSO-$d_6$) δ ppm 7.93 (s, 1H) 7.20-7.39 (m, 3H) 7.02-7.17 (m, 3H) 6.88-6.99 (m, 2H) 3.50 (s, 3H) 3.20 (s, 3H). MS calcd. for $C_{15}H_{15}ClN_2O_2$ [(M+H)$^+$] 291.0, obsd. 291.0, [(M-$C_2H_6NO)^+$] 230.0, obsd. 230.0.

Step 3: Preparation of 1-(4-chloro-2-phenylamino-phenyl)-propan-1-one

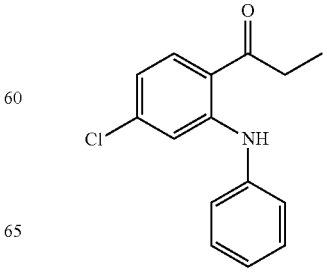

To a solution of 4-chloro-N-methoxy-N-methyl-2-phenylamino-benzamide (5.0 g, 17.2 mmol) in THF (60 mL) was added ethylmagnesium bromide (1M solution in THF, 70 mL, 70 mmol) dropwise at 0° C. under nitrogen. The mixture was slowly warmed to room temperature and stirred for 2 hr. Completion of the reaction was monitored by silica TLC (mobile phase; hexane:ethyl acetate=4:1; $R_f$=0.5). Reaction was quenched with an aqueous solution of 1N HCl (50 mL) at 0° C. and was extracted with ethyl acetate (2×300 mL). The combined organic layers were washed with water (100 mL), brine (100 mL), dried over anhydrous $Na_2SO_4$, and concentrated under reduced pressure. The crude material was purified using silica gel (100-200 mesh) column chromatography, using gradient polarity mobile phase (ethyl acetate:hexane=1:91:4), to give 1-(4-chloro-2-phenylamino-phenyl)-propan-1-one (4.15 g, 92.9% yield) as a yellow oil. $^1$H NMR (DMSO-$d_6$) δ ppm 10.53 (s, 1H) 8.00 (d, J=8.7 Hz, 1H) 7.34-7.51 (m, 2H) 7.28 (d, J=7.7 Hz, 2H) 7.13-7.23 (m, 1H) 7.07 (d, J=1.8 Hz, 1H) 6.82 (dd, J=8.6, 1.9 Hz, 1H) 3.07 (q, J=7.2 Hz, 2H) 1.09 (t, J=7.3 Hz, 3H).

Step 4: Preparation of oxazole-2-carbonyl chloride

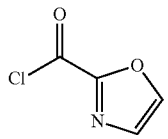

In a 10 mL round-bottomed flask, oxazole-2-carboxylic acid (300 mg, 2.65 mmol) and DMF (10.3 μL, 0.133 mmol) were combined with dichloromethane (2 mL) to give a white suspension. Oxalyl chloride (381 mg, 254 μL, 3.00 mmol) was added slowly over 15 min. and the reaction mixture turned into a clear solution. The reaction mixture was stirred at room temperature for 2 hr. After this time, the solvent was removed to give crude oxazole-2-carbonyl chloride as a yellow oil which solidified over time. The crude material was used in the next step without further purification.

Step 5: Preparation of 7-chloro-3-methyl-2-oxazol-2-yl-1-phenyl-1H-quinolin-4-one

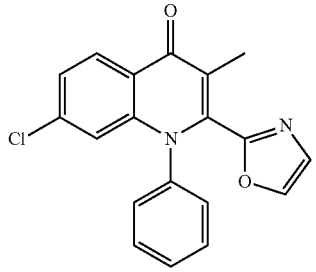 [SMILES: Cc1c(-c2ncco2)n(-c2ccccc2)c2cc(Cl)ccc2c1=O]

In a 25 mL round-bottomed flask, 1-(4-chloro-2-phenylamino-phenyl)-propan-1-one (522 mg, 2.01 mmol) was combined with THF (4 mL) to give a yellow solution. Sodium bis(trimethylsilyl)amide (1.0 M in THF) (5.02 mL, 5.02 mmol) was added slowly dropwise, resulting in a dark red solution. A mixture of oxazole-2-carbonyl chloride (344 mg, 2.61 mmol) in THF (8 mL) and 8 drops of DMF were added to the reaction mixture. The resulting mixture was stirred at room temperature for 5 hr. The reaction mixture was quenched by the addition of water and the aqueous layer was extracted with ethyl acetate. The organic phase was dried ($MgSO_4$), filtered, then concentrated to afford a yellow oil. The crude material was purified by flash chromatography (silica gel, 80 g, 25-65% ethyl acetate in hexanes) to give 7-chloro-3-methyl-2-oxazol-2-yl-1-phenyl-1H-quinolin-4-one (160 mg, 23.6%) as a yellowish solid. MS calcd. for $C_{19}H_{13}ClN_2O_2$ [(M+H)$^+$] 337, obsd. 337.

Step 6: Preparation 3-bromomethyl-7-chloro-2-oxazol-2-yl-1-phenyl-1H-quinolin-4-one

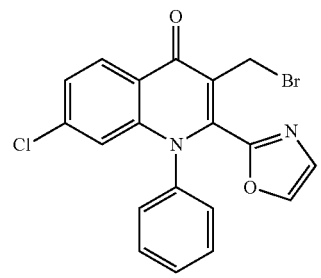 [SMILES: O=c1c(CBr)c(-c2ncco2)n(-c2ccccc2)c2cc(Cl)ccc12]

In a 250 mL round bottom flask, 7-chloro-3-methyl-2-oxazol-2-yl-1-phenyl-1H-quinolin-4-one (0.50 g, 1.48 mmol), N-bromosuccinimide (291 mg, 1.63 mmol) and 2,2'-azobisisobutyronitrile (AIBN, 36.6 mg, 0.223 mmol) were combined with carbon tetrachloride (20 mL). The mixture was heated to reflux for 2 hr. The reaction was cooled to room temperature and solids were filtered off. The mother liquor was concentrated and purified by flash chromatography using 3:2 hexane-ethyl acetate to afford 3-bromomethyl-7-chloro-2-oxazol-2-yl-1-phenyl-1H-quinolin-4-one (300 mg, 49% yield) as a white solid.

Step 7: Preparation of 3-aminomethyl-7-chloro-2-oxazol-2-yl-1-phenyl-1H-quinolin-4-one bis(tert-butyl carbamate)

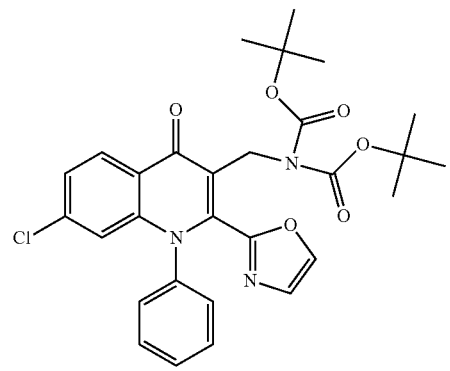 [SMILES: CC(C)(C)OC(=O)N(Cc1c(-c2ncco2)n(-c2ccccc2)c2cc(Cl)ccc2c1=O)C(=O)OC(C)(C)C]

In a 10 mL round bottom flask, di-tert butyl iminodicarboxylate (52.3 mg, 0.24 mmol) and 60% sodium hydride (20 mg, 0.5 mmol) were added sequentially to anhydrous DMF (3 mL). The reaction was stirred at room temperature for 30 min. to give a light yellow solution. Then 3-bromomethyl-7-chloro-2-oxazol-2-yl-1-phenyl-1H-quinolin-4-one (0.10 g, 0.24 mmol) was added and the mixture was stirred at room temperature for 5 hr. The reaction was quenched with a few drops of water and concentrated to dryness. The crude material was purified by HPLC using 25% ethyl acetate-hexane to obtain 3-aminomethyl-7-chloro-2-oxazol-2-yl-1-phenyl-1H-quinolin-4-one bis(tert-butyl-carbamate) (50 mg, 38% yield). MS calcd. for $C_{29}H_{30}ClN_3O_6$ [(M+H)$^+$] 553, obsd. 553.

Step 8: Preparation of 3-aminomethyl-7-chloro-2-oxazol-2-yl-1-phenyl-1H-quinolin-4-one trifluoroacetate salt

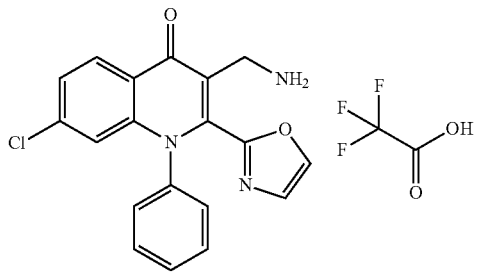

In a 10 mL round bottom flask, 3-aminomethyl-7-chloro-2-oxazol-2-yl-1-phenyl-1H-quinolin-4-one bis(tert-butyl-carbamate) (50 mg, 0.09 mmol) and trifluoroacetic acid (1 mL) were added to anhydrous dichloromethane (1 mL). The reaction mixture was stirred at room temperature for 2 hr. The mixture was concentrated to dryness to give 3-aminomethyl-7-chloro-2-oxazol-2-yl-1-phenyl-1H-quinolin-4-one trifluoroacetate salt. The intermediate was used in the next step without further purification. MS calcd. for $C_{19}H_{14}ClN_3O_2$ [(M+H)$^+$] 352, obsd 352.

Preparation of 3-aminomethyl-2-oxazol-2-yl-1-phenyl-1H-[1,8]naphthyridin-4-one trifluoroacetate salt (Intermediate B)

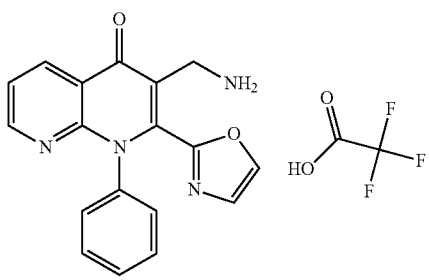

Step 1: Preparation of 1-(2-phenylamino-pyridin-3-yl)-propan-1-one

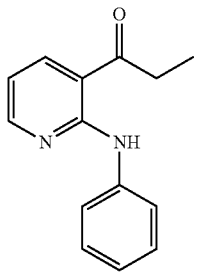 [SMILES: CCC(=O)c1cccnc1Nc1ccccc1]

A solution of 1-(2-chloro-pyridin-3-yl)-propan-1-one (6.0 g, 35.4 mmol) in 1,4-dioxane (59.0 mL) in a high pressure reaction tube was treated with (1S)-(+)-10-camphorsulfonic acid (20.5 g, 88.4 mmol). The resulting mixture was heated to 70° C. until all of the solids went into solution. The reaction was raised out of the heating bath, opened and treated with aniline (4.94 g, 4.84 mL, 53.1 mmol). The vessel was then re-sealed and heated at 95° C. overnight. After cooling to room temperature, the reaction was diluted with methylene chloride (75 mL) and was washed with a saturated aqueous sodium bicarbonate solution (2×100 mL). The organics were then dried over sodium sulfate, filtered, concentrated in vacuo and dried under high vacuum. The residue was then recrystallized from methanol. Collection by filtration (washing with 10 mL of methanol and 30 mL of hexanes) afforded 1-(2-phenylamino-pyridin-3-yl)-propan-1-one (5.64 g) of the desired product as a yellow, crystalline solid. The mother liquor was dry loaded onto silica gel. Flash chromatography (40 g, 10-25% ethyl acetate-hexanes) afforded an additional amount (1.28 g, 86% total yield) of the desired product as a yellow solid.

Step 2: Preparation of 3-methyl-2-oxazol-2-yl-1-phenyl-1H-[1,8]naphthyridin-4-one

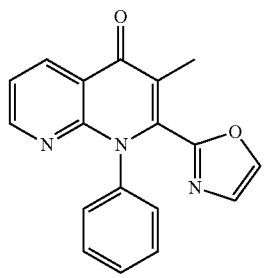 [SMILES: Cc1c(-c2ncco2)n(-c2ccccc2)c2ncccc2c1=O]

A solution of 1-(2-phenylamino-pyridin-3-yl)-propan-1-one (2.0 g, 8.84 mmol) in THF (17.7 mL) at 25° C. was treated with sodium bis(trimethylsilyl)amide (1.0 M in THF) (22.1 mL, 22.1 mmol). The resulting red solution was then treated with a mixture of oxazole-2-carbonyl chloride (1.51 g, 11.5 mmol) in THF (8 mL) and 10 drops of DMF. The reaction was then stirred at 25° C. overnight. The reaction was diluted with water (50 mL) and was then extracted into ethyl acetate (3×50 mL). The organics were dried over sodium sulfate, filtered and concentrated in vacuo. The resulting residue was absorbed onto silica and dried under high vacuum. Flash chromatography (25 g, 25%-75% ethyl acetate-hexanes) afforded 3-methyl-2-oxazol-2-yl-1-phenyl-1H-[1,8]naphthyridin-4-one (540 mg, 20.1%) as a light yellow solid.

Step 3: Preparation of 3-bromomethyl-2-oxazol-2-yl-1-phenyl-1H-[1,8]naphthyridin-4-one

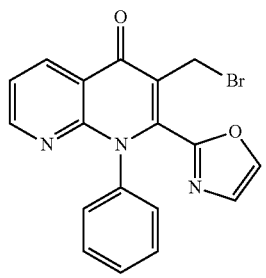 [SMILES: O=c1c(CBr)c(-c2ncco2)n(-c2ccccc2)c2ncccc12]

A mixture of 2,2'-azobis(2-methylpropionitrile) (AIBN, 43.4 mg, 0.265 mmol), N-bromosuccinimide (345 mg, 1.94 mmol) and 3-methyl-2-oxazol-2-yl-1-phenyl-1H-[1,8]naphthyridin-4-one (535 mg, 1.76 mmol) in carbon tetrachloride (22.0 mL) was heated at 90° C. for 2 hr. The reaction was cooled to 25° C. and sat overnight. The reaction was diluted with water (30 mL) and extracted into methylene chloride (2×50 mL). The combined organics were then washed with a saturated aqueous solution of sodium bicarbonate (2×50 mL), dried over sodium sulfate, filtered and concentrated in vacuo. The residue was dissolved in methylene chloride and methanol, treated with silica gel, re-concentrated and dried in vacuo. Flash chromatography (40 g, 15%-40% ethyl acetate-hexanes) gave 3-bromomethyl-2-oxazol-2-yl-1-phenyl-1H-[1,8]naphthyridin-4-one (321.7 mg, 47.7%).

Step 4: Preparation of 3-aminomethyl-2-oxazol-2-yl-1-phenyl-1H-[1,8]naphthyridin-4-one bis(tert-butyl carbamate)

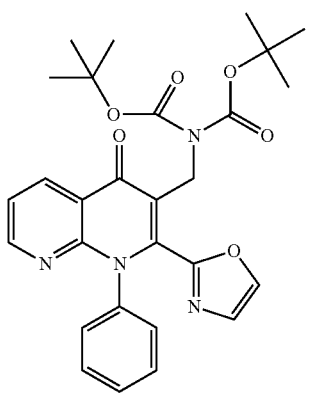 [SMILES: CC(C)(C)OC(=O)N(Cc1c(-c2ncco2)n(-c2ccccc2)c2ncccc2c1=O)C(=O)OC(C)(C)C]

To a mixture of 3-bromomethyl-2-oxazol-2-yl-1-phenyl-1H-[1,8]naphthyridin-4-one (320 mg, 0.837 mmol), THF (2.79 mL) and DMF (2.79 mL) was added di-tert-butyl iminodicarboxylate (182 mg, 0.837 mmol) and sodium hydride (60% in mineral oil, 33.5 mg, 0.837 mmol). The reaction mixture was heated at 45° C. overnight which turned into a clear yellow solution. The reaction was diluted with a saturated aqueous ammonium chloride solution (30 mL) and was extracted into methylene chloride (3×50 mL). The combined organic layers were dried over sodium sulfate, filtered and concentrated in vacuo. Flash chromatography (30%-50% ethyl acetate-hexanes) afforded 3-aminomethyl-2-oxazol-2-yl-1-phenyl-1H-[1,8]naphthyridin-4-one bis(tert-butyl carbamate) (298.7 mg, 68.8%) as an off-white solid.

Step 5: Preparation of 3-aminomethyl-2-oxazol-2-yl-1-phenyl-1H-[1,8]naphthyridin-4-one trifluoroacetate salt

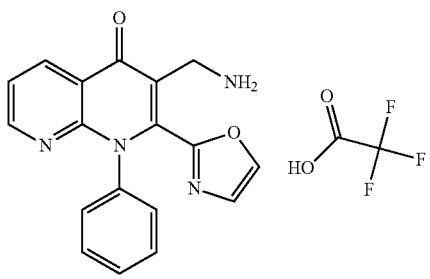

A solution of 3-aminomethyl-2-oxazol-2-yl-1-phenyl-1H-[1,8]naphthyridin-4-one bis(tert-butyl carbamate) (26 mg, 50.1 µmol) in methylene chloride (167 µL) at 25° C. was treated with TFA (83.6 µL). The reaction was stirred at 25° C. for 4 hr. The reaction was concentrated in vacuo, triturated with diethyl ether and then dried under high vacuum to give 3-aminomethyl-2-oxazol-2-yl-1-phenyl-1H-[1,8]naphthyridin-4-one trifluoroacetate salt. The product was used in subsequent steps without further purification.

Preparation of 3-aminomethyl-7-chloro-4-oxo-1-phenyl-1,4-dihydro-quinoline-2-carboxylic acid dimethylamide hydrochloride salt (Intermediate C)

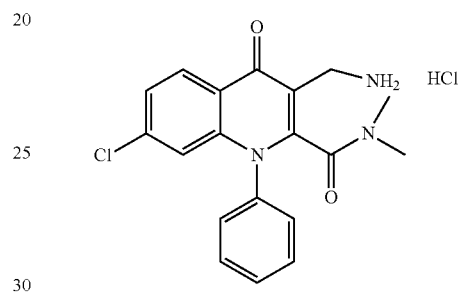

Step 1: Preparation of N-(5-chloro-2-propionyl-phenyl)-N-phenyl-oxalamic acid methyl ester

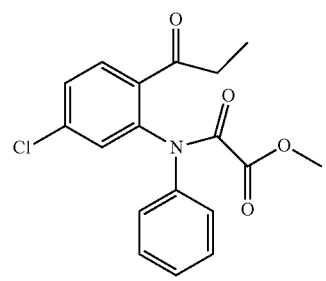 [SMILES: CCC(=O)c1ccc(Cl)cc1N(C(=O)C(=O)OC)c1ccccc1]

To a solution of 1-(4-chloro-2-phenylamino-phenyl)-propan-1-one (13.0 g, 50.2 mmol) in toluene (150 mL) was added methyl chlorooxoacetate (42.86 g, 350.0 mmol) at room temperature under nitrogen. The reaction mixture was heated at reflux at 110° C. for 16 hr. Completion of the reaction was monitored by silica TLC (mobile phase; hexane:ethyl acetate=1:1; $R_f$=0.5). The reaction mixture was concentrated under vacuum to afford 15.2 g (87.6% crude yield) of N-(5-chloro-2-propionyl-phenyl)-N-phenyl-oxalamic acid methyl ester. The crude product was used in the next step without further purification.

Step 2: Preparation of 7-chloro-3-methyl-4-oxo-1-phenyl-1,4-dihydro-quinoline-2-carboxylic acid methyl ester

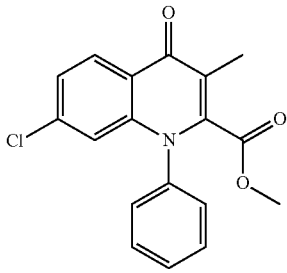 [SMILES: Cc1c(C(=O)O)n(-c2ccccc2)c2cc(Cl)ccc2c1=O]

To a stirred suspension of N-(5-chloro-2-propionyl-phenyl)-N-phenyl-oxalamic acid methyl ester (15.0 g, 43.5 mmol) in methanol (200 mL) was added potassium carbonate (35.0 g, 253 mmol) at room temperature. The mixture was heated at 80° C. for 1 hr. Completion of the reaction was monitored by silica TLC (mobile phase; hexane:ethyl acetate=7:3; $R_f$=0.6). The reaction mixture was cooled to room temperature. The reaction mixture was filtered through a sintered glass funnel and the solids were washed with MeOH (2×50 mL). The combined filtrates were concentrated under reduced pressure. The residue obtained was taken up in ethyl acetate (500 mL), washed with water (2×200 mL), dried over anhydrous $Na_2SO_4$, and concentrated under reduced pressure. The crude material was purified by washing with a mixture of hexane-ether to afford 7-chloro-3-methyl-4-oxo-1-phenyl-1,4-dihydro-quinoline-2-carboxylic acid methyl ester (10.5 g, 73.4% yield). $^1$H NMR (DMSO-$d_6$) δ 8.24 (d, J=8.7 Hz, 1H) 7.28-7.78 (m, 6H) 6.69 (d, J=1.7 Hz, 1H) 3.49 (s, 3H) 1.97 (s, 3H); MS calcd. for $C_{18}H_{14}ClNO_3$ [(M+H)$^+$] 328.0, obsd. 327.9.

Step 3: Preparation of 7-chloro-3-methyl-4-oxo-1-phenyl-1,4-dihydro-quinoline-2-carboxylic acid

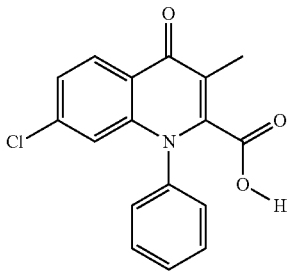

In a sealed tube, 7-chloro-3-methyl-4-oxo-1-phenyl-1,4-dihydro-quinoline-2-carboxylic acid methyl ester (3.84 g, 11.7 mmol) and 1N sodium hydroxide (70 mL, 70 mmol) were added to dioxane (150 mL). The reaction mixture was heated to 150° C. overnight. The reaction mixture was poured into 500 mL ethyl acetate and extracted with 1N HCl (1×400 mL) and brine (1×100 mL). The organic layers were dried over $Na_2SO_4$ and concentrated in vacuo. The crude material was triturated with diethyl ether (1×100 mL) to give 7-chloro-3-methyl-4-oxo-1-phenyl-1,4-dihydro-quinoline-2-carboxylic acid (3.40 g, 92.5% yield) as a white solid. MS calcd for $C_{17}H_{12}ClNO_3$ [(M+H)$^+$] 314, obsd. 314.

Step 4: Preparation of 7-chloro-3-methyl-4-oxo-1-phenyl-1,4-dihydro-quinoline-2-carboxylic acid dimethylamide

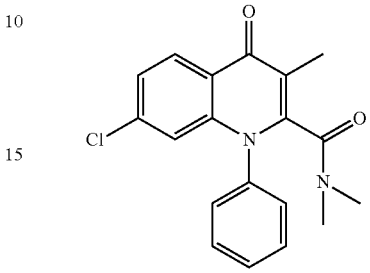

In a 50 mL round bottom flask, 7-chloro-3-methyl-4-oxo-1-phenyl-1,4-dihydro-quinoline-2-carboxylic acid (0.5 g, 1.60 mmol), bromo-tris-pyrrolidino-phosphonium hexafluorophosphate (PyBrOP, 1.11 g, 2.39 mmol) and N,N-diisopropylethylamine (1.11 mL, 6.37 mmol) were added to anhydrous DMF (5.0 mL). The mixture was stirred at room temperature for 30 min. Dimethylamine (2M in THF, 1.6 mL, 3.2 mmol) was added and the reaction mixture was stirred at room temperature for 48 hr. The mixture was concentrated to dryness and the crude was purified by flash chromatography using 3:2 hexane-ethyl acetate to afford 7-chloro-3-methyl-4-oxo-1-phenyl-1,4-dihydro-quinoline-2-carboxylic acid dimethylamide (600 mg, >100% yield). MS calcd for $C_{19}H_{17}ClN_2O_2$ [(M+H)$^+$] 341, obsd 341.

Step 5: Preparation of 3-azidomethyl-7-chloro-4-oxo-1-phenyl-1,4-dihydro-quinoline-2-carboxylic acid dimethylamide

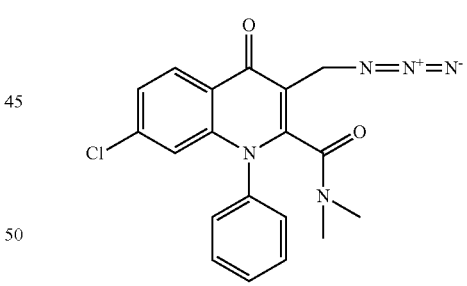

In a 50 mL round bottom flask, 7-chloro-3-methyl-4-oxo-1-phenyl-1,4-dihydro-quinoline-2-carboxylic acid dimethylamide (0.54 g, 1.58 mmol), N-bromosuccinimide (0.367 g, 2.06 mmol) and AIBN (78 mg, 0.475 mmol) were added to dichloroethane (6.0 mL). The reaction mixture was heated to reflux for 5 hr. The mixture was concentrated to dryness and the crude (containing 3-bromomethyl-7-chloro-4-oxo-1-phenyl-1,4-dihydro-quinoline-2-carboxylic acid dimethylamide) was redissolved in DMF (6.0 mL). To the reaction mixture was added sodium azide (0.515 g, 7.92 mmol). The reaction was stirred at room temperature overnight. The mixture was partitioned between ethyl acetate and water and the organic layer was washed with aqueous sodium bicarbonate solution. The organic layer was dried, evaporated to dryness and purified by flash chromatography using 40% ethyl acetate-hexane to afford 3-azidomethyl-7-chloro-4-oxo-1-phenyl-1,4-dihydro-quinoline-2-carboxylic acid dimethylamide (260 mg, 43% yield).

Step 6: Preparation of 3-aminomethyl-7-chloro-4-oxo-1-phenyl-1,4-dihydro-quinoline-2-carboxylic acid dimethylamide hydrochloride salt

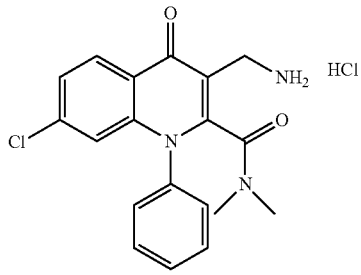 [SMILES: CN(C)C(=O)c1c(CN)c(=O)c2ccc(Cl)cc2n1-c1ccccc1 ; Cl]

In a 50 mL round-bottomed flask, 3-azidomethyl-7-chloro-4-oxo-1-phenyl-1,4-dihydro-quinoline-2-carboxylic acid dimethylamide (0.40 g, 1.05 mmol), platinum (IV) oxide (0.05 g, 0.204 mmol) and 4N HCl (0.1 mL) were added to 1:1 $CH_2Cl_2$/ethyl acetate (10 mL). The reaction was charged with 1 atm $H_2$ using a balloon and stirred at room temperature for 4 hr. The catalyst was filtered off and washed with methanol. The filtrate was evaporated to afford 3-aminomethyl-7-chloro-4-oxo-1-phenyl-1,4-dihydro-quinoline-2-carboxylic acid dimethylamide hydrochloride salt (0.303 g, 74% yield). The intermediate was used in the next step without further purification. MS calcd. for $C_{19}H_{18}ClN_3O_2$ [(M+H)$^+$] 356, obsd 356.

Preparation of 3-aminomethyl-7-chloro-1-phenyl-1H-quinolin-4-one (Intermediate D)

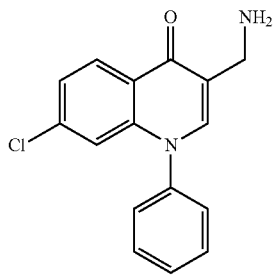 [SMILES: NCc1cn(-c2ccccc2)c2cc(Cl)ccc2c1=O]

Step 1: Preparation of 7-chloro-3-methyl-1-phenyl-1H-quinolin-4-one

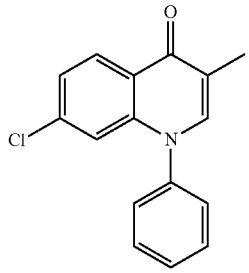 [SMILES: Cc1cn(-c2ccccc2)c2cc(Cl)ccc2c1=O]

To a mixture of THF (60 mL) and DMF (7.5 mL) at 0° C. under nitrogen was added oxalyl chloride (6.5 mL, 76.8 mmol) during which time a white precipitate formed. The temperature was slowly raised to room temp. and stirred for 1.5 hr. THF was distilled off from the reaction mixture under reduced pressure and under nitrogen. The gummy residue was further diluted with DMF (100 mL). A solution of 1-(4-chloro-2-phenylamino-phenyl)-propan-1-one (5.0 g, 19.30 mmol) in DMF (50 mL) was added to the reaction mixture at room temperature. The reaction was heated at 115° C. for 2 hr. The reaction mixture was brought down to room temperature, then diluted with water (750 mL), and the mixture was extracted with ethyl acetate (2×750 mL). The combined organic layers were washed with brine (500 mL), dried, and concentrated under reduced pressure to yield 7-chloro-3-methyl-1-phenyl-1H-quinolin-4-one (4.25 g, 81.6%) as an off-white solid. $^1$H NMR (DMSO-d$_6$) δ ppm 8.24 (d, J=8.8 Hz, 1H) 8.01 (s, 1H) 7.52-7.80 (m, 5H) 7.40 (dd, J=8.8, 1.8 Hz, 1H) 6.87 (d, J=1.8 Hz, 1H) 2.01 (s, 3H). MS calcd. for $C_{16}H_{12}ClNO$ [(M+H)$^+$] 270.0, obsd. 269.8.

Step 2: Preparation of 3-bromomethyl-7-chloro-1-phenyl-1H-quinolin-4-one

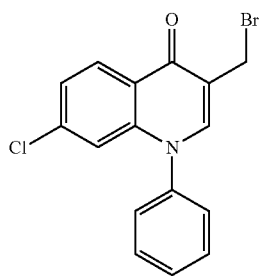 [SMILES: O=c1c(CBr)cn(-c2ccccc2)c2cc(Cl)ccc12]

In a 50 mL round-bottomed flask, 7-chloro-3-methyl-1-phenyl-1H-quinolin-4-one (0.142 g, 0.526 mmol), NBS (103 mg, 0.579 mol) and AIBN (13.0 mg, 0.079 mmol) were combined with carbon tetrachloride (3.5 mL) to give a colorless solution. The reaction mixture was heated at 115° C. for 1 h. The reaction mixture was cooled to room temp and then cooled to 0° C. The mixture was filtered to remove succinimide and the filtrate was concentrated. The crude product was used in the next step without further purification.

Step 3: Preparation of 3-azidomethyl-7-chloro-1-phenyl-1H-quinolin-4-one

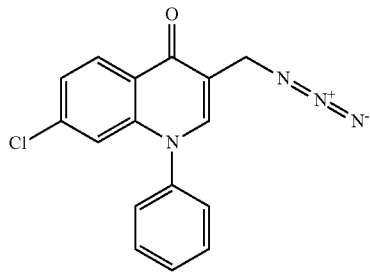 [SMILES: [N-]=[N+]=NCc1cn(-c2ccccc2)c2cc(Cl)ccc2c1=O]

In a 25 mL round-bottomed flask, crude 3-bromomethyl-7-chloro-1-phenyl-1H-quinolin-4-one (0.184 g, 0.528 mmol) and sodium azide (34.3 mg, 0.528 mmol) were combined with DMF (3.5 mL) to give a yellow solution. The reaction mixture was stirred overnight at room temperature. The reaction mixture was poured over ice and the resulting white suspension was extracted with ethyl acetate. The organic phase was dried over magnesium sulfate, filtered, then concentrated to afford the crude product as slightly yellow oil. The crude was purified by flash chromatography using 15%-45% ethyl acetate/hexanes to afford 3-azidomethyl-7-chloro-1-phenyl-1H-quinolin-4-one (75 mg, 46% yield) as a white solid.

Step 4: Preparation of 3-aminomethyl-7-chloro-1-phenyl-1H-quinolin-4-one

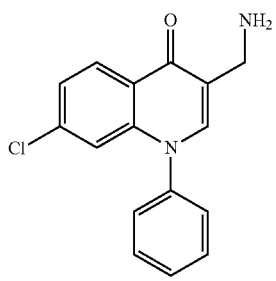 [SMILES: NCc1cn(-c2ccccc2)c2cc(Cl)ccc2c1=O]

To a 250 mL round-bottomed flask was added 3-azidomethyl-7-chloro-1-phenyl-1H-quinolin-4-one (2.00 g, 6.44 mmol), ethyl acetate (120 mL) followed by platinum (IV) oxide (152 mg, 0.671 mmol). The reaction mixture was evacuated and back-filled with hydrogen gas using an atmospheric hydrogenation apparatus. The reaction mixture was stirred under hydrogen gas (1 atm.) at room temperature for 5 hr. TLC (40% ethyl acetate-hexanes) and LCMS indicated the absence of starting material. The reaction mixture was filtered through celite under $N_2$ atmosphere, then the celite layer was washed with ethyl acetate. The combined filtrate and washings were concentrated to give 3-aminomethyl-7-chloro-1-phenyl-1H-quinolin-4-one (1.77 g, 96.6% crude yield) as a light beige/greyish solid. The material was used in the next step without further purification.

Preparation of 6-Chloro-N-(7-chloro-4-oxo-1-phenyl-1,4-dihydro-quinolin-3-ylmethyl)-nicotinamide (Intermediate E)

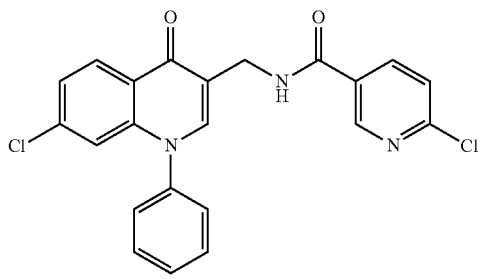 [SMILES: O=C(NCc1cn(-c2ccccc2)c2cc(Cl)ccc2c1=O)c1ccc(Cl)nc1]

To a stirred solution of 6-chloronicotinic acid (183 mg, 1.16 mmol) and N,N-diisopropylethylamine (409 mg, 552 µL, 3.16 mmol) in methylene chloride was added (benzotriazol-1-yloxy)tris(dimethylamino)phosphonium hexafluorophosphonate (BOP) (559 mg, 1.26 mmol). After 15 min., 3-(aminomethyl)-7-chloro-1-phenylquinolin-4(1H)-one (intermediate D) (300 mg, 1.05 mmol) was added. After 1.5 hr., the suspension was diluted with $CH_2Cl_2$ and washed with water followed by citric acid solution (5%) and finally potassium carbonate solution. The organic layer was dried, filtered and concentrated to afford 6-chloro-N-(7-chloro-4-oxo-1-phenyl-1,4-dihydro-quinolin-3-ylmethyl)-nicotinamide (340 mg, 76%). The product was used in subsequent reactions without further purification.

Preparation of 2-bromo-thiazole-5-carboxylic acid (7-chloro-4-oxo-1-phenyl-1,4-dihydro-quinolin-3-ylmethyl)-amide (Intermediate F)

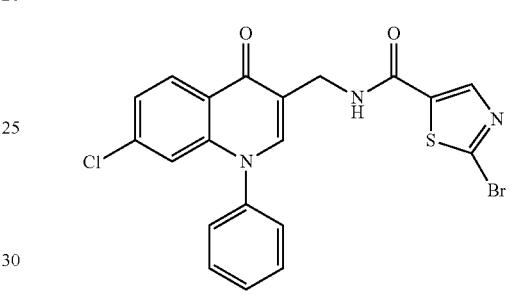

To a stirred solution of 2-bromothiazole-5-carboxylic acid (241 mg, 1.16 mmol) and N,N-diisopropylethylamine (409 mg, 552 µL, 3.16 mmol) in methylene chloride was added (benzotriazol-1-yloxy)tris(dimethylamino)phosphonium hexafluorophosphate (BOP) (559 mg, 1.26 mmol). After 15 min., 3-(aminomethyl)-7-chloro-1-phenylquinolin-4(1H)-one (intermediate D) (300 mg, 1.05 mmol) was added. The reaction mixture was stirred at room temperature. The mixture was diluted with $CH_2Cl_2$ and washed with water followed by 1N aqueous HCl and finally saturated aqueous sodium carbonate solution. The organic layer was dried ($Na_2SO_4$), filtered and concentrated. The product 2-bromo-thiazole-5-carboxylic acid (7-chloro-4-oxo-1-phenyl-1,4-dihydro-quinolin-3-ylmethyl)-amide (464 mg, 93%) was obtained without further purification.

Preparation of 3-aminomethyl-7-chloro-1-(2-chlorophenyl)-1H-quinolin-4-one (Intermediate G)

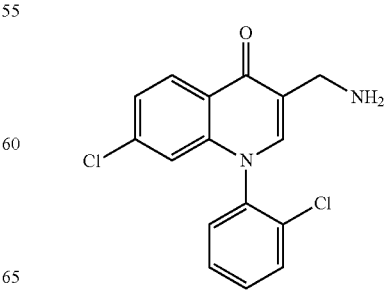

Step 1: Preparation of 4-chloro-2-(2-chloro-phenylamino)-benzoic acid

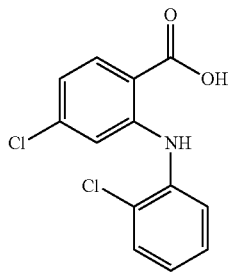 [SMILES: O=C(O)c1ccc(Cl)cc1Nc1ccccc1Cl]

In a 250 mL round bottom flask, 2-bromo-4-chloro-benzoic acid (10 g, 42.5 mmol), 2-chloroaniline (8.49 g, 7.0 mL, 66.6 mmol), potassium carbonate (9.39 g, 68.0 mmol), copper (0.092 g, 1.44 mmol) and copper (I) oxide (0.126 g, 0.88 mmol) were combined with 2-ethoxyethanol (20 mL). The mixture was heated to 130° C. for 4 hr. The mixture was cooled to room temp. and 150 mL of water was added. The slurry was stirred at room temperature for 2 days. The slurry was filtered and rinsed with 2-ethoxyethanol. The pH of the filtrate was adjusted to 7 using 4N HCl and the solid was filtered off. The green solid was then air-dried for 4 hr. to give 4-chloro-2-(2-chloro-phenylamino)-benzoic acid (3.5 g, 29% yield). The material was used in the next step without further purification. MS calcd. for $C_{13}H_9Cl_2N_3O_2$ [(M−H)−1] 280.0, obsd. 280.0.

Step 2: Preparation of 4-chloro-2-(2-chloro-phenylamino)-N-methoxy-N-methyl-benzamide

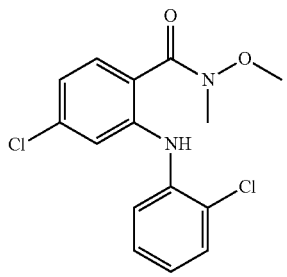 [SMILES: CON(C)C(=O)c1ccc(Cl)cc1Nc1ccccc1Cl]

In a 500 mL round bottom flask, 4-chloro-2-(2-chloro-phenylamino)-benzoic acid (1.15 g, 4.08 mmol), bromo-tris-pyrrolidino-phosphonium hexafluorophosphate (PyBrOP, 2.28 g, 4.89 mmol), N,O-dimethylhydroxylamine hydrochloride (0.80 g, 8.2 mmol) and N,N-diisopropylethylamine (7.5 mL, 42.9 mmol) were added to dichloromethane (60.0 mL). The mixture was stirred at room temperature overnight. LCMS the next day indicated a mixture of starting material and product. The reaction was further charged with N,O-dimethylhydroxylamine hydrochloride (1.61 g, 16.5 mmol) and 2-(1H-benzotriazol-1-yl)-1,1,3,3-tetramethyluronium hexafluorophosphate (HBTU, 1.86 g, 4.89 mmol) and the mixture was stirred overnight at room temperature. LCMS the next day showed complete consumption of starting material. The reaction mixture was poured into ethyl acetate. The organic layer was washed with saturated sodium bicarbonate, water and brine. The organic layer was dried, filtered and concentrated. The crude was purified by flash chromatography using 0-15% ethyl acetate-hexanes to give 4-chloro-2-(2-chloro-phenylamino)-N-methoxy-N-methyl-benzamide as an orange oil. $^1$H NMR (DMSO-d6) δ ppm 8.03 (s, 1H) 7.39-7.58 (m, 2H) 7.20-7.37 (m, 2H) 6.92-7.17 (m, 3H) 3.52 (s, 3H) 3.24 (s, 3H). MS calcd. for $C_{15}H_{14}Cl_2N_2O_2$ [(M+H)+] 326.0, obsd. 324.9, [(M-$C_2H_6NO_2$)+] 265.0, obsd. 264.0.

Step 3: Preparation of 1-[4-chloro-2-(2-chloro-phenylamino)-phenyl]-propan-1-one

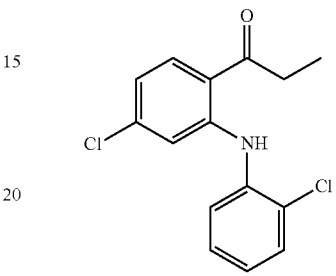

In a 500 mL round bottom flask, 4-chloro-2-(2-chloro-phenylamino)-N-methoxy-N-methyl-benzamide (1.0 g, 3.08 mmol) was added to THF (60 mL) to give a colorless solution. The reaction was cooled to 0° C. in an ice bath and ethyl magnesium bromide (3.0 M in THF, 3.59 mL, 10.8 mmol) was added slowly dropwise. The mixture was stirred at 0° C. for 1 hr. TLC and HPLC indicated the presence of starting material. The reaction was warmed to room temperature overnight. TLC the next day still showed the presence of starting material. The reaction was re-cooled to 0° C. and additional amount of ethylmagnesium bromide (3.59 mL, 10.8 mmol) was added. The reaction was stirred at 15° C. for 2.5 hr. TLC indicated complete consumption of starting material. The reaction mixture was quenched with cold water and extracted twice with ethyl acetate. The combined organic layers were washed with brine. The organic layer was dried over magnesium sulfate, filtered and concentrated. The crude material was purified by flash chromatography using 0-20% dichloromethane-hexanes to give 1-[4-chloro-2-(2-chloro-phenylamino)-phenyl]-propan-1-one (584 mg, 65% yield) as a yellow oil. $^1$H NMR (DMSO-d6) δ ppm 10.67 (s, 1H) 8.05 (d, J=8.7 Hz, 1H) 7.58 (ddd, J=12.8, 8.1, 1.1 Hz, 2H) 7.32-7.48 (m, 1H) 7.12-7.27 (m, 1H) 7.02 (d, J=2.0 Hz, 1H) 6.91 (dd, J=8.6, 1.9 Hz, 1H) 3.10 (q, J=7.3 Hz, 2H) 1.09 (t, J=7.2 Hz, 3H). MS calcd. for $C_{15}H_{13}Cl_2NO$ [(M+H)+] 295.0, obsd. 294.1.

Step 4: Preparation of 7-chloro-1-(2-chloro-phenyl)-3-methyl-1H-quinolin-4-one

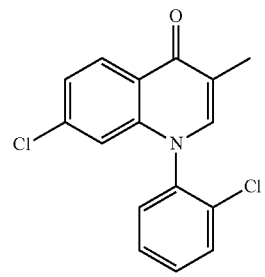 [SMILES: Cc1cn(-c2ccccc2Cl)c2cc(Cl)ccc2c1=O]

To a 3-necked, 100 mL round-bottom flask was added DMF (26 mL) which was then cooled to −4° C. To the reaction was slowly added oxalyl chloride (2.8 g, 1.93 mL, 22.1 mmol) dropwise. Once the addition was complete, the reaction was warmed to room temperature. To the above mixture was added 1-[4-chloro-2-(2-chloro-phenylamino)-phenyl]-propan-1-one (1.3 g, 4.42 mmol) in DMF (10 mL). The reaction mixture was heated to 130° C. After 2 hr, HPLC showed a 35:65 product to SM ratio. The reaction was heated overnight at 130° C. HPLC the next day showed a 1:1 mixture of product to SM. The reaction mixture was poured over ice. Once the ice melted, the solids were filtered off. The recovery of solids was low so the filtrate was extracted with ethyl acetate. The combined organic layers were washed with water and brine, then dried over magnesium sulfate, filtered, and concentrated. The crude (~900 mg) was purified by flash chromatography (silica gel, 80 g, 0-40% ethyl acetate in hexanes). The starting material of 1-[4-chloro-2-(2-chloro-phenylamino)-phenyl]-propan-1-one (694 mg 53.4%) was recovered as a yellow oil. The desired product 7-chloro-1-(2-chloro-phenyl)-3-methyl-1H-quinolin-4-one (200 mg, 14.9%) of 7-chloro-1-(2-chloro-phenyl)-3-methyl-1H-quinolin-4-one was obtained as a red solid. $^1$H NMR (DMSO-d6) δ ppm (d, J=8.7 Hz, 1H) 7.97 (d, J=0.6 Hz, 1H) 7.82 (dd, J=7.8, 1.7 Hz, 1H) 7.76 (dd, J=7.5, 2.0 Hz, 1H) 7.56-7.73 (m, 2H) 7.40 (dd, J=8.6, 1.9 Hz, 1H) 6.63 (d, J=1.8 Hz, 1H) 1.98 (s, 3H). MS calcd. for $C_{16}H_{11}Cl_2NO$ [(M+H)$^+$] 305.0, obsd. 304.0.

Step 5: Preparation of 3-bromomethyl-7-chloro-1-(2-chloro-phenyl)-1H-quinolin-4-one

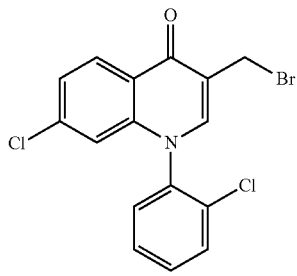 [SMILES: O=c1c(CBr)cn(-c2ccccc2Cl)c2cc(Cl)ccc12]

To a 25 mL round-bottom flask was added 7-chloro-1-(2-chloro-phenyl)-3-methyl-1H-quinolin-4-one (324 mg, 1.07 mmol), N-bromosuccinimide (219 mg, 1.23 mmol), AIBN (33.0 mg, 201 µmol) and carbon tetrachloride (9 mL). The mixture was heated at reflux for 2 hr. The reaction mixture was cooled to room temperature and then placed in an ice bath. The solvent was decanted and the residue was then rinsed with a very small amount of dichloromethane. The supernatant was concentrated and the crude 3-bromomethyl-7-chloro-1-(2-chloro-phenyl)-1H-quinolin-4-one was used in the next step without further purification.

Step 6: Preparation of 3-azidomethyl-7-chloro-1-(2-chloro-phenyl)-1H-quinolin-4-one

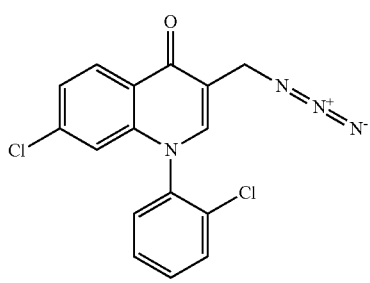 [SMILES: [N-]=[N+]=NCc1cn(-c2ccccc2Cl)c2cc(Cl)ccc2c1=O]

To a 25 mL round-bottom flask containing the crude 3-bromomethyl-7-chloro-1-(2-chloro-phenyl)-1H-quinolin-4-one (410 mg, 1.07 mmol) was added sodium azide (83.5 mg, 1.28 mmol) and DMF (9 mL). The reaction mixture was stirred overnight at room temperature. The mixture was diluted with ethyl acetate (100 mL) and washed with brine (100 mL). The organic layer was dried over magnesium sulfate, filtered, and concentrated. The crude was purified by flash chromatography (silica gel, 24 g, 0-50% ethyl acetate in hexanes) to yield 3-azidomethyl-7-chloro-1-(2-chloro-phenyl)-1H-quinolin-4-one (215 mg, 58%) as a light yellow solid. $^1$H NMR (DMSO-d6) δ ppm 8.17-8.36 (m, 2H) 7.83 (ddd, J=9.8, 7.9, 1.7 Hz, 2H) 7.68 (ddd, J=9.8, 7.8, 1.6 Hz, 2H) 7.48 (dd, J=8.7, 1.8 Hz, 1H) 6.70 (d, J=1.8 Hz, 1H) 4.09-4.44 (m, 2H). MS calcd. for $C_{16}H_{10}Cl_2N_4O$ [(M+H)$^+$] 346.0, obsd. 345.0.

Step 7: Preparation of 3-aminomethyl-7-chloro-1-(2-chloro-phenyl)-1H-quinolin-4-one

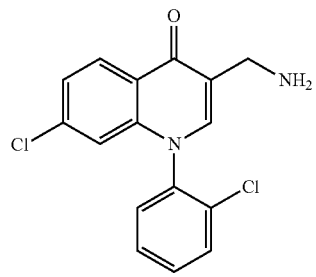 [SMILES: NCc1cn(-c2ccccc2Cl)c2cc(Cl)ccc2c1=O]

To a 100 mL round-bottom flask was added 3-azidomethyl-7-chloro-1-(2-chloro-phenyl)-1H-quinolin-4-one (215 mg, 0.623 mmol), ethyl acetate (20 mL) followed by platinum (IV) oxide (18.0 mg, 0.079 mmol). The reaction vessel was evacuated and back-filled with hydrogen gas via a balloon. Almost immediately the reddish color of the $PtO_2$ turned black. The reaction mixture was stirred under a balloon of hydrogen gas at room temp overnight. The reaction mixture was filtered through a bed of celite. The filtrate was concentrated to give the crude 3-aminomethyl-7-chloro-1-(2-chloro-phenyl)-1H-quinolin-4-one (152 mg, 76.4%, 81% purity by HPLC). $^1$H NMR (DMSO-d6) δ ppm 8.23 (d, J=8.7 Hz, 1H) 7.80-7.92 (m, 2H) 7.59-7.79 (m, 3H) 7.41 (dd, J=8.7, 1.8 Hz, 1H) 6.66 (d, J=1.8 Hz, 1H) 3.58 (s, 2H) 1.69 (br. s., 2H). MS calcd. for $C_{16}H_{12}Cl_2N_2O$ [(M+H)$^+$] 320.0, obsd. 318.9, [(M-NH$_2$)$^+$] 303.0, obsd. 301.9.

Preparation of 3-aminomethyl-7-fluoro-1-(2-fluoro-phenyl)-1H-quinolin-4-one hydrochloride salt (Intermediate H)

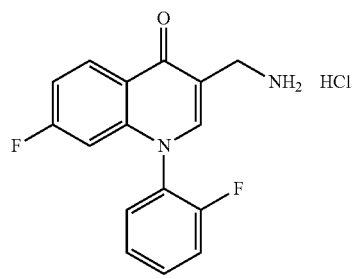 [SMILES: NCc1cn(-c2ccccc2F)c2cc(F)ccc2c1=O ; Cl]

Step 1: Preparation of 4-fluoro-2-(2-fluoro-phenylamino)-benzoic acid

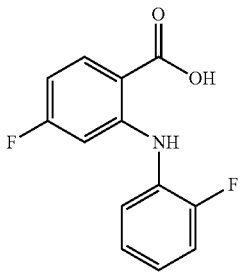 [SMILES: O=C(O)c1ccc(F)cc1Nc1ccccc1F]

In a 50 mL round bottom flask, 2-bromo-4-fluorobenzoic acid (12.78 g, 58.4 mmol), 2-fluoroaniline (7.33 mL, 75.9 mmol), potassium carbonate (9.68 g, 70.0 mmol), copper (0.371 g, 5.84 mmol) and copper (I) iodide (0.556 g, 2.92 mmol) were added to 2-ethoxyethanol (50 mL). The mixture was heated to 135° C. overnight. The mixture was cooled and 100 mL of water was added. The slurry was stirred at room temperature overnight. The slurry was filtered through a bed of celite and washed with 2-ethoxyethanol. The pH of the filtrate was adjusted to 2 using 4N HCl and the solid was filtered off. The solid was then dried in high vacuum to give 4-fluoro-2-(2-fluoro-phenylamino)-benzoic acid (16.5 g, >100% yield).

Step 2: Preparation of 4-fluoro-2-(2-fluoro-phenylamino)-N-methoxy-N-methyl-benzamide

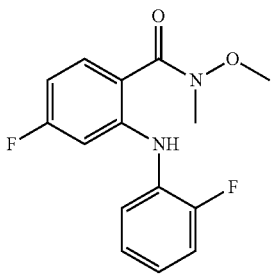 [SMILES: CON(C)C(=O)c1ccc(F)cc1Nc1ccccc1F]

In a 500 mL round bottom flask, 4-fluoro-2-(2-fluoro-phenylamino)-benzoic acid (6.0 g, 24.1 mmol), O-benzotriazole-N,N,N',N'-tetramethyl-uronium-hexafluorophosphate (HBTU) (18.5 g, 48 mmol) and triethylamine (20 mL, 144 mmol) were added to DMF (80.0 mL). The reaction mixture was stirred for 1 hr. at room temperature, then N,O-dimethylhydroxylamine hydrochloride (4.7 g, 48 mmol) was added. The mixture was stirred for 2 hr. The reaction mixture was poured into 300 mL of ethyl acetate and washed with saturated ammonium chloride (2×150 mL), water (2×200 mL) and brine (1×200 mL). The organic layer was evaporated and purified by flash chromatography using 30% ethyl acetate-hexanes to give 4-fluoro-2-(2-fluoro-phenylamino)-N-methoxy-N-methyl-benzamide (6.0 g, 85.3%).

Step 3: Preparation of 1-[4-fluoro-2-(2-fluoro-phenylamino)-phenyl]-propan-1-one

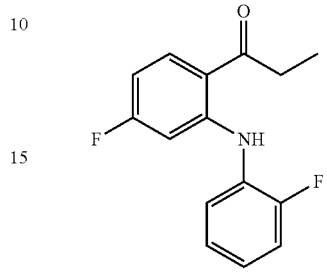

In a 500 mL round bottom flask, 4-fluoro-2-(2-fluoro-phenylamino)-N-methoxy-N-methyl-benzamide (6.0 g, 20.5 mmol) was added to THF (60 mL) to give a colorless solution. The reaction was cooled to 0° C. in an ice bath and ethyl magnesium bromide (3.0 M in THF, 27.4 mL, 82.2 mmol) was added slowly over a 15 min. period. The mixture was stirred at 0° C. for 4 hr. The reaction mixture was poured into ethyl acetate (250 mL) and washed with 1N HCl (1×150 mL), water (2×150 mL) and brine (2×150 mL). The combined organic layers were dried over sodium sulfate, filtered and concentrated in vacuum. The crude material was purified by flash chromatography using 20% ethyl acetate-hexanes to give 1-[4-fluoro-2-(2-fluoro-phenylamino)-phenyl]-propan-1-one (3.0 g, 56%).

Step 4: Preparation of 7-fluoro-1-(2-fluoro-phenyl)-3-methyl-1H-quinolin-4-one

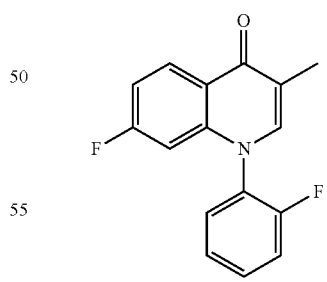

In a 250 mL round bottom flask, 1-[4-fluoro-2-(2-fluoro-phenylamino)-phenyl]-propan-1-one (3.05 g, 11.7 mmol) was added to DMF (4.3 mL) at 0° C. Oxalyl chloride (8.18 mL, 96.7 mmol) was added slowly and the reaction mixture stirred at 0° C. The mixture was then warmed up to room temperature and stirred for 1.5 hr. The mixture was concentrated to dryness and the crude redissolved in toluene (80 mL). The reaction mixture was heated at 115° C. for 24 hr.

The mixture was concentrated to dryness and triturated from methanol to afford 7-fluoro-1-(2-fluoro-phenyl)-3-methyl-1H-quinolin-4-one (1.20 g, 37.8%) as a white solid.

Step 5: Preparation of 3-azidomethyl-7-fluoro-1-(2-fluoro-phenyl)-1H-quinolin-4-one

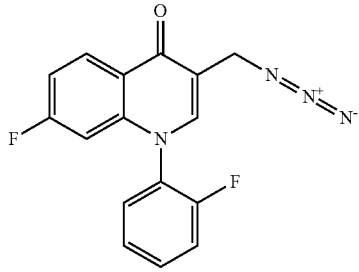 [SMILES: [N-]=[N+]=NCc1cn(-c2ccccc2F)c2cc(F)ccc2c1=O]

In a 50 mL round bottom flask, 7-fluoro-1-(2-fluoro-phenyl)-3-methyl-1H-quinolin-4-one (1.20 g, 4.42 mmol), N-bromosuccinimide (0.787 g, 4.42 mmol) and V65 [2,2'-azobis(2,4-dimethylvaleronitrile)](0.33 g, 1.33 mmol) were combined with carbon tetrachloride (35.0 mL). The reaction mixture was heated to reflux for 5 hr. The reaction was concentrated to dryness and the crude (containing 3-bromomethyl-7-fluoro-1-(2-fluoro-phenyl)-1H-quinolin-4-one) was redissolved in DMF (10.0 mL). To this reaction mixture was added sodium azide (1.44 g, 22.1 mmol) and the reaction was stirred at room temperature overnight. The reaction was partitioned between ethyl acetate and water and the organic layer was washed with saturated aqueous sodium bicarbonate solution. The organic layer was evaporated to dryness and purified by flash chromatography using 40% ethyl acetate-hexanes to afford 3-azidomethyl-7-fluoro-1-(2-fluoro-phenyl)-1H-quinolin-4-one (740 mg, 53.6%).

Step 6: Preparation of 3-aminomethyl-7-fluoro-1-(2-fluoro-phenyl)-1H-quinolin-4-one hydrochloride salt

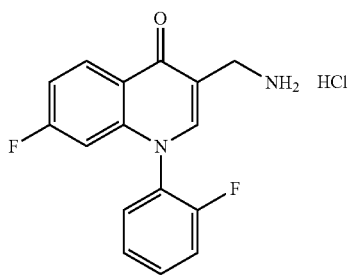 [SMILES: NCc1cn(-c2ccccc2F)c2cc(F)ccc2c1=O ; Cl]

In a 50 mL round bottom flask, 3-azidomethyl-7-fluoro-1-(2-fluoro-phenyl)-1H-quinolin-4-one (0.290 g, 0.929 mmol) was added platinum (IV) oxide (0.040 g, 0.176 mmol) and 4 N HCl (2 mL) in 1:1 dichloroethane-ethyl acetate (15 mL). The reaction was charged with 1 atm. $H_2$ using a balloon and stirred at room temperature for 3 hr. The catalyst was filtered off and the filtrate evaporated to dryness to give 3-aminomethyl-7-fluoro-1-(2-fluoro-phenyl)-1H-quinolin-4-one hydrochloride salt (200 mg, 67% yield). The crude was used in subsequent steps without further purification.

Preparation of 3-aminomethyl-7-chloro-1-phenyl-1H-quinolin-4-one (Intermediate I)

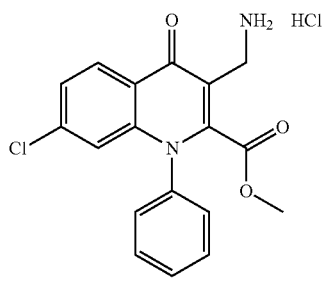 [SMILES: COC(=O)c1c(CN)c(=O)c2ccc(Cl)cc2n1-c1ccccc1 ; Cl]

Step 1: Preparation of N-(5-chloro-2-propionyl-phenyl)-N-phenyl-oxalamic acid methyl ester

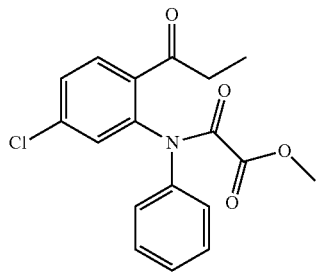 [SMILES: CCC(=O)c1ccc(Cl)cc1N(C(=O)C(=O)OC)c1ccccc1]

A solution of 1-(4-chloro-2-phenylamino-phenyl)-propan-1-one (13.0 g, 50.2 mmol) in toluene (150 mL) at 25° C. was treated with methyl chlorooxoacetate (42.86 g, 350 mmol). The reaction mixture was then heated at 110° C. for 16 hr. At this time, the reaction mixture was concentrated in vacuo to afford N-(5-chloro-2-propionyl-phenyl)-N-phenyl-oxalamic acid methyl ester (15.2 g, 87.6%). The material was used without further purification.

Step 2: Preparation of 7-chloro-3-methyl-4-oxo-1-phenyl-1,4-dihydro-quinoline-2-carboxylic acid methyl ester

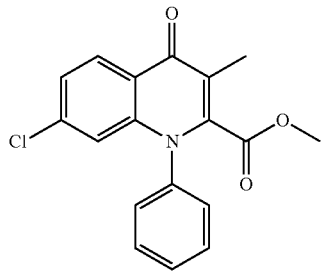 [SMILES: COC(=O)c1c(C)c(=O)c2ccc(Cl)cc2n1-c1ccccc1]

A stirred suspension of N-(5-chloro-2-propionyl-phenyl)-N-phenyl-oxalamic acid methyl ester (15.0 g, 43.5 mmol) in methanol (200 mL) was treated with potassium carbonate (35.0 g, 253 mmol) at 25° C. The mixture was then heated at 80° C. for 1 hr. At this time, the reaction was cooled to 25° C. The resulting solids were collected by filtration through a sintered glass funnel and then washed with methanol (2×50 mL). The filtrate was concentrated in vacuo. The resulting residue was dissolved in ethyl acetate (500 mL) and was washed with water (2×200 mL). The organics were dried over sodium sulfate, filtered and concentrated in vacuo. The resulting solids were triturated with hexanes and diethyl ether to afford 7-chloro-3-methyl-4-oxo-1-phenyl-1,4-dihydro-quinoline-2-carboxylic acid methyl ester (10.5 g, 73.4%). $^1$H NMR (DMSO-d$_6$) δ ppm 8.24 (d, J=8.7 Hz, 1H) 7.28-7.78 (m, 6H) 6.69 (d, J=1.7 Hz, 1H) 3.49 (s, 3H) 1.97 (s, 3H). MS calcd. for C$_{18}$H$_{14}$ClNO$_3$ [(M+H)$^+$] 328.0 found 327.9.

Step 3: Preparation of 3-bromomethyl-7-chloro-4-oxo-1-phenyl-1,4-dihydro-quinoline-2-carboxylic acid methyl ester

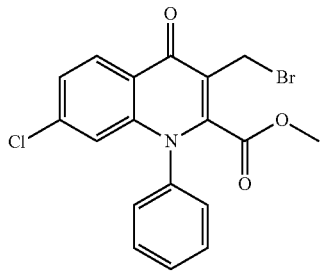 [SMILES: COC(=O)c1c(CBr)c(=O)c2ccc(Cl)cc2n1-c1ccccc1]

A solution of 7-chloro-3-methyl-4-oxo-1-phenyl-1,4-dihydro-quinoline-2-carboxylic acid methyl ester (1.6 g, 4.88 mmol), N-bromosuccinimide (869 mg, 4.88 mmol) and benzoyl peroxide (118 mg, 0.488 mmol) in carbon tetrachloride (50 mL) was heated at 100° C. for 5 hr. At this time, the reaction was cooled to 25° C. The resulting solids were collected by filtration to afford 3-bromomethyl-7-chloro-4-oxo-1-phenyl-1,4-dihydro-quinoline-2-carboxylic acid methyl ester (1.7 g, 85.6%) as a white solid. The material was used without further purification.

Step 4: Preparation of 3-azidomethyl-7-chloro-4-oxo-1-phenyl-1,4-dihydro-quinoline-2-carboxylic acid methyl ester

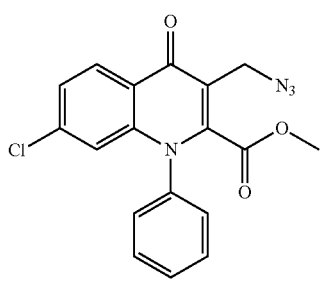 [SMILES: COC(=O)c1c(CN=[N+]=[N-])c(=O)c2ccc(Cl)cc2n1-c1ccccc1]

In a 250 mL round-bottomed flask, methyl 3-(bromomethyl)-7-chloro-4-oxo-1-phenyl-1,4-dihydroquinoline-2-carboxylate (2.7 g, 6.64 mmol) and sodium azide (1.25 g, 19.2 mmol) were combined with DMF (40 mL). The reaction mixture was stirred at room temperature overnight, then it was concentrated and triturated in ethyl acetate. The product 3-azidomethyl-7-chloro-4-oxo-1-phenyl-1,4-dihydro-quinoline-2-carboxylic acid methyl ester (2.3 g, 94%) was obtained as a white solid.

Step 5: Preparation of 3-aminomethyl-7-chloro-4-oxo-1-phenyl-1,4-dihydro-quinoline-2-carboxylic acid methyl ester hydrochloride

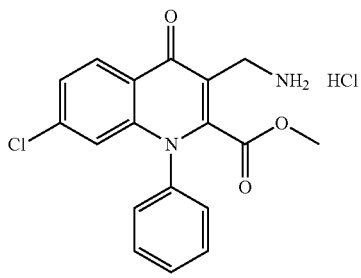 [SMILES: COC(=O)c1c(CN)c(=O)c2ccc(Cl)cc2n1-c1ccccc1 ; Cl]

In a 250 mL round-bottomed flask, 3-azidomethyl-7-chloro-4-oxo-1-phenyl-1,4-dihdro-quinoline-1-carboxylic acid methyl ester (2.00 g, 5.42 mmol), platinum (IV) oxide (0.200 g, 0.881 mmol) and 4.0N aqueous HCl were combined with 1:1 dichloromethane/ethyl acetate (30 mL). The reaction flask was charged with 1 atmosphere H$_2$ and was stirred at room temperature for 4 hr. The catalyst was filtered off, and the filter bed was washed with methanol. The combined filtrates were evaporated to afford of 3-aminomethyl-7-chloro-4-oxo-1-phenyl-1,4-dihydro-quinoline-2-carboxylic acid methyl ester hydrochloride (1.70 g, 82.5%).

3-Aminomethyl-4-oxo-1-phenyl-7-trifluoromethyl-1,4-dihydro-[1,8]naphthyridine-2-carboxylic acid methyl ester hydrochloride salt (Intermediate J)

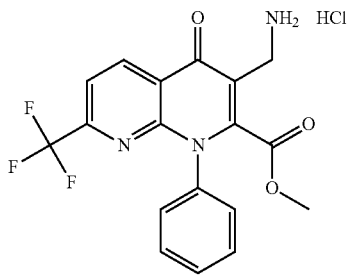 [SMILES: COC(=O)c1c(CN)c(=O)c2ccc(C(F)(F)F)nc2n1-c1ccccc1 ; Cl]

Step 1: 2-Phenylamino-6-trifluoromethyl-nicotinic acid

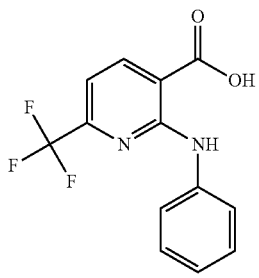 [SMILES: O=C(O)c1ccc(C(F)(F)F)nc1Nc1ccccc1]

In a 50 mL round-bottomed flask, 2-chloro-6-(trifluoromethyl)-nicotinic acid (5 g, 22.2 mmol) was combined with THF (20 mL) to give a dark red solution. The reaction solution was cooled to −78° C., lithium hexamethyldisilazane (LiHMDS, 1.0 M in THF) (66.5 mL, 66.5 mmol) was added and stirred for 2 hr. A solution of aniline (19.6 g, 19.2 mL, 210 mmol) in THF (20 mL) was added dropwise to the reaction and the reaction was allowed to gradually warm at room temperature. The resultant reaction was stirred overnight. The reaction mixture was diluted with ethyl acetate (250 mL). The organic layers were combined, washed with saturated aqueous NaHCO$_3$ (2×150 mL), H$_2$O (1×50 mL), and brine (1×50 mL). The organic layers were dried over MgSO$_4$ and concentrated in vacuo. The compound was triturated in ether to give of 2-phenylamino-6-trifluoromethyl-nicotinic acid (6.19 g, 98.9%) as a light brown solid. The material was not further purified.

Step 2: N-Methoxy-N-methyl-2-phenylamino-6-trifluoromethyl-nicotinamide

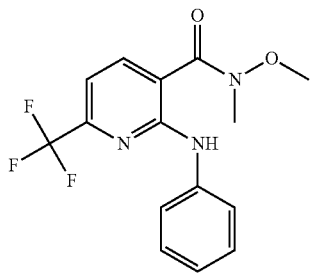 [SMILES: CON(C)C(=O)c1ccc(C(F)(F)F)nc1Nc1ccccc1]

In a 1 L pear-shaped flask, 2-phenylamino-6-trifluoromethyl-nicotinic acid (6.2 g, 22.0 mmol) was combined with DMF (120 mL) to give a dark brown solution. N,O-dimethylhydroxyl-amine hydrochloride (2.79 g, 28.6 mmol) and HBTU (13.3 g, 35.2 mmol) were added. N,N-diisopropylethylamine (8.88 g, 12 mL, 68.7 mmol) was added. The reaction mixture was stirred at 25° C. for 4 hr. The reaction mixture was diluted with methylene chloride (400 mL), washed with saturated NH$_4$Cl (1×300 mL), saturated NaHCO$_3$ (1×300 mL), and brine (1×200 mL). The organic phase was dried over Na$_2$SO$_4$ and concentrated in vacuo to give 20.5 g of crude product as a brown oil. The crude material was purified by flash chromatography (silica gel, 250 g, 10% to 35% ethyl acetate-hexanes). Fractions containing the desired product were concentrated, treated with ether and concentrated again to give N-methoxy-N-methyl-2-phenylamino-6-trifluoromethyl-nicotinamide (6.86 g, 96%) as a brown oil which solidified on standing overnight at room temperature. $^1$H NMR (DMSO-d$_6$) δ ppm 8.85 (s, 1H) 7.93 (d, J=7.5 Hz, 1H) 7.64 (d, J=7.8 Hz, 2H) 7.14-7.48 (m, 3H) 6.78-7.14 (m, 1H) 3.55 (s, 3H) 3.31 (s, 3H). MS calcd. for C$_{15}$H$_{14}$F$_3$N$_3$O$_2$ [(M+H)$^+$] 326.0, obsd. 326.0.

Step 3: 1-(2-Phenylamino-6-trifluoromethyl-pyridin-3-yl)-propan-1-one

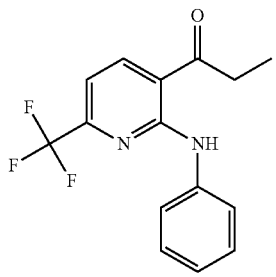 [SMILES: CCC(=O)c1ccc(C(F)(F)F)nc1Nc1ccccc1]

In a 250 mL round-bottomed flask, N-methoxy-N-methyl-2-phenylamino-6-trifluoromethyl-nicotinamide (1.73 g, 5.32 mmol) was combined with THF (20 mL) to give a brown solution and the solution was cooled to 0° C. Ethylmagnesium bromide (1.0 M in THF) (16 mL, 16.0 mmol) was added dropwise at 0° C. over 5 min. The reaction mixture was stirred in an ice bath for 2.5 hr and 1 hr at room temperature. Additional ethylmagnesium bromide (1.0 M in THF) (6 mL, 6.00 mmol) was introduced over 3 min and the mixture was stirred for 2 hr at room temperature. The reaction mixture was cautiously quenched with water (50 mL) and extracted with ethyl acetate (3×50 mL). The organic layers were combined, washed with brine (1×50 mL), dried over MgSO$_4$ and concentrated in vacuo to give 1.56 g of crude product as a yellow solid. The crude material was purified by flash chromatography (silica gel, 150 g, 15% ethyl acetate in hexanes) to give 1-(2-phenylamino-6-trifluoromethyl-pyridin-3-yl)-propan-1-one (1.35 g, 86.3% yield) as a yellow solid. $^1$H NMR (DMSO-d$_6$) δ ppm 11.13 (s, 7H) 8.67 (d, J=8.2 Hz, 1H) 7.74 (d, J=7.8 Hz, 2H) 7.20-7.54 (m, 3H) 6.81-7.19 (m, 1H) 3.19 (q, J=7.2 Hz, 2H) 1.12 (t, J=7.1 Hz, 3H). MS calcd. for C$_{15}$H$_{13}$F$_3$N$_2$O [(M+H)$^+$] 295.0, obsd. 295.0.

Step 4: N-Phenyl-N-(3-propionyl-6-trifluoromethyl-pyridin-2-yl)-oxalamic acid methyl ester

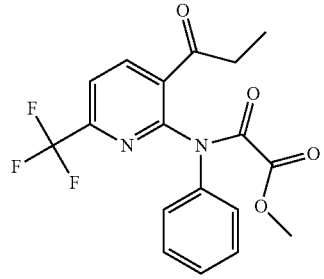 [SMILES: CCC(=O)c1ccc(C(F)(F)F)nc1N(C(=O)C(=O)OC)c1ccccc1]

In a 250 mL pear-shaped flask, 1-(2-(phenylamino-6-trifluoromethyl-pyridin-3-yl)-propan-1-one (1.35 g, 4.59 mmol) was combined with toluene (40 mL) to give a yellow solution. Methyl oxalyl chloride (3.99 g, 3 mL, 32.5 mmol) was added. The reaction mixture was refluxed for 18 hr. The crude reaction mixture was cooled, concentrated in vacuo to give 1.86 g (107% crude yield) of crude N-phenyl-N-(3-propionyl-6-trifluoromethyl-pyridin-2-yl)-oxalamic acid methyl ester as a dark yellow solid. The material was not further purified.

Step 5: 3-Methyl-4-oxo-1-phenyl-7-trifluoromethyl-1,4-dihydro-[1,8]naphthyridine-2-carboxylic acid methyl ester

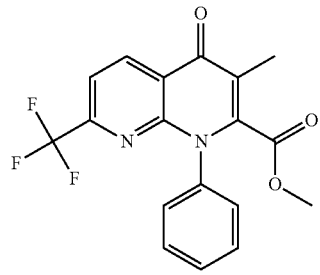 [SMILES: COC(=O)c1c(C)c(=O)c2ccc(C(F)(F)F)nc2n1-c1ccccc1]

In a 250 mL pear-shaped flask, N-phenyl-N-(3-propionyl-6-trifluoromethyl-pyridin-2-yl)-oxalamic acid methyl ester (1.74 g, 4.58 mmol) was combined with methanol (25 mL) to give a yellow solution. Potassium carbonate (3.8 g, 27.5 mmol) was added and the reaction mixture was refluxed for 2 hr. The reaction mixture was cooled, diluted with H$_2$O (75 mL) and extracted with ethyl acetate (3×75 mL). The organic layers were combined, washed with brine (1×50 mL), dried over MgSO$_4$, and concentrated in vacuo to give 1.7 g crude product as a yellow solid. The crude material was purified by flash chromatography (silica gel, 120 g, 20% to 50% ethyl acetate in hexanes) to give 3-methyl-4-oxo-1-phenyl-7-trifluoromethyl-1,4-dihydro-[1,8]naphthyridine-2-carboxylic acid methyl ester (0.89 g, 3.7%) as an off-white solid. $^1$H NMR (DMSO-d$_6$) δ ppm 8.84 (d, J=8.2 Hz, 1H) 7.91 (d, J=8.2 Hz, 1H) 7.32-7.70 (m, 5H) 3.51 (s, 3H) 2.01 (s, 3H). MS calcd. for C$_{18}$H$_{13}$F$_3$N$_2$O$_3$ [(M+H)$^+$] 363.0, obsd. 363.0.

Step 6: 3-Bromomethyl-4-oxo-1-phenyl-7-trifluoromethyl-1,4-dihydro-[1,8]naphthyridine-2-carboxylic acid methyl ester

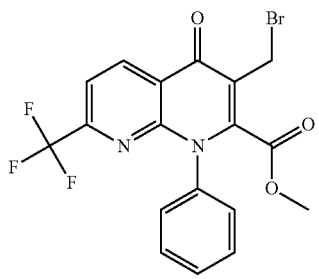 [SMILES: COC(=O)c1c(CBr)c(=O)c2ccc(C(F)(F)F)nc2n1-c1ccccc1]

In a 50 mL pear-shaped flask, 3-methyl-4-oxo-1-phenyl-7-trifluoromethyl-1,4-dihydro-[1,8]naphthyridine-2-carboxylic acid methyl ester (0.45 g, 1.24 mmol), NBS (221 mg, 1.24 mmol) and benzoyl peroxide (60.2 mg, 0.248 mmol) were combined with carbon tetrachloride (12 mL) to give a light yellow suspension. The reaction mixture was refluxed for 2 hr. The reaction mixture was cooled, diluted with methylene chloride (50 mL), washed with saturated aqueous NaHCO$_3$ (1×20 mL), and brine (1×20 mL). The organic phase was dried over MgSO$_4$, filtered, and concentrated in vacuo to give crude 3-bromomethyl-4-oxo-1-phenyl-7-trifluoromethyl-1,4-dihydro-[1,8]naphthyridine-2-carboxylic acid methyl ester (536.6 mg, 97.9%) as a pale yellow solid. The material was not further purified. $^1$H NMR (DMSO-d$_6$) δ ppm 8.89 (d, J=8.2 Hz, 1H) 7.99 (d, J=8.2 Hz, 1H) 7.44-7.62 (m, 5H) 4.53 (s, 2H) 3.55 (s, 3H). MS calcd. for C$_{18}$H$_{12}$BrF$_3$N$_2$O$_3$ [(M+H)$^+$] 442.0, obsd. 443.0.

Step 7: 3-Azidomethyl-4-oxo-1-phenyl-7-trifluoromethyl-1,4-dihydro-[1,8]naphthyridine-2-carboxylic acid methyl ester

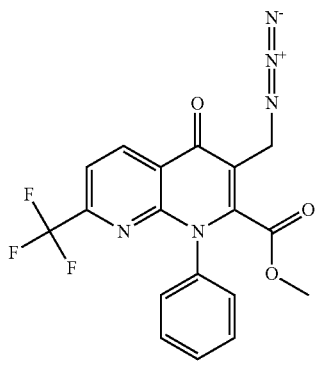 [SMILES: COC(=O)c1c(CN=[N+]=[N-])c(=O)c2ccc(C(F)(F)F)nc2n1-c1ccccc1]

In a 25 mL pear-shaped flask, 3-bromomethyl-4-oxo-1-phenyl-7-trifluoromethyl-1,4-dihydro-[1,8]naphthyridine-2-carboxylic acid methyl ester (150.6 mg, 0.341 mmol) and sodium azide (66.6 mg, 1.02 mmol) were combined with DMF (2 mL) to give a light yellow solution. The reaction mixture was stirred at 25° C. for 16 h. The reaction mixture was diluted with H$_2$O (25 mL) and extracted with ethyl acetate (3×30 mL). The organic layers were combined, washed with brine (2×25 mL), dried over MgSO$_4$, and concentrated in vacuo to give 3-azidomethyl-4-oxo-1-phenyl-7-trifluoromethyl-1,4-dihydro-[1,8]naphthyridine-2-carboxylic acid methyl ester (134.7 mg, 97.8%) as a yellow oil which contained DMF as an impurity. $^1$H NMR (DMSO-d$_6$) δ ppm 8.89 (d, J=8.2 Hz, 1H) 7.78-8.27 (m, 1H) 7.26-7.76 (m, 5H) 4.30 (s, 2H) 3.52 (s, 2H). MS calcd. for C$_{18}$H$_{12}$F$_3$N$_5$O$_3$ [(M+H)$^+$] 404.0, obsd. 404.0, [(M+H-N$_2$)$^+$] 376.0, obsd. 376.0.

Step 8: 3-Aminomethyl-4-oxo-1-phenyl-7-trifluoromethyl-1,4-dihydro-[1,8]naphthyridine-2-carboxylic acid methyl ester hydrochloride

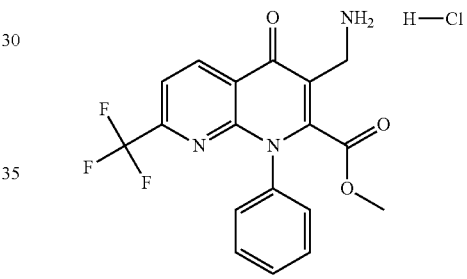

In a 100 mL pear-shaped flask, 3-azidomethyl-4-oxo-1-phenyl-7-trifluoromethyl-1,4-dihydro-[1,8]naphthyridine-2-carboxylic acid methyl ester (490 mg, 1.21 mmol), platinum (IV) oxide (100 mg, 0.440 mmol) and a 4N HCl in 1,4-dioxane (2.4 g, 2 mL) were combined with ethyl acetate (12 mL) to give a brown suspension which was hydrogenated at atmospheric pressure at 25° C. for 11 hr. The reaction mixture was diluted with methanol (200 mL), stirred for 1 hr at room temperature, filtered through a small celite pad, and concentrated under vacuum to give 3-aminomethyl-4-oxo-1-phenyl-7-trifluoromethyl-1,4-dihydro-[1,8]naphthyridine-2-carboxylic acid methyl ester hydrochloride (0.54 g, 107% crude yield) as a light brown solid. Material was used without any further purification. $^1$H NMR (DMSO-d$_6$) δ ppm 8.93 (d, J=8.2 Hz, 1H) 8.21 (br. s., 2H) 8.04 (d, J=8.2 Hz, 1H) 6.80-7.72 (m, 4H) 3.88 (br. s., 2H) 3.54 (s, 3H). MS calcd. for C$_{18}$H$_{14}$F$_3$N$_3$O$_3$ [(M+H)$^+$] 378.0, obsd. 378.0, [(M+H-NH$_3$)$^+$] 361.0, obsd. 361.0, [(M+H-NH$_3$+CH$_3$CN)$^+$] 402.0, obsd. 402.0.

Preparation of 3-aminomethyl-7-methoxy-1-phenyl-1H-quinolin-4-one hydrochloride salt (Intermediate K)

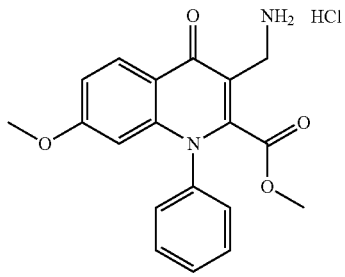

Step 1: Preparation of 4-fluoro-2-phenylamino-benzoic acid

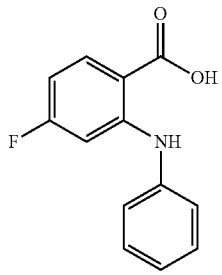 [SMILES: O=C(O)c1ccc(F)cc1Nc1ccccc1]

A mixture of 4-fluoro-2-bromo-benzoic acid (25 g, 114 mmol), aniline (12.5 mL, 137 mmol), potassium carbonate (17.4 g, 126 mmol), copper powder (725 mg, 11.4 mmol), and copper (I) iodide (1.09 g, 5.71 mmol) in 2-ethoxyethanol (70 mL) was stirred at 138° C. for 70 hr. under an argon atmosphere. The reaction mixture was cooled to room temperature, then water (60 mL) was added. The mixture was filtered through celite. The filtrate was adjusted to pH<2, then an additional 200 mL of water was added. The mixture was allowed to stir for 1 hr. The precipitated solids were collected via filtrated. The solids were taken up into 5% sodium carbonate solution, then filtered. The product was dried under vacuum overnight at 85° C.

Step 2: Preparation of 4-fluoro-N-methoxy-N-methyl-2-phenylamino-benzamide

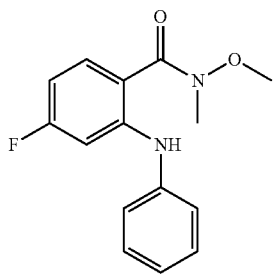 [SMILES: CON(C)C(=O)c1ccc(F)cc1Nc1ccccc1]

To a solution of 4-fluoro-2-phenylamino-benzoic acid (10 g, 43.2 mmol) in DMF (100 mL) was added O-benzotriazole-N,N,N',N'-tetramethyl-uronium-hexafluorophosphate (HBTU) (32.8 g, 86.5 mmol), N,O-dimethylhydroxylamine hydrochloride (5.3 g, 86.5 mmol), and triethylamine (26.0 g, 36.2 mL, 259 mmol) at room temp. The resulting mixture was stirred for 24 hr at room temperature. The reaction mixture was diluted with ethyl acetate and the organic layer was washed with water and brine. The organic layer was dried over anhydrous Na$_2$SO$_4$ and volatiles were removed under reduced pressure. The crude material was purified using silica gel column chromatography (100% hexanes ramped to 30% ethyl acetate in hexanes). Further purification was accomplished by recrystallization from 10% ethyl acetate in petroleum ether. The product 4-fluoro-N-methoxy-N-methyl-2-phenylamino-benzamide (9.35 g, 79%) was obtained as an off-white solid.

Step 3: Preparation of 1-(4-fluoro-2-phenylamino-phenyl)-propan-1-one

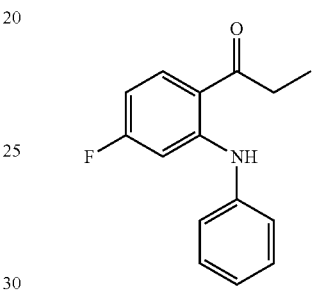

To a solution of 4-fluoro-N-methoxy-N-methyl-2-phenylamino-benzamide (9.35 g, 34.1 mmol) in THF (170 mL) was added ethylmagnesium bromide (1M solution in THF) (136 mL, 136 mmol) dropwise at 0° C. under nitrogen. The mixture was slowly warmed to room temperature and stirred for 4 hr. At this time, only 50% of the starting material was consumed. The reaction mixture was cooled again to 0° C. To push the reaction to completion, a 3M solution of ethylmagnesium bromide in diethyl ether (50 mL, 150 mmol) was added slowly to the cooled reaction mixture. The reaction was quenched with an aqueous solution of 1N HCl at 0° C. and was extracted with ethyl acetate. The combined organic layer was washed with water and brine. The organic phase was dried over anhydrous Na$_2$SO$_4$, filtered, and concentrated under reduced pressure. The crude material was purified using silica gel column chromatography (100% hexanes ramped to 6% ethyl acetate in hexanes) to give 1-(4-fluoro-2-phenylamino-phenyl)-propan-1-one.

Step 4: Preparation of N-(5-fluoro-2-propionyl-phenyl)-N-phenyl-oxalamic acid methyl ester

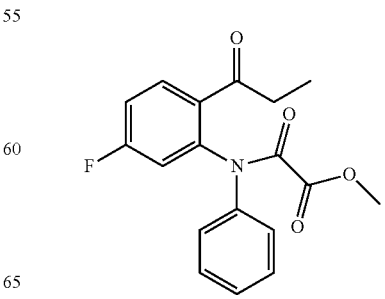

To a solution of 1-(4-fluoro-2-phenylamino-phenyl)-propan-1-one (6.0 g, 24.7 mmol) in toluene (75 mL) was added methyl chlorooxoacetate (14.2 mL, 148 mmol) at room temperature under nitrogen. The reaction mixture was heated at reflux at 110° C. for 16 hr. The reaction mixture was concentrated under vacuum to afford N-(5-fluoro-2-propionyl-phenyl)-N-phenyl-oxalamic acid methyl ester. The crude product was used in the next step without further purification.

Step 5: Preparation of 7-methoxy-3-methyl-4-oxo-1-phenyl-1,4-dihydro-quinoline-2-carboxylic acid methyl ester

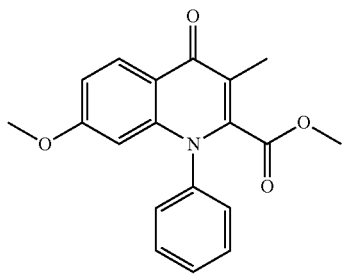

A mixture of N-(5-fluoro-2-propionyl-phenyl)-N-phenyl-oxalamic acid methyl ester (8 g, 24.3 mmol) and potassium carbonate (20.1 g, 146 mmol) in methanol (150 mL) was refluxed for 3 hr. The crude product was recrystallized from methanol to afford a mixture of 7-fluoro-3-methyl-4-oxo-1-phenyl-1,4-dihydro-quinoline-2-carboxylic acid methyl ester and 7-methoxy-3-methyl-4-oxo-1-phenyl-1,4-dihydro-quinoline-2-carboxylic acid methyl ester as approximately 5 g of a white solid.

Step 6: Preparation of 3-azidomethyl-7-methoxy-4-oxo-1-phenyl-1,4-dihydro-quinoline-2-carboxylic acid methyl ester

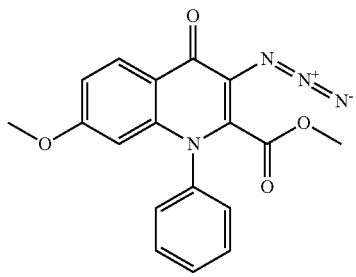 [SMILES: COC(=O)c1c(N=[N+]=[N-])c(=O)c2ccc(OC)cc2n1-c1ccccc1]

The mixture of obtained from step 5 above (7-fluoro-3-methyl-4-oxo-1-phenyl-1,4-dihydro-quinoline-2-carboxylic acid methyl ester and 7-methoxy-3-methyl-4-oxo-1-phenyl-1,4-dihydro-quinoline-2-carboxylic acid methyl ester), N-bromosuccinimide (3.6 g, 20 mmol) and V65 (2,2'-azobis (2,4-dimethylvaleronitrile)) (118 mg, 0.488 mmol) in dichloromethane (75 mL) was heated at 45° C. overnight. At this time, the reaction was concentrated. The crude product was dissolved in 100 mL DMF and sodium azide (4 g, 60 mmol) was added. The resulting mixture was heated at 70° C. for 2 hr. The crude product was purified using a 200 g silica gel column (100% hexanes ramped to 50% ethyl acetate in hexanes). Two products were isolated: 3-azidomethyl-7-fluoro-4-oxo-1-phenyl-1,4-dihydro-quinoline-2-carboxylic acid methyl ester (290 mg) and 3-azidomethyl-7-methoxy-4-oxo-1-phenyl-1,4-dihydro-quinoline-2-carboxylic acid methyl ester (570 mg).

Step 7: Preparation of 3-aminomethyl-7-methoxy-4-oxo-1-phenyl-1,4-dihydro-quinoline-2-carboxylic acid methyl ester hydrochloride salt

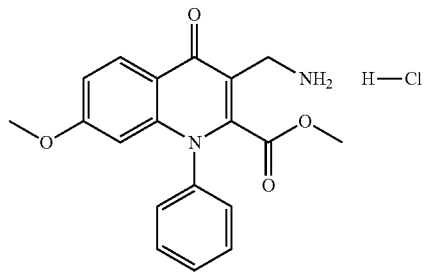

A mixture of 3-azidomethyl-7-methoxy-4-oxo-1-phenyl-1,4-dihdro-quinoline-1-carboxylic acid methyl ester (570 mg, 1.56 mmol), platinum (IV) oxide (50 mg, 0.220 mmol) and 4.0 M HCl in dioxane (2 mL) were combined with 1:1:1 dichloromethane/ethyl acetate/methanol (20 mL). The reaction flask was charged with 1 atmosphere $H_2$ and was stirred at room temperature for 4 hr. The catalyst was carefully filtered off, and the filter bed was washed with methanol. The combined filtrates were evaporated to afford 3-aminomethyl-7-methoxy-4-oxo-1-phenyl-1,4-dihydro-quinoline-2-carboxylic acid methyl ester hydrochloride.

Preparation of 3-Aminomethyl-7-fluoro-1-phenyl-1H-quinolin-4-one hydrochloride salt (Intermediate L)

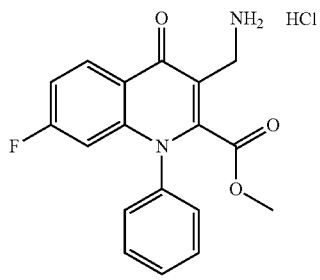 [SMILES: COC(=O)c1c(CN)c(=O)c2ccc(F)cc2n1-c1ccccc1 ; Cl]

Step 1: Preparation of 7-fluoro-3-methyl-4-oxo-1-phenyl-1,4-dihydro-quinoline-2-carboxylic

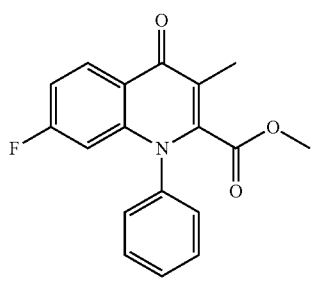 [SMILES: COC(=O)c1c(C)c(=O)c2ccc(F)cc2n1-c1ccccc1]

A mixture of N-(5-fluoro-2-propionyl-phenyl)-N-phenyl-oxalamic acid methyl ester (8 g, 24.3 mmol) and potassium carbonate (20.1 g, 146 mmol) in methanol (150 mL) was refluxed for 3 hr. The crude product was recrystallized from methanol to afford a mixture of 7-fluoro-3-methyl-4-oxo-1-phenyl-1,4-dihydro-quinoline-2-carboxylic acid methyl ester and 7-methoxy-3-methyl-4-oxo-1-phenyl-1,4-dihydro-quinoline-2-carboxylic acid methyl ester as approximately 5 g of a white solid.

Step 2: Preparation of 3-azidomethyl-7-fluoro-4-oxo-1-phenyl-1,4-dihydro-quinoline-2-carboxylic acid methyl ester

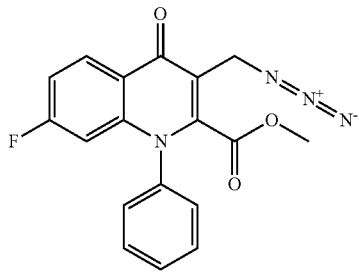 [SMILES: COC(=O)c1c(CN=[N+]=[N-])c(=O)c2ccc(F)cc2n1-c1ccccc1]

The mixture of obtained from step 1 above (7-fluoro-3-methyl-4-oxo-1-phenyl-1,4-dihydro-quinoline-2-carboxylic acid methyl ester and 7-methoxy-3-methyl-4-oxo-1-phenyl-1,4-dihydro-quinoline-2-carboxylic acid methyl ester), N-bromosuccinimide (3.6 g, 20 mmol) and V65 (2,2'-azobis (2,4-dimethylvaleronitrile)) (118 mg, 488 µmol) in dichloromethane (75 mL) was heated at 45° C. overnight. At this time, the reaction was concentrated. The crude product was dissolved in 100 mL DMF and sodium azide (4 g, 60 mmol) was added. The resulting mixture was heated at 70° C. for 2 hr. The crude product was purified using a 200 g silica gel column (100% hexanes ramped to 50% ethyl acetate in hexanes). Two products were isolated: 3-azidomethyl-7-fluoro-4-oxo-1-phenyl-1,4-dihydro-quinoline-2-carboxylic acid methyl ester (290 mg) and 3-azidomethyl-7-methoxy-4-oxo-1-phenyl-1,4-dihydro-quinoline-2-carboxylic acid methyl ester (570 mg).

Step 3: Preparation of 3-aminomethyl-7-fluoro-4-oxo-1-phenyl-1,4-dihydro-quinoline-2-carboxylic acid methyl ester hydrochloride salt

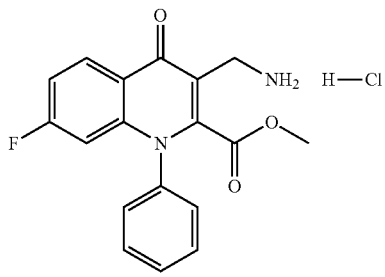

A mixture of 3-azidomethyl-7-fluoro-4-oxo-1-phenyl-1,4-dihdro-quinoline-1-carboxylic acid methyl ester (290 mg, 823 µmol), platinum (IV) oxide (40 mg, 0.176 mmol) and 4.0 M HCl in dioxane (2 mL) were combined with 1:1 dichloromethane/ethyl acetate (15 mL). The reaction flask was charged with 1 atmosphere H₂ and was stirred at room temperature for 3 hr. After this time, starting material still remained. The reaction flask was charged with an additional portion of platinum (IV) oxide. After additional stirring at room temperature under 1 atmosphere H₂, the catalyst was carefully filtered off, and the filter bed was washed with methanol. The combined filtrates were evaporated to afford 3-aminomethyl-7-fluoro-4-oxo-1-phenyl-1,4-dihydro-quinoline-2-carboxylic acid methyl ester hydrochloride (200 mg, 75%).

Preparation of (7-Chloro-4-oxo-1-phenyl-1,4-dihydro-quinolin-3-ylmethyl)-carbamic acid 4-nitro-phenyl ester (Intermediate M)

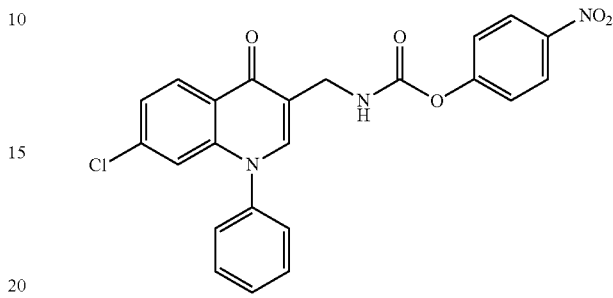

In a 250 mL round-bottomed flask, 3-(aminomethyl)-7-chloro-1-phenylquinolin-4(1H)-one (intermediate D) (1 g, 3.51 mmol), 4-nitrophenyl chloroformate (708 mg, 3.51 mmol) and N,N-diisopropylethylamine (1.36 g, 1.84 mL, 10.5 mmol) were combined with CH₂Cl₂ (30 mL). The reaction mixture was stirred overnight at room temperature. After this time, the reaction mixture was concentrated to dryness to afford (7-chloro-4-oxo-1-phenyl-1,4-dihydro-quinolin-3-ylmethyl)-carbamic acid 4-nitro-phenyl ester (1.6 g, 100%)

Preparation of 1-(7-Chloro-4-oxo-1-phenyl-1,4-dihydroquinolin-3-ylmethyl)-3-piperidin-4-yl-urea hydrochloride salt (Intermediate N)

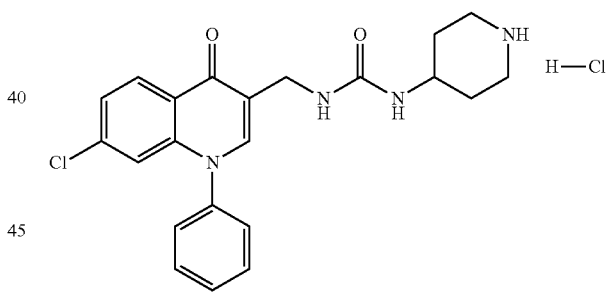

Step 1: Preparation of 4-[3-(7-Chloro-4-oxo-1-phenyl-1,4-dihydro-quinolin-3-ylmethyl)-ureido]-piperidine-1-carboxylic acid tert-butyl ester

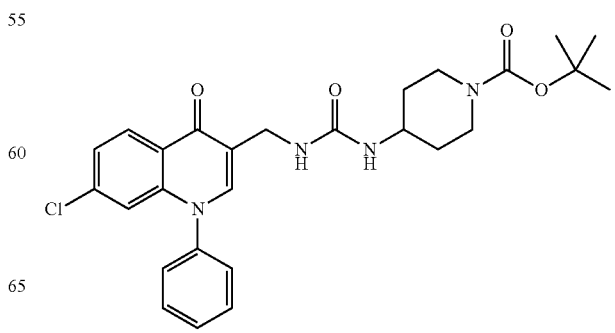

In a 25 mL round-bottomed flask, 4-nitrophenyl (7-chloro-4-oxo-1-phenyl-1,4-dihydroquinolin-3-yl)methylcarbamate (intermediate M) (1.6 g, 3.56 mmol), 4-boc-amino-piperidine (712 mg, 3.56 mmol) and N,N-diisopropylethylamine (1.38 g, 1.86 mL, 10.7 mmol) were combined with methylene chloride (5.00 mL). The reaction mixture was stirred at room temperature. The mixture was partitioned between $CH_2Cl_2$ and water. The organic phase was dried over magnesium sulfate, filtered, and concentrated to afford 4-[3-(7-chloro-4-oxo-1-phenyl-1,4-dihydro-quinolin-3-ylmethyl)-ureido]-piperidine-1-carboxylic acid tert-butyl ester (1.7 g, 94%).

Step 2: Preparation of 1-(7-chloro-4-oxo-1-phenyl-1,4-dihydroquinolin-3-ylmethyl)-3-piperidin-4-yl-urea hydrochloride salt

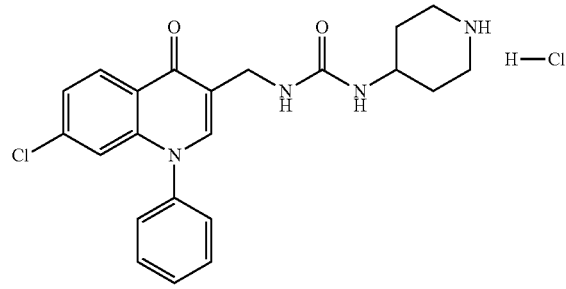

In a 250 mL flask, tert-butyl 4-(3-((7-chloro-4-oxo-1-phenyl-1,4-dihydroquinolin-3-yl)methyl)ureido)piperidine-1-carboxylate (1.6 g, 3.13 mmol) and HCl gas were combined with dioxane (30 mL). The reaction mixture was stirred overnight at room temperature. After this time, LC/MS showed the reaction to be complete. The product 1-(7-chloro-4-oxo-1-phenyl-1,4-dihydroquinolin-3-ylmethyl)-3-piperidin-4-yl-urea hydro-chloride salt (1.4 g, 100%) was used in subsequent steps without further purification.

Part II

Preparation of Compounds

Example I-1

1-Benzyl-2-oxo-1,2-dihydro-pyridine-4-carboxylic acid (7-chloro-2-oxazol-2-yl-4-oxo-1-phenyl-1,4-dihydro-quinolin-3-ylmethyl)-amide

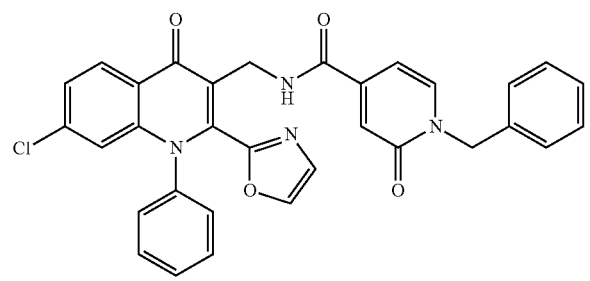 [SMILES: O=C(NCc1c(-c2ncco2)n(-c2ccccc2)c2cc(Cl)ccc2c1=O)c1ccn(Cc2ccccc2)c(=O)c1]

In a 10 mL round-bottomed flask, 1-benzyl-2-oxo-1,2-dihydropyridine-4-carboxylic acid (32.6 mg, 0.142 mmol), bromo-tris-pyrrolidino-phosphonium hexafluorophosphate (PyBrOP) (66.3 mg, 0.142 mmol) and N,N-diisopropylethylamine (73.5 mg, 0.099 mL, 0.569 mmol) were combined with DMF (2 mL). The reaction mixture was stirred at room temperature for 10 min. After this time, 3-aminomethyl-7-chloro-2-oxazol-2-yl-1-phenyl-1H-quinolin-4-one (intermediate A) was added (0.050 g, 0.142 mmol). The reaction mixture was stirred at room temperature for 3 hr. The product was purified using flash chromatography (40% ethyl acetate/hexane ramped to 100% ethyl acetate/hexanes). MS calcd. for $C_{32}H_{24}ClN_4O_4$ [(M+H)$^+$] 563.1, obsd. 563.3.

Examples I-2 to I-5

The following examples I-2 to I-5 were prepared in an analogous manner to example I-1, starting with intermediate A, an appropriate commercially available carboxylic acid, and a commercially available amide coupling reagent (for example, bromo-tris-pyrrolidino-phosphonium hexafluorophosphate (PyBrOP) or 1-(3-dimethylaminopropyl)-3-ethyl-carbodiimide hydrochloride (EDC) and 1-hydroxybenzotriazole (HOBT).

Example I-2

N-(7-Chloro-2-oxazol-2-yl-4-oxo-1-phenyl-1,4-dihydro-quinolin-3-ylmeth yl)-2-morpholin-4-yl-isonicotinamide

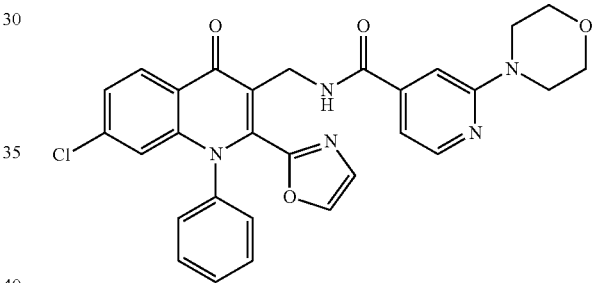

N-(7-Chloro-2-oxazol-2-yl-4-oxo-1-phenyl-1,4-dihydro-quinolin-3-ylmethyl)-2-morpholin-4-yl-isonicotinamide was prepared starting from intermediate A and 2-morpholinoisonicotinic acid. MS calcd. for $C_{29}H_{25}ClN_5O_4$ [(M+H)$^+$] 542.2, obsd. 542.2.

Example I-3

N-(7-Chloro-2-oxazol-2-yl-4-oxo-1-phenyl-1,4-dihydro-quinolin-3-ylmeth yl)-6-morpholin-4-yl-nicotinamide

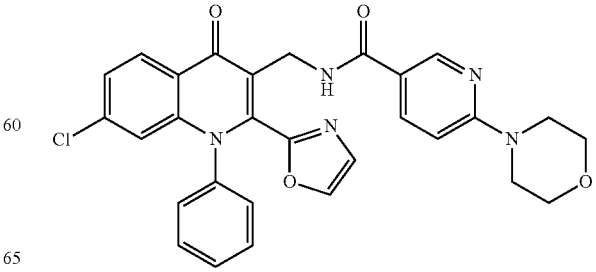

N-(7-Chloro-2-oxazol-2-yl-4-oxo-1-phenyl-1,4-dihydro-quinolin-3-ylmethyl)-6-morpho-lin-4-yl-nicotinamide was prepared starting from intermediate A and 6-morpholinonicotinic acid. $^1$H NMR (400 MHz, DMSO-d$_6$) δ ppm 8.47 (d, J=1.76 Hz, 1H) 8.33 (d, J=8.28 Hz, 1H) 8.12 (t, J=4.50 Hz, 1H) 7.98 (d, J=0.75 Hz, 1H) 7.85 (dd, J=9.03, 2.51 Hz, 1H) 7.47-7.57 (m, 4H) 7.36-7.44 (m, 2H) 7.17 (s, 1H) 6.79 (d, J=9.03 Hz, 1H) 6.73 (d, J=2.01 Hz, 1H) 4.24 (d, J=4.52 Hz, 2H) 3.63-3.71 (m, 4H) 3.48-3.55 (m, 4H). MS calcd. for C$_{29}$H$_{24}$ClN$_5$O$_4$ [(M+H)$^+$] 542.2, obsd. 542.0.

Example I-4

N-(7-Chloro-2-oxazol-2-yl-4-oxo-1-phenyl-1,4-dihydro-quinolin-3-ylmethyl)-terephthalamide

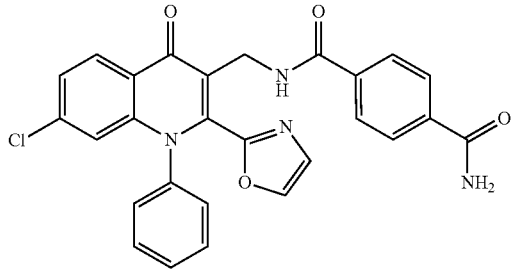 [SMILES: NC(=O)c1ccc(C(=O)NCc2c(-c3ncco3)n(-c3ccccc3)c3cc(Cl)ccc3c2=O)cc1]

N-(7-Chloro-2-oxazol-2-yl-4-oxo-1-phenyl-1,4-dihydro-quinolin-3-ylmethyl)-terephthal-amide was prepared starting from intermediate A and 4-(aminocarbonyl)benzoic acid. $^1$H NMR (400 MHz, DMSO-d$_6$) δ ppm 8.40 (t, J=4.50 Hz, 1H) 8.31 (d, J=8.59 Hz, 1H) 8.02 (br. s, 1H) 7.97 (d, J=0.78 Hz, 1H) 7.83-7.87 (m, 2H) 7.73-7.78 (m, 2H) 7.37-7.54 (m, 7H) 7.16 (d, J=0.78 Hz, 1H) 6.72 (d, J=1.56 Hz, 1H) 4.25 (d, J=4.30 Hz, 2H). MS calcd. for C$_{27}$H$_{19}$ClN$_4$O$_4$ [(M+H)$^+$] 499.1, obsd. 499.

Example I-5

5-[(7-Chloro-2-oxazol-2-yl-4-oxo-1-phenyl-1,4-dihydro-quinolin-3-ylmethyl)-carbamoyl]-pyridine-2-carboxylic acid methyl ester

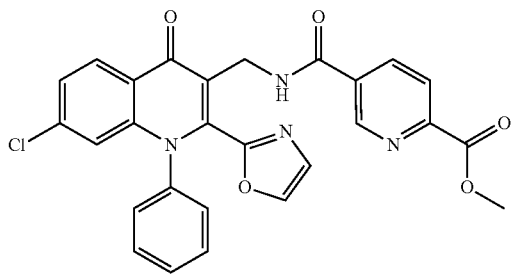 [SMILES: COC(=O)c1ccc(C(=O)NCc2c(-c3ncco3)n(-c3ccccc3)c3cc(Cl)ccc3c2=O)cn1]

5-[(7-Chloro-2-oxazol-2-yl-4-oxo-1-phenyl-1,4-dihydro-quinolin-3-ylmethyl)-carbamoyl]-pyridine-2-carboxylic acid methyl ester was prepared starting from intermediate A and 6-(methoxycarbonyl)nicotinic acid. MS calcd. for C$_{27}$H$_{20}$ClN$_4$O$_5$ [(M+H)$^+$] 515.1, obsd. 515.0.

Example I-6

6-Chloro-N-(7-chloro-2-oxazol-2-yl-4-oxo-1-phenyl-1,4-dihydro-quinolin-3-ylmethyl)-nicotinamide

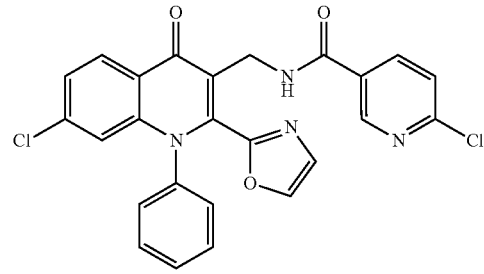 [SMILES: O=C(NCc1c(-c2ncco2)n(-c2ccccc2)c2cc(Cl)ccc2c1=O)c1ccc(Cl)nc1]

A 5 mL round-bottomed flask was charged with 6-chloronicotinamide (14 mg, 0.091 mmol), sodium hydride (60% suspension in mineral oil, 5.0 mg, 0.013 mmol) and DMF (1 mL) to give a slightly white suspension. This mixture was stirred at 50° C. for 15 min. During this time, the reaction mixture became more cloudy and difficult to stir. The reaction mixture was cooled to room temperature. A solution of 3-(bromomethyl)-7-chloro-2-(oxazol-2-yl)-1-phenylquinolin-4(1H)-one (38 mg, 0.091 mmol) in DMF (1 mL) was added dropwise to the room temperature reaction mixture. The reaction was stirred at 50° C. over 1 hr. LC/MS at this time suggested formation of the desired product. The reaction mixture was allowed to cool gradually to room temperature, then it was stirred at room temperature overnight. The reaction was quenched via addition of 1 mL water slowly. The quenched reaction mixture was then partitioned between 20 mL ethyl acetate and 20 mL water. The organic phase was dried (MgSO$_4$), filtered, then concentrated over silica gel. The silica gel supported crude product was loaded onto a 40 gram silica gel column. Flash chromatography (75% ethyl acetate-hexanes ramped to 100% ethyl acetate) was used to partially purify the desired product 6-chloro-N-(7-chloro-2-(oxazol-2-yl)-4-oxo-1-phenyl-1,4-dihydroquinolin-3-ylmethyl)nicotinamide from the side product 6-chloro-N,N-bis((7-chloro-2-(oxazol-2-yl)-4-oxo-1-phenyl-1,4-dihydroquinolin-3-yl)methyl)nicotinamide. Homogeneous fractions were concentrated to provide 6-chloro-N-(7-chloro-2-(oxazol-2-yl)-4-oxo-1-phenyl-1,4-dihydroquinolin-3-ylmethyl)nicotin-amide as 1 mg (2% yield) of a white solid. $^1$H NMR (chloroform-d) δ ppm 8.75 (d, J=2.4 Hz, 1H) 8.42 (d, J=8.6 Hz, 1H) 7.99 (dd, J=8.2, 2.7 Hz, 1H) 7.68 (bs, 1H), 7.58 (s, 1H), 7.45 (m, 3H), 7.39 (dd, J=8.5, 2.0 Hz, 1H) 7.34 (d, J=8.2 Hz, 1H) 7.28 (m, 2H) 7.13 (s, 1H) 6.85 (d, J=2.0 Hz, 1H) 4.47 (d, J=5.5 Hz, 2H). MS calcd. for C$_{25}$H$_{16}$C$_{12}$N$_4$O$_3$ [(M+H)$^+$] 490.1, obsd. 490.9.

Example I-7

3,4,5,6-Tetrahydro-2H-[1,2']bipyridinyl-5'-carboxylic acid (7-chloro-2-oxazol-2-yl-4-oxo-1-phenyl-1,4-dihydro-quinolin-3-ylmethyl)-amide

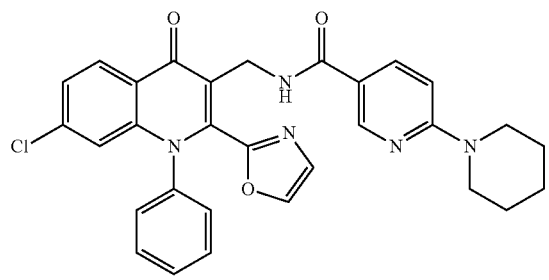 [SMILES: O=C(NCc1c(-c2ncco2)n(-c2ccccc2)c2cc(Cl)ccc2c1=O)c1ccc(N2CCCCC2)nc1]

In a 20 mL flask, 6-chloro-N-((7-chloro-2-(oxazol-2-yl)-4-oxo-1-phenyl-1,4-dihydroquinolin-3-yl)methyl)nicotinamide (Example I-6) (6 mg, 0.012 mmol) and piperidine (10.4 mg, 0.012 mL, 0.122 mmol) were combined with NMP (0.500 mL) to give a light yellow solution. The reaction mixture was heated at 120° C. for 1.5 hr. After this time, LC/MS showed that the reaction was complete. The reaction mixture was cooled to room temperature, and the solvent was evaporated. The crude product was purified using preparatory reverse-phase HPLC. The product 3,4,5,6-tetrahydro-2H-[1,2']bipyridinyl-5'-carboxylic acid (7-chloro-2-oxazol-2-yl-4-oxo-1-phenyl-1,4-dihydro-quinolin-3-ylmethyl)-amide was obtained as an off-white solid. $^1$H NMR (400 MHz, DMSO-$d_6$) δ ppm 8.39 (d, J=2.30 Hz, 1H) 8.31 (d, J=8.59 Hz, 1H) 8.08 (br. s, 1H) 7.96 (d, J=0.80 Hz, 1H) 7.78-7.83 (m, 1H) 7.45-7.54 (m, 4H) 7.38 (d, J=8.20 Hz, 2H) 7.15 (d, J=0.80 Hz, 1H) 6.78-6.85 (m, 1H) 6.71 (d, J=1.95 Hz, 1H) 4.21 (d, J=4.69 Hz, 2H) 3.54-3.61 (m, 4H) 1.45-1.63 (m, 6H). MS calcd. for $C_{30}H_{26}ClN_5O_3$ [(M+H)$^+$] 540.2, obsd. 540.1

Example I-8

Benzo[1,3]dioxole-5-carboxylic acid (7-chloro-2-oxazol-2-yl-4-oxo-1-phenyl-1,4-dihydro-quinolin-3-ylmethyl)-amide

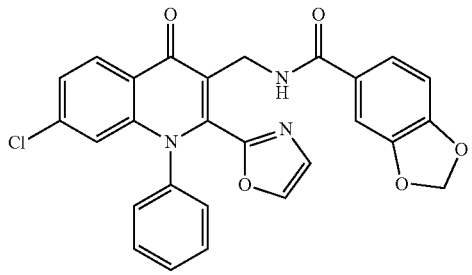 [SMILES: O=C(NCc1c(-c2ncco2)n(-c2ccccc2)c2cc(Cl)ccc2c1=O)c1ccc2c(c1)OCO2]

In a 20 mL vial, 3-(aminomethyl)-7-chloro-2-(oxazol-2-yl)-1-phenylquinolin-4(1H)-one (intermediate A) (20 mg, 0.057 mmol), benzo[d][1,3]dioxole-5-carbonyl chloride (12 mg, 0.065 mmol) and N,N-(dimethylamino)pyridine (DMAP) (1.0 mg, 0.085 mmol) were combined with methylene chloride (1.5 mL) to give a brown solution. N,N-diisopropylethylamine (37 mg, 0.050 mL, 0.28 mmol) was added. The reaction mixture was stirred overnight at room temperature. In the morning, LC/MS indicated complete conversion to the desired product. The reaction mixture was diluted with 10 mL methylene chloride, then the organic solution was washed with water. The organic phase was dried over $Na_2SO_4$, filtered, then concentrated over silica gel. The silica gel-supported crude product was loaded onto a 25 gram SiliCycle column. Flash chromatography (50% ethyl acetate-hexanes ramped to 75% ethyl acetate-hexanes) afforded benzo[1,3]dioxole-5-carboxylic acid (7-chloro-2-oxazol-2-yl-4-oxo-1-phenyl-1,4-dihydro-quinolin-3-ylmethyl)-amide as a brown oil. $^1$H NMR (300 MHz, chloroform-d) δ ppm 8.36 (d, J=8.67 Hz, 1H) 7.50 (d, J=0.94 Hz, 1H) 7.34-7.42 (m, 4H) 7.30 (dd, J=8.67, 1.88 Hz, 1H) 7.15-7.26 (m, 6H) 7.05 (d, J=0.94 Hz, 1H) 6.77 (d, J=1.88 Hz, 1H) 6.70 (d, J=8.10 Hz, 1H) 5.91 (s, 2H) 4.37 (s, 2H). MS calcd. for $C_{27}H_{18}ClN_3O_5$ [(M+H)$^+$] 499.9, obsd. 500.0.

Example I-9

1-Benzyl-2-oxo-1,2-dihydro-pyridine-4-carboxylic acid (2-oxazol-2-yl-4-oxo-1-phenyl-1,4-dihydro-[1,8]naphthyridin-3-ylmethyl)-amide

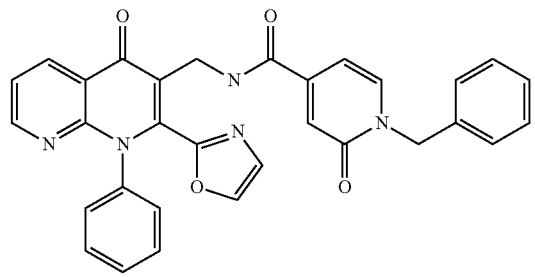 [SMILES: O=C(NCc1c(-c2ncco2)n(-c2ccccc2)c2ncccc2c1=O)c1ccn(Cc2ccccc2)c(=O)c1]

In a 50 mL round-bottomed flask, 1-benzyl-2-oxo-1,2-dihydropyridine-4-carboxylic acid (21 mg, 0.93 mmol), 1-(3-dimethylaminopropyl)-3-ethylcarbodiimide (23.0 mg, 0.148 mmol), 1H-benzo[d][1,2,3]triazol-1-ol (20.0 mg, 0.148 mmol) and N,N-diisopropylethylamine were combined with methylene chloride (5 mL). The reaction mixture was stirred at room temperature for 10 min. After this time, 3-(aminomethyl)-2-(oxazol-2-yl)-1-phenyl-1,8-naphthyridin-4(1H)-one (intermediate B) was added. The reaction mixture was stirred at room temperature over the weekend. The reaction mixture was partitioned between methylene chloride and water. The organic phase was dried over sodium sulfate, then filtered and concentrated. The crude product was purified using flash chromatography (Isco, 0% ethyl acetate-hexanes ramped to 70% ethyl acetate-hexanes) to afford 1-Benzyl-2-oxo-1,2-dihydro-pyridine-4-carboxylic acid (2-oxazol-2-yl-4-oxo-1-phenyl-1,4-dihydro-[1,8]naphthyridin-3-ylmethyl)-amide as a light brown powder (12 mg). MS calcd. for $C_{31}H_{24}N_5O_4$ [(M+H)$^+$] 530.2, obsd. 530.3

Examples I-10 to I-11

The following examples I-10 to I-11 were prepared in an analogous manner to example I-9, starting with intermediate B, an appropriate commercially available carboxylic acid, and a commercially available amide coupling reagent (for example, bromo-tris-pyrrolidino-phosphonium hexafluorophosphate (PyBrOP) or 1-(3-dimethylaminopropyl)-3-ethylcarbodiimide hydrochloride (EDC) and 1-hydroxybenzotriazole (HOBT).

Example I-10

6-Morpholin-4-yl-N-(2-oxazol-2-yl-4-oxo-1-phenyl-1,4-dihydro-[1,8]naphthyridin-3-ylmethyl)-nicotinamide

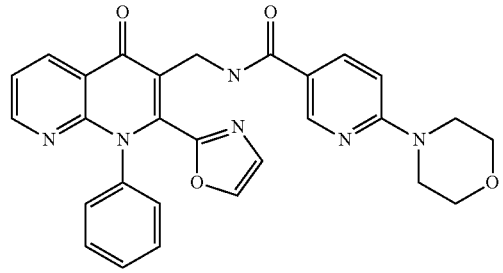 [SMILES: O=C(NCc1c(-c2ncco2)n(-c2ccccc2)c2ncccc2c1=O)c1ccc(N2CCOCC2)nc1]

6-Morpholin-4-yl-N-(2-oxazol-2-yl-4-oxo-1-phenyl-1,4-dihydro-[1,8]naphthyridin-3-yl-methyl)-nicotinamide was prepared starting from intermediate B and 6-morpholin-4-yl-nicotinic acid. $^1$H NMR (300 MHz, DMSO-$d_6$) δ ppm 8.65-8.67 (m, 2H) 8.48 (d, J=2.90 Hz, 1H) 8.05-8.15 (m, 1H) 7.98 (d, J=0.75 Hz, 1H) 7.85 (dd, J=8.70, 2.90 Hz, 1H) 7.55 (dd, J=8.20, 4.40 Hz, 1H) 7.23-7.45 (m, 5H) 7.18 (d, J=0.75 Hz, 1H) 6.79 (d, J=8.30 Hz, 1H) 4.25 (d, J=4.20 Hz, 2H) 3.62-3.73 (m, 4H) 3.47-3.57 (m, 4H).

Example I-11

1-Methyl-1H-pyrazole-4-carboxylic acid (2-oxazol-2-yl-4-oxo-1-phenyl-1,4-dihydro-[1,8]naphthyridin-3-ylmethyl)-amide

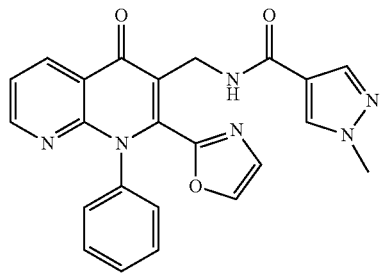 [SMILES: Cn1cc(C(=O)NCc2c(-c3ncco3)n(-c3ccccc3)c3ncccc3c2=O)cn1]

Methyl-1H-pyrazole-4-carboxylic acid (2-oxazol-2-yl-4-oxo-1-phenyl-1,4-dihydro-[1,8]naphthyridin-3-ylmethyl)-amide was prepared starting from intermediate B and 1-methyl-1H-pyrazole-4-carboxylic acid. MS calcd. for $C_{23}H_{19}N_6O_3$ [(M+H)$^+$] 427.1, obsd. 427.2.

Example I-12

4-Hydroxymethyl-3,4,5,6-tetrahydro-2H-[1,2']bipyridinyl-5'-carboxylic acid (2-oxazol-2-yl-4-oxo-1-phenyl-1,4-dihydro-[1,8]naphthyridin-3-ylmethyl)-amide

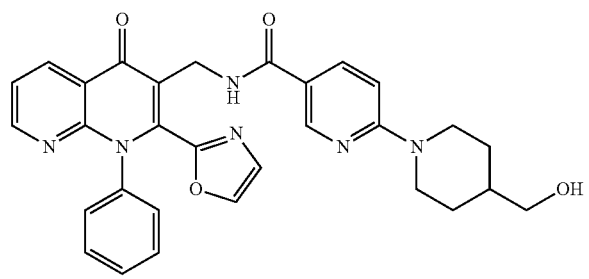 [SMILES: O=C(NCc1c(-c2ncco2)n(-c2ccccc2)c2ncccc2c1=O)c1ccc(N2CCC(CO)CC2)nc1]

In a 50 mL round-bottomed flask, 6-chloronicotinic acid (18.2 mg, 0.116 mmol), 1-(3-dimethylaminopropyl)-3-ethylcarbodiimide (28.7 mg, 0.185 mmol) and 1H-benzo[d][1,2,3]triazol-1-ol (15.6 mg, 0.116 mmol) and N,N-diisopropylethylamine (0.200 mL, 1.16 mmol) were combined with CH$_2$Cl$_2$ (5.00 ml). The reaction mixture was stirred at room temperature for 10 min. After this time, 3-(aminomethyl)-2-(oxazol-2-yl)-1-phenyl-1,8-naphthyridin-4(1H)-one (intermediate B) (50 mg, 0.116 mmol) was added, then the mixture was stirred at room temperature over the weekend. The reaction mixture was partitioned between CH$_2$Cl$_2$ and water. The organic phase was dried over MgSO$_4$, filtered, and concentrated. The intermediate 6-chloro-N-(2-oxazol-2-yl-4-oxo-1-phenyl-1,4-dihydro-[1,8]naphthyridin-3-ylmethyl)-nicotinamide was used in the next step without further purification.

The product from above was combined with piperidin-4-ylmethanol (25 mg, 0.218 mmol), N,N-diisopropylethylamine (0.095 mL, 0.546 mmol) and NMP (5.00 ml). The mixture was stirred at room temperature over the weekend. The solvent was evaporated and the crude product was purified using flash chromatography (Isco, 0% ethyl acetate-hexanes ramped to 100% ethyl acetate-hexanes) to give 4-hydroxymethyl-3,4,5,6-tetrahydro-2H-[1,2']bipyridinyl-5'-carboxylic acid (2-oxazol-2-yl-4-oxo-1-phenyl-1,4-dihydro-[1,8]naphthyridin-3-ylmethyl)-amide. MS calcd. for $C_{30}H_{29}N_6O_4$ [(M+H)$^+$] 537.2, obsd. 537.3.

Example I-13

7-Chloro-3-{[(6-morpholin-4-yl-pyridine-3-carbonyl)-amino]-methyl}-4-oxo-1-phenyl-1,4-dihydro-quinoline-2-carboxylic acid dimethylamide

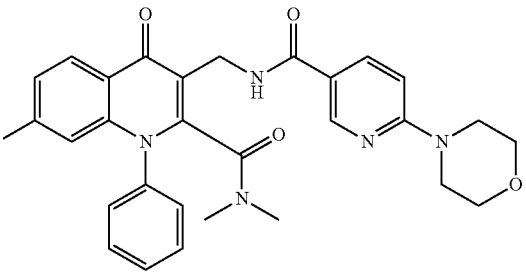

6-Morpholinonicotinic acid (32.6 mg, 0.142 mmol), bromo-tris-pyrrolidino-phosphonium hexafluorophosphate (PyBrOP) (120 mg, 0.374 mmol) and triethylamine (100 mg, 0.137 mL, 0.988 mmol) were combined with DMF (4 mL). The reaction mixture was stirred at room temperature for 10 min. After this time, 3-(aminomethyl)-7-chloro-N,N-dimethyl-4-oxo-1-phenyl-1,4-dihydroquinoline-2-carboxamide (intermediate C) (0.052 g, 0.156 mmol) was added. The reaction mixture was stirred at room temperature for 15 hr. The crude material was purified by flash chromatography (10% ethyl acetate-hexanes ramped to 100% ethyl acetate). MS calcd. for $C_{29}H_{28}ClN_5O_4$ [(M+H)$^+$] 546.2, obsd. 546.0.

Examples I-14 to I-21

The following examples I-14 to I-21 were prepared in an analogous manner to example I-13, starting with intermediate C, an appropriate commercially available carboxylic acid, and a commercially available amide coupling reagent (for example, bromo-tris-pyrrolidino phosphonium hexafluorophosphate (PyBrOP), 1-(3-dimethylaminopropyl)-3-ethylcarbodiimide hydrochloride (EDC) and 1-hydroxybenzotriazole (HOBT), or O-benzotriazole-1-yl)-N,N,N',N'-tetramethyluronium hexafluorophosphate (HBTU).

Example I-14

7-Chloro-3-{[(2-morpholin-4-yl-thiazole-5-carbonyl)-amino]-methyl}-4-oxo-1-phenyl-1,4-dihydro-quinoline-2-carboxylic acid dimethylamide

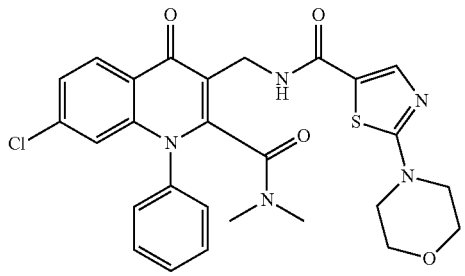 [SMILES: CN(C)C(=O)c1c(CNC(=O)c2cnc(N3CCOCC3)s2)c(=O)c2ccc(Cl)cc2n1-c1ccccc1]

7-Chloro-3-{[(2-morpholin-4-yl-thiazole-5-carbonyl)-amino]-methyl}-4-oxo-1-phenyl-1,4-dihydro-quinoline-2-carboxylic acid dimethylamide was prepared starting from intermediate C and 2-morpholin-4-yl-thiazole-5-carboxylic acid. MS calcd. for $C_{27}H_{26}ClN_5O_4S$ [(M+H)$^+$] 552.1, obsd. 552.0.

Example I-15

7-Chloro-3-[(4-methoxy-benzoylamino)-methyl]-4-oxo-1-phenyl-1,4-dihydro-quinoline-2-carboxylic acid dimethylamide

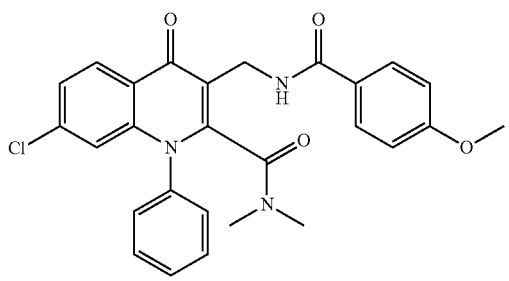 [SMILES: COc1ccc(C(=O)NCc2c(C(=O)N(C)C)n(-c3ccccc3)c3cc(Cl)ccc3c2=O)cc1]

7-Chloro-3-[(4-methoxy-benzoylamino)-methyl]-4-oxo-1-phenyl-1,4-dihydro-quinoline-2-carboxylic acid dimethylamide was prepared starting from intermediate C and 4-methoxybenzoic acid. MS calcd. for $C_{27}H_{24}ClN_3O_4$ [(M+H)$^+$] 490.2, obds. 490.0.

Example I-16

3-{[(Benzothiazole-6-carbonyl)-amino]-methyl}-7-chloro-4-oxo-1-phenyl-1,4-dihydro-quinoline-2-carboxylic acid dimethylamide

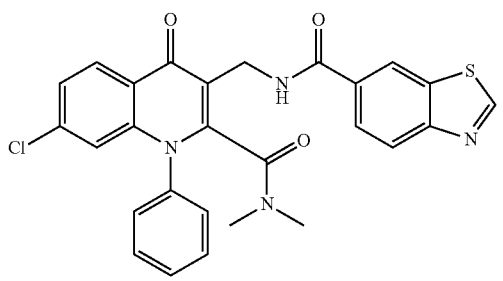 [SMILES: CN(C)C(=O)c1c(CNC(=O)c2ccc3ncsc3c2)c(=O)c2ccc(Cl)cc2n1-c1ccccc1]

3-{[(Benzothiazole-6-carbonyl)-amino]-methyl}-7-chloro-4-oxo-1-phenyl-1,4-dihydro-quinoline-2-carboxylic acid dimethylamide was prepared starting from intermediate C and benzothiazole-6-carboxylic acid. MS calcd. for $C_{27}H_{21}ClN_4O_3S$ [(M+H)$^+$] 517.1, obsd. 516.9.

Example I-17

7-Chloro-3-[(4-morpholin-4-yl-benzoylamino)-methyl]-4-oxo-1-phenyl-1,4-dihydro-quinoline-2-carboxylic acid dimethylamide

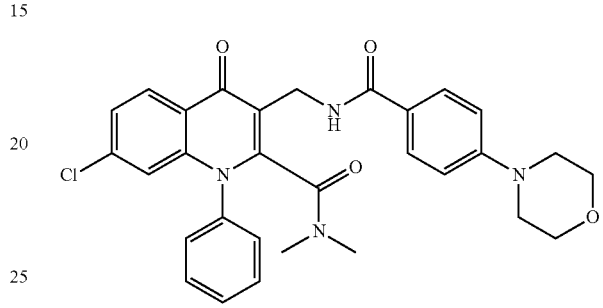

7-Chloro-3-[(4-morpholin-4-yl-benzoylamino)-methyl]-4-oxo-1-phenyl-1,4-dihydro-quinoline-2-carboxylic acid dimethylamide was prepared starting from intermediate C and 4-morpholin-4-yl-benzoic acid. MS calcd. for $C_{30}H_{29}ClN_4O_4$ [(M+H)$^+$] 545.2, obsd. 545.2.

Example I-18

7-Chloro-3-[(4-oxazol-5-yl-benzoylamino)-methyl]-4-oxo-1-phenyl-1,4-dihydro-quinoline-2-carboxylic acid dimethylamide

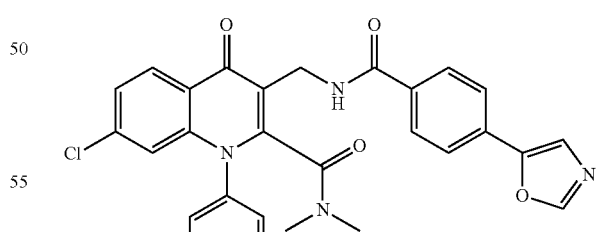

7-Chloro-3-[(4-oxazol-5-yl-benzoylamino)-methyl]-4-oxo-1-phenyl-1,4-dihydro-quinoline-2-carboxylic acid dimethylamide was prepared starting from intermediate C and 4-(oxazol-4-yl)benzoic acid. MS calcd. for $C_{29}H_{23}ClN_4O_4$ [(M+H)$^+$] 527.1, obsd. 527.0.

Example I-19

7-Chloro-3-[(4-methanesulfonyl-benzoylamino)-methyl]-4-oxo-1-phenyl-1,4-di-hydro-quinoline-2-carboxylic acid dimethylamide

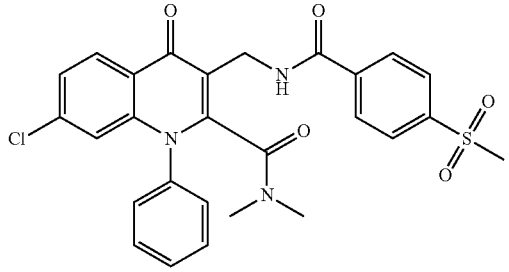 [SMILES: CN(C)C(=O)c1c(CNC(=O)c2ccc(S(C)(=O)=O)cc2)c(=O)c2ccc(Cl)cc2n1-c1ccccc1]

7-Chloro-3-[(4-methanesulfonyl-benzoylamino)-methyl]-4-oxo-1-phenyl-1,4-di-hydro-quinoline-2-carboxylic acid dimethylamide was prepared starting from intermediate C and 4-(methylsulfonyl)benzoic acid. MS calcd. for $C_{27}H_{24}ClN_3O_5S$ [(M+H)$^+$] 538.1, obsd. 538.2.

Example I-20

7-Chloro-3-[(4-fluoro-benzoylamino)-methyl]-4-oxo-1-phenyl-1,4-di-hydro-quinoline-2-carboxylic acid dimethylamide

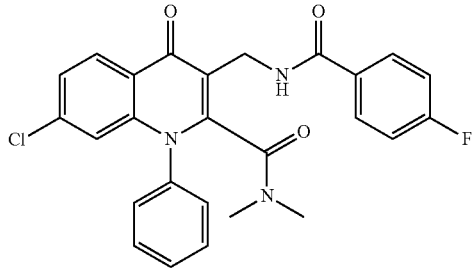 [SMILES: CN(C)C(=O)c1c(CNC(=O)c2ccc(F)cc2)c(=O)c2ccc(Cl)cc2n1-c1ccccc1]

7-Chloro-3-[(4-fluoro-benzoylamino)-methyl]-4-oxo-1-phenyl-1,4-di-hydro-quinoline-2-carboxylic acid dimethylamide was prepared starting from intermediate C and 4-fluorobenzoic acid. MS calcd. for $C_{26}H_{21}ClFN_3O_3$ [(M+H)$^+$] 478.1, obsd. 477.9.

Example I-21

7-Chloro-3-{[(2,3-dihydro-benzo[1,4]dioxine-6-carbonyl)-amino]-methyl}-4-oxo-1-phenyl-1,4-dihydro-quinoline-2-carboxylic acid dimethylamide

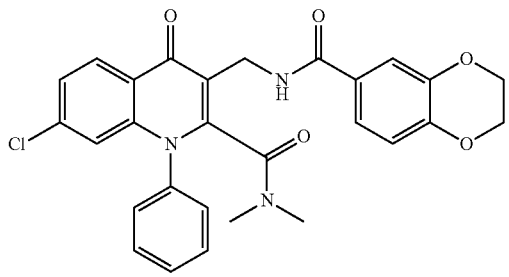 [SMILES: CN(C)C(=O)c1c(CNC(=O)c2ccc3c(c2)OCCO3)c(=O)c2ccc(Cl)cc2n1-c1ccccc1]

7-Chloro-3-{[(2,3-dihydro-benzo[1,4]dioxine-6-carbonyl)-amino]-methyl}-4-oxo-1-phenyl-1,4-dihydro-quinoline-2-carboxylic acid dimethylamide was prepared starting from intermediate C and 2,3-dihydrobenzo[1,4]dioxine-6-carboxylic acid. MS calcd. for $C_{28}H_{24}ClN_3O_5$ [(M+H)$^+$] 518, obsd. 518.

Example I-22

3-{[(1-Benzyl-2-oxo-1,2-dihydro-pyridine-4-carbonyl)-amino]-methyl}-7-chloro-4-oxo-1-phenyl-1,4-dihydro-quinoline-2-carboxylic acid dimethylamide

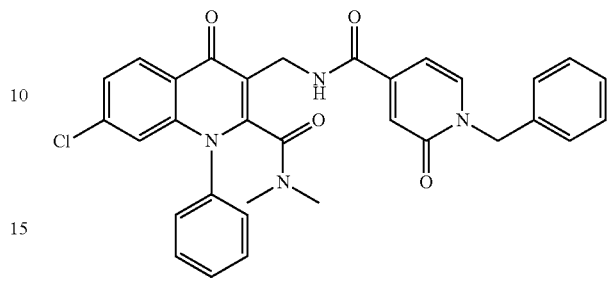

3-{[(1-Benzyl-2-oxo-1,2-dihydro-pyridine-4-carbonyl)-amino]-methyl}-7-chloro-4-oxo-1-phenyl-1,4-dihydro-quinoline-2-carboxylic acid dimethylamide was prepared starting from intermediate C and 1-benzyl-2-oxo-1,2-dihydro-pyridine-4-carboxylic acid. MS calcd. for $C_{32}H_{28}ClN_4O_4$ [(M+H)$^+$] 567.2, obsd. 567.1.

Example I-23

7-Chloro-3-{[(1-methyl-1H-pyrazole-4-carbonyl)-amino]-methyl}-4-oxo-1-phenyl-1,4-dihydro-quinoline-2-carboxylic acid dimethylamide

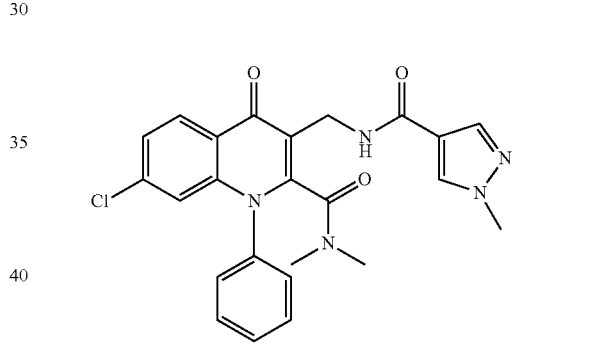

7-Chloro-3-{[(1-methyl-1H-pyrazole-4-carbonyl)-amino]-methyl}-4-oxo-1-phenyl-1,4-dihydro-quinoline-2-carboxylic acid dimethylamide was prepared starting from intermediate D and 1-methyl-1H-pyrazole-4-carboxylic acid. MS calcd. for $C_{24}H_{23}ClN_5O_3$ [(M+H)$^+$] 464.1, obsd. 464.2.

Example I-24

4-Hydroxymethyl-3,4,5,6-tetrahydro-2H-[1,2']bipyridinyl-5'-carboxylic acid (7-chloro-2-dimethylcarbamoyl-4-oxo-1-phenyl-1,4-dihydro-quinolin-3-ylmethyl)-amide

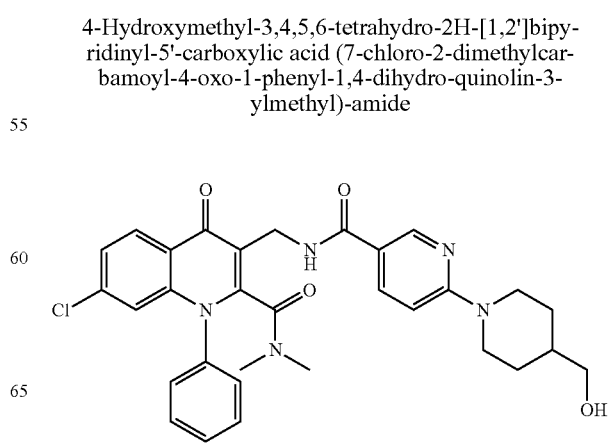

Step 1: Preparation of 7-chloro-3-{[(6-chloro-pyridine-3-carbonyl)-amino]-methyl}-4-oxo-1-phenyl-1,4-dihydro-quinoline-2-carboxylic acid dimethylamide

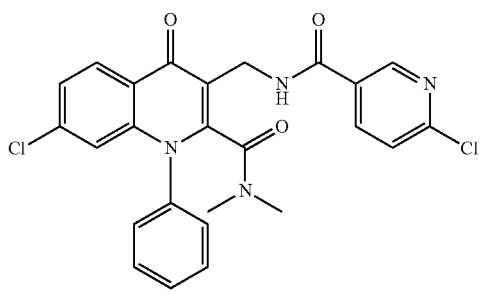 [SMILES: CN(C)C(=O)c1c(CNC(=O)c2ccc(Cl)nc2)c(=O)c2ccc(Cl)cc2n1-c1ccccc1]

A mixture of 3-(aminomethyl)-7-chloro-N,N-dimethyl-4-oxo-1-phenyl-1,4-dihydroquinoline-2-carboxamide (intermediate C, 200 mg, 0.562 mmol), 6-chloronicotinoyl chloride (109 mg, 0.618 mmol), triethylamine (0.157 mL, 1.13 mmol) and methylene chloride (30 mL) was stirred at room temperature. The crude material was purified by flash chromatography (10% ethyl acetate in hexanes ramped to 70% ethyl acetate in hexanes) to give 7-chloro-3-{[(6-chloro-pyridine-3-carbonyl)-amino]-methyl}-4-oxo-1-phenyl-1,4-dihydro-quinoline-2-carboxylic acid dimethylamide.

Step 2: Preparation of 4-hydroxymethyl-3,4,5,6-tetrahydro-2H-[1,2']bipyridinyl-5'-carboxylic acid (7-chloro-2-dimethylcarbamoyl-4-oxo-1-phenyl-1,4-dihydro-quinolin-3-ylmethyl)-amide

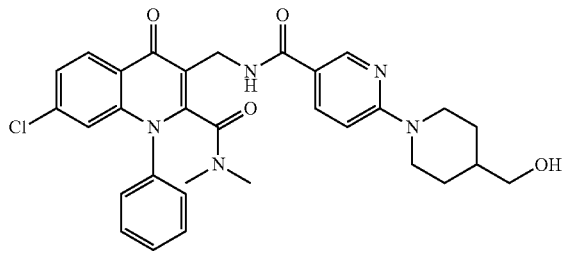 [SMILES: CN(C)C(=O)c1c(CNC(=O)c2ccc(N3CCC(CO)CC3)nc2)c(=O)c2ccc(Cl)cc2n1-c1ccccc1]

The intermediate 7-chloro-3-{[(6-chloro-pyridine-3-carbonyl)-amino]-methyl}-4-oxo-1-phenyl-1,4-dihydro-quinoline-2-carboxylic acid dimethylamide (70 mg, 0.141 mmol) was combined with piperidin-4-ylmethanol (40 mg, 0.346 mmol) and NMP (2 mL). The reaction mixture was heated at 125° C. for 2 hr. After this time, the crude product was subjected to preparative reverse-phase HPLC purification. The product, 4-hydroxymethyl-3,4,5,6-tetrahydro-2H[1,2'] bipyridinyl-5'-carboxylic acid (7-chloro-2-dimethylcarbamoyl-4-oxo-1-phenyl-1,4-dihydro-quinolin-3-ylmethyl)-amide was obtained as 30 mg (37%) of a white solid. MS calcd. for $C_{31}H_{32}ClN_5O_4$ [(M+H)$^+$] 574.2, obsd. 574.3.

Example I-25

4-(2-Hydroxy-ethyl)-3,4,5,6-tetrahydro-2H-[1,2'] bipyridinyl-5'-carboxylic acid (7-chloro-2-dimethylcarbamoyl-4-oxo-1-phenyl-1,4-dihydro-quinolin-3-ylmethyl)-amide

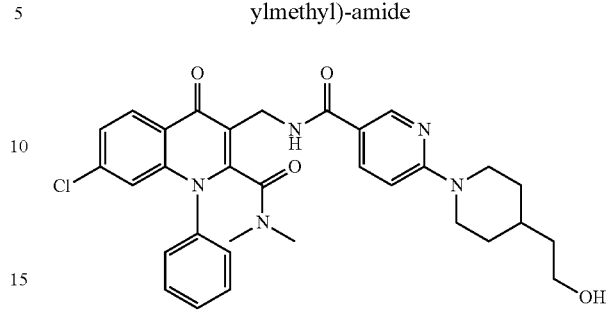

4-(2-Hydroxy-ethyl)-3,4,5,6-tetrahydro-2H-[1,2]bipyridinyl-5'-carboxylic acid (7-chloro 2-dimethylcarbamoyl-4-oxo-1-phenyl-1,4-dihydro-quinolin-3-ylmethyl)-amide was prepared according to the procedure described for example 3-11, starting from the intermediate 7-chloro-3-{[(6-chloro-pyridine-3-carbonyl)-amino]-methyl}-4-oxo-1-phenyl-1,4-dihydro-quinoline-2-carboxylic acid dimethylamide and 2-(piperidin-4-yl)ethanol. MS calcd. for $C_{32}H_{34}ClN_5O_4$ [(M+H)$^+$] 588.2, obsd. 588.3.

Example I-26

3-({[2-(4-hydroxymethyl-piperidin-1-yl)-thiazole-5-carbonyl]-amino}-methyl)-4-oxo-1-phenyl-1,4-dihydro-quinoline-2-carboxylic acid dimethylamide

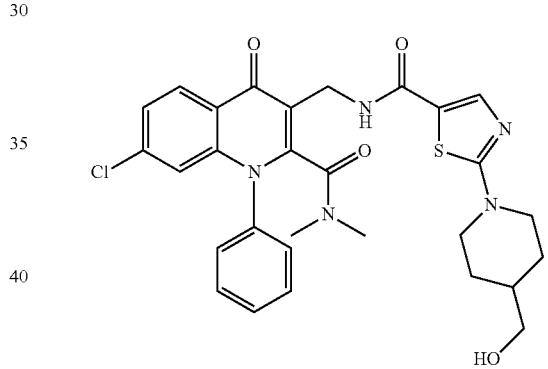

Step 1: Preparation of 3-{[(2-Bromo-thiazole-5-carbonyl)-amino]-methyl}-7-chloro-4-oxo-1-phenl-1,4-dihydro-quinoline-2-carboxylic acid dimethylamide

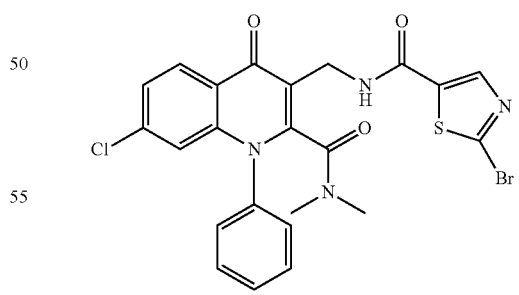

In a 250 mL round-bottomed flask, 2-bromothiazole-5-carboxylic acid (182 mg, 0.877 mmol), bromo-tris-pyrrolidino phosphonium (PyBrOP) (352 mg, 1.1 mmol) and triethylamine (222 mg, 2.19 mmol) were combined with DMF (6 mL) to give a yellow solution. Intermediate C (3-(aminomethyl)-7-chloro-N,N-dimethyl-4-oxo-1-phenyl-1,4-dihydro-quinoline-2-carboxamide) (260 mg, 0.731 mmol) was added. The reaction mixture was stirred overnight at room temperature.

Step 2: Preparation of 3-({[2-(4-hydroxymethyl-piperidin-1-yl)-thiazole-5-carbonyl]-amino}-methyl)-4-oxo-1-phenyl-1,4-dihydro-quinoline-2-carboxylic acid dimethylamide

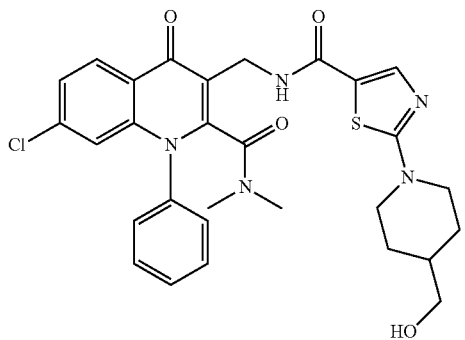 [SMILES: CN(C)C(=O)c1c(CNC(=O)c2cnc(N3CCC(CO)CC3)s2)c(=O)c2ccc(Cl)cc2n1-c1ccccc1]

The intermediate 3-{[(2-bromo-thiazole-5-carbonyl)-amino]-methyl}-7-chloro-4-oxo-1-phenyl-1,4-dihydro-quinoline-2-carboxylic acid dimethylamide (70 mg, 0.128 mmol) was combined with piperidin-4-ylmethanol (65 mg, 0.564 mmol) and NMP (2 mL). The reaction mixture was heated at 125° C. for 2 hr. After this time, the crude product was subjected to preparative SFC purification (PYR-AMIDE; modifier: 25% ethanol; flow rate: 70 mL/min). The product, 3-({[2-(4-hydroxymethylpiperidinl-yl)-thiazole-5-carbonyl]-amino}-methyl)-4-oxo-1-phenyl-1,4-dihydro-quinoline-2-carboxylic acid dimethylamide (53 mg, 57%) was obtained as an off-white solid. MS calcd. for $C_{29}H_{30}ClN_5O_4S$ $[(M+H)^+]$ 580.2, obsd. 580.3.

Example I-27

7-Chloro-3-[4({2-[4-(2-hydroxy-ethyl)-piperidin-1-yl]-thiazole-5-carbonyl}-amino)-methyl]-4-oxo-1-phenyl-1,4-dihydro-quinoline-2-carboxylic acid dimethylamide

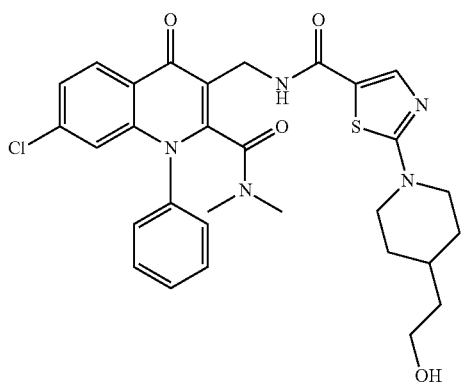 [SMILES: CN(C)C(=O)c1c(CNC(=O)c2cnc(N3CCC(CCO)CC3)s2)c(=O)c2ccc(Cl)cc2n1-c1ccccc1]

7-Chloro-3-[({2-[4-(2-hydroxy-ethyl)-piperidin-1-yl]-thiazole-5-carbonyl}-amino)-methyl]-4-oxo-1-phenyl-1,4-dihydro-quinoline-2-carboxylic acid dimethylamide was prepared according to the procedure described for example 3-13, starting from the intermediate 3-{[(2-bromo-thiazole-5-carbonyl)-amino]-methyl}-7-chloro-4-oxo-1-phenl-1,4-dihydro-quinoline-2-carboxylic acid dimethylamide and 2-(piperidin-4-yl)ethanol. MS calcd. for $C_{30}H_{32}ClN_5O_4S$ $[(M+H)^+]$ 594.2, obsd. 594.1.

Example I-28

3,4,5,6-Tetrahydro-2H-[1,2']bipyridinyl-5'-carboxylic acid (7-chloro-2-dimethylcarbamoyl-4-oxo-1-phenyl-1,4-dihydro-quinolin-3-ylmethyl)-amide trifluoroacetate salt

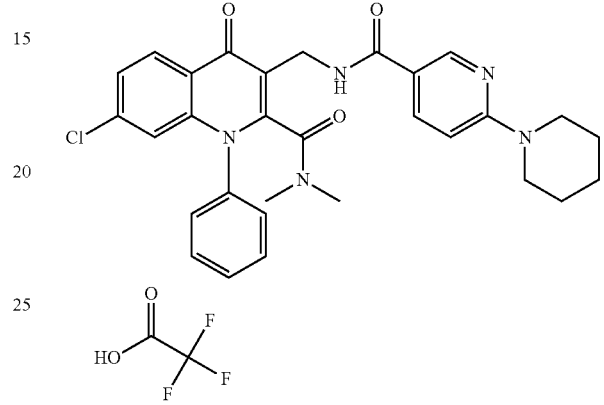

A mixture of 6-chloronicotinoyl chloride (40 mg, 0.227 mmol), piperidine (50 mg, 0.587 mmol), 3-(aminomethyl)-7-chloro-N,N-dimethyl-4-oxo-1-phenyl-1,4-dihydroquinoline-2-carboxamide (intermediate C) (50 mg, 0.141 mmol), triethylamine (100 mg, 0.998 mmol), and THF was heated at 140° C. for 30 min. using a microwave reactor. The desired product 3,4,5,6-tetrahydro-2H-[1,2]bipyridinyl-5'-carboxylic acid (7-chloro-2-dimethylcarbamoyl-4-oxo-1-phenyl-1,4-dihydro-quinolin-3-ylmethyl)-amide trifluoro-acetate (20 mg, 26%) was obtained using preparative reverse-phase HPLC MS calcd. for $C_{30}H_{30}ClN_5O_3$ $[(M+H)^+]$ 544.2, obsd. 544.3. The de-chlorination product 3,4,5,6-tetrahydro-2H-[1,2]bipyridinyl-5'-carboxylic acid (2-dimethylcarbamoyl-4-oxo-1-phenyl-1,4-dihydro-quinolin-3-ylmethyl)-amide (15 mg, 21%) was also obtained.

Example I-29

1-Benzyl-2-oxo-1,2-dihydro-pyridine-4-carboxylic acid (7-chloro-4-oxo-1-phenyl-1,4-dihydro-quinolin-3-ylmethyl)-amide

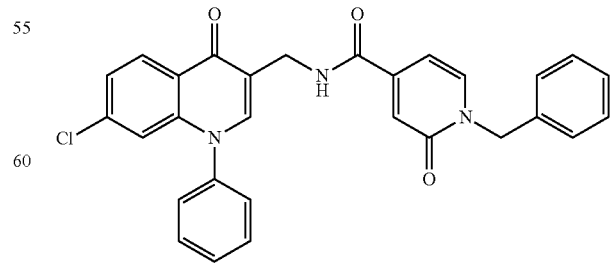

In a 20 mL round-bottomed flask, 3-(aminomethyl)-7-chloro-1-phenylquinolin-4(1H)-one (intermediate D) (50 mg, 0.176 mmol), 1-benzyl-2-oxo-1,2-dihydropyridine-4-carboxylic acid (40.3 mg, 0.176 mmol), bromo-tris-pyrrolidino-phosphonium hexafluorophosphate (PyBrOP) (81.8 mg, 176 mmol) and N,N-diisopropylethylamine (0.092 mL, 0.527 mmol) were combined with $CH_2Cl_2$ (5.00 mL). The reaction mixture was stirred at room temperature, and the crude product was purified using preparative reverse-phase HPLC. MS calcd. for $C_{29}H_{23}ClN_3O_3$ [(M+H)$^+$] 496.1, obsd. 496.0.

Examples I-30 to I-56

The following examples I-30 to I-56 were prepared in an analogous manner to example I-29, starting with intermediate D, an appropriate carboxylic acid, and a commercially available amide coupling reagent (for example, bromo-tris-pyrrolidino-phosphonium hexafluorophosphate (PyBrOP), 1-(3-dimethylaminopropyl)-3-ethylcarbodiimide hydrochloride (EDC) and 1-hydroxybenzotriazole (HOBT), or O-benzotriazole-1-yl)-N,N,N',N'-tetramethyluronium hexafluorophosphate (HBTU).

Example I-30

1-Methyl-1H-pyrazole-4-carboxylic acid (7-chloro-4-oxo-1-phenyl-1,4-di hydro-quinolin-3-ylmethyl)-amide

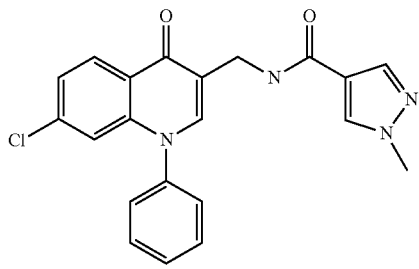 [SMILES: Cn1cc(C(=O)NCc2cn(-c3ccccc3)c3cc(Cl)ccc3c2=O)cn1]

Methyl-1H-pyrazole-4-carboxylic acid (7-chloro-4-oxo-1-phenyl-1,4-dihydro-quinolin-3-ylmethyl)-amide was prepared starting from intermediate D and 1-methyl-1H-pyrazole-4-carboxylic acid. MS calcd. for $C_{21}H_{18}ClN_4O_2$ [(M+H)$^+$] 393.1, obsd. 393.0.

Example I-31

N-(7-Chloro-4-oxo-1-phenyl-1,4-dihydro-quinolin-3-ylmethyl)-2-morpholin-4-yl-isonicotinamide

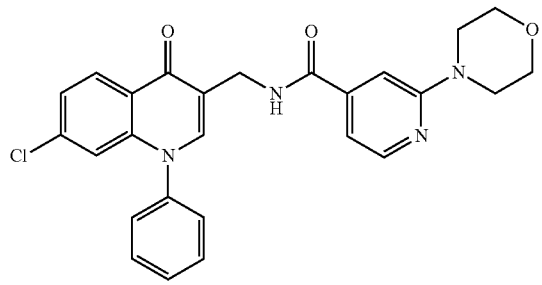 [SMILES: O=C(NCc1cn(-c2ccccc2)c2cc(Cl)ccc2c1=O)c1ccnc(N2CCOCC2)c1]

N-(7-Chloro-4-oxo-1-phenyl-1,4-dihydro-quinolin-3-ylmethyl)-2-morpholin-4-yl-iso-nicotinamide was prepared starting from intermediate D and 2-morpholinoisonicotinic acid. MS calcd. for $C_{26}H_{24}ClN_4O_3$ [(M+H)$^+$] 475.2, obsd. 475.0.

Example I-32

N-(7-Chloro-4-oxo-1-phenyl-1,4-dihydro-quinolin-3-ylmethyl)-2-pyrrolidin-1-yl-isonicotinamide

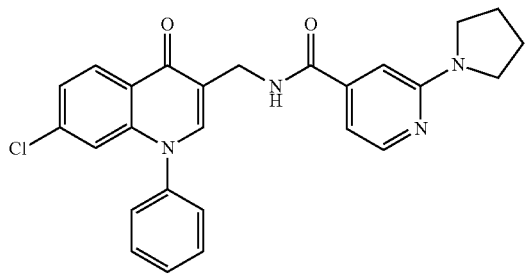 [SMILES: O=C(NCc1cn(-c2ccccc2)c2cc(Cl)ccc2c1=O)c1ccnc(N2CCCC2)c1]

N-(7-Chloro-4-oxo-1-phenyl-1,4-dihydro-quinolin-3-ylmethyl)-2-pyrrolidin-1-yl-iso-nicotinamide was prepared starting from intermediate D and 2-(pyrrolidin-1-yl)isonicotinic acid. MS calcd. for $C_{26}H_{24}ClN_4O_2$ [(M+H)$^+$] 459.2, obsd. 459.0.

Example I-33

3H-Benzoimidazole-5-carboxylic acid (7-chloro-4-oxo-1-phenyl-1,4-dihydro-quinolin-3-ylmethyl)-amide

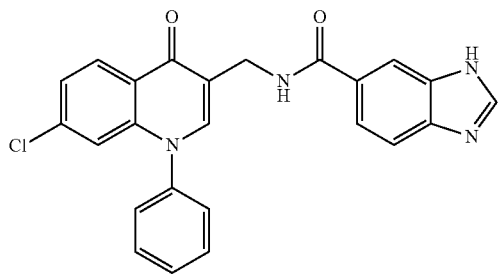 [SMILES: O=C(NCc1cn(-c2ccccc2)c2cc(Cl)ccc2c1=O)c1ccc2nc[nH]c2c1]

3H-Benzoimidazole-5-carboxylic acid (7-chloro-4-oxo-1-phenyl-1,4-dihydro-quinolin-3-ylmethyl)-amide was prepared starting from intermediate D and 1H-benzimidazole-5-carboxylic acid. MS calcd. for $C_{24}H_{18}ClN_4O_2$ [(M+H)$^+$] 429.1, obsd. 429.0.

Example I-34

1-(4-Chloro-benzyl)-2-oxo-1,2-dihydro-pyridine-4-carboxylic acid (7-chloro-4-oxo-1-phenyl-1,4-dihydro-quinolin-3-ylmethyl)-amide

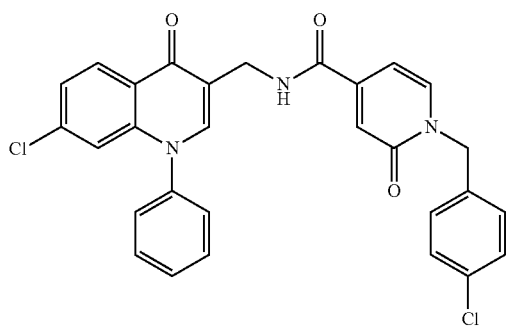 [SMILES: O=C(NCc1cn(-c2ccccc2)c2cc(Cl)ccc2c1=O)c1ccn(Cc2ccc(Cl)cc2)c(=O)c1]

1-(4-Chloro-benzyl)-2-oxo-1,2-dihydro-pyridine-4-carboxylic acid (7-chloro-4-oxo-1-phenyl-1,4-dihydro-quinolin-3-ylmethyl)-amide was prepared starting from intermediate D and 1-(4-chlorobenzyl)-2-oxo-1,2-dihydro-pyridine-4-carboxylic acid. MS calcd. for $C_{29}H_{21}Cl_2N_3O_3$ [(M+H)$^+$] 530.1, obsd. 530.0.

Example I-35

N-(7-Chloro-4-oxo-1-phenyl-1,4-dihydro-quinolin-3-ylmethyl)-6-methoxy-nicotinamide

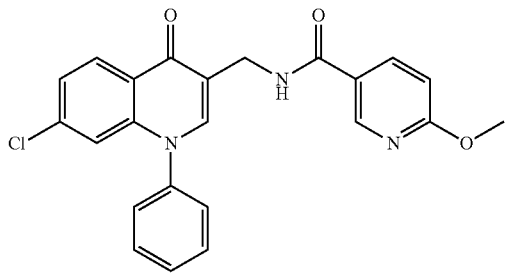 [SMILES: COc1ccc(C(=O)NCc2cn(-c3ccccc3)c3cc(Cl)ccc3c2=O)cn1]

N-(7-Chloro-4-oxo-1-phenyl-1,4-dihydro-quinolin-3-ylmethyl)-6-methoxy-nicotinamide was prepared starting from intermediate D and 6-methoxy-nicotinic acid. MS calcd. for $C_{23}H_{18}ClN_3O_3$ [(M+H)$^+$] 419.1, obsd. 420 [(M+H)$^+$].

Example I-36

N-(7-Chloro-4-oxo-1-phenyl-1,4-dihydro-quinolin-3-ylmethyl)-4-sulfamoyl-benzamide

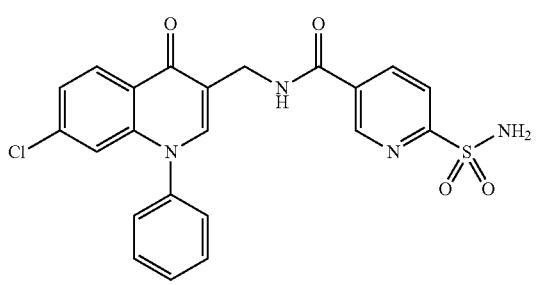 [SMILES: NS(=O)(=O)c1ccc(C(=O)NCc2cn(-c3ccccc3)c3cc(Cl)ccc3c2=O)cn1]

N-(7-Chloro-4-oxo-1-phenyl-1,4-dihydro-quinolin-3-ylmethyl)-4-sulfamoyl-benzamide was prepared starting from intermediate D and 4-carboxybenzenesulfonamide. MS calcd. for $C_{23}H_{18}ClN_3O_4S$ [(M+H)$^+$] 467.9, obsd. 468.0.

Example I-37

1-Phenyl-1H-pyrazole-4-carboxylic acid (7-chloro-4-oxo-1-phenyl-1,4-dihydro-quinolin-3-ylmethyl)-amide

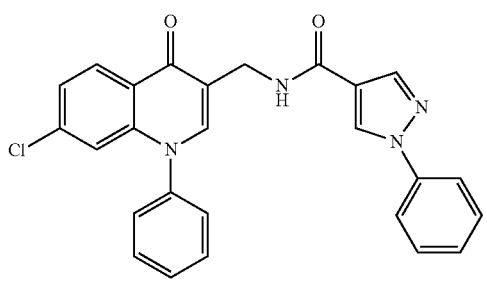 [SMILES: O=C(NCc1cn(-c2ccccc2)c2cc(Cl)ccc2c1=O)c1cnn(-c2ccccc2)c1]

Phenyl-1H-pyrazole-4-carboxylic acid (7-chloro-4-oxo-1-phenyl-1,4-dihydro-quinolin-3-ylmethyl)-amide was prepared starting from intermediate D and 1-phenyl-1H-pyrazole-4-carboxylic acid. MS calcd. for $C_{26}H_{20}ClN_4O_2$ [(M+H)$^+$] 455.1, obsd. 455.0.

Example I-38

1-(3-Methoxy-benzyl)-2-oxo-1,2-dihydro-pyridine-4-carboxylic acid (7-chloro-4-oxo-1-phenyl-1,4-dihydro-quinolin-3-ylmethyl)-amide

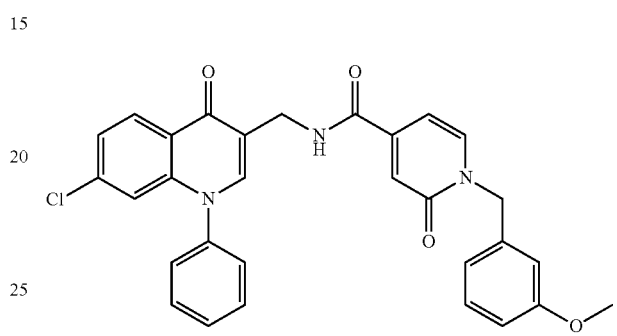

1-(3-Methoxy-benzyl)-2-oxo-1,2-dihydro-pyridine-4-carboxylic acid (7-chloro-4-oxo-1-phenyl-1,4-dihydro-quinolin-3-ylmethyl)-amide was prepared starting from intermediate D and 1-(3-methoxy-benzyl)-2-oxo-1,2-dihydro-pyridine-4-carboxylic acid. MS calcd. for $C_{30}H_{25}ClN_3O_4$ [(M+H)$^+$] 526.2, obsd. 526.0.

Example I-39

1-(2-Chloro-benzyl)-2-oxo-1,2-dihydro-pyridine-4-carboxylic acid (7-chloro-4-oxo-1-phenyl-1,4-dihydro-quinolin-3-ylmethyl)-amide

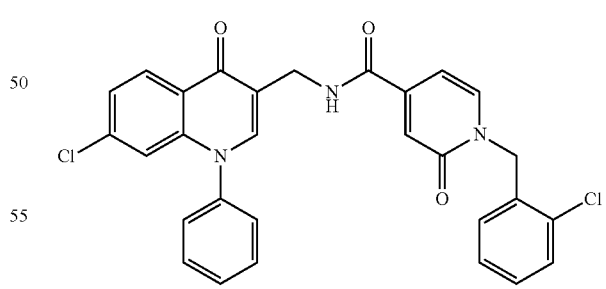

1-(2-Chloro-benzyl)-2-oxo-1,2-dihydro-pyridine-4-carboxylic acid (7-chloro-4-oxo-1-phenyl-1,4-dihydro-quinolin-3-ylmethyl)-amide was prepared starting from intermediate D and 1-(2-chloro-benzyl)-2-oxo-1,2-dihydro-pyridine-4-carboxylic acid. MS calcd. for $C_{29}H_{22}Cl_2N_3O_3$ [(M+H)$^+$] 530.1, obsd. 530.0.

Example I-40

N-(7-Chloro-4-oxo-1-phenyl-1,4-dihydro-quinolin-3-ylmethyl)-6-morpholin-4-yl-nicotinamide

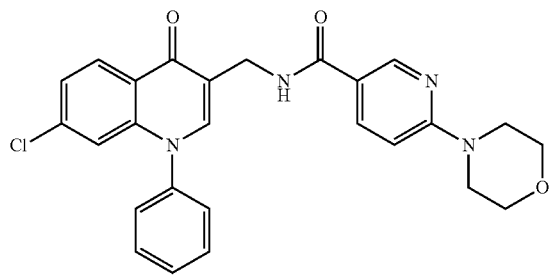

N-(7-Chloro-4-oxo-1-phenyl-1,4-dihydro-quinolin-3-ylmethyl)-6-morpholin-4-yl-nicotinamide was prepared starting from intermediate D and 6-morpholin-4-yl-nicotinic acid. MS calcd. for $C_{26}H_{23}ClN_4O_3$ [(M+H)$^+$] 474.9, obsd. 474.9.

Example I-41

N-(7-Chloro-4-oxo-1-phenyl-1,4-dihydro-quinolin-3-ylmethyl)-2-dimethyl amino-isonicotinamide

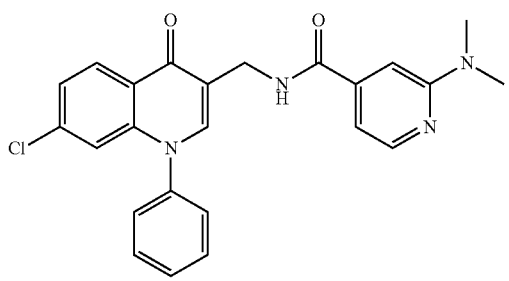 [SMILES: CN(C)c1cc(C(=O)NCc2cn(-c3ccccc3)c3cc(Cl)ccc3c2=O)ccn1]

N-(7-Chloro-4-oxo-1-phenyl-1,4-dihydro-quinolin-3-ylmethyl)-2-dimethylamino-iso-nicotinamide was prepared starting from intermediate D and 2-dimethylamino-isonicotinic acid. MS calcd. for $C_{24}H_{22}ClN_4O_2$ [(M+H)$^+$] 433.1, obsd. 432.9.

Example I-42

Benzothiazole-5-carboxylic acid (7-chloro-4-oxo-1-phenyl-1,4-dihydro-quinolin-3-ylmethyl)-amide

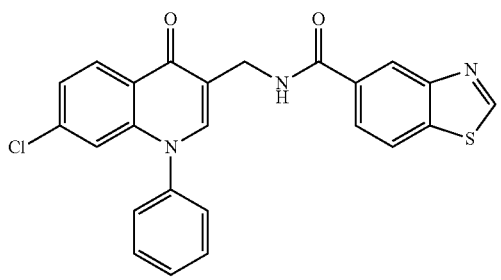 [SMILES: O=C(NCc1cn(-c2ccccc2)c2cc(Cl)ccc2c1=O)c1ccc2scnc2c1]

Benzothiazole-5-carboxylic acid (7-chloro-4-oxo-1-phenyl-1,4-dihydro-quinolin-3-ylmethyl)-amide was prepared starting from intermediate D and benzothiazole-5-carboxylic acid. MS calcd. for $C_{24}H_{17}ClN_3O_2S$ [(M+H)$^+$] 446.1, obsd. 445.9.

Example I-43

N-(7-Chloro-4-oxo-1-phenyl-1,4-dihydro-quinolin-3-ylmethyl)-4-(2H-[1,2,4]triazol-3-yl)-benzamide

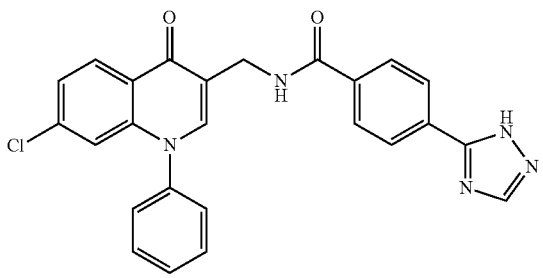 [SMILES: O=C(NCc1cn(-c2ccccc2)c2cc(Cl)ccc2c1=O)c1ccc(-c2ncn[nH]2)cc1]

N-(7-Chloro-4-oxo-1-phenyl-1,4-dihydro-quinolin-3-ylmethyl)-4-(2H-[1,2,4]triazol-3-yl)-benzamide was prepared starting from intermediate D and 4-(2H-[1,2,4]triazol-3-yl)-benzoic acid. MS calcd. for $C_{25}H_{18}ClN_5O_2$ [(M+H)$^+$] 455.9, obsd. 456.0.

Example I-44

1-(3-Chloro-benzyl)-2-oxo-1,2-dihydro-pyridine-4-carboxylic acid (7-chloro-4-oxo-1-phenyl-1,4-dihydro-quinolin-3-ylmethyl)-amide

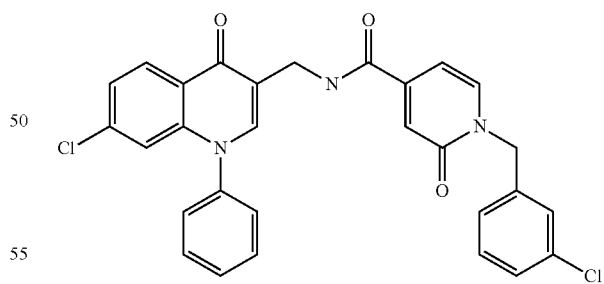

1-(3-Chloro-benzyl)-2-oxo-1,2-dihydro-pyridine-4-carboxylic acid (7-chloro-4-oxo-1-phenyl-1,4-dihydro-quinolin-3-ylmethyl)-amide was prepared starting from intermediate D and 1-(3-chloro-benzyl)-2-oxo-1,2-dihydro-pyridine-4-carboxylic acid. MS calcd. for $C_{29}H_{22}Cl_2N_3O_3$ [(M+H)$^+$] 530.1, obsd. 530.0.

Example I-45

3-Methyl-3H-imidazo[4,5-b]pyridine-6-carboxylic acid (7-chloro-4-oxo-1-phenyl-1,4-dihydro-quinolin-3-ylmethyl)-amide

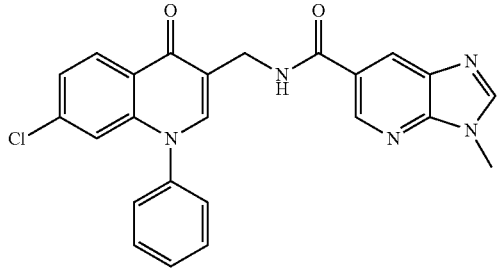 [SMILES: Cn1cnc2cc(C(=O)NCc3cn(-c4ccccc4)c4cc(Cl)ccc4c3=O)cnc21]

3-Methyl-3H-imidazo[4,5-b]pyridine-6-carboxylic acid (7-chloro-4-oxo-1-phenyl-1,4-dihydro-quinolin-3-ylmethyl)-amide was prepared starting from intermediate D and 3-Methyl-3H-imidazo[4,5-b]pyridine-6-carboxylic acid. MS calcd. for $C_{24}H_{19}ClN_5O_2$ [(M+H)$^+$] 444.1, obsd. 444.0.

Example I-46

1H-Indole-6-carboxylic acid (7-chloro-4-oxo-1-phenyl-1,4-dihydro-quinolin-3-ylmethyl)-amide

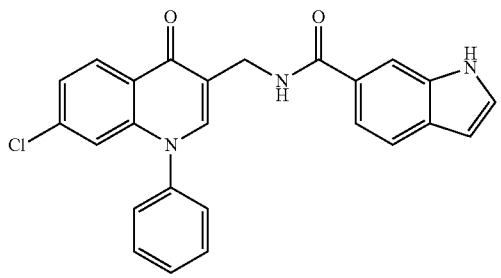 [SMILES: O=C(NCc1cn(-c2ccccc2)c2cc(Cl)ccc2c1=O)c1ccc2cc[nH]c2c1]

1H-Indole-6-carboxylic acid (7-chloro-4-oxo-1-phenyl-1,4-dihydro-quinolin-3-ylmethyl)-amide was prepared starting from intermediate D and 1H-Indole-6-carboxylic acid. MS calcd. for $C_{25}H_{19}ClN_3O_2$ [(M+H)$^+$] 428.1, obsd. 427.9.

Example I-47

N-(7-Chloro-4-oxo-1-phenyl-1,4-dihydro-quinolin-3-ylmethyl)-4-oxazol-5-yl-benzamide

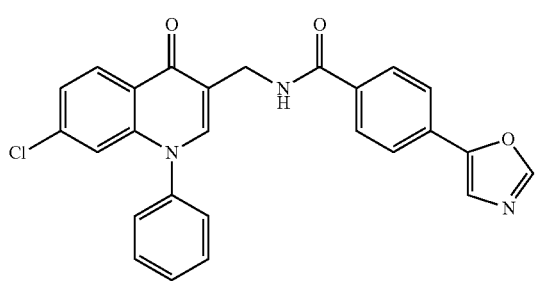 [SMILES: O=C(NCc1cn(-c2ccccc2)c2cc(Cl)ccc2c1=O)c1ccc(-c2cnco2)cc1]

N-(7-Chloro-4-oxo-1-phenyl-1,4-dihydro-quinolin-3-yl-methyl)-4-oxazol-5-yl-benzamide was prepared starting from intermediate D and 4-oxazol-5-yl-benzoic acid. MS calcd. for $C_{26}H_{18}ClN_3O_3$ [(M+H)$^+$] 455.9, obsd. 456.0.

Example I-48

1-(2-Methoxy-benzyl)-2-oxo-1,2-dihydro-pyridine-4-carboxylic acid (7-chloro-4-oxo-1-phenyl-1,4-dihydro-quinolin-3-ylmethyl)-amide

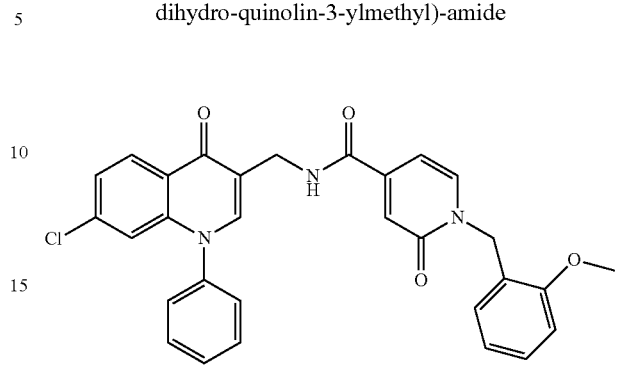

1-(2-Methoxy-benzyl)-2-oxo-1,2-dihydro-pyridine-4-carboxylic acid (7-chloro-4-oxo-1-phenyl-1,4-dihydro-quinolin-3-ylmethyl)-amide was prepared starting from intermediate D and 1-(2-methoxy-benzyl)-2-oxo-1,2-dihydro-pyridine-4-carboxylic acid. MS calcd. for $C_{30}H_{25}ClN_3O_4$ [(M+H)$^+$] 526.2, obsd. 526.0.

Example I-49

1H-Imidazo[4,5-b]pyridine-6-carboxylic acid (7-chloro-4-oxo-1-phenyl-1,4-dihydro-quinolin-3-ylmethyl)-amide

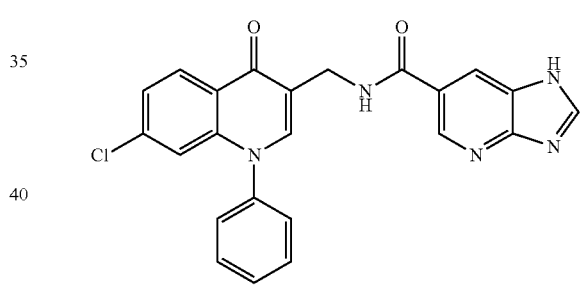

1-(2-Methoxy-benzyl)-2-oxo-1,2-dihydro-pyridine-4-carboxylic acid (7-chloro-4-oxo-1-phenyl-1,4-dihydro-quinolin-3-ylmethyl)-amide was prepared starting from intermediate D and 1H-imidazo[4,5-b]pyridine-6-carboxylic acid. MS calcd. for $C_{23}H_{17}ClN_5O_2$ [(M+H)$^+$] 430.1, obsd. 429.9.

Example I-50

N-(7-Chloro-4-oxo-1-phenyl-1,4-dihydro-quinolin-3-ylmethyl)-terephthal-amide

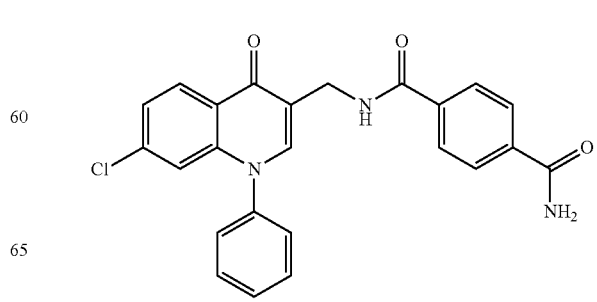

N-(7-Chloro-4-oxo-1-phenyl-1,4-dihydro-quinolin-3-ylmethyl)-terephthalamide was prepared starting from intermediate D and 4-(aminocarbonyl)benzoic acid. MS calcd. for $C_{24}H_{18}ClN_3O_3$ [(M+H)$^+$] 431.9, obsd. 432.0.

Example I-51

3-[(7-Chloro-4-oxo-1-phenyl-1,4-dihydro-quinolin-3-ylmethyl)-carbamoyl]-pyrrolidine-1-carboxylic acid tert-butyl ester

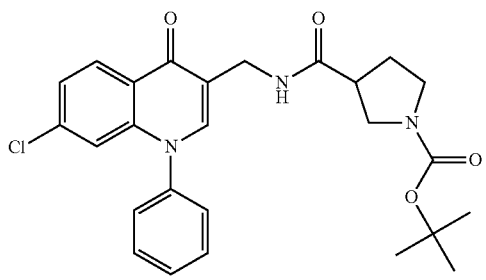 [SMILES: CC(C)(C)OC(=O)N1CCC(C(=O)NCc2cn(-c3ccccc3)c3cc(Cl)ccc3c2=O)C1]

3-[(7-Chloro-4-oxo-1-phenyl-1,4-dihydro-quinolin-3-ylmethyl)-carbamoyl]-pyrrolidine-1-carboxylic acid tert-butyl ester was prepared starting from intermediate D and 1-(tert-butoxycarbonyl)-pyrrolidine-3-carboxylic acid. MS calcd. for $C_{26}H_{29}ClN_3O_4$ [(M+H)$^+$] 481.3, obsd. 482.0.

Example I-52

1-Benzyl-6-oxo-1,6-dihydro-pyridine-3-carboxylic acid (7-chloro-4-oxo-1-phenyl-1,4-dihydro-quinolin-3-ylmethyl)-amide

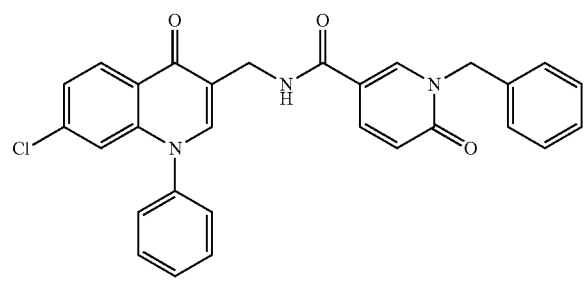 [SMILES: O=C(NCc1cn(-c2ccccc2)c2cc(Cl)ccc2c1=O)c1ccc(=O)n(Cc2ccccc2)c1]

Benzyl-6-oxo-1,6-dihydro-pyridine-3-carboxylic acid (7-chloro-4-oxo-1-phenyl-1,4-dihydro-quinolin-3-ylmethyl)-amide was prepared starting from intermediate D and 1-benzyl-6-oxo-1,6-dihydro-pyridine-3-carboxylic acid. MS calcd. for $C_{29}H_{23}ClN_3O_3$ [(M+H)$^+$] 496.1, obsd. 496.1.

Example I-53

1-Methyl-1H-[1,2,3]triazole-4-carboxylic acid (7-chloro-4-oxo-1-phenyl-1,4-dihydro-quinolin-3-ylmethyl)-amide

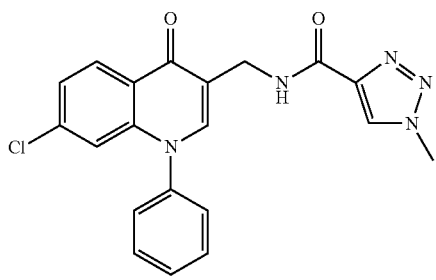 [SMILES: Cn1cc(C(=O)NCc2cn(-c3ccccc3)c3cc(Cl)ccc3c2=O)nn1]

Methyl-1H-[1,2,3]triazole-4-carboxylic acid (7-chloro-4-oxo-1-phenyl-1,4-dihydro-quinolin-3-ylmethyl)-amide was prepared starting from intermediate D and 1-methyl-1H-[1,2,3]triazole-4-carboxylic acid. MS calcd. for $C_{20}H_{17}ClN_5O_2$ [(M+H)$^+$] 394.1, obsd. 394.0.

Example I-54

1-Methyl-2-oxo-1,2-dihydro-pyridine-4-carboxylic acid (7-chloro-4-oxo-1-phenyl-1,4-dihydro-quinolin-3-ylmethyl)-amide

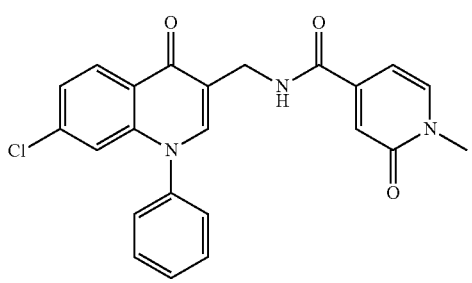 [SMILES: Cn1ccc(C(=O)NCc2cn(-c3ccccc3)c3cc(Cl)ccc3c2=O)cc1=O]

Methyl-2-oxo-1,2-dihydro-pyridine-4-carboxylic acid (7-chloro-4-oxo-1-phenyl-1,4-dihydro-quinolin-3-ylmethyl)-amide was prepared starting from intermediate D and 1-methyl-2-oxo-1,2-dihydro-pyridine-4-carboxylic acid. MS calcd. for $C_{23}H_{19}ClN_3O_3$ [(M+H)$^+$] 420.1, obsd. 420.0.

Example I-55

1-Benzyl-1H-[1,2,3]triazole-4-carboxylic acid (7-chloro-4-oxo-1-phenyl-1,4-dihydro-quinolin-3-ylmethyl)-amide

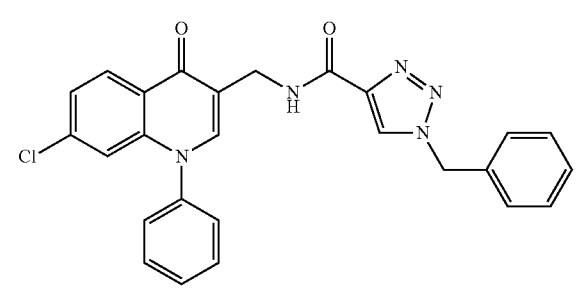 [SMILES: O=C(NCc1cn(-c2ccccc2)c2cc(Cl)ccc2c1=O)c1cn(Cc2ccccc2)nn1]

Benzyl-1H-[1,2,3]triazole-4-carboxylic acid (7-chloro-4-oxo-1-phenyl-1,4-dihydro-quinolin-3-ylmethyl)-amide was prepared starting from intermediate D and 1-benzyl-1H-[1,2,3]triazole-4-carboxylic acid. MS calcd. for $C_{26}H_{21}ClN_5O_2$ [(M+H)$^+$] 470.1, obsd. 469.9.

Example I-56

2-Morpholin-4-yl-pyrimidine-5-carboxylic acid (7-chloro-4-oxo-1-phenyl-1,4-dihydro-quinolin-3-ylmethyl)-amide

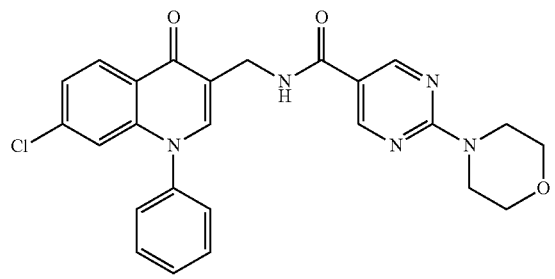 [SMILES: O=C(NCc1cn(-c2ccccc2)c2cc(Cl)ccc2c1=O)c1cnc(N2CCOCC2)nc1]

2-Morpholin-4-yl-pyrimidine-5-carboxylic acid (7-chloro-4-oxo-1-phenyl-1,4-dihydro-quinolin-3-ylmethyl)-amide was prepared starting from intermediate D and 2-morpholin-4-yl-pyrimidine-5-carboxylic acid. $^1$H NMR (400 MHz, DMSO-$d_6$) δ ppm 8.67 (s, 2H) 8.55 (t, J=5.50 Hz, 1H) 8.21 (d, J=8.78 Hz, 1H) 7.90 (s, 1H) 7.56-7.67 (m, 3H) 7.49-7.55 (m, 2H) 7.39 (dd, J=8.66, 1.88 Hz, 1H) 6.84 (d, J=2.01 Hz, 1H) 4.29 (d, J=5.52 Hz, 2H) 3.67-3.76 (m, 3H) 1.52-1.61 (m, 2H) 1.39-1.48 (m, 3H).

Example I-57

N-(7-Chloro-4-oxo-1-phenyl-1,4-dihydro-quinolin-3-ylmethyl)-3,4-dimethoxy-benzamide

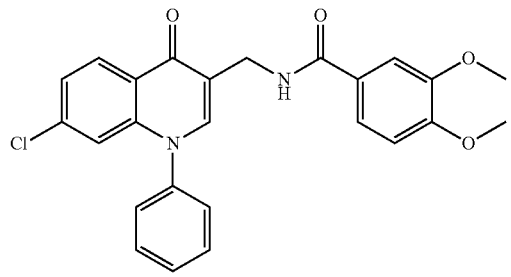 [SMILES: COc1ccc(C(=O)NCc2cn(-c3ccccc3)c3cc(Cl)ccc3c2=O)cc1OC]

In a 200 mL round-bottomed flask, 3-(aminomethyl)-7-chloro-1-phenylquinolin-4(1H)-one (intermediate D) (25 mg, 0.088 mmol) and 3,4-dimethoxybenzoyl chloride (17.6 mg, 0.088 mmol) were combined with methylene chloride (3 mL) to give a yellow suspension. The reaction mixture was cooled to 0° C. After 15 min. stirring at reduced temperature, N,N-diisopropylethylamine (56.7 mg, 76.6 µL, 0.439 mmol) was added. The reaction mixture quickly became a yellow solution, then was stirred at 0° C. for 1 hr. After this time, LC/MS indicated that the reaction was complete. The reaction mixture was warmed to room temperature, then stirred overnight. In the morning, the reaction mixture was concentrated over silica gel. Flash chromatography (25 gram Analogix column, 20% ethyl acetate-hexanes ramped to 100% ethyl acetate) was used to purify the product. N-(7-Chloro-4-oxo-1-phenyl-1,4-dihydro-quinolin-3-ylmethyl)-3,4-dimethoxy-benzamide (26 mg, 59%) was obtained as a white solid. MS calcd. for $C_{25}H_{21}ClN_2O_4$ [(M+H)$^+$] 448.9, obsd. 449.1.

Example I-58

N-(7-Chloro-4-oxo-1-phenyl-1,4-dihydro-quinolin-3-ylmethyl)-3,5-difluoro-benzamide

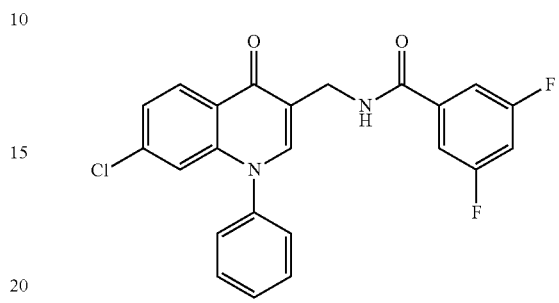

A 10 mL round bottom flask was charged with 3,5-difluorobenzoyl chloride (78.0 mg, 0.442 mmol) and anhydrous methylene chloride (5 mL) and was treated with 3-(aminomethyl)-7-chloro-1-phenylquinolin-4(1H)-one (intermediate D) (49.8 mg, 0.175 mmol), triethylamine (87.1 mg, 0.12 mL, 0.861 mmol), and catalytic N,N-(dimethylamino)pyridine (DMAP) (one spatula tip). The flask was capped with a glass stopper and the reaction stirred at room temperature over the weekend. The reaction was partitioned between methylene chloride (25 mL) and water (25 mL). The organic portions were dried over magnesium sulfate, filtered and rinsed with methylene chloride, concentrated on a rotary evaporator, and briefly dried on a vacuum pump. The material was then purified via Analogix Intelliflash 280 chromatography using a 12 g silica gel column and a 1%-5% MeOH/CH$_2$Cl$_2$ gradient elution. Two columns were required to isolate the desired product from the bis-acylation side product. Fractions containing the two products were separately combined and concentrated. The second product to elute was the desired product N-(7-chloro-4-oxo-1-phenyl-1,4-dihydro-quinolin-3-ylmethyl)-3,5-difluoro-benzamide, isolated as an off-white solid (44 mg, 60%). $^1$H NMR (400 MHz, DMSO-$d_6$) δ ppm 8.91 (t, J=5.14 Hz, 1H) 8.27 (d, J=8.66 Hz, 1H) 8.03 (s, 1H) 7.38-7.73 (m, 9H) 6.90 (d, J=1.81 Hz, 1H) 4.37 (d, J=5.24 Hz, 2H).

Examples I-59 to I-61

The following examples I-59 to I-61 were prepared in an analogous manner to example I-58, starting with intermediate D and an appropriate commercially available benzoyl chloride.

Example I-59

N-(7-Chloro-4-oxo-1-phenyl-1,4-dihydro-quinolin-3-ylmethyl)-2,3-difluoro-benzamide

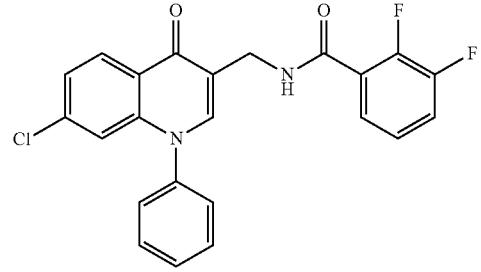 [SMILES: O=C(NCc1cn(-c2ccccc2)c2cc(Cl)ccc2c1=O)c1cccc(F)c1F]

N-(7-Chloro-4-oxo-1-phenyl-1,4-dihydro-quinolin-3-yl-methyl)-2,3-difluoro-benzamide was prepared starting from intermediate D and 2,3-difluoro-benzoyl chloride. $^1$H NMR (400 MHz, DMSO-d$_6$) δ ppm 8.75 (s, 1H) 8.28 (d, J=8.66 Hz, 1H) 8.00 (s, 1H) 7.15-7.80 (m, 9H) 6.92 (d, J=1.81 Hz, 1H) 0.39 (d, J=5.64 Hz, 2H).

Example I-60

N-(7-Chloro-4-oxo-1-phenyl-1,4-dihydro-quinolin-3-ylmethyl)-2,5-difluoro-benzamide

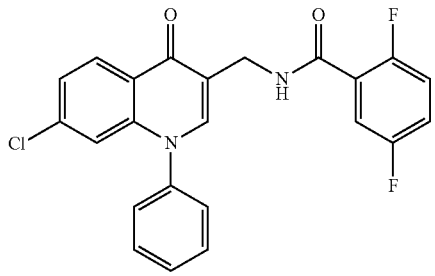 [SMILES: O=C(NCc1cn(-c2ccccc2)c2cc(Cl)ccc2c1=O)c1cc(F)ccc1F]

N-(7-Chloro-4-oxo-1-phenyl-1,4-dihydro-quinolin-3-yl-methyl)-2,5-difluoro-benzamide was prepared starting from intermediate D and 2,5-difluoro-benzoyl chloride. $^1$H NMR (400 MHz, DMSO-d$_6$) δ ppm 8.70 (br. s., 1H) 8.28 (d, J=8.66 Hz, 1H) 8.00 (s, 1H) 7.53-7.79 (m, 5 H) 7.21-7.52 (m, 4H) 6.92 (d, J=1.81 Hz, 1H) 4.39 (d, J=5.64 Hz, 2H).

Example I-61

6-Chloro-N-(7-chloro-4-oxo-1-phenyl-1,4-dihydro-quinolin-3-ylmethyl)-nicotinamide

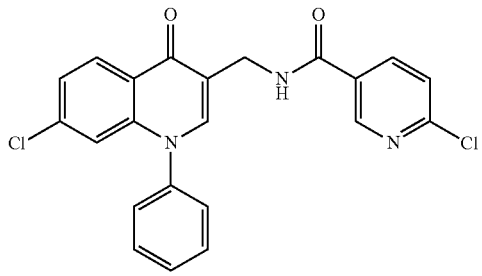 [SMILES: O=C(NCc1cn(-c2ccccc2)c2cc(Cl)ccc2c1=O)c1ccc(Cl)nc1]

6-Chloro-N-(7-chloro-4-oxo-1-phenyl-1,4-dihydro-quinolin-3-ylmethyl)-nicotinamide (intermediate E) was prepared as described above in the intermediates section. MS calcd. for $C_{22}H_{15}Cl_2N_3O_2$ [(M+H)$^+$] 424.0, obsd. 424.

Example I-62

5-{5-[(7-Chloro-4-oxo-1-phenyl-1,4-dihydro-quino-lin-3-ylmethyl)-carbamoyl]-pyridin-2-yl}-2,5-diaza-bicyclo[2.2.1]heptane-2-carboxylic acid tert-butyl ester

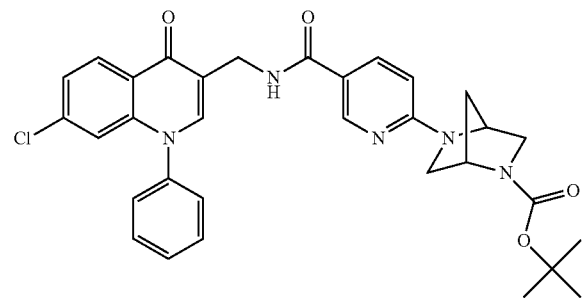 [SMILES: CC(C)(C)OC(=O)N1CC2CC1CN2c1ccc(C(=O)NCc2cn(-c3ccccc3)c3cc(Cl)ccc3c2=O)cn1]

A mixture of 6-chloro-N-((7-chloro-4-oxo-1-phenyl-1,4-dihydroquinolin-3-yl)methyl)nicotinamide (intermediate E) (30 mg, 0.071 mmol), (1S,4S)-tert-butyl 2,5-diazabicyclo[2.2.1]heptane-2-carboxylate (43 mg, 0.212 mmol) and N,N-diisopropylethylamine (59.2 mg, 80.0 µL, 0.456 mmol) in NMP (500 µL) was stirred at 115° C. in a sealed tube overnight. The reaction mixture was transferred to a vial with CH$_3$CN, then concentrated under a stream of nitrogen. The crude product was purified using preparative reverse-phase HPLC. The product 5-{5-[(7-chloro-4-oxo-1-phenyl-1,4-di-hydro-quinolin-3-ylmethyl)-carbamoyl]-pyridin-2-yl}-2,5-diaza-bicyclo-[2.2.1]-heptane-2-carboxylic acid tert-butyl ester (28 mg, 68%) was obtained as a white solid. MS calcd. for $C_{32}H_{32}ClN_5O_4$ [(M+H)$^+$] 586.2, obsd. 586.0.

Examples I-63 to I-88

The following examples I-63 to I-88 were prepared in an analogous manner to example I-62, starting with intermediate E and the appropriate amine.

Example I-63

4-(2-Hydroxy-ethyl)-3,4,5,6-tetrahydro-2H-[1,2']bipyridinyl-5'-carboxylic acid (7-chloro-4-oxo-1-phenyl-1,4-dihydro-quinolin-3-ylmethyl)-amide

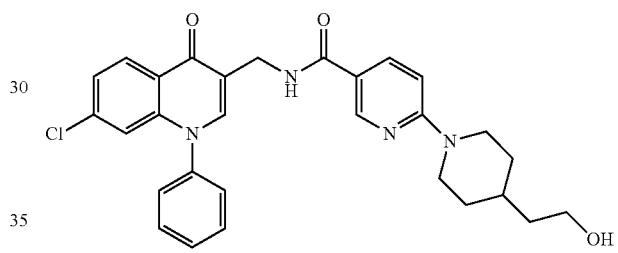

4-(2-Hydroxy-ethyl)-3,4,5,6-tetrahydro-2H-[1,2']bipyridinyl-5'-carboxylic acid (7-chloro-4-oxo-1-phenyl-1,4-dihydro-quinolin-3-ylmethyl)-amide was prepared starting from intermediate E and 4-(hydroxyethyl)piperidine. $^1$H NMR (400 MHz, DMSO-d$_6$) δ ppm 8.50 (d, J=2.01 Hz, 1H) 8.43 (t, J=5.65 Hz, 1H) 8.21 (d, J=9.04 Hz, 1H) 7.80-7.88 (m, 2H) 7.54-7.65 (m, 3H) 7.49-7.53 (m, 2H) 7.38 (dd, J=8.66, 1.88 Hz, 1H) 6.84 (d, J=2.00 Hz, 1H) 6.72 (d, J=8.78 Hz, 1H) 4.25-4.33 (m, 5H) 3.38 (q, J=6.10 Hz, 2H) 2.75 (t, J=12.50 Hz, 2H) 1.58-1.67 (m, 3H) 1.28 (q, J=6.53 Hz, 2H) 0.92-1.05 (m, 2H).

Example I-64

6-[Bis-(2-hydroxy-ethyl)-amino]-N-(7-chloro-4-oxo-1-phenyl-1,4-dihydro-quinolin-3-ylmethyl)-nicotinamide

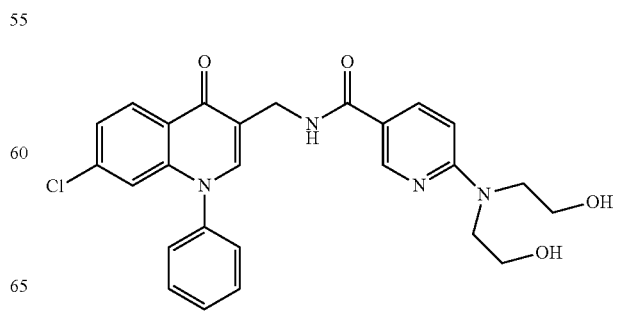

6-[Bis-(2-hydroxy-ethyl)-amino]-N-(7-chloro-4-oxo-1-phenyl-1,4-dihydro-quinolin-3-yl-methyl)-nicotinamide was prepared starting from intermediate E and diethanolamine. MS calcd. for $C_{26}H_{25}ClN_4O_4$ [(M+H)$^+$] 493, obsd. 493.

Example I-65

3,4,5,6-Tetrahydro-2H-[1,2']bipyridinyl-5'-carboxylic acid (7-chloro-4-oxo-1-phenyl-1,4-dihydro-quinolin-3-ylmethyl)-amide

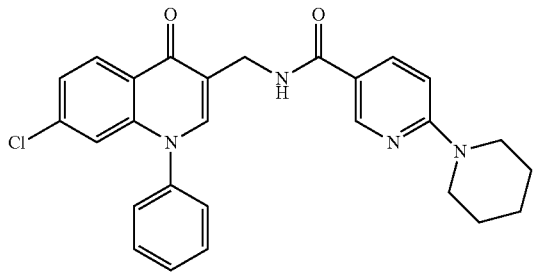 [SMILES: O=C(NCc1cn(-c2ccccc2)c2cc(Cl)ccc2c1=O)c1ccc(N2CCCCC2)nc1]

3,4,5,6-Tetrahydro-2H-[1,2']bipyridinyl-5'-carboxylic acid (7-chloro-4-oxo-1-phenyl-1,4-dihydro-quinolin-3-ylmethyl)-amide was prepared starting from intermediate E and piperidine. MS calcd. for $C_{27}H_{25}ClN_4O_2$ [(M+H)$^+$] 473.2, obsd. 473.

Example I-66

N-(7-Chloro-4-oxo-1-phenyl-1,4-dihydro-quinolin-3-ylmethyl)-6-[(2-hydroxy-ethyl)-methyl-amino]-nicotinamide

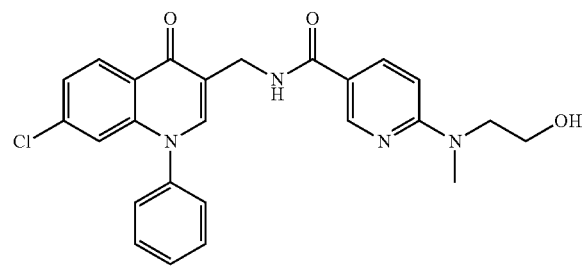

N-(7-Chloro-4-oxo-1-phenyl-1,4-dihydro-quinolin-3-ylmethyl)-6-[(2-hydroxy-ethyl)-methyl-amino]-nicotinamide was prepared starting from intermediate E and N-(methylamino)ethanol. MS calcd. for $C_{25}H_{23}ClN_4O_3$ [(M+H)$^+$] 463.2, obsd. 463.0.

Example I-67

4-Hydroxymethyl-3,4,5,6-tetrahydro-2H-[1,2']bipyridinyl-5'-carboxylic acid (7-chloro-4-oxo-1-phenyl-1,4-dihydro-quinolin-3-ylmethyl)-amide

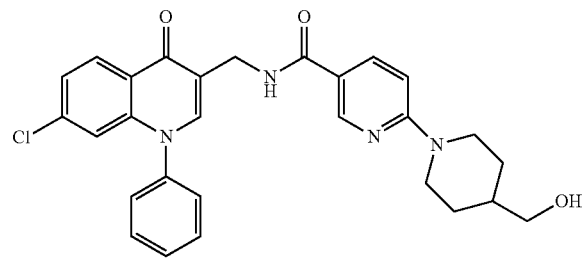 [SMILES: O=C(NCc1cn(-c2ccccc2)c2cc(Cl)ccc2c1=O)c1ccc(N2CCC(CO)CC2)nc1]

4-Hydroxymethyl-3,4,5,6-tetrahydro-2H-[1,2']bipyridinyl-5'-carboxylic acid (7-chloro-4-oxo-1-phenyl-1,4-dihydro-quinolin-3-ylmethyl)-amide was prepared starting from intermediate E and 4-piperidinemethanol. MS calcd. for $C_{28}H_{27}ClN_4O_3$ [(M+H)$^+$] 503.2, obsd. 503.

Example I-68

6-Azepan-1-yl-N-(7-chloro-4-oxo-1-phenyl-1,4-dihydro-quinolin-3-ylmethyl)-nicotinamide

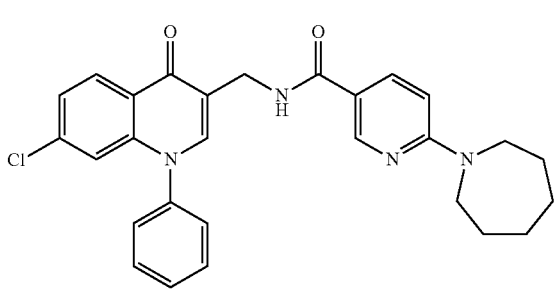 [SMILES: O=C(NCc1cn(-c2ccccc2)c2cc(Cl)ccc2c1=O)c1ccc(N2CCCCCC2)nc1]

Azepan-1-yl-N-(7-chloro-4-oxo-1-phenyl-1,4-dihydro-quinolin-3-ylmethyl)-nicotinamide was prepared starting from intermediate E and hexamethyleneimine. MS calcd. for $C_{28}H_{27}ClN_4O_2$ [(M+H)$^+$] 487.2, obsd. 487.

Example I-69

4-Methanesulfonyl-3,4,5,6-tetrahydro-2H-[1,2']bipyridinyl-5'-carboxylic acid (7-chloro-4-oxo-1-phenyl-1,4-dihydro-quinolin-3-ylmethyl)-amide

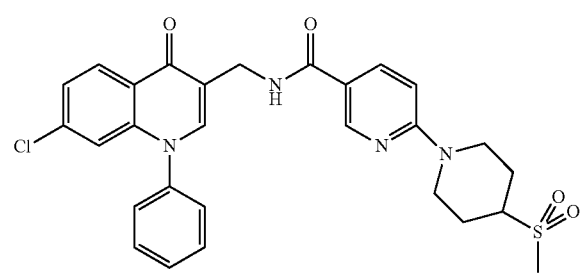 [SMILES: CS(=O)(=O)C1CCN(c2ccc(C(=O)NCc3cn(-c4ccccc4)c4cc(Cl)ccc4c3=O)cn2)CC1]

4-Methanesulfonyl-3,4,5,6-tetrahydro-2H-[1,2']bipyridinyl-5'-carboxylic acid (7-chloro-4-oxo-1-phenyl-1,4-dihydro-quinolin-3-ylmethyl)-amide was prepared starting from intermediate E and 4-methanesulfonyl piperidine hydrochloride. MS calcd. for $C_{28}H_{27}ClN_4O_4S$ [(M+H)$^+$] 551.1, obsd. 551.

Example I-70

N-(7-Chloro-4-oxo-1-phenyl-1,4-dihydro-quinolin-3-ylmethyl)-6-(R)-3-hydroxy-pyrrolidin-1-yl)-nicotinamide

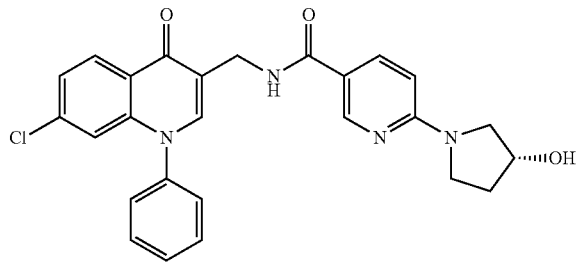 [SMILES: O=C(NCc1cn(-c2ccccc2)c2cc(Cl)ccc2c1=O)c1ccc(N2CC[C@@H](O)C2)nc1]

N-(7-Chloro-4-oxo-1-phenyl-1,4-dihydro-quinolin-3-ylmethyl)-6-(R)-3-hydroxy-pyrrolidin-1-yl)-nicotinamide was prepared starting from intermediate E and 3-pyrrolidinol. MS calcd. for $C_{26}H_{23}ClN_4O_3$ $[(M+H)^+]$ 475.2, obsd. 475.0.

Example I-71

4-Methoxy-3,4,5,6-tetrahydro-2H-[1,2']bipyridinyl-5'-carboxylic acid (7-chloro-4-oxo-1-phenyl-1,4-dihydro-quinolin-3-ylmethyl)-amide

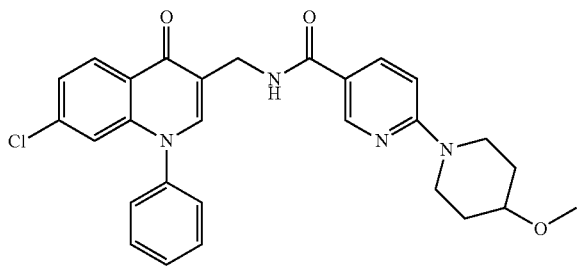 [SMILES: COC1CCN(c2ccc(C(=O)NCc3cn(-c4ccccc4)c4cc(Cl)ccc4c3=O)cn2)CC1]

4-Methoxy-3,4,5,6-tetrahydro-2H-[1,2']bipyridinyl-5'-carboxylic acid (7-chloro-4-oxo-1-phenyl-1,4-dihydro-quinolin-3-ylmethyl)-amide was prepared starting from intermediate E and 4-methoxypiperidine. MS calcd. for $C_{28}H_{27}ClN_4O_3$ $[(M+H)^+]$ 503.2, obsd. 503.0.

Example I-72

3,4,5,6-Tetrahydro-2H-[1,2']bipyridinyl-4,5'-dicarboxylic acid 5'-[(7-chloro-4-oxo-1-phenyl-1,4-dihydro-quinolin-3-ylmethyl)-amide]-4-methylamide

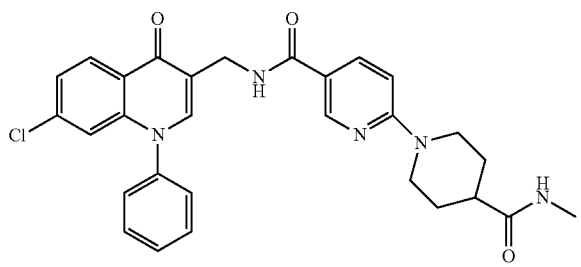 [SMILES: CNC(=O)C1CCN(c2ccc(C(=O)NCc3cn(-c4ccccc4)c4cc(Cl)ccc4c3=O)cn2)CC1]

3,4,5,6-Tetrahydro-2H-[1,2]bipyridinyl-4,5'-dicarboxylic acid 5'-[(7-chloro-4-oxo-1-phenyl-1,4-dihydro-quinolin-3-ylmethyl)-amide]-4-methylamide was prepared starting from intermediate E and piperidine 4-carboxylic acid methyl amide. MS calcd. for $C_{29}H_{28}ClN_5O_3$ $[(M+H)^+]$ 530.2, obsd. 530.0.

Example I-73

4-{5-[(7-Chloro-4-oxo-1-phenyl-1,4-dihydro-quinolin-3-ylmethyl)-carbamoyl]-pyridin-2-yl}-piperazine-1-carboxylic acid amide

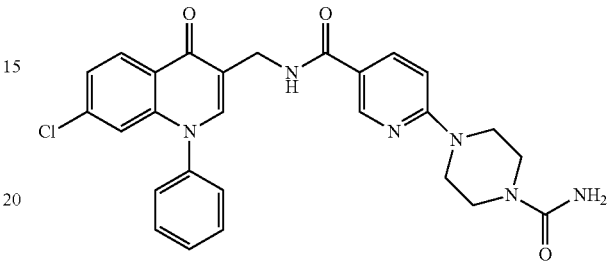

4-{5-[(7-Chloro-4-oxo-1-phenyl-1,4-dihydro-quinolin-3-ylmethyl)-carbamoyl]-pyridin-2-yl}-piperazine-1-carboxylic acid amide was prepared starting from intermediate E and piperazine-1-carboxylic acid amide. MS calcd. for $C_{27}H_{25}ClN_6O_3$ $[(M+H)^+]$ 517.2, obsd. 517.0.

Example I-74

N-(7-Chloro-4-oxo-1-phenyl-1,4-dihydro-quinolin-3-ylmethyl)-6-(2-methoxy-ethylamino)-nicotinamide

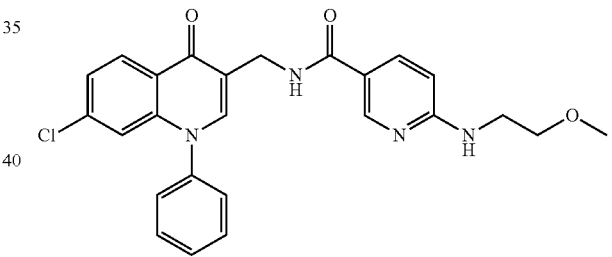

N-(7-Chloro-4-oxo-1-phenyl-1,4-dihydro-quinolin-3-ylmethyl)-6-(2-methoxy-ethyl-amino)-nicotinamide was prepared starting from intermediate E and 2-methoxyethylamine. MS calcd. for $C_{25}H_{23}ClN_4O_3$ $[(M+H)^+]$ 463.2, obsd. 463.0.

Example I-75

4-Dimethylamino-3,4,5,6-tetrahydro-2H-[1,2']bipyridinyl-5'-carboxylic acid (7-chloro-4-oxo-1-phenyl-1,4-dihydro-quinolin-3-ylmethyl)-amide

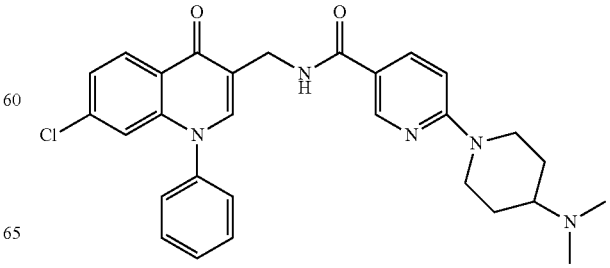

4-Dimethylamino-3,4,5,6-tetrahydro-2H-[1,2]bipyridinyl-5'-carboxylic acid (7-chloro-4-oxo-1-phenyl-1,4-dihydro-quinolin-3-ylmethyl)-amide was prepared starting from intermediate E and dimethyl-piperidin-4-yl-amine. MS calcd. for $C_{29}H_{30}ClN_5O_2$ [(M+H)$^+$] 516.2, obsd 516.0.

Example I-76

4-Hydroxy-3,4,5,6-tetrahydro-2H-[1,2']bipyridinyl-5'-carboxylic acid (7-chloro-4-oxo-1-phenyl-1,4-dihydro-quinolin-3-ylmethyl)-amide

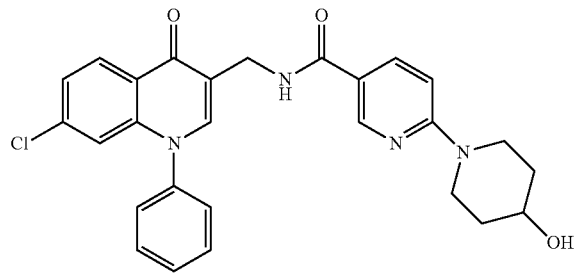 [SMILES: O=C(NCc1cn(-c2ccccc2)c2cc(Cl)ccc2c1=O)c1ccc(N2CCC(O)CC2)nc1]

4-Hydroxy-3,4,5,6-tetrahydro-2H-[1,2]bipyridinyl-5'-carboxylic acid (7-chloro-4-oxo-1-phenyl-1,4-dihydro-quinolin-3-ylmethyl)-amide was prepared starting from intermediate E and 4-hydroxypiperidine. MS calcd. for $C_{27}H_{25}ClN_4O_3$ [(M+H)$^+$] 489.2, obsd. 489.

Example I-77

N-(7-Chloro-4-oxo-1-phenyl-1,4-dihydro-quinolin-3-ylmethyl)-6-(2-hydroxy-ethylamino)-nicotinamide

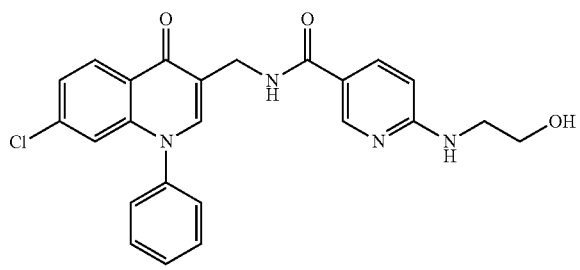

N-(7-Chloro-4-oxo-1-phenyl-1,4-dihydro-quinolin-3-ylmethyl)-6-(2-hydroxy-ethyl-amino)-nicotinamide was prepared starting from intermediate E and ethanolamine. MS calcd. for $C_{24}H_{21}ClN_4O_3$ [(M+H)$^+$] 449.1, obsd. 449.0.

Example I-78

N-(7-Chloro-4-oxo-1-phenyl-1,4-dihydro-quinolin-3-ylmethyl)-6-(tetrahydro-pyran-4-ylamino)-nicotinamide

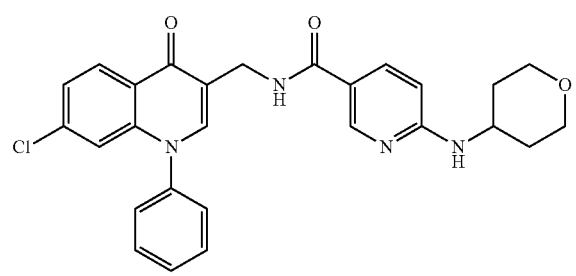 [SMILES: O=C(NCc1cn(-c2ccccc2)c2cc(Cl)ccc2c1=O)c1ccc(NC2CCOCC2)nc1]

N-(7-Chloro-4-oxo-1-phenyl-1,4-dihydro-quinolin-3-ylmethyl)-6-(tetrahydro-pyran-4-yl-amino)-nicotinamide was prepared starting from intermediate E and 4-aminotetrahydropyran. MS calcd. for $C_{27}H_{25}ClN_4O_3$ [(M+H)$^+$] 489.2, obsd. 489.0.

Example I-79

N-(7-Chloro-4-oxo-1-phenyl-1,4-dihydro-quinolin-3-ylmethyl)-6-dimethylamino-nicotinamide

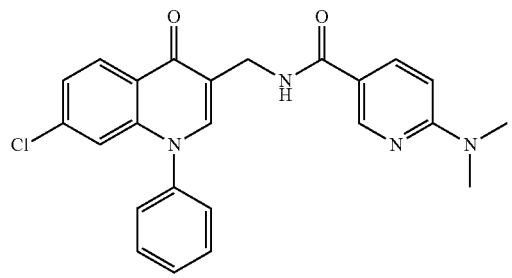

N-(7-Chloro-4-oxo-1-phenyl-1,4-dihydro-quinolin-3-ylmethyl)-6-dimethylamino-nicotinamide was prepared starting from intermediate E and dimethylamine. MS calcd. for $C_{24}H_{21}ClN_4O_2$ [(M+H)$^+$] 433.1, obsd. 432.

Example I-80

N-(7-Chloro-4-oxo-1-phenyl-1,4-dihydro-quinolin-3-ylmethyl)-6-(1,1-dioxo-thiomorpholin-4-yl)-nicotinamide

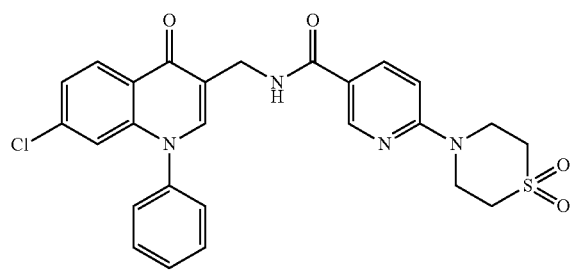 [SMILES: O=C(NCc1cn(-c2ccccc2)c2cc(Cl)ccc2c1=O)c1ccc(N2CCS(=O)(=O)CC2)nc1]

N-(7-Chloro-4-oxo-1-phenyl-1,4-dihydro-quinolin-3-ylmethyl)-6-(1,1-dioxo-thiomorph-olin-4-yl)-nicotinamide was prepared starting from intermediate E and thiomorpholine-1,1-dioxide. MS calcd. for $C_{26}H_{23}ClN_4O_4S$ [(M+H)$^+$] 523.1, obsd. 523.0.

Example I-81

{5'-[(7-Chloro-4-oxo-1-phenyl-1,4-dihydro-quinolin-3-ylmethyl)-carbamoyl]-3,4,5,6-tetrahydro-2H-[1,2]bipyridinyl-4-yl}-carbamic acid tert-butyl ester

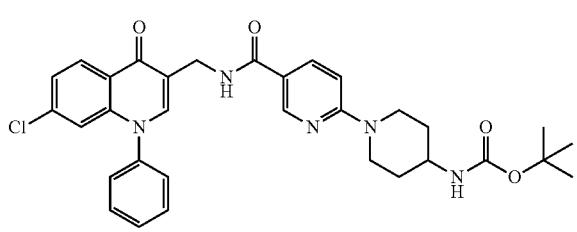 [SMILES: CC(C)(C)OC(=O)NC1CCN(c2ccc(C(=O)NCc3cn(-c4ccccc4)c4cc(Cl)ccc4c3=O)cn2)CC1]

{5'-[(7-Chloro-4-oxo-1-phenyl-1,4-dihydro-quinolin-3-ylmethyl)-carbamoyl]-3,4,5,6-tetra-hydro-2H[1,2']bipyridinyl-4-yl}-carbamic acid tert-butyl ester was prepared starting from intermediate E and 4-boc-aminopiperidine. MS calcd. for $C_{32}H_{34}ClN_5O_4$ [(M+H)$^+$] 588.2, obsd. 588.0.

Example I-82

N-(7-Chloro-4-oxo-1-phenyl-1,4-dihydro-quinolin-3-ylmethyl)-6-(4-methyl-[1,4]diazepan-1-yl)-nicotinamide

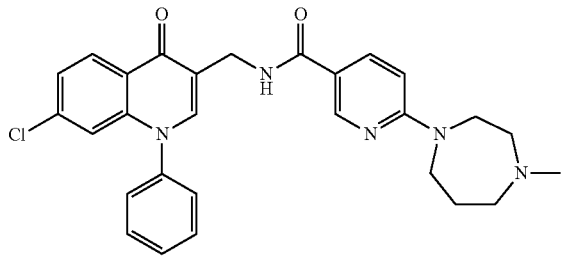 [SMILES: CN1CCCN(c2ccc(C(=O)NCc3cn(-c4ccccc4)c4cc(Cl)ccc4c3=O)cn2)CC1]

N-(7-Chloro-4-oxo-1-phenyl-1,4-dihydro-quinolin-3-ylmethyl)-6-(4-methyl-[1,4]-diazepan-1-yl)-nicotinamide was prepared starting from intermediate E and N-methylhomopiperazine. MS calcd. for $C_{28}H_{28}ClN_5O_2$ [(M+H)$^+$] 502.2, obsd. 502.0.

Example I-83

N-(7-Chloro-4-oxo-1-phenyl-1,4-dihydro-quinolin-3-ylmethyl)-6-[4-(2-hydroxy-ethyl)-piperazin-1-yl]-nicotinamide

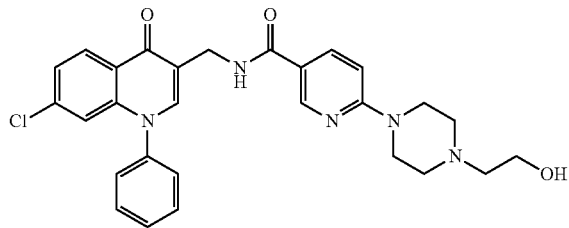 [SMILES: O=C(NCc1cn(-c2ccccc2)c2cc(Cl)ccc2c1=O)c1ccc(N2CCN(CCO)CC2)nc1]

N-(7-Chloro-4-oxo-1-phenyl-1,4-dihydro-quinolin-3-ylmethyl)-6-[4-(2-hydroxy-ethyl)-piperazin-1-yl]-nicotinamide was prepared starting from intermediate E and N-(2-hydroxyethyl)piperazine. MS calcd. for $C_{28}H_{28}ClN_5O_3$ [(M+H)$^+$] 518.2, obsd. 518.0.

Example I-84

N-(7-Chloro-4-oxo-1-phenyl-1,4-dihydro-quinolin-3-ylmethyl)-6-pyrrolidin-1-yl-nicotinamide

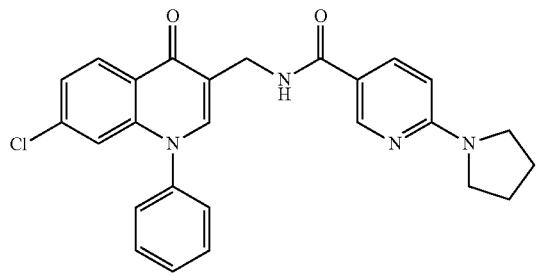 [SMILES: O=C(NCc1cn(-c2ccccc2)c2cc(Cl)ccc2c1=O)c1ccc(N2CCCC2)nc1]

N-(7-Chloro-4-oxo-1-phenyl-1,4-dihydro-quinolin-3-ylmethyl)-6-pyrrolidin-1-yl-nicotin-amide was prepared starting from intermediate E and pyrrolidine. MS calcd. $C_{26}H_{23}ClN_4O_2$ for [(M+H)$^+$] 459, obsd. 459.

Example I-85

N-(7-Chloro-4-oxo-1-phenyl-1,4-dihydro-quinolin-3-ylmethyl)-6-piperazin-1-yl-nicotinamide

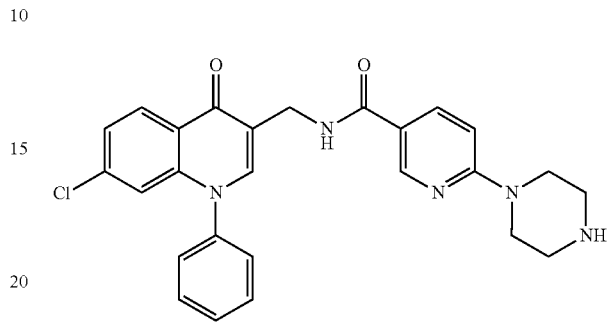

N-(7-Chloro-4-oxo-1-phenyl-1,4-dihydro-quinolin-3-ylmethyl)-6-piperazin-1-yl-nicotin-amide was prepared starting from intermediate E and piperazine. MS calcd. for $C_{26}H_{24}ClN_5O_2$ [(M+H)$^+$] 474.2, obsd. 474.

Example I-86

3,4,5,6-Tetrahydro-2H-[1,2']bipyridinyl-4,5'-dicarboxylic acid 4-amide-5'-[(7-chloro-4-oxo-1-phenyl-1,4-dihydro-quinolin-3-ylmethyl)-amide]

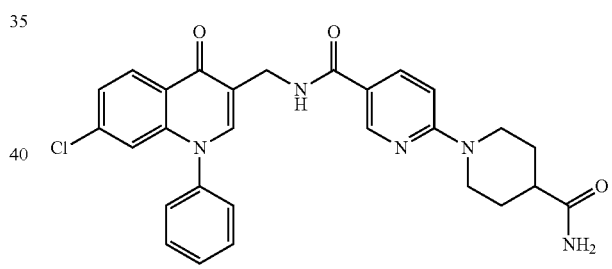

3,4,5,6-Tetrahydro-2H-[1,2]bipyridinyl-4,5'-dicarboxylic acid 4-amide-5'-[(7-chloro-4-oxo-1-phenyl-1,4-dihydro-quinolin-3-ylmethyl)-amide] was prepared starting from intermediate E and piperidine-4-carboxamide. MS calcd. for $C_{28}H_{26}ClN_5O_3$ [(M+H)$^+$] 516.2, obsd. 516.1.

Example I-87

N-(7-Chloro-4-oxo-1-phenyl-1,4-dihydro-quinolin-3-ylmethyl)-6-((S)-3-hydroxy-pyrrolidin-1-yl)-nicotinamide

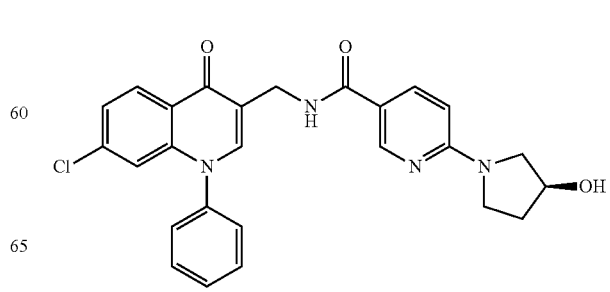

N-(7-Chloro-4-oxo-1-phenyl-1,4-dihydro-quinolin-3-yl-methyl)-6-(S)-3-hydroxypyrrolidin-1-yl)-nicotinamide was prepared starting from intermediate E and (S)-3-hydroxypyrrolidine. MS calcd. for $C_{26}H_{23}ClN_4O_3$ [(M+H)$^+$] 475.2, obsd. 475.0.

Example I-88

N-(7-Chloro-4-oxo-1-phenyl-1,4-dihydro-quinolin-3-ylmethyl)-6-(4-methyl-piperazin-1-yl)-nicotinamide

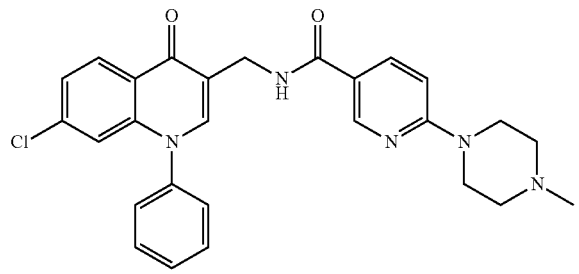 [SMILES: CN1CCN(c2ccc(C(=O)NCc3cn(-c4ccccc4)c4cc(Cl)ccc4c3=O)cn2)CC1]

N-(7-Chloro-4-oxo-1-phenyl-1,4-dihydro-quinolin-3-yl-methyl)-6-(4-methyl-piperazin-1-yl)-nicotinamide was prepared starting from intermediate E and 4-methylpiperazine. MS calcd. for $C_{27}H_{26}ClN_5O_2$ [(M+H)$^+$] 488.2, obsd. 488.

Example I-89

N-(7-Chloro-4-oxo-1-phenyl-1,4-dihydro-quinolin-3-ylmethyl)-6-(4-methyl-piperazin-1-yl)-nicotinamide trifluoroacetate

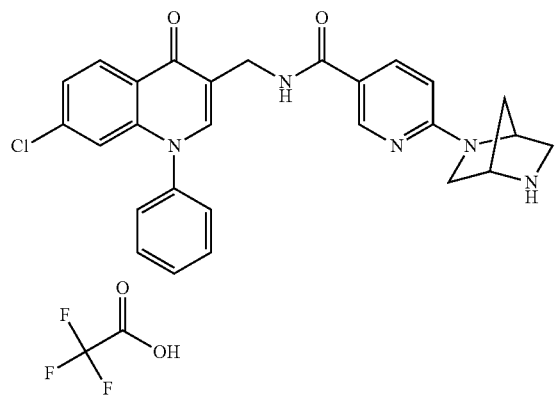

To a solution of (1S,4S)-tert-butyl 5-(5-((7-chloro-4-oxo-1-phenyl-1,4-dihydroquinolin-3-yl)methylcarbamoyl)pyridin-2-yl)-2,5-diazabicyclo[2.2.1]heptane-2-carboxylate (23 mg, 0.039 mmol) in dichloromethane (3 mL) was added trifluoroacetic acid (1.48 g, 1 mL, 13.0 mmol). The resulting solution was shaken at room temperature for 5 hr. in a screw-capped vial. The reaction mixture was concentrated then triturated with ether to give the trifluoroacetate salt of N-(7-chloro-4-oxo-1-phenyl-1,4-dihydro-quinolin-3-ylmethyl)-6-(4-methyl-piperazin-1-yl)-nicotinamide (23 mg, 98%) of light brown solid. MS calcd. for $C_{27}H_{24}ClN_5O_2$ [(M+H)$^+$] 486.2, obsd. 486.0.

Example I-90

4-Amino-3,4,5,6-tetrahydro-2H-[1,2']bipyridinyl-5'-carboxylic acid (7-chloro-4-oxo-1-phenyl-1,4-dihydro-quinolin-3-ylmethyl)-amide trifluoroacetate

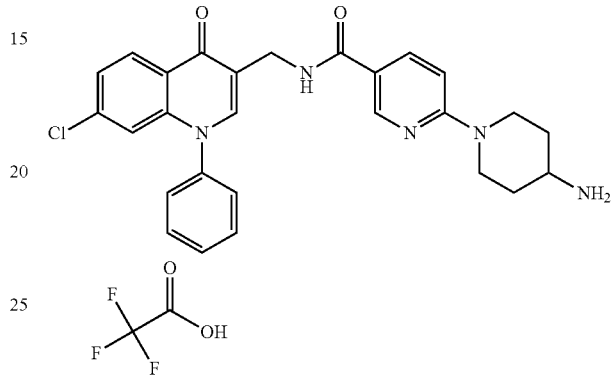

The trifluoroacetate salt of 4-amino-3,4,5,6-tetrahydro-2H-[1,2']bipyridinyl-5'-carboxylic acid (7-chloro-4-oxo-1-phenyl-1,4-dihydro-quinolin-3-ylmethyl)-amide was prepared in an analogous manner to example 4-61, starting from {5'-[(7-chloro-4-oxo-1-phenyl-1,4-dihydro-quinolin-3-ylmethyl)-carbamoyl]-3,4,5,6-tetra-hydro-2H-[1,2']bipyridinyl-4-yl}-carbamic acid tert-butyl ester. MS calcd. for $C_{27}H_{26}ClN_5O_2$ [(M+H)$^+$] 488.2, obsd. 488.1.

Example I-91

2-Piperidin-1-yl-thiazole-5-carboxylic acid (7-chloro-4-oxo-1-phenyl-1,4-dihydro-quinolin-3-ylmethyl)-amide

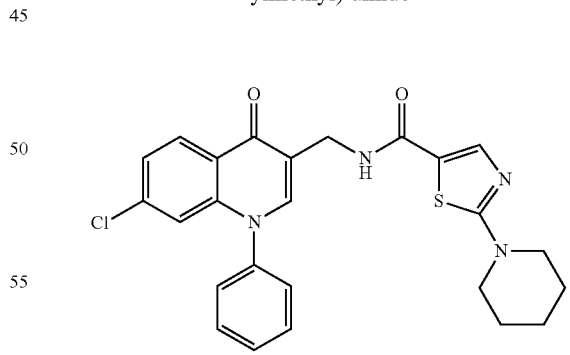

A mixture of 2-bromo-N-((7-chloro-4-oxo-1-phenyl-1,4-dihydroquinolin-3-yl)methyl)-thiazole-5-carboxamide (intermediate F) (30 mg, 0.063 mmol) and piperidine (10.8 mg, 0.126 mmol) in NMP was heated to 120° C. in a sealed microwave tube. After heating for 2 hr., the mixture was allowed to cool to room temperature. The crude product was purified using preparative reverse-phase HPLC, providing 2-piperidin-1-yl-thiazole-5-carboxylic acid (7-chloro-4-oxo- 1-phenyl-1,4-dihydro-quinolin-3-ylmethyl)-amide. MS calcd. for $C_{25}H_{23}ClN_4O_2S$ [(M+H)+] 479.1, obsd. 478.

Examples I-92 to I-97

The following examples I-92 to I-97 were prepared in an analogous manner to example I-91, starting with intermediate F and an appropriate amine.

Example I-92

2-(4-Methanesulfonyl-piperidin-1-yl)-thiazole-5-carboxylic acid (7-chloro-4-oxo-1-phenyl-1,4-dihydro-quinolin-3-ylmethyl)-amide

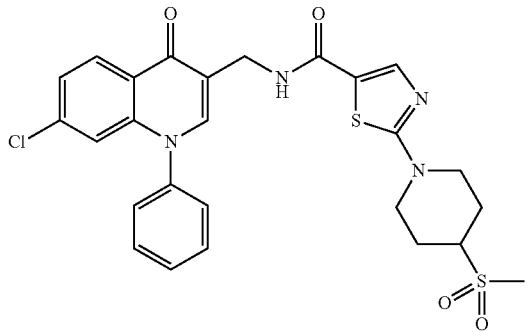 [SMILES: CS(=O)(=O)C1CCN(c2ncc(C(=O)NCc3cn(-c4ccccc4)c4cc(Cl)ccc4c3=O)s2)CC1]

2-(4-Methanesulfonyl-piperidin-1-yl)-thiazole-5-carboxylic acid (7-chloro-4-oxo-1-phenyl-1,4-dihydro-quinolin-3-ylmethyl)-amide was prepared starting from intermediate F and 4-methanesulfonyl piperidine hydrochloride. MS calcd. for $C_{26}H_{25}ClN_4O_4S_2$ [(M+H)+] 557.1, obsd. 557.

Example I-93

2-(4-Hydroxymethyl-piperidin-1-yl)-thiazole-5-carboxylic acid (7-chloro-4-oxo-1-phenyl-1,4-dihydro-quinolin-3-ylmethyl)-amide

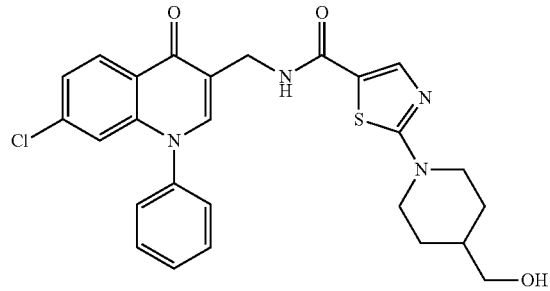 [SMILES: O=C(NCc1cn(-c2ccccc2)c2cc(Cl)ccc2c1=O)c1cnc(N2CCC(CO)CC2)s1]

2-(4-Hydroxymethyl-piperidin-1-yl)-thiazole-5-carboxylic acid (7-chloro-4-oxo-1-phenyl-1,4-dihydro-quinolin-3-ylmethyl)-amide was prepared starting from intermediate F and 4-hydroxymethyl piperidine. MS calcd. for $C_{26}H_{25}ClN_4O_3S$ [(M+H)+] 509.1, obsd. 509.

Example I-94

2-(4-Hydroxypiperidin-1-yl)-thiazole-5-carboxylic acid (7-chloro-4-oxo-1-phenyl-1,4-dihydro-quinolin-3-ylmethyl)-amide

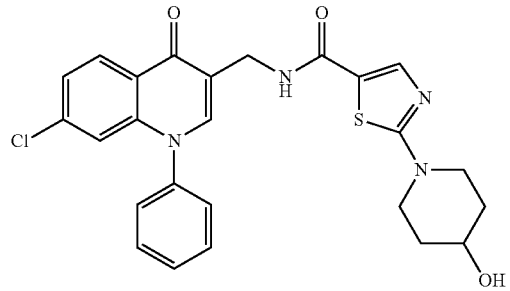 [SMILES: O=C(NCc1cn(-c2ccccc2)c2cc(Cl)ccc2c1=O)c1cnc(N2CCC(O)CC2)s1]

2-(4-Hydroxypiperidin-1-yl)-thiazole-5-carboxylic acid (7-chloro-4-oxo-1-phenyl-1,4-dihydro-quinolin-3-ylmethyl)-amide was prepared starting from intermediate F and 4-hydroxypiperidine. $^1$H NMR (400 MHz, DMSO-d$_6$) δ ppm 8.48 (t, J=5.54 Hz, 1H) 8.25 (d, J=8.66 Hz, 1H) 7.91 (s, 1H) 7.78 (s, 1H) 7.59-7.71 (m, 3H) 7.54-7.59 (m, 1H) 7.43 (dd, J=8.66, 2.01 Hz, 1H) 6.88 (d, J=1.81 Hz, 1H) 4.79 (d, J=4.03 Hz, 1H) 4.26 (d, J=5.44 Hz, 2H) 3.69 (dd, J=12.59, 4.53 Hz, 3H) 3.20 (ddd, J=13.09, 9.37, 3.53 Hz, 2H) 1.70-1.81 (m, 2H) 1.39 (td, J=8.66, 4.23 Hz, 2H).

Example I-95

2-(4-Methyl-piperazin-1-yl)-thiazole-5-carboxylic acid (7-chloro-4-oxo-1-phenyl-1,4-dihydro-quinolin-3-ylmethyl)-amide

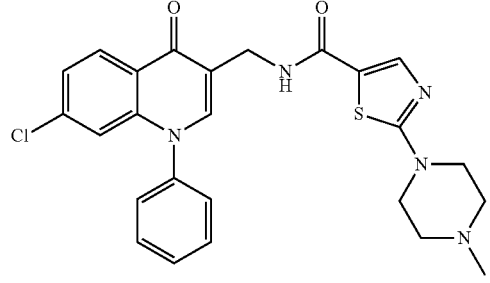 [SMILES: CN1CCN(c2ncc(C(=O)NCc3cn(-c4ccccc4)c4cc(Cl)ccc4c3=O)s2)CC1]

2-(4-Methyl-piperazin-1-yl)-thiazole-5-carboxylic acid (7-chloro-4-oxo-1-phenyl-1,4-dihydro-quinolin-3-ylmethyl)-amide was prepared starting from intermediate F and 4-methylpiperazine. MS calcd. for $C_{25}H_{24}ClN_5O_2S$ [(M+H)+] 494.1, obsd. 494.

Example I-96

2-Morpholin-4-yl-thiazole-5-carboxylic acid (7-chloro-4-oxo-1-phenyl-1,4-dihydro-quinolin-3-ylmethyl)-amide

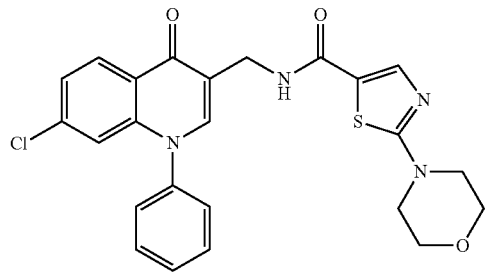 [SMILES: O=C(NCc1cn(-c2ccccc2)c2cc(Cl)ccc2c1=O)c1cnc(N2CCOCC2)s1]

2-Morpholin-4-yl-thiazole-5-carboxylic acid (7-chloro-4-oxo-1-phenyl-1,4-dihydro-quinolin-3-ylmethyl)-amide was prepared starting from intermediate F and morpholine. MS calcd. for $C_{24}H_{21}ClN_4O_3S$ [(M+H)$^+$] 481.1, obsd. 481.

Example I-97

2-(1,1-Dioxo-thiomorpholin-4-yl)-thiazole-5-carboxylic acid (7-chloro-4-oxo-1-phenyl-1,4-dihydro-quinolin-3-ylmethyl)-amide

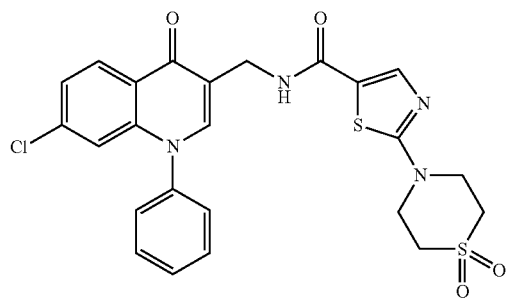 [SMILES: O=C(NCc1cn(-c2ccccc2)c2cc(Cl)ccc2c1=O)c1cnc(N2CCS(=O)(=O)CC2)s1]

2-(1,1-Dioxo-thiomorpholin-4-yl)-thiazole-5-carboxylic acid (7-chloro-4-oxo-1-phenyl-1,4-dihydro-quinolin-3-ylmethyl)-amide was prepared starting from intermediate F and thiomorpholine-1,1-dioxide. MS calcd. for $C_{24}H_{21}ClN_4O_4S_2$ [(M+H)$^+$] 529.1, obsd. 529.

Example I-98

N-(7-Chloro-4-oxo-1-phenyl-1,4-dihydro-quinolin-3-ylmethyl)-N-(2-hydroxy-2-methyl-propyl)-terephthalamide

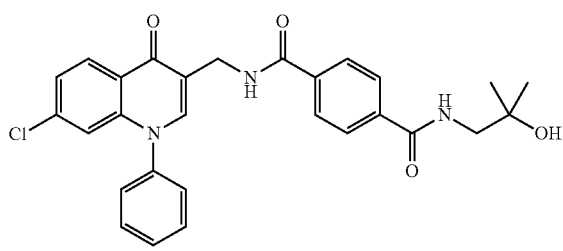 [SMILES: CC(C)(O)CNC(=O)c1ccc(C(=O)NCc2cn(-c3ccccc3)c3cc(Cl)ccc3c2=O)cc1]

Step 1

A mixture of 3-(aminomethyl)-7-chloro-1-phenylquinolin-4(1H)-one (100 mg, 0.351 mmol) and methyl 4-(chlorocarbonyl)benzoate (73.2 mg, 0.369 mmol) in methylene chloride (3.51 mL) was treated with triethylamine (178 mg, 247 µL, 1.76 mmol) and N,N-(dimethylamino)pyridine (DMAP) (one spatula tip). The reaction mixture was stirred for 4 hr. At this time, LCMS indicated completed conversion to desired product. The reaction was directly loaded onto a 12 inch silica gel column. Elution with 2% methanol/methylene chloride ramped to 4% methanol/methylene chloride furnished the intermediate methyl 4-((7-chloro-4-oxo-1-phenyl-1,4-dihydroquinolin-3-yl)methylcarbamoyl)benzoate (128 mg, 77%) as a light yellow solid.

Step 2

A solution of methyl 4-((7-chloro-4-oxo-1-phenyl-1,4-dihydroquinolin-3-yl)methylcarbamoyl)benzoate (128 mg, 0.286 mmol) in tetrahydrofuran (2.3 mL) at 25° C. was treated with a solution of lithium hydroxide monohydrate (24.0 mg, 0.573 mmol) in water (573 µL). The reaction was stirred at 25° C. for 24 hr. At this time, LC/MS indicated complete conversion to the desired acid. The reaction was diluted with water (30 mL) and was extracted with methylene chloride (1×50 mL). The aqueous layer was then acidified with a 1N aqueous hydrochloric acid solution, and then extracted with 90:10 methylene chloride-methanol (3×40 mL). The organic phase was dried over sodium sulfate, filtered, and concentrated in vacuo to give the intermediate 4-((7-chloro-4-oxo-1-phenyl-1,4-dihydroquinolin-3-yl)methylcarbamoyl)benzoic acid (55.1 mg, 44%).

Step 3

A solution of 4-((7-chloro-4-oxo-1-phenyl-1,4-dihydroquinolin-3-yl)methylcarbamoyl)benzoic acid (25.3 mg, 0.058 mmol), 1-amino-2-methylpropan-2-ol (5.21 mg, 0.058 mmol), 1-hydroxybenzotriazole (HOBT) (12.9 mg, 0.094 mmol), and N-(3-dimethylaminopropyl)-N'-ethylcarbodiimide hydrochloride (EDC) (18.1 mg, 0.094 mmol) in methylene chloride at 25° C. was treated with N,N-diisopropylethylamine (76.3 mg, 103 µL, 0.584 mmol). The reaction was stirred at 25° C. overnight. The reaction was diluted with methylene chloride (20 mL) and was washed with a saturated aqueous ammonium chloride solution (1×50 mL) and a saturated aqueous sodium bicarbonate solution (1×50 mL). The organics were dried over sodium sulfate, filtered and concentrated in vacuo. Flash chromatography (2% methanol/methylene chloride ramped to 6% methanol/methylene chloride) provided N-(7-chloro-4-oxo-1-phenyl-1,4-dihydro-quinolin-3-ylmethyl)-N-(2-hydroxy-2-methyl-propyl)-terephthalamide (14.3 mg, 49%) $^1$H NMR (300 MHz, DMSO-d$_6$) δ ppm 8.85 (t, J=5.27 Hz, 1H) 8.33 (t, J=6.12 Hz, 1H) 8.28 (d, J=8.67 Hz, 1H) 7.91 (s, 4H) 7.99 (s, 1H) 7.54-7.74 (m, 5H) 7.46 (dd, J=8.67, 1.88 Hz, 1H) 6.91 (d, J=1.70 Hz, 1H) 4.54 (s, 1H) 4.40 (d, J=5.46 Hz, 2H) 3.25 (d, J=6.03 Hz, 2H) 1.08-1.14 (m, 6H).

Example I-99

N-(7-Chloro-4-oxo-1-phenyl-1,4-dihydro-quinolin-3-ylmethyl)-N'-(5-hydroxy-adamantan-2-yl)-terephthalamide

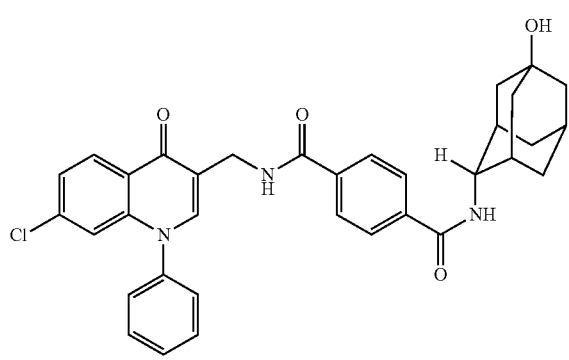 [SMILES: O=C(NCc1cn(-c2ccccc2)c2cc(Cl)ccc2c1=O)c1ccc(C(=O)NC2C3CC4CC2CC(O)(C4)C3)cc1]

N-(7-Chloro-4-oxo-1-phenyl-1,4-dihydro-quinolin-3-ylmethyl)-N-(5-hydroxy-adamantan-2-yl)-terephthalamide was prepared using a method analogous to the procedure described above for example I-98, using 4-((7-chloro-4-oxo-1-phenyl-1,4-dihydroquinolin-3-yl)methylcarbamoyl)benzoic acid and trans-4-aminoadamantan-1-ol.

$^1$H NMR (400 MHz, DMSO-$d_6$) δ ppm 8.89 (t, J=5.47 Hz, 1H) 8.29 (d, J=8.59 Hz, 1H) 7.95-8.08 (m, 2H) 7.81-7.95 (m, 4H) 7.62-7.76 (m, 3H) 7.56-7.62 (m, 2H) 7.47 (dd, J=8.59, 1.95 Hz, 1H) 6.92 (d, J=1.95 Hz, 1H) 4.44 (s, 1H) 4.41 (d, J=5.47 Hz, 2H) 3.94 (br. s., 1H) 1.90-2.19 (m, 5H) 1.55-1.83 (m, 6H) 1.34 (d, J=11.33 Hz, 2H).

Example I-100

N-[7-Chloro-1-(2-chloro-phenyl)-4-oxo-1,4-dihydro-quinolin-3-ylmethyl]-4-morpholin-4-yl-benzamide

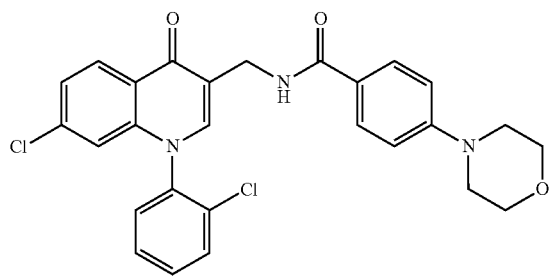 [SMILES: O=C(NCc1cn(-c2ccccc2Cl)c2cc(Cl)ccc2c1=O)c1ccc(N2CCOCC2)cc1]

While purging with argon, a 25 mL round-bottom flask was charged with 3-amino-methyl-7-chloro-1-(2-chloro-phenyl)-1H-quinolin-4-one (intermediate G) (50 mg, 0.157 mmol), 6-morpholinonicotinic acid (39.1 mg, 0.188 mmol), and O-(benzotriazol-1-yl)-N,N,N',N'-tetramethyluronium hexafluorophosphate (HBTU) (71.3 mg, 0.188 mmol). Methylene chloride (5 mL) and N,N-diisopropylethylamine (202 mg, 274 µL, 1.57 mmol) were added, then the reaction mixture was stirred overnight at room temperature. The reaction mixture was diluted with ethyl acetate and washed with water and brine. The organic phase was dried over MgSO$_4$, filtered, and concentrated. The crude product was purified using flash chromatography (12 g silica gel column, eluted with 100% methylene chloride ramped to 4% methanol in methylene chloride). Due to poor separation, a second purification was performed using a 23 g spherical silica column (100% methylene chloride ramped to 4% methanol in methylene chloride). N-[7-chloro-1-(2-chloro-phenyl)-4-oxo-1,4-dihydro-quinolin-3-ylmethyl]-4-morpholin-4-yl-benzamide (46.8 mg, 57%) was obtained as a white solid at 97% purity according to reverse-phase HPLC. By analytical SFC, two peaks were present, suggesting possible atropisomers. The product was submitted to preparative SFC (WHELK-O1 R,R 3×25; modifier: ethanol; flow rate: 70 mL/min); however, the two products were only partially resolved. $^1$H NMR (DMSO-$d_6$) δ ppm 8.45-8.69 (m, 2H) 8.26 (d, J=8.7 Hz, 1H) 7.56-8.07 (m, 6H) 7.45 (dd, J=8.7, 1.8 Hz, 1H) 6.81 (d, J=9.1 Hz, 1H) 6.67 (d, J=1.6 Hz, 1H) 4.34 (qd, J=15.0, 5.6 Hz, 2H) 3.58-3.78 (m, 4H) 3.38-3.58 (m, 4H). MS calcd. for $C_{26}H_{22}Cl_2N_4O_3$ [(M+H)$^+$] 510.0, obsd. 508.9.

Example I-101

6-Bromo-N-[7-chloro-1-(2-chloro-phenyl)-4-oxo-1,4-dihydro-quinolin-3-ylmethyl]-nicotinamide

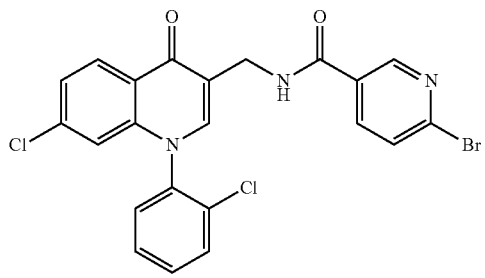 [SMILES: O=C(NCc1cn(-c2ccccc2Cl)c2cc(Cl)ccc2c1=O)c1ccc(Br)nc1]

6-Bromo-N-[7-chloro-1-(2-chloro-phenyl)-4-oxo-1,4-dihydro-quinolin-3-ylmethyl]-nico-tinamide was obtained using a procedure analogous to example 5-1, starting with intermediate G and 6-bromonicotinic acid. $^1$H NMR (DMSO-$d_6$) δ ppm 9.02 (br. s., 1H), 8.79 (d, J=2.1 Hz, 1H) 8.27 (d, J=8.8 Hz, 1H) 8.11 (dd, J=8.5, 2.4 Hz, 1H) 7.98 (s, 1H) 7.55-7.90 (m, 5H) 7.46 (dd, J=8.8, 1.8 Hz, 1H) 6.68 (d, J=1.5 Hz, 1H) 4.15-4.62 (m, 2H). MS calcd. for $C_{22}H_{14}BrCl_2N_eO_2$ [(M+H)$^+$] 504.0, obsd. 504.0.

Example I-102

N-[7-Chloro-1-(2-chloro-phenyl)-4-oxo-1,4-dihydro-quinolin-3-ylmethyl]-6-(1H-pyrazol-4-yl)-nicotinamide

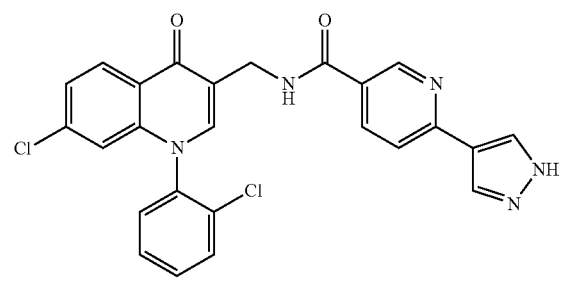 [SMILES: O=C(NCc1cn(-c2ccccc2Cl)c2cc(Cl)ccc2c1=O)c1ccc(-c2cn[nH]c2)nc1]

While purging with argon, a small microwave tube was charged with 4-(4,4,5,5-tetramethyl-1,3,2-dioxaborolan-2-yl)-1H-pyrazole (30.0 mg, 0.155 mmol), $K_3PO_4 \cdot H_2O$ (53 mg, 0.230 mmol), and $PdCl_2(dppf)$ (9.3 mg, 0.013 mmol). 6-Bromo-N-[7-chloro-1-(2-chloro-phenyl)-4-oxo-1,4-dihydro-quinolin-3-yl-methyl]-nicotinamide (Example I-101) (50 mg, 0.099 mmol) in DMF (0.50 mL) was added followed by water (0.05 mL). The reaction mixture was heated at 120° C. via microwave irradiation for 15 min. HPLC showed one or two new peaks forming; LC/MS showed one of the new peaks with the product mass. The reaction mixture was heated at 120° C. for another 40 min. After this time, most of the starting material was consumed, as observed by HPLC. The reaction mixture was diluted with $H_2O$, then extracted twice with ethyl acetate. The combined ethyl acetate layers were washed with brine. The organic phase was dried over $Na_2CO_3$, filtered, and concentrated. The crude product was purified using flash chromatography (12 g silica gel column eluting with 100% methylene chloride ramped to 0% methanol in methylene chloride). N-[7-Chloro-1-(2-chloro-phenyl)-4-oxo-1,4-dihydro-quinolin-3-ylmethyl]-6-(1H-pyrazol-4-yl)-nicotin-amide (3.7 mg, 7%) was obtained as a light brown solid at 90% purity by reverse-phase HPLC. MS calcd. for $C_{25}H_{17}Cl_2N_5O_2$ [(M+H)$^+$] 491.0, obsd. 489.9.

Example I-103

1-Phenyl-1H-pyrazole-4-carboxylic acid [7-fluoro-1-(2-fluoro-phenyl)-4-oxo-1,4-dihydro-quinolin-3-ylmethyl]-amide

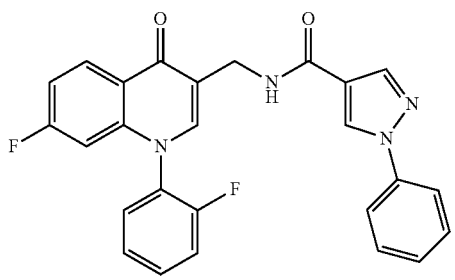 [SMILES: O=C(NCc1cn(-c2ccccc2F)c2cc(F)ccc2c1=O)c1cnn(-c2ccccc2)c1]

A mixture of 3-(aminomethyl)-7-fluoro-1-(2-fluorophenyl)quinolin-4(1H)-one (intermediate H) (50 mg, 0.175 mmol), 1-phenyl-1H-pyrazole-4-carboxylic acid (66 mg, 0.349 mmol), bromo-tris-pyrrolidino-phosphonium hexafluorophosphate (PyBrOP) (112 mg, 0.24 mmol), triethylamine (53 mg, 0.524 mmol), and DMF (3 mL) was stirred at room temperature overnight. The crude material was purified by flash chromatography (12 g silica gel eluting with 100% hexanes ramped to 70% ethyl acetate in hexanes). The product 1-phenyl-1H-pyrazole-4-carboxylic acid [7-fluoro-1-(2-fluoro-phenyl)-4-oxo-1,4-dihydro-quinolin-3-ylmethyl]-amide (46 mg, 58%) was obtained as an off-white solid. MS calcd. for $C_{22}H_{14}ClF_2N_3O_2$ [(M+H)$^+$] 426.1, obsd. 426.1.

Example I-104

1-Methyl-1H-pyrazole-4-carboxylic acid [7-fluoro-1-(2-fluoro-phenyl)-4-oxo-1,4-dihydro-quinolin-3-ylmethyl]-amide

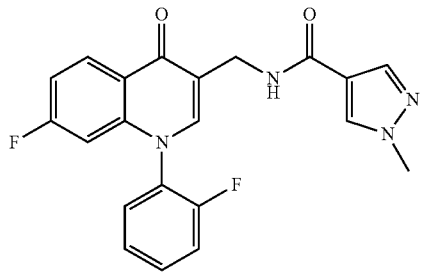 [SMILES: Cn1cc(C(=O)NCc2cn(-c3ccccc3F)c3cc(F)ccc3c2=O)cn1]

Methyl-1H-pyrazole-4-carboxylic acid [7-fluoro-1-(2-fluoro-phenyl)-4-oxo-1,4-dihydro-quinolin-3-ylmethyl]-amide was prepared using a procedure analogous to the procedure for example 6-1, starting from intermediate H and 1-methyl-1H-pyrazole carboxylic acid. MS calcd. for $C_{21}H_{16}F_2N_4O_2$ [(M+H)$^+$] 395.1, obsd. 395.1.

Example I-105

6-Chloro-N-[7-fluoro-1-(2-fluoro-phenyl)-4-oxo-1,4-dihydro-quinolin-3-yl-methyl]-nicotinamide

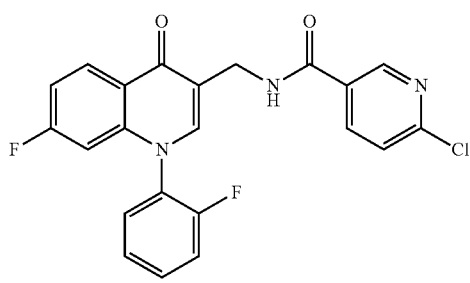 [SMILES: O=C(NCc1cn(-c2ccccc2F)c2cc(F)ccc2c1=O)c1ccc(Cl)nc1]

To a mixture of 3-(aminomethyl)-7-fluoro-1-(2-fluorophenyl)quinolin-4(1H)-one (intermediate H) (470 mg, 1.64 mmol), triethylamine (0.229 mL, 1.64 mmol), and 35 mL of a $CH_2Cl_2$-DMF mixture was added 6-chloronicotinoyl chloride (298 mg, 1.64 mmol). The resulting mixture was stirred at room temperature for 1 hr. After this time, the reaction was complete, giving 6-chloro-N-[7-fluoro-1-(2-fluoro-phenyl)-4-oxo-1,4-dihydro-quinolin-3-yl-methyl]-nicotinamide (500 mg, 72%). MS calcd. for $C_{22}H_{14}ClF_2N_3O_2$ [(M+H)$^+$] 426.1, obsd. 426.1.

Example I-106

4-Hydroxymethyl-3,4,5,6-tetrahydro-2H-[1,2']bipyridinyl-5'-carboxylic acid [7-fluoro-1-(2-fluoro-phenyl)-4-oxo-1,4-dihydro-quinolin-3-ylmethyl]-amide

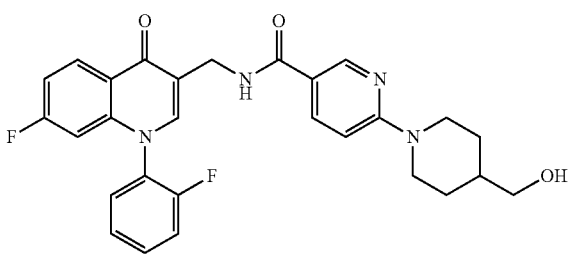 [SMILES: O=C(NCc1cn(-c2ccccc2F)c2cc(F)ccc2c1=O)c1ccc(N2CCC(CO)CC2)nc1]

A mixture of 6-chloro-N-[7-fluoro-1-(2-fluoro-phenyl)-4-oxo-1,4-dihydro-quinolin-3-yl-methyl]-nicotinamide (55 mg, 0.129 mmol), piperidin-4-yl methanol (22.3 mg, 0.194 mmol), triethylamine (0.036 mL, 258 mmol), and DMF (2 mL) was heated in a sealed tube at 140° C. for 5 hr. The crude material was purified by reverse phase chromatography (10% acetonitrile-water ramped to 60% acetonitrile-water). The product 4-hydroxymethyl-3,4,5,6-tetrahydro-2H-[1,2']bipyridinyl-5'-carboxylic acid [7-fluoro-1-(2-fluoro-phenyl)-4-oxo-1,4-dihydro-quinolin-3-ylmethyl]-amide (25 mg, 38%) was isolated as a light yellow solid. MS calcd. for $C_{28}H_{26}F_2N_4O_3$ [(M+H)$^+$] 505.2, obsd. 505.1.

Examples I-107 to I-108

The following examples I-107 to I-108 were prepared in an analogous manner to example I-106, starting with 6-chloro-N-[7-fluoro-1-(2-fluoro-phenyl)-4-oxo-1,4-dihydro-quinolin-3-yl-methyl]-nicotinamide (Example I-105) and an appropriate amine.

Example I-107

6-(1,1-Dioxo-1-thiomorpholin-4-yl)-N-[7-fluoro-1-(2-fluoro-phenyl)-4-oxo-1,4-dihydro-quinolin-3-ylmethyl]-nicotinamide

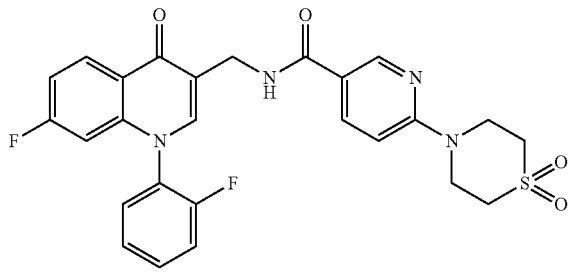 [SMILES: O=C(NCc1cn(-c2ccccc2F)c2cc(F)ccc2c1=O)c1ccc(N2CCS(=O)(=O)CC2)nc1]

6-(1,1-Dioxo-1-thiomorpholin-4-yl)-N-[7-fluoro-1-(2-fluoro-phenyl)-4-oxo-1,4-dihydro-quinolin-3-ylmethyl]-nicotinamide was prepared starting from 6-chloro-N-[7-fluoro-1-(2-fluoro-phenyl)-4-oxo-1,4-dihydro-quinolin-3-yl-methyl]-nicotinamide (example I-105) and thiomorpholine-1,1-dioxide. MS calcd. for $C_{26}H_{22}F_2N_4O_4S$ [(M+H)$^+$] 525.1, obsd. 525.2.

Example I-108

N-[7-Fluoro-1-(2-fluoro-phenyl)-4-oxo-1,4-dihydro-quinolin-3-ylmethyl]-6-morpholin-4-yl-nicotinamide

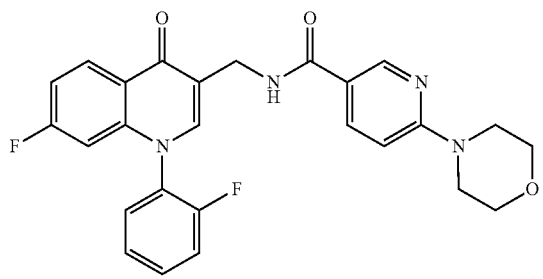 [SMILES: O=C(NCc1cn(-c2ccccc2F)c2cc(F)ccc2c1=O)c1ccc(N2CCOCC2)nc1]

N-[7-Fluoro-1-(2-fluoro-phenyl)-4-oxo-1,4-dihydro-quinolin-3-ylmethyl]-6-morpholin-4-yl-nicotinamide was prepared starting from 6-chloro-N-[7-fluoro-1-(2-fluoro-phenyl)-4-oxo-1,4-dihydro-quinolin-3-yl-methyl]-nicotinamide (Example I-105) and morpholine. $^1$H MS calcd. for $C_{26}H_{22}F_2N_4O_3$ [(M+H)$^+$] 477.2, obsd. 477.0.

Example I-109

1-Phenyl-1H-pyrazole-4-carboxylic acid [7-fluoro-1-(2-fluoro-phenyl)-4-oxo-1,4-dihydro-quinolin-3-ylmethyl]-amide

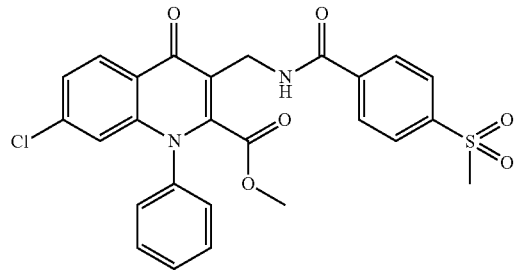 [SMILES: COC(=O)c1c(CNC(=O)c2ccc(S(C)(=O)=O)cc2)c(=O)c2ccc(Cl)cc2n1-c1ccccc1]

A mixture of 4-(methanesulfonyl)benzoic acid (50.2 mg, 0.251 mmol), bromo-tris-pyrrolidino-phosphonium hexafluorophosphate (PyBrOP) (140 mg, 0.301 mmol) N,N-diisopropylethylamine (162 mg, 1.25 mmol) and $CH_2Cl_2$ (10 mL) was stirred at room temperature for 5 min. After this time, 3-aminomethyl-7-chloro-4-oxo-1-phenyl-1,4-dihydro-quinoline-2-carboxylic acid methyl ester hydrochloride (intermediate I) (95 mg, 0.251 mmol) was added. The reaction mixture was stirred at room temperature for 3 hr. The reaction mixture was concentrated and purified by preparative reverse-phase HPLC, providing 7-chloro-3-[(4-methane-sulfonyl-benzoylamino)-methyl]-4-oxo-1-phenyl-1,4-dihydroquin-oline-2-carboxylic acid methyl ester. MS calcd. for $C_{26}H_{22}ClN_2O_6S$ [(M+H)$^+$] 525.1, obsd. 525.0.

Example I-110 to I-123

The following examples I-110 to I-123 were prepared in an analogous manner to example I-109, starting with intermediate I and an appropriate carboxylic acid.

Example I-110

7-Chloro-3-[(4-oxazol-5-yl-benzoylamino)-methyl]-4-oxo-1-phenyl-1,4-dihydro-quinoline-2-carboxylic acid methyl ester

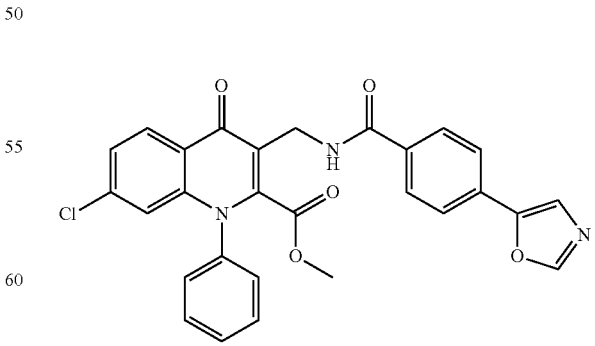

7-Chloro-3-[(4-oxazol-5-yl-benzoylamino)-methyl]-4-oxo-1-phenyl-1,4-dihydro-quinoline-2-carboxylic acid methyl ester was prepared starting from intermediate 1 and 4-oxazol-5-yl-benzoic acid. MS calcd. for $C_{28}H_{21}ClN_3O_5$ [(M+H)$^+$] 514.1, obsd. 514.0.

Example I-111

7-Chloro-4-oxo-1-phenyl-3-{[4-(4H-[1,2,4]triazol-3-yl)-benzoylamino]-methyl}-1,4-dihydro-quinoline-2-carboxylic acid methyl ester

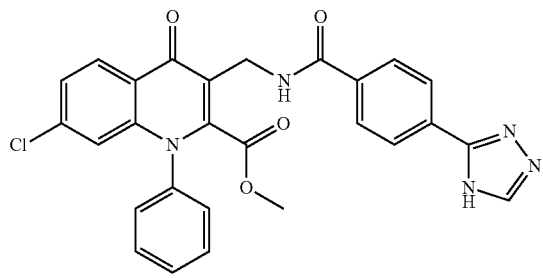 [SMILES: COC(=O)c1c(CNC(=O)c2ccc(-c3nnc[nH]3)cc2)c(=O)c2ccc(Cl)cc2n1-c1ccccc1]

7-Chloro-4-oxo-1-phenyl-3-{[4-(4H-[1,2,4]triazol-3-yl)-benzoylamino]-methyl}-1,4-di-hydro-quinoline-2-carboxylic acid methyl ester was prepared starting from intermediate 1 and 4-(4H-[1,2,4]triazol-3-yl)-benzoic acid. MS calcd. for $C_{27}H_{21}ClN_5O_4$ [(M+H)$^+$] 514.1, obsd. 514.0.

Example I-112

7-Chloro-3-{[(6-morpholin-4-yl-pyridine-3-carbonyl)-amino]-methyl}-4-oxo-1-phenyl-1,4-dihydro-quinoline-2-carboxylic acid methyl ester

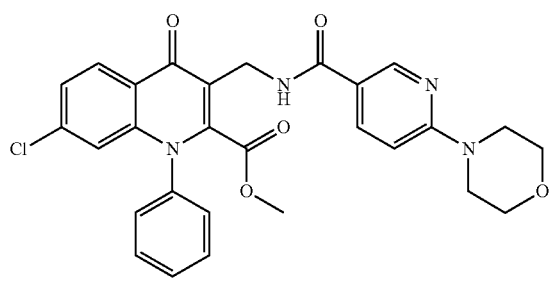 [SMILES: COC(=O)c1c(CNC(=O)c2ccc(N3CCOCC3)nc2)c(=O)c2ccc(Cl)cc2n1-c1ccccc1]

7-Chloro-3-{[(6-morpholin-4-yl-pyridine-3-carbonyl)-amino]-methyl}-4-oxo-1-phenyl-1,4-dihydro-quinoline-2-carboxylic acid methyl ester was prepared starting from intermediate 1 and 6-morpholin-4-yl-pyridine-3-carboxylic acid. MS calcd. for $C_{28}H_{26}ClN_4O_5$ [(M+H)$^+$] 533.2, obsd. 533.0.

Example I-113

3-{[(Benzothiazole-5-carbonyl)-amino]-methyl}-7-chloro-4-oxo-1-phenyl-1,4-dihydro-quinoline-2-carboxylic acid methyl ester

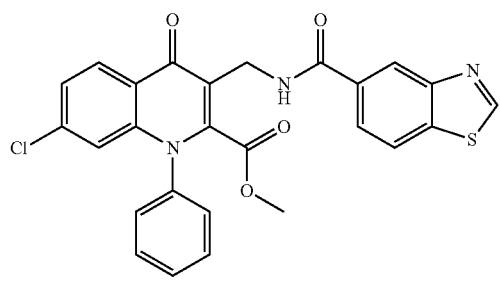 [SMILES: COC(=O)c1c(CNC(=O)c2ccc3scnc3c2)c(=O)c2ccc(Cl)cc2n1-c1ccccc1]

3-{[(Benzothiazole-5-carbonyl)-amino]-methyl}-7-chloro-4-oxo-1-phenyl-1,4-dihydro-quinoline-2-carboxylic acid methyl ester was prepared starting from intermediate I and benzothiazole-5-carboxylic acid. MS calcd. for $C_{26}H_{19}ClN_3O_4S$ [(M+H)$^+$] 504.1, obsd. 503.9.

Example I-114

7-Chloro-3-{[4-(1H-imidazol-2-yl)-benzoylamino]-methyl}-4-oxo-1-phenyl-1,4-dihydro-quinoline-2-carboxylic acid methyl ester

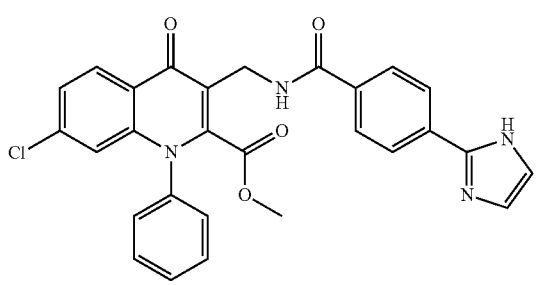 [SMILES: COC(=O)c1c(CNC(=O)c2ccc(-c3ncc[nH]3)cc2)c(=O)c2ccc(Cl)cc2n1-c1ccccc1]

7-Chloro-3-{[4-(1H-imidazol-2-yl)-benzoylamino]-methyl}-4-oxo-1-phenyl-1,4-dihydro-quinoline-2-carboxylic acid methyl ester was prepared starting from intermediate 1 and 4-(1H-imidazol-2-yl)-benzoic acid. MS calcd. for $C_{28}H_{22}ClN_4O_4$ [(M+H)$^+$] 513.1, obsd. 513.0.

Example I-115

7-Chloro-4-oxo-1-phenyl-3-[(4-sulfamoyl-benzoylamino)-methyl]-1,4-dihydro-quinoline-2-carboxylic acid methyl ester

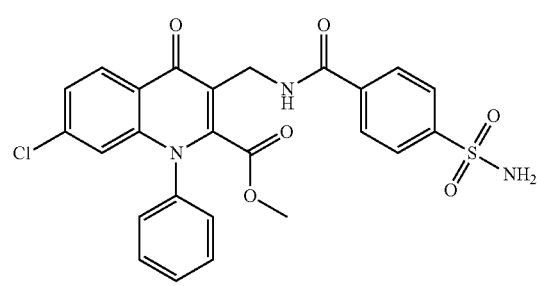 [SMILES: COC(=O)c1c(CNC(=O)c2ccc(S(N)(=O)=O)cc2)c(=O)c2ccc(Cl)cc2n1-c1ccccc1]

Chloro-4-oxo-1-phenyl-3-[(4-sulfamoyl-benzoylamino)-methyl]-1,4-dihydro-quinoline-2-carboxylic acid methyl ester was prepared starting from intermediate 1 and 4-sulfamoyl-benzoic acid. MS calcd. for $C_{25}H_{21}ClN_3O_6S$ [(M+H)$^+$] 526.1, obsd. 526.0.

Example I-116

Chloro-3-{[(2-morpholin-4-yl-thiazole-5-carbonyl)-amino]-methyl}-4-oxo-1-phenyl-1,4-dihydro-quinoline-2-carboxylic acid methyl ester

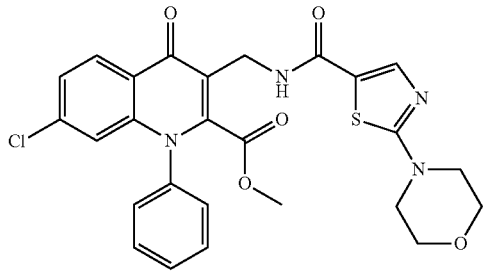 [SMILES: COC(=O)c1c(CNC(=O)c2cnc(N3CCOCC3)s2)c(=O)c2ccc(Cl)cc2n1-c1ccccc1]

Chloro-3-{[(2-morpholin-4-yl-thiazole-5-carbonyl)-amino]-methyl}-4-oxo-1-phenyl-1,4-dihydro-quinoline-2-carboxylic acid methyl ester was prepared starting from intermediate 1 and 2-morpholin-4-yl-thiazole-5-carboxylic acid. $^1$H NMR (400 MHz, DMSO-$d_6$) δ ppm 8.36 (t, J=4.94 Hz, 1H) 8.28 (d, J=8.66 Hz, 1H) 7.83 (s, 1H) 7.62-7.70 (m, 3H) 7.51 (dd, J=6.04, 2.42 Hz, 3H) 6.72 (d, J=1.81 Hz, 1H) 4.35 (d, J=4.83 Hz, 2H) 3.64-3.71 (m, 4H) 3.39-3.44 (m, 4H) 3.37 (s, 3H). MS calcd. for $C_{26}H_{23}ClN_4O_5S$ [(M+H)$^+$] 539.1, obsd. 539.1

Example I-117

3-[(4-Carbamoyl-benzoylamino)-methyl]-7-chloro-4-oxo-1-phenyl-1,4-dihydro-quinoline-2-carboxylic acid methyl ester

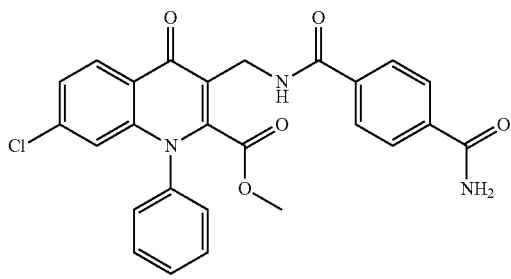 [SMILES: COC(=O)c1c(CNC(=O)c2ccc(C(N)=O)cc2)c(=O)c2ccc(Cl)cc2n1-c1ccccc1]

3-[(4-Carbamoyl-benzoylamino)-methyl]-7-chloro-4-oxo-1-phenyl-1,4-dihydroquinoline-2-carboxylic acid methyl ester was prepared starting from intermediate 1 and 4-(aminocarbonyl)benzoic acid. MS calcd. for $C_{26}H_{21}ClN_3O_5$ [(M+H)$^+$] 490.1, obsd. 490.0.

Example I-118

7-Chloro-3-[(4-methylcarbamoyl-benzoylamino)-methyl]-4-oxo-1-phenyl-1,4-dihydro-quinoline-2-carboxylic acid methyl ester

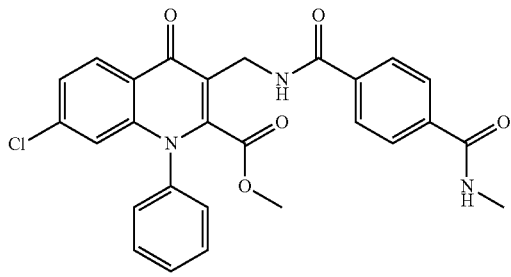 [SMILES: CNC(=O)c1ccc(C(=O)NCc2c(C(=O)OC)n(-c3ccccc3)c3cc(Cl)ccc3c2=O)cc1]

7-Chloro-3-[(4-methylcarbamoyl-benzoylamino)-methyl]-4-oxo-1-phenyl-1,4-dihydro-quinoline-2-carboxylic acid methyl ester was prepared starting from intermediate 1 and 4-methylcarbamoyl-benzoic acid. MS calcd. for $C_{27}H_{23}ClN_3O_5$ [(M+H)$^+$] 504.1, obsd. 504.0.

Example I-119

3-{[(1-Benzyl-1H-pyrazole-4-carbonyl)-amino]-methyl}-7-chloro-4-oxo-1-phenyl-1,4-dihydro-quinoline-2-carboxylic acid methyl ester

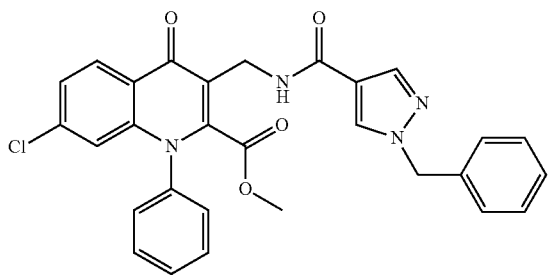 [SMILES: COC(=O)c1c(CNC(=O)c2cnn(Cc3ccccc3)c2)c(=O)c2ccc(Cl)cc2n1-c1ccccc1]

3-{[(1-Benzyl-1H-pyrazole-4-carbonyl)-amino]-methyl}-7-chloro-4-oxo-1-phenyl-1,4-dihydro-quinoline-2-carboxylic acid methyl ester was prepared starting from intermediate 1 and 1-benzyl-1H-pyrazole-4-carboxylic acid. $^1$H NMR (400 MHz, DMSO-$d_6$) δ ppm 8.28 (d, J=8.66 Hz, 1H) 8.23 (s, 1H) 8.14 (t, J=4.94 Hz, 1H) 7.85 (s, 1H) 7.61-7.67 (m, 3H) 7.46-7.54 (m, 3H) 7.27-7.37 (m, 3H) 7.22 (d, J=6.65 Hz, 2H) 6.71 (d, J=1.81 Hz, 1H) 5.31 (s, 2H) 4.34 (d, J=5.04 Hz, 2H) 3.34 (s, 3H). MS calcd. for $C_{29}H_{23}ClN_4O_4$ [(M+H)$^+$] 527.1, obsd. 527.0.

Example I-120

7-Chloro-3-{[(1H-indole-6-carbonyl)-amino]-methyl}-4-oxo-1-phenyl-1,4-dihydro-quinoline-2-carboxylic acid methyl ester

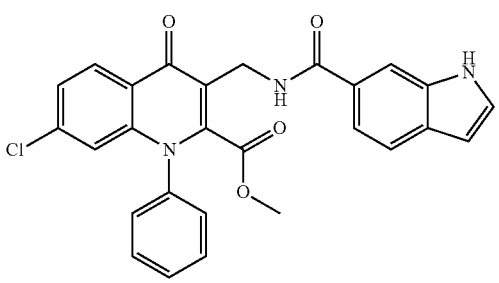 [SMILES: COC(=O)c1c(CNC(=O)c2ccc3cc[nH]c3c2)c(=O)c2ccc(Cl)cc2n1-c1ccccc1]

7-Chloro-3-{[(1H-indole-6-carbonyl)-amino]-methyl}-4-oxo-1-phenyl-1,4-dihydro-quin-oline-2-carboxylic acid methyl ester was prepared starting from intermediate 1 and 1H-indole-6-carboxylic acid. MS calcd. for $C_{27}H_{21}ClN_3O_4$ [(M+H)$^+$] 486.1, obsd. 485.9.

Example I-121

7-Chloro-3-{[(1-methyl-1H-pyrazole-4-carbonyl)-amino]-methyl}-4-oxo-1-phenyl-1,4-dihydro-quinoline-2-carboxylic acid methyl ester

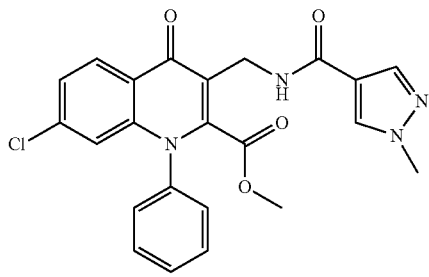

7-Chloro-3-{[(1-methyl-1H-pyrazole-4-carbonyl)-amino]-methyl}-4-oxo-1-phenyl-1,4-dihydro-quinoline-2-carboxylic acid methyl ester was prepared starting from intermediate 1 and 1-methyl-1H-pyrazole-4-carboxylic acid. $^1$H NMR (400 MHz, DMSO-d$_6$) δ ppm 8.29 (d, J=8.66 Hz, 1H) 8.10 (s, 2H) 7.80 (s, 1H) 7.61-7.69 (m, 3H) 7.51 (dt, J=6.50, 1.79 Hz, 3H) 6.72 (d, J=1.81 Hz, 1H) 4.35 (d, J=5.04 Hz, 2H) 3.81 (s, 3H) 3.36 (s, 3H) MS calcd. for $C_{23}H_{19}ClN_4O_4$ [(M+H)$^+$] 451.1, obsd. 451.0.

Example I-122

7-Chloro-4-oxo-1-phenyl-3-{[4-(1H-pyrazol-3-yl)-benzoylamino]-methyl}-1,4-dihydro-quinoline-2-carboxylic acid methyl ester

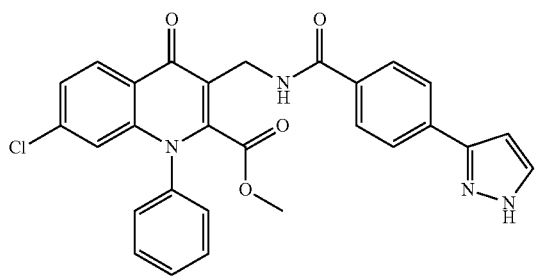 [SMILES: COC(=O)c1c(CNC(=O)c2ccc(-c3cc[nH]n3)cc2)c(=O)c2ccc(Cl)cc2n1-c1ccccc1]

7-Chloro-4-oxo-1-phenyl-3-{[4-(1H-pyrazol-3-yl)-benzoylamino]-methyl}-1,4-dihydro-quinoline-2-carboxylic acid methyl ester was prepared starting from intermediate 1 and 4-(1H-pyrazol-3-yl)-benzoic acid. MS calcd. for $C_{28}H_{22}ClN_4O_4$ [(M+H)$^+$] 513.1, obsd. 513.0.

Example I-123

7-Chloro-3-[(4-morpholin-4-yl-benzoylamino)-methyl]-4-oxo-1-phenyl-1,4-dihydro-quinoline-2-carboxylic acid methyl ester

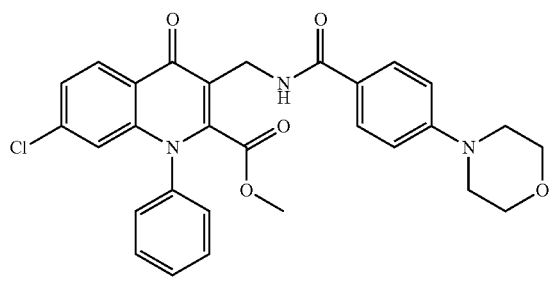

7-Chloro-3-[(4-morpholin-4-yl-benzoylamino)-methyl]-4-oxo-1-phenyl-1,4-dihydro-quinoline-2-carboxylic acid methyl ester was prepared starting from intermediate 1 and 4-morpholin-4-yl-benzoic acid. MS calcd. for $C_{29}H_{27}ClN_3O_5$ [(M+H)$^+$] 532.2, obsd. 532.0.

Example I-124

7-Chloro-4-oxo-1-phenyl-3-[(4-[1,2,3]thiadiazol-5-yl-benzoylamino)-methyl]-1,4-dihydro-quinoline-2-carboxylic acid methyl ester

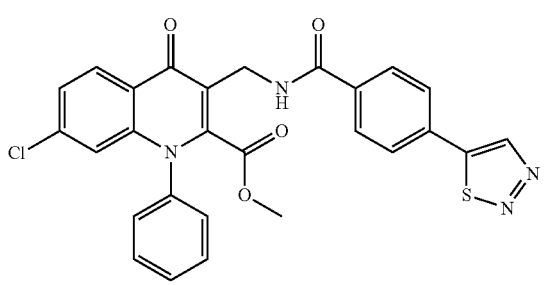 [SMILES: COC(=O)c1c(CNC(=O)c2ccc(-c3cnns3)cc2)c(=O)c2ccc(Cl)cc2n1-c1ccccc1]

7-Chloro-4-oxo-1-phenyl-3-[(4-[1,2,3]thiadiazol-5-yl-benzoylamino)-methyl]-1,4-di-hydro-quinoline-2-carboxylic acid methyl ester was prepared starting from intermediate 1 and 4-[1,2,3]thiadiazol-5-yl-benzoic acid. MS calcd. for $C_{27}H_{20}ClN_4O_4S$ [(M+H)$^+$] 531.1, obsd. 530.9.

Example I-125

7-Chloro-3-{[4-(5-methyl-[1,2,4]oxadiazol-3-yl)-benzoylamino]-methyl}-4-oxo-1-phenyl-1,4-dihydro-quinoline-2-carboxylic acid methyl ester

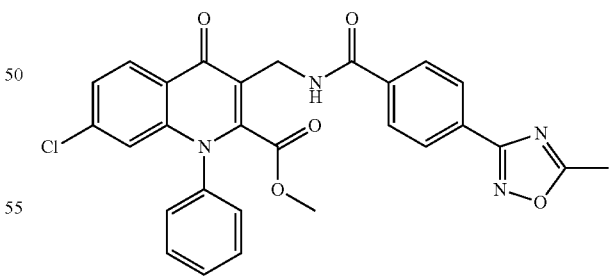

7-Chloro-3-{[4-(5-methyl-[1,2,4]oxadiazol-3-yl)-benzoylamino]-methyl}-4-oxo-1-phenyl-1,4-dihydro-quinoline-2-carboxylic acid methyl ester was prepared starting from intermediate 1 and 4-(5-methyl-[1,2,4]oxadiazol-3-yl)-benzoic acid. MS calcd. for $C_{28}H_{22}ClN_4O_5$ [(M+H)$^+$] 529.1, obsd. 529.0.

Example I-126

7-Chloro-3-{[4-(3-methyl-[1,2,4]oxadiazol-5-yl)-benzoylamino]-methyl}-4-oxo-1-phenyl-1,4-dihydro-quinoline-2-carboxylic acid methyl ester

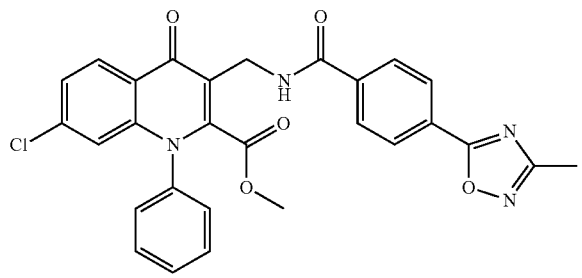 [SMILES: COC(=O)c1c(CNC(=O)c2ccc(-c3nc(C)no3)cc2)c(=O)c2ccc(Cl)cc2n1-c1ccccc1]

7-Chloro-3-{[4-(3-methyl-[1,2,4]oxadiazol-5-yl)-benzoylamino]-methyl}-4-oxo-1-phen-yl-1,4-dihydro-quinoline-2-carboxylic acid methyl ester was prepared starting from intermediate 1 and 4-(3-methyl-[1,2,4]oxadiazol-5-yl)-benzoic acid. MS calcd. for $C_{28}H_{22}ClN_4O_5$ [(M+H)$^+$] 529.1, obsd. 529.0.

Example I-127

7-Chloro-3-{[4-(2-methyl-thiazol-4-yl)-benzoylamino]-methyl}-4-oxo-1-phenyl-1,4-dihydro-quinoline-2-carboxylic acid methyl ester

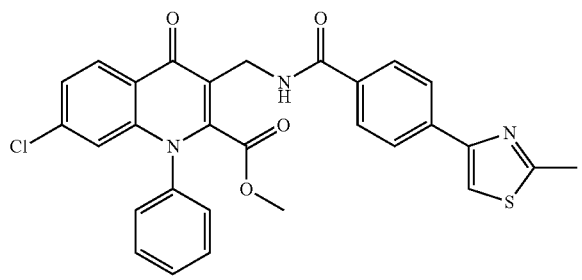 [SMILES: COC(=O)c1c(CNC(=O)c2ccc(-c3csc(C)n3)cc2)c(=O)c2ccc(Cl)cc2n1-c1ccccc1]

7-Chloro-3-{[4-(2-methyl-thiazol-4-yl)-benzoylamino]-methyl}-4-oxo-1-phenyl-1,4-dihydro-quinoline-2-carboxylic acid methyl ester was prepared starting from intermediate 1 and 4-(2-methyl-thiazol-4-yl)-benzoic acid. MS calcd. for $C_{29}H_{23}ClN_3O_4S$ [(M+H)$^+$] 544.1, obsd. 544.0.

Example I-128

3-{[(1-tert-Butoxycarbonyl-piperidine-4-carbonyl)-amino]-methyl}-7-chloro-4-oxo-1-phenyl-1,4-dihydro-quinoline-2-carboxylic acid methyl ester

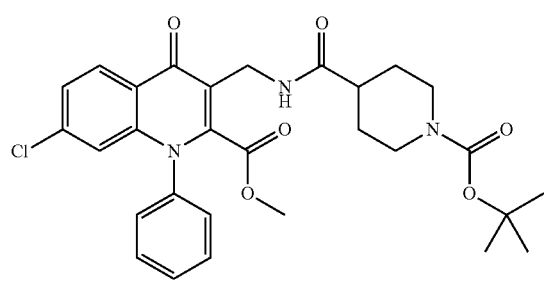 [SMILES: COC(=O)c1c(CNC(=O)C2CCN(C(=O)OC(C)(C)C)CC2)c(=O)c2ccc(Cl)cc2n1-c1ccccc1]

3-{[(1-tert-butoxycarbonyl-piperidine-4-carbonyl)-amino]-methyl}-7-chloro-4-oxo-1-phenyl-1,4-dihydro-quinoline-2-carboxylic acid methyl ester was prepared starting from intermediate 1 and 1-tert-butoxycarbonyl-piperidine-4-carboxylic acid. MS calcd. for $C_{29}H_{33}ClN_3O_6$ [(M+H)$^+$] 554.2, obsd. 554.1.

Example I-129

7-Chloro-3-{[4-(2-methyl-2H-tetrazol-5-yl)-benzoylamino]-methyl}-4-oxo-1-phenyl-1,4-dihydro-quinoline-2-carboxylic acid methyl ester

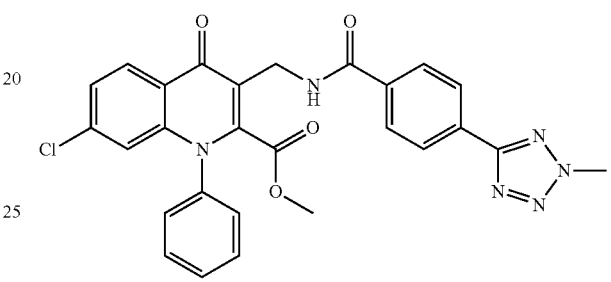

7-Chloro-3-{[4-(2-methyl-2H-tetrazol-5-yl)-benzoylamino]-methyl}-4-oxo-1-phenyl-1,4-dihydro-quinoline-2-carboxylic acid methyl ester was prepared starting from intermediate 1 and 4-(1-methyl-1H-tetrazol-5-yl)-benzoic acid. $^1$H NMR (400 MHz, DMSO-d$_6$) δ ppm 8.69 (t, J=4.90 Hz, 1H) 8.30 (d, J=8.66 Hz, 1H) 8.10 (d, J=8.66 Hz, 2H) 7.98 (d, J=8.66 Hz, 2H) 7.63-7.68 (m, 3H) 7.46-7.55 (m, 3H) 6.73 (d, J=2.01 Hz, 1H) 4.45 (d, J=4.90 Hz, 2H) 4.44 (s, 3 H) 3.37 (s, 3H). MS calcd. for $C_{27}H_{21}ClN_6O_4$ [(M+H)$^+$] 529.1, obsd. 529.1.

Example I-130

3-{[(1-Acetyl-piperidine-4-carbonyl)-amino]-methyl}-7-chloro-4-oxo-1-phenyl-1,4-dihydro-quinoline-2-carboxylic acid methyl ester

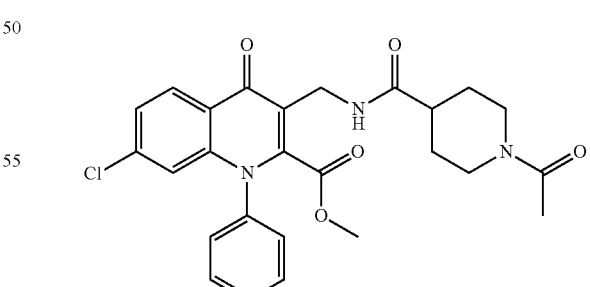

3-{[(1-Acetyl-piperidine-4-carbonyl)-amino]-methyl}-7-chloro-4-oxo-1-phenyl-1,4-dihydro-quinoline-2-carboxylic acid methyl ester was prepared starting from intermediate 1 and 1-acetyl-piperidine-4-carboxylic acid. MS calcd. for $C_{26}H_{27}ClN_3O_5$ [(M+H)$^+$] 496.2, obsd. 496.0.

Example I-131

7-Chloro-3-{[(1-methanesulfonyl-piperidine-4-carbonyl)-amino]-methyl}-4-oxo-1-phenyl-1,4-dihydroquinoline-2-carboxylic acid methyl ester

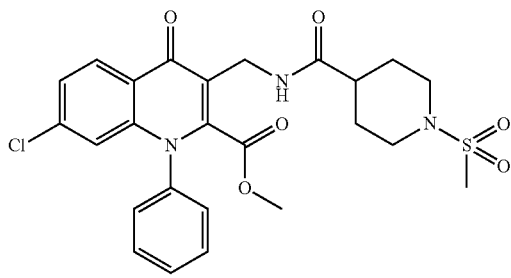 [SMILES: COC(=O)c1c(CNC(=O)C2CCN(S(C)(=O)=O)CC2)c(=O)c2ccc(Cl)cc2n1-c1ccccc1]

7-Chloro-3-{[(1-methanesulfonyl-piperidine-4-carbonyl)-amino]-methyl}-4-oxo-1-phenyl-1,4-dihydroquinoline-2-carboxylic acid methyl ester was prepared starting from intermediate 1 and 1-methanesulfonyl-piperidine-4-carboxylic acid. MS calcd. for $C_{25}H_{27}ClN_3O_6S$ $[(M+H)^+]$ 532.1, obsd. 532.0.

Example I-132

7-Chloro-3-[(4-chloro-benzoylamino)-methyl]-4-oxo-1-phenyl-1,4-dihydro-quinoline-2-carboxylic acid methyl ester

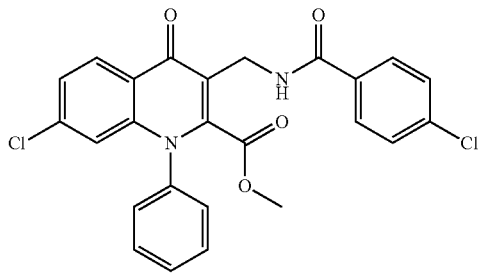 [SMILES: COC(=O)c1c(CNC(=O)c2ccc(Cl)cc2)c(=O)c2ccc(Cl)cc2n1-c1ccccc1]

In a 50 mL round-bottomed flask, 3-aminomethyl-7-chloro-4-oxo-1-phenyl-1,4-dihydro-quinoline-2-carboxylic acid methyl ester hydrochloride (intermediate I) (0.30 g, 0.791 mmol) and 4-chlorobenzoyl chloride (138 mg, 0.791 mmol) were added at 0° C. to 15 mL $CH_2Cl_2$. The reaction was stirred at 0° C. for 5 min. and then N,N-diisopropylethylamine (511 mg, 3.96 mmol) was added. The reaction mixture was stirred at 0° C. for 1 hr. The mixture was concentrated to dryness and then purified by flash chromatography using 40% ethyl acetate-hexanes. The desired product 7-chloro-3-[(4-chloro-benzoylamino)-methyl]-4-oxo-1-phenyl-1,4-dihydro-quinoline-2-carboxylic acid methyl ester (171 mg, 45%) was obtained as a white solid.

Examples I-133 to I-150

The following examples I-133 to I-150 were prepared in an analogous manner to example I-132, starting with intermediate I and an appropriate acid chloride.

Example I-133

7-Chloro-3-[(4-methoxycarbonyl-benzoylamino)-methyl]-4-oxo-1-phenyl-1,4-dihydro-quinoline-2-carboxylic acid methyl ester

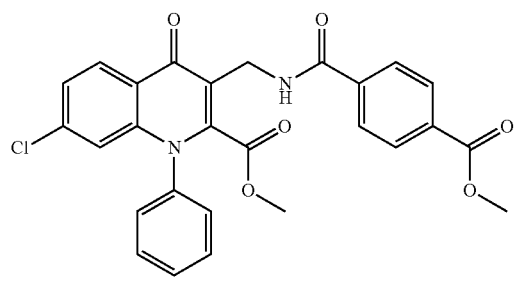 [SMILES: COC(=O)c1ccc(C(=O)NCc2c(C(=O)OC)n(-c3ccccc3)c3cc(Cl)ccc3c2=O)cc1]

7-Chloro-3-[(4-methoxycarbonyl-benzoylamino)-methyl]-4-oxo-1-phenyl-1,4-dihydro-quinoline-2-carboxylic acid methyl ester was prepared starting from intermediate 1 and 4-(methoxy)benzoyl chloride. MS calcd. for $C_{27}H_{22}ClN_2O_6$ $[(M+H)^+]$ 505.1, obsd. 504.9.

Example I-134

7-Chloro-3-[(4-methoxybenzoylamino)-methyl]-4-oxo-1-phenyl-1,4-dihydro-quinoline-2-carboxylic acid methyl ester

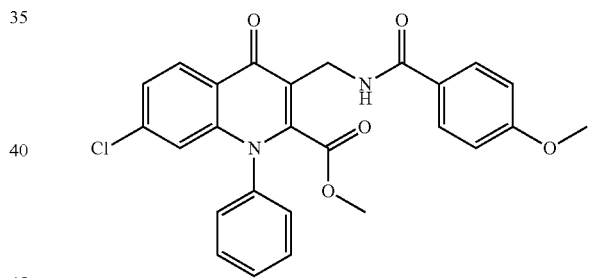

7-Chloro-3-[4-(methoxybenzoylamino)-methyl]-4-oxo-1-phenyl-1,4-dihydro-quinoline-2-carboxylic acid methyl ester was prepared starting from intermediate 1 and 4-(methoxy)benzoyl chloride. MS calcd. for $C_{26}H_{22}ClN_2O_5$ $[(M+H)^+]$ 477.1, obsd. 477.0.

Example I-135

7-Chloro-3-[(3-methoxybenzoylamino)-methyl]-4-oxo-1-phenyl-1,4-dihydro-quinoline-2-carboxylic acid methyl ester

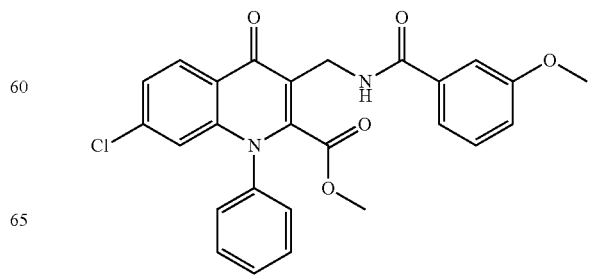

7-Chloro-3-[3-(methoxybenzoylamino)-methyl]-4-oxo-1-phenyl-1,4-dihydro-quinoline-2-carboxylic acid methyl ester was prepared starting from intermediate 1 and 3-(methoxy)benzoyl chloride. MS calcd. for $C_{26}H_{22}ClN_2O_5$ [(M+H)$^+$] 477.1, obsd. 477.0.

Example I-136

7-Chloro-4-oxo-1-phenyl-3-{[(pyridine-4-carbonyl)-amino]-methyl}-1,4-di-hydro-quinoline-2-carboxylic acid methyl ester

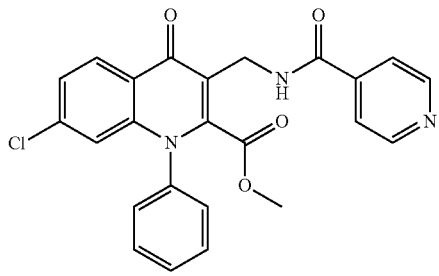 [SMILES: COC(=O)c1c(CNC(=O)c2ccncc2)c(=O)c2ccc(Cl)cc2n1-c1ccccc1]

7-Chloro-4-oxo-1-phenyl-3-{[(pyridine-4-carbonyl)-amino]-methyl}-1,4-dihydro-quinoline-2-carboxylic acid methyl ester was prepared starting from intermediate I and isonicotinoyl chloride. MS calcd. for $C_{24}H_{19}ClN_3O_4$ [(M+H)$^+$] 448.1, obsd. 447.9.

Example I-137

7-Chloro-3-[(3,4-difluoro-benzoylamino)-methyl]-4-oxo-1-phenyl-1,4-dihydro-quinoline-2-carboxylic acid methyl ester

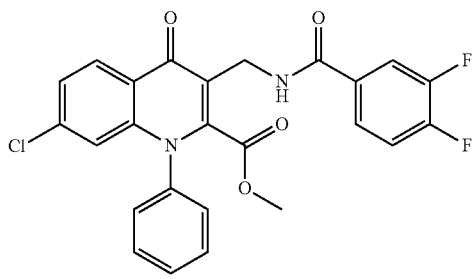 [SMILES: COC(=O)c1c(CNC(=O)c2ccc(F)c(F)c2)c(=O)c2ccc(Cl)cc2n1-c1ccccc1]

7-Chloro-3-[(3,4-difluoro-benzoylamino)-methyl]-4-oxo-1-phenyl-1,4-dihydro-quinoline-2-carboxylic acid methyl ester was prepared starting from intermediate 1 and 3,4-difluorobenzoyl chloride. MS calcd. for $C_{25}H_{18}ClF_2N_2O_4$ [(M+H)$^+$] 483.1, obsd. 482.9.

Example I-138

7-Chloro-3-[(3-fluoro-benzoylamino)-methyl]-4-oxo-1-phenyl-1,4-dihydro-quinoline-2-carboxylic acid methyl ester

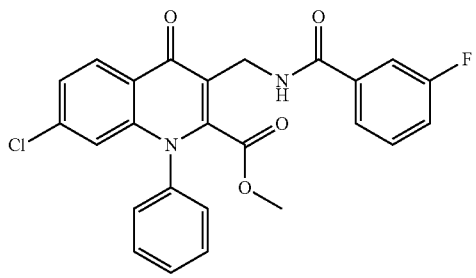 [SMILES: COC(=O)c1c(CNC(=O)c2cccc(F)c2)c(=O)c2ccc(Cl)cc2n1-c1ccccc1]

7-Chloro-3-[(3-fluoro-benzoylamino)-methyl]-4-oxo-1-phenyl-1,4-dihydro-quinoline-2-carboxylic acid methyl ester was prepared starting from intermediate 1 and 3-fluorobenzoyl chloride. MS calcd. for $C_{25}H_{19}ClFN_2O_4$ [(M+H)$^+$] 465.1, obsd. 464.9.

Example I-139

7-Chloro-4-oxo-1-phenyl-3-{[(pyridine-3-carbonyl)-amino]-methyl}-1,4-dihydro-quinoline-2-carboxylic acid methyl ester

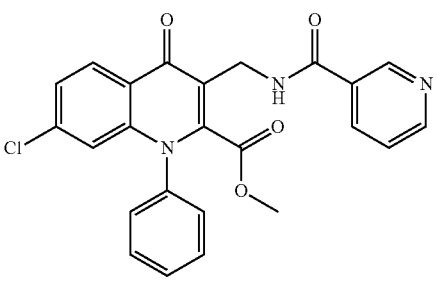 [SMILES: COC(=O)c1c(CNC(=O)c2cccnc2)c(=O)c2ccc(Cl)cc2n1-c1ccccc1]

7-Chloro-4-oxo-1-phenyl-3-{[(pyridine-3-carbonyl)-amino]-methyl}-1,4-dihydro-quinoline-2-carboxylic acid methyl ester was prepared starting from intermediate I and nicotinoyl chloride. MS calcd. for $C_{24}H_{19}ClN_3O_4$ [(M+H)$^+$] 448.1, obsd. 447.9.

Example I-140

7-Chloro-3-[(4-fluoro-benzoylamino)-methyl]-4-oxo-1-phenyl-1,4-dihydro-quinoline-2-carboxylic acid methyl ester

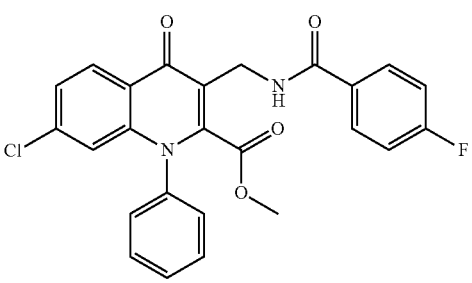 [SMILES: COC(=O)c1c(CNC(=O)c2ccc(F)cc2)c(=O)c2ccc(Cl)cc2n1-c1ccccc1]

7-Chloro-3-[(4-fluoro-benzoylamino)-methyl]-4-oxo-1-phenyl-1,4-dihydro-quinoline-2-carboxylic acid methyl ester was prepared starting from intermediate 1 and 4-fluorobenzoyl chloride. MS calcd. for $C_{25}H_{19}ClFN_2O_4$ [(M+H)$^+$] 465.1, obsd. 464.9.

Example I-141

7-Chloro-3-[(3-chloro-4-fluoro-benzoylamino)-methyl]-4-oxo-1-phenyl-1,4-dihydro-quinoline-2-carboxylic acid methyl ester

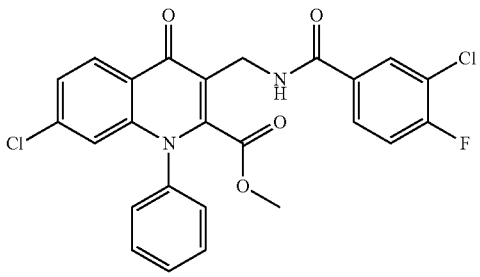 [SMILES: COC(=O)c1c(CNC(=O)c2ccc(F)c(Cl)c2)c(=O)c2ccc(Cl)cc2n1-c1ccccc1]

7-Chloro-3-[(3-chloro-4-fluoro-benzoylamino)-methyl]-4-oxo-1-phenyl-1,4-dihydro-quinoline-2-carboxylic acid methyl ester was prepared starting from intermediate 1 and 3-chloro-4-fluorobenzoyl chloride. MS calcd. for $C_{25}H_{18}Cl_2FN_2O_4$ [(M+H)$^+$] 499.1, obsd. 498.9.

Example I-142

7-Chloro-3-[(3-chloro-benzoylamino)-methyl]-4-oxo-1-phenyl-1,4-dihydro-quinoline-2-carboxylic acid methyl ester

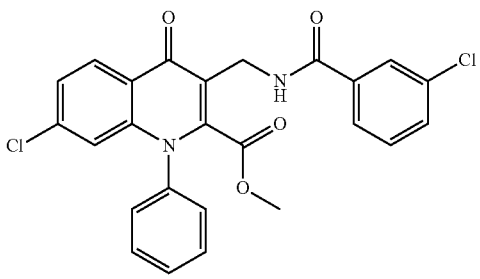 [SMILES: COC(=O)c1c(CNC(=O)c2cccc(Cl)c2)c(=O)c2ccc(Cl)cc2n1-c1ccccc1]

7-Chloro-3-[(3-chloro-benzoylamino)-methyl]-4-oxo-1-phenyl-1,4-dihydro-quinoline-2-carboxylic acid methyl ester was prepared starting from intermediate 1 and 3-chloro-benzoyl chloride. MS calcd. for $C_{25}H_{19}Cl_2N_2O_4$ [(M+H)$^+$] 481.1, obsd. 481.0.

Example I-143

7-Chloro-3-[(3,4-dimethoxy-benzoylamino)-methyl]-4-oxo-1-phenyl-1,4-dihydro-quinoline-2-carboxylic acid methyl ester

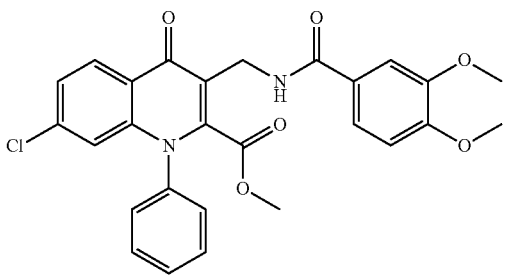 [SMILES: COC(=O)c1c(CNC(=O)c2ccc(OC)c(OC)c2)c(=O)c2ccc(Cl)cc2n1-c1ccccc1]

7-Chloro-3-[(3,4-dimethoxy-benzoylamino)-methyl]-4-oxo-1-phenyl-1,4-dihydro-quinoline-2-carboxylic acid methyl ester was prepared starting from intermediate 1 and 3,4-dimethoxybenzoyl chloride. MS calcd. for $C_{27}H_{24}ClN_2O_6$ [(M+H)$^+$] 507.1, obsd. 507.0.

Example I-144

7-Chloro-3-[(3,4-dichloro-benzoylamino)-methyl]-4-oxo-1-phenyl-1,4-dihydro-quinoline-2-carboxylic acid methyl ester

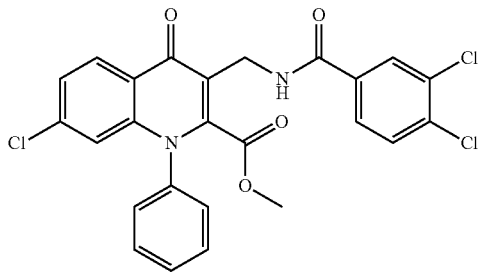 [SMILES: COC(=O)c1c(CNC(=O)c2ccc(Cl)c(Cl)c2)c(=O)c2ccc(Cl)cc2n1-c1ccccc1]

7-Chloro-3-[(3,4-dichloro-benzoylamino)-methyl]-4-oxo-1-phenyl-1,4-dihydro-quinoline-2-carboxylic acid methyl ester was prepared starting from intermediate 1 and 3,4-dichlorobenzoyl chloride. MS calcd. for $C_{25}H_{18}Cl_3N_2O_4$ [(M+H)$^+$] 515.0, obsd. 515.0.

Example I-145

7-Chloro-3-[(2-fluoro-benzoylamino)-methyl]-4-oxo-1-phenyl-1,4-dihydro-quinoline-2-carboxylic acid methyl ester

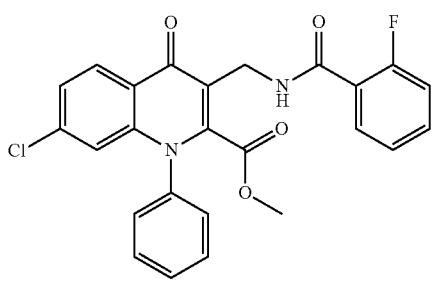

7-Chloro-3-[(2-fluoro-benzoylamino)-methyl]-4-oxo-1-phenyl-1,4-dihydro-quinoline-2-carboxylic acid methyl ester was prepared starting from intermediate 1 and 2-fluorobenzoyl chloride. MS calcd. for $C_{25}H_{19}ClFN_2O_4$ [(M+H)$^+$] 465.1, obsd. 464.9.

Example I-146

7-Chloro-4-oxo-1-phenyl-3-{[(pyridine-2-carbonyl)-amino]-methyl}-1,4-dihydro-quinoline-2-carboxylic acid methyl ester

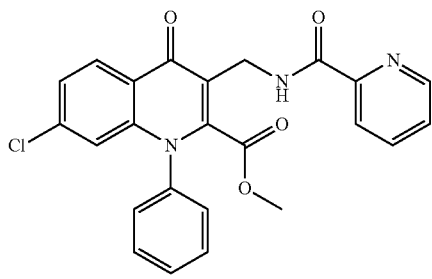 [SMILES: COC(=O)c1c(CNC(=O)c2ccccn2)c(=O)c2ccc(Cl)cc2n1-c1ccccc1]

7-Chloro-4-oxo-1-phenyl-3-{[(pyridine-2-carbonyl)-amino]-methyl}-1,4-dihydro-quino-line-2-carboxylic acid methyl ester was prepared starting from intermediate 1 and 2-pyridine carboxylic acid chloride. MS calcd. for $C_{24}H_{19}ClN_3O_4$ [(M+H)$^+$] 448.1, obsd. 447.9.

Example I-147

7-Chloro-3-(isobutyrylamino-methyl)-4-oxo-1-phenyl-1,4-dihydro-quinoline-2-carboxylic acid methyl ester

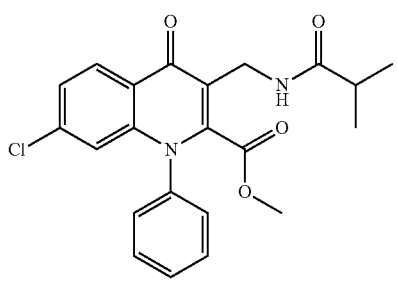 [SMILES: COC(=O)c1c(CNC(=O)C(C)C)c(=O)c2ccc(Cl)cc2n1-c1ccccc1]

7-Chloro-3-(isobutyrylamino-methyl)-4-oxo-1-phenyl-1,4-dihydro-quinoline-2-carboxylic acid methyl ester was prepared starting from intermediate I and isobutyryl chloride. MS calcd. for $C_{22}H_{22}ClN_2O_4$ [(M+H)$^+$] 413.1, obsd. 413.0.

Example I-148

7-Chloro-3-[(2-chloro-benzoylamino)-methyl]-4-oxo-1-phenyl-1,4-dihydro-quinoline-2-carboxylic acid methyl ester

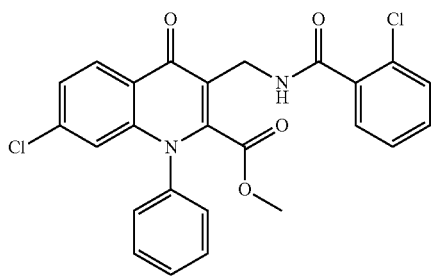

7-Chloro-3-[(2-chloro-benzoylamino)-methyl]-4-oxo-1-phenyl-1,4-dihydro-quinoline-2-carboxylic acid methyl ester was prepared starting from intermediate 1 and 2-chlorobenzoyl chloride. MS calcd. for $C_{25}H_{19}Cl_2N_2O_4$ [(M+H)$^+$] 481.1, obsd. 481.0.

Example I-149

7-Chloro-3-[(2-methoxy-benzoylamino)-methyl]-4-oxo-1-phenyl-1,4-dihydro-quinoline-2-carboxylic acid methyl ester

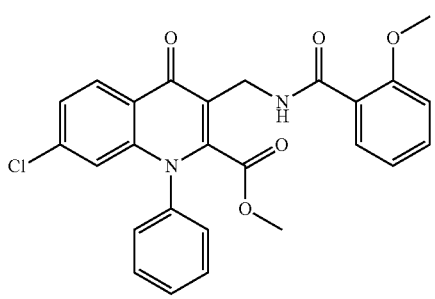 [SMILES: COC(=O)c1c(CNC(=O)c2ccccc2OC)c(=O)c2ccc(Cl)cc2n1-c1ccccc1]

7-Chloro-3-[(2-methoxy-benzoylamino)-methyl]-4-oxo-1-phenyl-1,4-dihydro-quinoline-2-carboxylic acid methyl ester was prepared starting from intermediate 1 and 2-methoxybenzoyl chloride. MS calcd. for $C_{26}H_{22}ClN_2O_5$ [(M+H)$^+$] 477.1, obsd. 477.0.

Example I-150

7-Chloro-3-[(benzoylamino)-methyl]-4-oxo-1-phenyl-1,4-dihydro-quinoline-2-carboxylic acid methyl ester

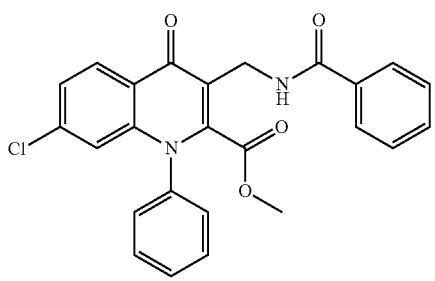 [SMILES: COC(=O)c1c(CNC(=O)c2ccccc2)c(=O)c2ccc(Cl)cc2n1-c1ccccc1]

7-Chloro-3-[(benzoylamino)-methyl]-4-oxo-1-phenyl-1,4-dihydro-quinoline-2-carboxylic acid methyl ester was prepared starting from intermediate I and benzoyl chloride. MS calcd. for $C_{25}H_{20}ClN_2O_4$ [(M+H)$^+$] 447.1, obsd. 446.9.

Example I-151

3-(Benzoylamino-methyl)-4-oxo-1-phenyl-1,4-dihydro-quinoline-2-carboxylic acid methyl ester

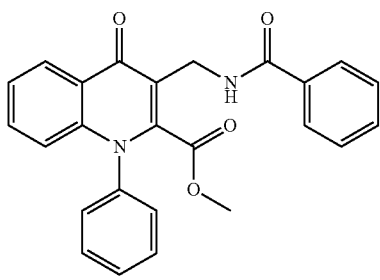 [SMILES: COC(=O)c1c(CNC(=O)c2ccccc2)c(=O)c2ccccc2n1-c1ccccc1]

3-(Benzoylamino-methyl)-4-oxo-1-phenyl-1,4-dihydro-quinoline-2-carboxylic acid methyl ester was prepared starting from an over-reduced batch of intermediate I and benzoyl chloride. MS calcd. for $C_{25}H_{21}N_2O_4$ [(M+H)$^+$] 413.1, obsd. 412.9

Example I-152

3-{[(6-Morpholin-4-yl-pyridine-3-carbonyl)-amino]-methyl}-4-oxo-1-phenyl-7-trifluoromethyl-1,4-dihydro-[1,8]naphthyridine-2-carboxylic acid methyl ester

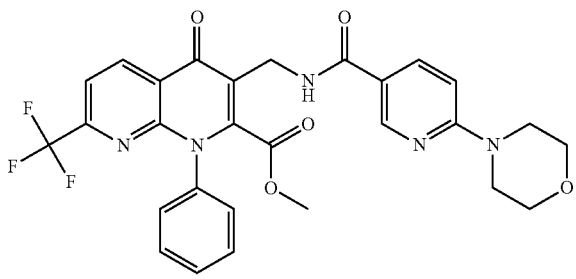 [SMILES: COC(=O)c1c(CNC(=O)c2ccc(N3CCOCC3)nc2)c(=O)c2ccc(C(F)(F)F)nc2n1-c1ccccc1]

A mixture of 6-morpholinenicotinic acid (20.1 mg, 0.097 mmol), bromo-tris-pyrrolidino-phosphonium hexafluorophosphate (PyBrOP) (54.2 mg, 0.116 mmol) and N,N-diisopropylethylamine (74.0 mg, 100 µL, 0.573 mmol) were combined with DMF (2 mL) to give a light yellow solution. The reaction mixture was stirred at room temperature for 45 min, cooled to 0° C. and methyl 3-(aminomethyl)-4-oxo-1-phenyl-7-(trifluoromethyl)-1,4-dihydro-1,8-naphthyridine-2-carboxylate hydrochloride (intermediate J) (40 mg, 0.097 mmol) in DMF (1 mL) was added over 1 min. The reaction mixture was slowly warmed to room temperature and stirred at room temperature overnight. The reaction mixture was diluted with ethyl acetate (30 mL), washed with saturated aqueous $NaHCO_3$ (1×10 mL), dried over $MgSO_4$ and concentrated in vacuo. The crude product was purified with preparative reverse-phase HPLC. $^1$H NMR (400 MHz, DMSO-$d_6$) δ ppm 8.89 (d, J=8.26 Hz, 1H) 8.55 (d, J=2.22 Hz, 1H) 8.33-8.42 (m, 1H) 7.89-8.02 (m, 2H) 7.51-7.60 (m, 3H) 7.39-7.47 (m, 2H) 6.80-6.92 (m, 1H) 4.43 (d, J=4.83 Hz, 2H) 3.63-3.73 (m, 4H) 3.49-3.57 (m, 4H) 3.37 (s, 3H). MS calcd. for $C_{28}H_{24}F_3N_5O_5$ [(M+H)$^+$] 568.1, obsd. 568.1.

Examples I-153 to I-59

The following examples I-153 to I-159 were prepared in an analogous manner to example I-152, starting with intermediate J and an appropriate carboxylic acid.

Example I-153

3-{[4-(1H-Imidazol-2-yl)-benzoylamino]-methyl}-4-oxo-1-phenyl-7-trifluoromethyl-1,4-dihydro-[1,8]naphthyridine-2-carboxylic acid methyl ester

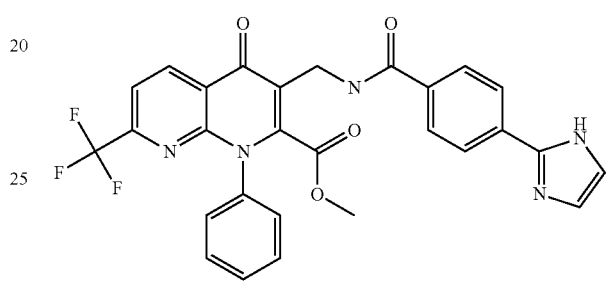

3-{[4-(1H-Imidazol-2-yl)-benzoylamino]-methyl}-4-oxo-1-phenyl-7-trifluoromethyl-1,4-dihydro-[1,8]naphthyridine-2-carboxylic acid methyl ester was prepared starting from intermediate J and 4-(1H-imidazol-2-yl)-benzoic acid. $^1$H NMR (DMSO-$d_6$) δ ppm 8.90 (d, J=8.1 Hz, 1H) 8.77 (t, J=4.6 Hz, 1H) 7.91-8.00 (m, 3H) 7.83-7.89 (m, 2H) 7.52-7.59 (m, 3H) 7.47 (s, 2H) 7.43 (dd, J=6.7, 2.7 Hz, 2H) 4.46 (d, J=4.8 Hz, 2H) 3.40 (s, 3H). MS calcd. for $C_{28}H_{20}F_3N_5O_4$ [(M+H)$^+$] 548.1, obsd. 548.1.

Example I-154

4-Oxo-1-phenyl-3-[(4-sulfamoyl-benzoylamino)-methyl]-7-trifluoromethyl-1,4-dihydro-[1,8]naphthyridine-2-carboxylic acid methyl ester

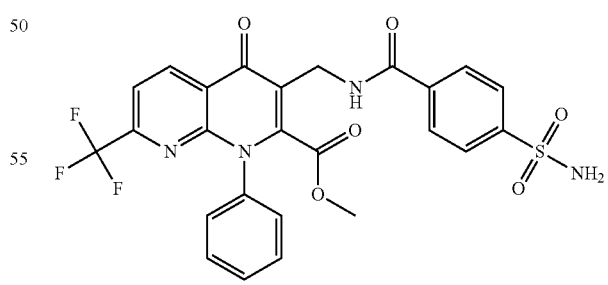

4-Oxo-1-phenyl-3-[(4-sulfamoyl-benzoylamino)-methyl]-7-trifluoromethyl-1,4-dihydro-[1,8]naphthyridine-2-carboxylic acid methyl ester was prepared starting from intermediate J and 4-sulfamoyl-benzoic acid. $^1$H NMR (400 MHz, DMSO-$d_6$) δ ppm 8.90 (d, J=8.06 Hz, 1H) 8.77 (t, J=4.63 Hz, 1H) 7.91-8.00 (m, 3H) 7.83-7.89 (m, 2H) 7.52-7.59 (m, 3H)

7.47 (s, 2H) 7.43 (dd, J=6.75, 2.72 Hz, 2H) 4.46 (d, J=4.83 Hz, 2H) 3.40 (s, 3H). MS calcd. for $C_{25}H_{19}F_3N_4O_6S$ [(M+H)$^+$] 561.1, obsd. 561.1.

Example I-155

3-[(4-Carbamoyl-benzoylamino)-methyl]-4-oxo-1-phenyl-7-trifluoromethyl-1,4-dihydro-[1,8]naphthyridine-2-carboxylic acid methyl ester

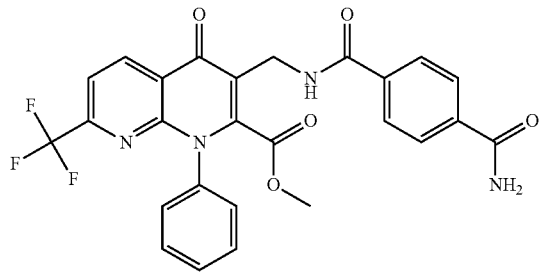 [SMILES: COC(=O)c1c(CNC(=O)c2ccc(C(N)=O)cc2)c(=O)c2ccc(C(F)(F)F)nc2n1-c1ccccc1]

3-[4(4-Carbamoyl-benzoylamino)-methyl]-4-oxo-1-phenyl-7-trifluoromethyl-1,4-dihydro-[1,8]naphthyridine-2-carboxylic acid methyl ester was prepared starting from intermediate J and 4-(aminocarbonyl)benzoic acid. $^1$H NMR (400 MHz, DMSO-d$_6$) δ ppm 8.90 (d, J=8.06 Hz, 1H) 8.66 (t, J=4.73 Hz, 1H) 8.06 (s, 1H) 7.97 (d, J=8.26 Hz, 1H) 7.83-7.93 (m, 4H) 7.53-7.60 (m, 3H) 7.49 (br. s., 1H) 7.40-7.45 (m, 2H) 4.46 (d, J=4.63 Hz, 2H) 3.40 (br. s., 3H). MS calcd. for $C_{26}H_{19}F_3N_4O_5$ [(M+H)$^+$] 525.1, obsd. 525.1.

Example I-156

4-Oxo-1-phenyl-3-{[4-(2H-pyrazol-3-yl)-benzoylamino]-methyl}-7-trifluoromethyl-1,4-dihydro-[1,8]naphthyridine-2-carboxylic acid methyl ester

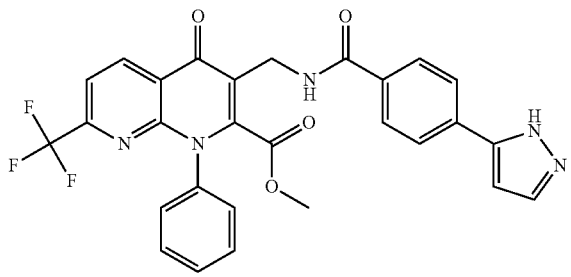 [SMILES: COC(=O)c1c(CNC(=O)c2ccc(-c3ccn[nH]3)cc2)c(=O)c2ccc(C(F)(F)F)nc2n1-c1ccccc1]

4-oxo-1-phenyl-3-{[4-(2H-pyrazol-3-yl)-benzoylamino]-methyl}-7-trifluoromethyl-1,4-dihydro-[1,8]naphthyridine-2-carboxylic acid methyl ester was prepared starting from intermediate J and 4-(2H-pyrazol-3-yl)-benzoic acid. $^1$H NMR (300 MHz, DMSO-d$_6$) δ ppm 12.99 (br. s., 1H) 8.90 (d, J=7.85 Hz, 1H) 8.52 (br. s., 1H) 7.97 (d, J=8.15 Hz, 1H) 7.77-7.90 (m, 5H) 7.51-7.60 (m, 3H) 7.43 (dd, J=6.79, 2.87 Hz, 2H) 6.79 (s, 1H) 4.46 (d, J=4.53 Hz, 2 H) 3.38 (s, 3H) LCMS calcd. for $C_{28}H_{20}F_3N_5O_4$ [(M+H)$^+$] 547.1, obsd. 548.1.

Example I-157

3-{[4-(2-Methyl-2H-tetrazol-5-yl)-benzoylamino]-methyl}-4-oxo-1-phenyl-7-trifluoromethyl-1,4-dihydro-[1,8]-naphthyridine-2-carboxylic acid methyl ester

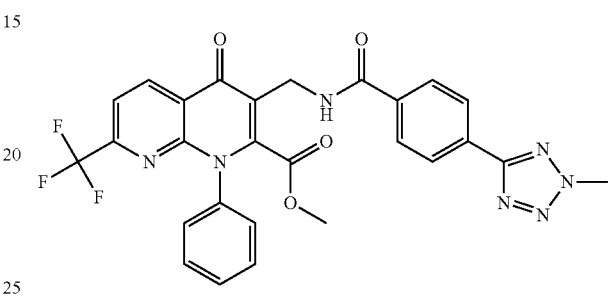

3-{[4-(2-Methyl-2H-tetrazol-5-yl)-benzoylamino]-methyl}-4-oxo-1-phenyl-7-trifluoromethyl-1,4-dihydro-[1,8]-naphthyridine-2-carboxylic acid methyl ester was prepared starting from intermediate J and 4-(2-methyl-2H-tetrazol-5-yl)-benzoic acid. $^1$H NMR (300 MHz, DMSO-d$_6$) δ ppm 8.91 (d, J=8.15 Hz, 1H) 8.71 (br. s., 1H) 8.07-8.17 (m, 2H) 7.90-8.03 (m, 3H) 7.52-7.62 (m, 3H) 7.39-7.50 (m, 2H) 4.48 (d, J=4.83 Hz, 2H) 4.44 (s, 3H) 3.41 (s, 3H). LCMS calcd. for $C_{27}H_{20}F_3N_7O_4$ [(M+H)$^+$] 563.1, obsd. 564.1.

Example I-158

3-{[(1H-Indole-6-carbonyl)-amino]-methyl}-4-oxo-1-phenyl-7-trifluoromethyl-1,4-dihydro-[1,8]naphthyridine-2-carboxylic acid methyl ester

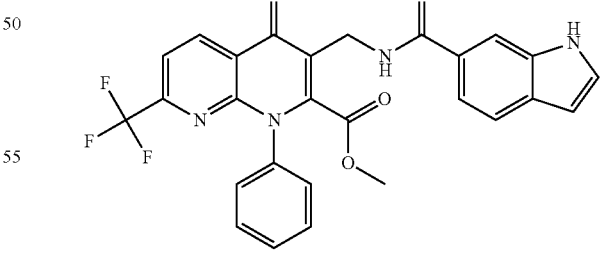

3-{[(1H-Indole-6-carbonyl)-amino]-methyl}-4-oxo-1-phenyl-7-trifluoromethyl-1,4-di-hydro-[1,8]naphthyridine-2-carboxylic acid methyl ester was prepared starting from intermediate J and 1H-indole-6-carboxylic acid. $^1$H NMR (300 MHz, DMSO-d$_6$) δ ppm 11.35 (br. s., 1H) 8.90 (d, J=8.15 Hz, 1H) 8.36 (br. s., 1H) 7.96 (d, J=8.15 Hz, 1H) 7.89

(s, 1H) 7.37-7.59 (m, 8 H) 6.46 (br. s., 1H) 4.47 (d, J=4.83 Hz, 2H) 3.37 (s, 3H) MS calcd. for $C_{27}H_{19}F_3N_4O_4$ [(M+H)$^+$] 521.1 obsd. 521.0.

Example I-159

3-[(3,4-Dichloro-benzoylamino)-methyl]-4-oxo-1-phenyl-7-trifluoromethyl-1,4-dihydro-[1,8]naphthyridine-2-carboxylic acid methyl ester

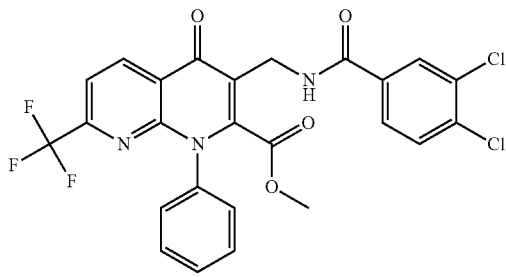 [SMILES: COC(=O)c1c(CNC(=O)c2ccc(Cl)c(Cl)c2)c(=O)c2ccc(C(F)(F)F)nc2n1-c1ccccc1]

3-[(3,4-Dichloro-benzoylamino)-methyl]-4-oxo-1-phenyl-7-trifluoromethyl-1,4-dihydro-[1,8]-naphthyridine-2-carboxylic acid methyl ester was prepared starting from intermediate J and 3,4-dichlorobenzoic acid. $^1$H NMR (400 MHz, DMSO-d$_6$) δ ppm 8.90 (d, J=8.06 Hz, 1H) 8.80 (t, J=4.63 Hz, 1H) 8.04 (d, J=1.81 Hz, 1H) 7.97 (d, J=8.06 Hz, 1H) 7.67-7.83 (m, 2H) 7.51-7.60 (m, 3H) 7.35-7.47 (m, 2H) 4.44 (d, J=4.83 Hz, 2H) 3.39 (s, 3H). MS calcd. for $C_{25}H_{16}Cl_2F_3N_3O_4$ [(M+H)$^+$] 549.0, obsd. 549.9.

Example I-160

3-[(3-Chloro-benzoylamino)-methyl]-7-methoxy-4-oxo-1-phenyl-1,4-dihydro-quinoline-2-carboxylic acid methyl ester

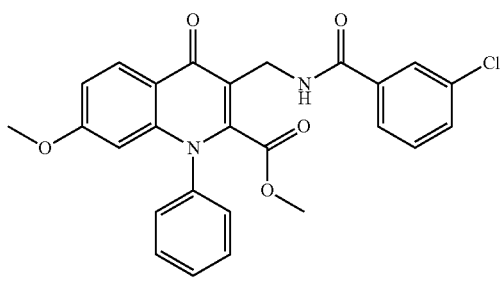 [SMILES: COC(=O)c1c(CNC(=O)c2cccc(Cl)c2)c(=O)c2ccc(OC)cc2n1-c1ccccc1]

A mixture of methyl 3-(aminomethyl)-7-methoxy-4-oxo-1-phenyl-1,4-dihydroquinoline-2-carboxylate (intermediate K) (30 mg, 0.089 mmol), 3-chlorobenzoyl chloride (35 mg, 0.200 mmol), and triethylamine (40 mg, 0.305 mmol) in methylene chloride (4 mL) was stirred at 0° C. for 1 hr. After this time, the reaction mixture was concentrated, and the crude material was triturated with diethyl ether. The product 3-[(3-chloro-benzoylamino)-methyl]-7-methoxy-4-oxo-1-phenyl-1,4-dihydro-quinoline-2-carboxylic acid methyl ester was obtained without further purification. MS calcd. for $C_{26}H_{21}ClN_2O_5$ [(M+H)$^+$] 477.1, obsd. 476.9.

Examples I-161 to I-168

The following examples I-161 to I-168 were prepared in an analogous manner to example I-160, starting with intermediate K and an appropriate acid chloride.

Example I-161

7-Methoxy-3-[(3-methoxy-benzoylamino)-methyl]-4-oxo-1-phenyl-1,4-dihydro-quinoline-2-carboxylic acid methyl ester

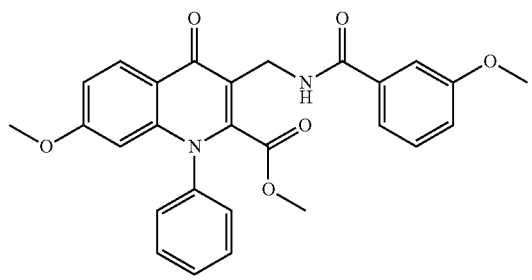

7-Methoxy-3-[(3-methoxy-benzoylamino)-methyl]-4-oxo-1-phenyl-1,4-dihydro-quino-line-2-carboxylic acid methyl ester was prepared starting from intermediate K and 3-methoxybenzoyl chloride. MS calcd. for $C_{27}H_{24}N_2O_6$ [(M+H)$^+$] 473.2, obsd. 473.0.

Example I-162

7-Methoxy-3-[(3,4-difluorobenzoylamino)-methyl]-4-oxo-1-phenyl-1,4-dihydro-quinoline-2-carboxylic acid methyl ester

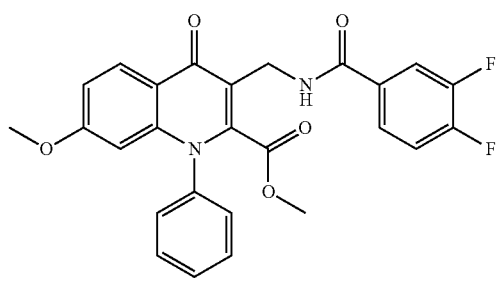 [SMILES: COC(=O)c1c(CNC(=O)c2ccc(F)c(F)c2)c(=O)c2ccc(OC)cc2n1-c1ccccc1]

7-Methoxy-3-[(3,4-difluoro-benzoylamino)-methyl]-4-oxo-1-phenyl-1,4-dihydro-quino-line-2-carboxylic acid methyl ester was prepared starting from intermediate K and 3,4-difluorobenzoyl chloride. MS calcd. for $C_{26}H_{20}F_2N_2O_5$ [(M+H)$^+$] 479.1, obsd. 479.1.

Example I-163

3-[(4-tert-Butyl-benzoylamino)-methyl]-7-methoxy-4-oxo-1-phenyl-1,4-dihydro-quinoline-2-carboxylic acid methyl ester

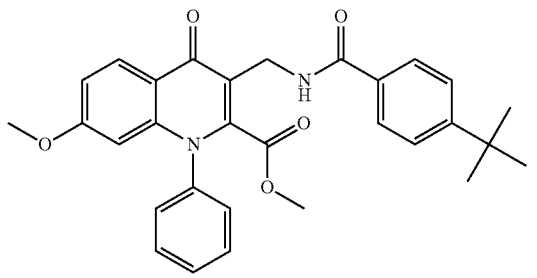 [SMILES: COC(=O)c1c(CNC(=O)c2ccc(C(C)(C)C)cc2)c(=O)c2ccc(OC)cc2n1-c1ccccc1]

3-[(4-tert-Butyl-benzoylamino)-methyl]-7-methoxy-4-oxo-1-phenyl-1,4-dihydro-quino-line-2-carboxylic acid methyl ester was prepared starting from intermediate K and 4-tert-butyl-benzoyl chloride. MS calcd. for $C_{30}H_{30}N_2O_5$ [(M+H)$^+$] 499.2, obsd. 499.2.

Example I-164

3-[(4-methoxy-benzoylamino)-methyl]-7-methoxy-4-oxo-1-phenyl-1,4-dihydro-quinoline-2-carboxylic acid methyl ester

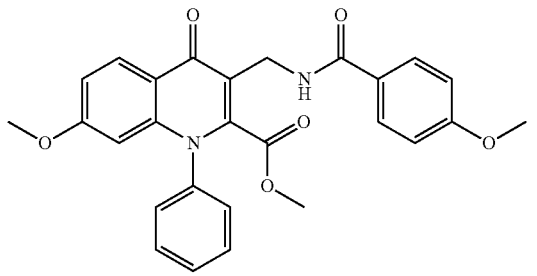

3-[(4-methoxy-benzoylamino)-methyl]-7-methoxy-4-oxo-1-phenyl-1,4-dihydro-quino-line-2-carboxylic acid methyl ester was prepared starting from intermediate K and 4-methoxybenzoyl chloride. MS calcd. for $C_{27}H_{24}N_2O_6$ [(M+H)$^+$] 473.2, obsd. 473.2.

Example I-165

7-Methoxy-4-oxo-1-phenyl-3-{[(pyridine-3-carbo-nyl)-amino]-methyl}-1,4-dihydro-quinoline-2-car-boxylic acidmethyl ester

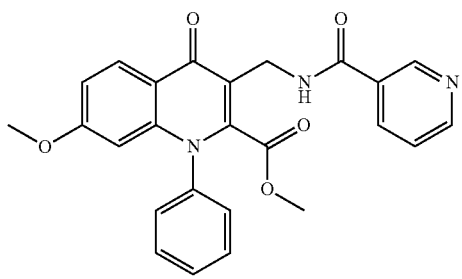 [SMILES: COC(=O)c1c(CNC(=O)c2cccnc2)c(=O)c2ccc(OC)cc2n1-c1ccccc1]

7-Methoxy-4-oxo-1-phenyl-3-{[(pyridine-3-carbonyl)-amino]-methyl}-1,4-dihydroquin-oline-2-carboxylic acid methyl ester was prepared starting from intermediate K and pyridine-3-carbonyl chloride. MS calcd. for $C_{25}H_{21}N_3O_5$ [(M+H)$^+$] 444.2, obsd. 444.0.

Example I-166

3-[(4-Fluoro-benzoylamino)-methyl]-7-methoxy-4-oxo-1-phenyl-1,4-dihydro-quinoline-2-carboxylic acid methyl ester

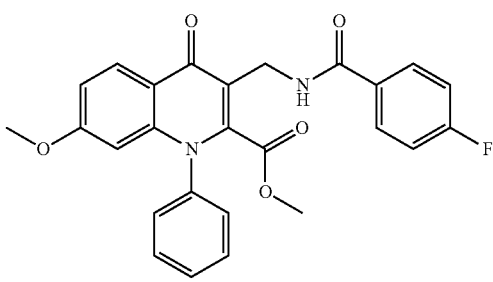 [SMILES: COC(=O)c1c(CNC(=O)c2ccc(F)cc2)c(=O)c2ccc(OC)cc2n1-c1ccccc1]

3-[(4-Fluoro-benzoylamino)-methyl]-7-methoxy-4-oxo-1-phenyl-1,4-dihydro-quinoline-2-carboxylic acid methyl ester was prepared starting from intermediate K and 4-fluorobenzoyl chloride. MS calcd. for $C_{26}H_{21}FN_2O_5$ [(M+H)$^+$] 461.1, obsd. 460.9.

Example I-167

3-[(4-Dimethylamino-benzoylamino)-methyl]-7-methoxy-4-oxo-1-phenyl-1,4-dihydro-quinoline-2-carboxylic acid methyl ester

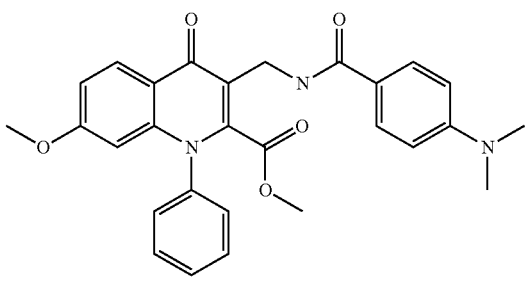

3-[(4-Dimethylamino-benzoylamino)-methyl]-7-methoxy-4-oxo-1-phenyl-1,4-dihydro-quinoline-2-carboxylic acid methyl ester as prepared starting from intermediate K and 4-(dimethylamino)benzoyl chloride. MS calcd. for $C_{28}H_{27}N_3O_5$ [(M+H)$^+$] 486.2, obsd. 486.2.

Example I-168

3-[(4-Chloro-benzoylamino)-methyl]-7-methoxy-4-oxo-1-phenyl-1,4-dihydro-quinoline-2-carboxylic acid methyl ester

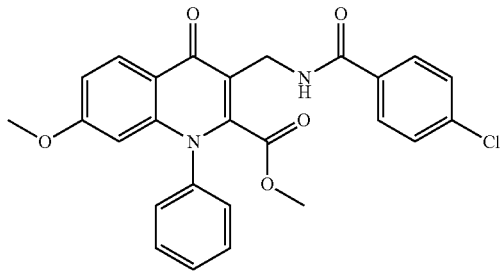 [SMILES: COC(=O)c1c(CNC(=O)c2ccc(Cl)cc2)c(=O)c2ccc(OC)cc2n1-c1ccccc1]

3-[(4-Dimethylamino-benzoylamino)-methyl]-7-methoxy-4-oxo-1-phenyl-1,4-dihydro-quinoline-2-carboxylic acid methyl ester as prepared starting from intermediate K and 4-chloro-benzoyl chloride. MS calcd. for $C_{26}H_{21}ClN_2O_5$ [(M+H)$^+$] 477.1, obsd. 477.1.

Example I-169

7-Fluoro-3-{[(6-morpholin-4-yl-pyridine-3-carbonyl)-amino]-methyl}-4-oxo-1-phenyl-1,4-dihydro-quinoline-2-carboxylic acid methyl ester

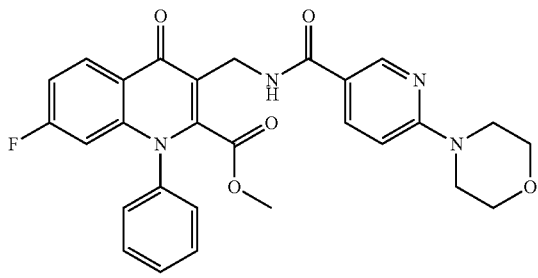 [SMILES: COC(=O)c1c(CNC(=O)c2ccc(N3CCOCC3)nc2)c(=O)c2ccc(F)cc2n1-c1ccccc1]

In a 50 mL round-bottomed flask, methyl 3-(aminomethyl)-7-fluoro-4-oxo-1-phenyl-1,4-dihydroquinoline-2-carboxylate methyl ester hydrochloride salt (intermediate L) (50 mg, 0.153 mmol), 6-morpholinonicotinic acid (63.8 mg, 0.306 mmol), bromotripyrrolidin-1-ylphosphonium (148 mg, 0.460 mmol) and triethylamine (62.0 mg, 0.613 mmol) were combined with DMF (4 mL) to give a white suspension at room temperature. The reaction mixture was stirred for 1 hr. The crude product was purified by preparative reverse phase chromatography, giving 7-fluoro-3-{[(6-morpholin-4-yl-pyridine-3-carbonyl)-amino]-methyl}-4-oxo-1-phenyl-1,4-dihydro-quinoline-2-carboxylic acid methyl ester (6 mg, 7.6%). MS calcd. for $C_{28}H_{25}FN_4O_5$ [(M+H)$^+$] 517.2, obsd. 517.2.

Example I-170

3-{[(6-Chloro-pyridine-3-carbonyl)-amino]-methyl}-7-fluoro-4-oxo-1-phenyl-1,4-dihydroquinoline-2-carboxylic acid methyl ester

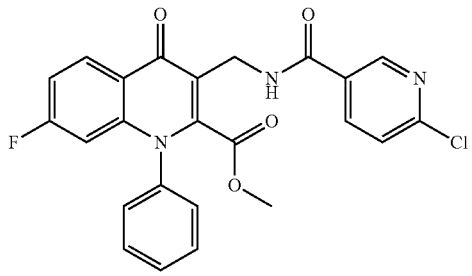 [SMILES: COC(=O)c1c(CNC(=O)c2ccc(Cl)nc2)c(=O)c2ccc(F)cc2n1-c1ccccc1]

3-{[(6-Chloro-pyridine-3-carbonyl)-amino]-methyl}-7-fluoro-4-oxo-1-phenyl-1,4-di-hydro-quinoline-2-carboxylic acid methyl ester was prepared starting from intermediate K and 6-chloronicotinic acid. MS calcd. for $C_{24}H_{17}ClFN_3O_4$ [(M+H)$^+$] 466.1, obsd. 466.1.

Example I-171

7-Chloro-3-[(6,7-dimethoxy-quinazolin-4-ylamino)-methyl]-1-phenyl-1H-quinolin-4-one

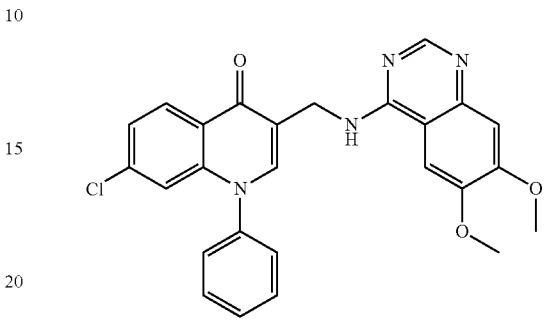

In a 25 mL round-bottomed flask, 6,7-dimethoxyquinazolin-4-amine (69.3 mg, 0.338 mmol) was combined with DMF (2.0 mL) to give a colorless solution. Sodium hydride (60% suspension in oil) (23.0 mg, 0.575 mmol) was added in three portions. The reaction mixture was stirred at room temperature for 15 min. After this time, the reaction mixture was a yellow solution. A DMF solution of the crude 3-bromomethyl-7-chloro-1-phenyl-1H-quinolin-4-one was next added dropwise via a syringe. The reaction mixture was stirred at 50° C. for 3 hr. After this time, TLC is quite messy, but LC/MS gives a strong peak for the desired product (approx 44%). The reaction mixture was cooled to room temperature, then was partitioned between water and ethyl acetate. The organic layer was dried over $Na_2SO_4$, filtered, then concentrated to furnish a brown oil. This crude product was dissolved in methylene chloride, then this solution was concentrated over silica gel. The silica gel-supported crude product was loaded onto a 80 gram SiliCycle column. Flash chromatography (2.5% methanol-methylene chloride ramped to 6% methanol-methylene chloride) afforded 7-chloro-3-[(6,7-dimethoxy-quinazolin-4-ylamino)-methyl]-1-phenyl-1H-quinolin-4-one. MS calcd. for $C_{26}H_{21}ClN_4O_3$ [(M+H)$^+$] 472.9, obsd. 473.0.

Example I-172

7-Chloro-3-[(7-fluoro-quinazolin-4-ylamino)-methyl]-1-phenyl-1H-quinolin-4-one

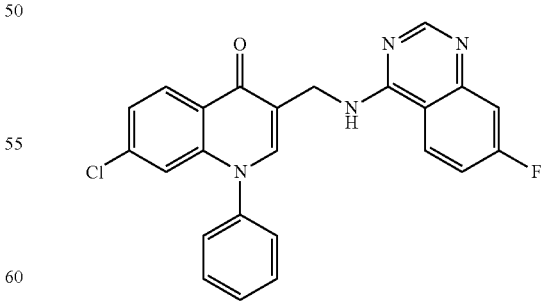

7-Chloro-3-[(7-fluoro-quinazolin-4-ylamino)-methyl]-1-phenyl-1H-quinolin-4-one was prepared according to the procedure described above for example 12-1, starting with intermediate M and 7-fluoro-quinazolin-4-amine. MS calcd. for $C_{24}H_{16}ClFN_4O$ [(M+H)$^+$] 430.9, obsd. 431.3

Example I-173

7-Chloro-1-phenyl-3-[(6-piperidin-1-yl-pyrimidin-4-ylamino)-methyl]-1H-quinolin-4-one

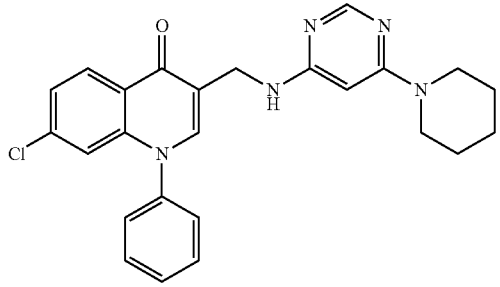 [SMILES: O=c1c(CNc2cc(N3CCCCC3)ncn2)cn(-c2ccccc2)c2cc(Cl)ccc12]

To a stirred solution of 3-(aminomethyl)-7-chloro-1-phenylquinolin-4(1H)-one (intermediate D) (30 mg, 0.105 mmol) and N,N-diisopropylethylamine (40.9 mg, 55.2 µL, 0.316 mmol) in NMP (500 µL) was added 4,6-dichloropyrimidine (15.7 mg, 0.105 mmol). The mixture was warmed to 120° C. in a sealed microwave tube. After 1.5 hr, piperidine (35.9 mg, 41.7 µL, 0.421 mmol) was added and heating at 120° C. continued for 9 hr. The reaction mixture was cooled to room temperature. The crude product was purified by preparative reverse-phase HPLC, giving 7-chloro-1-phenyl-3-[(6-piperidin-1-yl-pyrimidin-4-ylamino)-methyl]-1H-quinolin-4-one (25 mg, 53%) as an off-white solid. MS calcd. for $C_{25}H_{24}ClN_5O$ $[(M+H)^+]$ 446, obsd. 446.

Example I-174

7-Chloro-1-phenyl-3-[(2-piperidin-1-yl-pyrimidin-4-ylamino)-methyl]-1H-quinolin-4-one trifluoroacetate salt

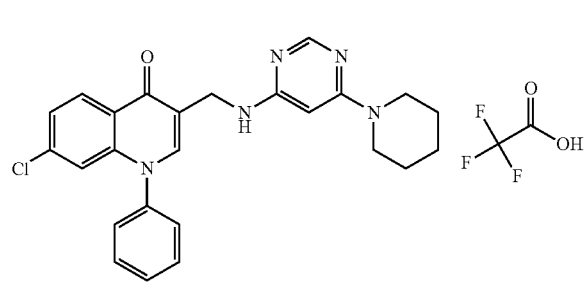

7-Chloro-1-phenyl-3-[(2-piperidin-1-yl-pyrimidin-4-ylamino)-methyl]-1H-quinolin-4 one trifluoroacetate salt was prepared according to the procedure described above for example 12-4, starting with intermediate D, 2,4-dichloropyrimidine, and piperidine. $^1$H NMR (400 MHz, DMSO-$d_6$) δ ppm 11.81 (br. s., 1H) 9.09 (t, J=5.50 Hz, 1H) 8.25 (d, J=8.30 Hz, 1H) 8.16 (s, 1 H) 7.52-7.79 (m, 4H) 7.46 (dd, J=8.86, 2.01 Hz, 1H) 6.91 (d, J=1.81 Hz, 1H) 6.12 (d, J=7.25 Hz, 1H) 4.42 (d, J=5.44 Hz, 2H) 1.28-1.66 (m, 5H).

Example I-175

3-(Benzothiazol-2-ylaminomethyl)-7-chloro-1-phenyl-1H-quinolin-4-one

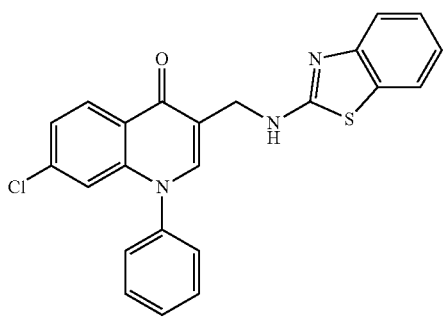 [SMILES: O=c1c(CNc2nc3ccccc3s2)cn(-c2ccccc2)c2cc(Cl)ccc12]

A mixture of 3-(aminomethyl)-7-chloro-1-phenylquinolin-4(1H)-one (intermediate D) (40 mg, 0.140 mmol), N,N-diisopropylethylamine (74.0 mg, 100 µL, 0.567 mmol) and 2-chlorobenzothiazole (31 mg, 0.181 mmol) in NMP (0.5 mL) was heated at 115° C. in a sealed tube. After 2 hr., LCMS indicated the desired product to be present with some remaining starting material and minor impurities. Heating continued overnight. In the morning, more 2-chlorobenzothiazole (12 mg, 0.070 mmol) was added. Heating continued for another 24 hr. The reaction mixture was concentrated under a stream of nitrogen, and the crude product was purified by preparative reverse phase HPLC. The desired product 3-(benzothiazol-2-ylaminomethyl)-7-chloro-1-phenyl-1H-quinolin-4-one (13 mg, 22%) was obtained an off-white solid. MS calcd. for $C_{23}H_{16}ClN_3OS$ $[(M+H)^+]$ 418.1, obsd. 418.

Example I-176

3-[(1H-Benzoimidazol-2-ylamino)-methyl]-7-chloro-1-phenyl-1H-quinolin-4-one

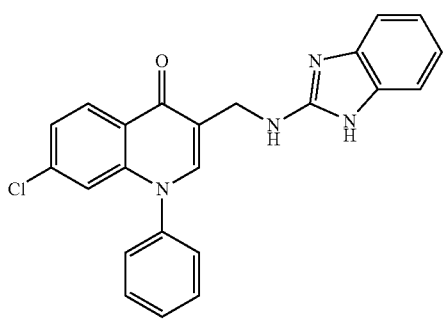 [SMILES: O=c1c(CNc2nc3ccccc3[nH]2)cn(-c2ccccc2)c2cc(Cl)ccc12]

A mixture of 3-(aminomethyl)-7-chloro-1-phenylquinolin-4(1H)-one (intermediate D) (40 mg, 0.140 mmol), N,N-diisopropylethylamine (74.0 mg, 100 µL, 0.570 mmol) and 2-chlorobenzimidazole (29 mg, 0.186 mmol) in NMP (500 µL) was heated at 115° C. in a sealed tube overnight. After this time, very little desired product was observed via LC/MS. Additional 2-chlorobenzimidazole (30 mg, 0.196 mmol), N,N-diisopropylethylamine (74.0 mg, 100 µL, 0.570 mmol), and NMP (0.2 mL) were added, and the reaction mixture was transferred to a small microwave tube. The mixture was heated via microwave irradiation at 180° C. for 2 hr. The reaction mixture was concentrated under a stream of nitrogen, and the crude product was purified by preparative reverse-phase HPLC. The product 3-[(1H-Benzoimidazol-2-ylamino)-methyl]-7-chloro-1-phenyl-1H-quinolin-4-one (4 mg, 6.8%) was obtained as an off-white solid. MS calcd. for $C_{23}H_{17}ClN_4O$ [(M+H)$^+$] 401.1, obsd. 401.

Example I-177

[(7-Chloro-4-oxo-1-phenyl-1,4-dihydro-quinolin-3-ylmethyl)-amino]-morpholin-4-yl-methylene-cyanamide

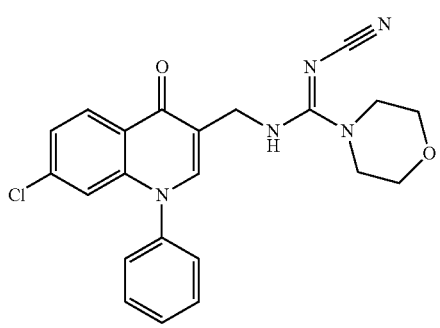 [SMILES: N#C/N=C(/NCc1cn(-c2ccccc2)c2cc(Cl)ccc2c1=O)N1CCOCC1]

To a stirred solution of 3-(aminomethyl)-7-chloro-1-phenylquinolin-4(1H)-one (intermediate D) (30 mg, 0.105 mmol) and N,N-diisopropylethylamine (40.9 mg, 55.2 μL, 0.316 mmol) in NMP (0.5 mL) was added diphenyl-cyano-carbonimidate (25.1 mg, 0.105 mmol). After 1 hr., morpholine (11.9 mg, 12.0 μL, 0.137 mmol) was added and the mixture was warmed to 120° C. in a sealed microwave tube. After 1 hr., LCMS showed complete conversion to product. The mixture was allowed to cool to room temp. and the crude product was purified using preparative reverse-phase HPLC. The product [(7-chloro-4-oxo-1-phenyl-1,4-dihydro-quinolin-3-ylmethyl)-amino]-morpholin-4-yl-methylene-cyanamide (25 mg, 56%) was obtained as a white solid. $^1$H NMR (400 MHz, DMSO-d$_6$) δ ppm 8.26 (d, J=8.8 Hz, 1H) 8.07 (s, 1H) 7.61-7.76 (m, 3H) 7.57-7.62 (m, 2H) 7.48-7.53 (m, 1H) 7.46 (dd, J=8.8, 1.9 Hz, 1H) 6.93 (d, J=1.9 Hz, 1H) 4.36 (d, J=4.8 Hz, 2H) 3.51-3.62 (m, 4H) 3.35-3.46 (m, 4H).

Example I-178

[(7-Chloro-4-oxo-1-phenyl-1,4-dihydro-quinolin-3-ylmethyl)-amino]-phenylamino-methylene-cyanamide

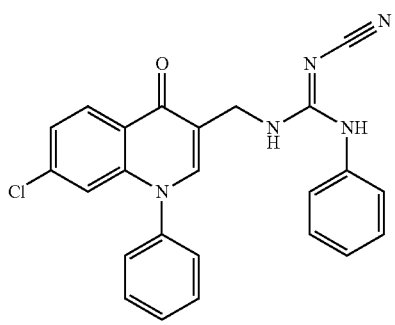 [SMILES: N#C/N=C(/NCc1cn(-c2ccccc2)c2cc(Cl)ccc2c1=O)Nc1ccccc1]

[(7-Chloro-4-oxo-1-phenyl-1,4-dihydro-quinolin-3-ylmethyl)-amino]-phenylamino-methylene-cyanamide was prepared according to the procedure described above for example 13-1, using intermediate D and aniline. MS calcd. for $C_{24}H_{18}ClN_5O$ [(M+H)$^+$] 428.1, obsd. 428.

Example I-179

(7-Chloro-4-oxo-1-phenyl-1,4-dihydro-quinolin-3-ylmethyl)-carbamic acid phenyl ester

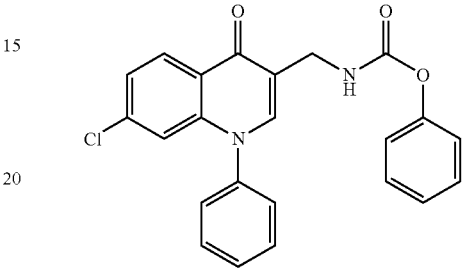

In a 10 mL round-bottomed flask, 3-(aminomethyl)-7-chloro-1-phenylquinolin-4(1H)-one intermediate D (0.05 g, 0.176 mmol), phenyl chloroformate (27.5 mg, 0.176 mmol) and N,N-diisopropylethylamine (68.1 mg, 92.0 μL, 0.527 mmol) were combined with CH$_2$Cl$_2$ (3 mL). The reaction mixture was stirred at room temperature for 1 hr. The reaction mixture was concentrated, then the crude product was purified using preparative reverse-phase HPLC to provide (7-chloro-4-oxo-1-phenyl-1,4-dihydro-quinolin-3-ylmethyl)-carbamic acid phenyl ester. MS calcd. for $C_{24}H_{18}ClN_5O$ [(M+H)$^+$] 405.1, obsd. 404.9.

Example I-180

4-Phenyl-piperazine-1-carboxylic acid (7-chloro-4-oxo-1-phenyl-1,4-dihydro-quinolin-3-ylmethyl)-amide

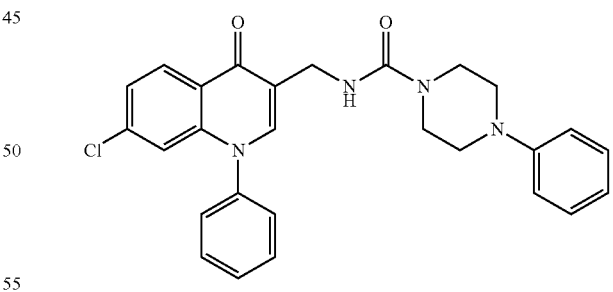

In a 25 mL round-bottomed flask, 4-nitrophenyl (7-chloro-4-oxo-1-phenyl-1,4-dihydroquinolin-3-yl)methylcarbamate (intermediate M) (0.05 g, 0.111 mmol), 1-phenylpiperazine (18.0 mg, 0.111 mmol) and N,N-diisopropylethylamine (43.1 mg, 58.2 μA, 333 mmol) were combined with methylene chloride (5 mL). The reaction mixture was stirred at room temperature. The crude product was purified using preparative reverse-phase HPLC, giving 4-phenyl-piperazine-1-carboxylic acid (7-chloro-4-oxo-1-phenyl-1,4-dihydro-quinolin-3-ylmethyl)-amide MS calcd. for $C_{27}H_{26}ClN_4O_2$ [(M+H)$^+$] 473.2, obsd. 473.0.

Examples I-181 to I-191

The following examples I-181 to I-191 were prepared in an analogous manner to example I-180, starting with intermediate M and the appropriate amine.

Example I-181

{4-[3-(7-Chloro-4-oxo-1-phenyl-1,4-dihydro-quinolin-3-ylmethyl)-ureido]-cyclohexyl}-carbamic acid tert-butyl ester

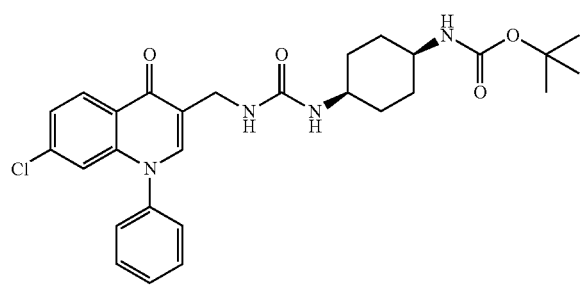 [SMILES: CC(C)(C)OC(=O)N[C@H]1CC[C@@H](NC(=O)NCc2cn(-c3ccccc3)c3cc(Cl)ccc3c2=O)CC1]

{4-[3-(7-Chloro-4-oxo-1-phenyl-1,4-dihydro-quinolin-3-ylmethyl)-ureido]-cyclohexyl}-carbamic acid tert-butyl ester was prepared starting from intermediate M and cis-(4-amino-cyclohexyl)-carbamic acid tert-butyl ester. MS calcd. for $C_{28}H_{34}ClN_4O_4$ [(M+H)$^+$] 525.2, obsd. 525.1.

Example I-182

{4-[3-(7-Chloro-4-oxo-1-phenyl-1,4-dihydro-quinolin-3-ylmethyl)-ureido]-cyclohexyl}-carbamic acid tert-butyl ester

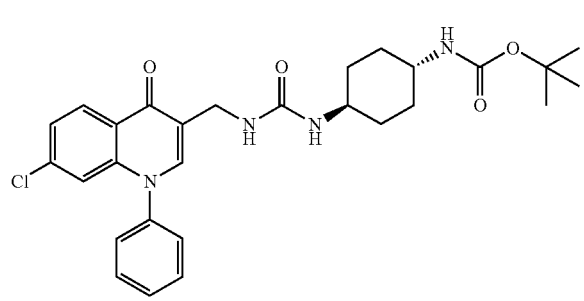 [SMILES: CC(C)(C)OC(=O)N[C@H]1CC[C@H](NC(=O)NCc2cn(-c3ccccc3)c3cc(Cl)ccc3c2=O)CC1]

{4-[3-(7-Chloro-4-oxo-1-phenyl-1,4-dihydro-quinolin-3-ylmethyl)-ureido]-cyclohexyl}-carbamic acid tert-butyl ester was prepared was prepared starting from intermediate M and trans-(4-amino-cyclohexyl)-carbamic acid tert-butyl ester. MS calcd. for $C_{28}H_{34}ClN_4O_4$ [(M+H)$^+$] 525.2, obsd. 525.1.

Example I-183

3-[3-(7-Chloro-4-oxo-1-phenyl-1,4-dihydro-quinolin-3-ylmethyl)-ureido]-pyrrolidine-1-carboxylic acid tert-butyl ester

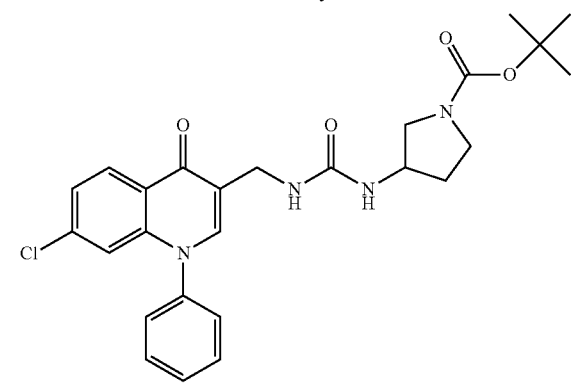

3-[3-(7-Chloro-4-oxo-1-phenyl-1,4-dihydro-quinolin-3-ylmethyl)-ureido]-pyrrolidine-1-carboxylic acid tert-butyl ester was prepared was prepared starting from intermediate M and 3-amino-pyrrolidine-1-carboxylic acid tert-butyl ester. MS calcd. for $C_{26}H_{30}ClN_4O_4$ [(M+H)$^+$] 497.2, obsd. 497.2.

Example I-184

1-(7-Chloro-4-oxo-1-phenyl-1,4-dihydro-quinolin-3-ylmethyl)-3-cyclopentyl-urea

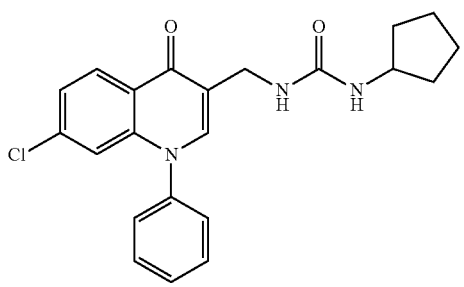 [SMILES: O=C(NCc1cn(-c2ccccc2)c2cc(Cl)ccc2c1=O)NC1CCCC1]

7-Chloro-4-oxo-1-phenyl-1,4-dihydro-quinolin-3-ylmethyl)-3-cyclopentyl-urea was prepared starting from intermediate M and cyclopentylamine. MS calcd. for $C_{22}H_{23}ClN_3O_2$ [(M+H)$^+$] 396.1, obsd. 396.0.

Example I-185

4-[3-(7-Chloro-4-oxo-1-phenyl-1,4-dihydro-quinolin-3-ylmethyl)-ureido]-cyclohexanecarboxylic acid methyl ester

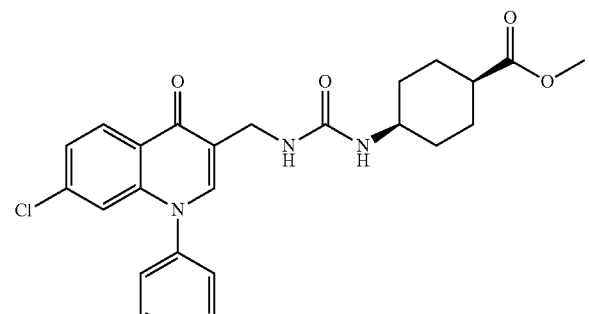

4-[3-(7-Chloro-4-oxo-1-phenyl-1,4-dihydro-quinolin-3-ylmethyl)-ureido]-cyclohexane-carboxylic acid methyl ester was prepared starting from intermediate M and cis-4-amino-cyclohexane carboxylic acid methyl ester. MS calcd. for $C_{25}H_{27}ClN_3O_4$ [(M+H)$^+$] 468.2, obsd. 468.0.

Example I-186

Pyrrolidine-1-carboxylic acid (7-chloro-4-oxo-1-phenyl-1,4-dihydro-quinolin-3-ylmethyl)-amide

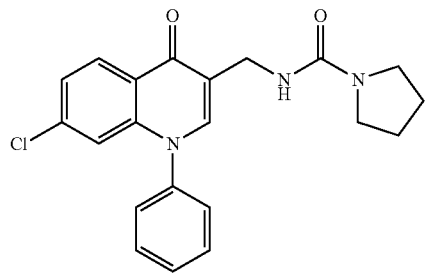 [SMILES: O=C(NCc1cn(-c2ccccc2)c2cc(Cl)ccc2c1=O)N1CCCC1]

Pyrrolidine-1-carboxylic acid (7-chloro-4-oxo-1-phenyl-1,4-dihydro-quinolin-3-yl-methyl)-amide was prepared starting from intermediate M and pyrrolidine. MS calcd. for $C_{21}H_{21}ClN_3O_2$ [(M+H)$^+$] 382.1, obsd. 381.9.

Example I-187

4-Methyl-piperazine-1-carboxylic acid (7-chloro-4-oxo-1-phenyl-1,4-dihydro-quinolin-3-ylmethyl)-amide

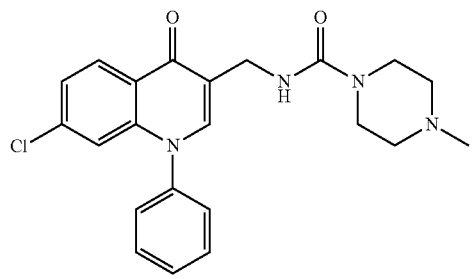 [SMILES: CN1CCN(C(=O)NCc2cn(-c3ccccc3)c3cc(Cl)ccc3c2=O)CC1]

4-Methyl-piperazine-1-carboxylic acid (7-chloro-4-oxo-1-phenyl-1,4-dihydro-quinolin-3-ylmethyl)-amide was prepared starting from intermediate M and 4-methyl-piperazine. MS calcd. for $C_{22}H_{24}ClN_4O_2$ [(M+H)$^+$] 411.2, obsd. 411.0.

Example I-188

Piperidine-1-carboxylic acid (7-chloro-4-oxo-1-phenyl-1,4-dihydro-quinolin-3-yl-methyl)-amide

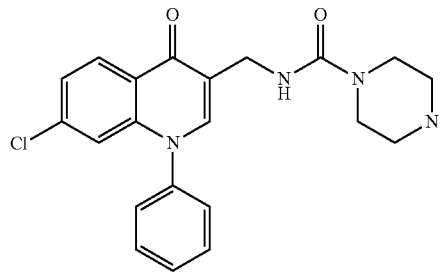 [SMILES: O=C(NCc1cn(-c2ccccc2)c2cc(Cl)ccc2c1=O)N1CCNCC1]

Piperidine-1-carboxylic acid (7-chloro-4-oxo-1-phenyl-1,4-dihydro-quinolin-3-ylmethyl)-amide was prepared starting from intermediate M and piperidine. MS calcd. for $C_{22}H_{23}ClN_3O_2$ [(M+H)$^+$] 396.1, obsd. 395.9.

Example I-189

4-[3-(7-Chloro-4-oxo-1-phenyl-1,4-dihydro-quinolin-3-ylmethyl)-ureido]-cyclohexanecarboxylic acid methyl ester

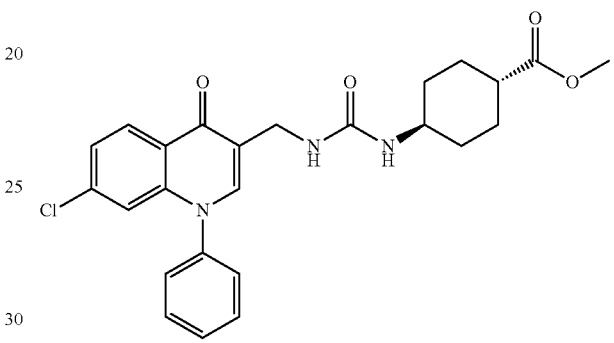

4-[3-(7-Chloro-4-oxo-1-phenyl-1,4-dihydro-quinolin-3-ylmethyl)-ureido]-cyclohexane-carboxylic acid methyl ester was prepared starting from intermediate M and trans-4-amino-cyclohexane carboxylic acid methyl ester. MS calcd. for $C_{25}H_{27}ClN_3O_4$ [(M+H)$^+$] 468.2, obsd. 468.1.

Example I-190

4-Phenyl-piperidine-1-carboxylic acid (7-chloro-4-oxo-1-phenyl-1,4-dihydro-quinolin-3-ylmethyl)-amide

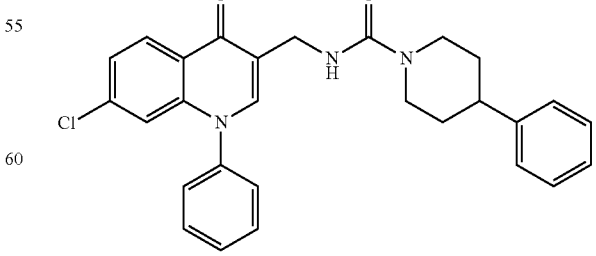

4-Phenyl-piperidine-1-carboxylic acid (7-chloro-4-oxo-1-phenyl-1,4-dihydro-quinolin-3-ylmethyl)-amide was prepared starting from intermediate M and 4-phenyl-piperidine. MS calcd. for $C_{28}H_{27}ClN_3O_2$ [(M+H)$^+$] 472.2, obsd. 472.2.

Example I-191

1-(7-Chloro-4-oxo-1-phenyl-1,4-dihydro-quinolin-3-ylmethyl)-3-(5-hydroxy-adamantan-2-yl)-urea

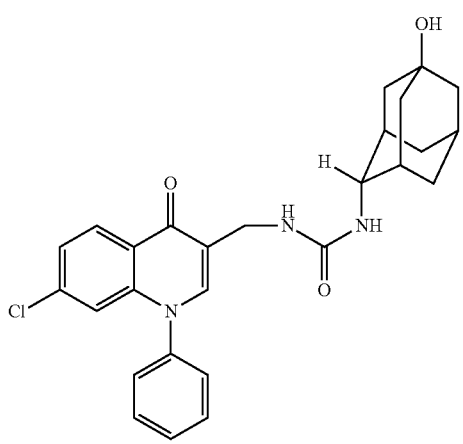 [SMILES: O=C(NCc1cn(-c2ccccc2)c2cc(Cl)ccc2c1=O)NC1C2CC3CC1CC(O)(C3)C2]

1-(7-Chloro-4-oxo-1-phenyl-1,4-dihydro-quinolin-3-ylmethyl)-3-(5-hydroxy-adamantan-2-yl)-urea was prepared starting from intermediate M and trans-4-aminoadamantan-1-ol. MS calcd. for $C_{27}H_{29}ClN_3O_3$ [(M+H)$^+$] 478.2, obsd. 478.0.

Example I-192

4-[3-(7-Chloro-4-oxo-1-phenyl-1,4-dihydro-quinolin-3-ylmethyl)-ureido]-piperidine-1-carboxylic acid tert-butyl ester

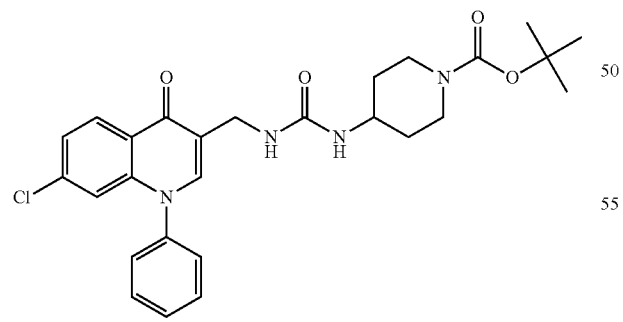

4-[3-(7-Chloro-4-oxo-1-phenyl-1,4-dihydro-quinolin-3-ylmethyl)-ureido]-piperidine-1-carboxylic acid tert-butyl ester was prepared as described above in the intermediates section, starting from 4-boc-aminopiperidine and intermediate M. MS calcd. for $C_{27}H_{32}ClN_4O_4$ [(M+H)$^+$] 511.2, obsd. 511.1.

Example I-193

4-[3-(7-Chloro-4-oxo-1-phenyl-1,4-dihydro-quinolin-3-ylmethyl)-ureido]-piperidine-yl-carboxylic acid phenyl ester

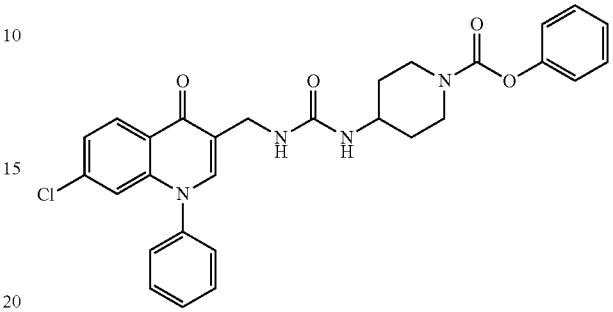

In a 20 mL round-bottomed flask, 1-((7-chloro-4-oxo-1-phenyl-1,4-dihydroquinolin-3-yl)methyl)-3-(piperidin-4-yl)urea (intermediate N) (0.100 g, 0.243 mmol), phenyl chloroformate (38.1 mg, 30.6 μL, 0.243 mmol) and N,N-diisopropylethylamine (157 mg, 213 μL, 1.22 mmol) were combined with $CH_2Cl_2$ (5 ml). The reaction mixture was stirred at room temperature for 1 hr. The reaction mixture was concentrated. The crude product was purified using preparative reverse-phase HPLC to give 4-[3-(7-chloro-4-oxo-1-phenyl-1,4-dihydro-quinolin-3-ylmethyl)-ureido]-piperidine-1-carboxylic acid phenyl ester. MS calcd. for $C_{29}H_{28}ClN_4O_4$ [(M+H)$^+$] 531.2, obsd. 531.0.

Examples I-194 to I-198

The following examples I-194 to I-198 were prepared in an analogous manner to example I-193, starting with intermediate N and the appropriate chloroformate, acid chloride, or sulfonyl chloride.

Example I-194

1-(1-Benzoyl-piperidin-4-yl)-3-(7-chloro-4-oxo-1-phenyl-1,4-dihydro-quinolin-3-yl-methyl)-urea

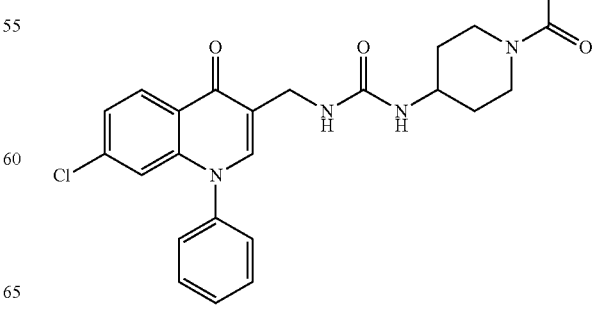

1-(1-Benzoyl-piperidin-4-yl)-3-(7-chloro-4-oxo-1-phenyl-1,4-dihydro-quinolin-3-yl methyl)-urea was prepared starting from intermediate N and benzoyl chloride. MS calcd. for $C_{29}H_{28}ClN_4O_3$ [(M+H)$^+$] 515.2, obsd. 515.2.

Example I-195

4-[3-(7-Chloro-4-oxo-1-phenyl-1,4-dihydro-quinolin-3-ylmethyl)-ureido]-piperidine-1-carboxylic acid benzyl ester

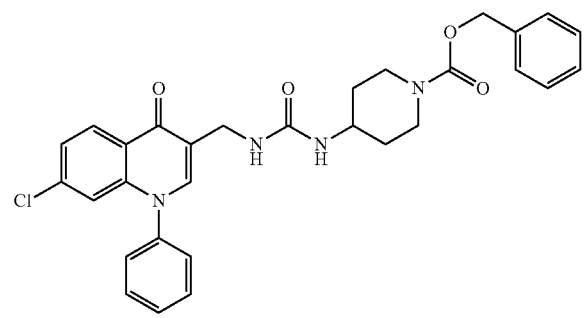 [SMILES: O=C(NCc1cn(-c2ccccc2)c2cc(Cl)ccc2c1=O)NC1CCN(C(=O)OCc2ccccc2)CC1]

4-[3-(7-Chloro-4-oxo-1-phenyl-1,4-dihydro-quinolin-3-ylmethyl)-ureido]-piperidine-1-carboxylic acid benzyl ester was prepared starting from intermediate N and benzyl chloroformate MS calcd. for $C_{30}H_{30}ClN_4O_4$ [(M+H)$^+$] 545.2, obsd. 545.0.

Example I-196

1-(7-Chloro-4-oxo-1-phenyl-1,4-dihydro-quinolin-3-ylmethyl)-3-(1-phenylsulfonyl-piperidin-4-yl)-urea

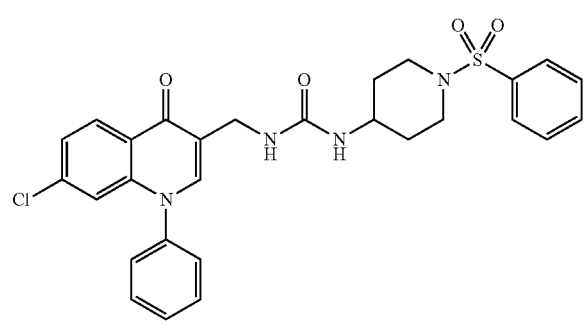 [SMILES: O=C(NCc1cn(-c2ccccc2)c2cc(Cl)ccc2c1=O)NC1CCN(S(=O)(=O)c2ccccc2)CC1]

1-(7-Chloro-4-oxo-1-phenyl-1,4-dihydro-quinolin-3-yl-methyl)-3-(1-phenylsulfonyl-piperidin-4-yl)-urea was prepared starting from intermediate N and benzenesulfonyl chloride. MS calcd. for $C_{28}H_{28}ClN_4O_4S$ [(M+H)$^+$] 551.1, obsd. 551.1.

Example I-197

1-(7-Chloro-4-oxo-1-phenyl-1,4-dihydro-quinolin-3-ylmethyl)-3-(1-methanesulfonyl-piperidin-4-yl)-urea

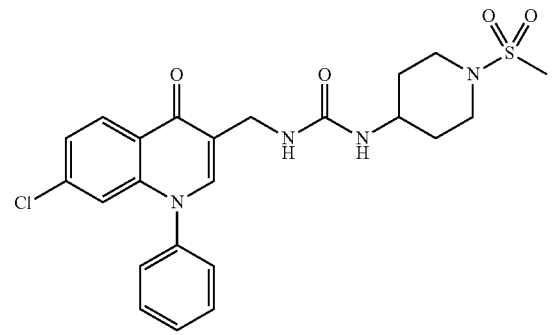 [SMILES: CS(=O)(=O)N1CCC(NC(=O)NCc2cn(-c3ccccc3)c3cc(Cl)ccc3c2=O)CC1]

1-(7-Chloro-4-oxo-1-phenyl-1,4-dihydro-quinolin-3-yl-methyl)-3-(1-methanesulfonyl-piperidin-4-yl)-urea was prepared starting from intermediate N and methanesulfonyl chloride. MS calcd. for $C_{23}H_{26}ClN_4O_4S$ [(M+H)$^+$] 489.1, obsd. 489.1.

Example I-198

1-(1-Acetyl-piperidin-4-yl)-3-(7-chloro-4-oxo-1-phenyl-1,4-dihydro-quinolin-3-ylmethyl)-urea

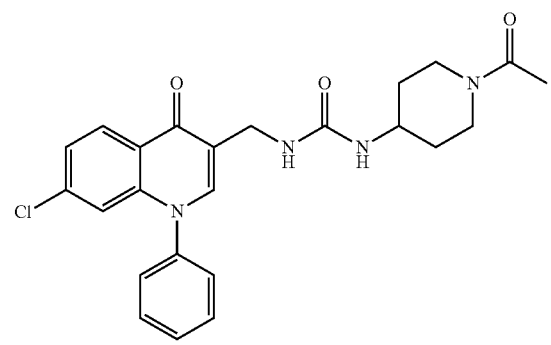 [SMILES: CC(=O)N1CCC(NC(=O)NCc2cn(-c3ccccc3)c3cc(Cl)ccc3c2=O)CC1]

1-(1-Acetyl-piperidin-4-yl)-3-(7-chloro-4-oxo-1-phenyl-1,4-dihydro-quinolin-3-yl-methyl)-urea was prepared starting from intermediate N and acetyl chloride. MS calcd. for $C_{24}H_{26}ClN_4O_3$ [(M+H)$^+$] 453.2, obsd. 453.1.

Example I-199

1-(7-Chloro-4-oxo-1-phenyl-1,4-dihydro-quinolin-3-ylmethyl)-3-[1-(4-methanesulfonyl-piperidine-1-carbonyl)-piperidin-4-yl]-urea

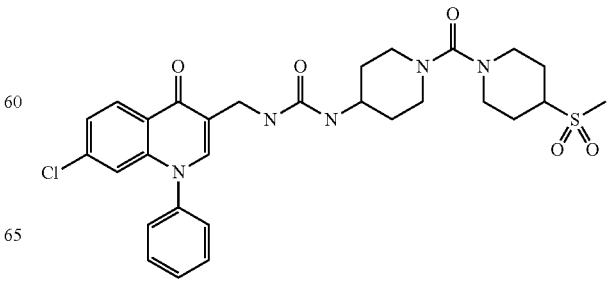

Step 1

In a 250 mL round-bottomed flask, 1-((7-chloro-4-oxo-1-phenyl-1,4-dihydroquinolin-3-yl)methyl)-3-(piperidin-4-yl) urea (intermediate N) (2.0 g, 4.9 mmol), 4-nitrophenyl chloroformate (981 mg, 4.87 mmol) and N,N-diisopropylethylamine (2.52 g, 3.4 mL, 19.5 mmol) were combined with CH$_2$Cl$_2$ (20 ml). The reaction mixture was stirred at room temperature overnight. The reaction mixture was concentrated, then the crude product, 4-[3-(7-Chloro-4-oxo-1-phenyl-1,4-dihydro-quinolin-3-ylmethyl)-ureido]-piperidine-1-carboxylic acid 4-nitrophenyl ester, was used in subsequent reactions without further purification.

Step 2

In a 20 mL round-bottomed flask, 4-nitrophenyl 4-(3-((7-chloro-4-oxo-1-phenyl-1,4-dihydroquinolin-3-yl)methyl) ureido)piperidine-1-carboxylate (0.100 g, 0.174 mmol), N,N-diisopropylethylamine (112 mg, 152 µL, 0.868 mmol) and 4-(methylsulfonyl)-piperidine (28.3 mg, 0.174 mmol) were combined with DMF (5 mL). The reaction mixture was stirred at 100° C. over the weekend. The reaction mixture was concentrated. The crude product was purified by preparative reverse-phase HPLC, giving the product 1-(7-chloro-4-oxo-1-phenyl-1,4-dihydro-quinolin-3-ylmethyl)-3-[1-(4-methanesulfonyl-piperidine-1-carbonyl)-piperidin-4-yl]-urea. MS calcd. for C$_{29}$H$_{35}$ClN$_5$O$_5$S [(M+H)$^+$] 600.2, obsd. 600.0.

Example I-200

Morpholine-4-carboxylic acid (7-chloro-4-oxo-1-phenyl-1,4-dihydro-quinolin-3-ylmethyl)-amide

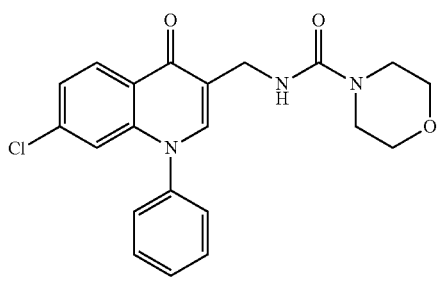

In a 10 mL round-bottomed flask, 3-(aminomethyl)-7-chloro-1-phenylquinolin-4(1H)-one (intermediate D) (0.05 g, 0.176 mmol), morpholine-4-carbonyl chloride (26.3 mg, 0.176 mmol) and N,N-diisopropylethylamine (68.1 mg, 92.0 µL, 0.527 mmol) were combined with CH$_2$Cl$_2$ (3 mL). The reaction mixture was stirred at room temperature for 1 hr and monitored by LC/MS. The crude product was purified using preparative reverse-phase HPLC, giving the desired product morpholine-4-carboxylic acid (7-chloro-4-oxo-1-phenyl-1,4-dihydro-quinolin-3-ylmethyl)-amide. MS calcd. for C$_{21}$H$_{21}$ClN$_3$O$_3$ [(M+H)$^+$] 398.1, obsd. 398.0.

Example I-201

1-(7-Chloro-4-oxo-1-phenyl-1,4-dihydro-quinolin-3-ylmethyl)-3-phenyl-urea

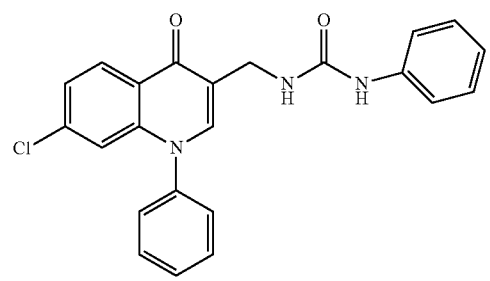 [SMILES: O=C(NCc1cn(-c2ccccc2)c2cc(Cl)ccc2c1=O)Nc1ccccc1]

In a 10 mL round-bottomed flask, 3-(aminomethyl)-7-chloro-1-phenylquinolin-4(1H)-one (intermediate D) (0.05 g, 0.176 mmol), phenyl isocyanate (20.9 mg, 19.2 µL, 0.176 mmol) and N,N-diisopropylethylamine (68.1 mg, 92.0 µL, 0.527 mmol) were combined with CH$_2$Cl$_2$ (3 mL). The reaction mixture was stirred at room temperature for 1 hr. The crude product was purified using preparative reverse-phase HPLC, giving 1-(7-chloro-4-oxo-1-phenyl-1,4-dihydro-quinolin-3-ylmethyl)-3-phenyl-urea. MS calcd. for C$_{23}$H$_{19}$ClN$_3$O$_2$ [(M+H)$^+$] 404.1 obsd. 403.9.

Examples I-202 to I-206

The following examples I-202 to I-206 were prepared in an analogous manner to example I-201, starting with intermediate D and the appropriate isocyanate.

Example I-202

1-(7-Chloro-4-oxo-1-phenyl-1,4-dihydro-quinolin-3-ylmethyl)-3-(4-dimethylamino-phenyl)-urea

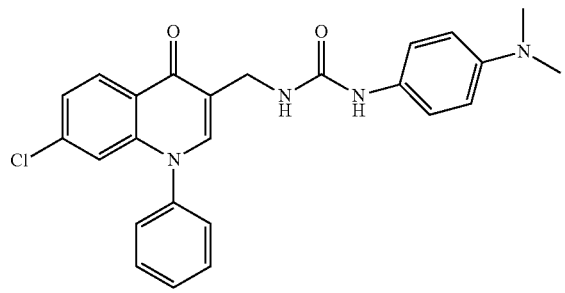 [SMILES: CN(C)c1ccc(NC(=O)NCc2cn(-c3ccccc3)c3cc(Cl)ccc3c2=O)cc1]

1-(7-Chloro-4-oxo-1-phenyl-1,4-dihydro-quinolin-3-yl-methyl)-3-(4-dimethylamino-phenyl)-urea was prepared starting from intermediate D and 4-(dimethylamino)-phenyl-isocyanate. MS calcd. for $C_{25}H_{24}ClN_4O_2$ [(M+H)$^+$] 447.2, obsd. 447.2.

Example I-203

1-(7-Chloro-4-oxo-1-phenyl-1,4-dihydro-quinolin-3-ylmethyl)-3-(4-methoxy-phenyl)-urea

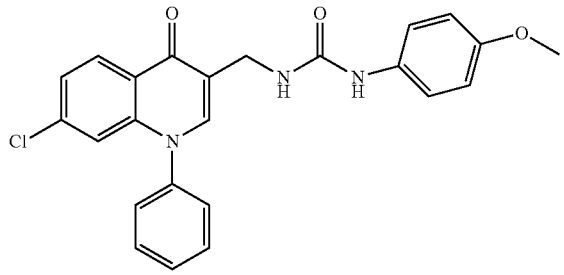 [SMILES: COc1ccc(NC(=O)NCc2cn(-c3ccccc3)c3cc(Cl)ccc3c2=O)cc1]

1-(7-Chloro-4-oxo-1-phenyl-1,4-dihydro-quinolin-3-ylmethyl)-3-(4-methoxy-phenyl)-urea was prepared starting from intermediate D and 4-(methoxy)-phenylisocyanate. MS calcd. for $C_{24}H_{21}ClN_3O_3$ [(M+H)$^+$] 434.1, obsd. 434.0.

Example I-204

1-(4-Chloro-3-fluoro-phenyl)-3-(7-chloro-4-oxo-1-phenyl-1,4-dihydro-quinolin-3-yl-methyl)-urea

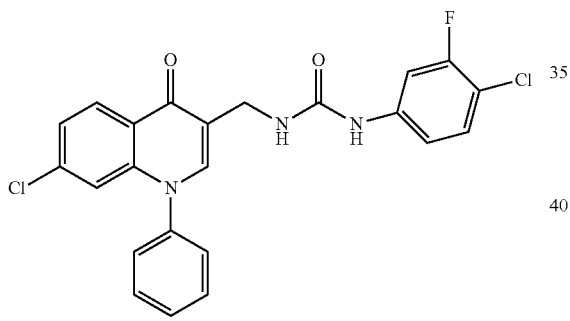

1-(4-Chloro-3-fluoro-phenyl)-3-(7-chloro-4-oxo-1-phenyl-1,4-dihydro-quinolin-3-yl-methyl)-urea was prepared starting from intermediate D and 4-chloro-3-fluoro-phenyl-isocyanate. MS calcd. for $C_{23}H_{17}Cl_2FN_3O_2$ [(M+H)$^+$] 456.1, obsd. 455.9.

Example I-205

1-(4-trifluoromethoxy-phenyl)-3-(7-chloro-4-oxo-1-phenyl-1,4-dihydro-quinolin-3-yl-methyl)-urea

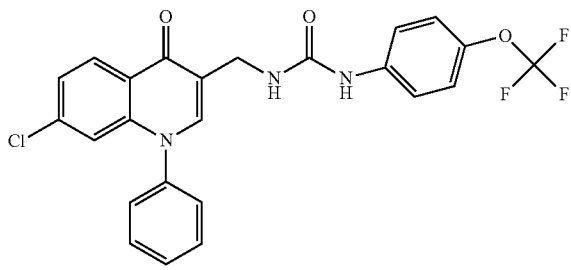 [SMILES: O=C(NCc1cn(-c2ccccc2)c2cc(Cl)ccc2c1=O)Nc1ccc(OC(F)(F)F)cc1]

1-(4-trifluoromethoxy-phenyl)-3-(7-chloro-4-oxo-1-phenyl-1,4-dihydro-quinolin-3-yl-methyl)-urea was prepared starting from intermediate D and 4-trifluoromethoxy-phenyl-isocyanate. MS calcd. for $C_{24}H_8ClF_3N_3O_3$ [(M+H)$^+$] 488.1, obsd. 488.0.

Example I-206

4-[3-(7-Chloro-4-oxo-1-phenyl-1,4-dihydro-quinolin-3-ylmethyl)-ureido]-benzoic acid methyl ester

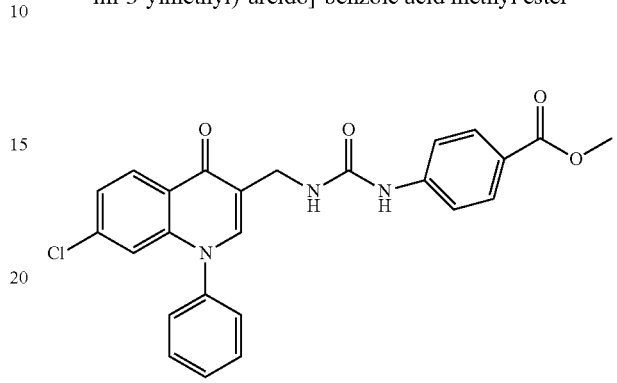

4-[3-(7-Chloro-4-oxo-1-phenyl-1,4-dihydro-quinolin-3-ylmethyl)-ureido]-benzoic acid methyl ester was prepared starting from intermediate D and 4-isocyanato-benzoic acid methyl ester. MS calcd. for $C_{25}H_{21}ClN_3O_4$ [(M+H)$^+$] 462.1, obsd. 462.0.

Example I-207

7-Chloro-3-(isoquinolin-1-ylaminomethyl)-4-oxo-1-phenyl-1,4-dihydro-quinoline-2-carboxylic acid methyl ester

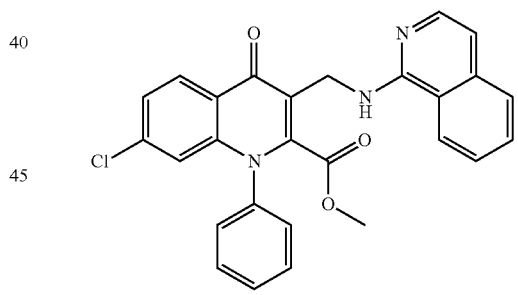

In a 10 mL round-bottomed flask, methyl 3-(bromomethyl)-7-chloro-4-oxo-1-phenyl-1,4-dihydroquinoline-2-carboxylate (50 mg, 0.123 mmol) was combined with methylene chloride (5 mL) to give a colorless solution. To this solution, N,N-diisopropylethylamine and 1-aminoisoquinoline were added. The reaction mixture was stirred at room temperature overnight. The reaction mixture was poured into 25 mL H$_2$O and extracted with ethyl acetate (1×25 mL). The organic layer was washed with 1 M HCl (1×10 mL), saturated aqueous NaHCO$_3$ (1×10 mL), and H$_2$O (1×10 mL). The organic layers were dried over Na$_2$SO$_4$, filtered, and concentrated in vacuo. The crude material was purified by flash chromatography (silica gel, 4 g, 5% to 40% ethyl acetate in hexanes), giving 7-chloro-3-(isoquinolin-1-ylaminomethyl)-4-oxo-1-phenyl-1,4-dihydro-quinoline-2-carboxylic acid methyl ester (4 mg, 7%). MS calcd. for $C_{27}H_{20}ClN_3O_3$ [(M+H)$^+$] 470.1, obsd. 470.9.

Example I-208

7-Chloro-4-oxo-1-phenyl-3-(quinazolin-4-ylaminomethyl)-1,4-dihydro-quinoline-2-carboxylic acid methyl ester

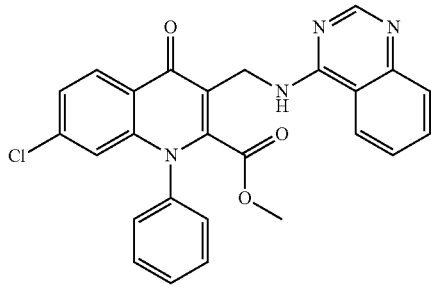 [SMILES: COC(=O)c1c(CNc2nccc3ccccc23)c(=O)c2ccc(Cl)cc2n1-c1ccccc1]

In a 10 mL round-bottomed flask, methyl 3-(bromomethyl)-7-chloro-4-oxo-1-phenyl-1,4-dihydroquinoline-2-carboxylate (50 mg, 0.123 mmol) was combined with dichloromethane (5 mL) to give a colorless solution. Quinazolin-4-ylamine (17.8 mg, 0.123 mmol) and N,N-diisopropylethylamine (19.1 mg, 0.148 mmol) were added. The reaction mixture was stirred at room temperature overnight. TLC showed only starting material present after this time. Sodium hydride (60% suspension) (9.8 mg, 0.264 mmol) and 2 mL of THF were added. The reaction mixture was stirred at room temperature. The reaction mixture was poured into 25 mL H$_2$O and extracted with ethyl acetate (1×25 mL). The organic layer was washed with 1 M HCl (1×10 mL), sat aqueous NaHCO$_3$ (1×10 mL), and H$_2$O (1×10 mL). The organic layers were dried over Na$_2$SO$_4$, filtered and concentrated in vacuo. The crude material was purified by flash chromatography (silica gel, 4 g, 30% to 100% ethyl acetate in hexanes) to yield 7-chloro-4-oxo-1-phenyl-3-(quinazolin-4-ylaminomethyl)-1,4-dihydro-quinoline-2-carboxylic acid methyl ester. MS calcd. for C$_{26}$H$_{19}$ClN$_4$O$_3$ [(M+H)$^+$] 471.1, obsd. 471.1.

Example I-209

7-Chloro-3-{[(morpholine-4-carbonyl)-amino]-methyl}-4-oxo-1-phenyl-1,4-dihydro-quinoline-2-carboxylic acid methyl ester

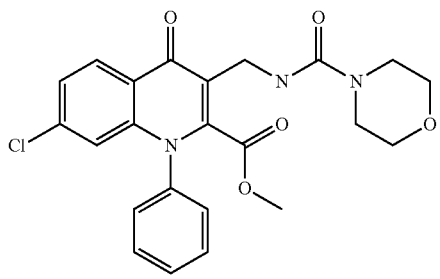 [SMILES: COC(=O)c1c(CNC(=O)N2CCOCC2)c(=O)c2ccc(Cl)cc2n1-c1ccccc1]

In a 50 mL flask, 3-aminomethyl-7-chloro-1-phenyl-1H-quinolin-4-one hydrochloride salt (intermediate I) (50 mg, 0.132 mmol) and morpholine-4-carbonyl chloride (21.7 mg, 0.145 mmol) were combined with CH$_2$Cl$_2$ (5 mL) and stirred at 0° C. for 10 min. Then N,N-diisopropylethylamine was added at 0° C. over 1 hr. The reaction mixture was stirred at and stirred at 0° C. for 4 hr. The reaction mixture was concentrated. The crude product was purified using preparative reverse phase HPLC to yield the product 7-chloro-3-{[(morpholine-4-carbonyl)-amino]-methyl}-4-oxo-1-phenyl-1,4-dihydro-quino-line-2-carboxylic acid methyl ester. MS calcd. for C$_{23}$H$_{23}$ClN$_3$O$_5$ [(M+H)$^+$] 456.1, obsd. 455.9.

Example I-210

7-Chloro-4-oxo-3-(phenoxycarbonylamino-methyl)-1-phenyl-1,4-dihydro-quinoline-2-carboxylic acid methyl ester

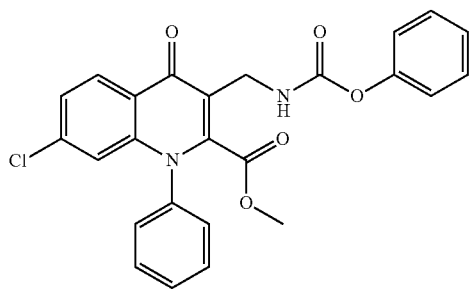 [SMILES: COC(=O)c1c(CNC(=O)Oc2ccccc2)c(=O)c2ccc(Cl)cc2n1-c1ccccc1]

A mixture of 3-aminomethyl-7-chloro-4-oxo-1-phenyl-1,4-dihydro-quinoline-2-carboxylic acid methyl ester hydrochloride (intermediate I) (0.050 g, 0.130 mmol), phenyl chloroformate (0.020 mL, 0.59 mmol) and N,N-diisopropylethylamine (0.10 mL, 0.574 mmol) in CH$_2$Cl$_2$ (10 mL) was stirred at room temperature, then concentrated to dryness. The crude product was purified using preparative reverse-phase HPLC to provide 7-chloro-4-oxo-3-(phenoxycarbonylamino-methyl)-1-phenyl-1,4-dihydro-quinoline-2-carboxylic acid methyl ester. MS calcd. for C$_{25}$H$_{20}$ClN$_2$O$_5$ [(M+H)$^+$] 463.1, obsd. 462.9.

Example I-211

7-Chloro-3-{[(4-methanesulfonyl-benzoyl)-methylamino]-methyl}-4-oxo-1-phenyl-1,4-dihydro-quinoline-2-carboxylic acid methyl ester

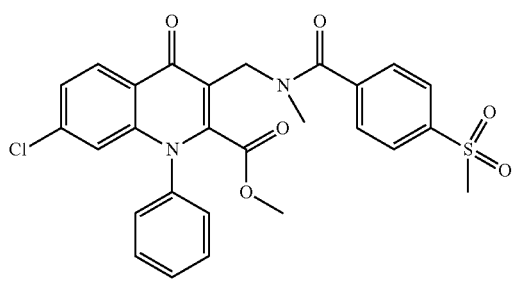 [SMILES: COC(=O)c1c(CN(C)C(=O)c2ccc(S(C)(=O)=O)cc2)c(=O)c2ccc(Cl)cc2n1-c1ccccc1]

To a stirred solution of N-methyl-4-(methylsulfonyl)benzamide (25.2 mg, 0.118 mmol) in NMP was added sodium hydride (60% suspension) (3.54 mg, 0.148 mmol). After 5 min., methyl 3-(bromomethyl)-7-chloro-4-oxo-1-phenyl-1,4-dihydroquinoline-2-carboxylate (40 mg, 0.098 mmol) was added and the mixture was allowed to stir for 3 hr. at room temp. The mixture was then quenched with water and acidified with 1N aqueous HCl. The mixture was then extracted with $CH_2Cl_2$. The extracts were dried ($Na_2SO_4$), filtered and concentrated in vacuo. Preparative reverse-phase HPLC afforded 7-chloro-3-{[(4-methanesulfonyl-benzoyl)-methyl-amino]-methyl}-4-oxo-1-phenyl-1,4-dihydro-quinoline-2-carboxylic acid methyl ester (11 mg, 20%) as an off-white foam. MS calcd. for $C_{27}H_{23}ClN_2O_6S$ [(M+H)$^+$] 539, obsd. 539.

Biological Examples

In Vitro JNK1 Assay

Phosphorylation of GST-c-Jun protein (amino acid residues 1-79) was measured as JNK1 activity. The kinase reaction contained 0.2 nM of active JNK1 kinase and 26.7 nM of GST-c-Jun in the presence of 2 μM ATP. The reaction buffer contained 50 mM HEPES, pH 7.0, mM $MgCl_2$, 1 mM DTT, 0.1 mM $Na_3VO_4$ and 0.2 mg/mL BSA. After 30 min. incubation at room temperature, the reaction was terminated by adding buffer containing 8 mM EDTA and a polyclonal anti-phospho-c-Jun antibody (Cell Signaling #9261L), followed by an additional incubation of 30 min. at room temperature. A detection reagent mixture containing 2 nM Europium labeled goat anti-rabbit antibody and 20 nM of Allophycocyanin labeled anti-GST antibody (Columbia Biosciences #D3-1310), was then added. Time-resolved Fluorescence Resonance Energy Transfer (TR-FRET) signals were measured 1 hr. later on the EnVision reader (Perkin Elmer). Compound potency was assessed at 10 serially diluted concentrations. Percentage of inhibition at each concentration was determined to generate an $IC_{50}$ value for each compound.

TABLE II

Representative Compound $IC_{50}$'s for JNK1

| Compound | JNK1, $IC_{50}$ (μM) | HK-2, $EC_{50}$ (μM) |
| --- | --- | --- |
| I-1 | 0.001 | 0.5 |
| I-2 | 0.007 | 2.7 |
| I-3 | 0.009 | 3.1 |
| I-4 | 0.014 | 3.0 |
| I-5 | 0.025 | N.D. |
| I-6 | 0.029 | N.D. |
| I-7 | 0.014 | 4.5 |
| I-8 | 0.025 | 4.2 |
| I-9 | 0.004 | 1.2 |
| I-10 | 0.029 | 5.2 |
| I-11 | 0.047 | 15 |
| I-12 | 0.007 | 2.5 |
| I-13 | 0.035 | 37 |
| I-14 | 0.036 | 25 |
| I-15 | 0.064 | 54 |
| I-16 | 0.066 | 35 |
| I-17 | 0.14 | N.D. |
| I-18 | 0.15 | N.D. |
| I-19 | 0.18 | 30 |
| I-20 | 0.24 | N.D. |
| I-21 | 0.46 | N.D. |
| I-22 | 0.33 | 25 |
| I-23 | 0.78 | 87 |
| I-24 | 0.14 | 11 |
| I-25 | 0.051 | 9.6 |
| I-26 | 0.098 | 14 |
| I-27 | 0.082 | 8.0 |
| I-28 | 0.091 | 9.7 |
| I-29 | 0.013 | 5.0 |
| I-30 | 0.018 | 42 |
| I-31 | 0.031 | 30 |
| I-32 | 0.038 | 29 |
| I-33 | 0.041 | 100 |
| I-34 | 0.044 | 12 |
| I-35 | 0.054 | 100 |
| I-36 | 0.055 | 100 |
| I-37 | 0.072 | 25 |
| I-38 | 0.072 | 16 |
| I-39 | 0.076 | 10 |
| I-40 | 0.084 | 100 |
| I-41 | 0.088 | 28 |
| I-42 | 0.089 | 25 |
| I-43 | 0.10 | 100 |
| I-44 | 0.11 | N.D. |
| I-45 | 0.11 | N.D. |
| I-46 | 0.14 | N.D. |
| I-47 | 0.17 | N.D. |
| I-48 | 0.18 | N.D. |
| I-49 | 0.23 | N.D. |
| I-50 | 0.30 | N.D. |
| I-51 | 0.33 | N.D. |
| I-52 | 0.38 | N.D. |
| I-53 | 0.56 | N.D. |
| I-54 | 0.67 | N.D. |
| I-55 | 0.70 | N.D. |
| I-56 | 0.19 | N.D. |
| I-57 | 0.08 | 26 |
| I-58 | 0.63 | N.D. |
| I-59 | 1.7 | N.D. |
| I-60 | 1.9 | N.D. |
| I-61 | 0.43 | N.D. |
| I-62 | 0.011 | 13 |
| I-63 | 0.017 | 3.8 |
| I-64 | 0.018 | 100 |
| I-65 | 0.019 | 40 |
| I-66 | 0.019 | 29 |
| I-67 | 0.020 | 6.3 |
| I-68 | 0.021 | 17 |
| I-69 | 0.024 | 39 |
| I-70 | 0.024 | 33 |
| I-71 | 0.026 | 17 |
| I-72 | 0.027 | 100 |
| I-73 | 0.029 | 100 |
| I-74 | 0.030 | 27 |
| I-75 | 0.031 | 14 |
| I-76 | 0.034 | 48 |
| I-77 | 0.047 | 63 |
| I-78 | 0.049 | 22 |
| I-79 | 0.055 | 46 |
| I-80 | 0.056 | 12 |
| I-81 | 0.065 | 100 |
| I-82 | 0.071 | 19 |
| I-83 | 0.081 | 12 |
| I-84 | 0.10 | 52 |
| I-85 | 0.11 | 72 |
| I-86 | 0.11 | N.D. |
| I-87 | 0.12 | N.D. |
| I-88 | 0.25 | N.D. |
| I-89 | 0.24 | 31 |
| I-90 | 0.13 | N.D. |
| I-91 | 0.016 | 19 |
| I-92 | 0.021 | 26 |
| I-93 | 0.033 | 100 |
| I-94 | 0.036 | 14 |
| I-95 | 0.040 | 22 |
| I-96 | 0.055 | 100 |
| I-97 | 0.069 | 39 |
| I-98 | 0.22 | N.D. |
| I-99 | 0.052 | 6.2 |
| I-100 | 0.090 | 29 |
| I-101 | 0.60 | N.D. |
| I-102 | 0.74 | N.D. |
| I-103 | 0.040 | 12 |
| I-104 | 0.12 | 100 |
| I-105 | 0.15 | N.D. |
| I-106 | 0.052 | 50 |
| I-107 | 0.10 | N.D. |
| I-108 | 0.12 | 47 |
| I-109 | 0.004 | 5.7 |
| I-110 | 0.004 | 4.0 |
| I-111 | 0.005 | 1.3 |
| I-112 | 0.006 | 1.2 |

TABLE II-continued

Representative Compound IC$_{50}$'s for JNK1

| Compound | JNK1, IC$_{50}$ (µM) | HK-2, EC$_{50}$ (µM) |
|---|---|---|
| I-113 | 0.007 | 2.0 |
| I-114 | 0.007 | 4.1 |
| I-115 | 0.008 | 2.4 |
| I-116 | 0.008 | 2.2 |
| I-117 | 0.010 | 3.8 |
| I-118 | 0.011 | 3.7 |
| I-119 | 0.013 | 6.3 |
| I-120 | 0.015 | 3.0 |
| I-121 | 0.015 | 1.8 |
| I-122 | 0.015 | 3.3 |
| I-123 | 0.016 | 2.2 |
| I-124 | 0.017 | 7.8 |
| I-125 | 0.022 | 18 |
| I-126 | 0.029 | 14 |
| I-127 | 0.031 | 38 |
| I-128 | 0.035 | 100 |
| I-129 | 0.050 | 11 |
| I-130 | 0.22 | 100 |
| I-131 | 0.64 | N.D. |
| I-132 | 0.015 | 9.2 |
| I-133 | 0.006 | 13 |
| I-134 | 0.007 | 1.9 |
| I-135 | 0.008 | 4.8 |
| I-136 | 0.012 | 7.9 |
| I-137 | 0.012 | 10 |
| I-138 | 0.013 | 10 |
| I-139 | 0.013 | 9.8 |
| I-140 | 0.014 | 10 |
| I-141 | 0.015 | 7.0 |
| I-142 | 0.017 | 9.7 |
| I-143 | 0.039 | 1.0 |
| I-144 | 0.048 | 8.8 |
| I-145 | 0.065 | 100 |
| I-146 | 0.10 | N.D. |
| I-147 | 0.20 | N.D. |
| I-148 | 0.43 | N.D. |
| I-149 | 0.67 | N.D. |
| I-150 | 0.012 | 7.7 |
| I-151 | 0.039 | 14 |
| I-152 | 0.018 | 7.8 |
| I-153 | 0.023 | 4.6 |
| I-154 | 0.026 | 9.9 |
| I-155 | 0.027 | 14 |
| I-156 | 0.030 | 8.7 |
| I-157 | 0.038 | 16 |
| I-158 | 0.079 | 10 |
| I-159 | 0.17 | 43 |
| I-160 | 0.026 | 22 |
| I-161 | 0.032 | 18 |
| I-162 | 0.039 | 38 |
| I-163 | 0.047 | 14 |
| I-164 | 0.054 | 8.9 |
| I-165 | 0.065 | 100 |
| I-166 | 0.073 | 100 |
| I-167 | 0.18 | N.D. |
| I-168 | 0.10 | 32 |
| I-169 | 0.004 | 2.4 |
| I-170 | 0.01 | 44 |
| I-171 | 0.023 | 88 |
| I-172 | 0.079 | 100 |
| I-173 | 0.14 | N.D. |
| I-174 | 0.35 | N.D. |
| I-175 | 0.70 | N.D. |
| I-176 | 0.85 | N.D. |
| I-177 | 1.2 | N.D. |
| I-178 | 2.7 | N.D. |
| I-179 | 2.0 | N.D. |
| I-180 | 0.12 | N.D. |
| I-181 | 0.20 | N.D. |
| I-182 | 0.70 | N.D. |
| I-183 | 0.91 | N.D. |
| I-184 | 0.92 | N.D. |
| I-185 | 1.1 | N.D. |
| I-186 | 1.2 | N.D. |
| I-187 | 1.4 | N.D. |
| I-188 | 1.7 | N.D. |
| I-189 | 2.0 | N.D. |
| I-190 | 2.1 | N.D. |
| I-191 | 0.24 | N.D. |
| I-192 | 0.06 | N.D. |
| I-193 | 0.18 | N.D. |
| I-194 | 0.19 | N.D. |
| I-195 | 0.58 | N.D. |
| I-196 | 1.1 | N.D. |
| I-197 | 2.1 | N.D. |
| I-198 | 2.2 | N.D. |
| I-199 | 1.6 | N.D. |
| I-200 | 0.85 | N.D. |
| I-201 | 0.55 | N.D. |
| I-202 | 0.63 | N.D. |
| I-203 | 0.65 | N.D. |
| I-204 | 1.1 | N.D. |
| I-205 | 1.8 | N.D. |
| I-206 | 2.7 | N.D. |
| I-207 | 0.11 | N.D. |
| I-208 | 0.06 | 8.4 |
| I-209 | 0.15 | N.D. |
| I-210 | 1.1 | N.D. |
| I-211 | 0.92 | N.D. |

Cell-Based Assay for JNK Inhibitors

The cell-based assay employed the in-cell ELISA method to determine the ability of compounds to prevent the generation of phospho(Ser63)-c-jun in HK-2 cells (human proximal tubule cells) in response to stimulation with tumor necrosis factor α (TNFα). In brief, for quantification of phospho (Ser63)-c-jun, the cells (in 96-well format) were fixed and permeablized then incubated sequentially with a rabbit anti-phospho-c-jun First Antibody specific for the presence of the phospho-Ser63 epitope and a donkey anti-rabbit IgG Second Antibody linked to horseradish peroxidase (HRP) for colorimetric quantitation of binding. For determination of non-specific binding of the First Antibody, Blank wells were pre-incubated with a mouse anti-phospho(Ser63)-c-jun Blocking Antibody that prevented specific binding of the First Antibody to the phospho-Ser63 epitope, but which was not recognized by the donkey anti-rabbit IgG Second Antibody. Thus the remaining signal represented non-specific binding only and this was used as the value for 100% inhibition (Blank value). Blank wells received no TNFα stimulation or compound. Additional Control wells received TNFα stimulation, but no compound. The signal obtained in this case was considered the value for 0% inhibition (Control value).

Stock cultures of HK-2 cells (ATCC, Manassas, Va.) were grown under a 5% CO2/95% O2 atmosphere at 37 degrees C. in Keratinocyte-SFM medium (KSFM, Invitrogen, Grand Island, N.Y.) containing 5 µg/L epidermal growth factor and 5 mg/L bovine pituitary extract (both supplied with the medium), additionally supplemented with 10% (v/v) fetal calf serum (FCS; Invitrogen, Grand Island, N.Y.) and 1% (v/v) antibiotic-antimycotic (ABAM: Sigma, St. Louis, Mo.). For assays, cells were seeded in collagen coated 96-well polystyrene plates (BD Biosciences, Franklin Lakes, N.J.) at a density of 40,000 cells/well and cultured for 24 h in the same medium (100 µL/well) followed by a further 16-24 h in 100 µL of similar medium, but without FCS. The medium was then replaced by 100 µL/well of Assay Medium (KSFM supplemented only with ABAM as above and 0.2% (w/v) low-endotoxin bovine serum albumin (BSA, Sigma, St. Louis, Mo.). Stock solutions of test compounds in dimethyl-sulfoxide (DMSO) were diluted into Assay Medium to the desired concentrations such that the final DMSO concentration was 1% (v/v) in all cases. For determination of $EC_{50}$s, six concentrations of compound were used (4-fold dilutions). Assay Medium for Blank and Control wells was made 1% with respect to DMSO, but without compound. To initiate the assay, the medium was replaced with the Assay Medium containing compound and culture was continued for 60 minutes after which time 5 µL of a solution of TNFα (Sigma, St. Louis, Mo.) in phosphate buffered saline (PBS; Invitrogen, Grand Island, N.Y.) was added to give a final concentration of 10 ng/mL TNFα (except Blank and PBS Control wells that received PBS alone). Cells were incubated for a further 30 minutes and then the medium was aspirated and the wells washed with 100 µL/well PBS followed by the addition of 100 µL 3.7% (v/v) Formaldehyde (Fisher Scientific, Fair Lawn, N.J.) in PBS. Plates were then allowed to stand at room temperature for 20 minutes before being washed with 200 µL/well of PBS. (Further steps were performed immediately or the plates were stored at 4 degrees C. and the assay completed the next day.) To each well was added 100 µL 1% (v/v) TritonX-100 (Sigma, St. Louis, Mo.) in PBS followed by 20 minutes standing at room temperature, washing with 200 µL/well PBS, the addition of 100 µL/well of Quenching buffer (1% (v/v) hydrogen peroxide (Sigma, St. Louis, Mo.) and 0.1% (w/v) sodium azide (Fisher Scientific, Fair Lawn, N.J.)) in PBS and a further 20 minutes at room temperature. Plates were then washed twice with 200 µL/well of 0.1% (v/v) Tween-20 (Teknova, Hollister, Calif.) in PBS before addition of 200 µL/well of 2% BSA/0.1% Tween-20 in PBS and a further 1 hour at room temperature. At this time, buffer was removed from Blank wells and replaced with 90 µL/well of mouse anti-phospho-c-jun-Ser63 (BD Bioscience, 558036) diluted 1:4000 in PBS containing 1% BSA/0.1% Tween-20 (Antibody Dilution Buffer). All other wells are replaced with 90 µL/well of rabbit anti-phospho-c-jun-Ser63 (Cell Signaling, 9261) diluted 1:250 in Antibody Dilution Buffer. After a further one hour, rabbit anti-phospho-c-jun-Ser63 is added directly to the solution in the Blank wells resulting in 1:250 dilution of this antibody. Plates were then placed on a slowly rotating platform at 4 degrees C. overnight. Wells were then washed thrice with 200 µL/well PBS/0.1% Tween-20. After addition of the third wash, the plates were placed on a slowly rotating platform for 15 minutes at room temperature. The final PBS/Tween20 wash was then replaced with 100 µL/well of donkey anti-rabbit HRP-labeled Second Antibody (Jackson ImmunoResearch Laboratory, West Grove, Pa.) diluted 1:10,000 in Antibody Dilution Buffer and the plates placed on a slowly rotating platform for 1 hour at room temperature. Wells were then washed four times with 200 µL/well PBS/ 0.1% Tween-20, including slow rotation for 30 minutes for the third wash and 10 minutes for the final wash. The wells were then washed once with 200 µL PBS without Tween-20. To each well was then added 1004 of TMB solution (Sigma, St. Louis, Mo.) followed by incubation at room temperature for 8 minutes and then the addition of 100 µL/well of 3% v/v phosphoric acid (Sigma, St. Louis, Mo.). Absorbance was determined at a 450 nm wavelength using a spectrophotometer (Molecular Devices SpectraMax 250).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

We claim:
1. A compound of formula I

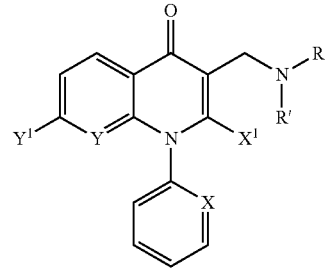

wherein:
R is —C(=O)A, —C(=O)OA, —C(=O)NHA, —C(=N—C=N)A, —C(=N—C=N)NHA, or A;
A is lower alkyl, phenyl, cycloalkyl, adamantyl, heterocycloalkyl, heteroaryl, or bicyclic heteroaryl, optionally substituted with one or more $A^1$;
each $A^1$ is independently $A^2$ or $A^3$;
each $A^2$ is independently hydroxy, halo, or oxo;
each $A^3$ is independently lower alkyl, lower alkoxy, phenyl, benzyl, heterocycloalkyl, bicyclic heterocycloalkyl, heteroaryl, amino, lower alkyl amino, lower dialkyl amino, amido, lower alkyl ester, sulfonyl, sulfonamido, —C(=O), or —C(=O)O, optionally substituted with one or more halo, hydroxy, lower alkyl, lower alkoxy, phenyl, hydroxy cycloalkyl, amino, lower alkyl amino, lower dialkyl amino, carbamic acid tert-butyl ester, sulfonyl, lower alkyl sulfonyl heterocycloalkyl, or hydroxy lower alkyl;
R' is H or methyl;
X is CX';
X' is H or halo;
$X^1$ is H, 2-oxazolyl, dimethyl amido, or lower alkyl ester;
Y is CH or N; and
$Y^1$ is H, halo, lower alkoxy, or halo lower alkyl;
or a pharmaceutically acceptable salt thereof.
2. The compound of claim 1, wherein R' is H.
3. The compound of claim 2, wherein X is CH.
4. The compound of claim 3, wherein Y is CH.
5. The compound of claim 4, wherein $Y^1$ is Cl.
6. The compound of claim 5, wherein R is —C(=O)A.
7. The compound of claim 6, wherein A is phenyl, heteroaryl or bicyclic heteroaryl, optionally substituted with one or more $A^1$.
8. The compound of claim 7, wherein $X^1$ is 2-oxazolyl.
9. The compound of claim 7, wherein $X^1$ is dimethyl amido.
10. The compound of claim 7, wherein $X^1$ is H or methyl ester.
11. The compound of claim 3, wherein Y is N, $Y^1$ is H or $CF_3$, and $X^1$ is 2-oxazolyl.
12. The compound of claim 5, wherein R is —C(=O) NHA.
13. The compound of claim 7, wherein A is phenyl, optionally substituted with one or more $A^1$.
14. A compound selected from the group consisting of:
1-Benzyl-2-oxo-1,2-dihydro-pyridine-4-carboxylic acid (7-chloro-2-oxazol-2-yl-4-oxo-1-phenyl-1,4-dihydro-quinolin-3-ylmethyl)-amide;

N-(7-Chloro-2-oxazol-2-yl-4-oxo-1-phenyl-1,4-dihydro-quinolin-3-ylmethyl)-2-morpholin-4-yl-isonicotinamide;
N-(7-Chloro-2-oxazol-2-yl-4-oxo-1-phenyl-1,4-dihydro-quinolin-3-ylmethyl)-6-morpholin-4-yl-nicotinamide;
N-(7-Chloro-2-oxazol-2-yl-4-oxo-1-phenyl-1,4-dihydro-quinolin-3-ylmethyl)-terephthalamide;
5-[(7-Chloro-2-oxazol-2-yl-4-oxo-1-phenyl-1,4-dihydro-quinolin-3-ylmethyl)-carbamoyl]-pyridine-2-carboxylic acid methyl ester;
6-Chloro-N-(7-chloro-2-oxazol-2-yl-4-oxo-1-phenyl-1,4-dihydro-quinolin-3-ylmethyl)-nicotinamide;
3,4,5,6-Tetrahydro-2H-[1,2]bipyridinyl-5'-carboxylic acid (7-chloro-2-oxazol-2-yl-4-oxo-1-phenyl-1,4-dihydro-quinolin-3-ylmethyl)-amide;
Benzo[1,3]dioxole-5-carboxylic acid (7-chloro-2-oxazol-2-yl-4-oxo-1-phenyl-1,4-dihydro-quinolin-3-ylmethyl)-amide;
1-Benzyl-2-oxo-1,2-dihydro-pyridine-4-carboxylic acid (2-oxazol-2-yl-4-oxo-1-phenyl-1,4-dihydro-[1,8]naphthyridin-3-ylmethyl)-amide;
6-Morpholin-4-yl-N-(2-oxazol-2-yl-4-oxo-1-phenyl-1,4-dihydro-[1,8]naphthyridin-3-ylmethyl)-nicotinamide;
1-Methyl-1H-pyrazole-4-carboxylic acid (2-oxazol-2-yl-4-oxo-1-phenyl-1,4-dihydro-[1,8]naphthyridin-3-ylmethyl)-amide;
4-Hydroxymethyl-3,4,5,6-tetrahydro-2H-[1,2]bipyridinyl-5'-carboxylic acid (2-oxazol-2-yl-4-oxo-1-phenyl-1,4-dihydro-[1,8]naphthyridin-3-ylmethyl)-amide;
7-Chloro-3-{[(6-morpholin-4-yl-pyridine-3-carbonyl)-amino]-methyl}-4-oxo-1-phenyl-1,4-dihydro-quinoline-2-carboxylic acid dimethylamide;
7-Chloro-3-{[(2-morpholin-4-yl-thiazole-5-carbonyl)-amino]-methyl}-4-oxo-1-phenyl-1,4-dihydro-quinoline-2-carboxylic acid dimethylamide;
7-Chloro-3-[(4-methoxy-benzoylamino)-methyl]-4-oxo-1-phenyl-1,4-dihydro-quinoline-2-carboxylic acid dimethylamide;
3-{[(Benzothiazole-6-carbonyl)-amino]-methyl}-7-chloro-4-oxo-1-phenyl-1,4-dihydro-quinoline-2-carboxylic acid dimethylamide;
7-Chloro-3-[(4-morpholin-4-yl-benzoylamino)-methyl]-4-oxo-1-phenyl-1,4-dihydro-quinoline-2-carboxylic acid dimethylamide;
7-Chloro-3-[(4-oxazol-5-yl-benzoylamino)-methyl]-4-oxo-1-phenyl-1,4-dihydro-quinoline-2-carboxylic acid dimethylamide;
7-Chloro-3-[(4-methanesulfonyl-benzoylamino)-methyl]-4-oxo-1-phenyl-1,4-dihydro-quinoline-2-carboxylic acid dimethylamide;
7-Chloro-3-[(4-fluoro-benzoylamino)-methyl]-4-oxo-1-phenyl-1,4-dihydro-quinoline-2-carboxylic acid dimethylamide;
7-Chloro-3-{[(2,3-dihydro-benzo[1,4]dioxine-6-carbonyl)-amino]-methyl}-4-oxo-1-phenyl-1,4-dihydro-quinoline-2-carboxylic acid dimethylamide;
3-{[(1-Benzyl-2-oxo-1,2-dihydro-pyridine-4-carbonyl)-amino]-methyl}-7-chloro-4-oxo-1-phenyl-1,4-dihydro-quinoline-2-carboxylic acid dimethylamide;
7-Chloro-3-{[(1-methyl-1H-pyrazole-4-carbonyl)-amino]-methyl}-4-oxo-1-phenyl-1,4-dihydro-quinoline-2-carboxylic acid dimethylamide;
4-Hydroxymethyl-3,4,5,6-tetrahydro-2H-[1,2]bipyridinyl-5'-carboxylic acid (7-chloro-2-dimethylcarbamoyl-4-oxo-1-phenyl-1,4-dihydro-quinolin-3-ylmethyl)-amide;
4-(2-Hydroxy-ethyl)-3,4,5,6-tetrahydro-2H-[1,2]bipyridinyl-5'-carboxylic acid (7-chloro-2-dimethylcarbamoyl-4-oxo-1-phenyl-1,4-dihydro-quinolin-3-ylmethyl)-amide;
7-Chloro-3-({[2-(4-hydroxymethyl-piperidin-1-yl)-thiazole-5-carbonyl]-amino}-methyl)-4-oxo-1-phenyl-1,4-dihydro-quinoline-2-carboxylic acid dimethylamide;
7-Chloro-3-[({2-[4-(2-hydroxy-ethyl)-piperidin-1-yl]-thiazole-5-carbonyl}-amino)-methyl]-4-oxo-1-phenyl-1,4-dihydro-quinoline-2-carboxylic acid dimethylamide;
3,4,5,6-Tetrahydro-2H-[1,2]bipyridinyl-5'-carboxylic acid (7-chloro-2-dimethylcarbamoyl-4-oxo-1-phenyl-1,4-dihydro-quinolin-3-ylmethyl)-amide;
1-Benzyl-2-oxo-1,2-dihydro-pyridine-4-carboxylic acid (7-chloro-4-oxo-1-phenyl-1,4-dihydro-quinolin-3-ylmethyl)-amide;
1-Methyl-1H-pyrazole-4-carboxylic acid (7-chloro-4-oxo-1-phenyl-1,4-dihydro-quinolin-3-ylmethyl)-amide;
N-(7-Chloro-4-oxo-1-phenyl-1,4-dihydro-quinolin-3-ylmethyl)-2-morpholin-4-yl-isonicotinamide;
N-(7-Chloro-4-oxo-1-phenyl-1,4-dihydro-quinolin-3-ylmethyl)-2-pyrrolidin-1-yl-isonicotinamide;
3H-Benzoimidazole-5-carboxylic acid (7-chloro-4-oxo-1-phenyl-1,4-dihydro-quinolin-3-ylmethyl)-amide;
1-(4-Chloro-benzyl)-2-oxo-1,2-dihydro-pyridine-4-carboxylic acid (7-chloro-4-oxo-1-phenyl-1,4-dihydro-quinolin-3-ylmethyl)-amide;
N-(7-Chloro-4-oxo-1-phenyl-1,4-dihydro-quinolin-3-ylmethyl)-6-methoxy-nicotinamide;
N-(7-Chloro-4-oxo-1-phenyl-1,4-dihydro-quinolin-3-ylmethyl)-4-sulfamoyl-benzamide;
1-Phenyl-1H-pyrazole-4-carboxylic acid (7-chloro-4-oxo-1-phenyl-1,4-dihydro-quinolin-3-ylmethyl)-amide;
1-(3-Methoxy-benzyl)-2-oxo-1,2-dihydro-pyridine-4-carboxylic acid (7-chloro-4-oxo-1-phenyl-1,4-dihydro-quinolin-3-ylmethyl)-amide;
1-(2-Chloro-benzyl)-2-oxo-1,2-dihydro-pyridine-4-carboxylic acid (7-chloro-4-oxo-1-phenyl-1,4-dihydro-quinolin-3-ylmethyl)-amide;
N-(7-Chloro-4-oxo-1-phenyl-1,4-dihydro-quinolin-3-ylmethyl)-6-morpholin-4-yl-nicotinamide;
N-(7-Chloro-4-oxo-1-phenyl-1,4-dihydro-quinolin-3-ylmethyl)-2-dimethylamino-isonicotinamide;
Benzothiazole-5-carboxylic acid (7-chloro-4-oxo-1-phenyl-1,4-dihydro-quinolin-3-ylmethyl)-amide;
N-(7-Chloro-4-oxo-1-phenyl-1,4-dihydro-quinolin-3-ylmethyl)-4-(2H-[1,2,4]triazol-3-yl)-benzamide;
1-(3-Chloro-benzyl)-2-oxo-1,2-dihydro-pyridine-4-carboxylic acid (7-chloro-4-oxo-1-phenyl-1,4-dihydro-quinolin-3-ylmethyl)-amide;
3-Methyl-3H-imidazo[4,5-b]pyridine-6-carboxylic acid (7-chloro-4-oxo-1-phenyl-1,4-dihydro-quinolin-3-ylmethyl)-amide;
1H-Indole-6-carboxylic acid (7-chloro-4-oxo-1-phenyl-1,4-dihydro-quinolin-3-ylmethyl)-amide;
N-(7-Chloro-4-oxo-1-phenyl-1,4-dihydro-quinolin-3-ylmethyl)-4-oxazol-5-yl-benzamide;
1-(2-Methoxy-benzyl)-2-oxo-1,2-dihydro-pyridine-4-carboxylic acid (7-chloro-4-oxo-1-phenyl-1,4-dihydro-quinolin-3-ylmethyl)-amide;
1H-Imidazo[4,5-b]pyridine-6-carboxylic acid (7-chloro-4-oxo-1-phenyl-1,4-dihydro-quinolin-3-ylmethyl)-amide;
N-(7-Chloro-4-oxo-1-phenyl-1,4-dihydro-quinolin-3-ylmethyl)-terephthalamide;

3-[(7-Chloro-4-oxo-1-phenyl-1,4-dihydro-quinolin-3-yl-methyl)-carbamoyl]-pyrrolidine-1-carboxylic acid tert-butyl ester;
1-Benzyl-6-oxo-1,6-dihydro-pyridine-3-carboxylic acid (7-chloro-4-oxo-1-phenyl-1,4-dihydro-quinolin-3-ylmethyl)-amide;
1-Methyl-1H-[1,2,3]triazole-4-carboxylic acid (7-chloro-4-oxo-1-phenyl-1,4-dihydro-quinolin-3-ylmethyl)-amide;
1-Methyl-2-oxo-1,2-dihydro-pyridine-4-carboxylic acid (7-chloro-4-oxo-1-phenyl-1,4-dihydro-quinolin-3-ylmethyl)-amide;
1-Benzyl-1H-[1,2,3]triazole-4-carboxylic acid (7-chloro-4-oxo-1-phenyl-1,4-dihydro-quinolin-3-ylmethyl)-amide;
2-Morpholin-4-yl-pyrimidine-5-carboxylic acid (7-chloro-4-oxo-1-phenyl-1,4-dihydro-quinolin-3-ylmethyl)-amide;
N-(7-Chloro-4-oxo-1-phenyl-1,4-dihydro-quinolin-3-yl-methyl)-3,4-dimethoxy-benzamide;
N-(7-Chloro-4-oxo-1-phenyl-1,4-dihydro-quinolin-3-yl-methyl)-3,5-difluoro-benzamide;
N-(7-Chloro-4-oxo-1-phenyl-1,4-dihydro-quinolin-3-yl-methyl)-2,3-difluoro-benzamide;
N-(7-Chloro-4-oxo-1-phenyl-1,4-dihydro-quinolin-3-yl-methyl)-2,5-difluoro-benzamide;
6-Chloro-N-(7-chloro-4-oxo-1-phenyl-1,4-dihydro-quinolin-3-ylmethyl)-nicotinamide;
(1S,4S)-5-{5-[(7-Chloro-4-oxo-1-phenyl-1,4-dihydro-quinolin-3-ylmethyl)-carbamoyl]-pyridin-2-yl}-2,5-diaza-bicyclo[2.2.1]heptane-2-carboxylic acid tert-butyl ester;
4-(2-Hydroxy-ethyl)-3,4,5,6-tetrahydro-2H-[1,2']bipyridinyl-5'-carboxylic acid (7-chloro-4-oxo-1-phenyl-1,4-dihydro-quinolin-3-ylmethyl)-amide;
6-[Bis-(2-hydroxy-ethyl)-amino]-N-(7-chloro-4-oxo-1-phenyl-1,4-dihydro-quinolin-3-ylmethyl)-nicotinamide;
3,4,5,6-Tetrahydro-2H-[1,2']bipyridinyl-5'-carboxylic acid (7-chloro-4-oxo-1-phenyl-1,4-dihydro-quinolin-3-ylmethyl)-amide;
N-(7-Chloro-4-oxo-1-phenyl-1,4-dihydro-quinolin-3-yl-methyl)-6-[(2-hydroxy-ethyl)-methyl-amino]-nicotinamide;
4-Hydroxymethyl-3,4,5,6-tetrahydro-2H-[1,2']bipyridinyl-5'-carboxylic acid (7-chloro-4-oxo-1-phenyl-1,4-dihydro-quinolin-3-ylmethyl)-amide;
6-Azepan-1-yl-N-(7-chloro-4-oxo-1-phenyl-1,4-dihydro-quinolin-3-ylmethyl)-nicotinamide;
4-Methanesulfonyl-3,4,5,6-tetrahydro-2H-[1,2']bipyridinyl-5'-carboxylic acid (7-chloro-4-oxo-1-phenyl-1,4-dihydro-quinolin-3-ylmethyl)-amide;
N-(7-Chloro-4-oxo-1-phenyl-1,4-dihydro-quinolin-3-yl-methyl)-6-((R)-3-hydroxy-pyrrolidin-1-yl)-nicotinamide;
4-Methoxy-3,4,5,6-tetrahydro-2H-[1,2]bipyridinyl-5'-carboxylic acid (7-chloro-4-oxo-1-phenyl-1,4-dihydro-quinolin-3-ylmethyl)-amide;
3,4,5,6-Tetrahydro-2H-[1,2]bipyridinyl-4,5'-dicarboxylic acid 5'-[(7-chloro-4-oxo-1-phenyl-1,4-dihydro-quinolin-3-ylmethyl)-amide]-4-methylamide;
4-{5-[(7-Chloro-4-oxo-1-phenyl-1,4-dihydro-quinolin-3-ylmethyl)-carbamoyl]-pyridin-2-yl}-piperazine-1-carboxylic acid amide;
N-(7-Chloro-4-oxo-1-phenyl-1,4-dihydro-quinolin-3-yl-methyl)-6-(2-methoxy-ethylamino)-nicotinamide;
4-Dimethylamino-3,4,5,6-tetrahydro-2H-[1,2]bipyridinyl-5'-carboxylic acid (7-chloro-4-oxo-1-phenyl-1,4-dihydro-quinolin-3-ylmethyl)-amide;
4-Hydroxy-3,4,5,6-tetrahydro-2H-[1,2]bipyridinyl-5'-carboxylic acid (7-chloro-4-oxo-1-phenyl-1,4-dihydro-quinolin-3-ylmethyl)-amide;
N-(7-Chloro-4-oxo-1-phenyl-1,4-dihydro-quinolin-3-yl-methyl)-6-(2-hydroxy-ethylamino)-nicotinamide;
N-(7-Chloro-4-oxo-1-phenyl-1,4-dihydro-quinolin-3-yl-methyl)-6-(tetrahydro-pyran-4-ylamino)-nicotinamide;
N-(7-Chloro-4-oxo-1-phenyl-1,4-dihydro-quinolin-3-yl-methyl)-6-dimethylamino-nicotinamide;
N-(7-Chloro-4-oxo-1-phenyl-1,4-dihydro-quinolin-3-yl-methyl)-6-(1,1-dioxo-1$\lambda^6$-thiomorpholin-4-yl)-nicotinamide;
{5'-[(7-Chloro-4-oxo-1-phenyl-1,4-dihydro-quinolin-3-ylmethyl)-carbamoyl]-3,4,5,6-tetrahydro-2H[1,2']bipyridinyl-4-yl}-carbamic acid tert-butyl ester;
N-(7-Chloro-4-oxo-1-phenyl-1,4-dihydro-quinolin-3-yl-methyl)-6-(4-methyl-[1,4]diazepan-1-yl)-nicotinamide;
N-(7-Chloro-4-oxo-1-phenyl-1,4-dihydro-quinolin-3-yl-methyl)-6-[4-(2-hydroxy-ethyl)-piperazin-1-yl]-nicotinamide;
N-(7-Chloro-4-oxo-1-phenyl-1,4-dihydro-quinolin-3-yl-methyl)-6-pyrrolidin-1-yl-nicotinamide;
N-(7-Chloro-4-oxo-1-phenyl-1,4-dihydro-quinolin-3-yl-methyl)-6-piperazin-1-yl-nicotinamide;
3,4,5,6-Tetrahydro-2H-[1,2]bipyridinyl-4,5'-dicarboxylic acid 4-amide 5'-[(7-chloro-4-oxo-1-phenyl-1,4-dihydro-quinolin-3-ylmethyl)-amide];
N-(7-Chloro-4-oxo-1-phenyl-1,4-dihydro-quinolin-3-yl-methyl)-6-((S)-3-hydroxy-pyrrolidin-1-yl)-nicotinamide;
N-(7-Chloro-4-oxo-1-phenyl-1,4-dihydro-quinolin-3-yl-methyl)-6-(4-methyl-piperazin-1-yl)-nicotinamide;
N-(7-Chloro-4-oxo-1-phenyl-1,4-dihydro-quinolin-3-yl-methyl)-6-(1S,4S)-2,5-diaza-bicyclo[2.2.1]hept-2-yl-nicotinamide
4-Amino-3,4,5,6-tetrahydro-2H-[1,2]bipyridinyl-5'-carboxylic acid (7-chloro-4-oxo-1-phenyl-1,4-dihydro-quinolin-3-ylmethyl)-amide;
2-Piperidin-1-yl-thiazole-5-carboxylic acid (7-chloro-4-oxo-1-phenyl-1,4-dihydro-quinolin-3-ylmethyl)-amide;
2-(4-Methanesulfonyl-piperidin-1-yl)-thiazole-5-carboxylic acid (7-chloro-4-oxo-1-phenyl-1,4-dihydro-quinolin-3-ylmethyl)-amide;
2-(4-Hydroxymethyl-piperidin-1-yl)-thiazole-5-carboxylic acid (7-chloro-4-oxo-1-phenyl-1,4-dihydro-quinolin-3-ylmethyl)-amide;
2-(4-Hydroxy-piperidin-1-yl)-thiazole-5-carboxylic acid (7-chloro-4-oxo-1-phenyl-1,4-dihydro-quinolin-3-ylmethyl)-amide;
2-(4-Methyl-piperazin-1-yl)-thiazole-5-carboxylic acid (7-chloro-4-oxo-1-phenyl-1,4-dihydro-quinolin-3-ylmethyl)-amide;
2-Morpholin-4-yl-thiazole-5-carboxylic acid (7-chloro-4-oxo-1-phenyl-1,4-dihydro-quinolin-3-ylmethyl)-amide;
2-(1,1-Dioxo-1$\lambda^6$-thiomorpholin-4-yl)-thiazole-5-carboxylic acid (7-chloro-4-oxo-1-phenyl-1,4-dihydro-quinolin-3-ylmethyl)-amide;
N-(7-Chloro-4-oxo-1-phenyl-1,4-dihydro-quinolin-3-yl-methyl)-N'-(2-hydroxy-2-methyl-propyl)-terephthala-mide;

N-(7-Chloro-4-oxo-1-phenyl-1,4-dihydro-quinolin-3-yl-methyl)-N'-((1R,3R)-5-hydroxy-adamantan-2-yl)-terephthalamide;

N-[7-Chloro-1-(2-chloro-phenyl)-4-oxo-1,4-dihydro-quinolin-3-ylmethyl]-6-morpholin-4-yl-nicotinamide;

6-Bromo-N-[7-chloro-1-(2-chloro-phenyl)-4-oxo-1,4-dihydro-quinolin-3-ylmethyl]-nicotinamide;

N-[7-Chloro-1-(2-chloro-phenyl)-4-oxo-1,4-dihydro-quinolin-3-ylmethyl]-6-(1H-pyrazol-4-yl)-nicotinamide;

1-Phenyl-1H-pyrazole-4-carboxylic acid [7-fluoro-1-(2-fluoro-phenyl)-4-oxo-1,4-dihydro-quinolin-3-ylmethyl]-amide;

1-Methyl-1H-pyrazole-4-carboxylic acid [7-fluoro-1-(2-fluoro-phenyl)-4-oxo-1,4-dihydro-quinolin-3-ylmethyl]-amide;

6-Chloro-N-[7-fluoro-1-(2-fluoro-phenyl)-4-oxo-1,4-dihydro-quinolin-3-ylmethyl]-nicotinamide;

4-Hydroxymethyl-3,4,5,6-tetrahydro-2H-[1,2']bipyridinyl-5'-carboxylic acid [7-fluoro-1-(2-fluoro-phenyl)-4-oxo-1,4-dihydro-quinolin-3-ylmethyl]-amide;

6-(1,1-Dioxo-1$\lambda^6$-thiomorpholin-4-yl)-N-[7-fluoro-1-(2-fluoro-phenyl)-4-oxo-1,4-dihydro-quinolin-3-ylmethyl]-nicotinamide;

N-[7-Fluoro-1-(2-fluoro-phenyl)-4-oxo-1,4-dihydro-quinolin-3-ylmethyl]-6-morpholin-4-yl-nicotinamide;

7-Chloro-3-[(4-methanesulfonyl-benzoylamino)-methyl]-4-oxo-1-phenyl-1,4-dihydro-quinoline-2-carboxylic acid methyl ester;

7-Chloro-3-[(4-oxazol-5-yl-benzoylamino)-methyl]-4-oxo-1-phenyl-1,4-dihydro-quinoline-2-carboxylic acid methyl ester;

7-Chloro-4-oxo-1-phenyl-3-{[4-(4H-[1,2,4]triazol-3-yl)-benzoylamino]-methyl}-1,4-dihydro-quinoline-2-carboxylic acid methyl ester;

7-Chloro-3-{[(6-morpholin-4-yl-pyridine-3-carbonyl)-amino]-methyl}-4-oxo-1-phenyl-1,4-dihydro-quinoline-2-carboxylic acid methyl ester;

3-{[(Benzothiazole-5-carbonyl)-amino]-methyl}-7-chloro-4-oxo-1-phenyl-1,4-dihydro-quinoline-2-carboxylic acid methyl ester;

7-Chloro-3-{[4-(1H-imidazol-2-yl)-benzoylamino]-methyl}-4-oxo-1-phenyl-1,4-dihydro-quinoline-2-carboxylic acid methyl ester;

7-Chloro-4-oxo-1-phenyl-3-[(4-sulfamoyl-benzoylamino)-methyl]-1,4-dihydro-quinoline-2-carboxylic acid methyl ester;

7-Chloro-3-{[(2-morpholin-4-yl-thiazole-5-carbonyl)-amino]-methyl}-4-oxo-1-phenyl-1,4-dihydro-quinoline-2-carboxylic acid methyl ester;

3-[(4-Carbamoyl-benzoylamino)-methyl]-7-chloro-4-oxo-1-phenyl-1,4-dihydro-quinoline-2-carboxylic acid methyl ester;

7-Chloro-3-[(4-methylcarbamoyl-benzoylamino)-methyl]-4-oxo-1-phenyl-1,4-dihydro-quinoline-2-carboxylic acid methyl ester;

3-{[(1-Benzyl-1H-pyrazole-4-carbonyl)-amino]-methyl}-7-chloro-4-oxo-1-phenyl-1,4-dihydro-quinoline-2-carboxylic acid methyl ester;

7-Chloro-3-{[(1H-indole-6-carbonyl)-amino]-methyl}-4-oxo-1-phenyl-1,4-dihydro-quinoline-2-carboxylic acid methyl ester;

7-Chloro-3-{[(1-methyl-1H-pyrazole-4-carbonyl)-amino]-methyl}-4-oxo-1-phenyl-1,4-dihydro-quinoline-2-carboxylic acid methyl ester;

7-Chloro-4-oxo-1-phenyl-3-{[4-(1H-pyrazol-3-yl)-benzoylamino]-methyl}-1,4-dihydro-quinoline-2-carboxylic acid methyl ester;

7-Chloro-3-[(4-morpholin-4-yl-benzoylamino)-methyl]-4-oxo-1-phenyl-1,4-dihydro-quinoline-2-carboxylic acid methyl ester;

7-Chloro-4-oxo-1-phenyl-3-[(4-[1,2,3]thiadiazol-5-yl-benzoylamino)-methyl]-1,4-dihydro-quinoline-2-carboxylic acid methyl ester;

7-Chloro-3-{[4-(5-methyl-[1,2,4]oxadiazol-3-yl)-benzoylamino]-methyl}-4-oxo-1-phenyl-1,4-dihydro-quinoline-2-carboxylic acid methyl ester;

7-Chloro-3-{[4-(3-methyl-[1,2,4]oxadiazol-5-yl)-benzoylamino]-methyl}-4-oxo-1-phenyl-1,4-dihydro-quinoline-2-carboxylic acid methyl ester;

7-Chloro-3-{[4-(2-methyl-thiazol-4-yl)-benzoylamino]-methyl}-4-oxo-1-phenyl-1,4-dihydro-quinoline-2-carboxylic acid methyl ester;

3-{[(1-tert-Butoxycarbonyl-piperidine-4-carbonyl)-amino]-methyl}-7-chloro-4-oxo-1-phenyl-1,4-dihydro-quinoline-2-carboxylic acid methyl ester;

7-Chloro-3-{[4-(2-methyl-2H-tetrazol-5-yl)-benzoylamino]-methyl}-4-oxo-1-phenyl-1,4-dihydro-quinoline-2-carboxylic acid methyl ester;

3-{[(1-Acetyl-piperidine-4-carbonyl)-amino]-methyl}-7-chloro-4-oxo-1-phenyl-1,4-dihydro-quinoline-2-carboxylic acid methyl ester;

7-Chloro-3-{[(1-methanesulfonyl-piperidine-4-carbonyl)-amino]-methyl}-4-oxo-1-phenyl-1,4-dihydro-quinoline-2-carboxylic acid methyl ester;

7-Chloro-3-[(4-chloro-benzoylamino)-methyl]-4-oxo-1-phenyl-1,4-dihydro-quinoline-2-carboxylic acid methyl ester;

7-Chloro-3-[(4-methoxycarbonyl-benzoylamino)-methyl]-4-oxo-1-phenyl-1,4-dihydro-quinoline-2-carboxylic acid methyl ester;

7-Chloro-3-[(4-methoxy-benzoylamino)-methyl]-4-oxo-1-phenyl-1,4-dihydro-quinoline-2-carboxylic acid methyl ester;

7-Chloro-3-[(3-methoxy-benzoylamino)-methyl]-4-oxo-1-phenyl-1,4-dihydro-quinoline-2-carboxylic acid methyl ester;

7-Chloro-4-oxo-1-phenyl-3-{[(pyridine-4-carbonyl)-amino]-methyl}-1,4-dihydro-quinoline-2-carboxylic acid methyl ester;

7-Chloro-3-[(3,4-difluoro-benzoylamino)-methyl]-4-oxo-1-phenyl-1,4-dihydro-quinoline-2-carboxylic acid methyl ester;

7-Chloro-3-[(3-fluoro-benzoylamino)-methyl]-4-oxo-1-phenyl-1,4-dihydro-quinoline-2-carboxylic acid methyl ester;

7-Chloro-4-oxo-1-phenyl-3-{[(pyridine-3-carbonyl)-amino]-methyl}-1,4-dihydro-quinoline-2-carboxylic acid methyl ester;

7-Chloro-3-[(4-fluoro-benzoylamino)-methyl]-4-oxo-1-phenyl-1,4-dihydro-quinoline-2-carboxylic acid methyl ester;

7-Chloro-3-[(3-chloro-4-fluoro-benzoylamino)-methyl]-4-oxo-1-phenyl-1,4-dihydro-quinoline-2-carboxylic acid methyl ester;

7-Chloro-3-[(3-chloro-benzoylamino)-methyl]-4-oxo-1-phenyl-1,4-dihydro-quinoline-2-carboxylic acid methyl ester 7-Chloro-3-[(3,4-dimethoxy-benzoylamino)-methyl]-4-oxo-1-phenyl-1,4-dihydro-quinoline-2-carboxylic acid methyl ester 7-Chloro-3-[(3,4-dichloro-benzoylamino)-methyl]-4-oxo-1-phenyl-1,4-dihydro-quinoline-2-carboxylic acid methyl ester;
7-Chloro-3-[(2-fluoro-benzoylamino)-methyl]-4-oxo-1-phenyl-1,4-dihydro-quinoline-2-carboxylic acid methyl ester;
7-Chloro-4-oxo-1-phenyl-3-{[(pyridine-2-carbonyl)-amino]-methyl}-1,4-dihydro-quinoline-2-carboxylic acid methyl ester;
7-Chloro-3-(isobutyrylamino-methyl)-4-oxo-1-phenyl-1,4-dihydro-quinoline-2-carboxylic acid methyl ester;
7-Chloro-3-[(2-chloro-benzoylamino)-methyl]-4-oxo-1-phenyl-1,4-dihydro-quinoline-2-carboxylic acid methyl ester;
7-Chloro-3-[(2-methoxy-benzoylamino)-methyl]-4-oxo-1-phenyl-1,4-dihydro-quinoline-2-carboxylic acid methyl ester;
3-(Benzoylamino-methyl)-7-chloro-4-oxo-1-phenyl-1,4-dihydro-quinoline-2-carboxylic acid methyl ester;
3-(Benzoylamino-methyl)-4-oxo-1-phenyl-1,4-dihydro-quinoline-2-carboxylic acid methyl ester;
3-{[(6-Morpholin-4-yl-pyridine-3-carbonyl)-amino]-methyl}-4-oxo-1-phenyl-7-trifluoromethyl-1,4-dihydro-[1,8]naphthyridine-2-carboxylic acid methyl ester
3-{[4-(1H-Imidazol-2-yl)-benzoylamino]-methyl}-4-oxo-1-phenyl-7-trifluoromethyl-1,4-dihydro-[1,8]naphthyridine-2-carboxylic acid methyl ester;
4-oxo-1-phenyl-3-[(4-sulfamoyl-benzoylamino)-methyl]-7-trifluoromethyl-1,4-dihydro-[1,8]naphthyridine-2-carboxylic acid methyl ester;
3-[(4-Carbamoyl-benzoylamino)-methyl]-4-oxo-1-phenyl-7-trifluoromethyl-1,4-dihydro-[1,8]naphthyridine-2-carboxylic acid methyl ester;
4-Oxo-1-phenyl-3-{[4-(2H-pyrazol-3-yl)-benzoylamino]-methyl}-7-trifluoromethyl-1,4-dihydro-[1,8]naphthyridine-2-carboxylic acid methyl ester;
3-{[4-(2-Methyl-2H-tetrazol-5-yl)-benzoylamino]-methyl}-4-oxo-1-phenyl-7-trifluoromethyl-1,4-dihydro-[1,8]naphthyridine-2-carboxylic acid methyl ester;
3-{[(1H-Indole-6-carbonyl)-amino]-methyl}-4-oxo-1-phenyl-7-trifluoromethyl-1,4-dihydro-[1,8]naphthyridine-2-carboxylic acid methyl ester;
3-[(3,4-Dichloro-benzoylamino)-methyl]-4-oxo-1-phenyl-7-trifluoromethyl-1,4-dihydro-[1,8]naphthyridine-2-carboxylic acid methyl ester;
3-[(3-Chloro-benzoylamino)-methyl]-7-methoxy-4-oxo-1-phenyl-1,4-dihydro-quinoline-2-carboxylic acid methyl ester;
7-Methoxy-3-[(3-methoxy-benzoylamino)-methyl]-4-oxo-1-phenyl-1,4-dihydro-quinoline-2-carboxylic acid methyl ester;
3-[(3,4-Difluoro-benzoylamino)-methyl]-7-methoxy-4-oxo-1-phenyl-1,4-dihydro-quinoline-2-carboxylic acid methyl ester;
3-[(4-tert-Butyl-benzoylamino)-methyl]-7-methoxy-4-oxo-1-phenyl-1,4-dihydro-quinoline-2-carboxylic acid methyl ester;
7-Methoxy-3-[(4-methoxy-benzoylamino)-methyl]-4-oxo-1-phenyl-1,4-dihydro-quinoline-2-carboxylic acid methyl ester;
7-Methoxy-4-oxo-1-phenyl-3-{[(pyridine-3-carbonyl)-amino]-methyl}-1,4-dihydro-quinoline-2-carboxylic acid methyl ester;
3-[(4-Fluoro-benzoylamino)-methyl]-7-methoxy-4-oxo-1-phenyl-1,4-dihydro-quinoline-2-carboxylic acid methyl ester;
3-[(4-Dimethylamino-benzoylamino)-methyl]-7-methoxy-4-oxo-1-phenyl-1,4-dihydro-quinoline-2-carboxylic acid methyl ester;
3-[(4-Chloro-benzoylamino)-methyl]-7-methoxy-4-oxo-1-phenyl-1,4-dihydro-quinoline-2-carboxylic acid methyl ester;
7-Fluoro-3-{[(6-morpholin-4-yl-pyridine-3-carbonyl)-amino]-methyl}-4-oxo-1-phenyl-1,4-dihydro-quinoline-2-carboxylic acid methyl ester;
3-{[(6-Chloro-pyridine-3-carbonyl)-amino]-methyl}-7-fluoro-4-oxo-1-phenyl-1,4-dihydro-quinoline-2-carboxylic acid methyl ester;
7-Chloro-3-[(6,7-dimethoxy-quinazolin-4-ylamino)-methyl]-1-phenyl-1H-quinolin-4-one;
7-Chloro-3-[(7-fluoro-quinazolin-4-ylamino)-methyl]-1-phenyl-1H-quinolin-4-one;
7-Chloro-1-phenyl-3-[(6-piperidin-1-yl-pyrimidin-4-ylamino)-methyl]-1H-quinolin-4-one;
7-Chloro-1-phenyl-3-[(2-piperidin-1-yl-pyrimidin-4-ylamino)-methyl]-1H-quinolin-4-one;
3-(Benzothiazol-2-ylaminomethyl)-7-chloro-1-phenyl-1H-quinolin-4-one;
3-[(1H-Benzoimidazol-2-ylamino)-methyl]-7-chloro-1-phenyl-1H-quinolin-4-one;
[(7-Chloro-4-oxo-1-phenyl-1,4-dihydro-quinolin-3-ylmethyl)-amino]-morpholin-4-yl-methylene-cyanamide;
[(7-Chloro-4-oxo-1-phenyl-1,4-dihydro-quinolin-3-ylmethyl)-amino]-phenylamino-methylene-cyanamide;
(7-Chloro-4-oxo-1-phenyl-1,4-dihydro-quinolin-3-ylmethyl)-carbamic acid phenyl ester;
4-Phenyl-piperazine-1-carboxylic acid (7-chloro-4-oxo-1-phenyl-1,4-dihydro-quinolin-3-ylmethyl)-amide;
{4-[3-(7-Chloro-4-oxo-1-phenyl-1,4-dihydro-quinolin-3-ylmethyl)-ureido]-cyclohexyl}-carbamic acid tert-butyl ester;
{4-[3-(7-Chloro-4-oxo-1-phenyl-1,4-dihydro-quinolin-3-ylmethyl)-ureido]-cyclohexyl}-carbamic acid tert-butyl ester;
3-[3-(7-Chloro-4-oxo-1-phenyl-1,4-dihydro-quinolin-3-ylmethyl)-ureido]-pyrrolidine-1-carboxylic acid tert-butyl ester;
1-(7-Chloro-4-oxo-1-phenyl-1,4-dihydro-quinolin-3-ylmethyl)-3-cyclopentyl-urea;
4-[3-(7-Chloro-4-oxo-1-phenyl-1,4-dihydro-quinolin-3-ylmethyl)-ureido]-cyclohexanecarboxylic acid methyl ester;
Pyrrolidine-1-carboxylic acid (7-chloro-4-oxo-1-phenyl-1,4-dihydro-quinolin-3-ylmethyl)-amide;
4-Methyl-piperazine-1-carboxylic acid (7-chloro-4-oxo-1-phenyl-1,4-dihydro-quinolin-3-ylmethyl)-amide;
Piperidine-1-carboxylic acid (7-chloro-4-oxo-1-phenyl-1,4-dihydro-quinolin-3-ylmethyl)-amide;
4-[3-(7-Chloro-4-oxo-1-phenyl-1,4-dihydro-quinolin-3-ylmethyl)-ureido]-cyclohexanecarboxylic acid methyl ester;
4-Phenyl-piperidine-1-carboxylic acid (7-chloro-4-oxo-1-phenyl-1,4-dihydro-quinolin-3-ylmethyl)-amide;
1-(7-Chloro-4-oxo-1-phenyl-1,4-dihydro-quinolin-3-ylmethyl)-3-((1S,3R,7S)-5-hydroxy-adamantan-2-yl)-urea;
4-[3-(7-Chloro-4-oxo-1-phenyl-1,4-dihydro-quinolin-3-ylmethyl)-ureido]-piperidine-1-carboxylic acid tert-butyl ester
4-[3-(7-Chloro-4-oxo-1-phenyl-1,4-dihydro-quinolin-3-ylmethyl)-ureido]-piperidine-1-carboxylic acid phenyl ester;

1-(1-Benzoyl-piperidin-4-yl)-3-(7-chloro-4-oxo-1-phenyl-1,4-dihydro-quinolin-3-ylmethyl)-urea;
4-[3-(7-Chloro-4-oxo-1-phenyl-1,4-dihydro-quinolin-3-ylmethyl)-ureido]-piperidine-1-carboxylic acid benzyl ester;
1-(1-Benzenesulfonyl-piperidin-4-yl)-3-(7-chloro-4-oxo-1-phenyl-1,4-dihydro-quinolin-3-ylmethyl)-urea;
1-(7-Chloro-4-oxo-1-phenyl-1,4-dihydro-quinolin-3-ylmethyl)-3-(1-methanesulfonyl-piperidin-4-yl)-urea;
1-(1-Acetyl-piperidin-4-yl)-3-(7-chloro-4-oxo-1-phenyl-1,4-dihydro-quinolin-3-ylmethyl)-urea;
1-(7-Chloro-4-oxo-1-phenyl-1,4-dihydro-quinolin-3-ylmethyl)-3-[1-(4-methanesulfonyl-piperidine-1-carbonyl)-piperidin-4-yl]-urea;
Morpholine-4-carboxylic acid (7-chloro-4-oxo-1-phenyl-1,4-dihydro-quinolin-3-ylmethyl)-amide;
1-(7-Chloro-4-oxo-1-phenyl-1,4-dihydro-quinolin-3-ylmethyl)-3-phenyl-urea;
1-(7-Chloro-4-oxo-1-phenyl-1,4-dihydro-quinolin-3-ylmethyl)-3-(4-dimethylamino-phenyl)-urea;
1-(7-Chloro-4-oxo-1-phenyl-1,4-dihydro-quinolin-3-ylmethyl)-3-(4-methoxy-phenyl)-urea;
1-(3-Chloro-4-fluoro-phenyl)-3-(7-chloro-4-oxo-1-phenyl-1,4-dihydro-quinolin-3-ylmethyl)-urea;
1-(7-Chloro-4-oxo-1-phenyl-1,4-dihydro-quinolin-3-ylmethyl)-3-(4-trifluoromethoxy-phenyl)-urea;
4-[3-(7-Chloro-4-oxo-1-phenyl-1,4-dihydro-quinolin-3-ylmethyl)-ureido]-benzoic acid methyl ester;
7-Chloro-3-(isoquinolin-1-ylaminomethyl)-4-oxo-1-phenyl-1,4-dihydro-quinoline-2-carboxylic acid methyl ester;
7-Chloro-4-oxo-1-phenyl-3-(quinazolin-4-ylaminomethyl)-1,4-dihydro-quinoline-2-carboxylic acid methyl ester;
7-Chloro-3-{[(morpholine-4-carbonyl)-amino]-methyl}-4-oxo-1-phenyl-1,4-dihydro-quinoline-2-carboxylic acid methyl ester;
7-Chloro-4-oxo-3-(phenoxycarbonylamino-methyl)-1-phenyl-1,4-dihydro-quinoline-2-carboxylic acid methyl ester; and
7-Chloro-3-{[(4-methanesulfonyl-benzoyl)-methyl-amino]-methyl}-4-oxo-1-phenyl-1,4-dihydro-quinoline-2-carboxylic acid methyl ester.

15. A pharmaceutical composition comprising the compound of claim 1, admixed with at least one pharmaceutically acceptable carrier, excipient or diluent.

\* \* \* \* \*